US007754859B2

(12) United States Patent
Laing et al.

(10) Patent No.: US 7,754,859 B2
(45) Date of Patent: Jul. 13, 2010

(54) TARGETED BINDING AGENTS DIRECTED TO PDGFR-ALPHA AND USES THEREOF

(75) Inventors: Naomi Laing, Waltham, MA (US); Jaspal Singh Kang, Burnaby (CA); Ian Foltz, Burnaby (CA); Gadi Gazit-Bornstein, Waltham, MA (US); Xiao-Dang Yang, Palo Alco, CA (US); David Charles Blakey, Macclesfield (GB); Sue A. Cartlidge, Macclesfield (GB)

(73) Assignee: AstraZeneca AB, Soedertaelje (SE)

( * ) Notice: Subject to any disclaimer, the term of this patent is extended or adjusted under 35 U.S.C. 154(b) by 119 days.

(21) Appl. No.: 11/833,473

(22) Filed: Aug. 3, 2007

(65) Prior Publication Data

US 2008/0089837 A1 Apr. 17, 2008

Related U.S. Application Data

(60) Provisional application No. 60/835,647, filed on Aug. 3, 2006.

(51) Int. Cl.

| | |
|---|---|
| ***C12P 21/08*** | (2006.01) |
| ***C07K 16/00*** | (2006.01) |
| ***A61K 39/00*** | (2006.01) |
| *C07K 17/00* | (2006.01) |
| *C07K 17/14* | (2006.01) |

(52) U.S. Cl. ............................ 530/388.15; 530/387.1; 530/391.1; 424/133.1; 424/134.1; 424/178.1

(58) Field of Classification Search ...................... None
See application file for complete search history.

(56) References Cited

U.S. PATENT DOCUMENTS

| | | | | |
|---|---|---|---|---|
| 2003/0165831 A1 | 9/2003 | Lee et al. | | |
| 2005/0058649 A1* | 3/2005 | Landes et al. | ............ | 424/146.1 |
| 2005/0059113 A1* | 3/2005 | Bedian et al. | .............. | 435/69.1 |

FOREIGN PATENT DOCUMENTS

| | | | |
|---|---|---|---|
| CA | 2560046 | A1 | 9/2005 |
| WO | 90/10013 | A1 | 9/1990 |
| WO | 92/13867 | A1 | 8/1992 |
| WO | 92/13870 | A1 | 8/1992 |
| WO | 93/23068 | A1 | 11/1993 |
| WO | 95/00659 | A1 | 1/1995 |
| WO | 97/37029 | A1 | 10/1997 |
| WO | 2005/087269 | A1 | 9/2005 |
| WO | 2006/138729 | A2 | 12/2006 |

OTHER PUBLICATIONS

J Davies et al., "Affinity improvement of single antibody VH domains: residues in all three hypervariable regions affect antigen binding", Immunotechnology (1996) 169-179, vol. 2, No. 3.

M Little et al. "Of mice and men: hybridoma and recombinant antibodies", Immunology Today (2000) 364-370, vol. 21, No. 8.

T J MacDonald et al. "Expression profiling of medulloblastoma: PDGFRA and the RAS/MAPK pathway as therapeutic targets for metastatic disease" Nature Genetics (2001) 143-152, vol. 29, No. 2.

L J Holt et al. "Domain antibodies: proteins for therapy" Trends in Biotechnology (2003) 484-490, Vol. 21, No. 11.

N Loizos et al. "Targeting the platelet-derived growth factor receptor A with a neutralizing human monoclonal antibody inhibits the growth of tumor xenografts: Implications as a potential therapeutic target" Molecular Cancer Therapeutics (2005) 369-379, vol. 4, No. 3.

P Müller et al. "A novel therapeutic target in human hepatocellular cancer" FASEB, Journal Fed. Of American Soc. For Experimental Biology (2005) A1505-A1506, Vol. 19, No. 5, Suppl. S, Part 2.

D S Deevi et al. "Inhibition of human osteosarcoma xenograft growth by anti-Platelet derived growth factor receptor alpha antibody, IMC-3G3, alone and in combination with chemotherapy" Proceedings of the American Association for Cancer Research Annual Meeting (2006) 877, vol. 47, Abstract 3729.

W Li et al. "Platelet Derived Growth Factor Receptor Alpha Is Essential for Establishing a Microenvironment That Supports Definitive Erythropoiesis" Journal of Biochemistry (2006) 267-273, vol. 140, No. 2.

P Stock et al. "Platelet-derived growth factor receptor-A: a novel therapeutic target in human hepatocellular cancer" Molecular Cancer Therapeutics (2007) 1932-1941, vol. 6, No. 7.

Blakey, D, 'The Development of a Portfolio of Antibody Based Therapeutics for Cancer Therapy', Presentation given at ELRIG (2009) European Laboratory Robotics Interest Group - Drug Discovery 2009.

Blakey, D, 'Development of a Portfolio of Antibody Based Therapeutics for Oncology', Presentation given at PEGS (2009) Protein Engineering Summit - 5th Annual.

Blakey, D, 'Development of novel human therapeutic antibodies targeting the IGF and PDGF signalling pathways for cancer therapy', Presentation given at ICRA (2009) International Congress on Recombinant Antibodies - 8th.

Bosslet, K, 'Development of a Portfolio of Antibody Based Therapeutics for Cancer Therapy', Presentation given at MipTec, 2009.

Bosslet, K 'The Development of Therapeutic Antibodies for Cancer Therapy', Presentation given at BIO (2009) Bionnale.

Gaithersburg, MD, Press release - Medlmmune Advances Three Oncology Programs Into the Clinic, Aug. 10, 2009 (http://pressroom.medimmune.com/press-releases/2009/08/10/medimmune-advances-three-oncologyprograms-into-the-clinic/).

Grotendorst et al, 'Differential Binding, Biological and Biochemical Actions of Recombinant PDGF AA, AB, and BB Molecules on Connective Tissue Cells', Journal of Cellular Physiology, 149, (1991), 235-243.

(Continued)

*Primary Examiner*—Larry R. Helms
*Assistant Examiner*—Anne M. Gussow

(57) ABSTRACT

Targeted binding agents directed to the antigen PDGFR-alpha and uses of such agents are disclosed herein. More specifically the invention relates to fully human monoclonal antibodies directed to the antigen PDGFR-alpha and uses of these antibodies. Aspects of the invention also relate to hybridomas or other cell lines expressing such antibodies. The described targeted binding agents and antibodies are useful as diagnostics and for the treatment of diseases associated with the activity and/or overexpression of PDGFR-alpha.

18 Claims, 4 Drawing Sheets

OTHER PUBLICATIONS

Jermutus, L. et al, 'Challenges in the preclinical development of monoclonal antibodies', Presentation given at KS (2009) Keystone Symposia - Antibodies as Drugs (Joint Meeting).

Laing, N et al, 'Characterization of a fully human PDGFRa antibody that reduces tumor growth and stromal infiltration in a xenograft model of non-small cell lung cancer', Eur J Cancer Suppl (20th EORTC-NCI-AACR Symp Mol Targets Cancer Ther –Oct. 21-24, Geneva 2008), vol. 6 (12): Abst 535.

Matsui et al, 'Isolation of a Novel Receptor cDNA Establishes the Existence of Two PDGF Receptor Genes', Science, 243 (1989), 800-804.

MEDI-575 clinical study ClinicalTrials.gov, 'A Phase 1, Multicenter, Open-label, Single-arm, Dose-escalation Study to Evaluate the Safety, Tolerability, and Antitumor Activity of MEDI-575, a Fully Human Monocional Antibody Directed Against Platelet-derived Growth Factor Receptor Alpha (PDGFRa), in Subjects With Advanced Solid Tumors Refractory to Standard Therapy or for Which No Standard Therapy Exists', Sep. 2009, Identifier: NCT00816400 (http://clinicaltrials.gov/ct2/shown/NCT00816400).

Steiner, P et al, 'Inhibition of the Platelet-Derived Growth Factor Receptor Alpha (PDGFRa) Signaleng Pthway with the Human Monoclonal Antibody MEDI-575 in Preclinical Mouse Models of NSCLC', Abstract from WCLC (2009) World Conference of Lung Cancer –13th.

Zusmanovich, M et al, 'A Pharmacokinetic Study of Medi-575, a fully human IgG2 kappa monoclonal antibody in Cynomolgus Monkeys Following Intravenous Administration', An abstract from AAPS (2009) American Association of Pharmaceutical Scientists –2009 Annual Meeting and Exposition.

* cited by examiner

SEQUENCE LISTING

```
<160> NUMBER OF SEQ ID NOS: 154

<210> SEQ ID NO 1
<211> LENGTH: 360
<212> TYPE: DNA
<213> ORGANISM: Homo sapiens

<400> SEQUENCE: 1

caggtgcacc tggtggagtc tgggggaggc ttggtcaagc ctggagggtc cctgagactc      60

tcctgtgcag cctctggatt caccttcagt gactactaca tgcactggat ccgccaggct     120

ccagggaagg gcctggagtg ggtttcatac attagtagaa gtggcagtct catatactac     180

gtagactctg tgaagggccg attcaccatc tccagggaca acgccaagaa ctcactgaat     240

ctgcaaatga acagcctgag agccgaggac acggccgtgt actactgtgc gagagggggg     300

ccgtatagtg ggagcccctt tgactactgg ggccagggaa ccctggtcac cgtctcctca     360


<210> SEQ ID NO 2
<211> LENGTH: 120
<212> TYPE: PRT
<213> ORGANISM: Homo sapiens

<400> SEQUENCE: 2

Gln Val His Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met His Trp Ile Arg Gln Ala Pro Gly Lys Gly Leu Glu Trp Val
        35                  40                  45
```

-continued

Ser Tyr Ile Ser Arg Ser Gly Ser Leu Ile Tyr Tyr Val Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Ser Leu Arg Ala Glu Asp Thr Ala Val Tyr Tyr Cys
                85                  90                  95

Ala Arg Gly Gly Pro Tyr Ser Gly Ser Pro Phe Asp Tyr Trp Gly Gln
            100                 105                 110

Gly Thr Leu Val Thr Val Ser Ser
        115                 120

<210> SEQ ID NO 3
<211> LENGTH: 324
<212> TYPE: DNA
<213> ORGANISM: Homo sapiens

<400> SEQUENCE: 3
gacatccaga tgacccagtc tccatcctcc ctgtctgcat ctgtaggaga cagagtcacc 60
atcacttgcc ggccaagtca gagaattagc aggtatttaa attggtatca gcagaaacca 120
gggaaagccc ctaagttcct gatctatgct gcatccagtt tgccaagtgg ggtcccatca 180
aggttcagtg gcagtggatc tgggacagat ttcaccctca ccatcagcac tttacaacct 240
gaagattttg caacttacta ctgtcaacag agttacagta cccctccgtg gacgttcggc 300
caagggacca aggtggaaat caaa 324

<210> SEQ ID NO 4
<211> LENGTH: 108
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Arg Ile Ser Arg Tyr
            20                  25                  30

Leu Asn Trp Tyr Gln Gln Lys Pro Gly Lys Ala Pro Lys Phe Leu Ile
        35                  40                  45

Tyr Ala Ala Ser Ser Leu Pro Ser Gly Val Pro Ser Arg Phe Ser Gly
    50                  55                  60

Ser Gly Ser Gly Thr Asp Phe Thr Leu Thr Ile Ser Thr Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
            100                 105

<210> SEQ ID NO 5
<211> LENGTH: 360
<212> TYPE: DNA
<213> ORGANISM: Homo sapiens

<400> SEQUENCE: 5
caggtgcagc tggtggagtc tgggggaggc ttggtcaagc ctggagggtc cctgagactc 60
tcctgtgcag cctctggatt caccttcagt gactactaca tgaactggat ccgccaggct 120
ccagggaagg ggctggagtg ggtttcattc attagtagta gtggtagtac catatactac 180
gcagactctg tgaagggccg attcaccatc tccagggaca acgccaagaa ctcactgtat 240

-continued

```
ctgcaaatga acagcctgag agccgaggac acggccgtgt attactgtgc gagagatggt    300

catatagcag ctcgtggtat ggacgtctgg ggccaaggga ccacggtcac cgtctcctca    360


<210> SEQ ID NO 6
<211> LENGTH: 120
<212> TYPE: PRT
<213> ORGANISM: Homo sapiens

<400> SEQUENCE: 6

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser Phe Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly His Ile Ala Ala Arg Gly Met Asp Val Trp Gly Gln
            100                 105                 110

Gly Thr Thr Val Thr Val Ser Ser
        115                 120


<210> SEQ ID NO 7
<211> LENGTH: 336
<212> TYPE: DNA
<213> ORGANISM: Homo sapiens

<400> SEQUENCE: 7

gtcatccaga tgacccagtc tccatcctcc ctgtctgcat ctgtaggaga cagagtcacc     60

atcacttgcc gggcgagtca ggtcattacc aattatttag cctggtatca gcagaaacca    120

gggaaagttc ctaagctcct gatctttgct tcatccactt tgcaatcagg ggtcccatct    180

cggttcagtg gcagtggatc tgggacagat ttcactctca ccatcagcag cctgcagcct    240

gaagatgttg cgacttatta ctgtcagaag tataacagtg cccctccaag gactcgatcg    300

atcaccttcg gccaagggac acgactggag attaaa                              336


<210> SEQ ID NO 8
<211> LENGTH: 112
<212> TYPE: PRT
<213> ORGANISM: Homo sapiens

<400> SEQUENCE: 8

Val Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Thr Asn Tyr
            20                  25                  30

Leu Ala Trp Tyr Gln Gln Lys Pro Gly Lys Val Pro Lys Leu Leu Ile
        35                  40                  45

Phe Ala Ser Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

-continued

Glu Asp Val Ala Thr Tyr Tyr Cys Gln Lys Tyr Asn Ser Ala Pro Pro
85 90 95

Arg Thr Arg Ser Ile Thr Phe Gly Gln Gly Thr Arg Leu Glu Ile Lys
100 105 110

<210> SEQ ID NO 9
<211> LENGTH: 360
<212> TYPE: DNA
<213> ORGANISM: Homo sapiens

<400> SEQUENCE: 9
caggtgcagc tggtggagtc tgggggaggc ttggtcaagc ctggagggtc cctgaggctc 60
tcctgtgcag cctctggatt caccttcagt gactactaca tgaactggat ccgccaggct 120
ccagggaagg ggctggagtg ggtttcatac attagtagta gtggtagtat catatactac 180
gcagactctg tgaagggccg attcaccatc tccagggaca acgccaagaa ctcactgtat 240
ctgcaaatga acagcctgag agccgaggac acggccgtgt attactgtgc gagagaaggg 300
cgtatagcag ctcgtggtat ggacgtctgg ggccaaggga ccacggtcac cgtctcctca 360

<210> SEQ ID NO 10
<211> LENGTH: 120
<212> TYPE: PRT
<213> ORGANISM: Homo sapiens

<400> SEQUENCE: 10

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Asn Trp Ile Arg Gln Ala Pro Gly Lys Gly Leu Glu Trp Val
35 40 45

Ser Tyr Ile Ser Ser Ser Gly Ser Ile Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Glu Gly Arg Ile Ala Ala Arg Gly Met Asp Val Trp Gly Gln
100 105 110

Gly Thr Thr Val Thr Val Ser Ser
115 120

<210> SEQ ID NO 11
<211> LENGTH: 324
<212> TYPE: DNA
<213> ORGANISM: Homo sapiens

<400> SEQUENCE: 11
gacatccaga tgacccagtc tccatcctcc ctgtctgcat ctgtaggaga cagagtctcc 60
atcacttgcc ggccaagtca gagctttagc aggtatataa attggtatca gcagaaacca 120
gggaaagccc ctaagctcct gatccatgct gcatccagtt tggtaggtgg ggtcccatca 180
aggttcagtg gcagtggatc tgggacagat ttcactctca ccatcagcag tctgcaacct 240
gaagattttg caacttacta ctgtcaacag acttacagta accccccgat caccttcggc 300
caagggacac gactggagat gaaa 324

<210> SEQ ID NO 12
<211> LENGTH: 108
<212> TYPE: PRT
<213> ORGANISM: Homo sapiens

<400> SEQUENCE: 12

```
Asp Ile Gln Met Thr Gln Ser Pro Ser Ser Leu Ser Ala Ser Val Gly
1               5                   10                  15

Asp Arg Val Ser Ile Thr Cys Arg Pro Ser Gln Ser Phe Ser Arg Tyr
            20                  25                  30

Ile Asn Trp Tyr Gln Gln Lys Pro Gly Lys Ala Pro Lys Leu Leu Ile
        35                  40                  45

His Ala Ala Ser Ser Leu Val Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Asn Pro Pro
                85                  90                  95

Ile Thr Phe Gly Gln Gly Thr Arg Leu Glu Met Lys
            100                 105
```

<210> SEQ ID NO 13
<211> LENGTH: 351
<212> TYPE: DNA
<213> ORGANISM: Homo sapiens

<400> SEQUENCE: 13

```
cagctgcagc tgcaggagtc gggcccagga ctggtgaagc cttcggagac cctgtccctc      60

acctgcactg tctctggtga ctccatcagc agttttattt actactgggg ctggatccgc     120

cagcccccag ggaaggggct ggagtggatt gggactattt attatagtgg gagcacctac     180

tacaacccgt ccctcaagag tcgagtcacc atatccgtag acacgtccaa gaaccagttc     240

tccctgaagc tgaggtctgt gaccgccgca gacacggctg tgtattactg tgcgagacat     300

cactgggttt ttgactactg gggccaggga acccaggtca ccgtctcctc a              351
```

<210> SEQ ID NO 14
<211> LENGTH: 117
<212> TYPE: PRT
<213> ORGANISM: Homo sapiens

<400> SEQUENCE: 14

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Ser Ser Phe
            20                  25                  30

Ile Tyr Tyr Trp Gly Trp Ile Arg Gln Pro Pro Gly Lys Gly Leu Glu
        35                  40                  45

Trp Ile Gly Thr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg His His Trp Val Phe Asp Tyr Trp Gly Gln Gly Thr Gln
            100                 105                 110

Val Thr Val Ser Ser
```

-continued

115

<210> SEQ ID NO 15
<211> LENGTH: 321
<212> TYPE: DNA
<213> ORGANISM: Homo sapiens

<400> SEQUENCE: 15
gacattgtgc tgactcagtt tccagacttt cagtctgtga ctccaaagga gaaagtcacc 60
atcacttgcc gggccagtca ggtcattggt agtagcttac actggtacca gcagaaacca 120
gatcagtctc cgaagctcct catcaagtat gcttcccagt ccttctcagg ggtcccctcg 180
aggttcagtg gcagtggatc tgggacagat ttcaccctca ccatcaatag cctggaagtt 240
gaagatgctg caacgtatta ctgtcatcag agtactattt taccgtggac gttcggccaa 300
gggaccaagg tggaagtcaa a 321

<210> SEQ ID NO 16
<211> LENGTH: 107
<212> TYPE: PRT
<213> ORGANISM: Homo sapiens

<400> SEQUENCE: 16

Asp Ile Val Leu Thr Gln Phe Pro Asp Phe Gln Ser Val Thr Pro Lys
1 5 10 15

Glu Lys Val Thr Ile Thr Cys Arg Ala Ser Gln Val Ile Gly Ser Ser
20 25 30

Leu His Trp Tyr Gln Gln Lys Pro Asp Gln Ser Pro Lys Leu Leu Ile
35 40 45

Lys Tyr Ala Ser Gln Ser Phe Ser Gly Val Pro Ser Arg Phe Ser Gly
50 55 60

Ser Gly Ser Gly Thr Asp Phe Thr Leu Thr Ile Asn Ser Leu Glu Val
65 70 75 80

Glu Asp Ala Ala Thr Tyr Tyr Cys His Gln Ser Thr Ile Leu Pro Trp
85 90 95

Thr Phe Gly Gln Gly Thr Lys Val Glu Val Lys
100 105

<210> SEQ ID NO 17
<211> LENGTH: 351
<212> TYPE: DNA
<213> ORGANISM: Homo sapiens

<400> SEQUENCE: 17
cagctgcagc tgcaggagtc gggcccagga ctggtgaagc cttcggagac cctgtccctc 60
acctgcactg tctctggtgg cttcatcagc agtagtagtt actactgggg ctggatccgc 120
cagcccccag ggaagggact ggagtggatt gggaccatct attatagtgg gaccacctac 180
tacaattcgt ccctgaagag tcgagtcacc atatccgtag acacgtccca gaaccagttc 240
tccctgaagc tgagctctgt gaccgccgca gatacggctg tgtattactg tgcgagacat 300
cactgggttt ttgactactg gggccaggga accctggtca ccgtctcctc a 351

<210> SEQ ID NO 18
<211> LENGTH: 117
<212> TYPE: PRT
<213> ORGANISM: Homo sapiens

<400> SEQUENCE: 18

-continued

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Phe Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Thr Ile Tyr Tyr Ser Gly Thr Thr Tyr Tyr Asn Ser Ser
    50                  55                  60

Leu Lys Ser Arg Val Thr Ile Ser Val Asp Thr Ser Gln Asn Gln Phe
65                  70                  75                  80

Ser Leu Lys Leu Ser Ser Val Thr Ala Ala Asp Thr Ala Val Tyr Tyr
                85                  90                  95

Cys Ala Arg His His Trp Val Phe Asp Tyr Trp Gly Gln Gly Thr Leu
           100                 105                 110

Val Thr Val Ser Ser
        115
```

<210> SEQ ID NO 19
<211> LENGTH: 321
<212> TYPE: DNA
<213> ORGANISM: Homo sapiens

<400> SEQUENCE: 19

```
gaagttgtgc tgactcagtc tccagacttt cagtctgtga ctccaaagga gaaaatcacc      60

atcacctgcc gggccagtca gatcattggt actagcttac actggtatca gaagaaacca     120

gatcagtctc caaagctcct catcaagtat gcttcccagt ccttctcagg ggtcccctcg     180

aggttcagtg gcagtggatc tgggacagaa ttcaccctca ccatcaatag cctggaagct     240

gaagatactg caacgtatta ctgtcatcag agtactaatt taccgtggac gttcggccaa     300

gggaccaagg tggaaatcaa a                                               321
```

<210> SEQ ID NO 20
<211> LENGTH: 107
<212> TYPE: PRT
<213> ORGANISM: Homo sapiens

<400> SEQUENCE: 20

```
Glu Val Val Leu Thr Gln Ser Pro Asp Phe Gln Ser Val Thr Pro Lys
1               5                   10                  15

Glu Lys Ile Thr Ile Thr Cys Arg Ala Ser Gln Ile Ile Gly Thr Ser
            20                  25                  30

Leu His Trp Tyr Gln Lys Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Glu Phe Thr Leu Thr Ile Asn Ser Leu Glu Ala
65                  70                  75                  80

Glu Asp Thr Ala Thr Tyr Tyr Cys His Gln Ser Thr Asn Leu Pro Trp
                85                  90                  95

Thr Phe Gly Gln Gly Thr Lys Val Glu Ile Lys
            100                 105
```

<210> SEQ ID NO 21
<211> LENGTH: 324
<212> TYPE: DNA
<213> ORGANISM: Homo sapiens -continued

<400> SEQUENCE: 21

```
gacatccaga tgacccagtc tccatcctcc ctgtctgcat ctgtaggaga cagagtcacc     60

atcacttgcc gggcaagtca cagcattacc aggtatataa attggtatca gcagaaacca    120

gggaaagccc ctaacctcct gatctatgct gcatccagtt tgcaaagtgg ggtcccttca    180

aggttcagtg gcagtggatc tgggacagat ttcactctca ccatcagcag tccgcaacct    240

gaagattttg caacttacta ctgtcaacag agttacagtt cccctccgat caccttcggc    300

caagggacac gactggagat taaa                                           324
```

<210> SEQ ID NO 22
<211> LENGTH: 108
<212> TYPE: PRT
<213> ORGANISM: Homo sapiens

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Ala Ser His Ser Ile Thr Arg Tyr
            20                  25                  30

Ile Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Pro Gln Pro
65                  70                  75                  80

Glu Asp Phe Ala Thr Tyr Tyr Cys Gln Gln Ser Tyr Ser Ser Pro Pro
                85                  90                  95

Ile Thr Phe Gly Gln Gly Thr Arg Leu Glu Ile Lys
            100                 105
```

<210> SEQ ID NO 23
<211> LENGTH: 372
<212> TYPE: DNA
<213> ORGANISM: Homo sapiens

<400> SEQUENCE: 23

```
gaggtgcagc tagtggagtc tgggggaggc ttggtccagc ctggggggtc cctgagactc     60

tcctgtgcag cctctggatt cacctttagt agctattgga tgagctgggt ccgccaggct    120

ccagggaagg ggctggagtg ggtggccaac ataaagcaag atggaagtga gaagtactat    180

gtggactctg tgaagggccg attcaccatc tccagagaca acgccaagaa ctcactgtat    240

ctgcaaatga acagcctgag agccgaggac acggctgtgt attactgtgc gagatggggg    300

gtttttggtt cggggagtta ttatatccct tttgactact ggggccaggg aaccctggtc    360

accgtctcct ca                                                        372
```

<210> SEQ ID NO 24
<211> LENGTH: 124
<212> TYPE: PRT
<213> ORGANISM: Homo sapiens

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

-continued

```
Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Val Phe Gly Ser Gly Ser Tyr Tyr Ile Pro Phe Asp
            100                 105                 110

Tyr Trp Gly Gln Gly Thr Leu Val Thr Val Ser Ser
        115                 120
```

<210> SEQ ID NO 25
<211> LENGTH: 321
<212> TYPE: DNA
<213> ORGANISM: Homo sapiens

<400> SEQUENCE: 25

```
gacatccaga tgacccagtc tccatcctca ctgtctgcat ctgtgggaga cagagtcacc     60

atcacttgtc gggcgagtca gggcattagg aattatttag cctggtttca gcagaaacca    120

gggaaagccc ctaagtccct gatctatgct gcatccagtt tgcaaagtgg ggtcccatca    180

acgttcagcg gcagtggatc tgggacacat ttcactctca ccatcagtag tttgcagcct    240

gaagattttg caagttattt ctgccaacag tatgagattt atcctctcac tttcggcgga    300

gggaccaagg tggagatcaa a                                              321
```

<210> SEQ ID NO 26
<211> LENGTH: 107
<212> TYPE: PRT
<213> ORGANISM: Homo sapiens

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Thr Phe Ser Gly
    50                  55                  60

Ser Gly Ser Gly Thr His Phe Thr Leu Thr Ile Ser Ser Leu Gln Pro
65                  70                  75                  80

Glu Asp Phe Ala Ser Tyr Phe Cys Gln Gln Tyr Glu Ile Tyr Pro Leu
                85                  90                  95

Thr Phe Gly Gly Gly Thr Lys Val Glu Ile Lys
            100                 105
```

<210> SEQ ID NO 27
<211> LENGTH: 354
<212> TYPE: DNA
<213> ORGANISM: Homo sapiens

<400> SEQUENCE: 27

```
caggtgcagc tggtggagtc tgggggaggc gtggtccagc ctgggaggtc cctgagactc     60

tcctgtgcag cgtctggatt caccttcagt agctatggca tgcactgggt ccgccaggct    120
```

-continued

```
ccaggcaagg ggctggagtg ggtggcagtt atatggtatg atagaagtaa taaatactat    180

gcagactccg tgaagggccg gttcaccatc tccagagaca attccaagaa cacgctgtat    240

ctgcaaatgg acagcctgag agccgaggac acggctgtgt attactgtgc gggggggacga   300

tcccggggag cctttgacta ctggggccag ggaaccctgg tcaccgtctc ctca          354
```

<210> SEQ ID NO 28
<211> LENGTH: 118
<212> TYPE: PRT
<213> ORGANISM: Homo sapiens

<400> SEQUENCE: 28

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Arg Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asp Ser Leu Arg Ala Glu Asp Thr Ala Val Tyr Tyr Cys
                85                  90                  95

Ala Gly Gly Arg Ser Arg Gly Ala Phe Asp Tyr Trp Gly Gln Gly Thr
            100                 105                 110

Leu Val Thr Val Ser Ser
        115
```

<210> SEQ ID NO 29
<211> LENGTH: 321
<212> TYPE: DNA
<213> ORGANISM: Homo sapiens

<400> SEQUENCE: 29

```
gacatccaga tgacccagtc tccatcttcc gtgtctgcat ctgtaggaga cagagtcacc     60

atcacttgtc gggcgagtca gggtattagc agctggttag cctggtatca gcagaaaccc    120

gggaaagccc ctaagctcct gatttatgct gcatccagtt tgcaaagtgg ggtcccatca    180

agattcagcg gcagtggctc tgggacagat ttcactctca ccatcagcag cctgcagcct    240

gaagattttg caacttacta ttgtcaacgg actaacagtt tccctcggac gttcggccaa    300

gggaccaagg tggaaatcaa a                                              321
```

<210> SEQ ID NO 30
<211> LENGTH: 107
<212> TYPE: PRT
<213> ORGANISM: Homo sapiens

<400> SEQUENCE: 30

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

-continued

Ser Gly Ser Gly Thr Asp Phe Thr Leu Thr Ile Ser Ser Leu Gln Pro
65 70 75 80

Glu Asp Phe Ala Thr Tyr Tyr Cys Gln Arg Thr Asn Ser Phe Pro Arg
85 90 95

Thr Phe Gly Gln Gly Thr Lys Val Glu Ile Lys
100 105

<210> SEQ ID NO 31
<211> LENGTH: 351
<212> TYPE: DNA
<213> ORGANISM: Homo sapiens

<400> SEQUENCE: 31
cagctgcagt tgcaggagtc gggcccagga ctggtgaagc cttcggagac cctgtccctc 60
acctgcactg tctctggtgg ctccatcagc agtagtaatt actactgggg ctggatccgc 120
cagcccccag ggaaggggct ggagtggatt gggactatat attatactgg gagtacctac 180
tacaacccgt ccctcaagag tcgagtcacc atatccgtag acacgtccaa gaaccagttc 240
tccctgaagt tgagctctgt gaccgccgca gacacggctg tgtattactg tgcgagacat 300
cactgggttt ttgactactg gggccaggga accctggtca ccgtctcctc a 351

<210> SEQ ID NO 32
<211> LENGTH: 117
<212> TYPE: PRT
<213> ORGANISM: Homo sapiens

<400> SEQUENCE: 32

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Asn Tyr Tyr Trp Gly Trp Ile Arg Gln Pro Pro Gly Lys Gly Leu Glu
35 40 45

Trp Ile Gly Thr Ile Tyr Tyr Thr Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Arg His His Trp Val Phe Asp Tyr Trp Gly Gln Gly Thr Leu
100 105 110

Val Thr Val Ser Ser
115

<210> SEQ ID NO 33
<211> LENGTH: 321
<212> TYPE: DNA
<213> ORGANISM: Homo sapiens

<400> SEQUENCE: 33
gaaattgtgc tgactcagtc tccagacttt ctgtctgtga ctccaaagga gaaagtcacc 60
atcacctgcc gggccagtca gatcattggt agtagcttac actggtacca acagaaacca 120
gatcagtctc caaaactcct catcaagtat gcttcccagt ccttctcagg ggtcccctcg 180
aggttcagtg gcagtggatc tgggacagat ttcaccctca ccctcaatag cctggaagct 240
gaagatgctg caacgtatta ctgtcatcag agtactattt taccgtggac gttcggccaa 300

-continued gggaccaagg tggaaatcaa a 321

<210> SEQ ID NO 34
<211> LENGTH: 107
<212> TYPE: PRT
<213> ORGANISM: Homo sapiens

<400> SEQUENCE: 34

Glu Ile Val Leu Thr Gln Ser Pro Asp Phe Leu Ser Val Thr Pro Lys
1 5 10 15

Glu Lys Val Thr Ile Thr Cys Arg Ala Ser Gln Ile Ile Gly Ser Ser
20 25 30

Leu His Trp Tyr Gln Gln Lys Pro Asp Gln Ser Pro Lys Leu Leu Ile
35 40 45

Lys Tyr Ala Ser Gln Ser Phe Ser Gly Val Pro Ser Arg Phe Ser Gly
50 55 60

Ser Gly Ser Gly Thr Asp Phe Thr Leu Thr Leu Asn Ser Leu Glu Ala
65 70 75 80

Glu Asp Ala Ala Thr Tyr Tyr Cys His Gln Ser Thr Ile Leu Pro Trp
85 90 95

Thr Phe Gly Gln Gly Thr Lys Val Glu Ile Lys
100 105

<210> SEQ ID NO 35
<211> LENGTH: 351
<212> TYPE: DNA
<213> ORGANISM: Homo sapiens

<400> SEQUENCE: 35
cagctgcagt tgcaggagtc gggcccagga ctggtgaagc cttcggagac cctgtccctc 60
acctgcactg tctctggtgg ctccatcagc agtagtactt actactgggg ctggatccgc 120
cagcccccag ggaaggggct ggagtggatt gggactatat attatagtgg gagcacctac 180
tacaacccgt ccctcaagag tcgagtcacc atatccgtag acacgtccaa gaaccagttc 240
tccctgaagc tgaactctgt gaccgccgca gacacggctg tgtattactg tgcgagacat 300
cactgggttt ttgactactg gggccaggga accctggtca ccgtctcctc a 351

<210> SEQ ID NO 36
<211> LENGTH: 117
<212> TYPE: PRT
<213> ORGANISM: Homo sapiens

<400> SEQUENCE: 36

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Thr Tyr Tyr Trp Gly Trp Ile Arg Gln Pro Pro Gly Lys Gly Leu Glu
35 40 45

Trp Ile Gly Thr Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Asn Ser Val Thr Ala Ala Asp Thr Ala Val Tyr Tyr
85 90 95

Cys Ala Arg His His Trp Val Phe Asp Tyr Trp Gly Gln Gly Thr Leu

-continued

```
            100                 105                 110

Val Thr Val Ser Ser
        115


<210> SEQ ID NO 37
<211> LENGTH: 321
<212> TYPE: DNA
<213> ORGANISM: Homo sapiens

<400> SEQUENCE: 37

gaaattgtgc tgactcagtc tccagacttt ctgtctgtga ctccaaagga gaaagtcacc      60

atcacctgcc gggccagtca gatcattggt agtagtttac actggtacca acagaaacca     120

gatcagtctc caaacctcct catcaagtat gcttctcagt ccgtctcagg ggtcccctcg     180

aggttcagtg gcagtgggtc tgggacagat ttcaccctca ccctcaatag cctggaagct     240

gaagatgctg caacgtatta ctgtcatcag agtactattt taccgtggac gttcggccaa     300

gggaccaagg tggaaatcaa a                                               321


<210> SEQ ID NO 38
<211> LENGTH: 107
<212> TYPE: PRT
<213> ORGANISM: Homo sapiens

<400> SEQUENCE: 38

Glu Ile Val Leu Thr Gln Ser Pro Asp Phe Leu Ser Val Thr Pro Lys
1               5                   10                  15

Glu Lys Val Thr Ile Thr Cys Arg Ala Ser Gln Ile Ile Gly Ser Ser
            20                  25                  30

Leu His Trp Tyr Gln Gln Lys Pro Asp Gln Ser Pro Asn Leu Leu Ile
        35                  40                  45

Lys Tyr Ala Ser Gln Ser Val Ser Gly Val Pro Ser Arg Phe Ser Gly
    50                  55                  60

Ser Gly Ser Gly Thr Asp Phe Thr Leu Thr Leu Asn Ser Leu Glu Ala
65                  70                  75                  80

Glu Asp Ala Ala Thr Tyr Tyr Cys His Gln Ser Thr Ile Leu Pro Trp
                85                  90                  95

Thr Phe Gly Gln Gly Thr Lys Val Glu Ile Lys
            100                 105


<210> SEQ ID NO 39
<211> LENGTH: 360
<212> TYPE: DNA
<213> ORGANISM: Homo sapiens

<400> SEQUENCE: 39

caggtgcagc tggtggagtc tgggggaggc ttggtcaagc ctggagggtc cctgagactc      60

tcctgtgcag cctctggatt caccttcagg gactattaca tgagctggat ccgccaggct     120

ccagggaagg ggctggagtg ggttgcattc attagtagta gtggtagtat tatatactac     180

gcagactctg tgaagggccg attcaccatc tccagggaca acgccaagaa ctcactgttt     240

ctgcaaatga acagcctgag agccgaggac acggccgtgt attactgtgc gagagatggg     300

catatagcag ctcgtggtat ggacgtctgg ggccaaggga ccacggtcac cgtctcctca     360


<210> SEQ ID NO 40
<211> LENGTH: 120
<212> TYPE: PRT
<213> ORGANISM: Homo sapiens
```

<400> SEQUENCE: 40

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Arg Asp Tyr
20 25 30

Tyr Met Ser Trp Ile Arg Gln Ala Pro Gly Lys Gly Leu Glu Trp Val
35 40 45

Ala Phe Ile Ser Ser Ser Gly Ser Ile Ile Tyr Tyr Ala Asp Ser Val
50 55 60

Lys Gly Arg Phe Thr Ile Ser Arg Asp Asn Ala Lys Asn Ser Leu Phe
65 70 75 80

Leu Gln Met Asn Ser Leu Arg Ala Glu Asp Thr Ala Val Tyr Tyr Cys
85 90 95

Ala Arg Asp Gly His Ile Ala Ala Arg Gly Met Asp Val Trp Gly Gln
100 105 110

Gly Thr Thr Val Thr Val Ser Ser
115 120

<210> SEQ ID NO 41
<211> LENGTH: 324
<212> TYPE: DNA
<213> ORGANISM: Homo sapiens

<400> SEQUENCE: 41
gacatccaga tgacccagtc tccatcctcc ctgtctgcat ctgtaggaga cagagtcacc 60
atcacttgcc gggcaagtca gagcattaac aagtatataa attggtatca gcagaaacca 120
gggaaagccc ctaagctcct gatttatgct gcatccagtt tgcaaagtgg ggtcccatca 180
aggttcaatg gcagtggatc tgggacagat ttcactttca ccatcaacac tctgcaacct 240
gaagattttg caacttacta ctgtcagcag acttacagta cccctccgat caccttcggc 300
caagggacac gactggagat taaa 324

<210> SEQ ID NO 42
<211> LENGTH: 108
<212> TYPE: PRT
<213> ORGANISM: Homo sapiens

<400> SEQUENCE: 42

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asn Lys Tyr
20 25 30

Ile Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Asn Gly
50 55 60

Ser Gly Ser Gly Thr Asp Phe Thr Phe Thr Ile Asn Thr Leu Gln Pro
65 70 75 80

Glu Asp Phe Ala Thr Tyr Tyr Cys Gln Gln Thr Tyr Ser Thr Pro Pro
85 90 95

Ile Thr Phe Gly Gln Gly Thr Arg Leu Glu Ile Lys
100 105

<210> SEQ ID NO 43
<211> LENGTH: 360

-continued

<212> TYPE: DNA
<213> ORGANISM: Homo sapiens

<400> SEQUENCE: 43
caggtgcagc tggtggagtc tggggaggc ttggtcaagc ctggagggtc cctgagactc 60
tcctgtgcag cctctggatt caccttcagt gactactaca tgaactggat ccgccaggct 120
ccagggaagg ggctggagtg ggtttcattc attagtagta gtggtagtac catatactac 180
gcagactctg tgaagggccg attcaccatc tccagggaca acgccaagaa ctcactgtat 240
ctgcaaatga acagcctgag agccgaggac acggccgtgt attactgtgc gagagatggg 300
catatagcag ctcgtggtat ggacgtctgg ggccaaggga ccacggtcac cgtctcctca 360

<210> SEQ ID NO 44
<211> LENGTH: 120
<212> TYPE: PRT
<213> ORGANISM: Homo sapiens

<400> SEQUENCE: 44

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met Asn Trp Ile Arg Gln Ala Pro Gly Lys Gly Leu Glu Trp Val
35 40 45

Ser Phe Ile Ser Ser Ser Gly Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Asp Gly His Ile Ala Ala Arg Gly Met Asp Val Trp Gly Gln
100 105 110

Gly Thr Thr Val Thr Val Ser Ser
115 120

<210> SEQ ID NO 45
<211> LENGTH: 324
<212> TYPE: DNA
<213> ORGANISM: Homo sapiens

<400> SEQUENCE: 45
gacatccaga tgacccagtc tccatcctcc ctgtctgcat ctgtaggaga cagagtcacc 60
atcacttgcc gggcaagtca gagttttagc aggtatataa attggtatca gcagaaacca 120
gggaaagccc ctaaactcct gatctatgct gcatccagtt tgcaaggtgg ggtcccatca 180
aggttcagtg gcagtggatc tgggacagat ttcactctcg ccatcagcag tctgcaacct 240
gaagattttg caacttacta ctgtcaacag acttacagta cccctccgat caccttcggc 300
caagggacac gactggagat taaa 324

<210> SEQ ID NO 46
<211> LENGTH: 108
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Phe Ser Arg Tyr
            20                  25                  30

Ile Asn Trp Tyr Gln Gln Lys Pro Gly Lys Ala Pro Lys Leu Leu Ile
            35                  40                  45

Tyr Ala Ala Ser Ser Leu Gln Gly Gly Val Pro Ser Arg Phe Ser Gly
50                  55                  60

Ser Gly Ser Gly Thr Asp Phe Thr Leu Ala Ile Ser Ser Leu Gln Pro
65                  70                  75                  80

Glu Asp Phe Ala Thr Tyr Tyr Cys Gln Gln Thr Tyr Ser Thr Pro Pro
                85                  90                  95

Ile Thr Phe Gly Gln Gly Thr Arg Leu Glu Ile Lys
            100                 105

<210> SEQ ID NO 47
<211> LENGTH: 360
<212> TYPE: DNA
<213> ORGANISM: Homo sapiens

<400> SEQUENCE: 47
caggtgcagc tggtggagtc tgggggaggc ttggtcaagc ctggagggtc cctgagactc        60
tcctgtgcag cctctggatt caccttcagt gactactaca tgaactggat ccgccaggct       120
ccagggaagg ggctggagtg ggtttcatat attagtagta gtggtagtat tatatactac       180
gcagactctg tgaagggccg attcaccatc tccagggaca acgccaagaa ctcactgtat       240
ctgcaaatga acagcctgag agccgaggac acggccgtgt attactgtgc gagagatggg       300
cgtatagtag ctcgtggtat ggacgtctgg ggccaaggga ccacggtcac cgtctcctca       360

<210> SEQ ID NO 48
<211> LENGTH: 120
<212> TYPE: PRT
<213> ORGANISM: Homo sapiens

<400> SEQUENCE: 48

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
            35                  40                  45

Ser Tyr Ile Ser Ser Ser Gly Ser Ile Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Arg Ile Val Ala Arg Gly Met Asp Val Trp Gly Gln
            100                 105                 110

Gly Thr Thr Val Thr Val Ser Ser
        115                 120

<210> SEQ ID NO 49
<211> LENGTH: 324
<212> TYPE: DNA
<213> ORGANISM: Homo sapiens

<400> SEQUENCE: 49

-continued

```
gacatccaga tgacccagtc tccatcctcc ctgtgtgcat ctgtaggaga cagagtcacc      60

atcacttgcc gggcaagtcg gagcattacc aggtatttaa attggtatca gcagaaacca     120

gggaaagccc ctaagctcct gatctatggt gcatccagtt tgcaaagtgg ggtcccatcc     180

aggttcagtg gcagtggatc tgggacagat ttcactctca ccatcagcag tctgcaacct     240

gaagattttg caacttacta ctgtcaacag agttacagta cccctccgat caccttcggc     300

caagggacac gactggagat taaa                                            324
```

<210> SEQ ID NO 50
<211> LENGTH: 108
<212> TYPE: PRT
<213> ORGANISM: Homo sapiens

<400> SEQUENCE: 50

```
Asp Ile Gln Met Thr Gln Ser Pro Ser Ser Leu Cys Ala Ser Val Gly
1               5                   10                  15

Asp Arg Val Thr Ile Thr Cys Arg Ala Ser Arg Ser Ile Thr Arg Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

<210> SEQ ID NO 51
<211> LENGTH: 363
<212> TYPE: DNA
<213> ORGANISM: Homo sapiens

<400> SEQUENCE: 51

```
caggtgcagc tggtggagtc tgggggaggc gtggtccagc ctgggaggtc cctgagactc      60

tcctgtgcag cgtctggatt ctccttcagt atctatggca tgcactgggt ccgccaggct     120

ccaggcaagg ggctggagtg ggtggcagtt atttggtttg atggtagtaa taaatactat     180

gcagactccg tgaagggccg attcaccatc tccagagaca attccaagaa cacgctgtat     240

ctgcaaatga acagcctgag agccgaggac acggctttgt attactgtgc gagagataag     300

gcgtcttact atggttcggg gatggactac tggggccagg gaaccctggt caccgtctcc     360

tca                                                                   363
```

<210> SEQ ID NO 52
<211> LENGTH: 121
<212> TYPE: PRT
<213> ORGANISM: Homo sapiens

<400> SEQUENCE: 52

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Ile Tyr
            20                  25                  30

Gly Met His Trp Val Arg Gln Ala Pro Gly Lys Gly Leu Glu Trp Val
        35                  40                  45
```

-continued

```
Ala Val Ile Trp Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Arg Asp Lys Ala Ser Tyr Tyr Gly Ser Gly Met Asp Tyr Trp Gly
            100                 105                 110

Gln Gly Thr Leu Val Thr Val Ser Ser
        115                 120
```

```
<210> SEQ ID NO 53
<211> LENGTH: 327
<212> TYPE: DNA
<213> ORGANISM: Homo sapiens

<400> SEQUENCE: 53

gaaattgtgt tgacgcagtc tccaggcacc ctgtctttgt ctccagggga aagagccacc      60

ctctcctgca gggccagtca gagtgttagc agcacctact tagcctggta ccagcacaga     120

cctggccagg ctcccaggct cctcatctct ggtgcatcca ggagggccac tggcatccca     180

gacaggttca gtggcagtgg gtctgggaca gacttcactc tcaccatcag cagactggag     240

cctgaagatt ttgcagtgta ttactgtcag cactatggta gctcattcac gtggacgttc     300

ggccagggga ccaaggtgga aatcaaa                                         327
```

```
<210> SEQ ID NO 54
<211> LENGTH: 109
<212> TYPE: PRT
<213> ORGANISM: Homo sapiens

<400> SEQUENCE: 54

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln His Arg Pro Gly Gln Ala Pro Arg Leu Leu
        35                  40                  45

Ile Ser Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Phe
                85                  90                  95

Thr Trp Thr Phe Gly Gln Gly Thr Lys Val Glu Ile Lys
            100                 105
```

```
<210> SEQ ID NO 55
<211> LENGTH: 351
<212> TYPE: DNA
<213> ORGANISM: Homo sapiens

<400> SEQUENCE: 55

gaggtgcagt tggtggagag tgggggaggc ttggtccagc ctggggggtc cctgagactc      60

tcctgtgcag cctctggatt cacctttagt aacttttgga tgagctgggt ccgccaggct     120

ccagggaagg ggctggagtg ggtggccaac ataaagcacg gtggaagtga gaaatactat     180
```

-continued

```
gtggactctg tgaagggccg attcaccatc tccagagaca acgccaagaa ctcactgtat    240

ctgcaaatga acagactgag agccgaggac acggctgtgt attactgtgc gagagatcct    300

atgtactact ttgactactg gggccaggga accctggtca ccgtctcctc a             351


<210> SEQ ID NO 56
<211> LENGTH: 117
<212> TYPE: PRT
<213> ORGANISM: Homo sapiens

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Trp Met Ser Trp Val Arg Gln Ala Pro Gly Lys Gly Leu Glu Trp Val
        35                  40                  45

Ala Asn Ile Lys His Gly Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Arg Leu Arg Ala Glu Asp Thr Ala Val Tyr Tyr Cys
                85                  90                  95

Ala Arg Asp Pro Met Tyr Tyr Phe Asp Tyr Trp Gly Gln Gly Thr Leu
            100                 105                 110

Val Thr Val Ser Ser
        115


<210> SEQ ID NO 57
<211> LENGTH: 321
<212> TYPE: DNA
<213> ORGANISM: Homo sapiens

<400> SEQUENCE: 57

gacatccaga tgacccagtc tccatcctcc ctgtctgcat ctgtaggaga cagagtcacc     60

atcacttgcc gggcaagtca ggacattaga aatgatttag actggtatca gcagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag cataatggtt accctcgcag ttttggccag    300

gggaccaagc tggagatcaa a                                              321


<210> SEQ ID NO 58
<211> LENGTH: 107
<212> TYPE: PRT
<213> ORGANISM: Homo sapiens

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Asp Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
```

-continued

```
65                  70                  75                  80

Glu Asp Phe Ala Thr Tyr Tyr Cys Leu Gln His Asn Gly Tyr Pro Arg
                85                  90                  95

Ser Phe Gly Gln Gly Thr Lys Leu Glu Ile Lys
            100                 105
```

<210> SEQ ID NO 59
<211> LENGTH: 354
<212> TYPE: DNA
<213> ORGANISM: Homo sapiens

<400> SEQUENCE: 59

```
caggtgcagc tggtggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcagtt atatggtatg atagaagtaa taaatactat     180

gcagactccg tgaagggccg attcaccatc tccagagaca attccaagaa cacgctgtat     240

ctgcaaatga acagcctgag agccgaggac acggctgtgt attactgtgc ggggggacga     300

tcccggggag cctttgacta ctggggccag ggaaccctgg tcaccgtctc ctca           354
```

<210> SEQ ID NO 60
<211> LENGTH: 118
<212> TYPE: PRT
<213> ORGANISM: Homo sapiens

<400> SEQUENCE: 60

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Arg Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Ser Arg Gly Ala Phe Asp Tyr Trp Gly Gln Gly Thr
            100                 105                 110

Leu Val Thr Val Ser Ser
        115
```

<210> SEQ ID NO 61
<211> LENGTH: 321
<212> TYPE: DNA
<213> ORGANISM: Homo sapiens

<400> SEQUENCE: 61

```
gacatccaga tgacccagtc tccatcttcc gtgtctgcat ctgtaggaga cagagtcacc      60

atcacttgtc gggcgagtca gggtattagc agttggttag cctggtatca gcagaaacca     120

gggaaagccc ctaagctcct gatctttgct gcatccagtt tgcaaagtgg ggtcccatca     180

agattcagcg gcagtggatc tgggacagat ttcactctca ccatcagcag cctgcagcct     240

gaagattttg caacttacta ttgtcaacgg actaacagtt tccctcggac gttcggccaa     300

gggaccaagg tggaaatcaa a                                               321
```

-continued

<210> SEQ ID NO 62
<211> LENGTH: 107
<212> TYPE: PRT
<213> ORGANISM: Homo sapiens

<400> SEQUENCE: 62

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Thr Asn Ser Phe Pro Arg
                85                  90                  95

Thr Phe Gly Gln Gly Thr Lys Val Glu Ile Lys
            100                 105

<210> SEQ ID NO 63
<211> LENGTH: 363
<212> TYPE: DNA
<213> ORGANISM: Homo sapiens

<400> SEQUENCE: 63
gaggtgcagc tggtggagtc tgggggaggc ttggtacagc ctggggggtc cctgagactc      60
tcctgtgcag cctctggatt caccttcagt agctatagca tgaactgggt ccgccaggct     120
ccagggaagg ggctggagtg ggtttcattc attagtggta gtagtagtac catgtactac     180
gcagactctg tgaagggccg attcaccatc tccagagaca atgccaagaa ctcactgtat     240
ctgcaaatga acagcctgag agacgaggac acggctgtgt attactgtgc gagattacga     300
tattttgact ggtcatatgc ttttgatatc tggggccaag ggacaatggt caccgtctct     360
tca                                                                   363

<210> SEQ ID NO 64
<211> LENGTH: 121
<212> TYPE: PRT
<213> ORGANISM: Homo sapiens

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Phe Ile Ser Gly Ser Ser Ser Thr Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Leu Arg Tyr Phe Asp Trp Ser Tyr Ala Phe Asp Ile Trp Gly

-continued

```
        100                 105                 110

Gln Gly Thr Met Val Thr Val Ser Ser
        115                 120


<210> SEQ ID NO 65
<211> LENGTH: 321
<212> TYPE: DNA
<213> ORGANISM: Homo sapiens

<400> SEQUENCE: 65

gacatccaga tgacccagtc tccatcttcc gtgtctacat ctgtaggaga cagagtcacc      60

atcacttgtc gggcgagtca gggtattcgc agctggttag cctggtatca gcagagacca     120

gggaaagccc ctaagctcct gatctatgct gcatccagtt tacaaaatgg ggtcccatca     180

aggttcagcg gcagtggatc tgggacagat ttcactctca ccatcagcag cctgcagcct     240

gaagattttg caacttactt ttgtcaacag gctaccagtt tcccattcac tttcggccct     300

gggaccaaag tggatatcaa c                                               321


<210> SEQ ID NO 66
<211> LENGTH: 107
<212> TYPE: PRT
<213> ORGANISM: Homo sapiens

<400> SEQUENCE: 66

Asp Ile Gln Met Thr Gln Ser Pro Ser Ser Val Ser Thr Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Arg Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Thr Ser Phe Pro Phe
                85                  90                  95

Thr Phe Gly Pro Gly Thr Lys Val Asp Ile Asn
            100                 105


<210> SEQ ID NO 67
<211> LENGTH: 354
<212> TYPE: DNA
<213> ORGANISM: Homo sapiens

<400> SEQUENCE: 67

caggtgcagc tggtggagtc tgggggaggc gtggtccagc ctgggaggtc cctgagactc      60

tcctgtgcag cgtctggatt caccttcagt agctatggca tgcactgggt ccgccaggct     120

ccaggcaagg ggctggagtg ggtggcagtt atatggtatg atagaagtaa taaatactat     180

gtagactccg tgaagggccg attcaccatc tccagagaca attccaagaa cacgttgtat     240

ctgcaaatga acagcctgag agccgaggac acggctgtgt attactgtgc ggggggacga     300

tcccggggag cctttgacta ctggggccag ggaaccctgg tcaccgtctc ctca           354


<210> SEQ ID NO 68
<211> LENGTH: 118
<212> TYPE: PRT
<213> ORGANISM: Homo sapiens
```

-continued

<400> SEQUENCE: 68

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Arg Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Ser Arg Gly Ala Phe Asp Tyr Trp Gly Gln Gly Thr
            100                 105                 110

Leu Val Thr Val Ser Ser
        115
```

<210> SEQ ID NO 69
<211> LENGTH: 321
<212> TYPE: DNA
<213> ORGANISM: Homo sapiens

<400> SEQUENCE: 69

```
gacatccaga tgacccagtc tccatcttcc gtgtctgcat ctgtaggaga cagagtcacc      60

atcacttgtc gggcgagtca ggatattagc agctggttag cctggtatca gcagaaacca     120

gggaaagccc ctaagctcct gatctttgct gcatccagtt tgcaaagtgg ggtcccatca     180

agattcagcg gcagtggatc tgggacagat ttcactctca ccatcagcag cctgcagcct     240

gaagattttg caacttacta ttgtcaacgg actagcagtt tccctcggac gttcggccaa     300

gggaccaagg tggaaatcaa a                                               321
```

<210> SEQ ID NO 70
<211> LENGTH: 107
<212> TYPE: PRT
<213> ORGANISM: Homo sapiens

<400> SEQUENCE: 70

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Thr Ser Ser Phe Pro Arg
                85                  90                  95

Thr Phe Gly Gln Gly Thr Lys Val Glu Ile Lys
            100                 105
```

<210> SEQ ID NO 71
<211> LENGTH: 354

-continued

<212> TYPE: DNA
<213> ORGANISM: Homo sapiens

<400> SEQUENCE: 71
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atagaagtaa taaatactat 180
gcagactccg tgaagggccg attcaccatc tccagagaca attccaagaa cacgctgtat 240
ctgcaaatga acagcctgag agccgaggac acggctgtat attactgtgc ggggggacga 300
tcccggggag cctttgacta ctggggccag ggaaccctgg tcaccgtctc ctca 354

<210> SEQ ID NO 72
<211> LENGTH: 118
<212> TYPE: PRT
<213> ORGANISM: Homo sapiens

<400> SEQUENCE: 72

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Arg Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Gly Gly Arg Ser Arg Gly Ala Phe Asp Tyr Trp Gly Gln Gly Thr
100 105 110

Leu Val Thr Val Ser Ser
115

<210> SEQ ID NO 73
<211> LENGTH: 321
<212> TYPE: DNA
<213> ORGANISM: Homo sapiens

<400> SEQUENCE: 73
gacatccaga tgacccagtc tccatcttcc gtgtctgcat ctgttggaga cagagtcacc 60
atcacttgtc gggcgagtca gggtattagc agctggttag cctggtatca gcagaaaccc 120
gggaaagccc ctaacctcct gatttatgct gcatccagtt tgcaaagtgg ggtcccatca 180
agattcagcg gcagtggatc tgggacagat ttcactctca ccatcagcag cctgcagcct 240
gaagattttg caacttacta ttgtcaacgg actaacaatt tccctcggac gttcggccaa 300
gggaccaagg tggaaatcaa a 321

<210> SEQ ID NO 74
<211> LENGTH: 107
<212> TYPE: PRT
<213> ORGANISM: Homo sapiens

<400> SEQUENCE: 74

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Thr Asn Asn Phe Pro Arg
                85                  90                  95

Thr Phe Gly Gln Gly Thr Lys Val Glu Ile Lys
            100                 105

<210> SEQ ID NO 75
<211> LENGTH: 363
<212> TYPE: DNA
<213> ORGANISM: Homo sapiens

<400> SEQUENCE: 75
gaggtgcagc tggtggagtc tgggggaggc ttggtacagc ctggggggtc cctgagactc      60
tcctgtgcag cctctggatt caccttcagt agctatagca tgaactgggt ccgccaggct     120
ccagggaagg ggctggagtg ggtttcatac attagtggta gtagtactac catgtactac     180
gcagactctg tgaagggccg attcaccatc tccagagaca atgccaagaa ctcactgtat     240
ctgcaaatga acagcctgag agacgaggac acggctgtgt attactgtgc gagattacga     300
cattttgact ggtcatatgc ttttgatatc tggggccaag ggacaatggt caccgtctct     360
tca                                                                   363

<210> SEQ ID NO 76
<211> LENGTH: 121
<212> TYPE: PRT
<213> ORGANISM: Homo sapiens

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Gly Ser Ser Thr Thr Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Leu Arg His Phe Asp Trp Ser Tyr Ala Phe Asp Ile Trp Gly
            100                 105                 110

Gln Gly Thr Met Val Thr Val Ser Ser
        115                 120

<210> SEQ ID NO 77
<211> LENGTH: 321
<212> TYPE: DNA
<213> ORGANISM: Homo sapiens -continued

<400> SEQUENCE: 77
gacatccaga tgacccagtc tccatcttcc gtgtctacat ctgtaggaga cagagtcacc 60
atcacttgtc gggcgagtca gggtattagc agctggttag cctggtatca gcagagacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttactt ttgtcaacag gctaccagtt tcccattcac tttcggccct 300
gggaccaaag tgggtatcaa a 321

<210> SEQ ID NO 78
<211> LENGTH: 107
<212> TYPE: PRT
<213> ORGANISM: Homo sapiens

<400> SEQUENCE: 78

Asp Ile Gln Met Thr Gln Ser Pro Ser Ser Val Ser Thr Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Arg Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Ala Thr Ser Phe Pro Phe
85 90 95

Thr Phe Gly Pro Gly Thr Lys Val Gly Ile Lys
100 105

<210> SEQ ID NO 79
<211> LENGTH: 366
<212> TYPE: DNA
<213> ORGANISM: Homo sapiens

<400> SEQUENCE: 79
caggtgcagc tggtgcagtc tggggctgag gtgaagaaac ctggggcctc agtgaaggtc 60
tcctgcaagg cttctggata caccttcacc ggctaccata tgcactgggt gcgacaggcc 120
cctggacaag ggcttgagtg gatgggatgg atcaacccta acagtggtgg cacaaactat 180
gcacagaagt ttcagggcag ggtcaccatg accagggaca cgtccatcag cacagcctac 240
atggagctga gcaggctgag atctgacgac acggccgtgt attactgtgc gagagatagg 300
gctttttgga gtggttatca cggtttggac gtctggggcc aagggaccac ggtcaccgtc 360
tcctca 366

<210> SEQ ID NO 80
<211> LENGTH: 122
<212> TYPE: PRT
<213> ORGANISM: Homo sapiens

<400> SEQUENCE: 80

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

-continued

```
His Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Ala Phe Trp Ser Gly Tyr His Gly Leu Asp Val Trp
            100                 105                 110

Gly Gln Gly Thr Thr Val Thr Val Ser Ser
        115                 120


<210> SEQ ID NO 81
<211> LENGTH: 321
<212> TYPE: DNA
<213> ORGANISM: Homo sapiens

<400> SEQUENCE: 81

gacatccaga tgacccagtc tccatcctcc ctgtctgcat ctgtaggaga cagagtcacc      60

atcacttgcc gggcgagtca ggtcattgcc aattatttag cctggtatca gcagaaacca     120

ggaaaagttc ctaaactcct gatctatgct gcatccactt tgcaatcagg ggtcccatct     180

cggttcagtg gcagtggatc tgggacagat ttcactctca ccatcagcag cctgcagcct     240

gaagatgttg caacttatta ctgtcacacg tataagagtg ccccgtggac gttcggccaa     300

gggaccaagg tggaaatcaa a                                               321


<210> SEQ ID NO 82
<211> LENGTH: 107
<212> TYPE: PRT
<213> ORGANISM: Homo sapiens

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Ala Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys His Thr Tyr Lys Ser Ala Pro Trp
                85                  90                  95

Thr Phe Gly Gln Gly Thr Lys Val Glu Ile Lys
            100                 105


<210> SEQ ID NO 83
<211> LENGTH: 357
<212> TYPE: DNA
<213> ORGANISM: Homo sapiens

<400> SEQUENCE: 83

caggtgcagc tggtgcagtc tggggctgag gtgaagaagc ctggggcctc agtgaaggtt      60

tcctgcaagg cttctggata caccttcacc agttatgata tcaactgggt gcgacaggcc     120
```

-continued

```
actggacaag ggcttgagtg gatgggatgg atgaacccta acagtggtaa cacaggctat    180

gcacagcagt tccagggcag agtcaccatg accaggaaca cctccataac tacagcctac    240

atggagctga gcagcctgag atctgaggac acggccgtgt attactgtgc gagagaagag    300

tatagcagtt cgctctttga ctcctggggc cagggaaccc tggtcaccgt ctcctca       357


<210> SEQ ID NO 84
<211> LENGTH: 119
<212> TYPE: PRT
<213> ORGANISM: Homo sapiens

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Gln Phe
    50                  55                  60

Gln Gly Arg Val Thr Met Thr Arg Asn Thr Ser Ile Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Glu Tyr Ser Ser Ser Leu Phe Asp Ser Trp Gly Gln Gly
            100                 105                 110

Thr Leu Val Thr Val Ser Ser
        115


<210> SEQ ID NO 85
<211> LENGTH: 321
<212> TYPE: DNA
<213> ORGANISM: Homo sapiens

<400> SEQUENCE: 85

gacatccaga tgacccagtc tccatcctcc ctgtctgcat ctgtaggaga cagagtcacc     60

atcacttgcc gggcaagtca gggcattaga aataatttag gctggtttca gcagaagcca    120

gggaaagccc ctaagcgcct aatctatgct gcatccagtt tgcaaagtgg ggtcccatca    180

aggttcagcg gcagtggatc tgggacaaaa ttcactctca caatcagcag cctgcagcct    240

gaagattttg caacttattt ctgtctacag cataataggt accctctcac tttcggcgga    300

gggaccaagg tggagatcaa a                                              321


<210> SEQ ID NO 86
<211> LENGTH: 107
<212> TYPE: PRT
<213> ORGANISM: Homo sapiens

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Gly Trp Phe Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

-continued

Ser Gly Ser Gly Thr Lys Phe Thr Leu Thr Ile Ser Ser Leu Gln Pro
65 70 75 80

Glu Asp Phe Ala Thr Tyr Phe Cys Leu Gln His Asn Arg Tyr Pro Leu
85 90 95

Thr Phe Gly Gly Gly Thr Lys Val Glu Ile Lys
100 105

<210> SEQ ID NO 87
<211> LENGTH: 372
<212> TYPE: DNA
<213> ORGANISM: Homo sapiens

<400> SEQUENCE: 87
caggtgcagc tggtggagtc tgggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agctgaggac acggctgtgt tttactgtgc gagagataga 300
tattgtagta gtaccagctg ctataggggg ctaggctact ggggccaggg aaccctggtg 360
acggtttcat ca 372

<210> SEQ ID NO 88
<211> LENGTH: 124
<212> TYPE: PRT
<213> ORGANISM: Homo sapiens

<400> SEQUENCE: 88

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Phe Tyr Cys
85 90 95

Ala Arg Asp Arg Tyr Cys Ser Ser Thr Ser Cys Tyr Arg Gly Leu Gly
100 105 110

Tyr Trp Gly Gln Gly Thr Leu Val Thr Val Ser Ser
115 120

<210> SEQ ID NO 89
<211> LENGTH: 321
<212> TYPE: DNA
<213> ORGANISM: Homo sapiens

<400> SEQUENCE: 89
gacatccaga tgacccagtc tccatcctcc ctgtctgcat ctgtaggaga cagagtcagc 60
atcacttgcc gggcaagtca gggcattaga aatgatttag gctggtatca gcagaaacca 120
gggaaagccc ctacgcgcct gatctatgct gcatccagtt tgcaaagtgg ggtcccatca 180
aggttcagtg gcagtggatc tgggacagaa ttcactctca caatcagcag cctgcagcct 240

-continued

```
gaagattttg caagttatta ctgtctacag cataatagtt tcccgtggac gttcggccaa    300

gggaccaagg tggaaatcaa a                                              321


<210> SEQ ID NO 90
<211> LENGTH: 107
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Gly Ile Arg Asn Asp
            20                  25                  30

Leu Gly Trp Tyr Gln Gln Lys Pro Gly Lys Ala Pro Thr Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ser Tyr Tyr Cys Leu Gln His Asn Ser Phe Pro Trp
                85                  90                  95

Thr Phe Gly Gln Gly Thr Lys Val Glu Ile Lys
            100                 105


<210> SEQ ID NO 91
<211> LENGTH: 360
<212> TYPE: DNA
<213> ORGANISM: Homo sapiens

<400> SEQUENCE: 91

caggtgcagc tggtggagtc tgggggaggc ttggtcaagc ctggagggtc cctgagactc     60

tcctgtgcag cctctggatt caccttcagt gactactaca tgaactggat ccgccaggct    120

ccagggaagg ggctggagtg ggtttcatac attagtagta gtggtagtat tatatactac    180

gcagactctg tgaagggccg attcaccatc tccagggaca acgccaagaa ctcactgtat    240

ctgcaaatga acagcctgag agccgaggac acggccgtgt attactgtgc gagagatggg    300

catatagcag ctcgtggtat ggacgtctgg ggccaaggga ccacggtcac cgtctcctca    360


<210> SEQ ID NO 92
<211> LENGTH: 120
<212> TYPE: PRT
<213> ORGANISM: Homo sapiens

<400> SEQUENCE: 92

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Val
        35                  40                  45

Ser Tyr Ile Ser Ser Ser Gly Ser Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

-continued

```
Ala Arg Asp Gly His Ile Ala Ala Arg Gly Met Asp Val Trp Gly Gln
            100                 105                 110

Gly Thr Thr Val Thr Val Ser Ser
        115                 120
```

<210> SEQ ID NO 93
<211> LENGTH: 324
<212> TYPE: DNA
<213> ORGANISM: Homo sapiens

<400> SEQUENCE: 93

```
gacatccaga tgacccagtc tccatcctcc ctgtctgcat ctgtaggaga cagagtcacc     60

atcacttgcc gggcaagtca gagctttagc aggtatataa attggtatca gcagaaacca    120

gggaaagccc ctaagctcct gatctatgct gcatccagtt tgcaaggtgg ggtcccatca    180

aggttcagtg gcagtggatc tgggacagat ttcactctca ccatcagcag tctgcaacct    240

gaagattttg caacttacta ctgtcaacag acttacagta accctccgat caccttcggc    300

caagggacac gactggagat taaa                                           324
```

<210> SEQ ID NO 94
<211> LENGTH: 108
<212> TYPE: PRT
<213> ORGANISM: Homo sapiens

<400> SEQUENCE: 94

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Phe Ser Arg Tyr
            20                  25                  30

Ile Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Asn Pro Pro
                85                  90                  95

Ile Thr Phe Gly Gln Gly Thr Arg Leu Glu Ile Lys
            100                 105
```

<210> SEQ ID NO 95
<211> LENGTH: 360
<212> TYPE: DNA
<213> ORGANISM: Homo sapiens

<400> SEQUENCE: 95

```
caggtgcagc tggtggagtc tgggggaggc gtggtccagc ctgggaggtc cctgagactc     60

tcctgtgcag cgtctggatt caccttcagt agctatggca tgcactgggt ccgccaggcg    120

ccaggcaagg ggctggagtg ggtggcagtt atatggtatg atagaagtaa taaatactat    180

gcagactccg tgaagggccg attcaccatc tccagagaca attccaagaa cacgctgtat    240

ctgcaaatga acagcttgag agccgaggac acggctgtgt attactgtgc ggggggacga    300

tcccggggag cctttgactt ctggggccag ggaaccctgg tcaccgtctc ctcagcctcc    360
```

<210> SEQ ID NO 96
<211> LENGTH: 118

-continued

<212> TYPE: PRT
<213> ORGANISM: Homo sapiens

<400> SEQUENCE: 96

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Arg Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Ser Arg Gly Ala Phe Asp Phe Trp Gly Gln Gly Thr
            100                 105                 110

Leu Val Thr Val Ser Ser
        115
```

<210> SEQ ID NO 97
<211> LENGTH: 321
<212> TYPE: DNA
<213> ORGANISM: Homo sapiens

<400> SEQUENCE: 97

```
gacatccaga tgacccagtc tccatcttcc gtgtctgcat ctgtaggaga cagagtcacc      60

atcacttgtc gggcgagtca agatattagc agctggttag cctggtatca gcagaaagca     120

gggaaagccc ctaaactcct gatctatgct gcatccagtt tgcaaagtgg ggtcccatca     180

agattcagcg gcagtggatc tgggacagat ttcactctca ccatcagcag cctgcagcct     240

gaagattttg caacttacta ttgtcaacgg actaacagtt ttcctcggac gttcggccaa     300

gggaccaagg tggaaatcaa a                                               321
```

<210> SEQ ID NO 98
<211> LENGTH: 107
<212> TYPE: PRT
<213> ORGANISM: Homo sapiens

<400> SEQUENCE: 98

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Ala Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Thr Asn Ser Phe Pro Arg
                85                  90                  95

Thr Phe Gly Gln Gly Thr Lys Val Glu Ile Lys
            100                 105
```

-continued

<210> SEQ ID NO 99
<211> LENGTH: 351
<212> TYPE: DNA
<213> ORGANISM: Homo sapiens

<400> SEQUENCE: 99
caggtgcagc tggtgcagtc tggggctgag gtgaagaagc ctggggcctc agtgaaggtt 60
tcctgcaagg catctggata caccttcacc agctactata tgtactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagaggcagc 300
tcgccgttct ttgactactg gggccaggga accctggtca ccgtctcctc a 351

<210> SEQ ID NO 100
<211> LENGTH: 117
<212> TYPE: PRT
<213> ORGANISM: Homo sapiens

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Ser Pro Phe Phe Asp Tyr Trp Gly Gln Gly Thr Leu
            100                 105                 110

Val Thr Val Ser Ser
        115

<210> SEQ ID NO 101
<211> LENGTH: 321
<212> TYPE: DNA
<213> ORGANISM: Homo sapiens

<400> SEQUENCE: 101
gacatccaga tgacccagtc tccatcctcc ctgtctgcat ctgtaggaga cagagtcacc 60
atcacttgcc gggcaagtca gatcattagc cactttttaa attggtatca gcagaaacca 120
gggaaagccc ctaagctcct ggtctatgtt gcatccagtt tgcaaagtgg ggtcccatca 180
agattcagtg gcagtggatc tgggactgat ttcactctca ccatcagcag tctgcaacct 240
gaagattttg caacttacta ttgtcaacag agtttcagta taccgctcac tttcggcgga 300
gggaccaagg tggagatcaa a 321

<210> SEQ ID NO 102
<211> LENGTH: 107
<212> TYPE: PRT
<213> ORGANISM: Homo sapiens

<400> SEQUENCE: 102

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser His Phe
            20                  25                  30

Leu Asn Trp Tyr Gln Gln Lys Pro Gly Lys Ala Pro Lys Leu Leu Val
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ile Pro Leu
                85                  90                  95

Thr Phe Gly Gly Gly Thr Lys Val Glu Ile Lys
            100                 105


<210> SEQ ID NO 103
<211> LENGTH: 381
<212> TYPE: DNA
<213> ORGANISM: Homo sapiens

<400> SEQUENCE: 103

caggtgcagc tggtggagtc tgggggaggc gtggtccagc ctgggaggtc cctgagagtc      60

tcctgtgcag cgtctggatt tatgttcaga agctatggca tgcactgggt ccgccaggct     120

ccaggcaagg ggctggagtg ggtggcagtt atatggcatg atggaagtaa taaaaatcat     180

ggagactccg tgaagggccg attcaccatc tccagagaca attccaagaa cacgctgtat     240

ctgcaaatga acagcctgag agccgaggac acggctgtgt attactgtgc gagagggaga     300

ctggcagggg ggggccccta ttactattac tactacggta tggacgtctg gggccaaggg     360

accacggtca ccgtctcctc a                                               381


<210> SEQ ID NO 104
<211> LENGTH: 127
<212> TYPE: PRT
<213> ORGANISM: Homo sapiens

<400> SEQUENCE: 104

Gln Val Gln Leu Val Glu Ser Gly Gly Gly Val Val Gln Pro Gly Arg
1               5                   10                  15

Ser Leu Arg Val Ser Cys Ala Ala Ser Gly Phe Met Phe Arg Ser Tyr
            20                  25                  30

Gly Met His Trp Val Arg Gln Ala Pro Gly Lys Gly Leu Glu Trp Val
        35                  40                  45

Ala Val Ile Trp His Asp Gly Ser Asn Lys Asn His Gly Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Leu Ala Gly Gly Gly Pro Tyr Tyr Tyr Tyr Tyr Tyr
            100                 105                 110

Gly Met Asp Val Trp Gly Gln Gly Thr Thr Val Thr Val Ser Ser
        115                 120                 125


<210> SEQ ID NO 105
<211> LENGTH: 333
<212> TYPE: DNA
```

-continued

<213> ORGANISM: Homo sapiens

<400> SEQUENCE: 105
gatattgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc tcatcgggcc 180
tccggggtcc ctgacaggtt cagtggcagt ggatcaggca cagattttac actgaaaatc 240
agcagagtgg aggctgagga tgttgggctt tattactgca tgcaatctct acaaactatc 300
accttcggcc aagggacacg actggagatt aaa 333

<210> SEQ ID NO 106
<211> LENGTH: 111
<212> TYPE: PRT
<213> ORGANISM: Homo sapiens

<400> SEQUENCE: 106

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser His Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Leu Tyr Tyr Cys Met Gln Ser
85 90 95

Leu Gln Thr Ile Thr Phe Gly Gln Gly Thr Arg Leu Glu Ile Lys
100 105 110

<210> SEQ ID NO 107
<211> LENGTH: 360
<212> TYPE: DNA
<213> ORGANISM: Homo sapiens

<400> SEQUENCE: 107
caggtgcagc tggtggagtc tgggggaggc ttggtcaagc ctggagggtc cctgagactc 60
tcctgtgcag cctctggatt caccttcagt gactactaca tgaactggat ccgccaggct 120
ccagggaagg ggctggagtg ggtttcatac attagtagta gtggtagtat catatactac 180
gcagactctg tgaagggccg attcaccatc tccagggaca acgccaagaa ctcactgtat 240
ctgcaaatga acagcctgag agccgaggac acggccgtgt attactgtgc gagagatggg 300
cgtatagtag ctcgtggtat ggacgtctgg ggccaaggga ccacggtcac cgtctcctca 360

<210> SEQ ID NO 108
<211> LENGTH: 120
<212> TYPE: PRT
<213> ORGANISM: Homo sapiens

<400> SEQUENCE: 108

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

-continued

```
Tyr Met Asn Trp Ile Arg Gln Ala Pro Gly Lys Gly Leu Glu Trp Val
        35                  40                  45

Ser Tyr Ile Ser Ser Ser Gly Ser Ile Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Arg Ile Val Ala Arg Gly Met Asp Val Trp Gly Gln
            100                 105                 110

Gly Thr Thr Val Thr Val Ser Ser
        115                 120
```

<210> SEQ ID NO 109
<211> LENGTH: 324
<212> TYPE: DNA
<213> ORGANISM: Homo sapiens

<400> SEQUENCE: 109

```
gacatccaga tgacccagtc tccatcctcc ctgtctgcat ctgtaggaga cagagtcacc     60

ctcacttgcc gggcaagtca cagcattaac aggtatataa attggtatca gcagaaacca    120

gggaaagccc ctaaactcct gatctatgct gcatccagtt tgcaaagtgg ggtcccatct    180

aggttcagtg gcaatggatc tgggacagat ttcactctca ccatcagcag tctgcaacct    240

gaagattttg caacttacta ctgtcaacag agttacagta cccctccgat caccttcggc    300

caagggacac gactggagat tact                                           324
```

<210> SEQ ID NO 110
<211> LENGTH: 108
<212> TYPE: PRT
<213> ORGANISM: Homo sapiens

<400> SEQUENCE: 110

```
Asp Ile Gln Met Thr Gln Ser Pro Ser Ser Leu Ser Ala Ser Val Gly
1               5                   10                  15

Asp Arg Val Thr Leu Thr Cys Arg Ala Ser His Ser Ile Asn Arg Tyr
            20                  25                  30

Ile Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Asn Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Thr
            100                 105
```

<210> SEQ ID NO 111
<211> LENGTH: 360
<212> TYPE: DNA
<213> ORGANISM: Homo sapiens

<400> SEQUENCE: 111

```
caggtgcagc tggtggagtc tgggggaggc gtggtccagc ctgggaggtc cctgagactc     60

tcctgtgcag cgtctggatt caccttcagt agatatggca tgcactgggt ccgccaggct    120
```

-continued ccaggcaagg ggctggagtg ggtggcagtt atatggtatg atggaagaaa taaatactat 180
gtagactccg tgaagggccg attcaccatc tccagagaca attccaagaa cacgctgtat 240
ctgcaaatga acagcctgag agccgaggac acggctgtgt attattgtgt gggagtgggt 300
ataacagtga ctggtgcctt tgactactgg ggccagggaa ccctggtcac cgtctcctca 360

<210> SEQ ID NO 112
<211> LENGTH: 120
<212> TYPE: PRT
<213> ORGANISM: Homo sapiens

<400> SEQUENCE: 112

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Arg Tyr
20 25 30

Gly Met His Trp Val Arg Gln Ala Pro Gly Lys Gly Leu Glu Trp Val
35 40 45

Ala Val Ile Trp Tyr Asp Gly Arg Asn Lys Tyr Tyr Val Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Val Gly Val Gly Ile Thr Val Thr Gly Ala Phe Asp Tyr Trp Gly Gln
100 105 110

Gly Thr Leu Val Thr Val Ser Ser
115 120

<210> SEQ ID NO 113
<211> LENGTH: 321
<212> TYPE: DNA
<213> ORGANISM: Homo sapiens

<400> SEQUENCE: 113
gaaatagtga tgacgcagtc tccagccacc ctgtctgtgt ctccagggga aagagccacc 60
ctctcctgca gggccagtca gagtgttcgc agcaacttag cctggtacca acagaaacct 120
ggccaggctc ccaggctcct catctatggt gcatccacca gggtcactga tatcccaacc 180
aggttcagtg gcagtgggtc tgggacagag ttcactctct ccatcagcag cctgcagtct 240
gaagattttg cagtttatta ttgtcagcag tataataact ggcctcggac gtttggccaa 300
gggaccaagg tggaaatcaa a 321

<210> SEQ ID NO 114
<211> LENGTH: 107
<212> TYPE: PRT
<213> ORGANISM: Homo sapiens

<400> SEQUENCE: 114

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Arg Ser Asn
20 25 30

Leu Ala Trp Tyr Gln Gln Lys Pro Gly Gln Ala Pro Arg Leu Leu Ile
35 40 45

Tyr Gly Ala Ser Thr Arg Val Thr Asp Ile Pro Thr Arg Phe Ser Gly
50 55 60

-continued

Ser Gly Ser Gly Thr Glu Phe Thr Leu Ser Ile Ser Ser Leu Gln Ser
65 70 75 80

Glu Asp Phe Ala Val Tyr Tyr Cys Gln Gln Tyr Asn Asn Trp Pro Arg
85 90 95

Thr Phe Gly Gln Gly Thr Lys Val Glu Ile Lys
100 105

<210> SEQ ID NO 115
<211> LENGTH: 354
<212> TYPE: DNA
<213> ORGANISM: Homo sapiens

<400> SEQUENCE: 115
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagtt atatggtatg atagaagtaa taaatactat 180
gcagactccg tgaagggccg attcaccatc tccagagaca attccaagaa cacgctgtat 240
ctgcaaatga acagcctgag agccgaggac acggctgtgt attactgtgc ggggggacga 300
tcccggggag cctttgactt ctggggccag ggaaccctgg tcaccgtctc ctca 354

<210> SEQ ID NO 116
<211> LENGTH: 118
<212> TYPE: PRT
<213> ORGANISM: Homo sapiens

<400> SEQUENCE: 116

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Arg Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Gly Gly Arg Ser Arg Gly Ala Phe Asp Phe Trp Gly Gln Gly Thr
100 105 110

Leu Val Thr Val Ser Ser
115

<210> SEQ ID NO 117
<211> LENGTH: 306
<212> TYPE: DNA
<213> ORGANISM: Homo sapiens

<400> SEQUENCE: 117
cagtctccat cttccgtgtc tgcatctgta ggagacagag tcaccatcac ttgtcgggcg 60
agtcagggta ttagcagctg gttagcctgg tatcagcaga aagcagggaa agcccctaaa 120
ctcctgatct attctgcatc cagtttgcaa agtggggtcc catcaagatt cagcggcagt 180
ggatctggga cagatttcac tctcaccatc agcagcctgc agcctgaaga ttttgcaact 240
tactattgtc aacggactaa cagttttcct cggacgttcg gccaagggac caaggtggaa 300

-continued

```
atcaaa                                                               306

<210> SEQ ID NO 118
<211> LENGTH: 107
<212> TYPE: PRT
<213> ORGANISM: Homo sapiens

<400> SEQUENCE: 118

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Ala Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Thr Asn Ser Phe Pro Arg
                85                  90                  95

Thr Phe Gly Gln Gly Thr Lys Val Glu Ile Lys
            100                 105

<210> SEQ ID NO 119
<211> LENGTH: 351
<212> TYPE: DNA
<213> ORGANISM: Homo sapiens

<400> SEQUENCE: 119

cagctgcagc tgcaggagtc gggcccagga ctggtgaagc cttcggagac cctgtccctc     60

acctgcactg tctctggtgg cttcatcagc agtagtagtt actactgggg ctggatccgc    120

cagcccccag ggaagggact ggagtggatt gggaccatct attatagtgg gaccacctac    180

tacaattcgt ccctgaagag tcgagtcacc atatccgtag acacgtccca gaaccagttc    240

tccctgaagc tgagctctgt gaccgccgca gatacggctg tgtattactg tgcgagacat    300

cactgggttt ttgactactg gggccaggga accctggtca ccgtctcctc a             351

<210> SEQ ID NO 120
<211> LENGTH: 117
<212> TYPE: PRT
<213> ORGANISM: Homo sapiens

<400> SEQUENCE: 120

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Phe Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Thr Ile Tyr Tyr Ser Gly Thr Thr Tyr Tyr Asn Ser Ser
    50                  55                  60

Leu Lys Ser Arg Val Thr Ile Ser Val Asp Thr Ser Gln Asn Gln Phe
65                  70                  75                  80

Ser Leu Lys Leu Ser Ser Val Thr Ala Ala Asp Thr Ala Val Tyr Tyr
                85                  90                  95

Cys Ala Arg His His Trp Val Phe Asp Tyr Trp Gly Gln Gly Thr Leu
```

-continued

```
            100                 105                 110

Val Thr Val Ser Ser
        115


<210> SEQ ID NO 121
<211> LENGTH: 321
<212> TYPE: DNA
<213> ORGANISM: Homo sapiens

<400> SEQUENCE: 121

gaagttgtgc tgactcagtc tccagacttt cagtctgtga ctccaaagga gaaaatcacc      60

atcacctgcc gggccagtca gatcattggt actagcttac actggtatca gaagaaacca     120

gatcagtctc caaagctcct catcaagtat gcttcccagt ccttctcagg ggtcccctcg     180

aggttcagtg gcagtggatc tgggacagaa ttcaccctca ccatcaatag cctggaagct     240

gaagatactg caacgtatta ctgtcatcag agtactaatt taccgtggac gttcggccaa     300

gggaccaagg tggaaatcaa a                                               321


<210> SEQ ID NO 122
<211> LENGTH: 107
<212> TYPE: PRT
<213> ORGANISM: Homo sapiens

<400> SEQUENCE: 122

Glu Val Val Leu Thr Gln Ser Pro Asp Phe Gln Ser Val Thr Pro Lys
1               5                   10                  15

Glu Lys Ile Thr Ile Thr Cys Arg Ala Ser Gln Ile Ile Gly Thr Ser
            20                  25                  30

Leu His Trp Tyr Gln Lys Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Glu Phe Thr Leu Thr Ile Asn Ser Leu Glu Ala
65                  70                  75                  80

Glu Asp Thr Ala Thr Tyr Tyr Cys His Gln Ser Thr Asn Leu Pro Trp
                85                  90                  95

Thr Phe Gly Gln Gly Thr Lys Val Glu Ile Lys
            100                 105


<210> SEQ ID NO 123
<211> LENGTH: 384
<212> TYPE: DNA
<213> ORGANISM: Homo sapiens

<400> SEQUENCE: 123

caggtgcagc tggtgcagtc tggggctgag gtgaagaagc ctggggcctc agtgaaggtc      60

tcctgcaagg cttctggata caccttcatc ggctactatc ttcactgggt gcgacaggcc     120

cctggacaag ggcttgaatg gatgggatcg atcaacccta acagtggtgg cacaaactat     180

gcacagaagt ttcagggcag ggtcaccatg atcagggaca cgtccatcaa cacagcctac     240

atggagctga gcaggctgag atctgacgac acggccgtgt attactgtgc gagagataaa     300

cgtatcacta tggttcgggg agtccactat ctctactacg gttgggacgt ctggggccaa     360

gggaccacgg tcaccgtctc ctca                                            384


<210> SEQ ID NO 124
<211> LENGTH: 128
```

<212> TYPE: PRT
<213> ORGANISM: Homo sapiens

<400> SEQUENCE: 124

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Ile Gly Tyr
20 25 30

Tyr Leu His Trp Val Arg Gln Ala Pro Gly Gln Gly Leu Glu Trp Met
35 40 45

Gly Ser Ile Asn Pro Asn Ser Gly Gly Thr Asn Tyr Ala Gln Lys Phe
50 55 60

Gln Gly Arg Val Thr Met Ile Arg Asp Thr Ser Ile Asn Thr Ala Tyr
65 70 75 80

Met Glu Leu Ser Arg Leu Arg Ser Asp Asp Thr Ala Val Tyr Tyr Cys
85 90 95

Ala Arg Asp Lys Arg Ile Thr Met Val Arg Gly Val His Tyr Leu Tyr
100 105 110

Tyr Gly Trp Asp Val Trp Gly Gln Gly Thr Thr Val Thr Val Ser Ser
115 120 125

<210> SEQ ID NO 125
<211> LENGTH: 321
<212> TYPE: DNA
<213> ORGANISM: Homo sapiens

<400> SEQUENCE: 125
gacatccaga tgacccagtc tccatcctcc ctgtctgcat ctgtaggaga cagagtcacc 60
atcacttgcc gggcgagtca ggtcattagc aattatttag cctggtatca gcagaaacca 120
gggaaagttc ctcagctcct gatctatgct gcatccactt tgcaatcagg ggtcccatct 180
cggttcagtg gcagtggatc tgggacagat ttcactctca ccatcagcag cctgcagcct 240
gaagatgttg caacttatta ctgtcaaaac tataaaagtg ccccgtggac gttcggccaa 300
gggaccaagg tggaaatcaa a 321

<210> SEQ ID NO 126
<211> LENGTH: 107
<212> TYPE: PRT
<213> ORGANISM: Homo sapiens

<400> SEQUENCE: 126

Asp Ile Gln Met Thr Gln Ser Pro Ser Ser Leu Ser Ala Ser Val Gly
1 5 10 15

Asp Arg Val Thr Ile Thr Cys Arg Ala Ser Gln Val Ile Ser Asn Tyr
20 25 30

Leu Ala Trp Tyr Gln Gln Lys Pro Gly Lys Val Pro Gln Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Gln Asn Tyr Lys Ser Ala Pro Trp
85 90 95

Thr Phe Gly Gln Gly Thr Lys Val Glu Ile Lys
100 105

<210> SEQ ID NO 127
<211> LENGTH: 116
<212> TYPE: PRT
<213> ORGANISM: Homo sapiens

<400> SEQUENCE: 127

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Ser Gly Ser Phe Asp Tyr Trp Gly Gln Gly Thr Leu Val
            100                 105                 110

Thr Val Ser Ser
        115
```

<210> SEQ ID NO 128
<211> LENGTH: 118
<212> TYPE: PRT
<213> ORGANISM: Homo sapiens

<400> SEQUENCE: 128

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Ala Ala Arg Gly Met Asp Val Trp Gly Gln Gly Thr
            100                 105                 110

Thr Val Thr Val Ser Ser
        115
```

<210> SEQ ID NO 129
<211> LENGTH: 114
<212> TYPE: PRT
<213> ORGANISM: Homo sapiens

<400> SEQUENCE: 129

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45
```

-continued

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Trp Phe Asp Tyr Trp Gly Gln Gly Thr Leu Val Thr Val
            100                 105                 110

Ser Ser

<210> SEQ ID NO 130
<211> LENGTH: 108
<212> TYPE: PRT
<213> ORGANISM: Homo sapiens

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
            100                 105

<210> SEQ ID NO 131
<211> LENGTH: 107
<212> TYPE: PRT
<213> ORGANISM: Homo sapiens

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Ile
                85                  90                  95

Thr Phe Gly Gln Gly Thr Arg Leu Glu Ile Lys
            100                 105

<210> SEQ ID NO 132
<211> LENGTH: 107
<212> TYPE: PRT
<213> ORGANISM: Homo sapiens -continued

<400> SEQUENCE: 132

Glu Ile Val Leu Thr Gln Ser Pro Asp Phe Gln Ser Val Thr Pro Lys
1 5 10 15

Glu Lys Val Thr Ile Thr Cys Arg Ala Ser Gln Ser Ile Gly Ser Ser
20 25 30

Leu His Trp Tyr Gln Gln Lys Pro Asp Gln Ser Pro Lys Leu Leu Ile
35 40 45

Lys Tyr Ala Ser Gln Ser Phe Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

Glu Asp Ala Ala Thr Tyr Tyr Cys His Gln Ser Ser Ser Leu Pro Trp
85 90 95

Thr Phe Gly Gln Gly Thr Lys Val Glu Ile Lys
100 105

<210> SEQ ID NO 133
<211> LENGTH: 105
<212> TYPE: PRT
<213> ORGANISM: Homo sapiens

<400> SEQUENCE: 133

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ile Thr Phe
85 90 95

Gly Gln Gly Thr Arg Leu Glu Ile Lys
100 105

<210> SEQ ID NO 134
<211> LENGTH: 120
<212> TYPE: PRT
<213> ORGANISM: Homo sapiens

<400> SEQUENCE: 134

Gln Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Asp Tyr
20 25 30

Tyr Met His Trp Ile Arg Gln Ala Pro Gly Lys Gly Leu Glu Trp Val
35 40 45

Ser Tyr Ile Ser Arg Ser Gly Ser Leu Ile Tyr Tyr Val Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Gly Pro Tyr Ser Gly Ser Pro Phe Asp Tyr Trp Gly Gln

-continued

```
            100                 105                 110

Gly Thr Leu Val Thr Val Ser Ser
        115                 120


<210> SEQ ID NO 135
<211> LENGTH: 108
<212> TYPE: PRT
<213> ORGANISM: Homo sapiens

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Arg Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
            100                 105


<210> SEQ ID NO 136
<211> LENGTH: 108
<212> TYPE: PRT
<213> ORGANISM: Homo sapiens

<400> SEQUENCE: 136

Asp Ile Gln Met Thr Gln Ser Pro Ser Ser Leu Ser Ala Ser Val Gly
1               5                   10                  15

Asp Arg Val Ser Ile Thr Cys Arg Pro Ser Gln Ser Phe Ser Arg Tyr
            20                  25                  30

Ile Asn Trp Tyr Gln Gln Lys Pro Gly Lys Ala Pro Lys Leu Leu Ile
        35                  40                  45

Tyr Ala Ala Ser Ser Leu Val Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Asn Pro Pro
                85                  90                  95

Ile Thr Phe Gly Gln Gly Thr Arg Leu Glu Ile Lys
            100                 105


<210> SEQ ID NO 137
<211> LENGTH: 10
<212> TYPE: PRT
<213> ORGANISM: Homo sapiens

<400> SEQUENCE: 137

Gly Phe Thr Phe Ser Asp Tyr Tyr Met His
1               5                   10


<210> SEQ ID NO 138
<211> LENGTH: 17
<212> TYPE: PRT
<213> ORGANISM: Homo sapiens
```

<400> SEQUENCE: 138

Tyr Ile Ser Arg Ser Gly Ser Leu Ile Tyr Tyr Val Asp Ser Val Lys
1 5 10 15

Gly

<210> SEQ ID NO 139
<211> LENGTH: 11
<212> TYPE: PRT
<213> ORGANISM: Homo sapiens

<400> SEQUENCE: 139

Gly Gly Pro Tyr Ser Gly Ser Pro Phe Asp Tyr
1 5 10

<210> SEQ ID NO 140
<211> LENGTH: 11
<212> TYPE: PRT
<213> ORGANISM: Homo sapiens

<400> SEQUENCE: 140

Arg Pro Ser Gln Arg Ile Ser Arg Tyr Leu Asn
1 5 10

<210> SEQ ID NO 141
<211> LENGTH: 7
<212> TYPE: PRT
<213> ORGANISM: Homo sapiens

<400> SEQUENCE: 141

Ala Ala Ser Ser Leu Pro Ser
1 5

<210> SEQ ID NO 142
<211> LENGTH: 10
<212> TYPE: PRT
<213> ORGANISM: Homo sapiens

<400> SEQUENCE: 142

Gln Gln Ser Tyr Ser Thr Pro Pro Trp Thr
1 5 10

<210> SEQ ID NO 143
<211> LENGTH: 10
<212> TYPE: PRT
<213> ORGANISM: Homo sapiens

<400> SEQUENCE: 143

Gly Phe Thr Phe Ser Asp Tyr Tyr Met Asn
1 5 10

<210> SEQ ID NO 144
<211> LENGTH: 17
<212> TYPE: PRT
<213> ORGANISM: Homo sapiens

<400> SEQUENCE: 144

Tyr Ile Ser Ser Ser Gly Ser Ile Ile Tyr Tyr Ala Asp Ser Val Lys
1 5 10 15

Gly

<210> SEQ ID NO 145
<211> LENGTH: 11

-continued

<212> TYPE: PRT
<213> ORGANISM: Homo sapiens

<400> SEQUENCE: 145

Glu Gly Arg Ile Ala Ala Arg Gly Met Asp Val
1 5 10

<210> SEQ ID NO 146
<211> LENGTH: 11
<212> TYPE: PRT
<213> ORGANISM: Homo sapiens

<400> SEQUENCE: 146

Arg Pro Ser Gln Ser Phe Ser Arg Tyr Ile Asn
1 5 10

<210> SEQ ID NO 147
<211> LENGTH: 7
<212> TYPE: PRT
<213> ORGANISM: Homo sapiens

<400> SEQUENCE: 147

Ala Ala Ser Ser Leu Val Gly
1 5

<210> SEQ ID NO 148
<211> LENGTH: 10
<212> TYPE: PRT
<213> ORGANISM: Homo sapiens

<400> SEQUENCE: 148

Gln Gln Thr Tyr Ser Asn Pro Pro Ile Thr
1 5 10

<210> SEQ ID NO 149
<211> LENGTH: 12
<212> TYPE: PRT
<213> ORGANISM: Homo sapiens

<400> SEQUENCE: 149

Gly Asp Ser Ile Ser Ser Phe Ile Tyr Tyr Trp Gly
1 5 10

<210> SEQ ID NO 150
<211> LENGTH: 16
<212> TYPE: PRT
<213> ORGANISM: Homo sapiens

<400> SEQUENCE: 150

Thr Ile Tyr Tyr Ser Gly Ser Thr Tyr Tyr Asn Pro Ser Leu Lys Ser
1 5 10 15

<210> SEQ ID NO 151
<211> LENGTH: 7
<212> TYPE: PRT
<213> ORGANISM: Homo sapiens

<400> SEQUENCE: 151

His His Trp Val Phe Asp Tyr
1 5

<210> SEQ ID NO 152
<211> LENGTH: 11
<212> TYPE: PRT
<213> ORGANISM: Homo sapiens -continued

```
<400> SEQUENCE: 152

Arg Ala Ser Gln Val Ile Gly Ser Ser Leu His
1               5                   10


<210> SEQ ID NO 153
<211> LENGTH: 7
<212> TYPE: PRT
<213> ORGANISM: Homo sapiens

<400> SEQUENCE: 153

Tyr Ala Ser Gln Ser Phe Ser
1               5


<210> SEQ ID NO 154
<211> LENGTH: 9
<212> TYPE: PRT
<213> ORGANISM: Homo sapiens

<400> SEQUENCE: 154

His Gln Ser Thr Ile Leu Pro Trp Thr
1               5
```

TARGETED BINDING AGENTS DIRECTED TO PDGFR-ALPHA AND USES THEREOF

CROSS REFERENCE TO RELATED APPLICATIONS

This application claims priority under 35 U.S.C. § 119 to U.S. Provisional Application Ser. No. 60/835,647, filed Aug. 3, 2006, the entirety of which is hereby incorporated by reference.

BACKGROUND OF THE INVENTION

1. Field of the Invention

The invention relates to targeted binding agents against the target antigen PDGFR-alpha and uses of such agents. In some embodiments, the invention relates to fully human monoclonal antibodies directed to PDGFR-alpha and uses of these antibodies. Aspects of the invention also relate to hybridomas or other cell lines expressing such targeted binding agents or antibodies. The described targeted binding agents and antibodies are useful as diagnostics and for the treatment of diseases associated with the activity and/or overexpression of PDGFR-alpha.

2. Description of the Related Art

Platelet derived growth factor (PDGF) is a protein that regulates cell growth and division. There are five different isoforms of PDGF (A, B, C, D, and an AB heterodimer) that exist as dimers and activate the cellular response through two different receptors (PDGFR-alpha and PDGFR-beta). Specifically, PDGF dimers bind to two receptors simultaneously to induce receptor dimerization, autophosphorylation and intracellular signaling.

Platelet derived growth factor receptor-alpha (PDGFR-alpha, also known as CD140a), is a type III receptor tyrosine kinase characterized by an extracellular domain having five IgG-like domains, a transmembrane domain and a catalytic intracellular domain. PDGFR-alpha can form homodimers or heterodimers with the structurally similar PDGFR-beta. PDGF-AA activates only alpha-alpha receptor dimers, PDGF-AB and PDGF-CC activate alpha-alpha and/or alpha-beta receptor dimers and PDGF-BB activates all three combinations of receptor dimers.

PDGFR-alpha has been linked to tumorigenesis and has been implicated in a number of cancers including breast, lung, ovarian, prostate, colon and endometrial cancers, as well as hepatocellular carcinoma, glioblastoma, melanoma, and gastrointestinal stromal tumor (GIST)).

Several companies have developed therapeutic agents that target PDGFR-alpha. Gleevec® (Novartis®) and SUTENT/SU11248 (sunitinib malate, Pfizer®) are small molecule drugs that target PDGFR-alpha as well as other receptor tyrosine kinases. In addition, monoclonal antibodies that target PDGFR-alpha have been reported. International publication number WO 1992/013867 describes that mouse or rabbit monoclonal and/or polyclonal antibodies may be prepared to PDGF receptor constructs. International publication number WO 1995/000659 relates to a monoclonal antibody, specific for PDGFR-alpha, characterized in that it binds PDGFR-alpha and does not bind PDGFR-beta. The application discloses two antibodies; characterized as having half maximal binding affinity of 50 pM and 75 pM as measured by solid phase enzyme linked immunosorbent assay. International publication number WO2006/138729 discloses a fully human monoclonal antibody, termed 3G3 (ImClone Systems, Inc.), that targets PDGFR-alpha. This antibody has a reported affinity for soluble PDGFR-alpha of 40 pM as measured in a bivalent affinity assay; in which soluble PDGFR-alpha was immobilized on a sensor chip and antibody was injected at various concentrations. As discussed herein, in a bivalent assay, experimental artifacts may affect the measured affinity.

An antibody with an affinity higher than 40 pM, may be desirable as such an antibody may produce a greater extent and/or duration of PDGFR-alpha inhibition when administered to humans at standard doses. An antibody with an affinity higher than 40 pM may be administered at a lower effective dose than an antibody with a lower affinity, or may be administered at longer dosing intervals in comparison with a standard dosing interval for an antibody with a lower affinity.

SUMMARY OF THE INVENTION

Embodiments of the invention relate to targeted binding agents that specifically bind to PDGFR-alpha and inhibit the growth of cells that express PDGFR-alpha. Mechanisms by which this can be achieved can include, and are not limited to, blocking ligand binding and/or inhibiting cell signaling implicated in tumor cell growth as well as inhibition of the stromal fibroblast component leading to reduced angiogenesis. The targeted binding agents are useful for reducing tumour growth and angiogenesis.

In one embodiment of the invention, the targeted binding agent is a fully human antibody that binds to PDGFR-alpha and inhibits binding of PDGF-AA, PDGF-AB, PDGF-BB, and/or PDGF-CC ligands to PDGFR-alpha. Yet another embodiment of the invention is a fully human monoclonal antibody that binds to PDGFR-alpha and inhibits receptor autophosphorylation. Another embodiment of the invention is a fully human monoclonal antibody that binds to PDGFR-alpha and inhibits downstream cell signaling implicated in cell growth.

In some embodiments, the targeted binding agent binds to PDGFR-alpha and does not cross-react with PDGFR-beta receptor, that is, the agent is mono-specific. In some embodiments, the targeted binding agent binds to PDGFR-alpha and does not cross react with other Class III receptor tyrosine kinase family members, such as, for example, FLT3, c-kit, and/or CSF-1R.

Another embodiment of the invention is a targeted binding agent that competes for binding with any of the targeted binding agents or antibodies described herein.

In one embodiment, the targeted binding agent binds PDGFR-alpha with a KD of less than about 500 picomolar (pM). In another embodiment, the targeted binding agent binds with a KD less than about 400, 300, 200 or 100 pM. In one embodiment, the targeted binding agent binds with a KD of less than about 75, 60, 50, 40, 30, 20, 10 or 5 pM. Affinity and/or avidity measurements can be measured by FMAT, FACS, KinExA® and/or BIACORE®, as described herein.

In another embodiment, the targeted binding agent binds PDGFR-alpha with a KD less than about 400, 300, 200, or 100, 75, 60, 50, 40, 30, 20, 10, or 5 pM as measured in a monovalent affinity assay. Monovalent affinity may be measured in a BIACORE® assay in which soluble receptor is flowed over immobilized antibody. In comparison with a bivalent affinity assay, the KD as reported by a monovalent affinity assay is much less likely to be affected by experimental artifacts and is thus able to report a KD much closer to the true monovalent affinity of the antibody. In a bivalent affinity assay, the density of immobilized receptor influences the extent to which single antibody molecules bind twice and/or rebind immobilized receptor as they are flowed over. As such, in a bivalent affinity assay, the density of receptor can directly affect the reported KD. Thus, a monovalent affinity assay provides a much more biologically-relevant measurement of affinity.

In another embodiment, the targeted binding agent inhibits ligand-induced transphosphorylation within the receptor dimer with an IC50 less than about 400, 300, 200, or 100, 75, 60, 50, 40, 30, 20, 10, or 5 pM when performed at close to saturating ligand levels.

In another embodiment, the targeted binding agent inhibits ligand-induced receptor autophosphorylation with an IC50 less than about 400, 300, 200, 100, 75, 60, 50, 40, 30, 20, 10 or 5 pM when performed at close to saturating ligand levels.

In one embodiment of the invention, the targeted binding agent is an antibody. In one embodiment of the invention, the targeted binding agent is a monoclonal antibody. In one embodiment of the invention, the targeted binding agent is a fully human monoclonal antibody. In another embodiment of the invention, the targeted binding agent is a fully human monoclonal antibody of the IgG1, IgG2, IgG3 or IgG4 isotype. In another embodiment of the invention, the targeted binding agent is a fully human monoclonal antibody of the IgG2 isotype. This isotype has reduced potential to elicit effector function in comparison with other isotypes, which may lead to reduced toxicity.

A further embodiment is an antibody that binds to PDGFR-alpha and comprises a heavy chain amino acid sequence having one, two or three of the complementarity determining regions (CDR) sequences shown in Table 12 and a light chain amino acid sequence having one, two or three of the CDR sequences shown in Table 13. In certain embodiments the antibody is a fully human monoclonal antibody. In some embodiments, the invention provides an antibody that binds the same epitope as any of the antibodies disclosed herein.

In one embodiment, the heavy chain of antibody 2.175.3, 2.451.1, 2.449.1.3, 2.998.2 or 2.84.3 is paired with a heterologous light chain. Light-chain promiscuity is well established in the art. Thus, the heavy chain of any of antibodies 2.175.3, 2.451.1, 2.449.1.3, 2.998.2 or 2.84.3 or another antibody as disclosed herein may be paired with the light chain of any of antibodies 2.175.3, 2.451.1, 2.449.1.3, 2.998.2, 2.84.3, or other antibody as disclosed herein.

In one embodiment an antigen binding site may comprise a heavy chain CDR1, CDR2 and CDR3 and a light chain CDR1, CDR2 and CDR3 of any of antibodies 2.175.3, 2.451.1, 2.449.1.3, 2.998.2, 2.84.3 with as many as twenty, sixteen, ten, nine or fewer, e.g. one, two, three, four or five, amino acid additions, substitutions, deletions, and/or insertions within the disclosed CDRs. Such modifications may potentially be made at any residue within the CDRs.

In another embodiment the targeted binding agent or antibody may comprise a sequence comprising any one, two, three, four, five or six of the CDR1, CDR2 or CDR3 sequences as shown in Table 12 or Table 13. In another embodiment the targeted binding agent or antibody may comprise a sequence comprising a CDR1, CDR2 and CDR3 sequence as shown in Table 12. In another embodiment the targeted binding agent or antibody may comprise a sequence comprising a CDR1, CDR2 and CDR3 sequence as shown in Table 13. In another embodiment the targeted binding agent or antibody may comprise a sequence comprising a CDR1, CDR2 and CDR3 sequence as shown in Table 12 and a CDR1, CDR2 and CDR3 sequence as shown in Table 13. It is noted that those of ordinary skill in the art can readily accomplish CDR determinations. See for example, Kabat et al., Sequences of Proteins of Immunological Interest, Fifth Edition, NIH Publication 91-3242, Bethesda Md. (1991), vols. 1-3.

In another embodiment the targeted binding agent or antibody may comprise a sequence comprising any one, two, three, four, five or six of the CDR1, CDR2 and CDR3 sequences of any one of the fully human monoclonal antibodies 2.175.3, 2.449.1.3 or 2.998.2, as shown in Table 12 or in Table 13. In one embodiment the targeted binding agent or antibody may comprise a sequence comprising a CDR1, CDR2 and CDR3 sequence of fully human monoclonal antibody 2.175.3, 2.449.1.3 or 2.998.2, as shown in Table 12. In another embodiment the targeted binding agent or antibody may comprise a sequence comprising a CDR1, CDR2 and CDR3 sequence of fully human monoclonal antibody 2.175.3, 2.449.1.3 or 2.998.2, as shown in Table 13. In another embodiment the targeted binding agent or antibody may comprise a sequence comprising a CDR1, CDR2 and CDR3 sequence of fully human monoclonal antibody 2.175.3, 2.449.1.3 or 2.998.2 as shown in Table 12, and a CDR1, CDR2 and CDR3 sequence of fully human monoclonal antibody 2.175.3, 2.449.1.3 or 2.998.2 as shown in Table 13.

In another embodiment the targeted binding agent or antibody comprises a sequence comprising a CDR1, CDR2 and CDR3 sequence of fully human monoclonal antibody 2.175.3 (SEQ ID NO.:137, SEQ ID NO.:138 and SEQ ID NO.:139, respectively) as shown in Table 12 and a CDR1, CDR2 and CDR3 sequence of fully human monoclonal antibody 2.175.3 (SEQ ID NO.:140, SEQ ID NO.:141 and SEQ ID NO.:142, respectively) as shown in Table 13. In another embodiment the targeted binding agent or antibody comprises a sequence comprising a CDR1, CDR2 and CDR3 sequence of fully human monoclonal antibody 2.449.1.3 (SEQ ID NO.:143, SEQ ID NO.:144 and SEQ ID NO.:145, respectively) as shown in Table 12 and a CDR1, CDR2 and CDR3 sequence of fully human monoclonal antibody 2.449.1.3 (SEQ ID NO.: 146, SEQ ID NO.:147 and SEQ ID NO.:148, respectively) as shown in Table 13. In another embodiment the targeted binding agent or antibody comprises a sequence comprising a CDR1, CDR2 and CDR3 sequence of fully human monoclonal antibody 2.998.2 SEQ ID NO.:149, SEQ ID NO.:150 and SEQ ID NO.:151, respectively) as shown in Table 12 and a CDR1, CDR2 and CDR3 sequence of fully human monoclonal antibody 2.998.2 (SEQ ID NO.:152, SEQ ID NO.:153 and SEQ ID NO.:154, respectively) as shown in Table 13.

A further embodiment of the invention is a targeted binding agent which competes for binding to PDGFR-alpha with the targeted binding agent or antibodies of the invention. In another embodiment of the invention there is an antibody which competes for binding to PDGFR-alpha with the targeted binding agent or antibodies of the invention. In another embodiment the targeted binding agent or antibody competes for binding to PDGFR-alpha with any one of fully human monoclonal antibodies 2.175.3, 2.449.1.3 or 2.998.2. In one embodiment of the invention there is provided an antibody which competes with any one of fully human monoclonal antibodies 2.175.3, 2.449.1.3 or 2.998.2 for binding to PDGFR-alpha.

A further embodiment of the invention is a targeted binding agent or antibody that binds to the same epitope on PDGFR-alpha as the targeted binding agent or antibodies of the invention. In another embodiment of the invention there is an antibody that binds to the same epitope on PDGFR-alpha as the targeted binding agent or antibodies of the invention. In one embodiment of the invention there is provided a targeted binding agent that binds to the same epitope on PDGFR-alpha as any one of fully human monoclonal antibodies 2.175.3, 2.449.1.3 or 2.998.2. In one embodiment of the invention there is provided an antibody that binds to the same epitope on PDGFR-alpha as any one of fully human monoclonal antibodies 2.175.3, 2.449.1.3 or 2.998.2.

A further embodiment of the invention is a targeted binding agent or antibody comprising the contiguous heavy and light chain sequences spanning the framework regions and/or complementarity determining regions (CDR's), specifically from FR1 through FR4 or CDR1 through CDR3 of any one of the monoclonal antibodies as shown in Table 12 or Table 13.

One embodiment provides a targeted binding agent, or antigen-binding portion thereof, wherein the agent, or binding portion, comprises a heavy chain polypeptide having the sequence of SEQ ID NO.:2. In one embodiment, the agent, or binding portion thereof, further comprises a light chain polypeptide having the sequence of SEQ ID NO.:4. Another embodiment is a targeted binding agent, or antigen-binding portion thereof, wherein the agent, or binding portion, comprises a heavy chain polypeptide having the sequence of SEQ ID NO.:10. In one embodiment, the agent, or binding portion thereof, further comprises a light chain polypeptide having the sequence of SEQ ID NO.:12. Still another embodiment is a targeted binding agent, or antigen-binding portion thereof, wherein the agent, or binding portion, comprises a heavy chain polypeptide having the sequence of SEQ ID NO.:14. In one embodiment, the agent, or binding portion thereof, further comprises a light chain polypeptide having the sequence of SEQ ID NO.:16.

In one embodiment, the targeted binding agent comprises one or more of fully human monoclonal antibodies 2.175.3, 2.449.1.3 or 2.998.2.

In one embodiment, the targeted binding agent of the invention comprises a polypeptide comprising the sequence of SEQ ID NO.:2, wherein the sequence comprises any one of the unique combinations of germline and non-germline residues indicated by each row of Table 6. In one embodiment, the targeted binding agent of the invention comprises a polypeptide comprising the sequence of SEQ ID NO.: 10, wherein the sequence comprises any one of the unique combinations of germline and non-germline residues indicated by each row of Table 8. In one embodiment, the targeted binding agent of the invention comprises a polypeptide comprising the sequence of SEQ ID NO.: 14, wherein the sequence comprises any one of the unique combinations of germline and non-germline residues indicated by each row of Table 10. In one embodiment, the targeted binding agent of the invention comprises a polypeptide comprising the sequence of SEQ ID NO.:4, wherein the sequence comprises any one of the unique combinations of germline and non-germline residues indicated by each row of Table 7. In one embodiment, the targeted binding agent of the invention comprises a polypeptide comprising the sequence of SEQ ID NO.: 12, wherein the sequence comprises any one of the unique combinations of germline and non-germline residues indicated by each row of Table 9. In one embodiment, the targeted binding agent of the invention comprises a polypeptide comprising the sequence of SEQ ID NO.: 16, wherein the sequence comprises any one of the unique combinations of germline and non-germline residues indicated by each row of Table 11.

In one embodiment, the antibody of the invention comprises a heavy chain polypeptide comprising the sequence of SEQ ID NO.:2, wherein the sequence comprises any one of the unique combinations of germline and non-germline residues indicated by each row of Table 6. In one embodiment, the antibody of the invention comprises a heavy chain polypeptide comprising the sequence of SEQ ID NO.: 10, wherein the sequence comprises any one of the unique combinations of germline and non-germline residues indicated by each row of Table 8. In one embodiment, the antibody of the invention comprises a heavy chain polypeptide comprising the sequence of SEQ ID NO.: 14, wherein the sequence comprises any one of the unique combinations of germline and non-germline residues indicated by each row of Table 10. In one embodiment, the antibody of the invention comprises a light chain polypeptide comprising the sequence of SEQ ID NO.:4, wherein the sequence comprises any one of the unique combinations of germline and non-germline residues indicated by each row of Table 7. In one embodiment, the antibody of the invention comprises a light chain polypeptide comprising the sequence of SEQ ID NO.: 12, wherein the sequence comprises any one of the unique combinations of germline and non-germline residues indicated by each row of Table 9. In one embodiment, the antibody of the invention comprises a light chain polypeptide comprising the sequence of SEQ ID NO.: 16, wherein the sequence comprises any one of the unique combinations of germline and non-germline residues indicated by each row of Table 11.

In one embodiment, the targeted binding agent or antibody of the invention comprises a heavy chain sequence according to SEQ ID NO:2, 6 or 10, wherein the residue at position 30 is selected from: S or R;
the residue at position 31 is selected from: S, N or D;
the residue at position 33 is selected from: G or Y;
the residue at position 35 is selected from: S, H or N;
the residue at position 50 is selected from: Y, V or F;
the residue at position 53 is selected from: Y, S or R;
the residue at position 54 is selected from: S or D;
the residue at position 57 is selected from: T, L, N or I;
the residue at position 58 is selected from: K or I;
the residue at position 61 is selected from: V or A;
the residue at position 99 is selected from: G, D or E or the residue is deleted;
the residue at position 100 is selected from: G or the residue is deleted;
the residue at position 101 is selected from: S, H, P or R;
the residue at position 102 is selected from: Y or I;
the residue at position 103 is selected from: S, V or A;
the residue at position 104 is selected from: G or A;
the residue at position 105 is selected from: S or R;
the residue at position 106 is selected from: P or G;
the residue at position 107 is selected from: F or M; and
the residue at position 109 is selected from: Y or V. This group of heavy chain sequences is named "Group A".

In one embodiment, the targeted binding agent or antibody of the invention comprises a heavy chain sequence according to SEQ ID NO: 14 or 18, wherein the residue at position 27 is selected from: G or D;
the residue at position 28 is selected from: S or F;
the residue at position 32 is selected from: S or F;
the residue at position 33 is selected from: S, N, T or I;
the residue at position 52 is selected from: S or T;
the residue at position 56 is selected from: S or T;
the residue at position 58 is selected from: S or T;
the residue at position 63 is selected from: S or P;
the residue at position 100 is selected from: H or the residue is deleted;
the residue at position 101 is selected from: H or the residue is deleted; and
the residue at position 103 is selected from: V or the residue is deleted. This group of heavy chain sequences is named "Group B".

In one embodiment, the targeted binding agent or antibody of the invention comprises a light chain sequence according to SEQ ID NO:4, 8 or 12, wherein the residue at position 25 is selected from: A or P;
the residue at position 27 is selected from: Q, R or H;

the residue at position 28 is selected from: G, V, S, I, D or R;

the residue at position 29 is selected from: I or F;

the residue at position 30 is selected from: S, N, A, R or T;

the residue at position 31 is selected from: S, H, K, T or R;

the residue at position 32 is selected from: S, T, Y, D, N or F;

the residue at position 33 is selected from: L or I;

the residue at position 50 is selected from: A, G, L, Y, S or V;

the residue at position 51 is selected from: A, G or S;

the residue at position 53 is selected from: T, Q, N, H, R or S;

the residue at position 54 is selected from: L, R or S;

the residue at position 55 is selected from: Q, P, F, A or V;

the residue at position 56 is selected from: S, N, T or G;

the residue at position 91 is selected from: S or T;

the residue at position 92 is selected from: Y or F;

the residue at position 94 is selected from: N, T, S or the residue is deleted;

the residue at position 95 is selected from: F, W, P, I, A, L or the residue is deleted;

the residue at position 96 is selected from: P or the residue is deleted; and the residue at position 97 is selected from: W, L, R, I or the residue is deleted. This group of light chain sequences is named "Group C".

In one embodiment, the targeted binding agent or antibody of the invention comprises a light chain sequence according to SEQ ID NO: 16 or 20, wherein the residue at position 28 is selected from: S, I, G, D, R or V;

the residue at position 29 is selected from: F, I or V;

the residue at position 30 is selected from: S, A, T, G, R or N;

the residue at position 31 is selected from: S, R, K, N or T;

the residue at position 32 is selected from: Y, F, W, N, D or S;

the residue at position 33 is selected from: L or I;

the residue at position 34 is selected from: N, A or H;

the residue at position 50 is selected from: A, Y, G, L or V;

the residue at position 51 is selected from: A, G or S;

the residue at position 52 is selected from: A, Y, G, L or V;

the residue at position 54 is selected from: L, R or S;

the residue at position 55 is selected from: Q, F, V, A or P;

the residue at position 56 is selected from: S, N, T or G;

the residue at position 92 is selected from: S or T; and the residue at position 93 is selected from: S, N or I. This group of light chain sequences is named "Group D".

In one embodiment the targeted binding agent or antibody of the invention comprises any one of the Group A heavy chain sequences and any one of the Group C or Group D light chain sequences.

In one embodiment the targeted binding agent or antibody of the invention comprises any one of the Group B heavy chain sequences and any one of the Group C or Group D light chain sequences.

In one embodiment, the targeted binding agent comprises an antibody which comprises variants or derivative of the CDRs disclosed herein or the light or heavy chain sequences disclosed herein or the monoclonal antibodies disclosed herein. Variants include antibodies comprising light or heavy chain sequences which have at least about 60, 70, 80, 85, 90, 95, 98 or about 99% amino acid sequence identity with any of the CDR1, CDR2 or CDR3s as shown in Table 12 or Table 13, or with the light or heavy chain sequences disclosed herein, or with the monoclonal antibodies disclosed herein. In one embodiment variants comprise changes in the CDR sequences or light or heavy chain sequences disclosed herein that are naturally occurring or are introduced by in vitro engineering of native sequences using recombinant DNA techniques or mutagenesis techniques. Naturally occurring variants include those which are generated in vivo in the corresponding germline nucleotide sequences during the generation of an antibody to a foreign antigen. In one embodiment the derivative may be a heteroantibody, that is an antibody in which two or more antibodies are linked together. Derivatives include antibodies which have been chemically modified. Examples include covalent attachment of one or more polymers, such as water-soluble polymers, N-linked, or O-linked carbohydrates, sugars, phosphates, and/or other such molecules. The derivatives are modified in a manner that is different from naturally occurring or starting antibody, either in the type or location of the molecules attached. Derivatives further include deletion of one or more chemical groups which are naturally present on the antibody.

Other embodiments of the invention include human monoclonal antibodies that bind PDGFR-alpha and comprise a heavy chain polypeptide derived from a VH3-11 germ line sequence. Other embodiments of the invention include human monoclonal antibodies that bind PDGFR-alpha and comprise a heavy chain polypeptide derived from a VH4-39 germ line sequence. Other embodiments of the invention include human monoclonal antibodies that bind PDGFR-alpha and comprise a heavy chain polypeptide derived from a D1-26, D6-6 or D7-27 germ line sequence. Some embodiments of the invention include human monoclonal antibodies that bind PDGFR-alpha and comprise a Vκ light chain. Still other embodiments of the invention include a monoclonal antibody that comprises a Vκ light chain paired with a heavy chain encoded by, or derived from, a VH3-11 or VH4-39 heavy chain gene. In some embodiments, the Vκ light chain polypeptide is encoded by, or derived from, a JK1 light chain gene. In other embodiments, the Vκ light chain polypeptide is encoded by, or derived from, a JK5 light chain gene.

Other embodiments of the invention include human monoclonal antibodies that bind PDGFR-alpha and comprise a heavy chain polypeptide derived from a VH3-11 germ line sequence, and a Vk light chain polypeptide derived from a O12 light chain gene. Additional embodiments of the invention include human monoclonal antibodies that bind PDGFR-alpha and comprise a heavy chain polypeptide derived from a VH3-11 germ line sequence, and a Vk light chain polypeptide derived from the O12 germline sequence light chain wherein the second amino acid in CDR1 of the light chain encodes proline. This combination of VH3-11 heavy chain gene usage in combination with O12 light chain gene usage along with proline encoded for at the second amino acid position of CDR1 of the light chain is exemplified in antibodies derived from two antibodies from independent lineages with diverse CDR3 heavy chain and light chain sequences, namely 2.449.1.3 and 2.175.3 (see Tables 12 and 13).

Monoclonal antibodies 2.175.3 and 2.449.1.3 are both high affinity antibodies to PDGFRa, and block PDGF-driven cellular responses with high potency in vitro. Although these two antibodies share VH (VH3-11) and Vk (O12) usage, they diverge in D, JH and Jk usage. Thus, they are derived from different B-cell lineages. They do, however, share unusual sequence patterns in Vk. Residue 25 is a proline in both antibodies, mutated from the germline alanine. Proline is not used by any of the Vk germline genes, and occurs at this location in only 0.2% of human sequences in the Kabat database. Proline at position 25 would insert a rigid peptide bond and a sharp angle in the peptide backbone, and would therefore produce unique structural characteristics within this Vk region of the light chain of both of these antibodies. Similarly, a mutant arginine is used by both 2.175.3 and 2.449.1.3 in position 27e (Kabat numbering) of CDR1 of Vk. Arginine is not used in this canonical location in any Vk germline genes, and occurs in only 0.4% of human sequences in the Kabat database. In one embodiment of the invention there is provided a human monoclonal antibody that binds PDGFR-alpha and comprises a proline at residue 25. In one embodiment of the invention there is provided a human monoclonal antibody that binds PDGFR-alpha and comprises an arginine at position 27e of CDR1.

In other embodiments the invention provides compositions, including a targeted binding agent of the invention or binding fragment thereof, and a pharmaceutically acceptable carrier. In other embodiments the invention provides compositions, including an antibody of the invention or binding fragment thereof, and a pharmaceutically acceptable carrier.

Still further embodiments of the invention include methods of effectively treating an animal suffering from a neoplastic disease, including selecting an animal in need of treatment for a neoplastic disease, and administering to the animal a therapeutically effective dose of a targeted binding agent that specifically binds to PDGFR-alpha. In certain embodiments, the animal is human. In certain embodiments, the targeted binding agent is a fully human monoclonal antibody. In certain embodiments, the targeted binding agent is an antibody of the invention and may be selected from the group consisting of 2.175.3, 2.449.1.3, or 2.998.2.

Treatable neoplastic diseases, include, for example, cancers including, melanoma, small cell lung cancer, non-small cell lung cancer, glioma, hepatocellular (liver) carcinoma, thyroid tumor, gastric (stomach) cancer, prostate cancer, breast cancer, ovarian cancer, bladder cancer, lung cancer, glioblastoma, endometrial cancer, kidney cancer, colon cancer, pancreatic cancer, esophageal carcinoma, head and neck cancers, mesothelioma, sarcomas, biliary (cholangiocarcinoma), small bowel adenocarcinoma, pediatric malignancies, epidermoid carcinoma, and gastrointestinal stromal tumor (GIST).

In one embodiment the present invention is suitable for use in antagonizing PDGFR-alpha, in patients with a tumour which is dependent alone, or in part, on a PDGFR-alpha.

Additional embodiments of the invention include methods of inhibiting tumor cell growth in an animal. These methods include selecting an animal in need of treatment for tumor cell growth, and administering to the animal a therapeutically effective dose of a targeted binding agent, wherein said agent specifically binds to PDGFR-alpha. In another embodiment the method includes selecting an animal in need of treatment for tumor cell growth, and administering to the animal a therapeutically effective dose of a fully human monoclonal antibody, wherein said antibody specifically binds to PDGFR-alpha.

Further embodiments of the invention include the use of a targeted binding agent in the preparation of medicament for the treatment of diseases involving PDGFR-alpha expression in an animal, wherein the agent specifically binds to PDGFR-alpha. In another embodiment the invention includes the use of an antibody in the preparation of medicament for the treatment of diseases involving PDGFR-alpha expression in an animal, wherein the monoclonal antibody specifically binds to PDGFR-alpha.

In other embodiments, the targeted binding agents or antibodies described herein can be used for the preparation of a medicament for the treatment of neoplastic diseases in an animal, wherein the antibody specifically binds to PDGFR-alpha.

Embodiments of the invention described herein relate to monoclonal antibodies that bind PDGFR-alpha and affect PDGFR-alpha function. Other embodiments relate to fully human anti-PDGFR-alpha antibodies and anti-PDGFR-alpha antibody preparations with desirable properties from a therapeutic perspective, including high binding affinity for PDGFR-alpha, high selectivity for inhibition of PDGFR-alpha signaling, low toxicity, the ability to block PDGF-AA ligands from binding to PDGFR-alpha, the ability to block PDGF-AB ligands from binding to PDGFR-alpha, the ability to block PDGF-BB ligands from binding to PDGFR-alpha, the ability to block PDGF-CC ligands from binding to PDGFR-alpha, and/or the ability to inhibit tumor cell growth in vitro and in vivo. Some embodiments relate to fully human anti-PDGFR-alpha antibodies that do not substantially cross react with PDGFR-beta. Still other embodiments relate to fully human anti-PDGFR-alpha antibodies and anti-PDGFR-alpha antibody preparations that do not result in a significant Human Anti-Chimeric Antibody (HACA) response, thereby allowing for repeated administration.

In one embodiment, the invention includes antibodies that bind to PDGFR-alpha with very high affinities (Kd). For example a human, rabbit, mouse, chimeric or humanized antibody that is capable of binding PDGFR-alpha with a Kd less than, but not limited to, 10-5, 10-6, 10-7, 10-8, 10-9, 10-10 or 10-11M, or any range or value therein. Affinity and/or avidity measurements can be measured by KinExA® and/or BIACORE®, as described herein.

Accordingly, one embodiment described herein includes isolated antibodies, or fragments of those antibodies, that bind to PDGFR-alpha. As known in the art, the antibodies can advantageously be, for example, polyclonal, oligoclonal, monoclonal, chimeric, humanized, and/or fully human antibodies. Embodiments of the invention described herein also provide cells for producing these antibodies.

It will be appreciated that embodiments of the invention are not limited to any particular form of an antibody or method of generation or production. For example, the anti-PDGFR-alpha antibody can be a full-length antibody (e.g., having an intact human Fc region) or an antibody binding fragment (e.g., a Fab, Fab' or F(ab')2, FV or dAb). In addition, the antibody can be manufactured from a hybridoma that secretes the antibody, or from a recombinantly engineered cell that has been transformed or transfected with a gene or genes encoding the antibody. In addition, the antibodies can be single-domain antibodies such as camelid or human single VH or VL domains that bind to PDGFR-alpha, such as a dAb fragment.

Other embodiments of the invention include isolated nucleic acid molecules encoding any of the targeted binding agents or antibodies described herein, vectors having isolated nucleic acid molecules encoding anti-PDGFR-alpha antibodies or a host cell transformed with any of such nucleic acid molecules. In addition, one embodiment of the invention is a method of producing an anti-PDGFR-alpha antibody by culturing host cells under conditions wherein a nucleic acid molecule is expressed to produce the antibody followed by recovering the antibody.

A further embodiment herein includes a method of producing high affinity antibodies to PDGFR-alpha by immunizing a mammal with cells expressing human PDGFR-alpha, isolated cell membranes containing human PDGFR-alpha, purified human PDGFR-alpha, or a fragment thereof, and/or one or more orthologous sequences or fragments thereof.

Other embodiments are based upon the generation and identification of isolated antibodies that bind specifically to PDGFR-alpha. PDGFR-alpha is expressed on a number of tumor types. Antibodies that neutralize PDGFR-alpha can prevent PDGFR-alpha induced tumor growth and other desired effects.

Another embodiment of the invention includes a method of diagnosing diseases or conditions in which an antibody prepared as described herein is utilized to detect the level of PDGFR-alpha in a patient or patient sample. In further embodiments, methods for the identification of risk factors, diagnosis of disease, and staging of disease is presented which involves the identification of the expression and/or overexpression of PDGFR-alpha using anti-PDGFR-alpha antibodies. In some embodiments, the methods comprise administering to a patient a fully human antibody conjugate that selectively binds to a PDGFR-alpha protein on a cell. The antibody conjugate comprises an antibody that selectively binds to PDGFR-alpha and a label. The methods further comprise observing the presence of the label in the patient. A relatively high amount of the label will indicate a relatively high risk of the disease and a relatively low amount of the label will indicate a relatively low risk of the disease. In one embodiment, the label is a green fluorescent protein.

The invention further provides methods for assaying the level of PDGFR-alpha in a patient sample, comprising contacting an anti-PDGFR-alpha antibody with a biological sample from a patient, and detecting the level of binding between said antibody and PDGFR-alpha in said sample. In more specific embodiments, the biological sample is blood or serum.

Another embodiment of the invention includes a method for diagnosing a condition associated with the expression of PDGFR-alpha in a cell by contacting serum or a cell with an anti-PDGFR-alpha antibody, and thereafter detecting the presence of PDGFR-alpha.

In another embodiment, the invention includes an assay kit for detecting PDGFR-alpha in mammalian tissues, cells, or body fluids to screen for diseases involving cells that express PDGFR-alpha. The kit includes an antibody that binds to PDGFR-alpha and a means for indicating the reaction of the antibody with PDGFR-alpha, if present. Preferably the antibody is a monoclonal antibody. In one embodiment, the antibody that binds PDGFR-alpha is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radiopaque material.

Yet another embodiment includes methods for treating diseases or conditions associated with the expression of PDGFR-alpha in a patient, by administering to the patient an effective amount of an anti-PDGFR-alpha antibody. The anti-PDGFR-alpha antibody can be administered alone, or can be administered in combination with additional antibodies or chemotherapeutic drug or radiation therapy. For example, a monoclonal, oligoclonal or polyclonal mixture of PDGFR-alpha antibodies that inhibit tumor growth can be administered in combination with a drug shown to inhibit tumor cell proliferation directly. The method can be performed in vivo and the patient is preferably a human patient.

In some embodiments, the anti-PDGFR-alpha antibodies can be modified to enhance their capability of fixing complement and participating in complement-dependent cytotoxicity (CDC). In other embodiments, the anti-PDGFR-alpha antibodies can be modified to enhance their capability of activating effector cells and participating in antibody-dependent cytotoxicity (ADCC). In yet other embodiments, the anti-PDGFR-alpha antibodies can be modified both to enhance their capability of activating effector cells and participating in antibody-dependent cytotoxicity (ADCC) and to enhance their capability of fixing complement and participating in complement-dependent cytotoxicity (CDC).

In another embodiment, the invention provides an article of manufacture including a container. The container includes a composition containing an anti-PDGFR-alpha antibody, and a package insert or label indicating that the composition can be used to treat diseases characterized by the expression or overexpression of PDGFR-alpha.

In other embodiments, the invention provides a kit for treating diseases involving the expression of PDGFR-alpha, comprising anti-PDGFR-alpha monoclonal antibodies and instructions to administer the monoclonal antibodies to a subject in need of treatment.

In another aspect, a method of selectively killing a cancerous cell in a patient is provided. The method comprises administering a fully human antibody conjugate to a patient. The fully human antibody conjugate comprises an antibody that can bind to the extracellular domain of PDGFR-alpha and an agent. The agent is either a toxin, a radioisotope, or another substance that will kill a cancer cell. The antibody conjugate thereby selectively kills the cancer cell. The agent can be saporin.

In one aspect, a conjugated fully human antibody that binds to PDGFR-alpha is provided. Attached to the antibody is an agent, and the binding of the antibody to a cell results in the delivery of the agent to the cell. In one embodiment, the above conjugated fully human antibody binds to an extracellular domain of PDGFR-alpha. In another embodiment, the antibody and conjugated toxin are internalized by a cell that expresses PDGFR-alpha. In another embodiment, the agent is a cytotoxic agent. In another embodiment, the agent is, for example saporin, or auristatin, pseudomonas exotoxin, gelonin, ricin, calicheamicin or maytansine-based immunoconjugates, and the like. In still another embodiment, the agent is a radioisotope.

In some embodiments of the invention, the glycosylation patterns of the antibodies provided herein are modified to enhance ADCC and CDC effector function. See Shields R L et al., (2002) JBC. 277:26733; Shinkawa T et al., (2003) JBC. 278:3466 and Okazaki A et al., (2004) J. Mol. Biol., 336: 1239.

BRIEF DESCRIPTION OF THE DRAWINGS

FIG. 2*a* shows the average tumor size (mm3) vs. time (days) and FIG. 2*b* shows the average body weight (g) vs. time (days). The square points represent the vehicle treatment group; the circular points represent the 2.175.3 10 mg/kg treatment group; the triangular points represent the 2.449.1.3 10 mg/kg treatment group.

DETAILED DESCRIPTION OF THE PREFERRED EMBODIMENT

Figure 1:
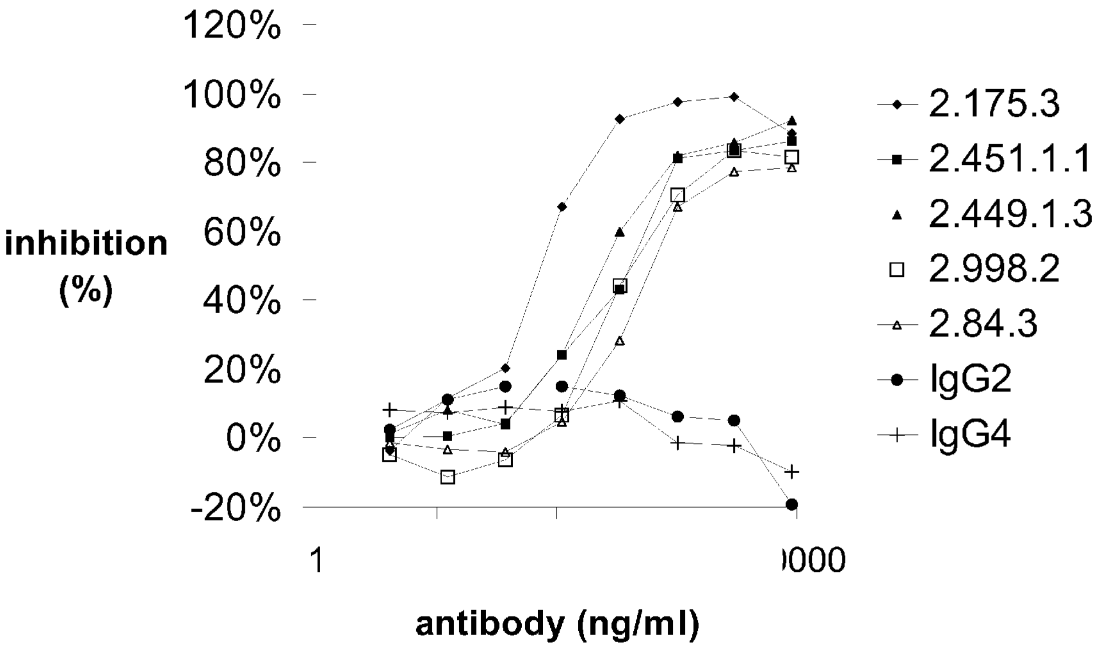
FIG. 1 is a graph showing the dose responses for 5 selected monoclonal antibodies for % inhibition of PDGF-AA-induced proliferation of MG-63 tumor cells against antibody in ng/ml. Cell stimulation was conducted using 100 ng/ml (3.45 nM) PDGF-AA.

Embodiments of the invention described herein relate to targeted binding agents that bind to PDGFR-alpha. In some embodiments, the targeted binding agents are antibodies that bind to PDGFR-alpha and inhibit tumor cell growth. Other embodiments of the invention include fully human anti-PDGFR-alpha antibodies, and antibody preparations that are therapeutically useful. Such anti-PDGFR-alpha antibody preparations preferably have desirable therapeutic properties, including strong binding affinity for PDGFR-alpha, high selectivity for inhibition of PDGFR-alpha signaling, low toxicity, the ability to block PDGF-AA ligands from binding to PDGFR-alpha, the ability to block PDGF-AB ligands from binding to PDGFR-alpha or PDGFR-alpha/beta heterodimers, the ability to block PDGF-BB ligands from binding to PDGFR-alpha or PDGFR-alpha/beta heterodimers, the ability to bock PDGF-CC ligands from binding to PDGFR-alpha or PDGFR-alpha/beta heterodimers, and/or the ability to inhibit tumor cell growth in vitro and in vivo. Some embodiments relate to fully human anti-PDGFR-alpha antibodies that do not cross-react with PDGFR-beta.

Embodiments of the invention also include targeted binding agents which are isolated binding fragments of anti-PDGFR-alpha antibodies. Preferably, the binding fragments are derived from fully human anti-PDGFR-alpha antibodies. Exemplary fragments include Fv, Fab' dAb or other well-known antibody fragments, as described in more detail below. Embodiments of the invention also include cells that express fully human antibodies against PDGFR-alpha. Examples of cells include hybridomas, or recombinantly created cells, such as Chinese hamster ovary (CHO) cells that produce antibodies against PDGFR-alpha.

In addition, embodiments of the invention include methods of using these antibodies for treating diseases. Anti-PDGFR-alpha antibodies are useful for inhibiting tumor growth. The mechanism of action can include, but is not limited to, blocking ligand binding and/or inhibiting cell signaling implicated in cell growth. Diseases that are treatable through this mechanism include, but are not limited to, neoplastic diseases, such as, cancers including, lung cancer, ovarian cancer, prostate cancer, colon cancer, glioblastoma, melanoma and gastrointestinal stromal tumor (GIST).

Other embodiments of the invention include diagnostic assays for specifically determining the presence and/or quantity of PDGFR-alpha in a patient or biological sample. The assay kit can include anti-PDGFR-alpha antibodies along with the necessary labels for detecting such antibodies. These diagnostic assays are useful to screen for PDGFR-alpha-related diseases including, but not limited to, neoplastic diseases, such as cancers including, breast cancer, lung cancer, ovarian cancer, prostate cancer, colon cancer, glioblastoma, melanoma and gastrointestinal stromal tumor (GIST).

Another embodiment is an antibody comprising a heavy chain polypeptide comprising the sequence of SEQ ID NO.:2. In one embodiment, the antibody further comprises a light chain polypeptide comprising the sequence of SEQ ID NO.:4. Another embodiment includes an antibody comprising a heavy chain polypeptide comprising the sequence of SEQ ID NO.:10. In one embodiment, the antibody further comprises a light chain polypeptide comprising the sequence of SEQ ID NO.:12. Still another embodiment is an antibody comprising a heavy chain polypeptide comprising the sequence of SEQ ID NO.:14. In one embodiment, the antibody further comprises a light chain polypeptide comprising the sequence of SEQ ID NO.:16.

Yet another embodiment is a hybridoma that produces the light chain and/or the heavy chain of antibody as described hereinabove. The hybridoma may produce a light chain and/or a heavy chain of a fully human monoclonal antibody. In one embodiment, the hybridoma produces the light chain and/or the heavy chain of the fully human monoclonal antibody 2.175.3, 2.449.1.3, and 2.998.2. Alternatively the hybridoma may produce an antibody that binds to the same epitope or epitopes as fully human monoclonal antibody 2.175.3, 2.449.1.3, and 2.998.2. Alternatively the hybridoma may produce an antibody that competes for binding to PDGFR-alpha with fully human monoclonal antibody 2.175.3, 2.449.1.3, and 2.998.2.

Still another embodiment is a nucleic acid molecule encoding the light chain or the heavy chain of the antibody as described hereinabove. In this embodiment, the nucleic acid molecule may encode the light chain or the heavy chain of a fully human monoclonal antibody. In one embodiment, the nucleic acid molecule encodes the light chain or the heavy chain of one of the fully human monoclonal antibodies 2.175.3, 2.449.1.3, or 2.998.2.

An additional embodiment is a vector comprising a nucleic acid molecule or molecules as described hereinabove, wherein the vector encodes a light chain and/or a heavy chain of an antibody as defined hereinabove.

One embodiment of the invention includes a host cell comprising a vector as described hereinabove. Alternatively the host cell may comprise more than one vector.

In addition, one embodiment of the invention is a method of producing an antibody by culturing host cells under conditions wherein a nucleic acid molecule is expressed to produce the antibody, followed by recovery of the antibody.

In one embodiment the invention includes a method of making a targeted binding agent by transfecting at least one host cell with at least one nucleic acid molecule encoding the targeted binding agent as described hereinabove, expressing the nucleic acid molecule in the host cell and isolating the targeted binding agent. Another embodiment of the invention is a method of making an antibody by transfecting at least one host cell with at least one nucleic acid molecule encoding the antibody as described hereinabove, expressing the nucleic acid molecule in the host cell and isolating the antibody.

Another aspect of the invention is a method of inhibiting the growth of cells that express PDGFR-alpha by administering a targeted binding agent as described hereinabove. The method may include selecting an animal in need of treatment for disease-related to PDGFR-alpha expression, and administering to the animal a therapeutically effective dose of a targeted binding agent that specifically binds to PDGFR-alpha.

Still another aspect is a method of treating a neoplastic disease in a mammal by administering a therapeutically effective amount of a targeted binding agent that specifically binds PDGFR-alpha. The method may include selecting an animal in need of treatment for a neoplastic disease, and administering to the animal a therapeutically effective dose of a targeted binding agent that specifically binds PDGFR-alpha. The agent can be administered alone, or can be administered in combination with a second anti-neoplastic agent selected from an antibody, a chemotherapeutic drug, or a radioactive drug.

One other aspect is a method of treating cancer in a mammal by administering a therapeutically effective amount of a targeted binding agent that specifically binds PDGFR-alpha. The method may include selecting an animal in need of treatment for cancer, and administering to the animal a therapeutically effective dose of a targeted binding agent that specifically binds PDGFR-alpha. The agent can be administered alone, or can be administered in combination with a second anti-neoplastic agent selected from an antibody, a chemotherapeutic drug, or a radioactive drug.

According to another aspect of the invention a targeted binding agent can be used that specifically binds PDGFR-alpha for the manufacture of a medicament for the treatment of a neoplastic disease.

One embodiment the invention is particularly suitable for use in inhibiting tumor growth in patients with a tumor that is dependent alone, or in part, on PDGFR-alpha expression.

Another embodiment of the invention includes an assay kit for detecting PDGFR-alpha in mammalian tissues, cells, or body fluids to screen for neoplastic and/or fibrotic and/or immune system diseases. The kit includes a targeted binding agent that binds to PDGFR-alpha and a means for indicating the reaction of the targeted binding agent with PDGFR-alpha, if present. The targeted binding agent may be a monoclonal antibody. In one embodiment, the antibody that binds PDGFR-alpha is labeled. In another embodiment the antibody is an unlabeled primary antibody and the kit further includes a means for detecting the primary antibody. In one embodiment, the means includes a labeled second antibody that is an anti-immunoglobulin. Preferably the antibody is labeled with a marker selected from the group consisting of a fluorochrome, an enzyme, a radionuclide and a radio-opaque material.

Further embodiments, features, and the like regarding anti-PDGFR-alpha antibodies are provided in additional detail below.

Definitions

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (3rd ed., Cold Spring Harbor Laboratory Press, Cold Spring Harbor, N.Y. (2001)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

A compound refers to any small molecular weight compound with a molecular weight of less than about 2000 Daltons.

The term "PDGFR-alpha" refers to the platelet derived growth factor tyrosine kinase receptor-alpha encoded by the PDGFR-alpha gene. PDGFR-alpha is also known as CD140a and PDGFR-$\alpha$.

The term "neutralizing" when referring to a targeted binding agent such as an antibody relates to the ability of said agent to eliminate, or significantly reduce, the activity of a target antigen. Accordingly, a "neutralizing" anti-PDGFR-alpha antibody of the invention is capable of eliminating or significantly reducing the activity of PDGFR-alpha. A neutralizing PDGFR-alpha antibody may, for example, act by blocking the binding of ligand to its receptor PDGFR-alpha.

The term "isolated polynucleotide" as used herein shall mean a polynucleotide that has been isolated from its naturally occurring environment. Such polynucleotides may be genomic, cDNA, or synthetic. Isolated polynucleotides preferably are not associated with all or a portion of the polynucleotides they associate with in nature. The isolated polynucleotides may be operably linked to another polynucleotide that it is not linked to in nature. In addition, isolated polynucleotides preferably do not occur in nature as part of a larger sequence.

The term "isolated protein" referred to herein means a protein that has been isolated from its naturally occurring environment. Such proteins may be derived from genomic DNA, cDNA, recombinant DNA, recombinant RNA, or synthetic origin or some combination thereof, which by virtue of its origin, or source of derivation, the "isolated protein" (1) is not associated with proteins found in nature, (2) is free of other proteins from the same source, e.g. free of murine proteins, (3) is expressed by a cell from a different species, or (4) does not occur in nature.

The term "polypeptide" is used herein as a generic term to refer to native protein, fragments, or analogs of a polypeptide sequence. Hence, native protein, fragments, and analogs are species of the polypeptide genus. Preferred polypeptides in accordance with the invention comprise the human heavy chain immunoglobulin molecules and the human kappa light chain immunoglobulin molecules, as well as antibody molecules formed by combinations comprising the heavy chain immunoglobulin molecules with light chain immunoglobulin molecules, such as the kappa or lambda light chain immunoglobulin molecules, and vice versa, as well as fragments and analogs thereof. Preferred polypeptides in accordance with the invention may also comprise solely the human heavy chain immunoglobulin molecules or fragments thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described that are in a relationship permitting them to function in their intended manner. For example, a control sequence "operably linked" to a coding sequence is connected in such a way that expression of the coding sequence is achieved under conditions compatible with the control sequences.

The term "control sequence" as used herein refers to polynucleotide sequences that are necessary either to effect or to affect the expression and processing of coding sequences to which they are connected. The nature of such control sequences differs depending upon the host organism; in prokaryotes, such control sequences generally include promoter, ribosomal binding site, and transcription termination sequence; in eukaryotes, generally, such control sequences may include promoters, enhancers, introns, transcription termination sequences, polyadenylation signal sequences, and 5' and '3 untranslated regions. The term "control sequences" is intended to include, at a minimum, all components whose presence is essential for expression and processing, and can also include additional components whose presence is advantageous, for example, leader sequences and fusion partner sequences.

The term "polynucleotide" as referred to herein means a polymeric form of nucleotides of at least 10 bases in length, either ribonucleotides or deoxynucleotides or a modified form of either type of nucleotide, or RNA-DNA hetero-duplexes. The term includes single and double stranded forms of DNA.

The term "oligonucleotide" referred to herein includes naturally occurring, and modified nucleotides linked together by naturally occurring, and non-naturally occurring linkages. Oligonucleotides are a polynucleotide subset generally comprising a length of 200 bases or fewer. Preferably, oligonucleotides are 10 to 60 bases in length and most preferably 12, 13, 14, 15, 16, 17, 18, 19, or 20 to 40 bases in length. Oligonucleotides are usually single stranded, e.g. for probes; although oligonucleotides may be double stranded, e.g. for use in the construction of a gene mutant. Oligonucleotides can be either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. See e.g., LaPlanche et al. Nucl. Acids Res. 14:9081 (1986); Stec et al. J. Am. Chem. Soc. 106:6077 (1984); Stein et al. Nucl. Acids Res. 16:3209 (1988); Zon et al. Anti-Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990), the disclosures of which are hereby incorporated by reference. An oligonucleotide can include a label for detection, if desired.

The term "selectively hybridize" referred to herein means to detectably and specifically bind. Polynucleotides, oligonucleotides and fragments thereof selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, or antibody fragments and a nucleic acid sequence of interest will be at least 80%, and more typically with preferably increasing homologies of at least 85%, 90%, 95%, 99%, and 100%.

The term "CDR region" or "CDR" is intended to indicate the hypervariable regions of the heavy and light chains of the immunoglobulin as defined by Kabat et al. 1991 (Kabat, E. A. et al. (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

The third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody (Segal et al., PNAS, 71:4298-4302, 1974, Amit et al., Science, 233:747-753, 1986, Chothia et al., J. Mol. Biol., 196:901-917, 1987, Chothia et al., Nature, 342:877-883, 1989, Caton et al., J. Immunol., 144:1965-1968, 1990, Sharon et al., PNAS, 87:4814-4817, 1990, Sharon et al., J. Immunol., 144:4863-4869, 1990, Kabat et al., J. Immunol., 147:1709-1719, 1991).

The term a "set of CDRs" referred to herein comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

Two amino acid sequences are "homologous" if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least about 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. It should be appreciated that there can be differing regions of homology within two orthologous sequences. For example, the functional sites of mouse and human orthologues may have a higher degree of homology than non-functional regions.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence.

In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The term "sequence identity" or "identity" with reference to a sequence means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U, or I) or amino acid residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more preferably at least 99 percent sequence identity, as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland, Mass. (1991)), which is incorporated herein by reference. Stereoisomers (e.g., D-amino acids) of the twenty conventional amino acids, unnatural amino acids such as $\alpha$-, $\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\sigma$-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity. Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99% sequence identity to the antibodies or immunoglobulin molecules described herein. In particular, conservative amino acid replacements are contemplated. Conservative replacements are those that take place within a family of amino acids that have related side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are an aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding function or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the antibodies described herein.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

Variants of the VH and VL domains and CDRs of the present invention, including those for which amino acid sequences are set out herein, and which can be employed in targeting agents and antibodies for PDGFR-alpha can be obtained by means of methods of sequence alteration or mutation and screening for antigen targeting with desired characteristics. Examples of desired characteristics include but are not limited to: increased binding affinity for antigen relative to known antibodies which are specific for the antigen; increased neutralization of an antigen activity relative to known antibodies which are specific for the antigen if the activity is known; specified competitive ability with a known antibody or ligand to the antigen at a specific molar ratio; ability to immunoprecipitate ligand-receptor complex; ability to bind to a specified epitope; linear epitope, e.g. peptide sequence identified using peptide-binding scan, e.g. using peptides screened in linear and/or constrained conformation; conformational epitope, formed by non-continuous residues; ability to modulate a new biological activity of PDGFR-alpha, or downstream molecule; ability to bind and/or neutralize and/or for any other desired property.

The techniques required to make substitutions within amino acid sequences of CDRs, antibody VH or VL domains and antigen binding sites are available in the art. Variants of antibody molecules disclosed herein may be produced and used in the present invention. Following the lead of computational chemistry in applying multivariate data analysis techniques to the structure/property-activity relationships (Wold, et al. Multivariate data analysis in chemistry. Chemometrics—Mathematics and Statistics in Chemistry (Ed.: B. Kowalski), D. Reidel Publishing Company, Dordrecht, Holland, 1984) quantitative activity-property relationships of antibodies can be derived using well-known mathematical techniques, such as statistical regression, pattern recognition and classification (Norman et al. Applied Regression Analysis. Wiley-Interscience; 3rd edition (April 1998); Kandel, Abraham & Backer, Eric. Computer-Assisted Reasoning in Cluster Analysis. Prentice Hall PTR, (May 11, 1995); Krzanowski, Wojtek. Principles of Multivariate Analysis: A User's Perspective (Oxford Statistical Science Series, No 22 (Paper)). Oxford University Press; (December 2000); Witten, Ian H. & Frank, Eibe. Data Mining: Practical Machine Learning Tools and Techniques with Java Implementations. Morgan Kaufmann; (Oct. 11, 1999); Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002); Ghose, Arup K. & Viswanadhan, Vellarkad N. Combinatorial Library Design and Evaluation Principles, Software, Tools, and Applications in Drug Discovery). The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions.

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule using any freely available or commercial package, such as WAM. A protein visualization and analysis software package, such as Insight II (Accelrys, Inc.) or Deep View may then be used to evaluate possible substitutions at each position in the CDR. This information may then be used to make substitutions likely to have a minimal or beneficial effect on activity or confer other desirable properties.

The term "polypeptide fragment" as used herein refers to a polypeptide that has an amino-terminal and/or carboxy-terminal deletion, but where the remaining amino acid sequence is identical to the corresponding positions in the naturally-occurring sequence deduced, for example, from a full-length cDNA sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long. The term "analog" as used herein refers to polypeptides which are comprised of a segment of at least 25 amino acids that has substantial identity to a portion of a deduced amino acid sequence and which has at least one of the following properties: (1) specific binding to a PDGFR-alpha, under suitable binding conditions, (2) ability to inhibit binding of PDGF-AA, (3) ability to inhibit binding of PDGF-AB, (4) ability to inhibit binding of PDGF-BB, and/or (5) ability to inhibit binding of PDGF-CC. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986); Veber and Freidinger TINS p.392 (1985); and Evans et al. J. Med. Chem. 30:1229 (1987), which are incorporated herein by reference. Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH2NH—, —CH2S—, —CH2—CH2-, —CH═CH-(cis and trans), —COCH2-, —CH(OH)CH2-, and —CH2SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference); for example, by adding internal cysteine residues capable of forming intramolecular disulfide bridges which cyclize the peptide.

As used herein, the term “antibody” refers to a polypeptide or group of polypeptides that are comprised of at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one “light” and one “heavy” chain. The variable regions of each light/heavy chain pair form an antibody binding site.

As used herein, a “targeted binding agent” is an agent, e.g. an antibody, or binding fragment thereof, that binds to a target site. In one embodiment, the targeted binding agent is specific for only one target site. In other embodiments, the targeted binding agent is specific for more than one target site. In one embodiment, the targeted binding agent may be a monoclonal antibody and the target site may be an epitope. As described below, a targeted binding agent may comprise at least one antigen binding domain (e.g. a CDR) of an antibody, wherein said domain is fused or contained within a heterologous protein scaffold, e.g. a non-antibody protein scaffold.

“Binding fragments” of an antibody are produced by recombinant DNA techniques, or by enzymatic or chemical cleavage of intact antibodies. Binding fragments include Fab, Fab', F(ab')2, Fv, dAb and single-chain antibodies. An antibody other than a “bispecific” or “bifunctional” antibody is understood to have each of its binding sites identical. An antibody substantially inhibits adhesion of a receptor to a counter-receptor when an excess of antibody reduces the quantity of receptor bound to counter-receptor by at least about 20%, 40%, 60% or 80%, and more usually greater than about 85% (as measured in an in vitro competitive binding assay).

An antibody may be oligoclonal, a polyclonal antibody, a monoclonal antibody, a chimeric antibody, a CDR-grafted antibody, a multi-specific antibody, a bi-specific antibody, a catalytic antibody, a chimeric antibody, a humanized antibody, a fully human antibody, an anti-idiotypic antibody and antibodies that can be labeled in soluble or bound form as well as fragments, variants or derivatives thereof, either alone or in combination with other amino acid sequences provided by known techniques. An antibody may be from any species. The term antibody also includes binding fragments of the antibodies of the invention; exemplary fragments include Fv, Fab, Fab', single stranded antibody (svFC), dimeric variable region (Diabody) and disulphide stabilized variable region (dsFv).

It has been shown that fragments of a whole antibody can perform the function of binding antigens. Examples of binding fragments are (Ward, E. S. et al., (1989) Nature 341, 544-546) the Fab fragment consisting of VL, VH, CL and CH1 domains; (McCafferty et al (1990) Nature, 348, 552-554) the Fd fragment consisting of the VH and CH1 domains; (Holt et al (2003) Trends in Biotechnology 21, 484-490) the Fv fragment consisting of the VL and VH domains of a single antibody; (iv) the dAb fragment (Ward, E. S. et al., Nature 341, 544-546 (1989), McCafferty et al (1990) Nature, 348, 552-554, Holt et al (2003) Trends in Biotechnology 21, 484-490], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, (1988) Science, 242, 423-426, Huston et al, (1988) PNAS USA, 85, 5879-5883); (viii) bispecific single chain Fv dimers (PCT/US92/09965) and (ix) “diabodies”, multivalent or multispecific fragments constructed by gene fusion (WO94/13804; Holliger, P. (1993) et al, Proc. Natl. Acad. Sci. USA 90 6444-6448). Fv, scFv or diabody molecules may be stabilized by the incorporation of disulphide bridges linking the VH and VL domains (Reiter, Y. et al, Nature Biotech, 14, 1239-1245, 1996). Minibodies comprising a scFv joined to a CH3 domain may also be made (Hu, S. et al, (1996) Cancer Res., 56, 3055-3061). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

The term “epitope” includes any protein determinant capable of specific binding to an immunoglobulin or T-cell receptor. Epitopic determinants usually consist of chemically active surface groupings of molecules such as amino acids or sugar side chains and may, but not always, have specific three-dimensional structural characteristics, as well as specific charge characteristics. An antibody is said to specifically bind an antigen when the dissociation constant is ≦1 μM, preferably ≦100 nM and most preferably ≦10 nM.

The term “agent” is used herein to denote a chemical compound, a mixture of chemical compounds, a biological macromolecule, or an extract made from biological materials.

“Active” or “activity” in regard to a PDGFR-alpha polypeptide refers to a portion of a PDGFR-alpha polypeptide that has a biological or an immunological activity of a native PDGFR-alpha polypeptide. “Biological” when used herein refers to a biological function that results from the activity of the native PDGFR-alpha polypeptide. A preferred PDGFR-alpha biological activity includes, for example, autophosphorylation.

“Mammal” when used herein refers to any animal that is considered a mammal. Preferably, the mammal is human.

Digestion of antibodies with the enzyme, papain, results in two identical antigen-binding fragments, known also as “Fab” fragments, and a “Fc” fragment, having no antigen-binding activity but having the ability to crystallize. Digestion of antibodies with the enzyme, pepsin, results in the a F(ab')2 fragment in which the two arms of the antibody molecule remain linked and comprise two-antigen binding sites. The F(ab')2 fragment has the ability to crosslink antigen.

“Fv” when used herein refers to the minimum fragment of an antibody that retains both antigen-recognition and antigen-binding sites.

“Fab” when used herein refers to a fragment of an antibody that comprises the constant domain of the light chain and the CH1 domain of the heavy chain.

A "dAb" is a single domain antibody and comprises either the variable domain of an antibody heavy chain (VH domain) or the variable domain of an antibody light chain (VL domain). Each dAb contains three of the six naturally occurring CDRs (Ward et al., Binding activities of a repertoire of single immunoglobulin variable domains secreted from *Escherichia coli*. Nature 341, 544-546 (1989); Holt, et al., Domain antibodies: protein for therapy, Trends Biotechnol. 21, 484-49 (2003)). With molecular weights ranging from 11 to 15 kDa, they are four times smaller than a fragment antigen binding (Fab)2 and half the size of a single chain Fv (scFv) molecule.

The term "mAb" refers to monoclonal antibody.

"Liposome" when used herein refers to a small vesicle that may be useful for delivery of drugs that may include the PDGFR-alpha polypeptide of the invention or antibodies to such a PDGFR-alpha polypeptide to a mammal.

"Label" or "labeled" as used herein refers to the addition of a detectable moiety to a polypeptide, for example, a radiolabel, fluorescent label, enzymatic label chemiluminescent labeled or a biotinyl group. Radioisotopes or radionuclides may include 3H, 14C, 15N, 35S, 90Y, 99Tc, 111In, 125I, 131I, fluorescent labels may include rhodamine, lanthanide phosphors or FITC and enzymatic labels may include horseradish peroxidase, β-galactosidase, luciferase, alkaline phosphatase.

Additional labels include, by way of illustration and not limitation: enzymes, such as glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase; dyes; additional fluorescent labels or fluorescers include, such as fluorescein and its derivatives, fluorochrome, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Biointernational); chemoluminescent labels or chemiluminescers, such as isoluminol, luminol and the dioxetanes; sensitizers; coenzymes; enzyme substrates; particles, such as latex or carbon particles; metal sol; crystallite; liposomes; cells, etc., which may be further labeled with a dye, catalyst or other detectable group; molecules such as biotin, digoxygenin or 5-bromodeoxyuridine; toxin moieties, such as for example a toxin moiety selected from a group of Pseudomonas exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The term "pharmaceutical agent or drug" as used herein refers to a chemical compound or composition capable of inducing a desired therapeutic effect when properly administered to a patient. Other chemistry terms herein are used according to conventional usage in the art, as exemplified by The McGraw-Hill Dictionary of Chemical Terms (Parker, S., Ed., McGraw-Hill, San Francisco (1985)), (incorporated herein by reference).

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

"Antibody-dependent cell-mediated cytotoxicity" and "ADCC" refer to a cell-mediated reaction in which non-specific cytotoxic cells that express Ig Fc receptors (FcRs) (e.g. Natural Killer (NK) cells, monocytes, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcRs expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. Nos. 5,500,362, or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in an animal model such as that disclosed in Clynes et al. PNAS (USA) 95:652-656 (1988).

"Complement dependent cytotoxicity" and "CDC" refer to the mechanism by which antibodies carry out their cell-killing function. It is initiated by the binding of C1q, a constituent of the first component of complement, to the Fc domain of Igs, IgG or IgM, which are in complex with antigen (Hughs-Jones, N. C., and B. Gardner. 1979. Mol. Immunol. 16:697). C1q is a large, structurally complex glycoprotein of ~410 kDa present in human serum at a concentration of 70 μg/ml (Cooper, N. R. 1985. Adv. Immunol. 37:151). Together with two serine proteases, C1r and C1s, C1q forms the complex C1, the first component of complement. At least two of the N-terminal globular heads of C1q must be bound to the Fc of Igs for C1 activation, hence for initiation of the complement cascade (Cooper, N. R. 1985. Adv. Immunol. 37:151).

"Whole blood assays" use unfractionated blood as a source of natural effectors. Blood contains complement in the plasma, together with FcR-expressing cellular effectors, such as polymorphonuclear cells (PMNs) and mononuclear cells (MNCs). Thus, whole blood assays allow simultaneous evaluation of the synergy of both ADCC and CDC effector mechanisms in vitro.

The term "patient" includes human and veterinary subjects.

The term "and/or" as used herein is to be taken as specific disclosure of each of the two specified features or components with or without the other. For example "A and/or B" is to be taken as specific disclosure of each of (i) A, (ii) B and (iii) A and B, just as if each is set out individually herein.

Antibody Structure

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site.

Thus, an intact antibody has two binding sites. Except in bifunctional or bispecific antibodies, the two binding sites are the same.

The chains all exhibit the same general structure of relatively conserved framework regions (FR) joined by three hyper variable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

A bispecific or bifunctional antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann Clin. Exp. Immunol. 79: 315-321 (1990), Kostelny et al. J. Immunol. 148:1547-1553 (1992). Bispecific antibodies do not exist in the form of fragments having a single binding site (e.g., Fab, Fab', and Fv).

Typically, a VH domain is paired with a VL domain to provide an antibody antigen-binding site, although a VH or VL domain alone may be used to bind antigen. The VH domain (see Table 12) may be paired with the VL domain (see Table 13), so that an antibody antigen-binding site is formed comprising both the VH and VL domains.

Human Antibodies and Humanization of Antibodies

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, fully human antibodies can be generated through the introduction of functional human antibody loci into a rodent, other mammal or animal so that the rodent, other mammal or animal produces fully human antibodies.

One method for generating fully human antibodies is through the use of XenoMouse® strains of mice that have been engineered to contain up to but less than 1000 kb-sized germline configured fragments of the human heavy chain locus and kappa light chain locus. See Mendez et al. Nature Genetics 15:146-156 (1997) and Green and Jakobovits J. Exp. Med. 188:483-495 (1998). The XenoMouse® strains are available from Amgen, Inc. (Fremont, Calif., U.S.A).

Such mice, then, are capable of producing human immunoglobulin molecules and antibodies and are deficient in the production of murine immunoglobulin molecules and antibodies. Technologies utilized for achieving the same are disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. Nature Genetics 15:146-156 (1997), the disclosure of which is hereby incorporated by reference.

The production of the XenoMouse® strains of mice is further discussed and delineated in U.S. patent application Ser. Nos. 07/466,008, filed Jan. 12, 1990, 07/610,515, filed Nov. 8, 1990, 07/919,297, filed Jul. 24, 1992, 07/922,649, filed Jul. 30, 1992, 08/031,801, filed Mar. 15, 1993, 08/112,848, filed Aug. 27, 1993, 08/234,145, filed Apr. 28, 1994, 08/376,279, filed Jan. 20, 1995, 08/430,938, filed Apr. 27, 1995, 08/464,584, filed Jun. 5, 1995, 08/464,582, filed Jun. 5, 1995, 08/463,191, filed Jun. 5, 1995, 08/462,837, filed Jun. 5, 1995, 08/486,853, filed Jun. 5, 1995, 08/486,857, filed Jun. 5, 1995, 08/486,859, filed Jun. 5, 1995, 08/462,513, filed Jun. 5, 1995, 08/724,752, filed Oct. 2, 1996, 08/759,620, filed Dec. 3, 1996, U.S. Publication 2003/0093820, filed Nov. 30, 2001 and U.S. Pat. Nos. 6,162,963, 6,150,584, 6,114,598, 6,075,181, and 5,939,598 and Japanese Patent Nos. 3 068 180 B2, 3 068 506 B2, and 3 068 507 B2. See also European Patent No., EP 0 463 151 B1, grant published Jun. 12, 1996, International Patent Application No., WO 94/02602, published Feb. 3, 1994, International Patent Application No., WO 96/34096, published Oct. 31, 1996, WO 98/24893, published Jun. 11, 1998, WO 00/76310, published Dec. 21, 2000. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. Nos. 5,591,669 and 6,023.010 to Krimpenfort and Berns, U.S. Pat. Nos. 5,612,205, 5,721,367, and 5,789,215 to Berns et al., and U.S. Pat. No. 5,643,763 to Choi and Dunn, and GenPharm International U.S. patent application Ser. Nos. 07/574,748, filed Aug. 29, 1990, 07/575,962, filed Aug. 31, 1990, 07/810,279, filed Dec. 17, 1991, 07/853,408, filed Mar. 18, 1992, 07/904,068, filed Jun. 23, 1992, 07/990,860, filed Dec. 16, 1992, 08/053,131, filed Apr. 26, 1993, 08/096,762, filed Jul. 22, 1993, 08/155,301, filed Nov. 18, 1993, 08/161,739, filed Dec. 3, 1993, 08/165,699, filed Dec. 10, 1993, 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Kirin has also demonstrated the generation of human antibodies from mice in which, through microcell fusion, large pieces of chromosomes, or entire chromosomes, have been introduced. See European Patent Application Nos. 773 288 and 843 961, the disclosures of which are hereby incorporated by reference. Additionally, KMTM—mice, which are the result of cross-breeding of Kirin's Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Human antibodies can also be derived by in vitro methods. Suitable examples include but are not limited to phage display (CAT, Morphosys, Dyax, Biosite/Medarex, Xoma, Symphogen, Alexion (formerly Proliferon), Affimed) ribosome display (CAT), yeast display, and the like.

In another embodiment, the antibodies of the invention the compete with the disclosed antibodies. Competition between antibodies may be assayed easily in vitro, for example using ELISA and/or by tagging a specific reporter molecule to one binding member which can be detected in the presence of one or more other untagged antibodies, to enable identification of antibodies which bind the same epitope or an overlapping epitope. Such methods are readily known to one of ordinary skill in the art, and are described in more detail herein. Thus, a further aspect of the present invention provides an antigen binding site comprising a human antibody antigen-binding site that competes with an antibody molecule, for example especially an antibody molecule comprising a VH and/or VL domain, CDR e.g. HCDR3 or set of CDRs of the parent antibody or any of antibodies disclosed herein that bind to PDGFR-alpha. In one embodiment, the an antibody of the invention competes with 2.175.3, 2.449.1.3 and/or 2.998.2.

Preparation of Antibodies

In general, antibodies produced by the fused hybridomas were human IgG2 or IgG4 heavy chains with fully human kappa or lambda light chains. Antibodies can also be of other human isotypes, including IgG1 heavy chains. The antibodies possessed high affinities, typically possessing a Kd of from about 10-6 through about 10-12 M or below, when measured against cells in FACS-based affinity measurement techniques. The affinity can also be measured by solid phase and solution phase techniques. In one embodiment, the antibodies described herein bind CD PDGFR-alpha 20 with a Kd of less than about 500, 400, 300, 200 or 100 picomolar (pM) and inhibit tumor growth. In some embodiments, the antibodies bind PDGFR-alpha with a Kd of less than about 75, 60, 50, 40, 30, 25, 20, 10, or 5 pM.

As will be appreciated, anti-PDGFR-alpha antibodies can be expressed in cell lines other than hybridoma cell lines. Sequences encoding particular antibodies can be used to transform a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Cell lines of particular preference are selected through determining which cell lines have high expression levels and produce antibodies with constitutive PDGFR-alpha binding properties.

Anti-PDGFR-alpha antibodies are useful in the detection of PDGFR-alpha in patient samples and accordingly are useful as diagnostics for disease states as described herein. In addition, based on their ability to inhibit tumor growth, anti-PDGFR-alpha antibodies have therapeutic effects in treating symptoms and conditions resulting from PDGFR-alpha expression. In specific embodiments, the antibodies and methods herein relate to the treatment of symptoms resulting from PDGFR-alpha induced tumor growth. Further embodiments involve using the antibodies and methods described herein to treat neoplastic diseases, such as cancers including, lung cancer, ovarian cancer, prostate cancer, colon cancer, glioblastoma, melanoma and gastrointestinal stromal tumor (GIST).

Antibody Sequences

Embodiments of the invention include the specific anti-PDGFR-alpha antibodies listed below in Table 1. This table reports the identification number of each anti-PDGFR-alpha antibody, along with the SEQ ID number of variable regions of the corresponding heavy chain and light chain genes.

Each antibody has been given an identification number that includes either two or three numbers separated by one or two decimal points. In some cases, only two identification numbers separated by one decimal point are listed. However, in some cases, several clones of one antibody were prepared. Although the clones have the identical nucleic acid and amino acid sequences as the parent sequence, they may also be listed separately, with the clone number indicated by the number to the right of a second decimal point. Thus, for example, the nucleic acid and amino acid sequences of antibody 2.84 are identical to the sequences of antibody 2.84.1, 2.84.2, and 2.84.3.

TABLE 1

| mAb ID No.: | Sequence | SEQ ID NO: |
|---|---|---|
| 2.175.3 | Nucleotide sequence encoding the variable region of the heavy chain | 1 |
| | Amino acid sequence encoding the variable region of the heavy chain | 2 |
| | Nucleotide sequence encoding the variable region of the light chain | 3 |
| | Amino acid sequence encoding the variable region of the light chain | 4 |
| 2.451.1.1 | Nucleotide sequence encoding the variable region of the heavy chain | 5 |
| | Amino acid sequence encoding the variable region of the heavy chain | 6 |
| | Nucleotide sequence encoding the variable region of the light chain O12/JK5 | 7 |

TABLE 1-continued

| mAb ID No.: | Sequence | SEQ ID NO: |
|---|---|---|
| | Amino acid sequence encoding the variable region of the light chain O12/JK5 | 8 |
| | Nucleotide sequence encoding the variable region of the light chain A20/JK5 | 21 |
| | Amino acid sequence encoding the variable region of the light chain A20/JK5 | 22 |
| 2.449.1.3 | Nucleotide sequence encoding the variable region of the heavy chain | 9 |
| | Amino acid sequence encoding the variable region of the heavy chain | 10 |
| | Nucleotide sequence encoding the variable region of the light chain | 11 |
| | Amino acid sequence encoding the variable region of the light chain | 12 |
| 2.998.2 | Nucleotide sequence encoding the variable region of the heavy chain | 13 |
| | Amino acid sequence encoding the vanable region of the heavy chain | 14 |
| | Nucleotide sequence encoding the variable region of the light chain | 15 |
| | Amino acid sequence encoding the variable region of the light chain | 16 |
| 2.84.3 | Nucleotide sequence encoding the variable region of the heavy chain | 17 |
| | Amino acid sequence encoding the variable region of the heavy chain | 18 |
| | Nucleotide sequence encoding the variable region of the light chain | 19 |
| | Amino acid sequence encoding the variable region of the light chain | 20 |
| 2.1576.1.2 | Nucleotide sequence encoding the variable region of the heavy chain | 23 |
| | Amino acid sequence encoding the variable region of the heavy chain | 24 |
| | Nucleotide sequence encoding the variable region of the light chain | 25 |
| | Amino acid sequence encoding the variable region of the light chain | 26 |
| 3.625.1 | Nucleotide sequence encoding the variable region of the heavy chain | 27 |
| | Amino acid sequence encoding the variable region of the heavy chain | 28 |
| | Nucleotide sequence encoding the variable region of the light chain | 29 |
| | Amino acid sequence encoding the variable region of the light chain | 30 |
| 2.414.2 | Nucleotide sequence encoding the variable region of the heavy chain | 31 |
| | Amino acid sequence encoding the variable region of the heavy chain | 32 |
| | Nucleotide sequence encoding the variable region of the light chain | 33 |
| | Amino acid sequence encoding the variable region of the light chain | 34 |
| 2.542.2 | Nucleotide sequence encoding the variable region of the heavy chain | 35 |
| | Amino acid sequence encoding the variable region of the heavy chain | 36 |
| | Nucleotide sequence encoding the variable region of the light chain | 37 |
| | Amino acid sequence encoding the variable region of the light chain | 38 |
| 2.737.1.4 | Nucleotide sequence encoding the variable region of the heavy chain | 39 |
| | Amino acid sequence encoding the variable region of the heavy chain | 40 |
| | Nucleotide sequence encoding the variable region of the light chain | 41 |
| | Amino acid sequence encoding the variable region of the light chain | 42 |
| 2.1623.2 | Nucleotide sequence encoding the variable region of the heavy chain | 43 |
| | Amino acid sequence encoding the variable region of the heavy chain | 44 |
| | Nucleotide sequence encoding the variable region of the light chain | 45 |
| | Amino acid sequence encoding the variable region of the light chain | 46 |
| 2.1853.3 | Nucleotide sequence encoding the variable region of the heavy chain | 47 |
| | Amino acid sequence encoding the variable region of the heavy chain | 48 |
| | Nucleotide sequence encoding the variable region of the light chain | 49 |
| | Amino acid sequence encoding the variable region of the light chain | 50 |
| 2.1954.2 | Nucleotide sequence encoding the variable region of the heavy chain | 51 |
| | Amino acid sequence encoding the variable region of the heavy chain | 52 |
| | Nucleotide sequence encoding the variable region of the light chain | 53 |
| | Amino acid sequence encoding the variable region of the light chain | 54 |
| 3.23.2 | Nucleotide sequence encoding the variable region of the heavy chain | 55 |
| | Amino acid sequence encoding the variable region of the heavy chain | 56 |
| | Nucleotide sequence encoding the variable region of the light chain | 57 |
| | Amino acid sequence encoding the variable region of the light chain | 58 |
| 3.87.1.1 | Nucleotide sequence encoding the variable region of the heavy chain | 59 |
| | Amino acid sequence encoding the variable region of the heavy chain | 60 |
| | Nucleotide sequence encoding the variable region of the light chain | 61 |
| | Amino acid sequence encoding the variable region of the light chain | 62 |
| 3.341.1 | Nucleotide sequence encoding the variable region of the heavy chain | 63 |
| | Amino acid sequence encoding the variable region of the heavy chain | 64 |
| | Nucleotide sequence encoding the variable region of the light chain | 65 |
| | Amino acid sequence encoding the variable region of the light chain | 66 |
| 3.472.1.1 | Nucleotide sequence encoding the variable region of the heavy chain | 67 |
| | Amino acid sequence encoding the variable region of the heavy chain | 68 |
| | Nucleotide sequence encoding the variable region of the light chain | 69 |
| | Amino acid sequence encoding the variable region of the light chain | 70 |
| 3.805.1.3 | Nucleotide sequence encoding the variable region of the heavy chain | 71 |
| | Amino acid sequence encoding the variable region of the heavy chain | 72 |
| | Nucleotide sequence encoding the variable region of the light chain | 73 |
| | Amino acid sequence encoding the variable region of the light chain | 74 |
| 3.818.4 | Nucleotide sequence encoding the variable region of the heavy chain | 75 |
| | Amino acid sequence encoding the variable region of the heavy chain | 76 |
| | Nucleotide sequence encoding the variable region of the light chain | 77 |
| | Amino acid sequence encoding the variable region of the light chain | 78 |
| 4.16.2 | Nucleotide sequence encoding the variable region of the heavy chain | 79 |
| | Amino acid sequence encoding the variable region of the heavy chain | 80 |

TABLE 1-continued

| mAb ID No.: | Sequence | SEQ ID NO: |
|---|---|---|
| | Nucleotide sequence encoding the variable region of the light chain | 81 |
| | Amino acid sequence encoding the variable region of the light chain | 82 |
| 5.1.1.1 | Nucleotide sequence encoding the variable region of the heavy chain | 83 |
| | Amino acid sequence encoding the variable region of the heavy chain | 84 |
| | Nucleotide sequence encoding the variable region of the light chain | 85 |
| | Amino acid sequence encoding the variable region of the light chain | 86 |
| 5.9.3 | Nucleotide sequence encoding the variable region of the heavy chain | 87 |
| | Amino acid sequence encoding the variable region of the heavy chain | 88 |
| | Nucleotide sequence encoding the variable region of the light chain | 89 |
| | Amino acid sequence encoding the variable region of the light chain | 90 |
| 2.796.2 | Nucleotide sequence encoding the variable region of the heavy chain | 91 |
| | Amino acid sequence encoding the variable region of the heavy chain | 92 |
| | Nucleotide sequence encoding the variable region of the light chain | 93 |
| | Amino acid sequence encoding the variable region of the light chain | 94 |
| 3.7772.2 | Nucleotide sequence encoding the variable region of the heavy chain | 95 |
| | Amino acid sequence encoding the variable region of the heavy chain | 96 |
| | Nucleotide sequence encoding the variable region of the light chain | 97 |
| | Amino acid sequence encoding the variable region of the light chain | 98 |
| 5.16.1 | Nucleotide sequence encoding the variable region of the heavy chain | 99 |
| | Amino acid sequence encoding the variable region of the heavy chain | 100 |
| | Nucleotide sequence encoding the variable region of the light chain | 101 |
| | Amino acid sequence encoding the variable region of the light chain | 102 |
| 2.2002.3 | Nucleotide sequence encoding the variable region of the heavy chain | 103 |
| | Amino acid sequence encoding the variable region of the heavy chain | 104 |
| | Nucleotide sequence encoding the variable region of the light chain | 105 |
| | Amino acid sequence encoding the variable region of the light chain | 106 |
| 2.2071.1.3 | Nucleotide sequence encoding the variable region of the heavy chain | 107 |
| | Amino acid sequence encoding the variable region of the heavy chain | 108 |
| | Nucleotide sequence encoding the variable region of the light chain | 109 |
| | Amino acid sequence encoding the variable region of the light chain | 110 |
| 3.23.3 | Nucleotide sequence encoding the variable region of the heavy chain | 111 |
| | Amino acid sequence encoding the variable region of the heavy chain | 112 |
| | Nucleotide sequence encoding the variable region of the light chain | 113 |
| | Amino acid sequence encoding the variable region of the light chain | 114 |
| 3.457.3.1 | Nucleotide sequence encoding the variable region of the heavy chain | 115 |
| | Amino acid sequence encoding the variable region of the heavy chain | 116 |
| | Nucleotide sequence encoding the variable region of the light chain | 117 |
| | Amino acid sequence encoding the variable region of the light chain | 118 |
| 2.84.1 | Nucleotide sequence encoding the variable region of the heavy chain | 119 |
| | Amino acid sequence encoding the variable region of the heavy chain | 120 |
| | Nucleotide sequence encoding the variable region of the light chain | 121 |
| | Amino acid sequence encoding the variable region of the light chain | 122 |
| 2.351.3 | Nucleotide sequence encoding the variable region of the heavy chain | 123 |
| | Amino acid sequence encoding the variable region of the heavy chain | 124 |
| | Nucleotide sequence encoding the variable region of the light chain | 125 |
| | Amino acid sequence encoding the variable region of the light chain | 126 |

Antibodies, as described herein in the Examples, were prepared through the utilization of the XenoMouse® technology, as described below. Such mice, then, are capable of producing human immunoglobulin molecules and antibodies and are deficient in the production of murine immunoglobulin molecules and antibodies. Technologies utilized for achieving the same are disclosed in the patents, applications, and references disclosed in the background section herein. In particular, however, a preferred embodiment of transgenic production of mice and antibodies therefrom is disclosed in U.S. patent application Ser. No. 08/759,620, filed Dec. 3, 1996 and International Patent Application Nos. WO 98/24893, published Jun. 11, 1998 and WO 00/76310, published Dec. 21, 2000, the disclosures of which are hereby incorporated by reference. See also Mendez et al. Nature Genetics 15:146-156 (1997), the disclosure of which is hereby incorporated by reference.

Through the use of such technology, fully human monoclonal antibodies to a variety of antigens have been produced. Essentially, XenoMouse® lines of mice are immunized with an antigen of interest (e.g. PDGFR-alpha), lymphatic cells (such as B-cells) are recovered from the hyper-immunized mice, and the recovered lymphocytes are fused with a myeloid-type cell line to prepare immortal hybridoma cell lines. These hybridoma cell lines are screened and selected to identify hybridoma cell lines that produced antibodies specific to the antigen of interest. Provided herein are methods for the production of multiple hybridoma cell lines that produce antibodies specific to PDGFR-alpha. Further, provided herein are characterization of the antibodies produced by such cell lines, including nucleotide and amino acid sequence analyses of the heavy and light chains of such antibodies.

Alternatively, instead of being fused to myeloma cells to generate hybridomas, B cells can be directly assayed. For example, CD19+ B cells can be isolated from hyperimmune XenoMouse® mice and allowed to proliferate and differentiate into antibody-secreting plasma cells. Antibodies from the cell supernatants are then screened by ELISA for reactivity against the PDGFR-alpha immunogen. The supernatants might also be screened for immunoreactivity against fragments of PDGFR-alpha to further map the different antibodies for binding to domains of functional interest on PDGFR-alpha. The antibodies may also be screened other related human receptors and against the rat, the mouse, and non-human primate, such as Cynomolgus monkey, orthologues of PDGFR-alpha, the last to determine species cross-reactivity. B cells from wells containing antibodies of interest may be immortalized by various methods including fusion to make hybridomas either from individual or from pooled wells, or by infection with EBV or transfection by known immortalizing genes and then plating in suitable medium. Alternatively, single plasma cells secreting antibodies with the desired specificities are then isolated using a PDGFR-alpha-specific hemolytic plaque assay (see for example Babcook et al., Proc. Natl. Acad. Sci. USA 93:7843-48 (1996)). Cells targeted for lysis are preferably sheep red blood cells (SRBCs) coated with the PDGFR-alpha antigen.

In the presence of a B-cell culture containing plasma cells secreting the immunoglobulin of interest and complement, the formation of a plaque indicates specific PDGFR-alpha-mediated lysis of the sheep red blood cells surrounding the plasma cell of interest. The single antigen-specific plasma cell in the center of the plaque can be isolated and the genetic information that encodes the specificity of the antibody is isolated from the single plasma cell. Using reverse-transcription followed by PCR (RT-PCR), the DNA encoding the heavy and light chain variable regions of the antibody can be cloned. Such cloned DNA can then be further inserted into a suitable expression vector, preferably a vector cassette such as a pcDNA, more preferably such a pcDNA vector containing the constant domains of immunoglobulin heavy and light chain. The generated vector can then be transfected into host cells, e.g., HEK293 cells, CHO cells, and cultured in conventional nutrient media modified as appropriate for inducing transcription, selecting transformants, or amplifying the genes encoding the desired sequences.

Anti-PDGFR-alpha antibodies can have therapeutic effects in treating symptoms and conditions related to PDGFR-alpha expression. For example, the antibodies can inhibit growth of cells expressing PDGFR-alpha, thereby inhibiting tumor growth, or the antibodies can be associated with an agent and deliver a lethal toxin to a targeted cell. Anti-PDGFR-alpha antibodies can have therapeutic effects in treating fibrotic diseases, such as cardiac, lung, liver, kidney or skin fibrosis. Anti-PDGFR-alpha antibodies can also have therapeutic effects in the treatment of allograft vasculopathy or restenosis. In addition, the anti-PDGFR-alpha antibodies are useful as diagnostics for the disease states, especially neoplastic, fibrotic and immune system diseases.

If desired, the isotype of an anti-PDGFR-alpha antibody can be switched, for example to take advantage of a biological property of a different isotype. For example, in some circumstances it can be desirable in connection with the generation of antibodies as therapeutic antibodies against PDGFR-alpha that the antibodies be capable of fixing complement and participating in complement-dependent cytotoxicity (CDC). There are a number of isotypes of antibodies that are capable of the same, including, without limitation, the following: murine IgM, murine IgG2a, murine IgG2b, murine IgG3, human IgM, human IgA, human IgG1, and human IgG3. In other embodiments it can be desirable in connection with the generation of antibodies as therapeutic antibodies against PDGFR-alpha that the antibodies be capable of binding Fc receptors on effector cells and participating in antibody-dependent cytotoxicity (ADCC). There are a number of isotypes of antibodies that are capable of the same, including, without limitation, the following: murine IgG2a, murine IgG2b, murine IgG3, human IgG1, and human IgG3. It will be appreciated that antibodies that are generated need not initially possess such an isotype but, rather, the antibody as generated can possess any isotype and the antibody can be isotype switched thereafter using conventional techniques that are well known in the art. Such techniques include the use of direct recombinant techniques (see e.g., U.S. Pat. No. 4,816,397), cell-cell fusion techniques (see e.g., U.S. Pat. Nos. 5,916,771 and 6,207,418), among others.

By way of example, the anti-PDGFR-alpha antibodies discussed herein are fully human antibodies. If an antibody possessed desired binding to PDGFR-alpha, it could be readily isotype switched to generate a human IgM, human IgG1, or human IgG3 isotype, while still possessing the same variable region (which defines the antibody's specificity and some of its affinity). Such molecule would then be capable of fixing complement and participating in CDC and/or be capable of binding to Fc receptors on effector cells and participating in ADCC.

In the cell-cell fusion technique, a myeloma, CHO cell or other cell line is prepared that possesses a heavy chain with any desired isotype and another myeloma, CHO cell or other cell line is prepared that possesses the light chain. Such cells can, thereafter, be fused and a cell line expressing an intact antibody can be isolated.

Accordingly, as antibody candidates are generated that meet desired "structural" attributes as discussed above, they can generally be provided with at least certain of the desired "functional" attributes through isotype switching.

Therapeutic Administration and Formulations

Embodiments of the invention include sterile pharmaceutical formulations of anti-PDGFR-alpha antibodies that are useful as treatments for diseases. Such formulations would inhibit cell growth, thereby effectively treating pathological conditions where, for example, PDGFR-alpha expression is abnormally elevated or PDGFR-alpha expressing cells mediate disease states. Anti-PDGFR-alpha antibodies preferably possess adequate affinity to specifically bind PDGFR-alpha, and preferably have an adequate duration of action to allow for infrequent dosing in humans. A prolonged duration of action will allow for less frequent and more convenient dosing schedules by alternate parenteral routes such as subcutaneous or intramuscular injection.

Sterile formulations can be created, for example, by filtration through sterile filtration membranes, prior to or following lyophilization and reconstitution of the antibody. The antibody ordinarily will be stored in lyophilized form or in solution. Therapeutic antibody compositions generally are placed into a container having a sterile access port, for example, an intravenous solution bag or vial having an adapter that allows retrieval of the formulation, such as a stopper pierceable by a hypodermic injection needle.

The route of antibody administration is in accord with known methods, e.g., injection or infusion by intravenous, intraperitoneal, intracerebral, intramuscular, intraocular, intraarterial, intrathecal, inhalation or intralesional routes, or by sustained release systems as noted below. The antibody is preferably administered continuously by infusion or by bolus injection.

An effective amount of antibody to be employed therapeutically will depend, for example, upon the therapeutic objectives, the route of administration, and the condition of the patient. Accordingly, it is preferred that the therapist titer the dosage and modify the route of administration as required to obtain the optimal therapeutic effect. Typically, the clinician will administer antibody until a dosage is reached that achieves the desired effect. The progress of this therapy is easily monitored by conventional assays or by the assays described herein.

Antibodies, as described herein, can be prepared in a mixture with a pharmaceutically acceptable carrier. This therapeutic composition can be administered intravenously or through the nose or lung, preferably as a liquid or powder aerosol (lyophilized). The composition can also be administered parenterally or subcutaneously as desired. When administered systemically, the therapeutic composition should be sterile, pyrogen-free and in a parenterally acceptable solution having due regard for pH, isotonicity, and stability. These conditions are known to those skilled in the art. Briefly, dosage formulations of the compounds described herein are prepared for storage or administration by mixing the compound having the desired degree of purity with physiologically acceptable carriers, excipients, or stabilizers. Such materials are non-toxic to the recipients at the dosages and concentrations employed, and include buffers such as TRIS HCl, phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium and/or nonionic surfactants such as TWEEN, PLURONICS or polyethyleneglycol. To set up animal xenograft studies, mouse cross-reactivity was determined using FACS analysis performed with NIH3T3 cells, a murine fibroblast line which expresses endogenous PDGFRa. NIH3T3 cells were incubated at 0.5x106 cells/ml with 10 ug/ml of test antibodies on ice for 1 h, rinsed and then resuspended in PBS with 5 ug/ml of goat-anti-human IgG antibodies labeled with Cy5. Cells were rinsed and analyzed by FACS for the presence of Cy5. Only 3 of the tested monoclonal antibodies exhibited mouse cross-reactivity. Results are summarized in Table 5.

Sterile compositions for injection can be formulated according to conventional pharmaceutical practice as described in Remington: The Science and Practice of Pharmacy (20th ed, Lippincott Williams & Wilkens Publishers (2003)). For example, dissolution or suspension of the active compound in a vehicle such as water or naturally occurring vegetable oil like sesame, peanut, or cottonseed oil or a synthetic fatty vehicle like ethyl oleate or the like can be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, films or microcapsules. Examples of sustained-release matrices include polyesters, hydrogels (e.g., poly(2-hydroxyethyl-methacrylate) as described by Langer et al., J. Biomed Mater. Res., (1981) 15:167-277 and Langer, Chem. Tech., (1982) 12:98-105, or poly(vinylalcohol)), polylactides (U.S. Pat. No. 3,773,919, EP 58,481), copolymers of L-glutamic acid and gamma ethyl-L-glutamate (Sidman et al., Biopolymers, (1983) 22:547-556), non-degradable ethylene-vinyl acetate (Langer et al., supra), degradable lactic acid-glycolic acid copolymers such as the LUPRON Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they can denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through disulfide interchange, stabilization can be achieved by modifying sulfhydryl residues, lyophilizing from acidic solutions, controlling moisture content, using appropriate additives, and developing specific polymer matrix compositions.

Sustained-released compositions also include preparations of crystals of the antibody suspended in suitable formulations capable of maintaining crystals in suspension. These preparations when injected subcutaneously or intraperitonealy can produce a sustained release effect. Other compositions also include liposomally entrapped antibodies. Liposomes containing such antibodies are prepared by methods known per se: U.S. Pat. No. DE 3,218,121; Epstein et al., Proc. Natl. Acad. Sci. USA, (1985) 82:3688-3692; Hwang et al., Proc. Natl. Acad. Sci. USA, (1980) 77:4030-4034; EP 52,322; EP 36,676; EP 88,046; EP 143,949; 142,641; Japanese patent application 83-118008; U.S. Pat. Nos. 4,485,045 and 4,544,545; and EP 102,324.

The dosage of the antibody formulation for a given patient will be determined by the attending physician taking into consideration various factors known to modify the action of drugs including severity and type of disease, body weight, sex, diet, time and route of administration, other medications and other relevant clinical factors. Therapeutically effective dosages can be determined by either in vitro or in vivo methods.

An effective amount of the antibodies, described herein, to be employed therapeutically will depend, for example, upon the therapeutic objectives, the route of administration, and the condition of the patient. Accordingly, it is preferred for the therapist to titer the dosage and modify the route of administration as required to obtain the optimal therapeutic effect. A typical daily dosage might range from about 0.001 mg/kg to up to 100 mg/kg or more, depending on the factors mentioned above. Typically, the clinician will administer the therapeutic antibody until a dosage is reached that achieves the desired effect. The progress of this therapy is easily monitored by conventional assays or as described herein.

It will be appreciated that administration of therapeutic entities in accordance with the compositions and methods herein will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures can be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol. Pharmacol. 32 (2): 210-8 (2000), Wang W. "Lyophilization and development of solid protein pharmaceuticals." Int. J. Pharm. 203 (1-2):1-60 (2000), Charman W N "Lipids, lipophilic drugs, and oral drug delivery-some emerging concepts." J Pharm Sci 0.89 (8):967-

78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Design and Generation of Other Therapeutics

In accordance with the present invention and based on the activity of the antibodies that are produced and characterized herein with respect to PDGFR-alpha, the design of other therapeutic modalities is facilitated and disclosed to one of skill in the art. Such modalities include, without limitation, advanced antibody therapeutics, such as bispecific antibodies, immunotoxins, radiolabeled therapeutics, and single antibody V domains, antibody-like binding agent based on other than V region scaffolds, generation of peptide therapeutics, gene therapies, particularly intrabodies, antisense therapeutics, and small molecules.

An antigen binding site may be provided by means of arrangement of CDRs on non-antibody protein scaffolds, such as fibronectin or cytochrome B etc. (Haan & Maggos (2004) BioCentury, 12 (5): A1-A6; Koide et al. (1998) Journal of Molecular Biology, 284: 1141-1151; Nygren et al. (1997) Current Opinion in Structural Biology, 7: 463-469) or by randomising or mutating amino acid residues of a loop within a protein scaffold to confer binding specificity for a desired target. Scaffolds for engineering novel binding sites in proteins have been reviewed in detail by Nygren et al. (Nygren et al. (1997) Current Opinion in Structural Biology, 7: 463-469). Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 (Wess, L. In: BioCentury, The Bernstein Report on BioBusiness, 12 (42), A1-A7, 2004). Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from S. aureus, transferrin, albumin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a targeted binding agent according to the present invention may comprise other amino acids, e.g. forming a peptide or polypeptide, such as a folded domain, or to impart to the molecule another functional characteristic in addition to ability to bind antigen. Targeted binding agents of the invention may carry a detectable label, or may be conjugated to a toxin or a targeting moiety or enzyme (e.g. via a peptidyl bond or linker). For example, a targeted binding agent may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

In connection with the generation of advanced antibody therapeutics, where complement fixation is a desirable attribute, it can be possible to sidestep the dependence on complement for cell killing through the use of bispecifics, immunotoxins, or radiolabels, for example.

For example, bispecific antibodies can be generated that comprise (i) two antibodies, one with a specificity to PDGFR-alpha and another to a second molecule, that are conjugated together, (ii) a single antibody that has one chain specific to PDGFR-alpha and a second chain specific to a second molecule, or (iii) a single chain antibody that has specificity to both PDGFR-alpha and the other molecule. Such bispecific antibodies can be generated using techniques that are well known; for example, in connection with (i) and (ii) see e.g., Fanger et al. Immunol Methods 4:72-81 (1994) and Wright and Harris, supra. and in connection with (iii) see e.g., Traunecker et al. Int. J. Cancer (Suppl.) 7:51-52 (1992). In each case, the second specificity can be made as desired. For example, the second specificity can be made to the heavy chain activation receptors, including, without limitation, CD16 or CD64 (see e.g., Deo et al. 18:127 (1997)) or CD89 (see e.g., Valerius et al. Blood 90:4485-4492 (1997)).

Antibodies can also be modified to act as immunotoxins utilizing techniques that are well known in the art. See e.g., Vitetta Immunol Today 14:252 (1993). See also U.S. Pat. No. 5,194,594. In connection with the preparation of radiolabeled antibodies, such modified antibodies can also be readily prepared utilizing techniques that are well known in the art. See e.g., Junghans et al. in Cancer Chemotherapy and Biotherapy 655-686 (2d edition, Chafner and Longo, eds., Lippincott Raven (1996)). See also U.S. Pat. Nos. 4,681,581, 4,735,210, 5,101,827, 5,102,990 (RE 35,500), 5,648,471, and 5,697,902. Each of immunotoxins and radiolabeled molecules would be likely to kill cells expressing the desired multimeric enzyme subunit oligomerization domain. In some embodiments, a pharmaceutical composition comprising an effective amount of the antibody in association with a pharmaceutically acceptable carrier or diluent is provided.

In some embodiments, an anti-PDGFR-alpha antibody is linked to an agent (e.g., radioisotope, pharmaceutical composition, or a toxin). Preferably, such antibodies can be used for the treatment of diseases, such diseases can relate cells expressing PDGFR-alpha or cells overexpressing PDGFR-alpha. For example, it is contemplated that the drug possesses the pharmaceutical property selected from the group of antimitotic, alkylating, antimetabolite, antiangiogenic, apoptotic, alkaloid, COX-2, and antibiotic agents and combinations thereof. The drug can be selected from the group of nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antimetabolites, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, oxaliplatin, doxorubicins and their analogs, and a combination thereof.

Examples of toxins further include gelonin, Pseudomonas exotoxin (PE), PE40, PE38, diphtheria toxin, ricin, ricin, abrin, alpha toxin, saporin, ribonuclease (RNase), DNase I, Staphylococcal enterotoxin-A, pokeweed antiviral protein, gelonin, Pseudomonas endotoxin, as well as derivatives, combinations and modifications thereof.

Examples of radioisotopes include gamma-emitters, positron-emitters, and x-ray emitters that can be used for localization and/or therapy, and beta-emitters and alpha-emitters that can be used for therapy. The radioisotopes described previously as useful for diagnostics, prognostics and staging are also useful for therapeutics. Non-limiting examples of anti-cancer or anti-leukemia agents include anthracyclines such as doxorubicin (adriamycin), daunorubicin (daunomycin), idarubicin, detorubicin, caminomycin, epirubicin, esorubicin, and morpholino and substituted derivatives, combinations and modifications thereof. Exemplary pharmaceutical agents include cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide, and bleomycin, and derivatives, combinations and modifications thereof. Preferably, the anti-cancer or anti-leukemia is doxorubicin, morpholinodoxorubicin, or morpholinodaunorubicin.

The antibodies of the invention also encompass antibodies that have half-lives (e.g., serum half-lives) in a mammal, preferably a human, of greater than that of an unmodified antibody. In one embodiment, said antibody half life is greater than about 15 days, greater than about 20 days, greater than about 25 days, greater than about 30 days, greater than about 35 days, greater than about 40 days, greater than about 45 days, greater than about 2 months, greater than about 3 months, greater than about 4 months, or greater than about 5 months. The increased half-lives of the antibodies of the present invention or fragments thereof in a mammal, preferably a human, result in a higher serum titer of said antibodies or antibody fragments in the mammal, and thus, reduce the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., International Publication Nos. WO 97/34631 and WO 02/060919, which are incorporated herein by reference in their entireties). Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

As will be appreciated by one of skill in the art, in the above embodiments, while affinity values can be important, other factors can be as important or more so, depending upon the particular function of the antibody. For example, for an immunotoxin (toxin associated with an antibody), the act of binding of the antibody to the target can be useful; however, in some embodiments, it is the internalization of the toxin into the cell that is the desired end result. As such, antibodies with a high percent internalization can be desirable in these situations. Thus, in one embodiment, antibodies with a high efficiency in internalization are contemplated. A high efficiency of internalization can be measured as a percent internalized antibody, and can be from a low value to 100%. For example, in varying embodiments, 0.1-5, 5-10, 10-20, 20-30, 30-40, 40-45, 45-50, 50-60, 60-70, 70-80, 80-90, 90-99, and 99-100% can be a high efficiency. As will be appreciated by one of skill in the art, the desirable efficiency can be different in different embodiments, depending upon, for example, the associated agent, the amount of antibody that can be administered to an area, the side effects of the antibody-agent complex, the type (e.g., cancer type) and severity of the problem to be treated.

In other embodiments, the antibodies disclosed herein provide an assay kit for the detection of PDGFR-alpha expression in mammalian tissues or cells in order to screen for a disease or disorder associated with changes in expression of PDGFR-alpha. The kit comprises an antibody that binds PDGFR-alpha and means for indicating the reaction of the antibody with the antigen, if present.

In some embodiments, an article of manufacture is provided comprising a container, comprising a composition containing an anti-PDGFR-alpha antibody, and a package insert or label indicating that the composition can be used to treat disease mediated by PDGFR-alpha expression. Preferably a mammal and, more preferably, a human, receives the anti-PDGFR-alpha antibody.

Combinations

The anti-neoplastic treatment defined herein may be applied as a sole therapy or may involve, in addition to the compounds of the invention, conventional surgery, bone marrow and peripheral stem cell transplantations or radiotherapy or chemotherapy. Such chemotherapy may include one or more of the following categories of anti tumor agents:

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents (for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341) and N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661), and metalloproteinase inhibitors like marimastat, inhibitors of urokinase plasminogen activator receptor function or, inhibitors of cathepsins, inhibitors of serine proteases for example matriptase, hepsin, urokinase, inhibitors of heparanase);

(iv) cytotoxic agents such as fludarabine, 2-chlorodeoxyadenosine, chlorambucil or doxorubicin and combination thereof such as Fludarabine+cyclophosphamide, CVP: cyclophosphamide+vincristine+prednisone, ACVBP: doxorubicin+cyclophosphamide+vindesine+bleomycin+prednisone, CHOP: cyclophosphamide+doxorubicin+vincristine+prednisone, CNOP: cyclophosphamide+mitoxantrone+vincristine+prednisone, m-BACOD: methotrexate+bleomycin+doxorubicin+cyclophosphamide+vincristine+dexamethasone+leucovorin, MACOP-B: methotrexate+doxorubicin+cyclophosphamide+vincristine+prednisone fixed dose+bleomycin+leucovorin, or ProMACE CytaBOM: prednisone+doxorubicin+cyclophosphamide+etoposide+cytarabine+bleomycin+vincristine+methotrexate+leucovorin.

(v) inhibitors of growth factor function, for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy) quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib, inhibitors of the hepatocyte growth factor family, inhibitors of the platelet-derived growth factor family such as imatinib, inhibitors of serine/threonine kinases (for example Ras/Raf signalling inhibitors such as farnesyl transferase inhibitors, for example sorafenib (BAY 43-9006)), inhibitors of cell signalling through MEK and/or AKT kinases, inhibitors of the hepatocyte growth factor family, c-kit inhibitors, abl kinase inhibitors, IGF receptor (insulin-like growth factor) kinase inhibitors, aurora kinase inhibitors (for example AZD1152, PH739358, VX-680, MLN8054, R763, MP235, MP529, VX-528 and AX39459), cyclin dependent kinase inhibitors such as CDK2 and/or CDK4 inhibitors, and inhibitors of survival signaling proteins such as Bcl-2, Bcl-XL for example ABT-737;

(vi) antiangiogenic agents such as those which inhibit the effects of vascular endothelial growth factor, [for example the anti-vascular endothelial cell growth factor antibody bevacizumab (Avastin™) and VEGF receptor tyrosine kinase inhibitors such as 4-(4-bromo-2-fluoroanilino)-6-methoxy-7-(1-methylpiperidin-4-ylmethoxy)quinazoline (ZD6474; Example 2 within WO 01/32651), 4-(4-fluoro-2-methylindol-5-yloxy)-6-methoxy-7-(3-pyrrolidin-1-ylpropoxy)quinazoline (AZD2171; Example 240 within WO 00/47212), vatalanib (PTK787; WO 98/35985) and SU11248 (sunitinib; WO 01/60814), compounds such as those disclosed in International Patent Applications WO97/22596, WO 97/30035, WO 97/32856, WO 98/13354, WO00/47212 and WO01/32651 and compounds that work by other mechanisms (for example linomide, inhibitors of integrin αvβ3 function and angiostatin)] or colony stimulating factor 1 (CSF1) or CSF1 receptor;

(vii) vascular damaging agents such as Combretastatin A4 and compounds disclosed in International Patent Applications WO 99/02166, WO 00/40529, WO 00/41669, WO 01/92224, WO 02/04434 and WO 02/08213;

(viii) antisense therapies, for example those which are directed to the targets listed above, such as G-3139 (Genasense), an anti bcl2 antisense;

(ix) gene therapy approaches, including for example approaches to replace aberrant genes such as aberrant p53 or aberrant BRCA1 or BRCA2, GDEPT (gene directed enzyme pro drug therapy) approaches such as those using cytosine deaminase, thymidine kinase or a bacterial nitroreductase enzyme and approaches to increase patient tolerance to chemotherapy or radiotherapy such as multi drug resistance gene therapy; and (x) immunotherapy approaches, including for example treatment with Alemtuzumab (campath-1H™), a monoclonal antibody directed at CD52, or treatment with antibodies directed at CD22, ex vivo and in vivo approaches to increase the immunogenicity of patient tumour cells, transfection with cytokines such as interleukin 2, interleukin 4 or granulocyte macrophage colony stimulating factor, approaches to decrease T cell anergy such as treatment with monoclonal antibodies inhibiting CTLA-4 function, approaches using transfected immune cells such as cytokine transfected dendritic cells, approaches using cytokine transfected tumour cell lines and approaches using anti idiotypic antibodies.

(xi) inhibitors of protein degradation such as proteasome inhibitor such as Velcade (bortezomid).

(xii) biotherapeutic therapeutic approaches for example those which use peptides or proteins (such as antibodies or soluble external receptor domain constructions) which either sequester receptor ligands, block ligand binding to receptor or decrease receptor signalling (e.g. due to enhanced receptor degradation or lowered expression levels).

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

In one embodiment of the invention the anti-neoplastic treatments of the invention are combined with agents which inhibit the effects of vascular endothelial growth factor (VEGF), (for example the anti-vascular endothelial cell growth factor antibody bevacizumab (Avastin®), anti-vascular endothelial growth factor receptor antibodies such anti-KDR antibodies and anti-flt1 antibodies, compounds such as those disclosed in International Patent Applications WO 97/22596, WO 97/30035, WO 97/3285, WO 98/13354, WO00/47212 and WO01/32651) and compounds that work by other mechanisms (for example linomide, inhibitors of integrin avb3 function and angiostatin); In another embodiment of the invention the anti-angiogenic treatments of the invention are combined agents which inhibit the tyrosine kinase activity of the vascular endothelial growth factor receptor, KDR (for example AZD2171 or AZD6474). Additional details on AZD2171 may be found in Wedge et al (2005) Cancer Research. 65 (10):4389-400. Additional details on AZD6474 may be found in Ryan & Wedge (2005) British Journal of Cancer. 92 Suppl 1:S6-13. Both publications are herein incorporated by reference in their entireties. In another embodiment of the invention, the fully human antibodies 1.1.2, 1.5.3, 2.1.2 are combined alone or in combination with Avastin™, AZD2171 or AZD6474.

Such conjoint treatment may be achieved by way of the simultaneous, sequential or separate dosing of the individual components of the treatment. Such combination products employ the compounds of this invention, or pharmaceutically acceptable salts thereof, within the dosage range described hereinbefore and the other pharmaceutically active agent within its approved dosage range.

EXAMPLES

The following examples, including the experiments conducted and results achieved are provided for illustrative purposes only and are not to be construed as limiting upon the teachings herein.

Example 1

Immunization and Titering

Immunogen

Recombinant soluble PDGFR-alpha extracellular domain was obtained from R&D Systems (Minneapolis, Minn. Catalog #: 322-PR/CF) and used as an immunogen. In addition, recombinant human PDGFR-alpha expressed in BHK (baby hamster kidney) cells was used as an antigen for immunization. The BHK cells were obtained from the American Type Tissue Collection, catalog no. CCL-10.

Immunization

Monoclonal antibodies against PDGFR-alpha were developed by sequentially immunizing XenoMouse® mice (XenoMouse strains: XMG2 (IgG2 kappa) and XM3C-1 (IgG4 kappa) Amgen, Inc. Fremont, Calif.) with the extracellular domain of PDGFR-alpha (R&D Systems, Catalog #: 322-PR/CF). XenoMouse animals were immunized via footpad route for all injections by conventional means. The total volume of each injection was 50 μl per mouse containing 10 micrograms of PDGFR-alpha extracellular domain, 25 μl per footpad. Adjuvants included Titermax GoldTM (Sigma, cat. T2684), aluminum phosphate gel adjuvant, HCL Biosector (cat 1452-250) and ImmuneEasy mouse adjuvant (qCpG, Qiagen cat. No 303105). The first injection was administered with Titermax GoldTM (Day 0). Boosts were administered as 5 ul of aluminum phosphate gel adjuvant (5 ul) and qCpG (15 ul) along with 10 ug of PDGFRalpha extracellular domain on days 3, 6, 10, 13, 20, 24, 27, 31 and 34.

Example 2

Recovery of Lymphocytes, B-Cell Isolations, Fusions and Generation of Hybridomas Immunized mice were sacrificed by cervical dislocation and the draining lymph nodes were harvested and pooled from each cohort. The lymphoid cells were dissociated by grinding in DMEM to release the cells from the tissues, and the cells were suspended in DMEM. The cells were counted, and 0.9 ml DMEM per 100 million lymphocytes was added to the cell pellet to resuspend the cells gently but completely. Using 100 μl of CD90+ magnetic beads per 100 million cells, the cells were labeled by incubating the cells with the magnetic beads at 4° C. for 15 minutes. The magnetically-labeled cell suspension containing up to 108 positive cells (or up to 2×109 total cells) was loaded onto an LS+ column and the column washed with DMEM. The total effluent was collected as the CD90-negative fraction (most of these cells were expected to be B cells).

A fusion was performed by mixing washed enriched B cells from above and nonsecretory myeloma P3×63Ag8.653 cells purchased from ATCC (cat. no. CRL 1580) (Kearney et al, J. Immunol. 123, 1979, 1548-1550) at a ratio of 1:1. The cell mixture was gently pelleted by centrifugation at 800×g. After complete removal of the supernatant, the cells were treated with 2-4 mL of Pronase solution (CalBiochem, cat. #53702; 0.5 mg/mL in PBS) for no more than 2 minutes. Then 3-5 ml of FBS was added to stop the enzyme activity and the suspension was adjusted to 40 mL total volume using electro cell fusion solution, ECFS (0.3 M Sucrose, Sigma, Cat# S7903, 0.1 mM Magnesium Acetate, Sigma, Cat# M2545, 0.1 mM Calcium Acetate, Sigma, Cat# C4705). The supernatant was removed after centrifugation and the cells were resuspended in 40 mL ECFS. This wash step was repeated and the cells again were resuspended in ECFS to a concentration of 2×106 cells/mL.

Electro-cell fusion was performed using a fusion generator, model ECM2001, Genetronic, Inc., San Diego, Calif. The fusion chamber size used was 2.0 mL, using the following instrument settings: Alignment condition: voltage: 50 V, time: 50 seconds; membrane breaking at: voltage: 3000 V, time: 30 μseconds; post-fusion holding time: 3 seconds.

After ECF, the cell suspensions were carefully removed from the fusion chamber under sterile conditions and transferred into a sterile tube containing the same volume of Hybridoma Culture Medium (DMEM (JRH Biosciences), 15% FBS (Hyclone), supplemented with L-glutamine, pen/strep, OPI (oxaloacetate, pyruvate, bovine insulin) (all from Sigma) and IL-6 (Boehringer Mannheim). The cells were incubated for 15-30 minutes at 37° C., and then centrifuged at 400×g (1000 rpm) for five minutes. The cells were gently resuspended in a small volume of Hybridoma Selection Medium (Hybridoma Culture Medium supplemented with 0.5×HA (Sigma, cat. # A9666)), and the volume was adjusted appropriately with more Hybridoma Selection Medium, based on a final plating of 5×106 B cells total per 96-well plate and 200 μL per well. The cells were mixed gently and pipetted into 96-well plates and allowed to grow. On day 7 or 10, one-half the medium was removed, and the cells were re-fed with Hybridoma Selection Medium.

ELISA Screening

For ELISA analysis, recombinant human PDGFR-alpha (R&D systems, cat#322-PR/CF), at a concentration of 4 ug/ml, was used as a capture reagent. ELISA plates were coated with recombinant human PDGFR-alpha in a volume of 50 µl/well in antigen coating buffer (0.1 M Carbonate Buffer, pH 9.6 $NaHCO_3$ (MW 84) 8.4 g/L) and incubated overnight at 4° C. The following day, the ELISA plate was washed 3 times with washing buffer (0.05% Tween 20 in 1×PBS) and subsequently blocked with 200 µl/well of blocking buffer (1% BSA, 0.1% Tween 20, 0.01% Thimerosal in 1×PBS) for 1 hour at room temperature. Upon completion of the blocking step, 50 µl/well of hybridoma supernatant was incubated at room temperature for 2 hours. After incubation, the ELISA plate was washed 3 times in washing buffer. Following the wash step, 50 µl/well of detection antibody was added to the wells and incubated at room temperature for 1 hour. The ELISA plate was subsequently washed 3 times with washing buffer and TMB substrate was added (50 µl/well). Following the addition of the stop solution (50 µl/well), the ELISA plate was read at 650 nm with an ELISA plate reader. The supernatants deemed positive by ELISA were subsequently evaluated by FMAT and FACS.

Example 3

Selection of Candidate Antibodies by FMAT and FACs

After 14 days of culture, hybridoma supernatants were screened for PDGFR-alpha-specific monoclonal antibodies by Fluorometric Microvolume Assay Technology (FMAT) by screening against either the human osteosarcoma MG-63 cell line or recombinant HEK293 cells that were transfected with human PDGFR-alpha and counter-screening against parental HEK293 cells.

The culture supernatants from the positive hybridoma cells growth wells based on the primary screen were removed and the PDGFR-alpha positive hybridoma cells were suspended with fresh hybridoma culture medium and were transferred to 24-well plates. After two days in culture, these supernatants were ready for a secondary confirmation screen. In the secondary confirmation screen, the positives in the first screening were screened by FACS with two sets or three sets of detection antibodies used separately: 1.25 ug/ml GAH-Gamma Cy5 (JIR#109-176-098) for human gamma chain detection; 1.25 ug/ml GAH-Kappa PE (S.B.#2063-09) for human kappa light chain detection and 1.25 ug/ml GAH-lambda PE (S.B.#2073-09) for human lambda light chain detection in order to confirm that the anti-PDGFR-alpha antibodies were fully human.

Example 4

PDGFR Tyrosine Phosphorylation Assay 791 antibody lines were interrogated using a PDGFR tyrosine phosphorylation (pTyr) assay to determine whether the antibody lines inhibited the phosphorylation of PDGFR-alpha in tumor cells.

Briefly, human osteosarcoma MG-63 cells were seeded at 10,000 cells per well in a 96-well FMAT assay plate in 100 µl Starvation Media (1% charcoal/dextran treated FBS) and incubated at 37° C. for approximately 20 hours. Starvation Media was removed and 37.5 µl of media was added to all wells receiving sample and 12.5 µl was added to wells receiving control (mouse mAb anti-PDGFRa (BD PharMingen catalog # 556001) or mouse IgG2a (serotech, 2× final concentration)) and incubated for 30 minutes at 37° C. 50 µl of PDGF-AA (R&D) in 1% assay media at 2× final concentration (50 ng/ml) was added to all plates and media added to column 12 of the control plate. Plates were incubated for 10 minutes at 37° C. Media was removed and 100 µl of 3.7% formaldehyde in PBS/3% BSA was added and incubated for 20 minutes at room temperature. Plates were washed two times with PBS and 100 µl permeabilization buffer (0.1% Triton-X in 3% BSA/PBS) was added to each well, incubated at room temperature for 10 minutes, and discarded. 100 ml of 0.6% hydrogen peroxide in PBS/3% BSA was added to inactivate any endogenous peroxidase activity and incubated at room temperature for 20 minutes. Plates were washed three times with PBS/0.1% Tween-20 and blocked with 100 µl 10% FBS in PBS/0.1% Tween-20. Plates were incubated for 1 hour at room temperature, blocking buffer removed, and 50 µl anti-phospho PDGFa antibody (sc-12910-R) (1 µg/ml) was added to each well in 10% FBS/PBS-T. Plates were incubated for 2 hours at room temperature, then washed three times with PBST, soaking for 5 minutes between each wash. 50 µl of Goat anti-Rabbit IgGFc-HRP secondary antibody diluted in Blocking Buffer was added and incubated at room temperature for 1 hour. Plates were washed three times for 5 minutes with PBST and tapped dry. 50 µl of ECL reagent (LumiGLO Reserve, KPL catalog # 54-71-01) was added and RLUs read immediately. Plates were washed two times with PBST and tapped dry. Plates where then frozen at −80° C. for 30-60 minutes. Plates were brought to room temperature and 100 µl of CyQuant added to each well. Plates were read at 485 nm excitation and 530 nm emission on a fluorescence reader.

103 lines were selected based on a greater than or equal to 90% neutralization in the pTyr assay, i.e. the selected antibody lines inhibited tyrosine phosphorylation of PDGF receptor-alpha by greater than or equal to 90%. (Data not shown).

Example 5

Affinity and Concentration Analysis of Hybridoma Supernatants High Antigen (HA)/Limited Antigen (LA) Analysis 103 antibody lines were interrogated using a high antigen (HA)/limited antigen (LA) analysis as described below. HA is an antibody concentration dependent reaction, and is thus a measure of antibody concentration. LA is largely an antibody affinity dependent reaction and thus, can be a measure of antibody affinity.

High Antigen Quantitation Assay

Briefly, ELISA plates were coated with a greater amount of human PDGFR-alpha antigen (R&D Systems, Inc., Minneapolis, Minn. Cat. No. 322-PR-050/CF) in comparison with the Limited Antigen Quantitation Assay described below. Antibody-containing hybridoma supernatants were titrated over a dilution range of 1:51 to 1:1656. A control of a known mouse anti-human PDGFR-alpha-specific antibody (PharMingen Catalog No. 556001) was used to define the linear range of the assay. Data within the linear range were then used to derive the relative concentration of the PDGFR-specific antibody in each titrated sample.

Limited Antigen Quantitation Assay

Microtiter plates were coated with a lower amount of human PDGFR-alpha antigen in comparison with the High Antigen Quantitation Assay described above. Fifty microliters (50 µL) of human PDGFR-alpha at 64, 32, 16, 8, 4, and 2 ng/ml (covering a range of 8.5 nM to 0.26 nM) in 1% skim milk/1×PBS pH 7.4/0.5% azide was added to each well. The plate was incubated for 30 minutes.

Plates were washed four times with water, and 50 µL of hybridoma supernatant containing test antibodies diluted 1:25 in 1% skim milk/1×PBS pH 7.4/0.5% azide were added to the wells. Plates were wrapped tightly with plastic wrap or paraffin film, and incubated overnight with shaking at room temperature.

On the following day, all plates were washed five times and 50 µL goat anti-Human IgG Fc HRP polyclonal antibody at a concentration of 0.5 ug/ml in 1% milk, 1×PBS pH 7.4 was added to each well. The plates were incubated for 1 hour at room temperature.

Plates were washed at least five times with tap water. Fifty microliters (50) µL of HPR substrate TMB was added to each well, and the plate were incubated for 30 minutes. The HRP-TMB reaction was stopped by adding 50 µL of 1M phosphoric acid to each well. Optical density (absorbance) at 450 nm was measured for each well of the plate.

Thirty-four (34) antibody lines were selected based on relative binding affinity. Selection was based on titration of antigen at 16 ng/ml and 2 ng/ml. Selected cut-offs were LA greater than 0.3 OD units and 3.3 µg/ml. Lines that exhibited weak reactivity at antigen concentration of 2 ng/ml of antigen were de-selected.

Nine (9) additional lines were added to increase the candidate pool based on inhibition of PDGFR-alpha phosphorylation in MG-63 cells, such that a total of 43 antibody lines that exhibited potent inhibition of tyrosine phosphorylation and high relative affinity based on HA/LA analysis were carried forward. The aforementioned nine additional lines exhibited complete inhibition of PDGFR-alpha phosphorylation (i.e. 100%). None of the lines cross-reacted with PDGFR-beta or homologs (FLT3, c-kit, CSF-1R).

TABLE 2

SUMMARY OF 43 ANTIBODY LINES SELECTED BASED ON ABILITY TO POTENTLY INHIBIT PDGFR-ALPHA PHOSPHORYLATION IN MG-63 CELLS

| Antibody Line | Average pTyr Inhibition |
|---|---|
| 3.197 | >100% |
| 3.476 | >100% |
| 2.1623 | >100% |
| 3.87 | >100% |
| 3.404 | >100% |
| 3.72 | >100% |
| 2.1795 | >100% |
| 2.1853 | >100% |
| 2.1954 | >100% |
| 2.2002 | >100% |
| 2.2071 | >100% |
| 3.156 | >100% |
| 3.341 | >100% |
| 3.456 | >100% |
| 3.818 | >100% |
| 2.1696 | >100% |
| 2.451 | >100% |
| 3.457 | >100% |
| 2.175 | 99% |
| 2.259 | 99% |
| 2.998 | 99% |
| 2.449 | 99% |
| 2.414 | 98% |
| 2.84 | 98% |
| 3.268 | 98% |
| 2.351 | 97% |
| 2.850 | 95% |
| 3.472 | 95% |
| 2.886 | 94% |
| 2.415 | 94% |
| 3.23 | 94% |
| 2.10 | 93% |
| 2.737 | 93% |

TABLE 2-continued

SUMMARY OF 43 ANTIBODY LINES SELECTED BASED ON ABILITY TO POTENTLY INHIBIT PDGFR-ALPHA PHOSPHORYLATION IN MG-63 CELLS

| Antibody Line | Average pTyr Inhibition |
|---|---|
| 2.796 | 93% |
| 2.565 | 92% |
| 2.12 | 92% |
| 2.624 | 92% |
| 2.862 | 92% |
| 3.805 | 92% |
| 2.542 | 91% |
| 3.289 | 91% |
| 3.772 | 91% |
| 2.889 | 90% |

Example 6

In Vitro Screening and Data Analysis of Cloned Monoclonal Antibodies

Thirty (30) antibody lines were cloned and interrogated further as follows.

pTyr Assay

PDGFR Tyrosine Phosphorylation (pTyr assay) was performed using MG-63 cells as described above in Example 4. Results are shown in Table 3.

Proliferation Assay

Inhibition of MG-63 cell growth by the purified monoclonal antibodies against PDGFR-alpha was evaluated using a PDGF-AA Proliferation Assay Screen.

Briefly, MG-63 cells were seeded at 5,000 cells per well in 100 µl full growth media in the inner wells of black clear bottom plates and incubated at 37° C., 5% CO2 for 3-4 hours. Cells were washed with PBS 1× with media and replaced with growth starvation culture media (MEM, 1% NEAA, 0.1% NaBicarb, 1% L glut) and starved overnight. Media was removed from plates and 50 µl of 2×mAb or media added to appropriate wells. 50 µl of PDGF-AA titration, 200 ng/ml PDGF-AA or media alone was added and plates incubated for 3 days. Plates were read out with Alamar Blue at 530 excitation and 580 nm emission (100 µl per well/100 µl).

Data for the top 15 monoclonal antibodies, i.e. exhibiting the lowest IC50 values, for a cell stimulation using 100 ng/ml (3.45 nM) PDGF-AA are summarized below in Table 3. Monoclonal antibodies selected for further analysis are shown in bold. The dose response curves for 5 of the selected antibodies are shown in FIG. 1. The preparation of 2.451.1.1 may contain two different antibodies, with the same heavy chain but different light chains, since there were two different light chain sequences detected during sequencing of the DNA for this monoclonal antibody.

TABLE 3

PROLIFERATION ASSAY: MG-63 CELLS

| mAb | $IC_{50}$ (ng/ml) |
|---|---|
| 2.175.3 | 56.1 (0.37 nM) |
| 2.414.2 | 349.1 (2.3 nM) |
| 2.451.1.1 | 283.1 (1.9 nM) |
| 2.542.2 | 651.6 (4.35 nM) |
| 2.737.1.4 | 558.5 (3.72 nM) |
| 2.1623.2 | 981.7 (6.5 nM) |

TABLE 3-continued

| PROLIFERATION ASSAY: MG-63 CELLS | |
|---|---|
| mAb | $IC_{50}$ (ng/ml) |
| 2.1853.3 | 2679.2 (18 nM) |
| 3.341.2 | 471.0 (3.1 nM) |
| 2.796.2 | 756.8 (5 nM) |
| 5.16.1 | 422.7 (2.8 nM) |
| 2.2071.1.3 | 492.0 (3.3 nM) |
| 2.449.1.3 | 236.6 (1.57 nM) |
| 2.84.3 | 480.8 (3.2 nM) |
| 2.998.2 | 315.5 (2.1 nM) |
| 2.351.3 | 648.6 (4.3 nM) |
| BD556001 | 2857.6 (19 nM) |
| Hu IgG2 | >10 μg/mL |
| Hu IgG4 | >10 μg/mL |

FACS Kd Affinity Determination

The affinity of purified monoclonal antibodies (mAbs 2.175.3, 2.449.1.3, 2.451.1.1, 2.998.2. 2.84.3) against PDGFR-alpha was determined by FACS analysis.

Briefly, MG-63 cells expressing PDGFR-alpha were resuspended in FACS buffer (2% FBS, 0.05% NaN3) at a concentration of approximately 3 to 5 million cells/mL. Cells were kept on ice. Purified antibodies and CD140a control were serially diluted in filtered 1×PBS (2×) across 11 wells in 96-well plates. The twelfth well in each row contained buffer only. 1×PBS and cells were added to each mAb well such that the final volume was 30 μL/well and each well contained approximately 100,000 cells. The final molecular concentration ranges for the mAbs were as follows:

| mAb | Concentration |
|---|---|
| 2.451.1.1 = | 19.1-0.019 nM |
| 2.175.3 = | 10.8-0.021 nM |
| 2.449.1.3 = | 10.7-0.021 nM |
| 2.449.1.3 = | 9.2-0.009 nM |
| 2.84.3 = | 4.4-0.009 nM |
| 2.449.1.3 = | 9.2-0.009 nM |
| 2.998.2 = | 4.6-0.009 nM |
| CD140a = | 20.2-0.020 nM |

Plates were placed on a plate shaker for 5 hours at 4° C., then spun and washed 3× with PBS. 200 μL of 100 or 131 nM Cy5 goat α-human polyclonal antibody (Jackson Laboratories, #109-175-008) was added to each well, and 200 μL of 100 nM Cy5 goat α-mouse polyclonal antibody was added to the cells complexed with CD140a antibody. Plates were then placed on a shaker for 40 minutes at 4° C., then spun and washed 3× with PBS.

The Geometric Mean Fluorescence (GMF) of 15,000 to 20,000 cell "events" for each mAb concentration was determined using a FACSCalibur instrument. For each mAb, the GMF data was normalized for both replicate titrations relative to an identical mAb concentration point in each titration. Corresponding normalized titration points were averaged to give one normalized GMF point for each mAb concentration. Only one titration data set for mAb 2.351.3 was of acceptable quality for analysis. A nonlinear plot of GMF as a function of molecular mAb concentration was fit using Scientist software using the equation:

$$F = P' \cdot \frac{(K_D + L_T + 1) - \sqrt{((K_D + L_T + 1))^2 - 4(L_T)}}{2}$$

In the above equation, F=Geometric mean fluorescence, LT=total molecular mAb concentration, P'=proportionality constant that relates arbitrary fluorescence units to bound mAb, and KD=equilibrium dissociation constant. For each mAb an estimate for KD was obtained as P' and KD were allowed to float freely in the nonlinear analysis. Table 4 below lists the resulting KDs for each mAb along with the 95% confidence interval of the fit. MAbs are listed in order of decreasing affinity.

TABLE 4

| Sample | $K_D$ (pM) | 95% CI (pM) |
|---|---|---|
| 2.175.3 | 328 | ±202 |
| 2.451.1.1 | 389 | ±196 |
| 2.449.1.3 (control) | 52 | ±51 |
| 2.449.1.3 | 53 | ±49 |
| 2.998.2 | 57 | ±68 (upper CI only) |
| CD140a | 146 | ±99 |
| 2.84.3 | 227 | ±121 |

Mouse Cross-reactivity

To set up animal xenograft studies, mouse cross-reactivity was determined using FACS analysis performed with NIH3T3 cells, a murine fibroblast line which expresses endogenous PDGFRa. NIH3T3 cells were incubated at 0.5×106 cells/ml with 10 ug/ml of test antibodies on ice for 1 h, rinsed and then resuspended in PBS with 5 ug/ml of goat-anti-human IgG antibodies labeled with Cy5. Cells were rinsed and analyzed by FACS for the presence of Cy5. Only 3 of the tested monoclonal antibodies exhibited mouse cross-reactivity. Results are summarized in Table 5.

Percent Internalization

The percentage of antibody being internalized in cells was determined using a standard internalization protocol. Percent internalization results at 10 μg/ml are summarized in Table 5.

Results

Results of in vitro screening and data analysis of the 30 cloned monoclonal antibodies are summarized in Table 5. mAbs are listed in order of increasing IC50 values. mAbs in italics were selected as the top ten mAbs and antibodies in boldface were selected as the three lead candidates. "( )" denotes ranking in Table 5.

As can be seen from Table 5, mAb 2.175.3 exhibited exceptional inhibition of PDGF-AA proliferation of MG-63 cells as well as exceptional inhibition of phosphorylation of PDGFR-alpha on MG-63 cells. MAbs 2.449.1.3 and 2.998.2 also inhibited phosphorylation of PDGFR-alpha on MG-63 cells and inhibited PDGF-AA proliferation of MG-63 cells. In addition, mAbs 2.449.1.3 and 2.998.2 also had a high binding affinity for PDGFR-alpha.

TABLE 5

PDGFR-ALPHA MONOCLONAL ANTIBODY SUMMARY

| Antibody | pTyr Assay: % Inhibition @ 2 μg/ml | Proliferation Assay: $IC_{50}$ ng/ml (1-6-06) | Proliferation Assay: $IC_{50}$ ng/ml (1-23-06) | % Internalization @ 10 μg/ml | Mouse-Cross Reactivity | Affinity: $K_D$ |
|---|---|---|---|---|---|---|
| ***2.175.3*** | 100 | 67.3 (1) (0.45 nM) | 56.1 (1) (0.37 nM) | 19% | Yes | 328 pM |
| ***2.449.1.3*** | 99 | 178.6 (2) (1.2 nM) | 236.6 (2) (1.57 nM) | 20% | — | 52 pM |
| *2.451.1.1* | 100 | 399.0 (6) (2.67 nM) | 283.1 (3) (1.9 nM) | 21% | — | 389 pM |
| ***2.998.2*** | 99 | 307.6 (4) (2.05 nM) | 315.5 (4) (2.1 nM) | 25% | — | 57 pM |
| *2.84.3* | 98 | 192.3 (3) (1.3 nM) | 480.9 (8) (3.2 nM) | 26% | — | 227 pM |
| *2.414.2* | 99 | 657.7 (9) (4.4 nM) | 349.1 (5) (2.3 nM) | 28% | — | |
| *5.16.1* | 99 | 385.5 (5) (2.57 nM) | 422.7 (6) (2.81 nM) | 31% | — | |
| *3.341.2* | 100 | 403.6 (7) (2.7 nM) | 471.0 (7) 3.1 nM) | 22% | — | |
| *2.2071.1.3* | 99 | 1,276.4 (10) (8.5 nM) | 492.0 (9) (3.3 nM) | 21% | — | |
| *2.737.1.4* | 99 | 550.8 (8) (3.7 nM) | 558.5 (10) (3.73 nM) | 22% | — | |
| 2.796.2 | 99 | 497.7 | 756.8 | 19% | — | |
| 2.542.2 | 99 | 1037.5 | 651.6 | 26% | — | |
| 2.351.3 | 97 | 1,078.9 | 648.6 | 21% | — | |
| 2.1623.2 | 97 | 755.1 | 981.7 | 46% | Yes | |
| 2.1853.3 | 98 | 1,122.0 | 2679.2 | 30% | Yes | |
| 3.818.4 | 92 | 4,602.6 | — | | | |
| 3.457.3.1 | 85 | — | — | | | |
| 3.23.3 | 84 | 61.9 | — | | | |
| 5.1.1.1 | 77 | >10 μg/mL | — | | | |
| 4.16.2 | 74 | >10 μg/mL | — | | | |
| 3.87.1.1 | 69 | 6,237.3 | — | | | |
| 2.1576.1.2 | 65 | >10 μg/mL | — | | | |
| 3.472.1.1 | 61 | — | — | | | |
| 3.805.1.3 | 58 | 1,016.2 | — | | | |
| 3.772.2 | 56 | 167.9 | — | | | |
| 5.9.3 | 31 | 2.2 | — | | | |
| 3.23.2 | 26 | 150.3 | — | | | |
| 2.1954.2 | −3 | — | — | | | |
| 3.625.1.7 | −3 | 3819.44 | — | | | |
| 2.2002.3 | −9 | — | — | | | |

Example 7

Structural Analysis of Anti-PDGFR-Alpha Antibodies

The heavy and light chain variable domains of the antibodies were sequenced to determine their DNA sequences. The complete sequence information for the anti-PDGFR-alpha antibodies is provided in the sequence listing with nucleotide and amino acid sequences for each gamma and kappa chain combination. The variable heavy sequences were analyzed to determine the VH family, the D-region sequence and the J-region sequence. The sequences were then translated to determine the primary amino acid sequence and compared to the germline VH, D and J-region sequences to assess somatic hypermutations. "-" indicates identity with the germline sequence. "#" indicates an additional amino acid in the antibody sequences that is not found in the germline.

Table 12 is a table comparing the antibody heavy chain regions to their cognate germline heavy chain region. Table 13 is a table comparing the antibody kappa light chain regions to their cognate germline light chain region.

The variable (V) regions of immunoglobulin chains are encoded by multiple germline DNA segments, which are joined into functional variable regions (VHDJH or VKJK) during B-cell ontogeny.

It should also be appreciated that where a particular antibody differs from its respective germline sequence at the amino acid level, the antibody sequence can be mutated back to the germline sequence. Such corrective mutations can occur at one, two, three or more positions, or a combination of any of the mutated positions, using standard molecular biological techniques. By way of non-limiting example, Table 12 shows that the heavy chain sequence of mAb 2.175.3 (SEQ ID NO.: 2) differs from the corresponding germline sequence inter alia through a Q to H mutation (mutation 1) in the FR1 region, a S to H mutation (mutation 2) in the CDR1 region, and a S to R mutation (mutation 3) in the CDR2 region. Thus, the amino acid or nucleotide sequence encoding the heavy chain of mAb 2.175.3 can be modified to change mutation 1 to yield the germline sequence at the site of mutation 1. Further, the amino acid or nucleotide sequence encoding the heavy chain of mAb 2.175.3 can be modified to change mutation 2 or mutation 3 to yield the germline sequence at the site of mutation 2 or mutation 3. Indeed the amino acid or nucleotide sequence encoding the heavy chain of mAb 2.175.3 can encompass any combination of two or more mutations to yield the germline sequence at those particular sites. Tables 6-11 below illustrate the position of such variations from the germline for mAb 2.175.3, 2.449.1.3 and 2.998.2. Each row represents a unique combination of germline and non-germline residues at the positions indicated. In the event of a discrepancy between the sequence listing and tables 6-11, the information provided in the table takes precedence.

TABLE 6

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| Q | S | S | T | A | Y | DELETED | DELETED | DELETED | DELETED |
| Q | S | S | T | A | Y | DELETED | DELETED | DELETED | P |
| Q | S | S | T | A | Y | DELETED | DELETED | P | DELETED |
| Q | S | S | T | A | Y | DELETED | DELETED | P | P |
| Q | S | S | T | A | Y | DELETED | G | DELETED | DELETED |
| Q | S | S | T | A | Y | DELETED | G | DELETED | P |
| Q | S | S | T | A | Y | DELETED | G | P | DELETED |
| Q | S | S | T | A | Y | DELETED | G | P | P |
| Q | S | S | T | A | Y | G | DELETED | DELETED | DELETED |
| Q | S | S | T | A | Y | G | DELETED | DELETED | P |
| Q | S | S | T | A | Y | G | DELETED | P | DELETED |
| Q | S | S | T | A | Y | G | DELETED | P | P |
| Q | S | S | T | A | Y | G | G | DELETED | DELETED |
| Q | S | S | T | A | Y | G | G | DELETED | P |
| Q | S | S | T | A | Y | G | G | P | DELETED |
| Q | S | S | T | A | Y | G | G | P | P |
| Q | S | S | T | A | N | DELETED | DELETED | DELETED | DELETED |
| Q | S | S | T | A | N | DELETED | DELETED | DELETED | P |
| Q | S | S | T | A | N | DELETED | DELETED | P | DELETED |
| Q | S | S | T | A | N | DELETED | DELETED | P | P |
| Q | S | S | T | A | N | DELETED | G | DELETED | DELETED |
| Q | S | S | T | A | N | DELETED | G | DELETED | P |
| Q | S | S | T | A | N | DELETED | G | P | DELETED |
| Q | S | S | T | A | N | DELETED | G | P | P |
| Q | S | S | T | A | N | G | DELETED | DELETED | DELETED |
| Q | S | S | T | A | N | G | DELETED | DELETED | P |
| Q | S | S | T | A | N | G | DELETED | P | DELETED |
| Q | S | S | T | A | N | G | DELETED | P | P |
| Q | S | S | T | A | N | G | G | DELETED | DELETED |
| Q | S | S | T | A | N | G | G | DELETED | P |
| Q | S | S | T | A | N | G | G | P | DELETED |
| Q | S | S | T | A | N | G | G | P | P |
| Q | S | S | T | V | Y | DELETED | DELETED | DELETED | DELETED |
| Q | S | S | T | V | Y | DELETED | DELETED | DELETED | P |
| Q | S | S | T | V | Y | DELETED | DELETED | P | DELETED |
| Q | S | S | T | V | Y | DELETED | DELETED | P | P |
| Q | S | S | T | V | Y | DELETED | G | DELETED | DELETED |
| Q | S | S | T | V | Y | DELETED | G | DELETED | P |
| Q | S | S | T | V | Y | DELETED | G | P | DELETED |
| Q | S | S | T | V | Y | DELETED | G | P | P |
| Q | S | S | T | V | Y | G | DELETED | DELETED | DELETED |
| Q | S | S | T | V | Y | G | DELETED | DELETED | P |
| Q | S | S | T | V | Y | G | DELETED | P | DELETED |
| Q | S | S | T | V | Y | G | DELETED | P | P |
| Q | S | S | T | V | Y | G | G | DELETED | DELETED |
| Q | S | S | T | V | Y | G | G | DELETED | P |
| Q | S | S | T | V | Y | G | G | P | DELETED |
| Q | S | S | T | V | Y | G | G | P | P |
| Q | S | S | T | V | N | DELETED | DELETED | DELETED | DELETED |
| Q | S | S | T | V | N | DELETED | DELETED | DELETED | P |
| Q | S | S | T | V | N | DELETED | DELETED | P | DELETED |
| Q | S | S | T | V | N | DELETED | DELETED | P | P |
| Q | S | S | T | V | N | DELETED | G | DELETED | DELETED |
| Q | S | S | T | V | N | DELETED | G | DELETED | P |
| Q | S | S | T | V | N | DELETED | G | P | DELETED |
| Q | S | S | T | V | N | DELETED | G | P | P |
| Q | S | S | T | V | N | G | DELETED | DELETED | DELETED |
| Q | S | S | T | V | N | G | DELETED | DELETED | P |
| Q | S | S | T | V | N | G | DELETED | P | DELETED |
| Q | S | S | T | V | N | G | DELETED | P | P |
| Q | S | S | T | V | N | G | G | DELETED | DELETED |
| Q | S | S | T | V | N | G | G | DELETED | P |
| Q | S | S | T | V | N | G | G | P | DELETED |
| Q | S | S | T | V | N | G | G | P | P |
| Q | S | S | L | A | Y | DELETED | DELETED | DELETED | DELETED |
| Q | S | S | L | A | Y | DELETED | DELETED | DELETED | P |
| Q | S | S | L | A | Y | DELETED | DELETED | P | DELETED |
| Q | S | S | L | A | Y | DELETED | DELETED | P | P |

TABLE 6-continued

| Exemplary Mutations of mAb 2.175.3 Heavy Chain (SEQ ID NO: 2) to Germline at the Indicated Residue Number. | | | | | | | | | |
|---|---|---|---|---|---|---|---|---|---|
| 3 | 35 | 53 | 57 | 61 | 80 | 99 | 100 | 101 | 106 |
| Q | S | S | L | A | Y | DELETED | G | DELETED | DELETED |
| Q | S | S | L | A | Y | DELETED | G | DELETED | P |
| Q | S | S | L | A | Y | DELETED | G | P | DELETED |
| Q | S | S | L | A | Y | DELETED | G | P | P |
| Q | S | S | L | A | Y | G | DELETED | DELETED | DELETED |
| Q | S | S | L | A | Y | G | DELETED | DELETED | P |
| Q | S | S | L | A | Y | G | DELETED | P | DELETED |
| Q | S | S | L | A | Y | G | DELETED | P | P |
| Q | S | S | L | A | Y | G | G | DELETED | DELETED |
| Q | S | S | L | A | Y | G | G | DELETED | P |
| Q | S | S | L | A | Y | G | G | P | DELETED |
| Q | S | S | L | A | Y | G | G | P | P |
| Q | S | S | L | A | N | DELETED | DELETED | DELETED | DELETED |
| Q | S | S | L | A | N | DELETED | DELETED | DELETED | P |
| Q | S | S | L | A | N | DELETED | DELETED | P | DELETED |
| Q | S | S | L | A | N | DELETED | DELETED | P | P |
| Q | S | S | L | A | N | DELETED | G | DELETED | DELETED |
| Q | S | S | L | A | N | DELETED | G | DELETED | P |
| Q | S | S | L | A | N | DELETED | G | P | DELETED |
| Q | S | S | L | A | N | DELETED | G | P | P |
| Q | S | S | L | A | N | G | DELETED | DELETED | DELETED |
| Q | S | S | L | A | N | G | DELETED | DELETED | P |
| Q | S | S | L | A | N | G | DELETED | P | DELETED |
| Q | S | S | L | A | N | G | DELETED | P | P |
| Q | S | S | L | A | N | G | G | DELETED | DELETED |
| Q | S | S | L | A | N | G | G | DELETED | P |
| Q | S | S | L | A | N | G | G | P | DELETED |
| Q | S | S | L | A | N | G | G | P | P |
| Q | S | S | L | V | Y | DELETED | DELETED | DELETED | DELETED |
| Q | S | S | L | V | Y | DELETED | DELETED | DELETED | P |
| Q | S | S | L | V | Y | DELETED | DELETED | P | DELETED |
| Q | S | S | L | V | Y | DELETED | DELETED | P | P |
| Q | S | S | L | V | Y | DELETED | G | DELETED | DELETED |
| Q | S | S | L | V | Y | DELETED | G | DELETED | P |
| Q | S | S | L | V | Y | DELETED | G | P | DELETED |
| Q | S | S | L | V | Y | DELETED | G | P | P |
| Q | S | S | L | V | Y | G | DELETED | DELETED | DELETED |
| Q | S | S | L | V | Y | G | DELETED | DELETED | P |
| Q | S | S | L | V | Y | G | DELETED | P | DELETED |
| Q | S | S | L | V | Y | G | DELETED | P | P |
| Q | S | S | L | V | Y | G | G | DELETED | DELETED |
| Q | S | S | L | V | Y | G | G | DELETED | P |
| Q | S | S | L | V | Y | G | G | P | DELETED |
| Q | S | S | L | V | Y | G | G | P | P |
| Q | S | S | L | V | N | DELETED | DELETED | DELETED | DELETED |
| Q | S | S | L | V | N | DELETED | DELETED | DELETED | P |
| Q | S | S | L | V | N | DELETED | DELETED | P | DELETED |
| Q | S | S | L | V | N | DELETED | DELETED | P | P |
| Q | S | S | L | V | N | DELETED | G | DELETED | DELETED |
| Q | S | S | L | V | N | DELETED | G | DELETED | P |
| Q | S | S | L | V | N | DELETED | G | P | DELETED |
| Q | S | S | L | V | N | DELETED | G | P | P |
| Q | S | S | L | V | N | G | DELETED | DELETED | DELETED |
| Q | S | S | L | V | N | G | DELETED | DELETED | P |
| Q | S | S | L | V | N | G | DELETED | P | DELETED |
| Q | S | S | L | V | N | G | DELETED | P | P |
| Q | S | S | L | V | N | G | G | DELETED | DELETED |
| Q | S | S | L | V | N | G | G | DELETED | P |
| Q | S | S | L | V | N | G | G | P | DELETED |
| Q | S | S | L | V | N | G | G | P | P |
| Q | S | R | T | A | Y | DELETED | DELETED | DELETED | DELETED |
| Q | S | R | T | A | Y | DELETED | DELETED | DELETED | P |
| Q | S | R | T | A | Y | DELETED | DELETED | P | DELETED |
| Q | S | R | T | A | Y | DELETED | DELETED | P | P |
| Q | S | R | T | A | Y | DELETED | G | DELETED | DELETED |
| Q | S | R | T | A | Y | DELETED | G | DELETED | P |
| Q | S | R | T | A | Y | DELETED | G | P | DELETED |
| Q | S | R | T | A | Y | DELETED | G | P | P |
| Q | S | R | T | A | Y | G | DELETED | DELETED | DELETED |
| Q | S | R | T | A | Y | G | DELETED | DELETED | P |
| Q | S | R | T | A | Y | G | DELETED | P | DELETED |
| Q | S | R | T | A | Y | G | DELETED | P | P |
| Q | S | R | T | A | Y | G | G | DELETED | DELETED |
| Q | S | R | T | A | Y | G | G | DELETED | P |

TABLE 6-continued

| Exemplary Mutations of mAb 2.175.3 Heavy Chain (SEQ ID NO: 2) to Germline at the Indicated Residue Number. | | | | | | | | | |
|---|---|---|---|---|---|---|---|---|---|
| 3 | 35 | 53 | 57 | 61 | 80 | 99 | 100 | 101 | 106 |
| Q | S | R | T | A | Y | G | G | P | DELETED |
| Q | S | R | T | A | Y | G | G | P | P |
| Q | S | R | T | A | N | DELETED | DELETED | DELETED | DELETED |
| Q | S | R | T | A | N | DELETED | DELETED | DELETED | P |
| Q | S | R | T | A | N | DELETED | DELETED | P | DELETED |
| Q | S | R | T | A | N | DELETED | DELETED | P | P |
| Q | S | R | T | A | N | DELETED | G | DELETED | DELETED |
| Q | S | R | T | A | N | DELETED | G | DELETED | P |
| Q | S | R | T | A | N | DELETED | G | P | DELETED |
| Q | S | R | T | A | N | DELETED | G | P | P |
| Q | S | R | T | A | N | G | DELETED | DELETED | DELETED |
| Q | S | R | T | A | N | G | DELETED | DELETED | P |
| Q | S | R | T | A | N | G | DELETED | P | DELETED |
| Q | S | R | T | A | N | G | DELETED | P | P |
| Q | S | R | T | A | N | G | G | DELETED | DELETED |
| Q | S | R | T | A | N | G | G | DELETED | P |
| Q | S | R | T | A | N | G | G | P | DELETED |
| Q | S | R | T | A | N | G | G | P | P |
| Q | S | R | T | V | Y | DELETED | DELETED | DELETED | DELETED |
| Q | S | R | T | V | Y | DELETED | DELETED | DELETED | P |
| Q | S | R | T | V | Y | DELETED | DELETED | P | DELETED |
| Q | S | R | T | V | Y | DELETED | DELETED | P | P |
| Q | S | R | T | V | Y | DELETED | G | DELETED | DELETED |
| Q | S | R | T | V | Y | DELETED | G | DELETED | P |
| Q | S | R | T | V | Y | DELETED | G | P | DELETED |
| Q | S | R | T | V | Y | DELETED | G | P | P |
| Q | S | R | T | V | Y | G | DELETED | DELETED | DELETED |
| Q | S | R | T | V | Y | G | DELETED | DELETED | P |
| Q | S | R | T | V | Y | G | DELETED | P | DELETED |
| Q | S | R | T | V | Y | G | DELETED | P | P |
| Q | S | R | T | V | Y | G | G | DELETED | DELETED |
| Q | S | R | T | V | Y | G | G | DELETED | P |
| Q | S | R | T | V | Y | G | G | P | DELETED |
| Q | S | R | T | V | Y | G | G | P | P |
| Q | S | R | T | V | N | DELETED | DELETED | DELETED | DELETED |
| Q | S | R | T | V | N | DELETED | DELETED | DELETED | P |
| Q | S | R | T | V | N | DELETED | DELETED | P | DELETED |
| Q | S | R | T | V | N | DELETED | DELETED | P | P |
| Q | S | R | T | V | N | DELETED | G | DELETED | DELETED |
| Q | S | R | T | V | N | DELETED | G | DELETED | P |
| Q | S | R | T | V | N | DELETED | G | P | DELETED |
| Q | S | R | T | V | N | DELETED | G | P | P |
| Q | S | R | T | V | N | G | DELETED | DELETED | DELETED |
| Q | S | R | T | V | N | G | DELETED | DELETED | P |
| Q | S | R | T | V | N | G | DELETED | P | DELETED |
| Q | S | R | T | V | N | G | DELETED | P | P |
| Q | S | R | T | V | N | G | G | DELETED | DELETED |
| Q | S | R | T | V | N | G | G | DELETED | P |
| Q | S | R | T | V | N | G | G | P | DELETED |
| Q | S | R | T | V | N | G | G | P | P |
| Q | S | R | L | A | Y | DELETED | DELETED | DELETED | DELETED |
| Q | S | R | L | A | Y | DELETED | DELETED | DELETED | P |
| Q | S | R | L | A | Y | DELETED | DELETED | P | DELETED |
| Q | S | R | L | A | Y | DELETED | DELETED | P | P |
| Q | S | R | L | A | Y | DELETED | G | DELETED | DELETED |
| Q | S | R | L | A | Y | DELETED | G | DELETED | P |
| Q | S | R | L | A | Y | DELETED | G | P | DELETED |
| Q | S | R | L | A | Y | DELETED | G | P | P |
| Q | S | R | L | A | Y | G | DELETED | DELETED | DELETED |
| Q | S | R | L | A | Y | G | DELETED | DELETED | P |
| Q | S | R | L | A | Y | G | DELETED | P | DELETED |
| Q | S | R | L | A | Y | G | DELETED | P | P |
| Q | S | R | L | A | Y | G | G | DELETED | DELETED |
| Q | S | R | L | A | Y | G | G | DELETED | P |
| Q | S | R | L | A | Y | G | G | P | DELETED |
| Q | S | R | L | A | Y | G | G | P | P |
| Q | S | R | L | A | N | DELETED | DELETED | DELETED | DELETED |
| Q | S | R | L | A | N | DELETED | DELETED | DELETED | P |
| Q | S | R | L | A | N | DELETED | DELETED | P | DELETED |
| Q | S | R | L | A | N | DELETED | DELETED | P | P |
| Q | S | R | L | A | N | DELETED | G | DELETED | DELETED |
| Q | S | R | L | A | N | DELETED | G | DELETED | P |
| Q | S | R | L | A | N | DELETED | G | P | DELETED |
| Q | S | R | L | A | N | DELETED | G | P | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| Q | S | R | L | A | N | G | DELETED | DELETED | DELETED |
| Q | S | R | L | A | N | G | DELETED | DELETED | P |
| Q | S | R | L | A | N | G | DELETED | P | DELETED |
| Q | S | R | L | A | N | G | DELETED | P | P |
| Q | S | R | L | A | N | G | G | DELETED | DELETED |
| Q | S | R | L | A | N | G | G | DELETED | P |
| Q | S | R | L | A | N | G | G | P | DELETED |
| Q | S | R | L | A | N | G | G | P | P |
| Q | S | R | L | V | Y | DELETED | DELETED | DELETED | DELETED |
| Q | S | R | L | V | Y | DELETED | DELETED | DELETED | P |
| Q | S | R | L | V | Y | DELETED | DELETED | P | DELETED |
| Q | S | R | L | V | Y | DELETED | DELETED | P | P |
| Q | S | R | L | V | Y | DELETED | G | DELETED | DELETED |
| Q | S | R | L | V | Y | DELETED | G | DELETED | P |
| Q | S | R | L | V | Y | DELETED | G | P | DELETED |
| Q | S | R | L | V | Y | DELETED | G | P | P |
| Q | S | R | L | V | Y | G | DELETED | DELETED | DELETED |
| Q | S | R | L | V | Y | G | DELETED | DELETED | P |
| Q | S | R | L | V | Y | G | DELETED | P | DELETED |
| Q | S | R | L | V | Y | G | DELETED | P | P |
| Q | S | R | L | V | Y | G | G | DELETED | DELETED |
| Q | S | R | L | V | Y | G | G | DELETED | P |
| Q | S | R | L | V | Y | G | G | P | DELETED |
| Q | S | R | L | V | Y | G | G | P | P |
| Q | S | R | L | V | N | DELETED | DELETED | DELETED | DELETED |
| Q | S | R | L | V | N | DELETED | DELETED | DELETED | P |
| Q | S | R | L | V | N | DELETED | DELETED | P | DELETED |
| Q | S | R | L | V | N | DELETED | DELETED | P | P |
| Q | S | R | L | V | N | DELETED | G | DELETED | DELETED |
| Q | S | R | L | V | N | DELETED | G | DELETED | P |
| Q | S | R | L | V | N | DELETED | G | P | DELETED |
| Q | S | R | L | V | N | DELETED | G | P | P |
| Q | S | R | L | V | N | G | DELETED | DELETED | DELETED |
| Q | S | R | L | V | N | G | DELETED | DELETED | P |
| Q | S | R | L | V | N | G | DELETED | P | DELETED |
| Q | S | R | L | V | N | G | DELETED | P | P |
| Q | S | R | L | V | N | G | G | DELETED | DELETED |
| Q | S | R | L | V | N | G | G | DELETED | P |
| Q | S | R | L | V | N | G | G | P | DELETED |
| Q | S | R | L | V | N | G | G | P | P |
| Q | H | S | T | A | Y | DELETED | DELETED | DELETED | DELETED |
| Q | H | S | T | A | Y | DELETED | DELETED | DELETED | P |
| Q | H | S | T | A | Y | DELETED | DELETED | P | DELETED |
| Q | H | S | T | A | Y | DELETED | DELETED | P | P |
| Q | H | S | T | A | Y | DELETED | G | DELETED | DELETED |
| Q | H | S | T | A | Y | DELETED | G | DELETED | P |
| Q | H | S | T | A | Y | DELETED | G | P | DELETED |
| Q | H | S | T | A | Y | DELETED | G | P | P |
| Q | H | S | T | A | Y | G | DELETED | DELETED | DELETED |
| Q | H | S | T | A | Y | G | DELETED | DELETED | P |
| Q | H | S | T | A | Y | G | DELETED | P | DELETED |
| Q | H | S | T | A | Y | G | DELETED | P | P |
| Q | H | S | T | A | Y | G | G | DELETED | DELETED |
| Q | H | S | T | A | Y | G | G | DELETED | P |
| Q | H | S | T | A | Y | G | G | P | DELETED |
| Q | H | S | T | A | Y | G | G | P | P |
| Q | H | S | T | A | N | DELETED | DELETED | DELETED | DELETED |
| Q | H | S | T | A | N | DELETED | DELETED | DELETED | P |
| Q | H | S | T | A | N | DELETED | DELETED | P | DELETED |
| Q | H | S | T | A | N | DELETED | DELETED | P | P |
| Q | H | S | T | A | N | DELETED | G | DELETED | DELETED |
| Q | H | S | T | A | N | DELETED | G | DELETED | P |
| Q | H | S | T | A | N | DELETED | G | P | DELETED |
| Q | H | S | T | A | N | DELETED | G | P | P |
| Q | H | S | T | A | N | G | DELETED | DELETED | DELETED |
| Q | H | S | T | A | N | G | DELETED | DELETED | P |
| Q | H | S | T | A | N | G | DELETED | P | DELETED |
| Q | H | S | T | A | N | G | DELETED | P | P |
| Q | H | S | T | A | N | G | G | DELETED | DELETED |
| Q | H | S | T | A | N | G | G | DELETED | P |
| Q | H | S | T | A | N | G | G | P | DELETED |
| Q | H | S | T | A | N | G | G | P | P |
| Q | H | S | T | V | Y | DELETED | DELETED | DELETED | DELETED |
| Q | H | S | T | V | Y | DELETED | DELETED | DELETED | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| Q | H | S | T | V | Y | DELETED | DELETED | P | DELETED |
| Q | H | S | T | V | Y | DELETED | DELETED | P | P |
| Q | H | S | T | V | Y | DELETED | G | DELETED | DELETED |
| Q | H | S | T | V | Y | DELETED | G | DELETED | P |
| Q | H | S | T | V | Y | DELETED | G | P | DELETED |
| Q | H | S | T | V | Y | DELETED | G | P | P |
| Q | H | S | T | V | Y | G | DELETED | DELETED | DELETED |
| Q | H | S | T | V | Y | G | DELETED | DELETED | P |
| Q | H | S | T | V | Y | G | DELETED | P | DELETED |
| Q | H | S | T | V | Y | G | DELETED | P | P |
| Q | H | S | T | V | Y | G | G | DELETED | DELETED |
| Q | H | S | T | V | Y | G | G | DELETED | P |
| Q | H | S | T | V | Y | G | G | P | DELETED |
| Q | H | S | T | V | Y | G | G | P | P |
| Q | H | S | T | V | N | DELETED | DELETED | DELETED | DELETED |
| Q | H | S | T | V | N | DELETED | DELETED | DELETED | P |
| Q | H | S | T | V | N | DELETED | DELETED | P | DELETED |
| Q | H | S | T | V | N | DELETED | DELETED | P | P |
| Q | H | S | T | V | N | DELETED | G | DELETED | DELETED |
| Q | H | S | T | V | N | DELETED | G | DELETED | P |
| Q | H | S | T | V | N | DELETED | G | P | DELETED |
| Q | H | S | T | V | N | DELETED | G | P | P |
| Q | H | S | T | V | N | G | DELETED | DELETED | DELETED |
| Q | H | S | T | V | N | G | DELETED | DELETED | P |
| Q | H | S | T | V | N | G | DELETED | P | DELETED |
| Q | H | S | T | V | N | G | DELETED | P | P |
| Q | H | S | T | V | N | G | G | DELETED | DELETED |
| Q | H | S | T | V | N | G | G | DELETED | P |
| Q | H | S | T | V | N | G | G | P | DELETED |
| Q | H | S | T | V | N | G | G | P | P |
| Q | H | S | L | A | Y | DELETED | DELETED | DELETED | DELETED |
| Q | H | S | L | A | Y | DELETED | DELETED | DELETED | P |
| Q | H | S | L | A | Y | DELETED | DELETED | P | DELETED |
| Q | H | S | L | A | Y | DELETED | DELETED | P | P |
| Q | H | S | L | A | Y | DELETED | G | DELETED | DELETED |
| Q | H | S | L | A | Y | DELETED | G | DELETED | P |
| Q | H | S | L | A | Y | DELETED | G | P | DELETED |
| Q | H | S | L | A | Y | DELETED | G | P | P |
| Q | H | S | L | A | Y | G | DELETED | DELETED | DELETED |
| Q | H | S | L | A | Y | G | DELETED | DELETED | P |
| Q | H | S | L | A | Y | G | DELETED | P | DELETED |
| Q | H | S | L | A | Y | G | DELETED | P | P |
| Q | H | S | L | A | Y | G | G | DELETED | DELETED |
| Q | H | S | L | A | Y | G | G | DELETED | P |
| Q | H | S | L | A | Y | G | G | P | DELETED |
| Q | H | S | L | A | Y | G | G | P | P |
| Q | H | S | L | A | N | DELETED | DELETED | DELETED | DELETED |
| Q | H | S | L | A | N | DELETED | DELETED | DELETED | P |
| Q | H | S | L | A | N | DELETED | DELETED | P | DELETED |
| Q | H | S | L | A | N | DELETED | DELETED | P | P |
| Q | H | S | L | A | N | DELETED | G | DELETED | DELETED |
| Q | H | S | L | A | N | DELETED | G | DELETED | P |
| Q | H | S | L | A | N | DELETED | G | P | DELETED |
| Q | H | S | L | A | N | DELETED | G | P | P |
| Q | H | S | L | A | N | G | DELETED | DELETED | DELETED |
| Q | H | S | L | A | N | G | DELETED | DELETED | P |
| Q | H | S | L | A | N | G | DELETED | P | DELETED |
| Q | H | S | L | A | N | G | DELETED | P | P |
| Q | H | S | L | A | N | G | G | DELETED | DELETED |
| Q | H | S | L | A | N | G | G | DELETED | P |
| Q | H | S | L | A | N | G | G | P | DELETED |
| Q | H | S | L | A | N | G | G | P | P |
| Q | H | S | L | V | Y | DELETED | DELETED | DELETED | DELETED |
| Q | H | S | L | V | Y | DELETED | DELETED | DELETED | P |
| Q | H | S | L | V | Y | DELETED | DELETED | P | DELETED |
| Q | H | S | L | V | Y | DELETED | DELETED | P | P |
| Q | H | S | L | V | Y | DELETED | G | DELETED | DELETED |
| Q | H | S | L | V | Y | DELETED | G | DELETED | P |
| Q | H | S | L | V | Y | DELETED | G | P | DELETED |
| Q | H | S | L | V | Y | DELETED | G | P | P |
| Q | H | S | L | V | Y | G | DELETED | DELETED | DELETED |
| Q | H | S | L | V | Y | G | DELETED | DELETED | P |
| Q | H | S | L | V | Y | G | DELETED | P | DELETED |
| Q | H | S | L | V | Y | G | DELETED | P | P |

TABLE 6-continued

| Exemplary Mutations of mAb 2.175.3 Heavy Chain (SEQ ID NO: 2) to Germline at the Indicated Residue Number. | | | | | | | | | |
|---|---|---|---|---|---|---|---|---|---|
| 3 | 35 | 53 | 57 | 61 | 80 | 99 | 100 | 101 | 106 |
| Q | H | S | L | V | Y | G | G | DELETED | DELETED |
| Q | H | S | L | V | Y | G | G | DELETED | P |
| Q | H | S | L | V | Y | G | G | P | DELETED |
| Q | H | S | L | V | Y | G | G | P | P |
| Q | H | S | L | V | N | DELETED | DELETED | DELETED | DELETED |
| Q | H | S | L | V | N | DELETED | DELETED | DELETED | P |
| Q | H | S | L | V | N | DELETED | DELETED | P | DELETED |
| Q | H | S | L | V | N | DELETED | DELETED | P | P |
| Q | H | S | L | V | N | DELETED | G | DELETED | DELETED |
| Q | H | S | L | V | N | DELETED | G | DELETED | P |
| Q | H | S | L | V | N | DELETED | G | P | DELETED |
| Q | H | S | L | V | N | DELETED | G | P | P |
| Q | H | S | L | V | N | G | DELETED | DELETED | DELETED |
| Q | H | S | L | V | N | G | DELETED | DELETED | P |
| Q | H | S | L | V | N | G | DELETED | P | DELETED |
| Q | H | S | L | V | N | G | DELETED | P | P |
| Q | H | S | L | V | N | G | G | DELETED | DELETED |
| Q | H | S | L | V | N | G | G | DELETED | P |
| Q | H | S | L | V | N | G | G | P | DELETED |
| Q | H | S | L | V | N | G | G | P | P |
| Q | H | R | T | A | Y | DELETED | DELETED | DELETED | DELETED |
| Q | H | R | T | A | Y | DELETED | DELETED | DELETED | P |
| Q | H | R | T | A | Y | DELETED | DELETED | P | DELETED |
| Q | H | R | T | A | Y | DELETED | DELETED | P | P |
| Q | H | R | T | A | Y | DELETED | G | DELETED | DELETED |
| Q | H | R | T | A | Y | DELETED | G | DELETED | P |
| Q | H | R | T | A | Y | DELETED | G | P | DELETED |
| Q | H | R | T | A | Y | DELETED | G | P | P |
| Q | H | R | T | A | Y | G | DELETED | DELETED | DELETED |
| Q | H | R | T | A | Y | G | DELETED | DELETED | P |
| Q | H | R | T | A | Y | G | DELETED | P | DELETED |
| Q | H | R | T | A | Y | G | DELETED | P | P |
| Q | H | R | T | A | Y | G | G | DELETED | DELETED |
| Q | H | R | T | A | Y | G | G | DELETED | P |
| Q | H | R | T | A | Y | G | G | P | DELETED |
| Q | H | R | T | A | Y | G | G | P | P |
| Q | H | R | T | A | N | DELETED | DELETED | DELETED | DELETED |
| Q | H | R | T | A | N | DELETED | DELETED | DELETED | P |
| Q | H | R | T | A | N | DELETED | DELETED | P | DELETED |
| Q | H | R | T | A | N | DELETED | DELETED | P | P |
| Q | H | R | T | A | N | DELETED | G | DELETED | DELETED |
| Q | H | R | T | A | N | DELETED | G | DELETED | P |
| Q | H | R | T | A | N | DELETED | G | P | DELETED |
| Q | H | R | T | A | N | DELETED | G | P | P |
| Q | H | R | T | A | N | G | DELETED | DELETED | DELETED |
| Q | H | R | T | A | N | G | DELETED | DELETED | P |
| Q | H | R | T | A | N | G | DELETED | P | DELETED |
| Q | H | R | T | A | N | G | DELETED | P | P |
| Q | H | R | T | A | N | G | G | DELETED | DELETED |
| Q | H | R | T | A | N | G | G | DELETED | P |
| Q | H | R | T | A | N | G | G | P | DELETED |
| Q | H | R | T | A | N | G | G | P | P |
| Q | H | R | T | V | Y | DELETED | DELETED | DELETED | DELETED |
| Q | H | R | T | V | Y | DELETED | DELETED | DELETED | P |
| Q | H | R | T | V | Y | DELETED | DELETED | P | DELETED |
| Q | H | R | T | V | Y | DELETED | DELETED | P | P |
| Q | H | R | T | V | Y | DELETED | G | DELETED | DELETED |
| Q | H | R | T | V | Y | DELETED | G | DELETED | P |
| Q | H | R | T | V | Y | DELETED | G | P | DELETED |
| Q | H | R | T | V | Y | DELETED | G | P | P |
| Q | H | R | T | V | Y | G | DELETED | DELETED | DELETED |
| Q | H | R | T | V | Y | G | DELETED | DELETED | P |
| Q | H | R | T | V | Y | G | DELETED | P | DELETED |
| Q | H | R | T | V | Y | G | DELETED | P | P |
| Q | H | R | T | V | Y | G | G | DELETED | DELETED |
| Q | H | R | T | V | Y | G | G | DELETED | P |
| Q | H | R | T | V | Y | G | G | P | DELETED |
| Q | H | R | T | V | Y | G | G | P | P |
| Q | H | R | T | V | N | DELETED | DELETED | DELETED | DELETED |
| Q | H | R | T | V | N | DELETED | DELETED | DELETED | P |
| Q | H | R | T | V | N | DELETED | DELETED | P | DELETED |
| Q | H | R | T | V | N | DELETED | DELETED | P | P |
| Q | H | R | T | V | N | DELETED | G | DELETED | DELETED |
| Q | H | R | T | V | N | DELETED | G | DELETED | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| Q | H | R | T | V | N | DELETED | G | P | DELETED |
| Q | H | R | T | V | N | DELETED | G | P | P |
| Q | H | R | T | V | N | G | DELETED | DELETED | DELETED |
| Q | H | R | T | V | N | G | DELETED | DELETED | P |
| Q | H | R | T | V | N | G | DELETED | P | DELETED |
| Q | H | R | T | V | N | G | DELETED | P | P |
| Q | H | R | T | V | N | G | G | DELETED | DELETED |
| Q | H | R | T | V | N | G | G | DELETED | P |
| Q | H | R | T | V | N | G | G | P | DELETED |
| Q | H | R | T | V | N | G | G | P | P |
| Q | H | R | L | A | Y | DELETED | DELETED | DELETED | DELETED |
| Q | H | R | L | A | Y | DELETED | DELETED | DELETED | P |
| Q | H | R | L | A | Y | DELETED | DELETED | P | DELETED |
| Q | H | R | L | A | Y | DELETED | DELETED | P | P |
| Q | H | R | L | A | Y | DELETED | G | DELETED | DELETED |
| Q | H | R | L | A | Y | DELETED | G | DELETED | P |
| Q | H | R | L | A | Y | DELETED | G | P | DELETED |
| Q | H | R | L | A | Y | DELETED | G | P | P |
| Q | H | R | L | A | Y | G | DELETED | DELETED | DELETED |
| Q | H | R | L | A | Y | G | DELETED | DELETED | P |
| Q | H | R | L | A | Y | G | DELETED | P | DELETED |
| Q | H | R | L | A | Y | G | DELETED | P | P |
| Q | H | R | L | A | Y | G | G | DELETED | DELETED |
| Q | H | R | L | A | Y | G | G | DELETED | P |
| Q | H | R | L | A | Y | G | G | P | DELETED |
| Q | H | R | L | A | Y | G | G | P | P |
| Q | H | R | L | A | N | DELETED | DELETED | DELETED | DELETED |
| Q | H | R | L | A | N | DELETED | DELETED | DELETED | P |
| Q | H | R | L | A | N | DELETED | DELETED | P | DELETED |
| Q | H | R | L | A | N | DELETED | DELETED | P | P |
| Q | H | R | L | A | N | DELETED | G | DELETED | DELETED |
| Q | H | R | L | A | N | DELETED | G | DELETED | P |
| Q | H | R | L | A | N | DELETED | G | P | DELETED |
| Q | H | R | L | A | N | DELETED | G | P | P |
| Q | H | R | L | A | N | G | DELETED | DELETED | DELETED |
| Q | H | R | L | A | N | G | DELETED | DELETED | P |
| Q | H | R | L | A | N | G | DELETED | P | DELETED |
| Q | H | R | L | A | N | G | DELETED | P | P |
| Q | H | R | L | A | N | G | G | DELETED | DELETED |
| Q | H | R | L | A | N | G | G | DELETED | P |
| Q | H | R | L | A | N | G | G | P | DELETED |
| Q | H | R | L | A | N | G | G | P | P |
| Q | H | R | L | V | Y | DELETED | DELETED | DELETED | DELETED |
| Q | H | R | L | V | Y | DELETED | DELETED | DELETED | P |
| Q | H | R | L | V | Y | DELETED | DELETED | P | DELETED |
| Q | H | R | L | V | Y | DELETED | DELETED | P | P |
| Q | H | R | L | V | Y | DELETED | G | DELETED | DELETED |
| Q | H | R | L | V | Y | DELETED | G | DELETED | P |
| Q | H | R | L | V | Y | DELETED | G | P | DELETED |
| Q | H | R | L | V | Y | DELETED | G | P | P |
| Q | H | R | L | V | Y | G | DELETED | DELETED | DELETED |
| Q | H | R | L | V | Y | G | DELETED | DELETED | P |
| Q | H | R | L | V | Y | G | DELETED | P | DELETED |
| Q | H | R | L | V | Y | G | DELETED | P | P |
| Q | H | R | L | V | Y | G | G | DELETED | DELETED |
| Q | H | R | L | V | Y | G | G | DELETED | P |
| Q | H | R | L | V | Y | G | G | P | DELETED |
| Q | H | R | L | V | Y | G | G | P | P |
| Q | H | R | L | V | N | DELETED | DELETED | DELETED | DELETED |
| Q | H | R | L | V | N | DELETED | DELETED | DELETED | P |
| Q | H | R | L | V | N | DELETED | DELETED | P | DELETED |
| Q | H | R | L | V | N | DELETED | DELETED | P | P |
| Q | H | R | L | V | N | DELETED | G | DELETED | DELETED |
| Q | H | R | L | V | N | DELETED | G | DELETED | P |
| Q | H | R | L | V | N | DELETED | G | P | DELETED |
| Q | H | R | L | V | N | DELETED | G | P | P |
| Q | H | R | L | V | N | G | DELETED | DELETED | DELETED |
| Q | H | R | L | V | N | G | DELETED | DELETED | P |
| Q | H | R | L | V | N | G | DELETED | P | DELETED |
| Q | H | R | L | V | N | G | DELETED | P | P |
| Q | H | R | L | V | N | G | G | DELETED | DELETED |
| Q | H | R | L | V | N | G | G | DELETED | P |
| Q | H | R | L | V | N | G | G | P | DELETED |
| Q | H | R | L | V | N | G | G | P | P |

TABLE 6-continued

| Exemplary Mutations of mAb 2.175.3 Heavy Chain (SEQ ID NO: 2) to Germline at the Indicated Residue Number. | | | | | | | | | |
|---|---|---|---|---|---|---|---|---|---|
| 3 | 35 | 53 | 57 | 61 | 80 | 99 | 100 | 101 | 106 |
| H | S | S | T | A | Y | DELETED | DELETED | DELETED | DELETED |
| H | S | S | T | A | Y | DELETED | DELETED | DELETED | P |
| H | S | S | T | A | Y | DELETED | DELETED | P | DELETED |
| H | S | S | T | A | Y | DELETED | DELETED | P | P |
| H | S | S | T | A | Y | DELETED | G | DELETED | DELETED |
| H | S | S | T | A | Y | DELETED | G | DELETED | P |
| H | S | S | T | A | Y | DELETED | G | P | DELETED |
| H | S | S | T | A | Y | DELETED | G | P | P |
| H | S | S | T | A | Y | G | DELETED | DELETED | DELETED |
| H | S | S | T | A | Y | G | DELETED | DELETED | P |
| H | S | S | T | A | Y | G | DELETED | P | DELETED |
| H | S | S | T | A | Y | G | DELETED | P | P |
| H | S | S | T | A | Y | G | G | DELETED | DELETED |
| H | S | S | T | A | Y | G | G | DELETED | P |
| H | S | S | T | A | Y | G | G | P | DELETED |
| H | S | S | T | A | Y | G | G | P | P |
| H | S | S | T | A | N | DELETED | DELETED | DELETED | DELETED |
| H | S | S | T | A | N | DELETED | DELETED | DELETED | P |
| H | S | S | T | A | N | DELETED | DELETED | P | DELETED |
| H | S | S | T | A | N | DELETED | DELETED | P | P |
| H | S | S | T | A | N | DELETED | G | DELETED | DELETED |
| H | S | S | T | A | N | DELETED | G | DELETED | P |
| H | S | S | T | A | N | DELETED | G | P | DELETED |
| H | S | S | T | A | N | DELETED | G | P | P |
| H | S | S | T | A | N | G | DELETED | DELETED | DELETED |
| H | S | S | T | A | N | G | DELETED | DELETED | P |
| H | S | S | T | A | N | G | DELETED | P | DELETED |
| H | S | S | T | A | N | G | DELETED | P | P |
| H | S | S | T | A | N | G | G | DELETED | DELETED |
| H | S | S | T | A | N | G | G | DELETED | P |
| H | S | S | T | A | N | G | G | P | DELETED |
| H | S | S | T | A | N | G | G | P | P |
| H | S | S | T | V | Y | DELETED | DELETED | DELETED | DELETED |
| H | S | S | T | V | Y | DELETED | DELETED | DELETED | P |
| H | S | S | T | V | Y | DELETED | DELETED | P | DELETED |
| H | S | S | T | V | Y | DELETED | DELETED | P | P |
| H | S | S | T | V | Y | DELETED | G | DELETED | DELETED |
| H | S | S | T | V | Y | DELETED | G | DELETED | P |
| H | S | S | T | V | Y | DELETED | G | P | DELETED |
| H | S | S | T | V | Y | DELETED | G | P | P |
| H | S | S | T | V | Y | G | DELETED | DELETED | DELETED |
| H | S | S | T | V | Y | G | DELETED | DELETED | P |
| H | S | S | T | V | Y | G | DELETED | P | DELETED |
| H | S | S | T | V | Y | G | DELETED | P | P |
| H | S | S | T | V | Y | G | G | DELETED | DELETED |
| H | S | S | T | V | Y | G | G | DELETED | P |
| H | S | S | T | V | Y | G | G | P | DELETED |
| H | S | S | T | V | Y | G | G | P | P |
| H | S | S | T | V | N | DELETED | DELETED | DELETED | DELETED |
| H | S | S | T | V | N | DELETED | DELETED | DELETED | P |
| H | S | S | T | V | N | DELETED | DELETED | P | DELETED |
| H | S | S | T | V | N | DELETED | DELETED | P | P |
| H | S | S | T | V | N | DELETED | G | DELETED | DELETED |
| H | S | S | T | V | N | DELETED | G | DELETED | P |
| H | S | S | T | V | N | DELETED | G | P | DELETED |
| H | S | S | T | V | N | DELETED | G | P | P |
| H | S | S | T | V | N | G | DELETED | DELETED | DELETED |
| H | S | S | T | V | N | G | DELETED | DELETED | P |
| H | S | S | T | V | N | G | DELETED | P | DELETED |
| H | S | S | T | V | N | G | DELETED | P | P |
| H | S | S | T | V | N | G | G | DELETED | DELETED |
| H | S | S | T | V | N | G | G | DELETED | P |
| H | S | S | T | V | N | G | G | P | DELETED |
| H | S | S | T | V | N | G | G | P | P |
| H | S | S | L | A | Y | DELETED | DELETED | DELETED | DELETED |
| H | S | S | L | A | Y | DELETED | DELETED | DELETED | P |
| H | S | S | L | A | Y | DELETED | DELETED | P | DELETED |
| H | S | S | L | A | Y | DELETED | DELETED | P | P |
| H | S | S | L | A | Y | DELETED | G | DELETED | DELETED |
| H | S | S | L | A | Y | DELETED | G | DELETED | P |
| H | S | S | L | A | Y | DELETED | G | P | DELETED |
| H | S | S | L | A | Y | DELETED | G | P | P |
| H | S | S | L | A | Y | G | DELETED | DELETED | DELETED |
| H | S | S | L | A | Y | G | DELETED | DELETED | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| H | S | S | L | A | Y | G | DELETED | P | DELETED |
| H | S | S | L | A | Y | G | DELETED | P | P |
| H | S | S | L | A | Y | G | G | DELETED | DELETED |
| H | S | S | L | A | Y | G | G | DELETED | P |
| H | S | S | L | A | Y | G | G | P | DELETED |
| H | S | S | L | A | Y | G | G | P | P |
| H | S | S | L | A | N | DELETED | DELETED | DELETED | DELETED |
| H | S | S | L | A | N | DELETED | DELETED | DELETED | P |
| H | S | S | L | A | N | DELETED | DELETED | P | DELETED |
| H | S | S | L | A | N | DELETED | DELETED | P | P |
| H | S | S | L | A | N | DELETED | G | DELETED | DELETED |
| H | S | S | L | A | N | DELETED | G | DELETED | P |
| H | S | S | L | A | N | DELETED | G | P | DELETED |
| H | S | S | L | A | N | DELETED | G | P | P |
| H | S | S | L | A | N | G | DELETED | DELETED | DELETED |
| H | S | S | L | A | N | G | DELETED | DELETED | P |
| H | S | S | L | A | N | G | DELETED | P | DELETED |
| H | S | S | L | A | N | G | DELETED | P | P |
| H | S | S | L | A | N | G | G | DELETED | DELETED |
| H | S | S | L | A | N | G | G | DELETED | P |
| H | S | S | L | A | N | G | G | P | DELETED |
| H | S | S | L | A | N | G | G | P | P |
| H | S | S | L | V | Y | DELETED | DELETED | DELETED | DELETED |
| H | S | S | L | V | Y | DELETED | DELETED | DELETED | P |
| H | S | S | L | V | Y | DELETED | DELETED | P | DELETED |
| H | S | S | L | V | Y | DELETED | DELETED | P | P |
| H | S | S | L | V | Y | DELETED | G | DELETED | DELETED |
| H | S | S | L | V | Y | DELETED | G | DELETED | P |
| H | S | S | L | V | Y | DELETED | G | P | DELETED |
| H | S | S | L | V | Y | DELETED | G | P | P |
| H | S | S | L | V | Y | G | DELETED | DELETED | DELETED |
| H | S | S | L | V | Y | G | DELETED | DELETED | P |
| H | S | S | L | V | Y | G | DELETED | P | DELETED |
| H | S | S | L | V | Y | G | DELETED | P | P |
| H | S | S | L | V | Y | G | G | DELETED | DELETED |
| H | S | S | L | V | Y | G | G | DELETED | P |
| H | S | S | L | V | Y | G | G | P | DELETED |
| H | S | S | L | V | Y | G | G | P | P |
| H | S | S | L | V | N | DELETED | DELETED | DELETED | DELETED |
| H | S | S | L | V | N | DELETED | DELETED | DELETED | P |
| H | S | S | L | V | N | DELETED | DELETED | P | DELETED |
| H | S | S | L | V | N | DELETED | DELETED | P | P |
| H | S | S | L | V | N | DELETED | G | DELETED | DELETED |
| H | S | S | L | V | N | DELETED | G | DELETED | P |
| H | S | S | L | V | N | DELETED | G | P | DELETED |
| H | S | S | L | V | N | DELETED | G | P | P |
| H | S | S | L | V | N | G | DELETED | DELETED | DELETED |
| H | S | S | L | V | N | G | DELETED | DELETED | P |
| H | S | S | L | V | N | G | DELETED | P | DELETED |
| H | S | S | L | V | N | G | DELETED | P | P |
| H | S | S | L | V | N | G | G | DELETED | DELETED |
| H | S | S | L | V | N | G | G | DELETED | P |
| H | S | S | L | V | N | G | G | P | DELETED |
| H | S | S | L | V | N | G | G | P | P |
| H | S | R | T | A | Y | DELETED | DELETED | DELETED | DELETED |
| H | S | R | T | A | Y | DELETED | DELETED | DELETED | P |
| H | S | R | T | A | Y | DELETED | DELETED | P | DELETED |
| H | S | R | T | A | Y | DELETED | DELETED | P | P |
| H | S | R | T | A | Y | DELETED | G | DELETED | DELETED |
| H | S | R | T | A | Y | DELETED | G | DELETED | P |
| H | S | R | T | A | Y | DELETED | G | P | DELETED |
| H | S | R | T | A | Y | DELETED | G | P | P |
| H | S | R | T | A | Y | G | DELETED | DELETED | DELETED |
| H | S | R | T | A | Y | G | DELETED | DELETED | P |
| H | S | R | T | A | Y | G | DELETED | P | DELETED |
| H | S | R | T | A | Y | G | DELETED | P | P |
| H | S | R | T | A | Y | G | G | DELETED | DELETED |
| H | S | R | T | A | Y | G | G | DELETED | P |
| H | S | R | T | A | Y | G | G | P | DELETED |
| H | S | R | T | A | Y | G | G | P | P |
| H | S | R | T | A | N | DELETED | DELETED | DELETED | DELETED |
| H | S | R | T | A | N | DELETED | DELETED | DELETED | P |
| H | S | R | T | A | N | DELETED | DELETED | P | DELETED |
| H | S | R | T | A | N | DELETED | DELETED | P | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| H | S | R | T | A | N | DELETED | G | DELETED | DELETED |
| H | S | R | T | A | N | DELETED | G | DELETED | P |
| H | S | R | T | A | N | DELETED | G | P | DELETED |
| H | S | R | T | A | N | DELETED | G | P | P |
| H | S | R | T | A | N | G | DELETED | DELETED | DELETED |
| H | S | R | T | A | N | G | DELETED | DELETED | P |
| H | S | R | T | A | N | G | DELETED | P | DELETED |
| H | S | R | T | A | N | G | DELETED | P | P |
| H | S | R | T | A | N | G | G | DELETED | DELETED |
| H | S | R | T | A | N | G | G | DELETED | P |
| H | S | R | T | A | N | G | G | P | DELETED |
| H | S | R | T | A | N | G | G | P | P |
| H | S | R | T | V | Y | DELETED | DELETED | DELETED | DELETED |
| H | S | R | T | V | Y | DELETED | DELETED | DELETED | P |
| H | S | R | T | V | Y | DELETED | DELETED | P | DELETED |
| H | S | R | T | V | Y | DELETED | DELETED | P | P |
| H | S | R | T | V | Y | DELETED | G | DELETED | DELETED |
| H | S | R | T | V | Y | DELETED | G | DELETED | P |
| H | S | R | T | V | Y | DELETED | G | P | DELETED |
| H | S | R | T | V | Y | DELETED | G | P | P |
| H | S | R | T | V | Y | G | DELETED | DELETED | DELETED |
| H | S | R | T | V | Y | G | DELETED | DELETED | P |
| H | S | R | T | V | Y | G | DELETED | P | DELETED |
| H | S | R | T | V | Y | G | DELETED | P | P |
| H | S | R | T | V | Y | G | G | DELETED | DELETED |
| H | S | R | T | V | Y | G | G | DELETED | P |
| H | S | R | T | V | Y | G | G | P | DELETED |
| H | S | R | T | V | Y | G | G | P | P |
| H | S | R | T | V | N | DELETED | DELETED | DELETED | DELETED |
| H | S | R | T | V | N | DELETED | DELETED | DELETED | P |
| H | S | R | T | V | N | DELETED | DELETED | P | DELETED |
| H | S | R | T | V | N | DELETED | DELETED | P | P |
| H | S | R | T | V | N | DELETED | G | DELETED | DELETED |
| H | S | R | T | V | N | DELETED | G | DELETED | P |
| H | S | R | T | V | N | DELETED | G | P | DELETED |
| H | S | R | T | V | N | DELETED | G | P | P |
| H | S | R | T | V | N | G | DELETED | DELETED | DELETED |
| H | S | R | T | V | N | G | DELETED | DELETED | P |
| H | S | R | T | V | N | G | DELETED | P | DELETED |
| H | S | R | T | V | N | G | DELETED | P | P |
| H | S | R | T | V | N | G | G | DELETED | DELETED |
| H | S | R | T | V | N | G | G | DELETED | P |
| H | S | R | T | V | N | G | G | P | DELETED |
| H | S | R | T | V | N | G | G | P | P |
| H | S | R | L | A | Y | DELETED | DELETED | DELETED | DELETED |
| H | S | R | L | A | Y | DELETED | DELETED | DELETED | P |
| H | S | R | L | A | Y | DELETED | DELETED | P | DELETED |
| H | S | R | L | A | Y | DELETED | DELETED | P | P |
| H | S | R | L | A | Y | DELETED | G | DELETED | DELETED |
| H | S | R | L | A | Y | DELETED | G | DELETED | P |
| H | S | R | L | A | Y | DELETED | G | P | DELETED |
| H | S | R | L | A | Y | DELETED | G | P | P |
| H | S | R | L | A | Y | G | DELETED | DELETED | DELETED |
| H | S | R | L | A | Y | G | DELETED | DELETED | P |
| H | S | R | L | A | Y | G | DELETED | P | DELETED |
| H | S | R | L | A | Y | G | DELETED | P | P |
| H | S | R | L | A | Y | G | G | DELETED | DELETED |
| H | S | R | L | A | Y | G | G | DELETED | P |
| H | S | R | L | A | Y | G | G | P | DELETED |
| H | S | R | L | A | Y | G | G | P | P |
| H | S | R | L | A | N | DELETED | DELETED | DELETED | DELETED |
| H | S | R | L | A | N | DELETED | DELETED | DELETED | P |
| H | S | R | L | A | N | DELETED | DELETED | P | DELETED |
| H | S | R | L | A | N | DELETED | DELETED | P | P |
| H | S | R | L | A | N | DELETED | G | DELETED | DELETED |
| H | S | R | L | A | N | DELETED | G | DELETED | P |
| H | S | R | L | A | N | DELETED | G | P | DELETED |
| H | S | R | L | A | N | DELETED | G | P | P |
| H | S | R | L | A | N | G | DELETED | DELETED | DELETED |
| H | S | R | L | A | N | G | DELETED | DELETED | P |
| H | S | R | L | A | N | G | DELETED | P | DELETED |
| H | S | R | L | A | N | G | DELETED | P | P |
| H | S | R | L | A | N | G | G | DELETED | DELETED |
| H | S | R | L | A | N | G | G | DELETED | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| H | S | R | L | A | N | G | G | P | DELETED |
| H | S | R | L | A | N | G | G | P | P |
| H | S | R | L | V | Y | DELETED | DELETED | DELETED | DELETED |
| H | S | R | L | V | Y | DELETED | DELETED | DELETED | P |
| H | S | R | L | V | Y | DELETED | DELETED | P | DELETED |
| H | S | R | L | V | Y | DELETED | DELETED | P | P |
| H | S | R | L | V | Y | DELETED | G | DELETED | DELETED |
| H | S | R | L | V | Y | DELETED | G | DELETED | P |
| H | S | R | L | V | Y | DELETED | G | P | DELETED |
| H | S | R | L | V | Y | DELETED | G | P | P |
| H | S | R | L | V | Y | G | DELETED | DELETED | DELETED |
| H | S | R | L | V | Y | G | DELETED | DELETED | P |
| H | S | R | L | V | Y | G | DELETED | P | DELETED |
| H | S | R | L | V | Y | G | DELETED | P | P |
| H | S | R | L | V | Y | G | G | DELETED | DELETED |
| H | S | R | L | V | Y | G | G | DELETED | P |
| H | S | R | L | V | Y | G | G | P | DELETED |
| H | S | R | L | V | Y | G | G | P | P |
| H | S | R | L | V | N | DELETED | DELETED | DELETED | DELETED |
| H | S | R | L | V | N | DELETED | DELETED | DELETED | P |
| H | S | R | L | V | N | DELETED | DELETED | P | DELETED |
| H | S | R | L | V | N | DELETED | DELETED | P | P |
| H | S | R | L | V | N | DELETED | G | DELETED | DELETED |
| H | S | R | L | V | N | DELETED | G | DELETED | P |
| H | S | R | L | V | N | DELETED | G | P | DELETED |
| H | S | R | L | V | N | DELETED | G | P | P |
| H | S | R | L | V | N | G | DELETED | DELETED | DELETED |
| H | S | R | L | V | N | G | DELETED | DELETED | P |
| H | S | R | L | V | N | G | DELETED | P | DELETED |
| H | S | R | L | V | N | G | DELETED | P | P |
| H | S | R | L | V | N | G | G | DELETED | DELETED |
| H | S | R | L | V | N | G | G | DELETED | P |
| H | S | R | L | V | N | G | G | P | DELETED |
| H | S | R | L | V | N | G | G | P | P |
| H | H | S | T | A | Y | DELETED | DELETED | DELETED | DELETED |
| H | H | S | T | A | Y | DELETED | DELETED | DELETED | P |
| H | H | S | T | A | Y | DELETED | DELETED | P | DELETED |
| H | H | S | T | A | Y | DELETED | DELETED | P | P |
| H | H | S | T | A | Y | DELETED | G | DELETED | DELETED |
| H | H | S | T | A | Y | DELETED | G | DELETED | P |
| H | H | S | T | A | Y | DELETED | G | P | DELETED |
| H | H | S | T | A | Y | DELETED | G | P | P |
| H | H | S | T | A | Y | G | DELETED | DELETED | DELETED |
| H | H | S | T | A | Y | G | DELETED | DELETED | P |
| H | H | S | T | A | Y | G | DELETED | P | DELETED |
| H | H | S | T | A | Y | G | DELETED | P | P |
| H | H | S | T | A | Y | G | G | DELETED | DELETED |
| H | H | S | T | A | Y | G | G | DELETED | P |
| H | H | S | T | A | Y | G | G | P | DELETED |
| H | H | S | T | A | Y | G | G | P | P |
| H | H | S | T | A | N | DELETED | DELETED | DELETED | DELETED |
| H | H | S | T | A | N | DELETED | DELETED | DELETED | P |
| H | H | S | T | A | N | DELETED | DELETED | P | DELETED |
| H | H | S | T | A | N | DELETED | DELETED | P | P |
| H | H | S | T | A | N | DELETED | G | DELETED | DELETED |
| H | H | S | T | A | N | DELETED | G | DELETED | P |
| H | H | S | T | A | N | DELETED | G | P | DELETED |
| H | H | S | T | A | N | DELETED | G | P | P |
| H | H | S | T | A | N | G | DELETED | DELETED | DELETED |
| H | H | S | T | A | N | G | DELETED | DELETED | P |
| H | H | S | T | A | N | G | DELETED | P | DELETED |
| H | H | S | T | A | N | G | DELETED | P | P |
| H | H | S | T | A | N | G | G | DELETED | DELETED |
| H | H | S | T | A | N | G | G | DELETED | P |
| H | H | S | T | A | N | G | G | P | DELETED |
| H | H | S | T | A | N | G | G | P | P |
| H | H | S | T | V | Y | DELETED | DELETED | DELETED | DELETED |
| H | H | S | T | V | Y | DELETED | DELETED | DELETED | P |
| H | H | S | T | V | Y | DELETED | DELETED | P | DELETED |
| H | H | S | T | V | Y | DELETED | DELETED | P | P |
| H | H | S | T | V | Y | DELETED | G | DELETED | DELETED |
| H | H | S | T | V | Y | DELETED | G | DELETED | P |
| H | H | S | T | V | Y | DELETED | G | P | DELETED |
| H | H | S | T | V | Y | DELETED | G | P | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| H | H | S | T | V | Y | G | DELETED | DELETED | DELETED |
| H | H | S | T | V | Y | G | DELETED | DELETED | P |
| H | H | S | T | V | Y | G | DELETED | P | DELETED |
| H | H | S | T | V | Y | G | DELETED | P | P |
| H | H | S | T | V | Y | G | G | DELETED | DELETED |
| H | H | S | T | V | Y | G | G | DELETED | P |
| H | H | S | T | V | Y | G | G | P | DELETED |
| H | H | S | T | V | Y | G | G | P | P |
| H | H | S | T | V | N | DELETED | DELETED | DELETED | DELETED |
| H | H | S | T | V | N | DELETED | DELETED | DELETED | P |
| H | H | S | T | V | N | DELETED | DELETED | P | DELETED |
| H | H | S | T | V | N | DELETED | DELETED | P | P |
| H | H | S | T | V | N | DELETED | G | DELETED | DELETED |
| H | H | S | T | V | N | DELETED | G | DELETED | P |
| H | H | S | T | V | N | DELETED | G | P | DELETED |
| H | H | S | T | V | N | DELETED | G | P | P |
| H | H | S | T | V | N | G | DELETED | DELETED | DELETED |
| H | H | S | T | V | N | G | DELETED | DELETED | P |
| H | H | S | T | V | N | G | DELETED | P | DELETED |
| H | H | S | T | V | N | G | DELETED | P | P |
| H | H | S | T | V | N | G | G | DELETED | DELETED |
| H | H | S | T | V | N | G | G | DELETED | P |
| H | H | S | T | V | N | G | G | P | DELETED |
| H | H | S | T | V | N | G | G | P | P |
| H | H | S | L | A | Y | DELETED | DELETED | DELETED | DELETED |
| H | H | S | L | A | Y | DELETED | DELETED | DELETED | P |
| H | H | S | L | A | Y | DELETED | DELETED | P | DELETED |
| H | H | S | L | A | Y | DELETED | DELETED | P | P |
| H | H | S | L | A | Y | DELETED | G | DELETED | DELETED |
| H | H | S | L | A | Y | DELETED | G | DELETED | P |
| H | H | S | L | A | Y | DELETED | G | P | DELETED |
| H | H | S | L | A | Y | DELETED | G | P | P |
| H | H | S | L | A | Y | G | DELETED | DELETED | DELETED |
| H | H | S | L | A | Y | G | DELETED | DELETED | P |
| H | H | S | L | A | Y | G | DELETED | P | DELETED |
| H | H | S | L | A | Y | G | DELETED | P | P |
| H | H | S | L | A | Y | G | G | DELETED | DELETED |
| H | H | S | L | A | Y | G | G | DELETED | P |
| H | H | S | L | A | Y | G | G | P | DELETED |
| H | H | S | L | A | Y | G | G | P | P |
| H | H | S | L | A | N | DELETED | DELETED | DELETED | DELETED |
| H | H | S | L | A | N | DELETED | DELETED | DELETED | P |
| H | H | S | L | A | N | DELETED | DELETED | P | DELETED |
| H | H | S | L | A | N | DELETED | DELETED | P | P |
| H | H | S | L | A | N | DELETED | G | DELETED | DELETED |
| H | H | S | L | A | N | DELETED | G | DELETED | P |
| H | H | S | L | A | N | DELETED | G | P | DELETED |
| H | H | S | L | A | N | DELETED | G | P | P |
| H | H | S | L | A | N | G | DELETED | DELETED | DELETED |
| H | H | S | L | A | N | G | DELETED | DELETED | P |
| H | H | S | L | A | N | G | DELETED | P | DELETED |
| H | H | S | L | A | N | G | DELETED | P | P |
| H | H | S | L | A | N | G | G | DELETED | DELETED |
| H | H | S | L | A | N | G | G | DELETED | P |
| H | H | S | L | A | N | G | G | P | DELETED |
| H | H | S | L | A | N | G | G | P | P |
| H | H | S | L | V | Y | DELETED | DELETED | DELETED | DELETED |
| H | H | S | L | V | Y | DELETED | DELETED | DELETED | P |
| H | H | S | L | V | Y | DELETED | DELETED | P | DELETED |
| H | H | S | L | V | Y | DELETED | DELETED | P | P |
| H | H | S | L | V | Y | DELETED | G | DELETED | DELETED |
| H | H | S | L | V | Y | DELETED | G | DELETED | P |
| H | H | S | L | V | Y | DELETED | G | P | DELETED |
| H | H | S | L | V | Y | DELETED | G | P | P |
| H | H | S | L | V | Y | G | DELETED | DELETED | DELETED |
| H | H | S | L | V | Y | G | DELETED | DELETED | P |
| H | H | S | L | V | Y | G | DELETED | P | DELETED |
| H | H | S | L | V | Y | G | DELETED | P | P |
| H | H | S | L | V | Y | G | G | DELETED | DELETED |
| H | H | S | L | V | Y | G | G | DELETED | P |
| H | H | S | L | V | Y | G | G | P | DELETED |
| H | H | S | L | V | Y | G | G | P | P |
| H | H | S | L | V | N | DELETED | DELETED | DELETED | DELETED |
| H | H | S | L | V | N | DELETED | DELETED | DELETED | P |

TABLE 6-continued

| Exemplary Mutations of mAb 2.175.3 Heavy Chain (SEQ ID NO: 2) to Germline at the Indicated Residue Number. | | | | | | | | | |
|---|---|---|---|---|---|---|---|---|---|
| 3 | 35 | 53 | 57 | 61 | 80 | 99 | 100 | 101 | 106 |
| H | H | S | L | V | N | DELETED | DELETED | P | DELETED |
| H | H | S | L | V | N | DELETED | DELETED | P | P |
| H | H | S | L | V | N | DELETED | G | DELETED | DELETED |
| H | H | S | L | V | N | DELETED | G | DELETED | P |
| H | H | S | L | V | N | DELETED | G | P | DELETED |
| H | H | S | L | V | N | DELETED | G | P | P |
| H | H | S | L | V | N | G | DELETED | DELETED | DELETED |
| H | H | S | L | V | N | G | DELETED | DELETED | P |
| H | H | S | L | V | N | G | DELETED | P | DELETED |
| H | H | S | L | V | N | G | DELETED | P | P |
| H | H | S | L | V | N | G | G | DELETED | DELETED |
| H | H | S | L | V | N | G | G | DELETED | P |
| H | H | S | L | V | N | G | G | P | DELETED |
| H | H | S | L | V | N | G | G | P | P |
| H | H | R | T | A | Y | DELETED | DELETED | DELETED | DELETED |
| H | H | R | T | A | Y | DELETED | DELETED | DELETED | P |
| H | H | R | T | A | Y | DELETED | DELETED | P | DELETED |
| H | H | R | T | A | Y | DELETED | DELETED | P | P |
| H | H | R | T | A | Y | DELETED | G | DELETED | DELETED |
| H | H | R | T | A | Y | DELETED | G | DELETED | P |
| H | H | R | T | A | Y | DELETED | G | P | DELETED |
| H | H | R | T | A | Y | DELETED | G | P | P |
| H | H | R | T | A | Y | G | DELETED | DELETED | DELETED |
| H | H | R | T | A | Y | G | DELETED | DELETED | P |
| H | H | R | T | A | Y | G | DELETED | P | DELETED |
| H | H | R | T | A | Y | G | DELETED | P | P |
| H | H | R | T | A | Y | G | G | DELETED | DELETED |
| H | H | R | T | A | Y | G | G | DELETED | P |
| H | H | R | T | A | Y | G | G | P | DELETED |
| H | H | R | T | A | Y | G | G | P | P |
| H | H | R | T | A | N | DELETED | DELETED | DELETED | DELETED |
| H | H | R | T | A | N | DELETED | DELETED | DELETED | P |
| H | H | R | T | A | N | DELETED | DELETED | P | DELETED |
| H | H | R | T | A | N | DELETED | DELETED | P | P |
| H | H | R | T | A | N | DELETED | G | DELETED | DELETED |
| H | H | R | T | A | N | DELETED | G | DELETED | P |
| H | H | R | T | A | N | DELETED | G | P | DELETED |
| H | H | R | T | A | N | DELETED | G | P | P |
| H | H | R | T | A | N | G | DELETED | DELETED | DELETED |
| H | H | R | T | A | N | G | DELETED | DELETED | P |
| H | H | R | T | A | N | G | DELETED | P | DELETED |
| H | H | R | T | A | N | G | DELETED | P | P |
| H | H | R | T | A | N | G | G | DELETED | DELETED |
| H | H | R | T | A | N | G | G | DELETED | P |
| H | H | R | T | A | N | G | G | P | DELETED |
| H | H | R | T | A | N | G | G | P | P |
| H | H | R | T | V | Y | DELETED | DELETED | DELETED | DELETED |
| H | H | R | T | V | Y | DELETED | DELETED | DELETED | P |
| H | H | R | T | V | Y | DELETED | DELETED | P | DELETED |
| H | H | R | T | V | Y | DELETED | DELETED | P | P |
| H | H | R | T | V | Y | DELETED | G | DELETED | DELETED |
| H | H | R | T | V | Y | DELETED | G | DELETED | P |
| H | H | R | T | V | Y | DELETED | G | P | DELETED |
| H | H | R | T | V | Y | DELETED | G | P | P |
| H | H | R | T | V | Y | G | DELETED | DELETED | DELETED |
| H | H | R | T | V | Y | G | DELETED | DELETED | P |
| H | H | R | T | V | Y | G | DELETED | P | DELETED |
| H | H | R | T | V | Y | G | DELETED | P | P |
| H | H | R | T | V | Y | G | G | DELETED | DELETED |
| H | H | R | T | V | Y | G | G | DELETED | P |
| H | H | R | T | V | Y | G | G | P | DELETED |
| H | H | R | T | V | Y | G | G | P | P |
| H | H | R | T | V | N | DELETED | DELETED | DELETED | DELETED |
| H | H | R | T | V | N | DELETED | DELETED | DELETED | P |
| H | H | R | T | V | N | DELETED | DELETED | P | DELETED |
| H | H | R | T | V | N | DELETED | DELETED | P | P |
| H | H | R | T | V | N | DELETED | G | DELETED | DELETED |
| H | H | R | T | V | N | DELETED | G | DELETED | P |
| H | H | R | T | V | N | DELETED | G | P | DELETED |
| H | H | R | T | V | N | DELETED | G | P | P |
| H | H | R | T | V | N | G | DELETED | DELETED | DELETED |
| H | H | R | T | V | N | G | DELETED | DELETED | P |
| H | H | R | T | V | N | G | DELETED | P | DELETED |
| H | H | R | T | V | N | G | DELETED | P | P |

TABLE 6-continued

Exemplary Mutations of mAb 2.175.3 Heavy Chain (SEQ ID NO: 2) to Germline at the Indicated Residue Number.

| 3 | 35 | 53 | 57 | 61 | 80 | 99 | 100 | 101 | 106 |
|---|---|---|---|---|---|---|---|---|---|
| H | H | R | T | V | N | G | G | DELETED | DELETED |
| H | H | R | T | V | N | G | G | DELETED | P |
| H | H | R | T | V | N | G | G | P | DELETED |
| H | H | R | T | V | N | G | G | P | P |
| H | H | R | L | A | Y | DELETED | DELETED | DELETED | DELETED |
| H | H | R | L | A | Y | DELETED | DELETED | DELETED | P |
| H | H | R | L | A | Y | DELETED | DELETED | P | DELETED |
| H | H | R | L | A | Y | DELETED | DELETED | P | P |
| H | H | R | L | A | Y | DELETED | G | DELETED | DELETED |
| H | H | R | L | A | Y | DELETED | G | DELETED | P |
| H | H | R | L | A | Y | DELETED | G | P | DELETED |
| H | H | R | L | A | Y | DELETED | G | P | P |
| H | H | R | L | A | Y | G | DELETED | DELETED | DELETED |
| H | H | R | L | A | Y | G | DELETED | DELETED | P |
| H | H | R | L | A | Y | G | DELETED | P | DELETED |
| H | H | R | L | A | Y | G | DELETED | P | P |
| H | H | R | L | A | Y | G | G | DELETED | DELETED |
| H | H | R | L | A | Y | G | G | DELETED | P |
| H | H | R | L | A | Y | G | G | P | DELETED |
| H | H | R | L | A | Y | G | G | P | P |
| H | H | R | L | A | N | DELETED | DELETED | DELETED | DELETED |
| H | H | R | L | A | N | DELETED | DELETED | DELETED | P |
| H | H | R | L | A | N | DELETED | DELETED | P | DELETED |
| H | H | R | L | A | N | DELETED | DELETED | P | P |
| H | H | R | L | A | N | DELETED | G | DELETED | DELETED |
| H | H | R | L | A | N | DELETED | G | DELETED | P |
| H | H | R | L | A | N | DELETED | G | P | DELETED |
| H | H | R | L | A | N | DELETED | G | P | P |
| H | H | R | L | A | N | G | DELETED | DELETED | DELETED |
| H | H | R | L | A | N | G | DELETED | DELETED | P |
| H | H | R | L | A | N | G | DELETED | P | DELETED |
| H | H | R | L | A | N | G | DELETED | P | P |
| H | H | R | L | A | N | G | G | DELETED | DELETED |
| H | H | R | L | A | N | G | G | DELETED | P |
| H | H | R | L | A | N | G | G | P | DELETED |
| H | H | R | L | A | N | G | G | P | P |
| H | H | R | L | V | Y | DELETED | DELETED | DELETED | DELETED |
| H | H | R | L | V | Y | DELETED | DELETED | DELETED | P |
| H | H | R | L | V | Y | DELETED | DELETED | P | DELETED |
| H | H | R | L | V | Y | DELETED | DELETED | P | P |
| H | H | R | L | V | Y | DELETED | G | DELETED | DELETED |
| H | H | R | L | V | Y | DELETED | G | DELETED | P |
| H | H | R | L | V | Y | DELETED | G | P | DELETED |
| H | H | R | L | V | Y | DELETED | G | P | P |
| H | H | R | L | V | Y | G | DELETED | DELETED | DELETED |
| H | H | R | L | V | Y | G | DELETED | DELETED | P |
| H | H | R | L | V | Y | G | DELETED | P | DELETED |
| H | H | R | L | V | Y | G | DELETED | P | P |
| H | H | R | L | V | Y | G | G | DELETED | DELETED |
| H | H | R | L | V | Y | G | G | DELETED | P |
| H | H | R | L | V | Y | G | G | P | DELETED |
| H | H | R | L | V | Y | G | G | P | P |
| H | H | R | L | V | N | DELETED | DELETED | DELETED | DELETED |
| H | H | R | L | V | N | DELETED | DELETED | DELETED | P |
| H | H | R | L | V | N | DELETED | DELETED | P | DELETED |
| H | H | R | L | V | N | DELETED | DELETED | P | P |
| H | H | R | L | V | N | DELETED | G | DELETED | DELETED |
| H | H | R | L | V | N | DELETED | G | DELETED | P |
| H | H | R | L | V | N | DELETED | G | P | DELETED |
| H | H | R | L | V | N | DELETED | G | P | P |
| H | H | R | L | V | N | G | DELETED | DELETED | DELETED |
| H | H | R | L | V | N | G | DELETED | DELETED | P |
| H | H | R | L | V | N | G | DELETED | P | DELETED |
| H | H | R | L | V | N | G | DELETED | P | P |
| H | H | R | L | V | N | G | G | DELETED | DELETED |
| H | H | R | L | V | N | G | G | DELETED | P |
| H | H | R | L | V | N | G | G | P | DELETED |
| H | H | R | L | V | N | G | G | P | P |

TABLE 7

Exemplary Mutations of mAb 2.175.3 Light Chain (SEQ ID NO: 4) to Germline at the Indicated Residue Number.

| 25 | 28 | 31 | 46 | 55 | 77 |
|---|---|---|---|---|---|
| A | S | S | L | Q | S |
| A | S | S | L | Q | T |
| A | S | S | L | P | S |
| A | S | S | L | P | T |
| A | S | S | F | Q | S |
| A | S | S | F | Q | T |
| A | S | S | F | P | S |
| A | S | S | F | P | T |
| A | S | R | L | Q | S |
| A | S | R | L | Q | T |
| A | S | R | L | P | S |
| A | S | R | L | P | T |
| A | S | R | F | Q | S |
| A | S | R | F | Q | T |
| A | S | R | F | P | S |
| A | S | R | F | P | T |
| A | R | S | L | Q | S |
| A | R | S | L | Q | T |
| A | R | S | L | P | S |
| A | R | S | L | P | T |
| A | R | S | F | Q | S |
| A | R | S | F | Q | T |
| A | R | S | F | P | S |
| A | R | S | F | P | T |
| A | R | R | L | Q | S |
| A | R | R | L | Q | T |
| A | R | R | L | P | S |
| A | R | R | L | P | T |
| A | R | R | F | Q | S |
| A | R | R | F | Q | T |
| A | R | R | F | P | S |
| A | R | R | F | P | T |
| P | S | S | L | Q | S |
| P | S | S | L | Q | T |
| P | S | S | L | P | S |
| P | S | S | L | P | T |
| P | S | S | F | Q | S |
| P | S | S | F | Q | T |
| P | S | S | F | P | S |
| P | S | S | F | P | T |
| P | S | R | L | Q | S |
| P | S | R | L | Q | T |
| P | S | R | L | P | S |
| P | S | R | L | P | T |
| P | S | R | F | Q | S |
| P | S | R | F | Q | T |
| P | S | R | F | P | S |
| P | S | R | F | P | T |
| P | R | S | L | Q | S |
| P | R | S | L | Q | T |
| P | R | S | L | P | S |
| P | R | S | L | P | T |
| P | R | S | F | Q | S |
| P | R | S | F | Q | T |
| P | R | S | F | P | S |
| P | R | S | F | P | T |
| P | R | R | L | Q | S |
| P | R | R | L | Q | T |
| P | R | R | L | P | S |
| P | R | R | L | P | T |
| P | R | R | F | Q | S |
| P | R | R | F | Q | T |
| P | R | R | F | P | S |
| P | R | R | F | P | T |

TABLE 8

Exemplary Mutations of mAb 2.449.1.3 Heavy Chain (SEQ ID NO: 10) to Germline at the Indicated Residue Number.

| 35 | 57 | 99 | 100 | 101 |
|---|---|---|---|---|
| S | T | DELETED | DELETED | S |
| S | T | DELETED | DELETED | R |
| S | T | DELETED | G | S |
| S | T | DELETED | G | R |
| S | T | E | DELETED | S |
| S | T | E | DELETED | R |
| S | T | E | G | S |
| S | T | E | G | R |
| S | I | DELETED | DELETED | S |
| S | I | DELETED | DELETED | R |
| S | I | DELETED | G | S |
| S | I | DELETED | G | R |
| S | I | E | DELETED | S |
| S | I | E | DELETED | R |
| S | I | E | G | S |
| S | I | E | G | R |
| N | T | DELETED | DELETED | S |
| N | T | DELETED | DELETED | R |
| N | T | DELETED | G | S |
| N | T | DELETED | G | R |
| N | T | E | DELETED | S |
| N | T | E | DELETED | R |
| N | T | E | G | S |
| N | T | E | G | R |
| N | I | DELETED | DELETED | S |
| N | I | DELETED | DELETED | R |
| N | I | DELETED | G | S |
| N | I | DELETED | G | R |
| N | I | E | DELETED | S |
| N | I | E | DELETED | R |
| N | I | E | G | S |
| N | I | E | G | R |

TABLE 9

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | L | Y | Q | S | S | DELETED | DELETED | DELETED | I |
| T | A | I | S | L | Y | Q | S | S | DELETED | DELETED | DELETED | M |
| T | A | I | S | L | Y | Q | S | S | DELETED | DELETED | P | I |
| T | A | I | S | L | Y | Q | S | S | DELETED | DELETED | P | M |
| T | A | I | S | L | Y | Q | S | S | DELETED | P | DELETED | I |
| T | A | I | S | L | Y | Q | S | S | DELETED | P | DELETED | M |
| T | A | I | S | L | Y | Q | S | S | DELETED | P | P | I |
| T | A | I | S | L | Y | Q | S | S | DELETED | P | P | M |
| T | A | I | S | L | Y | Q | S | S | N | DELETED | DELETED | I |
| T | A | I | S | L | Y | Q | S | S | N | DELETED | DELETED | M |
| T | A | I | S | L | Y | Q | S | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | L | Y | Q | S | S | N | DELETED | P | M |
| T | A | I | S | L | Y | Q | S | S | N | P | DELETED | I |
| T | A | I | S | L | Y | Q | S | S | N | P | DELETED | M |
| T | A | I | S | L | Y | Q | S | S | N | P | P | I |
| T | A | I | S | L | Y | Q | S | S | N | P | P | M |
| T | A | I | S | L | Y | Q | S | T | DELETED | DELETED | DELETED | I |
| T | A | I | S | L | Y | Q | S | T | DELETED | DELETED | DELETED | M |
| T | A | I | S | L | Y | Q | S | T | DELETED | DELETED | P | I |
| T | A | I | S | L | Y | Q | S | T | DELETED | DELETED | P | M |
| T | A | I | S | L | Y | Q | S | T | DELETED | P | DELETED | I |
| T | A | I | S | L | Y | Q | S | T | DELETED | P | DELETED | M |
| T | A | I | S | L | Y | Q | S | T | DELETED | P | P | I |
| T | A | I | S | L | Y | Q | S | T | DELETED | P | P | M |
| T | A | I | S | L | Y | Q | S | T | N | DELETED | DELETED | I |
| T | A | I | S | L | Y | Q | S | T | N | DELETED | DELETED | M |
| T | A | I | S | L | Y | Q | S | T | N | DELETED | P | I |
| T | A | I | S | L | Y | Q | S | T | N | DELETED | P | M |
| T | A | I | S | L | Y | Q | S | T | N | P | DELETED | I |
| T | A | I | S | L | Y | Q | S | T | N | P | DELETED | M |
| T | A | I | S | L | Y | Q | S | T | N | P | P | I |
| T | A | I | S | L | Y | Q | S | T | N | P | P | M |
| T | A | I | S | L | Y | Q | G | S | DELETED | DELETED | DELETED | I |
| T | A | I | S | L | Y | Q | G | S | DELETED | DELETED | DELETED | M |
| T | A | I | S | L | Y | Q | G | S | DELETED | DELETED | P | I |
| T | A | I | S | L | Y | Q | G | S | DELETED | DELETED | P | M |
| T | A | I | S | L | Y | Q | G | S | DELETED | P | DELETED | I |
| T | A | I | S | L | Y | Q | G | S | DELETED | P | DELETED | M |
| T | A | I | S | L | Y | Q | G | S | DELETED | P | P | I |
| T | A | I | S | L | Y | Q | G | S | DELETED | P | P | M |
| T | A | I | S | L | Y | Q | G | S | N | DELETED | DELETED | I |
| T | A | I | S | L | Y | Q | G | S | N | DELETED | DELETED | M |
| T | A | I | S | L | Y | Q | G | S | N | DELETED | P | I |
| T | A | I | S | L | Y | Q | G | S | N | DELETED | P | M |
| T | A | I | S | L | Y | Q | G | S | N | P | DELETED | I |
| T | A | I | S | L | Y | Q | G | S | N | P | DELETED | M |
| T | A | I | S | L | Y | Q | G | S | N | P | P | I |
| T | A | I | S | L | Y | Q | G | S | N | P | P | M |
| T | A | I | S | L | Y | Q | G | T | DELETED | DELETED | DELETED | I |
| T | A | I | S | L | Y | Q | G | T | DELETED | DELETED | DELETED | M |
| T | A | I | S | L | Y | Q | G | T | DELETED | DELETED | P | I |
| T | A | I | S | L | Y | Q | G | T | DELETED | DELETED | P | M |
| T | A | I | S | L | Y | Q | G | T | DELETED | P | DELETED | I |
| T | A | I | S | L | Y | Q | G | T | DELETED | P | DELETED | M |
| T | A | I | S | L | Y | Q | G | T | DELETED | P | P | I |
| T | A | I | S | L | Y | Q | G | T | DELETED | P | P | M |
| T | A | I | S | L | Y | Q | G | T | N | DELETED | DELETED | I |
| T | A | I | S | L | Y | Q | G | T | N | DELETED | DELETED | M |
| T | A | I | S | L | Y | Q | G | T | N | DELETED | P | I |
| T | A | I | S | L | Y | Q | G | T | N | DELETED | P | M |
| T | A | I | S | L | Y | Q | G | T | N | P | DELETED | I |
| T | A | I | S | L | Y | Q | G | T | N | P | DELETED | M |
| T | A | I | S | L | Y | Q | G | T | N | P | P | I |
| T | A | I | S | L | Y | Q | G | T | N | P | P | M |
| T | A | I | S | L | Y | V | S | S | DELETED | DELETED | DELETED | I |
| T | A | I | S | L | Y | V | S | S | DELETED | DELETED | DELETED | M |
| T | A | I | S | L | Y | V | S | S | DELETED | DELETED | P | I |
| T | A | I | S | L | Y | V | S | S | DELETED | DELETED | P | M |
| T | A | I | S | L | Y | V | S | S | DELETED | P | DELETED | I |
| T | A | I | S | L | Y | V | S | S | DELETED | P | DELETED | M |
| T | A | I | S | L | Y | V | S | S | DELETED | P | P | I |
| T | A | I | S | L | Y | V | S | S | DELETED | P | P | M |
| T | A | I | S | L | Y | V | S | S | N | DELETED | DELETED | I |
| T | A | I | S | L | Y | V | S | S | N | DELETED | DELETED | M |
| T | A | I | S | L | Y | V | S | S | N | DELETED | P | I |
| T | A | I | S | L | Y | V | S | S | N | DELETED | P | M |
| T | A | I | S | L | Y | V | S | S | N | P | DELETED | I |
| T | A | I | S | L | Y | V | S | S | N | P | DELETED | M |
| T | A | I | S | L | Y | V | S | S | N | P | P | I |
| T | A | I | S | L | Y | V | S | S | N | P | P | M |
| T | A | I | S | L | Y | V | S | T | DELETED | DELETED | DELETED | I |
| T | A | I | S | L | Y | V | S | T | DELETED | DELETED | DELETED | M |
| T | A | I | S | L | Y | V | S | T | DELETED | DELETED | P | I |
| T | A | I | S | L | Y | V | S | T | DELETED | DELETED | P | M |
| T | A | I | S | L | Y | V | S | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | L | Y | V | S | T | DELETED | P | DELETED | M |
| T | A | I | S | L | Y | V | S | T | DELETED | P | P | I |
| T | A | I | S | L | Y | V | S | T | DELETED | P | P | M |
| T | A | I | S | L | Y | V | S | T | N | DELETED | DELETED | I |
| T | A | I | S | L | Y | V | S | T | N | DELETED | DELETED | M |
| T | A | I | S | L | Y | V | S | T | N | DELETED | P | I |
| T | A | I | S | L | Y | V | S | T | N | DELETED | P | M |
| T | A | I | S | L | Y | V | S | T | N | P | DELETED | I |
| T | A | I | S | L | Y | V | S | T | N | P | DELETED | M |
| T | A | I | S | L | Y | V | S | T | N | P | P | I |
| T | A | I | S | L | Y | V | S | T | N | P | P | M |
| T | A | I | S | L | Y | V | G | S | DELETED | DELETED | DELETED | I |
| T | A | I | S | L | Y | V | G | S | DELETED | DELETED | DELETED | M |
| T | A | I | S | L | Y | V | G | S | DELETED | DELETED | P | I |
| T | A | I | S | L | Y | V | G | S | DELETED | DELETED | P | M |
| T | A | I | S | L | Y | V | G | S | DELETED | P | DELETED | I |
| T | A | I | S | L | Y | V | G | S | DELETED | P | DELETED | M |
| T | A | I | S | L | Y | V | G | S | DELETED | P | P | I |
| T | A | I | S | L | Y | V | G | S | DELETED | P | P | M |
| T | A | I | S | L | Y | V | G | S | N | DELETED | DELETED | I |
| T | A | I | S | L | Y | V | G | S | N | DELETED | DELETED | M |
| T | A | I | S | L | Y | V | G | S | N | DELETED | P | I |
| T | A | I | S | L | Y | V | G | S | N | DELETED | P | M |
| T | A | I | S | L | Y | V | G | S | N | P | DELETED | I |
| T | A | I | S | L | Y | V | G | S | N | P | DELETED | M |
| T | A | I | S | L | Y | V | G | S | N | P | P | I |
| T | A | I | S | L | Y | V | G | S | N | P | P | M |
| T | A | I | S | L | Y | V | G | T | DELETED | DELETED | DELETED | I |
| T | A | I | S | L | Y | V | G | T | DELETED | DELETED | DELETED | M |
| T | A | I | S | L | Y | V | G | T | DELETED | DELETED | P | I |
| T | A | I | S | L | Y | V | G | T | DELETED | DELETED | P | M |
| T | A | I | S | L | Y | V | G | T | DELETED | P | DELETED | I |
| T | A | I | S | L | Y | V | G | T | DELETED | P | DELETED | M |
| T | A | I | S | L | Y | V | G | T | DELETED | P | P | I |
| T | A | I | S | L | Y | V | G | T | DELETED | P | P | M |
| T | A | I | S | L | Y | V | G | T | N | DELETED | DELETED | I |
| T | A | I | S | L | Y | V | G | T | N | DELETED | DELETED | M |
| T | A | I | S | L | Y | V | G | T | N | DELETED | P | I |
| T | A | I | S | L | Y | V | G | T | N | DELETED | P | M |
| T | A | I | S | L | Y | V | G | T | N | P | DELETED | I |
| T | A | I | S | L | Y | V | G | T | N | P | DELETED | M |
| T | A | I | S | L | Y | V | G | T | N | P | P | I |
| T | A | I | S | L | Y | V | G | T | N | P | P | M |
| T | A | I | S | L | H | Q | S | S | DELETED | DELETED | DELETED | I |
| T | A | I | S | L | H | Q | S | S | DELETED | DELETED | DELETED | M |
| T | A | I | S | L | H | Q | S | S | DELETED | DELETED | P | I |
| T | A | I | S | L | H | Q | S | S | DELETED | DELETED | P | M |
| T | A | I | S | L | H | Q | S | S | DELETED | P | DELETED | I |
| T | A | I | S | L | H | Q | S | S | DELETED | P | DELETED | M |
| T | A | I | S | L | H | Q | S | S | DELETED | P | P | I |
| T | A | I | S | L | H | Q | S | S | DELETED | P | P | M |
| T | A | I | S | L | H | Q | S | S | N | DELETED | DELETED | I |
| T | A | I | S | L | H | Q | S | S | N | DELETED | DELETED | M |
| T | A | I | S | L | H | Q | S | S | N | DELETED | P | I |
| T | A | I | S | L | H | Q | S | S | N | DELETED | P | M |
| T | A | I | S | L | H | Q | S | S | N | P | DELETED | I |
| T | A | I | S | L | H | Q | S | S | N | P | DELETED | M |
| T | A | I | S | L | H | Q | S | S | N | P | P | I |
| T | A | I | S | L | H | Q | S | S | N | P | P | M |
| T | A | I | S | L | H | Q | S | T | DELETED | DELETED | DELETED | I |
| T | A | I | S | L | H | Q | S | T | DELETED | DELETED | DELETED | M |
| T | A | I | S | L | H | Q | S | T | DELETED | DELETED | P | I |
| T | A | I | S | L | H | Q | S | T | DELETED | DELETED | P | M |
| T | A | I | S | L | H | Q | S | T | DELETED | P | DELETED | I |
| T | A | I | S | L | H | Q | S | T | DELETED | P | DELETED | M |
| T | A | I | S | L | H | Q | S | T | DELETED | P | P | I |
| T | A | I | S | L | H | Q | S | T | DELETED | P | P | M |
| T | A | I | S | L | H | Q | S | T | N | DELETED | DELETED | I |
| T | A | I | S | L | H | Q | S | T | N | DELETED | DELETED | M |
| T | A | I | S | L | H | Q | S | T | N | DELETED | P | I |
| T | A | I | S | L | H | Q | S | T | N | DELETED | P | M |
| T | A | I | S | L | H | Q | S | T | N | P | DELETED | I |
| T | A | I | S | L | H | Q | S | T | N | P | DELETED | M |
| T | A | I | S | L | H | Q | S | T | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | L | H | Q | S | T | N | P | P | M |
| T | A | I | S | L | H | Q | G | S | DELETED | DELETED | DELETED | I |
| T | A | I | S | L | H | Q | G | S | DELETED | DELETED | DELETED | M |
| T | A | I | S | L | H | Q | G | S | DELETED | DELETED | P | I |
| T | A | I | S | L | H | Q | G | S | DELETED | DELETED | P | M |
| T | A | I | S | L | H | Q | G | S | DELETED | P | DELETED | I |
| T | A | I | S | L | H | Q | G | S | DELETED | P | DELETED | M |
| T | A | I | S | L | H | Q | G | S | DELETED | P | P | I |
| T | A | I | S | L | H | Q | G | S | DELETED | P | P | M |
| T | A | I | S | L | H | Q | G | S | N | DELETED | DELETED | I |
| T | A | I | S | L | H | Q | G | S | N | DELETED | DELETED | M |
| T | A | I | S | L | H | Q | G | S | N | DELETED | P | I |
| T | A | I | S | L | H | Q | G | S | N | DELETED | P | M |
| T | A | I | S | L | H | Q | G | S | N | P | DELETED | I |
| T | A | I | S | L | H | Q | G | S | N | P | DELETED | M |
| T | A | I | S | L | H | Q | G | S | N | P | P | I |
| T | A | I | S | L | H | Q | G | S | N | P | P | M |
| T | A | I | S | L | H | Q | G | T | DELETED | DELETED | DELETED | I |
| T | A | I | S | L | H | Q | G | T | DELETED | DELETED | DELETED | M |
| T | A | I | S | L | H | Q | G | T | DELETED | DELETED | P | I |
| T | A | I | S | L | H | Q | G | T | DELETED | DELETED | P | M |
| T | A | I | S | L | H | Q | G | T | DELETED | P | DELETED | I |
| T | A | I | S | L | H | Q | G | T | DELETED | P | DELETED | M |
| T | A | I | S | L | H | Q | G | T | DELETED | P | P | I |
| T | A | I | S | L | H | Q | G | T | DELETED | P | P | M |
| T | A | I | S | L | H | Q | G | T | N | DELETED | DELETED | I |
| T | A | I | S | L | H | Q | G | T | N | DELETED | DELETED | M |
| T | A | I | S | L | H | Q | G | T | N | DELETED | P | I |
| T | A | I | S | L | H | Q | G | T | N | DELETED | P | M |
| T | A | I | S | L | H | Q | G | T | N | P | DELETED | I |
| T | A | I | S | L | H | Q | G | T | N | P | DELETED | M |
| T | A | I | S | L | H | Q | G | T | N | P | P | I |
| T | A | I | S | L | H | Q | G | T | N | P | P | M |
| T | A | I | S | L | H | V | S | S | DELETED | DELETED | DELETED | I |
| T | A | I | S | L | H | V | S | S | DELETED | DELETED | DELETED | M |
| T | A | I | S | L | H | V | S | S | DELETED | DELETED | P | I |
| T | A | I | S | L | H | V | S | S | DELETED | DELETED | P | M |
| T | A | I | S | L | H | V | S | S | DELETED | P | DELETED | I |
| T | A | I | S | L | H | V | S | S | DELETED | P | DELETED | M |
| T | A | I | S | L | H | V | S | S | DELETED | P | P | I |
| T | A | I | S | L | H | V | S | S | DELETED | P | P | M |
| T | A | I | S | L | H | V | S | S | N | DELETED | DELETED | I |
| T | A | I | S | L | H | V | S | S | N | DELETED | DELETED | M |
| T | A | I | S | L | H | V | S | S | N | DELETED | P | I |
| T | A | I | S | L | H | V | S | S | N | DELETED | P | M |
| T | A | I | S | L | H | V | S | S | N | P | DELETED | I |
| T | A | I | S | L | H | V | S | S | N | P | DELETED | M |
| T | A | I | S | L | H | V | S | S | N | P | P | I |
| T | A | I | S | L | H | V | S | S | N | P | P | M |
| T | A | I | S | L | H | V | S | T | DELETED | DELETED | DELETED | I |
| T | A | I | S | L | H | V | S | T | DELETED | DELETED | DELETED | M |
| T | A | I | S | L | H | V | S | T | DELETED | DELETED | P | I |
| T | A | I | S | L | H | V | S | T | DELETED | DELETED | P | M |
| T | A | I | S | L | H | V | S | T | DELETED | P | DELETED | I |
| T | A | I | S | L | H | V | S | T | DELETED | P | DELETED | M |
| T | A | I | S | L | H | V | S | T | DELETED | P | P | I |
| T | A | I | S | L | H | V | S | T | DELETED | P | P | M |
| T | A | I | S | L | H | V | S | T | N | DELETED | DELETED | I |
| T | A | I | S | L | H | V | S | T | N | DELETED | DELETED | M |
| T | A | I | S | L | H | V | S | T | N | DELETED | P | I |
| T | A | I | S | L | H | V | S | T | N | DELETED | P | M |
| T | A | I | S | L | H | V | S | T | N | P | DELETED | I |
| T | A | I | S | L | H | V | S | T | N | P | DELETED | M |
| T | A | I | S | L | H | V | S | T | N | P | P | I |
| T | A | I | S | L | H | V | S | T | N | P | P | M |
| T | A | I | S | L | H | V | G | S | DELETED | DELETED | DELETED | I |
| T | A | I | S | L | H | V | G | S | DELETED | DELETED | DELETED | M |
| T | A | I | S | L | H | V | G | S | DELETED | DELETED | P | I |
| T | A | I | S | L | H | V | G | S | DELETED | DELETED | P | M |
| T | A | I | S | L | H | V | G | S | DELETED | P | DELETED | I |
| T | A | I | S | L | H | V | G | S | DELETED | P | DELETED | M |
| T | A | I | S | L | H | V | G | S | DELETED | P | P | I |
| T | A | I | S | L | H | V | G | S | DELETED | P | P | M |
| T | A | I | S | L | H | V | G | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | L | H | V | G | S | N | DELETED | DELETED | M |
| T | A | I | S | L | H | V | G | S | N | DELETED | P | I |
| T | A | I | S | L | H | V | G | S | N | DELETED | P | M |
| T | A | I | S | L | H | V | G | S | N | P | DELETED | I |
| T | A | I | S | L | H | V | G | S | N | P | DELETED | M |
| T | A | I | S | L | H | V | G | S | N | P | P | I |
| T | A | I | S | L | H | V | G | S | N | P | P | M |
| T | A | I | S | L | H | V | G | T | DELETED | DELETED | DELETED | I |
| T | A | I | S | L | H | V | G | T | DELETED | DELETED | DELETED | M |
| T | A | I | S | L | H | V | G | T | DELETED | DELETED | P | I |
| T | A | I | S | L | H | V | G | T | DELETED | DELETED | P | M |
| T | A | I | S | L | H | V | G | T | DELETED | P | DELETED | I |
| T | A | I | S | L | H | V | G | T | DELETED | P | DELETED | M |
| T | A | I | S | L | H | V | G | T | DELETED | P | P | I |
| T | A | I | S | L | H | V | G | T | DELETED | P | P | M |
| T | A | I | S | L | H | V | G | T | N | DELETED | DELETED | I |
| T | A | I | S | L | H | V | G | T | N | DELETED | DELETED | M |
| T | A | I | S | L | H | V | G | T | N | DELETED | P | I |
| T | A | I | S | L | H | V | G | T | N | DELETED | P | M |
| T | A | I | S | L | H | V | G | T | N | P | DELETED | I |
| T | A | I | S | L | H | V | G | T | N | P | DELETED | M |
| T | A | I | S | L | H | V | G | T | N | P | P | I |
| T | A | I | S | L | H | V | G | T | N | P | P | M |
| T | A | I | S | I | Y | Q | S | S | DELETED | DELETED | DELETED | I |
| T | A | I | S | I | Y | Q | S | S | DELETED | DELETED | DELETED | M |
| T | A | I | S | I | Y | Q | S | S | DELETED | DELETED | P | I |
| T | A | I | S | I | Y | Q | S | S | DELETED | DELETED | P | M |
| T | A | I | S | I | Y | Q | S | S | DELETED | P | DELETED | I |
| T | A | I | S | I | Y | Q | S | S | DELETED | P | DELETED | M |
| T | A | I | S | I | Y | Q | S | S | DELETED | P | P | I |
| T | A | I | S | I | Y | Q | S | S | DELETED | P | P | M |
| T | A | I | S | I | Y | Q | S | S | N | DELETED | DELETED | I |
| T | A | I | S | I | Y | Q | S | S | N | DELETED | DELETED | M |
| T | A | I | S | I | Y | Q | S | S | N | DELETED | P | I |
| T | A | I | S | I | Y | Q | S | S | N | DELETED | P | M |
| T | A | I | S | I | Y | Q | S | S | N | P | DELETED | I |
| T | A | I | S | I | Y | Q | S | S | N | P | DELETED | M |
| T | A | I | S | I | Y | Q | S | S | N | P | P | I |
| T | A | I | S | I | Y | Q | S | S | N | P | P | M |
| T | A | I | S | I | Y | Q | S | T | DELETED | DELETED | DELETED | I |
| T | A | I | S | I | Y | Q | S | T | DELETED | DELETED | DELETED | M |
| T | A | I | S | I | Y | Q | S | T | DELETED | DELETED | P | I |
| T | A | I | S | I | Y | Q | S | T | DELETED | DELETED | P | M |
| T | A | I | S | I | Y | Q | S | T | DELETED | P | DELETED | I |
| T | A | I | S | I | Y | Q | S | T | DELETED | P | DELETED | M |
| T | A | I | S | I | Y | Q | S | T | DELETED | P | P | I |
| T | A | I | S | I | Y | Q | S | T | DELETED | P | P | M |
| T | A | I | S | I | Y | Q | S | T | N | DELETED | DELETED | I |
| T | A | I | S | I | Y | Q | S | T | N | DELETED | DELETED | M |
| T | A | I | S | I | Y | Q | S | T | N | DELETED | P | I |
| T | A | I | S | I | Y | Q | S | T | N | DELETED | P | M |
| T | A | I | S | I | Y | Q | S | T | N | P | DELETED | I |
| T | A | I | S | I | Y | Q | S | T | N | P | DELETED | M |
| T | A | I | S | I | Y | Q | S | T | N | P | P | I |
| T | A | I | S | I | Y | Q | S | T | N | P | P | M |
| T | A | I | S | I | Y | Q | G | S | DELETED | DELETED | DELETED | I |
| T | A | I | S | I | Y | Q | G | S | DELETED | DELETED | DELETED | M |
| T | A | I | S | I | Y | Q | G | S | DELETED | DELETED | P | I |
| T | A | I | S | I | Y | Q | G | S | DELETED | DELETED | P | M |
| T | A | I | S | I | Y | Q | G | S | DELETED | P | DELETED | I |
| T | A | I | S | I | Y | Q | G | S | DELETED | P | DELETED | M |
| T | A | I | S | I | Y | Q | G | S | DELETED | P | P | I |
| T | A | I | S | I | Y | Q | G | S | DELETED | P | P | M |
| T | A | I | S | I | Y | Q | G | S | N | DELETED | DELETED | I |
| T | A | I | S | I | Y | Q | G | S | N | DELETED | DELETED | M |
| T | A | I | S | I | Y | Q | G | S | N | DELETED | P | I |
| T | A | I | S | I | Y | Q | G | S | N | DELETED | P | M |
| T | A | I | S | I | Y | Q | G | S | N | P | DELETED | I |
| T | A | I | S | I | Y | Q | G | S | N | P | DELETED | M |
| T | A | I | S | I | Y | Q | G | S | N | P | P | I |
| T | A | I | S | I | Y | Q | G | S | N | P | P | M |
| T | A | I | S | I | Y | Q | G | T | DELETED | DELETED | DELETED | I |
| T | A | I | S | I | Y | Q | G | T | DELETED | DELETED | DELETED | M |
| T | A | I | S | I | Y | Q | G | T | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | I | Y | Q | G | T | DELETED | DELETED | P | M |
| T | A | I | S | I | Y | Q | G | T | DELETED | P | DELETED | I |
| T | A | I | S | I | Y | Q | G | T | DELETED | P | DELETED | M |
| T | A | I | S | I | Y | Q | G | T | DELETED | P | P | I |
| T | A | I | S | I | Y | Q | G | T | DELETED | P | P | M |
| T | A | I | S | I | Y | Q | G | T | N | DELETED | DELETED | I |
| T | A | I | S | I | Y | Q | G | T | N | DELETED | DELETED | M |
| T | A | I | S | I | Y | Q | G | T | N | DELETED | P | I |
| T | A | I | S | I | Y | Q | G | T | N | DELETED | P | M |
| T | A | I | S | I | Y | Q | G | T | N | P | DELETED | I |
| T | A | I | S | I | Y | Q | G | T | N | P | DELETED | M |
| T | A | I | S | I | Y | Q | G | T | N | P | P | I |
| T | A | I | S | I | Y | Q | G | T | N | P | P | M |
| T | A | I | S | I | Y | V | S | S | DELETED | DELETED | DELETED | I |
| T | A | I | S | I | Y | V | S | S | DELETED | DELETED | DELETED | M |
| T | A | I | S | I | Y | V | S | S | DELETED | DELETED | P | I |
| T | A | I | S | I | Y | V | S | S | DELETED | DELETED | P | M |
| T | A | I | S | I | Y | V | S | S | DELETED | P | DELETED | I |
| T | A | I | S | I | Y | V | S | S | DELETED | P | DELETED | M |
| T | A | I | S | I | Y | V | S | S | DELETED | P | P | I |
| T | A | I | S | I | Y | V | S | S | DELETED | P | P | M |
| T | A | I | S | I | Y | V | S | S | N | DELETED | DELETED | I |
| T | A | I | S | I | Y | V | S | S | N | DELETED | DELETED | M |
| T | A | I | S | I | Y | V | S | S | N | DELETED | P | I |
| T | A | I | S | I | Y | V | S | S | N | DELETED | P | M |
| T | A | I | S | I | Y | V | S | S | N | P | DELETED | I |
| T | A | I | S | I | Y | V | S | S | N | P | DELETED | M |
| T | A | I | S | I | Y | V | S | S | N | P | P | I |
| T | A | I | S | I | Y | V | S | S | N | P | P | M |
| T | A | I | S | I | Y | V | S | T | DELETED | DELETED | DELETED | I |
| T | A | I | S | I | Y | V | S | T | DELETED | DELETED | DELETED | M |
| T | A | I | S | I | Y | V | S | T | DELETED | DELETED | P | I |
| T | A | I | S | I | Y | V | S | T | DELETED | DELETED | P | M |
| T | A | I | S | I | Y | V | S | T | DELETED | P | DELETED | I |
| T | A | I | S | I | Y | V | S | T | DELETED | P | DELETED | M |
| T | A | I | S | I | Y | V | S | T | DELETED | P | P | I |
| T | A | I | S | I | Y | V | S | T | DELETED | P | P | M |
| T | A | I | S | I | Y | V | S | T | N | DELETED | DELETED | I |
| T | A | I | S | I | Y | V | S | T | N | DELETED | DELETED | M |
| T | A | I | S | I | Y | V | S | T | N | DELETED | P | I |
| T | A | I | S | I | Y | V | S | T | N | DELETED | P | M |
| T | A | I | S | I | Y | V | S | T | N | P | DELETED | I |
| T | A | I | S | I | Y | V | S | T | N | P | DELETED | M |
| T | A | I | S | I | Y | V | S | T | N | P | P | I |
| T | A | I | S | I | Y | V | S | T | N | P | P | M |
| T | A | I | S | I | Y | V | G | S | DELETED | DELETED | DELETED | I |
| T | A | I | S | I | Y | V | G | S | DELETED | DELETED | DELETED | M |
| T | A | I | S | I | Y | V | G | S | DELETED | DELETED | P | I |
| T | A | I | S | I | Y | V | G | S | DELETED | DELETED | P | M |
| T | A | I | S | I | Y | V | G | S | DELETED | P | DELETED | I |
| T | A | I | S | I | Y | V | G | S | DELETED | P | DELETED | M |
| T | A | I | S | I | Y | V | G | S | DELETED | P | P | I |
| T | A | I | S | I | Y | V | G | S | DELETED | P | P | M |
| T | A | I | S | I | Y | V | G | S | N | DELETED | DELETED | I |
| T | A | I | S | I | Y | V | G | S | N | DELETED | DELETED | M |
| T | A | I | S | I | Y | V | G | S | N | DELETED | P | I |
| T | A | I | S | I | Y | V | G | S | N | DELETED | P | M |
| T | A | I | S | I | Y | V | G | S | N | P | DELETED | I |
| T | A | I | S | I | Y | V | G | S | N | P | DELETED | M |
| T | A | I | S | I | Y | V | G | S | N | P | P | I |
| T | A | I | S | I | Y | V | G | S | N | P | P | M |
| T | A | I | S | I | Y | V | G | T | DELETED | DELETED | DELETED | I |
| T | A | I | S | I | Y | V | G | T | DELETED | DELETED | DELETED | M |
| T | A | I | S | I | Y | V | G | T | DELETED | DELETED | P | I |
| T | A | I | S | I | Y | V | G | T | DELETED | DELETED | P | M |
| T | A | I | S | I | Y | V | G | T | DELETED | P | DELETED | I |
| T | A | I | S | I | Y | V | G | T | DELETED | P | DELETED | M |
| T | A | I | S | I | Y | V | G | T | DELETED | P | P | I |
| T | A | I | S | I | Y | V | G | T | DELETED | P | P | M |
| T | A | I | S | I | Y | V | G | T | N | DELETED | DELETED | I |
| T | A | I | S | I | Y | V | G | T | N | DELETED | DELETED | M |
| T | A | I | S | I | Y | V | G | T | N | DELETED | P | I |
| T | A | I | S | I | Y | V | G | T | N | DELETED | P | M |
| T | A | I | S | I | Y | V | G | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | I | Y | V | G | T | N | P | DELETED | M |
| T | A | I | S | I | Y | V | G | T | N | P | P | I |
| T | A | I | S | I | Y | V | G | T | N | P | P | M |
| T | A | I | S | I | H | Q | S | S | DELETED | DELETED | DELETED | I |
| T | A | I | S | I | H | Q | S | S | DELETED | DELETED | DELETED | M |
| T | A | I | S | I | H | Q | S | S | DELETED | DELETED | P | I |
| T | A | I | S | I | H | Q | S | S | DELETED | DELETED | P | M |
| T | A | I | S | I | H | Q | S | S | DELETED | P | DELETED | I |
| T | A | I | S | I | H | Q | S | S | DELETED | P | DELETED | M |
| T | A | I | S | I | H | Q | S | S | DELETED | P | P | I |
| T | A | I | S | I | H | Q | S | S | DELETED | P | P | M |
| T | A | I | S | I | H | Q | S | S | N | DELETED | DELETED | I |
| T | A | I | S | I | H | Q | S | S | N | DELETED | DELETED | M |
| T | A | I | S | I | H | Q | S | S | N | DELETED | P | I |
| T | A | I | S | I | H | Q | S | S | N | DELETED | P | M |
| T | A | I | S | I | H | Q | S | S | N | P | DELETED | I |
| T | A | I | S | I | H | Q | S | S | N | P | DELETED | M |
| T | A | I | S | I | H | Q | S | S | N | P | P | I |
| T | A | I | S | I | H | Q | S | S | N | P | P | M |
| T | A | I | S | I | H | Q | S | T | DELETED | DELETED | DELETED | I |
| T | A | I | S | I | H | Q | S | T | DELETED | DELETED | DELETED | M |
| T | A | I | S | I | H | Q | S | T | DELETED | DELETED | P | I |
| T | A | I | S | I | H | Q | S | T | DELETED | DELETED | P | M |
| T | A | I | S | I | H | Q | S | T | DELETED | P | DELETED | I |
| T | A | I | S | I | H | Q | S | T | DELETED | P | DELETED | M |
| T | A | I | S | I | H | Q | S | T | DELETED | P | P | I |
| T | A | I | S | I | H | Q | S | T | DELETED | P | P | M |
| T | A | I | S | I | H | Q | S | T | N | DELETED | DELETED | I |
| T | A | I | S | I | H | Q | S | T | N | DELETED | DELETED | M |
| T | A | I | S | I | H | Q | S | T | N | DELETED | P | I |
| T | A | I | S | I | H | Q | S | T | N | DELETED | P | M |
| T | A | I | S | I | H | Q | S | T | N | P | DELETED | I |
| T | A | I | S | I | H | Q | S | T | N | P | DELETED | M |
| T | A | I | S | I | H | Q | S | T | N | P | P | I |
| T | A | I | S | I | H | Q | S | T | N | P | P | M |
| T | A | I | S | I | H | Q | G | S | DELETED | DELETED | DELETED | I |
| T | A | I | S | I | H | Q | G | S | DELETED | DELETED | DELETED | M |
| T | A | I | S | I | H | Q | G | S | DELETED | DELETED | P | I |
| T | A | I | S | I | H | Q | G | S | DELETED | DELETED | P | M |
| T | A | I | S | I | H | Q | G | S | DELETED | P | DELETED | I |
| T | A | I | S | I | H | Q | G | S | DELETED | P | DELETED | M |
| T | A | I | S | I | H | Q | G | S | DELETED | P | P | I |
| T | A | I | S | I | H | Q | G | S | DELETED | P | P | M |
| T | A | I | S | I | H | Q | G | S | N | DELETED | DELETED | I |
| T | A | I | S | I | H | Q | G | S | N | DELETED | DELETED | M |
| T | A | I | S | I | H | Q | G | S | N | DELETED | P | I |
| T | A | I | S | I | H | Q | G | S | N | DELETED | P | M |
| T | A | I | S | I | H | Q | G | S | N | P | DELETED | I |
| T | A | I | S | I | H | Q | G | S | N | P | DELETED | M |
| T | A | I | S | I | H | Q | G | S | N | P | P | I |
| T | A | I | S | I | H | Q | G | S | N | P | P | M |
| T | A | I | S | I | H | Q | G | T | DELETED | DELETED | DELETED | I |
| T | A | I | S | I | H | Q | G | T | DELETED | DELETED | DELETED | M |
| T | A | I | S | I | H | Q | G | T | DELETED | DELETED | P | I |
| T | A | I | S | I | H | Q | G | T | DELETED | DELETED | P | M |
| T | A | I | S | I | H | Q | G | T | DELETED | P | DELETED | I |
| T | A | I | S | I | H | Q | G | T | DELETED | P | DELETED | M |
| T | A | I | S | I | H | Q | G | T | DELETED | P | P | I |
| T | A | I | S | I | H | Q | G | T | DELETED | P | P | M |
| T | A | I | S | I | H | Q | G | T | N | DELETED | DELETED | I |
| T | A | I | S | I | H | Q | G | T | N | DELETED | DELETED | M |
| T | A | I | S | I | H | Q | G | T | N | DELETED | P | I |
| T | A | I | S | I | H | Q | G | T | N | DELETED | P | M |
| T | A | I | S | I | H | Q | G | T | N | P | DELETED | I |
| T | A | I | S | I | H | Q | G | T | N | P | DELETED | M |
| T | A | I | S | I | H | Q | G | T | N | P | P | I |
| T | A | I | S | I | H | Q | G | T | N | P | P | M |
| T | A | I | S | I | H | V | S | S | DELETED | DELETED | DELETED | I |
| T | A | I | S | I | H | V | S | S | DELETED | DELETED | DELETED | M |
| T | A | I | S | I | H | V | S | S | DELETED | DELETED | P | I |
| T | A | I | S | I | H | V | S | S | DELETED | DELETED | P | M |
| T | A | I | S | I | H | V | S | S | DELETED | P | DELETED | I |
| T | A | I | S | I | H | V | S | S | DELETED | P | DELETED | M |
| T | A | I | S | I | H | V | S | S | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | S | I | H | V | S | S | DELETED | P | P | M |
| T | A | I | S | I | H | V | S | S | N | DELETED | DELETED | I |
| T | A | I | S | I | H | V | S | S | N | DELETED | DELETED | M |
| T | A | I | S | I | H | V | S | S | N | DELETED | P | I |
| T | A | I | S | I | H | V | S | S | N | DELETED | P | M |
| T | A | I | S | I | H | V | S | S | N | P | DELETED | I |
| T | A | I | S | I | H | V | S | S | N | P | DELETED | M |
| T | A | I | S | I | H | V | S | S | N | P | P | I |
| T | A | I | S | I | H | V | S | S | N | P | P | M |
| T | A | I | S | I | H | V | S | T | DELETED | DELETED | DELETED | I |
| T | A | I | S | I | H | V | S | T | DELETED | DELETED | DELETED | M |
| T | A | I | S | I | H | V | S | T | DELETED | DELETED | P | I |
| T | A | I | S | I | H | V | S | T | DELETED | DELETED | P | M |
| T | A | I | S | I | H | V | S | T | DELETED | P | DELETED | I |
| T | A | I | S | I | H | V | S | T | DELETED | P | DELETED | M |
| T | A | I | S | I | H | V | S | T | DELETED | P | P | I |
| T | A | I | S | I | H | V | S | T | DELETED | P | P | M |
| T | A | I | S | I | H | V | S | T | N | DELETED | DELETED | I |
| T | A | I | S | I | H | V | S | T | N | DELETED | DELETED | M |
| T | A | I | S | I | H | V | S | T | N | DELETED | P | I |
| T | A | I | S | I | H | V | S | T | N | DELETED | P | M |
| T | A | I | S | I | H | V | S | T | N | P | DELETED | I |
| T | A | I | S | I | H | V | S | T | N | P | DELETED | M |
| T | A | I | S | I | H | V | S | T | N | P | P | I |
| T | A | I | S | I | H | V | S | T | N | P | P | M |
| T | A | I | S | I | H | V | G | S | DELETED | DELETED | DELETED | I |
| T | A | I | S | I | H | V | G | S | DELETED | DELETED | DELETED | M |
| T | A | I | S | I | H | V | G | S | DELETED | DELETED | P | I |
| T | A | I | S | I | H | V | G | S | DELETED | DELETED | P | M |
| T | A | I | S | I | H | V | G | S | DELETED | P | DELETED | I |
| T | A | I | S | I | H | V | G | S | DELETED | P | DELETED | M |
| T | A | I | S | I | H | V | G | S | DELETED | P | P | I |
| T | A | I | S | I | H | V | G | S | DELETED | P | P | M |
| T | A | I | S | I | H | V | G | S | N | DELETED | DELETED | I |
| T | A | I | S | I | H | V | G | S | N | DELETED | DELETED | M |
| T | A | I | S | I | H | V | G | S | N | DELETED | P | I |
| T | A | I | S | I | H | V | G | S | N | DELETED | P | M |
| T | A | I | S | I | H | V | G | S | N | P | DELETED | I |
| T | A | I | S | I | H | V | G | S | N | P | DELETED | M |
| T | A | I | S | I | H | V | G | S | N | P | P | I |
| T | A | I | S | I | H | V | G | S | N | P | P | M |
| T | A | I | S | I | H | V | G | T | DELETED | DELETED | DELETED | I |
| T | A | I | S | I | H | V | G | T | DELETED | DELETED | DELETED | M |
| T | A | I | S | I | H | V | G | T | DELETED | DELETED | P | I |
| T | A | I | S | I | H | V | G | T | DELETED | DELETED | P | M |
| T | A | I | S | I | H | V | G | T | DELETED | P | DELETED | I |
| T | A | I | S | I | H | V | G | T | DELETED | P | DELETED | M |
| T | A | I | S | I | H | V | G | T | DELETED | P | P | I |
| T | A | I | S | I | H | V | G | T | DELETED | P | P | M |
| T | A | I | S | I | H | V | G | T | N | DELETED | DELETED | I |
| T | A | I | S | I | H | V | G | T | N | DELETED | DELETED | M |
| T | A | I | S | I | H | V | G | T | N | DELETED | P | I |
| T | A | I | S | I | H | V | G | T | N | DELETED | P | M |
| T | A | I | S | I | H | V | G | T | N | P | DELETED | I |
| T | A | I | S | I | H | V | G | T | N | P | DELETED | M |
| T | A | I | S | I | H | V | G | T | N | P | P | I |
| T | A | I | S | I | H | V | G | T | N | P | P | M |
| T | A | I | R | L | Y | Q | S | S | DELETED | DELETED | DELETED | I |
| T | A | I | R | L | Y | Q | S | S | DELETED | DELETED | DELETED | M |
| T | A | I | R | L | Y | Q | S | S | DELETED | DELETED | P | I |
| T | A | I | R | L | Y | Q | S | S | DELETED | DELETED | P | M |
| T | A | I | R | L | Y | Q | S | S | DELETED | P | DELETED | I |
| T | A | I | R | L | Y | Q | S | S | DELETED | P | DELETED | M |
| T | A | I | R | L | Y | Q | S | S | DELETED | P | P | I |
| T | A | I | R | L | Y | Q | S | S | DELETED | P | P | M |
| T | A | I | R | L | Y | Q | S | S | N | DELETED | DELETED | I |
| T | A | I | R | L | Y | Q | S | S | N | DELETED | DELETED | M |
| T | A | I | R | L | Y | Q | S | S | N | DELETED | P | I |
| T | A | I | R | L | Y | Q | S | S | N | DELETED | P | M |
| T | A | I | R | L | Y | Q | S | S | N | P | DELETED | I |
| T | A | I | R | L | Y | Q | S | S | N | P | DELETED | M |
| T | A | I | R | L | Y | Q | S | S | N | P | P | I |
| T | A | I | R | L | Y | Q | S | S | N | P | P | M |
| T | A | I | R | L | Y | Q | S | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | L | Y | Q | S | T | DELETED | DELETED | DELETED | M |
| T | A | I | R | L | Y | Q | S | T | DELETED | DELETED | P | I |
| T | A | I | R | L | Y | Q | S | T | DELETED | DELETED | P | M |
| T | A | I | R | L | Y | Q | S | T | DELETED | P | DELETED | I |
| T | A | I | R | L | Y | Q | S | T | DELETED | P | DELETED | M |
| T | A | I | R | L | Y | Q | S | T | DELETED | P | P | I |
| T | A | I | R | L | Y | Q | S | T | DELETED | P | P | M |
| T | A | I | R | L | Y | Q | S | T | N | DELETED | DELETED | I |
| T | A | I | R | L | Y | Q | S | T | N | DELETED | DELETED | M |
| T | A | I | R | L | Y | Q | S | T | N | DELETED | P | I |
| T | A | I | R | L | Y | Q | S | T | N | DELETED | P | M |
| T | A | I | R | L | Y | Q | S | T | N | P | DELETED | I |
| T | A | I | R | L | Y | Q | S | T | N | P | DELETED | M |
| T | A | I | R | L | Y | Q | S | T | N | P | P | I |
| T | A | I | R | L | Y | Q | S | T | N | P | P | M |
| T | A | I | R | L | Y | Q | G | S | DELETED | DELETED | DELETED | I |
| T | A | I | R | L | Y | Q | G | S | DELETED | DELETED | DELETED | M |
| T | A | I | R | L | Y | Q | G | S | DELETED | DELETED | P | I |
| T | A | I | R | L | Y | Q | G | S | DELETED | DELETED | P | M |
| T | A | I | R | L | Y | Q | G | S | DELETED | P | DELETED | I |
| T | A | I | R | L | Y | Q | G | S | DELETED | P | DELETED | M |
| T | A | I | R | L | Y | Q | G | S | DELETED | P | P | I |
| T | A | I | R | L | Y | Q | G | S | DELETED | P | P | M |
| T | A | I | R | L | Y | Q | G | S | N | DELETED | DELETED | I |
| T | A | I | R | L | Y | Q | G | S | N | DELETED | DELETED | M |
| T | A | I | R | L | Y | Q | G | S | N | DELETED | P | I |
| T | A | I | R | L | Y | Q | G | S | N | DELETED | P | M |
| T | A | I | R | L | Y | Q | G | S | N | P | DELETED | I |
| T | A | I | R | L | Y | Q | G | S | N | P | DELETED | M |
| T | A | I | R | L | Y | Q | G | S | N | P | P | I |
| T | A | I | R | L | Y | Q | G | S | N | P | P | M |
| T | A | I | R | L | Y | Q | G | T | DELETED | DELETED | DELETED | I |
| T | A | I | R | L | Y | Q | G | T | DELETED | DELETED | DELETED | M |
| T | A | I | R | L | Y | Q | G | T | DELETED | DELETED | P | I |
| T | A | I | R | L | Y | Q | G | T | DELETED | DELETED | P | M |
| T | A | I | R | L | Y | Q | G | T | DELETED | P | DELETED | I |
| T | A | I | R | L | Y | Q | G | T | DELETED | P | DELETED | M |
| T | A | I | R | L | Y | Q | G | T | DELETED | P | P | I |
| T | A | I | R | L | Y | Q | G | T | DELETED | P | P | M |
| T | A | I | R | L | Y | Q | G | T | N | DELETED | DELETED | I |
| T | A | I | R | L | Y | Q | G | T | N | DELETED | DELETED | M |
| T | A | I | R | L | Y | Q | G | T | N | DELETED | P | I |
| T | A | I | R | L | Y | Q | G | T | N | DELETED | P | M |
| T | A | I | R | L | Y | Q | G | T | N | P | DELETED | I |
| T | A | I | R | L | Y | Q | G | T | N | P | DELETED | M |
| T | A | I | R | L | Y | Q | G | T | N | P | P | I |
| T | A | I | R | L | Y | Q | G | T | N | P | P | M |
| T | A | I | R | L | Y | V | S | S | DELETED | DELETED | DELETED | I |
| T | A | I | R | L | Y | V | S | S | DELETED | DELETED | DELETED | M |
| T | A | I | R | L | Y | V | S | S | DELETED | DELETED | P | I |
| T | A | I | R | L | Y | V | S | S | DELETED | DELETED | P | M |
| T | A | I | R | L | Y | V | S | S | DELETED | P | DELETED | I |
| T | A | I | R | L | Y | V | S | S | DELETED | P | DELETED | M |
| T | A | I | R | L | Y | V | S | S | DELETED | P | P | I |
| T | A | I | R | L | Y | V | S | S | DELETED | P | P | M |
| T | A | I | R | L | Y | V | S | S | N | DELETED | DELETED | I |
| T | A | I | R | L | Y | V | S | S | N | DELETED | DELETED | M |
| T | A | I | R | L | Y | V | S | S | N | DELETED | P | I |
| T | A | I | R | L | Y | V | S | S | N | DELETED | P | M |
| T | A | I | R | L | Y | V | S | S | N | P | DELETED | I |
| T | A | I | R | L | Y | V | S | S | N | P | DELETED | M |
| T | A | I | R | L | Y | V | S | S | N | P | P | I |
| T | A | I | R | L | Y | V | S | S | N | P | P | M |
| T | A | I | R | L | Y | V | S | T | DELETED | DELETED | DELETED | I |
| T | A | I | R | L | Y | V | S | T | DELETED | DELETED | DELETED | M |
| T | A | I | R | L | Y | V | S | T | DELETED | DELETED | P | I |
| T | A | I | R | L | Y | V | S | T | DELETED | DELETED | P | M |
| T | A | I | R | L | Y | V | S | T | DELETED | P | DELETED | I |
| T | A | I | R | L | Y | V | S | T | DELETED | P | DELETED | M |
| T | A | I | R | L | Y | V | S | T | DELETED | P | P | I |
| T | A | I | R | L | Y | V | S | T | DELETED | P | P | M |
| T | A | I | R | L | Y | V | S | T | N | DELETED | DELETED | I |
| T | A | I | R | L | Y | V | S | T | N | DELETED | DELETED | M |
| T | A | I | R | L | Y | V | S | T | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | L | Y | V | S | T | N | DELETED | P | M |
| T | A | I | R | L | Y | V | S | T | N | P | DELETED | I |
| T | A | I | R | L | Y | V | S | T | N | P | DELETED | M |
| T | A | I | R | L | Y | V | S | T | N | P | P | I |
| T | A | I | R | L | Y | V | S | T | N | P | P | M |
| T | A | I | R | L | Y | V | G | S | DELETED | DELETED | DELETED | I |
| T | A | I | R | L | Y | V | G | S | DELETED | DELETED | DELETED | M |
| T | A | I | R | L | Y | V | G | S | DELETED | DELETED | P | I |
| T | A | I | R | L | Y | V | G | S | DELETED | DELETED | P | M |
| T | A | I | R | L | Y | V | G | S | DELETED | P | DELETED | I |
| T | A | I | R | L | Y | V | G | S | DELETED | P | DELETED | M |
| T | A | I | R | L | Y | V | G | S | DELETED | P | P | I |
| T | A | I | R | L | Y | V | G | S | DELETED | P | P | M |
| T | A | I | R | L | Y | V | G | S | N | DELETED | DELETED | I |
| T | A | I | R | L | Y | V | G | S | N | DELETED | DELETED | M |
| T | A | I | R | L | Y | V | G | S | N | DELETED | P | I |
| T | A | I | R | L | Y | V | G | S | N | DELETED | P | M |
| T | A | I | R | L | Y | V | G | S | N | P | DELETED | I |
| T | A | I | R | L | Y | V | G | S | N | P | DELETED | M |
| T | A | I | R | L | Y | V | G | S | N | P | P | I |
| T | A | I | R | L | Y | V | G | S | N | P | P | M |
| T | A | I | R | L | Y | V | G | T | DELETED | DELETED | DELETED | I |
| T | A | I | R | L | Y | V | G | T | DELETED | DELETED | DELETED | M |
| T | A | I | R | L | Y | V | G | T | DELETED | DELETED | P | I |
| T | A | I | R | L | Y | V | G | T | DELETED | DELETED | P | M |
| T | A | I | R | L | Y | V | G | T | DELETED | P | DELETED | I |
| T | A | I | R | L | Y | V | G | T | DELETED | P | DELETED | M |
| T | A | I | R | L | Y | V | G | T | DELETED | P | P | I |
| T | A | I | R | L | Y | V | G | T | DELETED | P | P | M |
| T | A | I | R | L | Y | V | G | T | N | DELETED | DELETED | I |
| T | A | I | R | L | Y | V | G | T | N | DELETED | DELETED | M |
| T | A | I | R | L | Y | V | G | T | N | DELETED | P | I |
| T | A | I | R | L | Y | V | G | T | N | DELETED | P | M |
| T | A | I | R | L | Y | V | G | T | N | P | DELETED | I |
| T | A | I | R | L | Y | V | G | T | N | P | DELETED | M |
| T | A | I | R | L | Y | V | G | T | N | P | P | I |
| T | A | I | R | L | Y | V | G | T | N | P | P | M |
| T | A | I | R | L | H | Q | S | S | DELETED | DELETED | DELETED | I |
| T | A | I | R | L | H | Q | S | S | DELETED | DELETED | DELETED | M |
| T | A | I | R | L | H | Q | S | S | DELETED | DELETED | P | I |
| T | A | I | R | L | H | Q | S | S | DELETED | DELETED | P | M |
| T | A | I | R | L | H | Q | S | S | DELETED | P | DELETED | I |
| T | A | I | R | L | H | Q | S | S | DELETED | P | DELETED | M |
| T | A | I | R | L | H | Q | S | S | DELETED | P | P | I |
| T | A | I | R | L | H | Q | S | S | DELETED | P | P | M |
| T | A | I | R | L | H | Q | S | S | N | DELETED | DELETED | I |
| T | A | I | R | L | H | Q | S | S | N | DELETED | DELETED | M |
| T | A | I | R | L | H | Q | S | S | N | DELETED | P | I |
| T | A | I | R | L | H | Q | S | S | N | DELETED | P | M |
| T | A | I | R | L | H | Q | S | S | N | P | DELETED | I |
| T | A | I | R | L | H | Q | S | S | N | P | DELETED | M |
| T | A | I | R | L | H | Q | S | S | N | P | P | I |
| T | A | I | R | L | H | Q | S | S | N | P | P | M |
| T | A | I | R | L | H | Q | S | T | DELETED | DELETED | DELETED | I |
| T | A | I | R | L | H | Q | S | T | DELETED | DELETED | DELETED | M |
| T | A | I | R | L | H | Q | S | T | DELETED | DELETED | P | I |
| T | A | I | R | L | H | Q | S | T | DELETED | DELETED | P | M |
| T | A | I | R | L | H | Q | S | T | DELETED | P | DELETED | I |
| T | A | I | R | L | H | Q | S | T | DELETED | P | DELETED | M |
| T | A | I | R | L | H | Q | S | T | DELETED | P | P | I |
| T | A | I | R | L | H | Q | S | T | DELETED | P | P | M |
| T | A | I | R | L | H | Q | S | T | N | DELETED | DELETED | I |
| T | A | I | R | L | H | Q | S | T | N | DELETED | DELETED | M |
| T | A | I | R | L | H | Q | S | T | N | DELETED | P | I |
| T | A | I | R | L | H | Q | S | T | N | DELETED | P | M |
| T | A | I | R | L | H | Q | S | T | N | P | DELETED | I |
| T | A | I | R | L | H | Q | S | T | N | P | DELETED | M |
| T | A | I | R | L | H | Q | S | T | N | P | P | I |
| T | A | I | R | L | H | Q | S | T | N | P | P | M |
| T | A | I | R | L | H | Q | G | S | DELETED | DELETED | DELETED | I |
| T | A | I | R | L | H | Q | G | S | DELETED | DELETED | DELETED | M |
| T | A | I | R | L | H | Q | G | S | DELETED | DELETED | P | I |
| T | A | I | R | L | H | Q | G | S | DELETED | DELETED | P | M |
| T | A | I | R | L | H | Q | G | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | L | H | Q | G | S | DELETED | P | DELETED | M |
| T | A | I | R | L | H | Q | G | S | DELETED | P | P | I |
| T | A | I | R | L | H | Q | G | S | DELETED | P | P | M |
| T | A | I | R | L | H | Q | G | S | N | DELETED | DELETED | I |
| T | A | I | R | L | H | Q | G | S | N | DELETED | DELETED | M |
| T | A | I | R | L | H | Q | G | S | N | DELETED | P | I |
| T | A | I | R | L | H | Q | G | S | N | DELETED | P | M |
| T | A | I | R | L | H | Q | G | S | N | P | DELETED | I |
| T | A | I | R | L | H | Q | G | S | N | P | DELETED | M |
| T | A | I | R | L | H | Q | G | S | N | P | P | I |
| T | A | I | R | L | H | Q | G | S | N | P | P | M |
| T | A | I | R | L | H | Q | G | T | DELETED | DELETED | DELETED | I |
| T | A | I | R | L | H | Q | G | T | DELETED | DELETED | DELETED | M |
| T | A | I | R | L | H | Q | G | T | DELETED | DELETED | P | I |
| T | A | I | R | L | H | Q | G | T | DELETED | DELETED | P | M |
| T | A | I | R | L | H | Q | G | T | DELETED | P | DELETED | I |
| T | A | I | R | L | H | Q | G | T | DELETED | P | DELETED | M |
| T | A | I | R | L | H | Q | G | T | DELETED | P | P | I |
| T | A | I | R | L | H | Q | G | T | DELETED | P | P | M |
| T | A | I | R | L | H | Q | G | T | N | DELETED | DELETED | I |
| T | A | I | R | L | H | Q | G | T | N | DELETED | DELETED | M |
| T | A | I | R | L | H | Q | G | T | N | DELETED | P | I |
| T | A | I | R | L | H | Q | G | T | N | DELETED | P | M |
| T | A | I | R | L | H | Q | G | T | N | P | DELETED | I |
| T | A | I | R | L | H | Q | G | T | N | P | DELETED | M |
| T | A | I | R | L | H | Q | G | T | N | P | P | I |
| T | A | I | R | L | H | Q | G | T | N | P | P | M |
| T | A | I | R | L | H | V | S | S | DELETED | DELETED | DELETED | I |
| T | A | I | R | L | H | V | S | S | DELETED | DELETED | DELETED | M |
| T | A | I | R | L | H | V | S | S | DELETED | DELETED | P | I |
| T | A | I | R | L | H | V | S | S | DELETED | DELETED | P | M |
| T | A | I | R | L | H | V | S | S | DELETED | P | DELETED | I |
| T | A | I | R | L | H | V | S | S | DELETED | P | DELETED | M |
| T | A | I | R | L | H | V | S | S | DELETED | P | P | I |
| T | A | I | R | L | H | V | S | S | DELETED | P | P | M |
| T | A | I | R | L | H | V | S | S | N | DELETED | DELETED | I |
| T | A | I | R | L | H | V | S | S | N | DELETED | DELETED | M |
| T | A | I | R | L | H | V | S | S | N | DELETED | P | I |
| T | A | I | R | L | H | V | S | S | N | DELETED | P | M |
| T | A | I | R | L | H | V | S | S | N | P | DELETED | I |
| T | A | I | R | L | H | V | S | S | N | P | DELETED | M |
| T | A | I | R | L | H | V | S | S | N | P | P | I |
| T | A | I | R | L | H | V | S | S | N | P | P | M |
| T | A | I | R | L | H | V | S | T | DELETED | DELETED | DELETED | I |
| T | A | I | R | L | H | V | S | T | DELETED | DELETED | DELETED | M |
| T | A | I | R | L | H | V | S | T | DELETED | DELETED | P | I |
| T | A | I | R | L | H | V | S | T | DELETED | DELETED | P | M |
| T | A | I | R | L | H | V | S | T | DELETED | P | DELETED | I |
| T | A | I | R | L | H | V | S | T | DELETED | P | DELETED | M |
| T | A | I | R | L | H | V | S | T | DELETED | P | P | I |
| T | A | I | R | L | H | V | S | T | DELETED | P | P | M |
| T | A | I | R | L | H | V | S | T | N | DELETED | DELETED | I |
| T | A | I | R | L | H | V | S | T | N | DELETED | DELETED | M |
| T | A | I | R | L | H | V | S | T | N | DELETED | P | I |
| T | A | I | R | L | H | V | S | T | N | DELETED | P | M |
| T | A | I | R | L | H | V | S | T | N | P | DELETED | I |
| T | A | I | R | L | H | V | S | T | N | P | DELETED | M |
| T | A | I | R | L | H | V | S | T | N | P | P | I |
| T | A | I | R | L | H | V | S | T | N | P | P | M |
| T | A | I | R | L | H | V | G | S | DELETED | DELETED | DELETED | I |
| T | A | I | R | L | H | V | G | S | DELETED | DELETED | DELETED | M |
| T | A | I | R | L | H | V | G | S | DELETED | DELETED | P | I |
| T | A | I | R | L | H | V | G | S | DELETED | DELETED | P | M |
| T | A | I | R | L | H | V | G | S | DELETED | P | DELETED | I |
| T | A | I | R | L | H | V | G | S | DELETED | P | DELETED | M |
| T | A | I | R | L | H | V | G | S | DELETED | P | P | I |
| T | A | I | R | L | H | V | G | S | DELETED | P | P | M |
| T | A | I | R | L | H | V | G | S | N | DELETED | DELETED | I |
| T | A | I | R | L | H | V | G | S | N | DELETED | DELETED | M |
| T | A | I | R | L | H | V | G | S | N | DELETED | P | I |
| T | A | I | R | L | H | V | G | S | N | DELETED | P | M |
| T | A | I | R | L | H | V | G | S | N | P | DELETED | I |
| T | A | I | R | L | H | V | G | S | N | P | DELETED | M |
| T | A | I | R | L | H | V | G | S | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | L | H | V | G | S | N | P | P | M |
| T | A | I | R | L | H | V | G | T | DELETED | DELETED | DELETED | I |
| T | A | I | R | L | H | V | G | T | DELETED | DELETED | DELETED | M |
| T | A | I | R | L | H | V | G | T | DELETED | DELETED | P | I |
| T | A | I | R | L | H | V | G | T | DELETED | DELETED | P | M |
| T | A | I | R | L | H | V | G | T | DELETED | P | DELETED | I |
| T | A | I | R | L | H | V | G | T | DELETED | P | DELETED | M |
| T | A | I | R | L | H | V | G | T | DELETED | P | P | I |
| T | A | I | R | L | H | V | G | T | DELETED | P | P | M |
| T | A | I | R | L | H | V | G | T | N | DELETED | DELETED | I |
| T | A | I | R | L | H | V | G | T | N | DELETED | DELETED | M |
| T | A | I | R | L | H | V | G | T | N | DELETED | P | I |
| T | A | I | R | L | H | V | G | T | N | DELETED | P | M |
| T | A | I | R | L | H | V | G | T | N | P | DELETED | I |
| T | A | I | R | L | H | V | G | T | N | P | DELETED | M |
| T | A | I | R | L | H | V | G | T | N | P | P | I |
| T | A | I | R | L | H | V | G | T | N | P | P | M |
| T | A | I | R | I | Y | Q | S | S | DELETED | DELETED | DELETED | I |
| T | A | I | R | I | Y | Q | S | S | DELETED | DELETED | DELETED | M |
| T | A | I | R | I | Y | Q | S | S | DELETED | DELETED | P | I |
| T | A | I | R | I | Y | Q | S | S | DELETED | DELETED | P | M |
| T | A | I | R | I | Y | Q | S | S | DELETED | P | DELETED | I |
| T | A | I | R | I | Y | Q | S | S | DELETED | P | DELETED | M |
| T | A | I | R | I | Y | Q | S | S | DELETED | P | P | I |
| T | A | I | R | I | Y | Q | S | S | DELETED | P | P | M |
| T | A | I | R | I | Y | Q | S | S | N | DELETED | DELETED | I |
| T | A | I | R | I | Y | Q | S | S | N | DELETED | DELETED | M |
| T | A | I | R | I | Y | Q | S | S | N | DELETED | P | I |
| T | A | I | R | I | Y | Q | S | S | N | DELETED | P | M |
| T | A | I | R | I | Y | Q | S | S | N | P | DELETED | I |
| T | A | I | R | I | Y | Q | S | S | N | P | DELETED | M |
| T | A | I | R | I | Y | Q | S | S | N | P | P | I |
| T | A | I | R | I | Y | Q | S | S | N | P | P | M |
| T | A | I | R | I | Y | Q | S | T | DELETED | DELETED | DELETED | I |
| T | A | I | R | I | Y | Q | S | T | DELETED | DELETED | DELETED | M |
| T | A | I | R | I | Y | Q | S | T | DELETED | DELETED | P | I |
| T | A | I | R | I | Y | Q | S | T | DELETED | DELETED | P | M |
| T | A | I | R | I | Y | Q | S | T | DELETED | P | DELETED | I |
| T | A | I | R | I | Y | Q | S | T | DELETED | P | DELETED | M |
| T | A | I | R | I | Y | Q | S | T | DELETED | P | P | I |
| T | A | I | R | I | Y | Q | S | T | DELETED | P | P | M |
| T | A | I | R | I | Y | Q | S | T | N | DELETED | DELETED | I |
| T | A | I | R | I | Y | Q | S | T | N | DELETED | DELETED | M |
| T | A | I | R | I | Y | Q | S | T | N | DELETED | P | I |
| T | A | I | R | I | Y | Q | S | T | N | DELETED | P | M |
| T | A | I | R | I | Y | Q | S | T | N | P | DELETED | I |
| T | A | I | R | I | Y | Q | S | T | N | P | DELETED | M |
| T | A | I | R | I | Y | Q | S | T | N | P | P | I |
| T | A | I | R | I | Y | Q | S | T | N | P | P | M |
| T | A | I | R | I | Y | Q | G | S | DELETED | DELETED | DELETED | I |
| T | A | I | R | I | Y | Q | G | S | DELETED | DELETED | DELETED | M |
| T | A | I | R | I | Y | Q | G | S | DELETED | DELETED | P | I |
| T | A | I | R | I | Y | Q | G | S | DELETED | DELETED | P | M |
| T | A | I | R | I | Y | Q | G | S | DELETED | P | DELETED | I |
| T | A | I | R | I | Y | Q | G | S | DELETED | P | DELETED | M |
| T | A | I | R | I | Y | Q | G | S | DELETED | P | P | I |
| T | A | I | R | I | Y | Q | G | S | DELETED | P | P | M |
| T | A | I | R | I | Y | Q | G | S | N | DELETED | DELETED | I |
| T | A | I | R | I | Y | Q | G | S | N | DELETED | DELETED | M |
| T | A | I | R | I | Y | Q | G | S | N | DELETED | P | I |
| T | A | I | R | I | Y | Q | G | S | N | DELETED | P | M |
| T | A | I | R | I | Y | Q | G | S | N | P | DELETED | I |
| T | A | I | R | I | Y | Q | G | S | N | P | DELETED | M |
| T | A | I | R | I | Y | Q | G | S | N | P | P | I |
| T | A | I | R | I | Y | Q | G | S | N | P | P | M |
| T | A | I | R | I | Y | Q | G | T | DELETED | DELETED | DELETED | I |
| T | A | I | R | I | Y | Q | G | T | DELETED | DELETED | DELETED | M |
| T | A | I | R | I | Y | Q | G | T | DELETED | DELETED | P | I |
| T | A | I | R | I | Y | Q | G | T | DELETED | DELETED | P | M |
| T | A | I | R | I | Y | Q | G | T | DELETED | P | DELETED | I |
| T | A | I | R | I | Y | Q | G | T | DELETED | P | DELETED | M |
| T | A | I | R | I | Y | Q | G | T | DELETED | P | P | I |
| T | A | I | R | I | Y | Q | G | T | DELETED | P | P | M |
| T | A | I | R | I | Y | Q | G | T | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | I | Y | Q | G | T | N | DELETED | DELETED | M |
| T | A | I | R | I | Y | Q | G | T | N | DELETED | P | I |
| T | A | I | R | I | Y | Q | G | T | N | DELETED | P | M |
| T | A | I | R | I | Y | Q | G | T | N | P | DELETED | I |
| T | A | I | R | I | Y | Q | G | T | N | P | DELETED | M |
| T | A | I | R | I | Y | Q | G | T | N | P | P | I |
| T | A | I | R | I | Y | Q | G | T | N | P | P | M |
| T | A | I | R | I | Y | V | S | S | DELETED | DELETED | DELETED | I |
| T | A | I | R | I | Y | V | S | S | DELETED | DELETED | DELETED | M |
| T | A | I | R | I | Y | V | S | S | DELETED | DELETED | P | I |
| T | A | I | R | I | Y | V | S | S | DELETED | DELETED | P | M |
| T | A | I | R | I | Y | V | S | S | DELETED | P | DELETED | I |
| T | A | I | R | I | Y | V | S | S | DELETED | P | DELETED | M |
| T | A | I | R | I | Y | V | S | S | DELETED | P | P | I |
| T | A | I | R | I | Y | V | S | S | DELETED | P | P | M |
| T | A | I | R | I | Y | V | S | S | N | DELETED | DELETED | I |
| T | A | I | R | I | Y | V | S | S | N | DELETED | DELETED | M |
| T | A | I | R | I | Y | V | S | S | N | DELETED | P | I |
| T | A | I | R | I | Y | V | S | S | N | DELETED | P | M |
| T | A | I | R | I | Y | V | S | S | N | P | DELETED | I |
| T | A | I | R | I | Y | V | S | S | N | P | DELETED | M |
| T | A | I | R | I | Y | V | S | S | N | P | P | I |
| T | A | I | R | I | Y | V | S | S | N | P | P | M |
| T | A | I | R | I | Y | V | S | T | DELETED | DELETED | DELETED | I |
| T | A | I | R | I | Y | V | S | T | DELETED | DELETED | DELETED | M |
| T | A | I | R | I | Y | V | S | T | DELETED | DELETED | P | I |
| T | A | I | R | I | Y | V | S | T | DELETED | DELETED | P | M |
| T | A | I | R | I | Y | V | S | T | DELETED | P | DELETED | I |
| T | A | I | R | I | Y | V | S | T | DELETED | P | DELETED | M |
| T | A | I | R | I | Y | V | S | T | DELETED | P | P | I |
| T | A | I | R | I | Y | V | S | T | DELETED | P | P | M |
| T | A | I | R | I | Y | V | S | T | N | DELETED | DELETED | I |
| T | A | I | R | I | Y | V | S | T | N | DELETED | DELETED | M |
| T | A | I | R | I | Y | V | S | T | N | DELETED | P | I |
| T | A | I | R | I | Y | V | S | T | N | DELETED | P | M |
| T | A | I | R | I | Y | V | S | T | N | P | DELETED | I |
| T | A | I | R | I | Y | V | S | T | N | P | DELETED | M |
| T | A | I | R | I | Y | V | S | T | N | P | P | I |
| T | A | I | R | I | Y | V | S | T | N | P | P | M |
| T | A | I | R | I | Y | V | G | S | DELETED | DELETED | DELETED | I |
| T | A | I | R | I | Y | V | G | S | DELETED | DELETED | DELETED | M |
| T | A | I | R | I | Y | V | G | S | DELETED | DELETED | P | I |
| T | A | I | R | I | Y | V | G | S | DELETED | DELETED | P | M |
| T | A | I | R | I | Y | V | G | S | DELETED | P | DELETED | I |
| T | A | I | R | I | Y | V | G | S | DELETED | P | DELETED | M |
| T | A | I | R | I | Y | V | G | S | DELETED | P | P | I |
| T | A | I | R | I | Y | V | G | S | DELETED | P | P | M |
| T | A | I | R | I | Y | V | G | S | N | DELETED | DELETED | I |
| T | A | I | R | I | Y | V | G | S | N | DELETED | DELETED | M |
| T | A | I | R | I | Y | V | G | S | N | DELETED | P | I |
| T | A | I | R | I | Y | V | G | S | N | DELETED | P | M |
| T | A | I | R | I | Y | V | G | S | N | P | DELETED | I |
| T | A | I | R | I | Y | V | G | S | N | P | DELETED | M |
| T | A | I | R | I | Y | V | G | S | N | P | P | I |
| T | A | I | R | I | Y | V | G | S | N | P | P | M |
| T | A | I | R | I | Y | V | G | T | DELETED | DELETED | DELETED | I |
| T | A | I | R | I | Y | V | G | T | DELETED | DELETED | DELETED | M |
| T | A | I | R | I | Y | V | G | T | DELETED | DELETED | P | I |
| T | A | I | R | I | Y | V | G | T | DELETED | DELETED | P | M |
| T | A | I | R | I | Y | V | G | T | DELETED | P | DELETED | I |
| T | A | I | R | I | Y | V | G | T | DELETED | P | DELETED | M |
| T | A | I | R | I | Y | V | G | T | DELETED | P | P | I |
| T | A | I | R | I | Y | V | G | T | DELETED | P | P | M |
| T | A | I | R | I | Y | V | G | T | N | DELETED | DELETED | I |
| T | A | I | R | I | Y | V | G | T | N | DELETED | DELETED | M |
| T | A | I | R | I | Y | V | G | T | N | DELETED | P | I |
| T | A | I | R | I | Y | V | G | T | N | DELETED | P | M |
| T | A | I | R | I | Y | V | G | T | N | P | DELETED | I |
| T | A | I | R | I | Y | V | G | T | N | P | DELETED | M |
| T | A | I | R | I | Y | V | G | T | N | P | P | I |
| T | A | I | R | I | Y | V | G | T | N | P | P | M |
| T | A | I | R | I | H | Q | S | S | DELETED | DELETED | DELETED | I |
| T | A | I | R | I | H | Q | S | S | DELETED | DELETED | DELETED | M |
| T | A | I | R | I | H | Q | S | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | I | H | Q | S | S | DELETED | DELETED | P | M |
| T | A | I | R | I | H | Q | S | S | DELETED | P | DELETED | I |
| T | A | I | R | I | H | Q | S | S | DELETED | P | DELETED | M |
| T | A | I | R | I | H | Q | S | S | DELETED | P | P | I |
| T | A | I | R | I | H | Q | S | S | DELETED | P | P | M |
| T | A | I | R | I | H | Q | S | S | N | DELETED | DELETED | I |
| T | A | I | R | I | H | Q | S | S | N | DELETED | DELETED | M |
| T | A | I | R | I | H | Q | S | S | N | DELETED | P | I |
| T | A | I | R | I | H | Q | S | S | N | DELETED | P | M |
| T | A | I | R | I | H | Q | S | S | N | P | DELETED | I |
| T | A | I | R | I | H | Q | S | S | N | P | DELETED | M |
| T | A | I | R | I | H | Q | S | S | N | P | P | I |
| T | A | I | R | I | H | Q | S | S | N | P | P | M |
| T | A | I | R | I | H | Q | S | T | DELETED | DELETED | DELETED | I |
| T | A | I | R | I | H | Q | S | T | DELETED | DELETED | DELETED | M |
| T | A | I | R | I | H | Q | S | T | DELETED | DELETED | P | I |
| T | A | I | R | I | H | Q | S | T | DELETED | DELETED | P | M |
| T | A | I | R | I | H | Q | S | T | DELETED | P | DELETED | I |
| T | A | I | R | I | H | Q | S | T | DELETED | P | DELETED | M |
| T | A | I | R | I | H | Q | S | T | DELETED | P | P | I |
| T | A | I | R | I | H | Q | S | T | DELETED | P | P | M |
| T | A | I | R | I | H | Q | S | T | N | DELETED | DELETED | I |
| T | A | I | R | I | H | Q | S | T | N | DELETED | DELETED | M |
| T | A | I | R | I | H | Q | S | T | N | DELETED | P | I |
| T | A | I | R | I | H | Q | S | T | N | DELETED | P | M |
| T | A | I | R | I | H | Q | S | T | N | P | DELETED | I |
| T | A | I | R | I | H | Q | S | T | N | P | DELETED | M |
| T | A | I | R | I | H | Q | S | T | N | P | P | I |
| T | A | I | R | I | H | Q | S | T | N | P | P | M |
| T | A | I | R | I | H | Q | G | S | DELETED | DELETED | DELETED | I |
| T | A | I | R | I | H | Q | G | S | DELETED | DELETED | DELETED | M |
| T | A | I | R | I | H | Q | G | S | DELETED | DELETED | P | I |
| T | A | I | R | I | H | Q | G | S | DELETED | DELETED | P | M |
| T | A | I | R | I | H | Q | G | S | DELETED | P | DELETED | I |
| T | A | I | R | I | H | Q | G | S | DELETED | P | DELETED | M |
| T | A | I | R | I | H | Q | G | S | DELETED | P | P | I |
| T | A | I | R | I | H | Q | G | S | DELETED | P | P | M |
| T | A | I | R | I | H | Q | G | S | N | DELETED | DELETED | I |
| T | A | I | R | I | H | Q | G | S | N | DELETED | DELETED | M |
| T | A | I | R | I | H | Q | G | S | N | DELETED | P | I |
| T | A | I | R | I | H | Q | G | S | N | DELETED | P | M |
| T | A | I | R | I | H | Q | G | S | N | P | DELETED | I |
| T | A | I | R | I | H | Q | G | S | N | P | DELETED | M |
| T | A | I | R | I | H | Q | G | S | N | P | P | I |
| T | A | I | R | I | H | Q | G | S | N | P | P | M |
| T | A | I | R | I | H | Q | G | T | DELETED | DELETED | DELETED | I |
| T | A | I | R | I | H | Q | G | T | DELETED | DELETED | DELETED | M |
| T | A | I | R | I | H | Q | G | T | DELETED | DELETED | P | I |
| T | A | I | R | I | H | Q | G | T | DELETED | DELETED | P | M |
| T | A | I | R | I | H | Q | G | T | DELETED | P | DELETED | I |
| T | A | I | R | I | H | Q | G | T | DELETED | P | DELETED | M |
| T | A | I | R | I | H | Q | G | T | DELETED | P | P | I |
| T | A | I | R | I | H | Q | G | T | DELETED | P | P | M |
| T | A | I | R | I | H | Q | G | T | N | DELETED | DELETED | I |
| T | A | I | R | I | H | Q | G | T | N | DELETED | DELETED | M |
| T | A | I | R | I | H | Q | G | T | N | DELETED | P | I |
| T | A | I | R | I | H | Q | G | T | N | DELETED | P | M |
| T | A | I | R | I | H | Q | G | T | N | P | DELETED | I |
| T | A | I | R | I | H | Q | G | T | N | P | DELETED | M |
| T | A | I | R | I | H | Q | G | T | N | P | P | I |
| T | A | I | R | I | H | Q | G | T | N | P | P | M |
| T | A | I | R | I | H | V | S | S | DELETED | DELETED | DELETED | I |
| T | A | I | R | I | H | V | S | S | DELETED | DELETED | DELETED | M |
| T | A | I | R | I | H | V | S | S | DELETED | DELETED | P | I |
| T | A | I | R | I | H | V | S | S | DELETED | DELETED | P | M |
| T | A | I | R | I | H | V | S | S | DELETED | P | DELETED | I |
| T | A | I | R | I | H | V | S | S | DELETED | P | DELETED | M |
| T | A | I | R | I | H | V | S | S | DELETED | P | P | I |
| T | A | I | R | I | H | V | S | S | DELETED | P | P | M |
| T | A | I | R | I | H | V | S | S | N | DELETED | DELETED | I |
| T | A | I | R | I | H | V | S | S | N | DELETED | DELETED | M |
| T | A | I | R | I | H | V | S | S | N | DELETED | P | I |
| T | A | I | R | I | H | V | S | S | N | DELETED | P | M |
| T | A | I | R | I | H | V | S | S | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | I | R | I | H | V | S | S | N | P | DELETED | M |
| T | A | I | R | I | H | V | S | S | N | P | P | I |
| T | A | I | R | I | H | V | S | S | N | P | P | M |
| T | A | I | R | I | H | V | S | T | DELETED | DELETED | DELETED | I |
| T | A | I | R | I | H | V | S | T | DELETED | DELETED | DELETED | M |
| T | A | I | R | I | H | V | S | T | DELETED | DELETED | P | I |
| T | A | I | R | I | H | V | S | T | DELETED | DELETED | P | M |
| T | A | I | R | I | H | V | S | T | DELETED | P | DELETED | I |
| T | A | I | R | I | H | V | S | T | DELETED | P | DELETED | M |
| T | A | I | R | I | H | V | S | T | DELETED | P | P | I |
| T | A | I | R | I | H | V | S | T | DELETED | P | P | M |
| T | A | I | R | I | H | V | S | T | N | DELETED | DELETED | I |
| T | A | I | R | I | H | V | S | T | N | DELETED | DELETED | M |
| T | A | I | R | I | H | V | S | T | N | DELETED | P | I |
| T | A | I | R | I | H | V | S | T | N | DELETED | P | M |
| T | A | I | R | I | H | V | S | T | N | P | DELETED | I |
| T | A | I | R | I | H | V | S | T | N | P | DELETED | M |
| T | A | I | R | I | H | V | S | T | N | P | P | I |
| T | A | I | R | I | H | V | S | T | N | P | P | M |
| T | A | I | R | I | H | V | G | S | DELETED | DELETED | DELETED | I |
| T | A | I | R | I | H | V | G | S | DELETED | DELETED | DELETED | M |
| T | A | I | R | I | H | V | G | S | DELETED | DELETED | P | I |
| T | A | I | R | I | H | V | G | S | DELETED | DELETED | P | M |
| T | A | I | R | I | H | V | G | S | DELETED | P | DELETED | I |
| T | A | I | R | I | H | V | G | S | DELETED | P | DELETED | M |
| T | A | I | R | I | H | V | G | S | DELETED | P | P | I |
| T | A | I | R | I | H | V | G | S | DELETED | P | P | M |
| T | A | I | R | I | H | V | G | S | N | DELETED | DELETED | I |
| T | A | I | R | I | H | V | G | S | N | DELETED | DELETED | M |
| T | A | I | R | I | H | V | G | S | N | DELETED | P | I |
| T | A | I | R | I | H | V | G | S | N | DELETED | P | M |
| T | A | I | R | I | H | V | G | S | N | P | DELETED | I |
| T | A | I | R | I | H | V | G | S | N | P | DELETED | M |
| T | A | I | R | I | H | V | G | S | N | P | P | I |
| T | A | I | R | I | H | V | G | S | N | P | P | M |
| T | A | I | R | I | H | V | G | T | DELETED | DELETED | DELETED | I |
| T | A | I | R | I | H | V | G | T | DELETED | DELETED | DELETED | M |
| T | A | I | R | I | H | V | G | T | DELETED | DELETED | P | I |
| T | A | I | R | I | H | V | G | T | DELETED | DELETED | P | M |
| T | A | I | R | I | H | V | G | T | DELETED | P | DELETED | I |
| T | A | I | R | I | H | V | G | T | DELETED | P | DELETED | M |
| T | A | I | R | I | H | V | G | T | DELETED | P | P | I |
| T | A | I | R | I | H | V | G | T | DELETED | P | P | M |
| T | A | I | R | I | H | V | G | T | N | DELETED | DELETED | I |
| T | A | I | R | I | H | V | G | T | N | DELETED | DELETED | M |
| T | A | I | R | I | H | V | G | T | N | DELETED | P | I |
| T | A | I | R | I | H | V | G | T | N | DELETED | P | M |
| T | A | I | R | I | H | V | G | T | N | P | DELETED | I |
| T | A | I | R | I | H | V | G | T | N | P | DELETED | M |
| T | A | I | R | I | H | V | G | T | N | P | P | I |
| T | A | I | R | I | H | V | G | T | N | P | P | M |
| T | A | F | S | L | Y | Q | S | S | DELETED | DELETED | DELETED | I |
| T | A | F | S | L | Y | Q | S | S | DELETED | DELETED | DELETED | M |
| T | A | F | S | L | Y | Q | S | S | DELETED | DELETED | P | I |
| T | A | F | S | L | Y | Q | S | S | DELETED | DELETED | P | M |
| T | A | F | S | L | Y | Q | S | S | DELETED | P | DELETED | I |
| T | A | F | S | L | Y | Q | S | S | DELETED | P | DELETED | M |
| T | A | F | S | L | Y | Q | S | S | DELETED | P | P | I |
| T | A | F | S | L | Y | Q | S | S | DELETED | P | P | M |
| T | A | F | S | L | Y | Q | S | S | N | DELETED | DELETED | I |
| T | A | F | S | L | Y | Q | S | S | N | DELETED | DELETED | M |
| T | A | F | S | L | Y | Q | S | S | N | DELETED | P | I |
| T | A | F | S | L | Y | Q | S | S | N | DELETED | P | M |
| T | A | F | S | L | Y | Q | S | S | N | P | DELETED | I |
| T | A | F | S | L | Y | Q | S | S | N | P | DELETED | M |
| T | A | F | S | L | Y | Q | S | S | N | P | P | I |
| T | A | F | S | L | Y | Q | S | S | N | P | P | M |
| T | A | F | S | L | Y | Q | S | T | DELETED | DELETED | DELETED | I |
| T | A | F | S | L | Y | Q | S | T | DELETED | DELETED | DELETED | M |
| T | A | F | S | L | Y | Q | S | T | DELETED | DELETED | P | I |
| T | A | F | S | L | Y | Q | S | T | DELETED | DELETED | P | M |
| T | A | F | S | L | Y | Q | S | T | DELETED | P | DELETED | I |
| T | A | F | S | L | Y | Q | S | T | DELETED | P | DELETED | M |
| T | A | F | S | L | Y | Q | S | T | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | L | Y | Q | S | T | DELETED | P | P | M |
| T | A | F | S | L | Y | Q | S | T | N | DELETED | DELETED | I |
| T | A | F | S | L | Y | Q | S | T | N | DELETED | DELETED | M |
| T | A | F | S | L | Y | Q | S | T | N | DELETED | P | I |
| T | A | F | S | L | Y | Q | S | T | N | DELETED | P | M |
| T | A | F | S | L | Y | Q | S | T | N | P | DELETED | I |
| T | A | F | S | L | Y | Q | S | T | N | P | DELETED | M |
| T | A | F | S | L | Y | Q | S | T | N | P | P | I |
| T | A | F | S | L | Y | Q | S | T | N | P | P | M |
| T | A | F | S | L | Y | Q | G | S | DELETED | DELETED | DELETED | I |
| T | A | F | S | L | Y | Q | G | S | DELETED | DELETED | DELETED | M |
| T | A | F | S | L | Y | Q | G | S | DELETED | DELETED | P | I |
| T | A | F | S | L | Y | Q | G | S | DELETED | DELETED | P | M |
| T | A | F | S | L | Y | Q | G | S | DELETED | P | DELETED | I |
| T | A | F | S | L | Y | Q | G | S | DELETED | P | DELETED | M |
| T | A | F | S | L | Y | Q | G | S | DELETED | P | P | I |
| T | A | F | S | L | Y | Q | G | S | DELETED | P | P | M |
| T | A | F | S | L | Y | Q | G | S | N | DELETED | DELETED | I |
| T | A | F | S | L | Y | Q | G | S | N | DELETED | DELETED | M |
| T | A | F | S | L | Y | Q | G | S | N | DELETED | P | I |
| T | A | F | S | L | Y | Q | G | S | N | DELETED | P | M |
| T | A | F | S | L | Y | Q | G | S | N | P | DELETED | I |
| T | A | F | S | L | Y | Q | G | S | N | P | DELETED | M |
| T | A | F | S | L | Y | Q | G | S | N | P | P | I |
| T | A | F | S | L | Y | Q | G | S | N | P | P | M |
| T | A | F | S | L | Y | Q | G | T | DELETED | DELETED | DELETED | I |
| T | A | F | S | L | Y | Q | G | T | DELETED | DELETED | DELETED | M |
| T | A | F | S | L | Y | Q | G | T | DELETED | DELETED | P | I |
| T | A | F | S | L | Y | Q | G | T | DELETED | DELETED | P | M |
| T | A | F | S | L | Y | Q | G | T | DELETED | P | DELETED | I |
| T | A | F | S | L | Y | Q | G | T | DELETED | P | DELETED | M |
| T | A | F | S | L | Y | Q | G | T | DELETED | P | P | I |
| T | A | F | S | L | Y | Q | G | T | DELETED | P | P | M |
| T | A | F | S | L | Y | Q | G | T | N | DELETED | DELETED | I |
| T | A | F | S | L | Y | Q | G | T | N | DELETED | DELETED | M |
| T | A | F | S | L | Y | Q | G | T | N | DELETED | P | I |
| T | A | F | S | L | Y | Q | G | T | N | DELETED | P | M |
| T | A | F | S | L | Y | Q | G | T | N | P | DELETED | I |
| T | A | F | S | L | Y | Q | G | T | N | P | DELETED | M |
| T | A | F | S | L | Y | Q | G | T | N | P | P | I |
| T | A | F | S | L | Y | Q | G | T | N | P | P | M |
| T | A | F | S | L | Y | V | S | S | DELETED | DELETED | DELETED | I |
| T | A | F | S | L | Y | V | S | S | DELETED | DELETED | DELETED | M |
| T | A | F | S | L | Y | V | S | S | DELETED | DELETED | P | I |
| T | A | F | S | L | Y | V | S | S | DELETED | DELETED | P | M |
| T | A | F | S | L | Y | V | S | S | DELETED | P | DELETED | I |
| T | A | F | S | L | Y | V | S | S | DELETED | P | DELETED | M |
| T | A | F | S | L | Y | V | S | S | DELETED | P | P | I |
| T | A | F | S | L | Y | V | S | S | DELETED | P | P | M |
| T | A | F | S | L | Y | V | S | S | N | DELETED | DELETED | I |
| T | A | F | S | L | Y | V | S | S | N | DELETED | DELETED | M |
| T | A | F | S | L | Y | V | S | S | N | DELETED | P | I |
| T | A | F | S | L | Y | V | S | S | N | DELETED | P | M |
| T | A | F | S | L | Y | V | S | S | N | P | DELETED | I |
| T | A | F | S | L | Y | V | S | S | N | P | DELETED | M |
| T | A | F | S | L | Y | V | S | S | N | P | P | I |
| T | A | F | S | L | Y | V | S | S | N | P | P | M |
| T | A | F | S | L | Y | V | S | T | DELETED | DELETED | DELETED | I |
| T | A | F | S | L | Y | V | S | T | DELETED | DELETED | DELETED | M |
| T | A | F | S | L | Y | V | S | T | DELETED | DELETED | P | I |
| T | A | F | S | L | Y | V | S | T | DELETED | DELETED | P | M |
| T | A | F | S | L | Y | V | S | T | DELETED | P | DELETED | I |
| T | A | F | S | L | Y | V | S | T | DELETED | P | DELETED | M |
| T | A | F | S | L | Y | V | S | T | DELETED | P | P | I |
| T | A | F | S | L | Y | V | S | T | DELETED | P | P | M |
| T | A | F | S | L | Y | V | S | T | N | DELETED | DELETED | I |
| T | A | F | S | L | Y | V | S | T | N | DELETED | DELETED | M |
| T | A | F | S | L | Y | V | S | T | N | DELETED | P | I |
| T | A | F | S | L | Y | V | S | T | N | DELETED | P | M |
| T | A | F | S | L | Y | V | S | T | N | P | DELETED | I |
| T | A | F | S | L | Y | V | S | T | N | P | DELETED | M |
| T | A | F | S | L | Y | V | S | T | N | P | P | I |
| T | A | F | S | L | Y | V | S | T | N | P | P | M |
| T | A | F | S | L | Y | V | G | S | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | L | Y | V | G | S | DELETED | DELETED | DELETED | M |
| T | A | F | S | L | Y | V | G | S | DELETED | DELETED | P | I |
| T | A | F | S | L | Y | V | G | S | DELETED | DELETED | P | M |
| T | A | F | S | L | Y | V | G | S | DELETED | P | DELETED | I |
| T | A | F | S | L | Y | V | G | S | DELETED | P | DELETED | M |
| T | A | F | S | L | Y | V | G | S | DELETED | P | P | I |
| T | A | F | S | L | Y | V | G | S | DELETED | P | P | M |
| T | A | F | S | L | Y | V | G | S | N | DELETED | DELETED | I |
| T | A | F | S | L | Y | V | G | S | N | DELETED | DELETED | M |
| T | A | F | S | L | Y | V | G | S | N | DELETED | P | I |
| T | A | F | S | L | Y | V | G | S | N | DELETED | P | M |
| T | A | F | S | L | Y | V | G | S | N | P | DELETED | I |
| T | A | F | S | L | Y | V | G | S | N | P | DELETED | M |
| T | A | F | S | L | Y | V | G | S | N | P | P | I |
| T | A | F | S | L | Y | V | G | S | N | P | P | M |
| T | A | F | S | L | Y | V | G | T | DELETED | DELETED | DELETED | I |
| T | A | F | S | L | Y | V | G | T | DELETED | DELETED | DELETED | M |
| T | A | F | S | L | Y | V | G | T | DELETED | DELETED | P | I |
| T | A | F | S | L | Y | V | G | T | DELETED | DELETED | P | M |
| T | A | F | S | L | Y | V | G | T | DELETED | P | DELETED | I |
| T | A | F | S | L | Y | V | G | T | DELETED | P | DELETED | M |
| T | A | F | S | L | Y | V | G | T | DELETED | P | P | I |
| T | A | F | S | L | Y | V | G | T | DELETED | P | P | M |
| T | A | F | S | L | Y | V | G | T | N | DELETED | DELETED | I |
| T | A | F | S | L | Y | V | G | T | N | DELETED | DELETED | M |
| T | A | F | S | L | Y | V | G | T | N | DELETED | P | I |
| T | A | F | S | L | Y | V | G | T | N | DELETED | P | M |
| T | A | F | S | L | Y | V | G | T | N | P | DELETED | I |
| T | A | F | S | L | Y | V | G | T | N | P | DELETED | M |
| T | A | F | S | L | Y | V | G | T | N | P | P | I |
| T | A | F | S | L | Y | V | G | T | N | P | P | M |
| T | A | F | S | L | H | Q | S | S | DELETED | DELETED | DELETED | I |
| T | A | F | S | L | H | Q | S | S | DELETED | DELETED | DELETED | M |
| T | A | F | S | L | H | Q | S | S | DELETED | DELETED | P | I |
| T | A | F | S | L | H | Q | S | S | DELETED | DELETED | P | M |
| T | A | F | S | L | H | Q | S | S | DELETED | P | DELETED | I |
| T | A | F | S | L | H | Q | S | S | DELETED | P | DELETED | M |
| T | A | F | S | L | H | Q | S | S | DELETED | P | P | I |
| T | A | F | S | L | H | Q | S | S | DELETED | P | P | M |
| T | A | F | S | L | H | Q | S | S | N | DELETED | DELETED | I |
| T | A | F | S | L | H | Q | S | S | N | DELETED | DELETED | M |
| T | A | F | S | L | H | Q | S | S | N | DELETED | P | I |
| T | A | F | S | L | H | Q | S | S | N | DELETED | P | M |
| T | A | F | S | L | H | Q | S | S | N | P | DELETED | I |
| T | A | F | S | L | H | Q | S | S | N | P | DELETED | M |
| T | A | F | S | L | H | Q | S | S | N | P | P | I |
| T | A | F | S | L | H | Q | S | S | N | P | P | M |
| T | A | F | S | L | H | Q | S | T | DELETED | DELETED | DELETED | I |
| T | A | F | S | L | H | Q | S | T | DELETED | DELETED | DELETED | M |
| T | A | F | S | L | H | Q | S | T | DELETED | DELETED | P | I |
| T | A | F | S | L | H | Q | S | T | DELETED | DELETED | P | M |
| T | A | F | S | L | H | Q | S | T | DELETED | P | DELETED | I |
| T | A | F | S | L | H | Q | S | T | DELETED | P | DELETED | M |
| T | A | F | S | L | H | Q | S | T | DELETED | P | P | I |
| T | A | F | S | L | H | Q | S | T | DELETED | P | P | M |
| T | A | F | S | L | H | Q | S | T | N | DELETED | DELETED | I |
| T | A | F | S | L | H | Q | S | T | N | DELETED | DELETED | M |
| T | A | F | S | L | H | Q | S | T | N | DELETED | P | I |
| T | A | F | S | L | H | Q | S | T | N | DELETED | P | M |
| T | A | F | S | L | H | Q | S | T | N | P | DELETED | I |
| T | A | F | S | L | H | Q | S | T | N | P | DELETED | M |
| T | A | F | S | L | H | Q | S | T | N | P | P | I |
| T | A | F | S | L | H | Q | S | T | N | P | P | M |
| T | A | F | S | L | H | Q | G | S | DELETED | DELETED | DELETED | I |
| T | A | F | S | L | H | Q | G | S | DELETED | DELETED | DELETED | M |
| T | A | F | S | L | H | Q | G | S | DELETED | DELETED | P | I |
| T | A | F | S | L | H | Q | G | S | DELETED | DELETED | P | M |
| T | A | F | S | L | H | Q | G | S | DELETED | P | DELETED | I |
| T | A | F | S | L | H | Q | G | S | DELETED | P | DELETED | M |
| T | A | F | S | L | H | Q | G | S | DELETED | P | P | I |
| T | A | F | S | L | H | Q | G | S | DELETED | P | P | M |
| T | A | F | S | L | H | Q | G | S | N | DELETED | DELETED | I |
| T | A | F | S | L | H | Q | G | S | N | DELETED | DELETED | M |
| T | A | F | S | L | H | Q | G | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | L | H | Q | G | S | N | DELETED | P | M |
| T | A | F | S | L | H | Q | G | S | N | P | DELETED | I |
| T | A | F | S | L | H | Q | G | S | N | P | DELETED | M |
| T | A | F | S | L | H | Q | G | S | N | P | P | I |
| T | A | F | S | L | H | Q | G | S | N | P | P | M |
| T | A | F | S | L | H | Q | G | T | DELETED | DELETED | DELETED | I |
| T | A | F | S | L | H | Q | G | T | DELETED | DELETED | DELETED | M |
| T | A | F | S | L | H | Q | G | T | DELETED | DELETED | P | I |
| T | A | F | S | L | H | Q | G | T | DELETED | DELETED | P | M |
| T | A | F | S | L | H | Q | G | T | DELETED | P | DELETED | I |
| T | A | F | S | L | H | Q | G | T | DELETED | P | DELETED | M |
| T | A | F | S | L | H | Q | G | T | DELETED | P | P | I |
| T | A | F | S | L | H | Q | G | T | DELETED | P | P | M |
| T | A | F | S | L | H | Q | G | T | N | DELETED | DELETED | I |
| T | A | F | S | L | H | Q | G | T | N | DELETED | DELETED | M |
| T | A | F | S | L | H | Q | G | T | N | DELETED | P | I |
| T | A | F | S | L | H | Q | G | T | N | DELETED | P | M |
| T | A | F | S | L | H | Q | G | T | N | P | DELETED | I |
| T | A | F | S | L | H | Q | G | T | N | P | DELETED | M |
| T | A | F | S | L | H | Q | G | T | N | P | P | I |
| T | A | F | S | L | H | Q | G | T | N | P | P | M |
| T | A | F | S | L | H | V | S | S | DELETED | DELETED | DELETED | I |
| T | A | F | S | L | H | V | S | S | DELETED | DELETED | DELETED | M |
| T | A | F | S | L | H | V | S | S | DELETED | DELETED | P | I |
| T | A | F | S | L | H | V | S | S | DELETED | DELETED | P | M |
| T | A | F | S | L | H | V | S | S | DELETED | P | DELETED | I |
| T | A | F | S | L | H | V | S | S | DELETED | P | DELETED | M |
| T | A | F | S | L | H | V | S | S | DELETED | P | P | I |
| T | A | F | S | L | H | V | S | S | DELETED | P | P | M |
| T | A | F | S | L | H | V | S | S | N | DELETED | DELETED | I |
| T | A | F | S | L | H | V | S | S | N | DELETED | DELETED | M |
| T | A | F | S | L | H | V | S | S | N | DELETED | P | I |
| T | A | F | S | L | H | V | S | S | N | DELETED | P | M |
| T | A | F | S | L | H | V | S | S | N | P | DELETED | I |
| T | A | F | S | L | H | V | S | S | N | P | DELETED | M |
| T | A | F | S | L | H | V | S | S | N | P | P | I |
| T | A | F | S | L | H | V | S | S | N | P | P | M |
| T | A | F | S | L | H | V | S | T | DELETED | DELETED | DELETED | I |
| T | A | F | S | L | H | V | S | T | DELETED | DELETED | DELETED | M |
| T | A | F | S | L | H | V | S | T | DELETED | DELETED | P | I |
| T | A | F | S | L | H | V | S | T | DELETED | DELETED | P | M |
| T | A | F | S | L | H | V | S | T | DELETED | P | DELETED | I |
| T | A | F | S | L | H | V | S | T | DELETED | P | DELETED | M |
| T | A | F | S | L | H | V | S | T | DELETED | P | P | I |
| T | A | F | S | L | H | V | S | T | DELETED | P | P | M |
| T | A | F | S | L | H | V | S | T | N | DELETED | DELETED | I |
| T | A | F | S | L | H | V | S | T | N | DELETED | DELETED | M |
| T | A | F | S | L | H | V | S | T | N | DELETED | P | I |
| T | A | F | S | L | H | V | S | T | N | DELETED | P | M |
| T | A | F | S | L | H | V | S | T | N | P | DELETED | I |
| T | A | F | S | L | H | V | S | T | N | P | DELETED | M |
| T | A | F | S | L | H | V | S | T | N | P | P | I |
| T | A | F | S | L | H | V | S | T | N | P | P | M |
| T | A | F | S | L | H | V | G | S | DELETED | DELETED | DELETED | I |
| T | A | F | S | L | H | V | G | S | DELETED | DELETED | DELETED | M |
| T | A | F | S | L | H | V | G | S | DELETED | DELETED | P | I |
| T | A | F | S | L | H | V | G | S | DELETED | DELETED | P | M |
| T | A | F | S | L | H | V | G | S | DELETED | P | DELETED | I |
| T | A | F | S | L | H | V | G | S | DELETED | P | DELETED | M |
| T | A | F | S | L | H | V | G | S | DELETED | P | P | I |
| T | A | F | S | L | H | V | G | S | DELETED | P | P | M |
| T | A | F | S | L | H | V | G | S | N | DELETED | DELETED | I |
| T | A | F | S | L | H | V | G | S | N | DELETED | DELETED | M |
| T | A | F | S | L | H | V | G | S | N | DELETED | P | I |
| T | A | F | S | L | H | V | G | S | N | DELETED | P | M |
| T | A | F | S | L | H | V | G | S | N | P | DELETED | I |
| T | A | F | S | L | H | V | G | S | N | P | DELETED | M |
| T | A | F | S | L | H | V | G | S | N | P | P | I |
| T | A | F | S | L | H | V | G | S | N | P | P | M |
| T | A | F | S | L | H | V | G | T | DELETED | DELETED | DELETED | I |
| T | A | F | S | L | H | V | G | T | DELETED | DELETED | DELETED | M |
| T | A | F | S | L | H | V | G | T | DELETED | DELETED | P | I |
| T | A | F | S | L | H | V | G | T | DELETED | DELETED | P | M |
| T | A | F | S | L | H | V | G | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | L | H | V | G | T | DELETED | P | DELETED | M |
| T | A | F | S | L | H | V | G | T | DELETED | P | P | I |
| T | A | F | S | L | H | V | G | T | DELETED | P | P | M |
| T | A | F | S | L | H | V | G | T | N | DELETED | DELETED | I |
| T | A | F | S | L | H | V | G | T | N | DELETED | DELETED | M |
| T | A | F | S | L | H | V | G | T | N | DELETED | P | I |
| T | A | F | S | L | H | V | G | T | N | DELETED | P | M |
| T | A | F | S | L | H | V | G | T | N | P | DELETED | I |
| T | A | F | S | L | H | V | G | T | N | P | DELETED | M |
| T | A | F | S | L | H | V | G | T | N | P | P | I |
| T | A | F | S | L | H | V | G | T | N | P | P | M |
| T | A | F | S | I | Y | Q | S | S | DELETED | DELETED | DELETED | I |
| T | A | F | S | I | Y | Q | S | S | DELETED | DELETED | DELETED | M |
| T | A | F | S | I | Y | Q | S | S | DELETED | DELETED | P | I |
| T | A | F | S | I | Y | Q | S | S | DELETED | DELETED | P | M |
| T | A | F | S | I | Y | Q | S | S | DELETED | P | DELETED | I |
| T | A | F | S | I | Y | Q | S | S | DELETED | P | DELETED | M |
| T | A | F | S | I | Y | Q | S | S | DELETED | P | P | I |
| T | A | F | S | I | Y | Q | S | S | DELETED | P | P | M |
| T | A | F | S | I | Y | Q | S | S | N | DELETED | DELETED | I |
| T | A | F | S | I | Y | Q | S | S | N | DELETED | DELETED | M |
| T | A | F | S | I | Y | Q | S | S | N | DELETED | P | I |
| T | A | F | S | I | Y | Q | S | S | N | DELETED | P | M |
| T | A | F | S | I | Y | Q | S | S | N | P | DELETED | I |
| T | A | F | S | I | Y | Q | S | S | N | P | DELETED | M |
| T | A | F | S | I | Y | Q | S | S | N | P | P | I |
| T | A | F | S | I | Y | Q | S | S | N | P | P | M |
| T | A | F | S | I | Y | Q | S | T | DELETED | DELETED | DELETED | I |
| T | A | F | S | I | Y | Q | S | T | DELETED | DELETED | DELETED | M |
| T | A | F | S | I | Y | Q | S | T | DELETED | DELETED | P | I |
| T | A | F | S | I | Y | Q | S | T | DELETED | DELETED | P | M |
| T | A | F | S | I | Y | Q | S | T | DELETED | P | DELETED | I |
| T | A | F | S | I | Y | Q | S | T | DELETED | P | DELETED | M |
| T | A | F | S | I | Y | Q | S | T | DELETED | P | P | I |
| T | A | F | S | I | Y | Q | S | T | DELETED | P | P | M |
| T | A | F | S | I | Y | Q | S | T | N | DELETED | DELETED | I |
| T | A | F | S | I | Y | Q | S | T | N | DELETED | DELETED | M |
| T | A | F | S | I | Y | Q | S | T | N | DELETED | P | I |
| T | A | F | S | I | Y | Q | S | T | N | DELETED | P | M |
| T | A | F | S | I | Y | Q | S | T | N | P | DELETED | I |
| T | A | F | S | I | Y | Q | S | T | N | P | DELETED | M |
| T | A | F | S | I | Y | Q | S | T | N | P | P | I |
| T | A | F | S | I | Y | Q | S | T | N | P | P | M |
| T | A | F | S | I | Y | Q | G | S | DELETED | DELETED | DELETED | I |
| T | A | F | S | I | Y | Q | G | S | DELETED | DELETED | DELETED | M |
| T | A | F | S | I | Y | Q | G | S | DELETED | DELETED | P | I |
| T | A | F | S | I | Y | Q | G | S | DELETED | DELETED | P | M |
| T | A | F | S | I | Y | Q | G | S | DELETED | P | DELETED | I |
| T | A | F | S | I | Y | Q | G | S | DELETED | P | DELETED | M |
| T | A | F | S | I | Y | Q | G | S | DELETED | P | P | I |
| T | A | F | S | I | Y | Q | G | S | DELETED | P | P | M |
| T | A | F | S | I | Y | Q | G | S | N | DELETED | DELETED | I |
| T | A | F | S | I | Y | Q | G | S | N | DELETED | DELETED | M |
| T | A | F | S | I | Y | Q | G | S | N | DELETED | P | I |
| T | A | F | S | I | Y | Q | G | S | N | DELETED | P | M |
| T | A | F | S | I | Y | Q | G | S | N | P | DELETED | I |
| T | A | F | S | I | Y | Q | G | S | N | P | DELETED | M |
| T | A | F | S | I | Y | Q | G | S | N | P | P | I |
| T | A | F | S | I | Y | Q | G | S | N | P | P | M |
| T | A | F | S | I | Y | Q | G | T | DELETED | DELETED | DELETED | I |
| T | A | F | S | I | Y | Q | G | T | DELETED | DELETED | DELETED | M |
| T | A | F | S | I | Y | Q | G | T | DELETED | DELETED | P | I |
| T | A | F | S | I | Y | Q | G | T | DELETED | DELETED | P | M |
| T | A | F | S | I | Y | Q | G | T | DELETED | P | DELETED | I |
| T | A | F | S | I | Y | Q | G | T | DELETED | P | DELETED | M |
| T | A | F | S | I | Y | Q | G | T | DELETED | P | P | I |
| T | A | F | S | I | Y | Q | G | T | DELETED | P | P | M |
| T | A | F | S | I | Y | Q | G | T | N | DELETED | DELETED | I |
| T | A | F | S | I | Y | Q | G | T | N | DELETED | DELETED | M |
| T | A | F | S | I | Y | Q | G | T | N | DELETED | P | I |
| T | A | F | S | I | Y | Q | G | T | N | DELETED | P | M |
| T | A | F | S | I | Y | Q | G | T | N | P | DELETED | I |
| T | A | F | S | I | Y | Q | G | T | N | P | DELETED | M |
| T | A | F | S | I | Y | Q | G | T | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | I | Y | Q | G | T | N | P | P | M |
| T | A | F | S | I | Y | V | S | S | DELETED | DELETED | DELETED | I |
| T | A | F | S | I | Y | V | S | S | DELETED | DELETED | DELETED | M |
| T | A | F | S | I | Y | V | S | S | DELETED | DELETED | P | I |
| T | A | F | S | I | Y | V | S | S | DELETED | DELETED | P | M |
| T | A | F | S | I | Y | V | S | S | DELETED | P | DELETED | I |
| T | A | F | S | I | Y | V | S | S | DELETED | P | DELETED | M |
| T | A | F | S | I | Y | V | S | S | DELETED | P | P | I |
| T | A | F | S | I | Y | V | S | S | DELETED | P | P | M |
| T | A | F | S | I | Y | V | S | S | N | DELETED | DELETED | I |
| T | A | F | S | I | Y | V | S | S | N | DELETED | DELETED | M |
| T | A | F | S | I | Y | V | S | S | N | DELETED | P | I |
| T | A | F | S | I | Y | V | S | S | N | DELETED | P | M |
| T | A | F | S | I | Y | V | S | S | N | P | DELETED | I |
| T | A | F | S | I | Y | V | S | S | N | P | DELETED | M |
| T | A | F | S | I | Y | V | S | S | N | P | P | I |
| T | A | F | S | I | Y | V | S | S | N | P | P | M |
| T | A | F | S | I | Y | V | S | T | DELETED | DELETED | DELETED | I |
| T | A | F | S | I | Y | V | S | T | DELETED | DELETED | DELETED | M |
| T | A | F | S | I | Y | V | S | T | DELETED | DELETED | P | I |
| T | A | F | S | I | Y | V | S | T | DELETED | DELETED | P | M |
| T | A | F | S | I | Y | V | S | T | DELETED | P | DELETED | I |
| T | A | F | S | I | Y | V | S | T | DELETED | P | DELETED | M |
| T | A | F | S | I | Y | V | S | T | DELETED | P | P | I |
| T | A | F | S | I | Y | V | S | T | DELETED | P | P | M |
| T | A | F | S | I | Y | V | S | T | N | DELETED | DELETED | I |
| T | A | F | S | I | Y | V | S | T | N | DELETED | DELETED | M |
| T | A | F | S | I | Y | V | S | T | N | DELETED | P | I |
| T | A | F | S | I | Y | V | S | T | N | DELETED | P | M |
| T | A | F | S | I | Y | V | S | T | N | P | DELETED | I |
| T | A | F | S | I | Y | V | S | T | N | P | DELETED | M |
| T | A | F | S | I | Y | V | S | T | N | P | P | I |
| T | A | F | S | I | Y | V | S | T | N | P | P | M |
| T | A | F | S | I | Y | V | G | S | DELETED | DELETED | DELETED | I |
| T | A | F | S | I | Y | V | G | S | DELETED | DELETED | DELETED | M |
| T | A | F | S | I | Y | V | G | S | DELETED | DELETED | P | I |
| T | A | F | S | I | Y | V | G | S | DELETED | DELETED | P | M |
| T | A | F | S | I | Y | V | G | S | DELETED | P | DELETED | I |
| T | A | F | S | I | Y | V | G | S | DELETED | P | DELETED | M |
| T | A | F | S | I | Y | V | G | S | DELETED | P | P | I |
| T | A | F | S | I | Y | V | G | S | DELETED | P | P | M |
| T | A | F | S | I | Y | V | G | S | N | DELETED | DELETED | I |
| T | A | F | S | I | Y | V | G | S | N | DELETED | DELETED | M |
| T | A | F | S | I | Y | V | G | S | N | DELETED | P | I |
| T | A | F | S | I | Y | V | G | S | N | DELETED | P | M |
| T | A | F | S | I | Y | V | G | S | N | P | DELETED | I |
| T | A | F | S | I | Y | V | G | S | N | P | DELETED | M |
| T | A | F | S | I | Y | V | G | S | N | P | P | I |
| T | A | F | S | I | Y | V | G | S | N | P | P | M |
| T | A | F | S | I | Y | V | G | T | DELETED | DELETED | DELETED | I |
| T | A | F | S | I | Y | V | G | T | DELETED | DELETED | DELETED | M |
| T | A | F | S | I | Y | V | G | T | DELETED | DELETED | P | I |
| T | A | F | S | I | Y | V | G | T | DELETED | DELETED | P | M |
| T | A | F | S | I | Y | V | G | T | DELETED | P | DELETED | I |
| T | A | F | S | I | Y | V | G | T | DELETED | P | DELETED | M |
| T | A | F | S | I | Y | V | G | T | DELETED | P | P | I |
| T | A | F | S | I | Y | V | G | T | DELETED | P | P | M |
| T | A | F | S | I | Y | V | G | T | N | DELETED | DELETED | I |
| T | A | F | S | I | Y | V | G | T | N | DELETED | DELETED | M |
| T | A | F | S | I | Y | V | G | T | N | DELETED | P | I |
| T | A | F | S | I | Y | V | G | T | N | DELETED | P | M |
| T | A | F | S | I | Y | V | G | T | N | P | DELETED | I |
| T | A | F | S | I | Y | V | G | T | N | P | DELETED | M |
| T | A | F | S | I | Y | V | G | T | N | P | P | I |
| T | A | F | S | I | Y | V | G | T | N | P | P | M |
| T | A | F | S | I | H | Q | S | S | DELETED | DELETED | DELETED | I |
| T | A | F | S | I | H | Q | S | S | DELETED | DELETED | DELETED | M |
| T | A | F | S | I | H | Q | S | S | DELETED | DELETED | P | I |
| T | A | F | S | I | H | Q | S | S | DELETED | DELETED | P | M |
| T | A | F | S | I | H | Q | S | S | DELETED | P | DELETED | I |
| T | A | F | S | I | H | Q | S | S | DELETED | P | DELETED | M |
| T | A | F | S | I | H | Q | S | S | DELETED | P | P | I |
| T | A | F | S | I | H | Q | S | S | DELETED | P | P | M |
| T | A | F | S | I | H | Q | S | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | I | H | Q | S | S | N | DELETED | DELETED | M |
| T | A | F | S | I | H | Q | S | S | N | DELETED | P | I |
| T | A | F | S | I | H | Q | S | S | N | DELETED | P | M |
| T | A | F | S | I | H | Q | S | S | N | P | DELETED | I |
| T | A | F | S | I | H | Q | S | S | N | P | DELETED | M |
| T | A | F | S | I | H | Q | S | S | N | P | P | I |
| T | A | F | S | I | H | Q | S | S | N | P | P | M |
| T | A | F | S | I | H | Q | S | T | DELETED | DELETED | DELETED | I |
| T | A | F | S | I | H | Q | S | T | DELETED | DELETED | DELETED | M |
| T | A | F | S | I | H | Q | S | T | DELETED | DELETED | P | I |
| T | A | F | S | I | H | Q | S | T | DELETED | DELETED | P | M |
| T | A | F | S | I | H | Q | S | T | DELETED | P | DELETED | I |
| T | A | F | S | I | H | Q | S | T | DELETED | P | DELETED | M |
| T | A | F | S | I | H | Q | S | T | DELETED | P | P | I |
| T | A | F | S | I | H | Q | S | T | DELETED | P | P | M |
| T | A | F | S | I | H | Q | S | T | N | DELETED | DELETED | I |
| T | A | F | S | I | H | Q | S | T | N | DELETED | DELETED | M |
| T | A | F | S | I | H | Q | S | T | N | DELETED | P | I |
| T | A | F | S | I | H | Q | S | T | N | DELETED | P | M |
| T | A | F | S | I | H | Q | S | T | N | P | DELETED | I |
| T | A | F | S | I | H | Q | S | T | N | P | DELETED | M |
| T | A | F | S | I | H | Q | S | T | N | P | P | I |
| T | A | F | S | I | H | Q | S | T | N | P | P | M |
| T | A | F | S | I | H | Q | G | S | DELETED | DELETED | DELETED | I |
| T | A | F | S | I | H | Q | G | S | DELETED | DELETED | DELETED | M |
| T | A | F | S | I | H | Q | G | S | DELETED | DELETED | P | I |
| T | A | F | S | I | H | Q | G | S | DELETED | DELETED | P | M |
| T | A | F | S | I | H | Q | G | S | DELETED | P | DELETED | I |
| T | A | F | S | I | H | Q | G | S | DELETED | P | DELETED | M |
| T | A | F | S | I | H | Q | G | S | DELETED | P | P | I |
| T | A | F | S | I | H | Q | G | S | DELETED | P | P | M |
| T | A | F | S | I | H | Q | G | S | N | DELETED | DELETED | I |
| T | A | F | S | I | H | Q | G | S | N | DELETED | DELETED | M |
| T | A | F | S | I | H | Q | G | S | N | DELETED | P | I |
| T | A | F | S | I | H | Q | G | S | N | DELETED | P | M |
| T | A | F | S | I | H | Q | G | S | N | P | DELETED | I |
| T | A | F | S | I | H | Q | G | S | N | P | DELETED | M |
| T | A | F | S | I | H | Q | G | S | N | P | P | I |
| T | A | F | S | I | H | Q | G | S | N | P | P | M |
| T | A | F | S | I | H | Q | G | T | DELETED | DELETED | DELETED | I |
| T | A | F | S | I | H | Q | G | T | DELETED | DELETED | DELETED | M |
| T | A | F | S | I | H | Q | G | T | DELETED | DELETED | P | I |
| T | A | F | S | I | H | Q | G | T | DELETED | DELETED | P | M |
| T | A | F | S | I | H | Q | G | T | DELETED | P | DELETED | I |
| T | A | F | S | I | H | Q | G | T | DELETED | P | DELETED | M |
| T | A | F | S | I | H | Q | G | T | DELETED | P | P | I |
| T | A | F | S | I | H | Q | G | T | DELETED | P | P | M |
| T | A | F | S | I | H | Q | G | T | N | DELETED | DELETED | I |
| T | A | F | S | I | H | Q | G | T | N | DELETED | DELETED | M |
| T | A | F | S | I | H | Q | G | T | N | DELETED | P | I |
| T | A | F | S | I | H | Q | G | T | N | DELETED | P | M |
| T | A | F | S | I | H | Q | G | T | N | P | DELETED | I |
| T | A | F | S | I | H | Q | G | T | N | P | DELETED | M |
| T | A | F | S | I | H | Q | G | T | N | P | P | I |
| T | A | F | S | I | H | Q | G | T | N | P | P | M |
| T | A | F | S | I | H | V | S | S | DELETED | DELETED | DELETED | I |
| T | A | F | S | I | H | V | S | S | DELETED | DELETED | DELETED | M |
| T | A | F | S | I | H | V | S | S | DELETED | DELETED | P | I |
| T | A | F | S | I | H | V | S | S | DELETED | DELETED | P | M |
| T | A | F | S | I | H | V | S | S | DELETED | P | DELETED | I |
| T | A | F | S | I | H | V | S | S | DELETED | P | DELETED | M |
| T | A | F | S | I | H | V | S | S | DELETED | P | P | I |
| T | A | F | S | I | H | V | S | S | DELETED | P | P | M |
| T | A | F | S | I | H | V | S | S | N | DELETED | DELETED | I |
| T | A | F | S | I | H | V | S | S | N | DELETED | DELETED | M |
| T | A | F | S | I | H | V | S | S | N | DELETED | P | I |
| T | A | F | S | I | H | V | S | S | N | DELETED | P | M |
| T | A | F | S | I | H | V | S | S | N | P | DELETED | I |
| T | A | F | S | I | H | V | S | S | N | P | DELETED | M |
| T | A | F | S | I | H | V | S | S | N | P | P | I |
| T | A | F | S | I | H | V | S | S | N | P | P | M |
| T | A | F | S | I | H | V | S | T | DELETED | DELETED | DELETED | I |
| T | A | F | S | I | H | V | S | T | DELETED | DELETED | DELETED | M |
| T | A | F | S | I | H | V | S | T | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | S | I | H | V | S | T | DELETED | DELETED | P | M |
| T | A | F | S | I | H | V | S | T | DELETED | P | DELETED | I |
| T | A | F | S | I | H | V | S | T | DELETED | P | DELETED | M |
| T | A | F | S | I | H | V | S | T | DELETED | P | P | I |
| T | A | F | S | I | H | V | S | T | DELETED | P | P | M |
| T | A | F | S | I | H | V | S | T | N | DELETED | DELETED | I |
| T | A | F | S | I | H | V | S | T | N | DELETED | DELETED | M |
| T | A | F | S | I | H | V | S | T | N | DELETED | P | I |
| T | A | F | S | I | H | V | S | T | N | DELETED | P | M |
| T | A | F | S | I | H | V | S | T | N | P | DELETED | I |
| T | A | F | S | I | H | V | S | T | N | P | DELETED | M |
| T | A | F | S | I | H | V | S | T | N | P | P | I |
| T | A | F | S | I | H | V | S | T | N | P | P | M |
| T | A | F | S | I | H | V | G | S | DELETED | DELETED | DELETED | I |
| T | A | F | S | I | H | V | G | S | DELETED | DELETED | DELETED | M |
| T | A | F | S | I | H | V | G | S | DELETED | DELETED | P | I |
| T | A | F | S | I | H | V | G | S | DELETED | DELETED | P | M |
| T | A | F | S | I | H | V | G | S | DELETED | P | DELETED | I |
| T | A | F | S | I | H | V | G | S | DELETED | P | DELETED | M |
| T | A | F | S | I | H | V | G | S | DELETED | P | P | I |
| T | A | F | S | I | H | V | G | S | DELETED | P | P | M |
| T | A | F | S | I | H | V | G | S | N | DELETED | DELETED | I |
| T | A | F | S | I | H | V | G | S | N | DELETED | DELETED | M |
| T | A | F | S | I | H | V | G | S | N | DELETED | P | I |
| T | A | F | S | I | H | V | G | S | N | DELETED | P | M |
| T | A | F | S | I | H | V | G | S | N | P | DELETED | I |
| T | A | F | S | I | H | V | G | S | N | P | DELETED | M |
| T | A | F | S | I | H | V | G | S | N | P | P | I |
| T | A | F | S | I | H | V | G | S | N | P | P | M |
| T | A | F | S | I | H | V | G | T | DELETED | DELETED | DELETED | I |
| T | A | F | S | I | H | V | G | T | DELETED | DELETED | DELETED | M |
| T | A | F | S | I | H | V | G | T | DELETED | DELETED | P | I |
| T | A | F | S | I | H | V | G | T | DELETED | DELETED | P | M |
| T | A | F | S | I | H | V | G | T | DELETED | P | DELETED | I |
| T | A | F | S | I | H | V | G | T | DELETED | P | DELETED | M |
| T | A | F | S | I | H | V | G | T | DELETED | P | P | I |
| T | A | F | S | I | H | V | G | T | DELETED | P | P | M |
| T | A | F | S | I | H | V | G | T | N | DELETED | DELETED | I |
| T | A | F | S | I | H | V | G | T | N | DELETED | DELETED | M |
| T | A | F | S | I | H | V | G | T | N | DELETED | P | I |
| T | A | F | S | I | H | V | G | T | N | DELETED | P | M |
| T | A | F | S | I | H | V | G | T | N | P | DELETED | I |
| T | A | F | S | I | H | V | G | T | N | P | DELETED | M |
| T | A | F | S | I | H | V | G | T | N | P | P | I |
| T | A | F | S | I | H | V | G | T | N | P | P | M |
| T | A | F | R | L | Y | Q | S | S | DELETED | DELETED | DELETED | I |
| T | A | F | R | L | Y | Q | S | S | DELETED | DELETED | DELETED | M |
| T | A | F | R | L | Y | Q | S | S | DELETED | DELETED | P | I |
| T | A | F | R | L | Y | Q | S | S | DELETED | DELETED | P | M |
| T | A | F | R | L | Y | Q | S | S | DELETED | P | DELETED | I |
| T | A | F | R | L | Y | Q | S | S | DELETED | P | DELETED | M |
| T | A | F | R | L | Y | Q | S | S | DELETED | P | P | I |
| T | A | F | R | L | Y | Q | S | S | DELETED | P | P | M |
| T | A | F | R | L | Y | Q | S | S | N | DELETED | DELETED | I |
| T | A | F | R | L | Y | Q | S | S | N | DELETED | DELETED | M |
| T | A | F | R | L | Y | Q | S | S | N | DELETED | P | I |
| T | A | F | R | L | Y | Q | S | S | N | DELETED | P | M |
| T | A | F | R | L | Y | Q | S | S | N | P | DELETED | I |
| T | A | F | R | L | Y | Q | S | S | N | P | DELETED | M |
| T | A | F | R | L | Y | Q | S | S | N | P | P | I |
| T | A | F | R | L | Y | Q | S | S | N | P | P | M |
| T | A | F | R | L | Y | Q | S | T | DELETED | DELETED | DELETED | I |
| T | A | F | R | L | Y | Q | S | T | DELETED | DELETED | DELETED | M |
| T | A | F | R | L | Y | Q | S | T | DELETED | DELETED | P | I |
| T | A | F | R | L | Y | Q | S | T | DELETED | DELETED | P | M |
| T | A | F | R | L | Y | Q | S | T | DELETED | P | DELETED | I |
| T | A | F | R | L | Y | Q | S | T | DELETED | P | DELETED | M |
| T | A | F | R | L | Y | Q | S | T | DELETED | P | P | I |
| T | A | F | R | L | Y | Q | S | T | DELETED | P | P | M |
| T | A | F | R | L | Y | Q | S | T | N | DELETED | DELETED | I |
| T | A | F | R | L | Y | Q | S | T | N | DELETED | DELETED | M |
| T | A | F | R | L | Y | Q | S | T | N | DELETED | P | I |
| T | A | F | R | L | Y | Q | S | T | N | DELETED | P | M |
| T | A | F | R | L | Y | Q | S | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | L | Y | Q | S | T | N | P | DELETED | M |
| T | A | F | R | L | Y | Q | S | T | N | P | P | I |
| T | A | F | R | L | Y | Q | S | T | N | P | P | M |
| T | A | F | R | L | Y | Q | G | S | DELETED | DELETED | DELETED | I |
| T | A | F | R | L | Y | Q | G | S | DELETED | DELETED | DELETED | M |
| T | A | F | R | L | Y | Q | G | S | DELETED | DELETED | P | I |
| T | A | F | R | L | Y | Q | G | S | DELETED | DELETED | P | M |
| T | A | F | R | L | Y | Q | G | S | DELETED | P | DELETED | I |
| T | A | F | R | L | Y | Q | G | S | DELETED | P | DELETED | M |
| T | A | F | R | L | Y | Q | G | S | DELETED | P | P | I |
| T | A | F | R | L | Y | Q | G | S | DELETED | P | P | M |
| T | A | F | R | L | Y | Q | G | S | N | DELETED | DELETED | I |
| T | A | F | R | L | Y | Q | G | S | N | DELETED | DELETED | M |
| T | A | F | R | L | Y | Q | G | S | N | DELETED | P | I |
| T | A | F | R | L | Y | Q | G | S | N | DELETED | P | M |
| T | A | F | R | L | Y | Q | G | S | N | P | DELETED | I |
| T | A | F | R | L | Y | Q | G | S | N | P | DELETED | M |
| T | A | F | R | L | Y | Q | G | S | N | P | P | I |
| T | A | F | R | L | Y | Q | G | S | N | P | P | M |
| T | A | F | R | L | Y | Q | G | T | DELETED | DELETED | DELETED | I |
| T | A | F | R | L | Y | Q | G | T | DELETED | DELETED | DELETED | M |
| T | A | F | R | L | Y | Q | G | T | DELETED | DELETED | P | I |
| T | A | F | R | L | Y | Q | G | T | DELETED | DELETED | P | M |
| T | A | F | R | L | Y | Q | G | T | DELETED | P | DELETED | I |
| T | A | F | R | L | Y | Q | G | T | DELETED | P | DELETED | M |
| T | A | F | R | L | Y | Q | G | T | DELETED | P | P | I |
| T | A | F | R | L | Y | Q | G | T | DELETED | P | P | M |
| T | A | F | R | L | Y | Q | G | T | N | DELETED | DELETED | I |
| T | A | F | R | L | Y | Q | G | T | N | DELETED | DELETED | M |
| T | A | F | R | L | Y | Q | G | T | N | DELETED | P | I |
| T | A | F | R | L | Y | Q | G | T | N | DELETED | P | M |
| T | A | F | R | L | Y | Q | G | T | N | P | DELETED | I |
| T | A | F | R | L | Y | Q | G | T | N | P | DELETED | M |
| T | A | F | R | L | Y | Q | G | T | N | P | P | I |
| T | A | F | R | L | Y | Q | G | T | N | P | P | M |
| T | A | F | R | L | Y | V | S | S | DELETED | DELETED | DELETED | I |
| T | A | F | R | L | Y | V | S | S | DELETED | DELETED | DELETED | M |
| T | A | F | R | L | Y | V | S | S | DELETED | DELETED | P | I |
| T | A | F | R | L | Y | V | S | S | DELETED | DELETED | P | M |
| T | A | F | R | L | Y | V | S | S | DELETED | P | DELETED | I |
| T | A | F | R | L | Y | V | S | S | DELETED | P | DELETED | M |
| T | A | F | R | L | Y | V | S | S | DELETED | P | P | I |
| T | A | F | R | L | Y | V | S | S | DELETED | P | P | M |
| T | A | F | R | L | Y | V | S | S | N | DELETED | DELETED | I |
| T | A | F | R | L | Y | V | S | S | N | DELETED | DELETED | M |
| T | A | F | R | L | Y | V | S | S | N | DELETED | P | I |
| T | A | F | R | L | Y | V | S | S | N | DELETED | P | M |
| T | A | F | R | L | Y | V | S | S | N | P | DELETED | I |
| T | A | F | R | L | Y | V | S | S | N | P | DELETED | M |
| T | A | F | R | L | Y | V | S | S | N | P | P | I |
| T | A | F | R | L | Y | V | S | S | N | P | P | M |
| T | A | F | R | L | Y | V | S | T | DELETED | DELETED | DELETED | I |
| T | A | F | R | L | Y | V | S | T | DELETED | DELETED | DELETED | M |
| T | A | F | R | L | Y | V | S | T | DELETED | DELETED | P | I |
| T | A | F | R | L | Y | V | S | T | DELETED | DELETED | P | M |
| T | A | F | R | L | Y | V | S | T | DELETED | P | DELETED | I |
| T | A | F | R | L | Y | V | S | T | DELETED | P | DELETED | M |
| T | A | F | R | L | Y | V | S | T | DELETED | P | P | I |
| T | A | F | R | L | Y | V | S | T | DELETED | P | P | M |
| T | A | F | R | L | Y | V | S | T | N | DELETED | DELETED | I |
| T | A | F | R | L | Y | V | S | T | N | DELETED | DELETED | M |
| T | A | F | R | L | Y | V | S | T | N | DELETED | P | I |
| T | A | F | R | L | Y | V | S | T | N | DELETED | P | M |
| T | A | F | R | L | Y | V | S | T | N | P | DELETED | I |
| T | A | F | R | L | Y | V | S | T | N | P | DELETED | M |
| T | A | F | R | L | Y | V | S | T | N | P | P | I |
| T | A | F | R | L | Y | V | S | T | N | P | P | M |
| T | A | F | R | L | Y | V | G | S | DELETED | DELETED | DELETED | I |
| T | A | F | R | L | Y | V | G | S | DELETED | DELETED | DELETED | M |
| T | A | F | R | L | Y | V | G | S | DELETED | DELETED | P | I |
| T | A | F | R | L | Y | V | G | S | DELETED | DELETED | P | M |
| T | A | F | R | L | Y | V | G | S | DELETED | P | DELETED | I |
| T | A | F | R | L | Y | V | G | S | DELETED | P | DELETED | M |
| T | A | F | R | L | Y | V | G | S | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | L | Y | V | G | S | DELETED | P | P | M |
| T | A | F | R | L | Y | V | G | S | N | DELETED | DELETED | I |
| T | A | F | R | L | Y | V | G | S | N | DELETED | DELETED | M |
| T | A | F | R | L | Y | V | G | S | N | DELETED | P | I |
| T | A | F | R | L | Y | V | G | S | N | DELETED | P | M |
| T | A | F | R | L | Y | V | G | S | N | P | DELETED | I |
| T | A | F | R | L | Y | V | G | S | N | P | DELETED | M |
| T | A | F | R | L | Y | V | G | S | N | P | P | I |
| T | A | F | R | L | Y | V | G | S | N | P | P | M |
| T | A | F | R | L | Y | V | G | T | DELETED | DELETED | DELETED | I |
| T | A | F | R | L | Y | V | G | T | DELETED | DELETED | DELETED | M |
| T | A | F | R | L | Y | V | G | T | DELETED | DELETED | P | I |
| T | A | F | R | L | Y | V | G | T | DELETED | DELETED | P | M |
| T | A | F | R | L | Y | V | G | T | DELETED | P | DELETED | I |
| T | A | F | R | L | Y | V | G | T | DELETED | P | DELETED | M |
| T | A | F | R | L | Y | V | G | T | DELETED | P | P | I |
| T | A | F | R | L | Y | V | G | T | DELETED | P | P | M |
| T | A | F | R | L | Y | V | G | T | N | DELETED | DELETED | I |
| T | A | F | R | L | Y | V | G | T | N | DELETED | DELETED | M |
| T | A | F | R | L | Y | V | G | T | N | DELETED | P | I |
| T | A | F | R | L | Y | V | G | T | N | DELETED | P | M |
| T | A | F | R | L | Y | V | G | T | N | P | DELETED | I |
| T | A | F | R | L | Y | V | G | T | N | P | DELETED | M |
| T | A | F | R | L | Y | V | G | T | N | P | P | I |
| T | A | F | R | L | Y | V | G | T | N | P | P | M |
| T | A | F | R | L | H | Q | S | S | DELETED | DELETED | DELETED | I |
| T | A | F | R | L | H | Q | S | S | DELETED | DELETED | DELETED | M |
| T | A | F | R | L | H | Q | S | S | DELETED | DELETED | P | I |
| T | A | F | R | L | H | Q | S | S | DELETED | DELETED | P | M |
| T | A | F | R | L | H | Q | S | S | DELETED | P | DELETED | I |
| T | A | F | R | L | H | Q | S | S | DELETED | P | DELETED | M |
| T | A | F | R | L | H | Q | S | S | DELETED | P | P | I |
| T | A | F | R | L | H | Q | S | S | DELETED | P | P | M |
| T | A | F | R | L | H | Q | S | S | N | DELETED | DELETED | I |
| T | A | F | R | L | H | Q | S | S | N | DELETED | DELETED | M |
| T | A | F | R | L | H | Q | S | S | N | DELETED | P | I |
| T | A | F | R | L | H | Q | S | S | N | DELETED | P | M |
| T | A | F | R | L | H | Q | S | S | N | P | DELETED | I |
| T | A | F | R | L | H | Q | S | S | N | P | DELETED | M |
| T | A | F | R | L | H | Q | S | S | N | P | P | I |
| T | A | F | R | L | H | Q | S | S | N | P | P | M |
| T | A | F | R | L | H | Q | S | T | DELETED | DELETED | DELETED | I |
| T | A | F | R | L | H | Q | S | T | DELETED | DELETED | DELETED | M |
| T | A | F | R | L | H | Q | S | T | DELETED | DELETED | P | I |
| T | A | F | R | L | H | Q | S | T | DELETED | DELETED | P | M |
| T | A | F | R | L | H | Q | S | T | DELETED | P | DELETED | I |
| T | A | F | R | L | H | Q | S | T | DELETED | P | DELETED | M |
| T | A | F | R | L | H | Q | S | T | DELETED | P | P | I |
| T | A | F | R | L | H | Q | S | T | DELETED | P | P | M |
| T | A | F | R | L | H | Q | S | T | N | DELETED | DELETED | I |
| T | A | F | R | L | H | Q | S | T | N | DELETED | DELETED | M |
| T | A | F | R | L | H | Q | S | T | N | DELETED | P | I |
| T | A | F | R | L | H | Q | S | T | N | DELETED | P | M |
| T | A | F | R | L | H | Q | S | T | N | P | DELETED | I |
| T | A | F | R | L | H | Q | S | T | N | P | DELETED | M |
| T | A | F | R | L | H | Q | S | T | N | P | P | I |
| T | A | F | R | L | H | Q | S | T | N | P | P | M |
| T | A | F | R | L | H | Q | G | S | DELETED | DELETED | DELETED | I |
| T | A | F | R | L | H | Q | G | S | DELETED | DELETED | DELETED | M |
| T | A | F | R | L | H | Q | G | S | DELETED | DELETED | P | I |
| T | A | F | R | L | H | Q | G | S | DELETED | DELETED | P | M |
| T | A | F | R | L | H | Q | G | S | DELETED | P | DELETED | I |
| T | A | F | R | L | H | Q | G | S | DELETED | P | DELETED | M |
| T | A | F | R | L | H | Q | G | S | DELETED | P | P | I |
| T | A | F | R | L | H | Q | G | S | DELETED | P | P | M |
| T | A | F | R | L | H | Q | G | S | N | DELETED | DELETED | I |
| T | A | F | R | L | H | Q | G | S | N | DELETED | DELETED | M |
| T | A | F | R | L | H | Q | G | S | N | DELETED | P | I |
| T | A | F | R | L | H | Q | G | S | N | DELETED | P | M |
| T | A | F | R | L | H | Q | G | S | N | P | DELETED | I |
| T | A | F | R | L | H | Q | G | S | N | P | DELETED | M |
| T | A | F | R | L | H | Q | G | S | N | P | P | I |
| T | A | F | R | L | H | Q | G | S | N | P | P | M |
| T | A | F | R | L | H | Q | G | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | L | H | Q | G | T | DELETED | DELETED | DELETED | M |
| T | A | F | R | L | H | Q | G | T | DELETED | DELETED | P | I |
| T | A | F | R | L | H | Q | G | T | DELETED | DELETED | P | M |
| T | A | F | R | L | H | Q | G | T | DELETED | P | DELETED | I |
| T | A | F | R | L | H | Q | G | T | DELETED | P | DELETED | M |
| T | A | F | R | L | H | Q | G | T | DELETED | P | P | I |
| T | A | F | R | L | H | Q | G | T | DELETED | P | P | M |
| T | A | F | R | L | H | Q | G | T | N | DELETED | DELETED | I |
| T | A | F | R | L | H | Q | G | T | N | DELETED | DELETED | M |
| T | A | F | R | L | H | Q | G | T | N | DELETED | P | I |
| T | A | F | R | L | H | Q | G | T | N | DELETED | P | M |
| T | A | F | R | L | H | Q | G | T | N | P | DELETED | I |
| T | A | F | R | L | H | Q | G | T | N | P | DELETED | M |
| T | A | F | R | L | H | Q | G | T | N | P | P | I |
| T | A | F | R | L | H | Q | G | T | N | P | P | M |
| T | A | F | R | L | H | V | S | S | DELETED | DELETED | DELETED | I |
| T | A | F | R | L | H | V | S | S | DELETED | DELETED | DELETED | M |
| T | A | F | R | L | H | V | S | S | DELETED | DELETED | P | I |
| T | A | F | R | L | H | V | S | S | DELETED | DELETED | P | M |
| T | A | F | R | L | H | V | S | S | DELETED | P | DELETED | I |
| T | A | F | R | L | H | V | S | S | DELETED | P | DELETED | M |
| T | A | F | R | L | H | V | S | S | DELETED | P | P | I |
| T | A | F | R | L | H | V | S | S | DELETED | P | P | M |
| T | A | F | R | L | H | V | S | S | N | DELETED | DELETED | I |
| T | A | F | R | L | H | V | S | S | N | DELETED | DELETED | M |
| T | A | F | R | L | H | V | S | S | N | DELETED | P | I |
| T | A | F | R | L | H | V | S | S | N | DELETED | P | M |
| T | A | F | R | L | H | V | S | S | N | P | DELETED | I |
| T | A | F | R | L | H | V | S | S | N | P | DELETED | M |
| T | A | F | R | L | H | V | S | S | N | P | P | I |
| T | A | F | R | L | H | V | S | S | N | P | P | M |
| T | A | F | R | L | H | V | S | T | DELETED | DELETED | DELETED | I |
| T | A | F | R | L | H | V | S | T | DELETED | DELETED | DELETED | M |
| T | A | F | R | L | H | V | S | T | DELETED | DELETED | P | I |
| T | A | F | R | L | H | V | S | T | DELETED | DELETED | P | M |
| T | A | F | R | L | H | V | S | T | DELETED | P | DELETED | I |
| T | A | F | R | L | H | V | S | T | DELETED | P | DELETED | M |
| T | A | F | R | L | H | V | S | T | DELETED | P | P | I |
| T | A | F | R | L | H | V | S | T | DELETED | P | P | M |
| T | A | F | R | L | H | V | S | T | N | DELETED | DELETED | I |
| T | A | F | R | L | H | V | S | T | N | DELETED | DELETED | M |
| T | A | F | R | L | H | V | S | T | N | DELETED | P | I |
| T | A | F | R | L | H | V | S | T | N | DELETED | P | M |
| T | A | F | R | L | H | V | S | T | N | P | DELETED | I |
| T | A | F | R | L | H | V | S | T | N | P | DELETED | M |
| T | A | F | R | L | H | V | S | T | N | P | P | I |
| T | A | F | R | L | H | V | S | T | N | P | P | M |
| T | A | F | R | L | H | V | G | S | DELETED | DELETED | DELETED | I |
| T | A | F | R | L | H | V | G | S | DELETED | DELETED | DELETED | M |
| T | A | F | R | L | H | V | G | S | DELETED | DELETED | P | I |
| T | A | F | R | L | H | V | G | S | DELETED | DELETED | P | M |
| T | A | F | R | L | H | V | G | S | DELETED | P | DELETED | I |
| T | A | F | R | L | H | V | G | S | DELETED | P | DELETED | M |
| T | A | F | R | L | H | V | G | S | DELETED | P | P | I |
| T | A | F | R | L | H | V | G | S | DELETED | P | P | M |
| T | A | F | R | L | H | V | G | S | N | DELETED | DELETED | I |
| T | A | F | R | L | H | V | G | S | N | DELETED | DELETED | M |
| T | A | F | R | L | H | V | G | S | N | DELETED | P | I |
| T | A | F | R | L | H | V | G | S | N | DELETED | P | M |
| T | A | F | R | L | H | V | G | S | N | P | DELETED | I |
| T | A | F | R | L | H | V | G | S | N | P | DELETED | M |
| T | A | F | R | L | H | V | G | S | N | P | P | I |
| T | A | F | R | L | H | V | G | S | N | P | P | M |
| T | A | F | R | L | H | V | G | T | DELETED | DELETED | DELETED | I |
| T | A | F | R | L | H | V | G | T | DELETED | DELETED | DELETED | M |
| T | A | F | R | L | H | V | G | T | DELETED | DELETED | P | I |
| T | A | F | R | L | H | V | G | T | DELETED | DELETED | P | M |
| T | A | F | R | L | H | V | G | T | DELETED | P | DELETED | I |
| T | A | F | R | L | H | V | G | T | DELETED | P | DELETED | M |
| T | A | F | R | L | H | V | G | T | DELETED | P | P | I |
| T | A | F | R | L | H | V | G | T | DELETED | P | P | M |
| T | A | F | R | L | H | V | G | T | N | DELETED | DELETED | I |
| T | A | F | R | L | H | V | G | T | N | DELETED | DELETED | M |
| T | A | F | R | L | H | V | G | T | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | L | H | V | G | T | N | DELETED | P | M |
| T | A | F | R | L | H | V | G | T | N | P | DELETED | I |
| T | A | F | R | L | H | V | G | T | N | P | DELETED | M |
| T | A | F | R | L | H | V | G | T | N | P | P | I |
| T | A | F | R | L | H | V | G | T | N | P | P | M |
| T | A | F | R | I | Y | Q | S | S | DELETED | DELETED | DELETED | I |
| T | A | F | R | I | Y | Q | S | S | DELETED | DELETED | DELETED | M |
| T | A | F | R | I | Y | Q | S | S | DELETED | DELETED | P | I |
| T | A | F | R | I | Y | Q | S | S | DELETED | DELETED | P | M |
| T | A | F | R | I | Y | Q | S | S | DELETED | P | DELETED | I |
| T | A | F | R | I | Y | Q | S | S | DELETED | P | DELETED | M |
| T | A | F | R | I | Y | Q | S | S | DELETED | P | P | I |
| T | A | F | R | I | Y | Q | S | S | DELETED | P | P | M |
| T | A | F | R | I | Y | Q | S | S | N | DELETED | DELETED | I |
| T | A | F | R | I | Y | Q | S | S | N | DELETED | DELETED | M |
| T | A | F | R | I | Y | Q | S | S | N | DELETED | P | I |
| T | A | F | R | I | Y | Q | S | S | N | DELETED | P | M |
| T | A | F | R | I | Y | Q | S | S | N | P | DELETED | I |
| T | A | F | R | I | Y | Q | S | S | N | P | DELETED | M |
| T | A | F | R | I | Y | Q | S | S | N | P | P | I |
| T | A | F | R | I | Y | Q | S | S | N | P | P | M |
| T | A | F | R | I | Y | Q | S | T | DELETED | DELETED | DELETED | I |
| T | A | F | R | I | Y | Q | S | T | DELETED | DELETED | DELETED | M |
| T | A | F | R | I | Y | Q | S | T | DELETED | DELETED | P | I |
| T | A | F | R | I | Y | Q | S | T | DELETED | DELETED | P | M |
| T | A | F | R | I | Y | Q | S | T | DELETED | P | DELETED | I |
| T | A | F | R | I | Y | Q | S | T | DELETED | P | DELETED | M |
| T | A | F | R | I | Y | Q | S | T | DELETED | P | P | I |
| T | A | F | R | I | Y | Q | S | T | DELETED | P | P | M |
| T | A | F | R | I | Y | Q | S | T | N | DELETED | DELETED | I |
| T | A | F | R | I | Y | Q | S | T | N | DELETED | DELETED | M |
| T | A | F | R | I | Y | Q | S | T | N | DELETED | P | I |
| T | A | F | R | I | Y | Q | S | T | N | DELETED | P | M |
| T | A | F | R | I | Y | Q | S | T | N | P | DELETED | I |
| T | A | F | R | I | Y | Q | S | T | N | P | DELETED | M |
| T | A | F | R | I | Y | Q | S | T | N | P | P | I |
| T | A | F | R | I | Y | Q | S | T | N | P | P | M |
| T | A | F | R | I | Y | Q | G | S | DELETED | DELETED | DELETED | I |
| T | A | F | R | I | Y | Q | G | S | DELETED | DELETED | DELETED | M |
| T | A | F | R | I | Y | Q | G | S | DELETED | DELETED | P | I |
| T | A | F | R | I | Y | Q | G | S | DELETED | DELETED | P | M |
| T | A | F | R | I | Y | Q | G | S | DELETED | P | DELETED | I |
| T | A | F | R | I | Y | Q | G | S | DELETED | P | DELETED | M |
| T | A | F | R | I | Y | Q | G | S | DELETED | P | P | I |
| T | A | F | R | I | Y | Q | G | S | DELETED | P | P | M |
| T | A | F | R | I | Y | Q | G | S | N | DELETED | DELETED | I |
| T | A | F | R | I | Y | Q | G | S | N | DELETED | DELETED | M |
| T | A | F | R | I | Y | Q | G | S | N | DELETED | P | I |
| T | A | F | R | I | Y | Q | G | S | N | DELETED | P | M |
| T | A | F | R | I | Y | Q | G | S | N | P | DELETED | I |
| T | A | F | R | I | Y | Q | G | S | N | P | DELETED | M |
| T | A | F | R | I | Y | Q | G | S | N | P | P | I |
| T | A | F | R | I | Y | Q | G | S | N | P | P | M |
| T | A | F | R | I | Y | Q | G | T | DELETED | DELETED | DELETED | I |
| T | A | F | R | I | Y | Q | G | T | DELETED | DELETED | DELETED | M |
| T | A | F | R | I | Y | Q | G | T | DELETED | DELETED | P | I |
| T | A | F | R | I | Y | Q | G | T | DELETED | DELETED | P | M |
| T | A | F | R | I | Y | Q | G | T | DELETED | P | DELETED | I |
| T | A | F | R | I | Y | Q | G | T | DELETED | P | DELETED | M |
| T | A | F | R | I | Y | Q | G | T | DELETED | P | P | I |
| T | A | F | R | I | Y | Q | G | T | DELETED | P | P | M |
| T | A | F | R | I | Y | Q | G | T | N | DELETED | DELETED | I |
| T | A | F | R | I | Y | Q | G | T | N | DELETED | DELETED | M |
| T | A | F | R | I | Y | Q | G | T | N | DELETED | P | I |
| T | A | F | R | I | Y | Q | G | T | N | DELETED | P | M |
| T | A | F | R | I | Y | Q | G | T | N | P | DELETED | I |
| T | A | F | R | I | Y | Q | G | T | N | P | DELETED | M |
| T | A | F | R | I | Y | Q | G | T | N | P | P | I |
| T | A | F | R | I | Y | Q | G | T | N | P | P | M |
| T | A | F | R | I | Y | V | S | S | DELETED | DELETED | DELETED | I |
| T | A | F | R | I | Y | V | S | S | DELETED | DELETED | DELETED | M |
| T | A | F | R | I | Y | V | S | S | DELETED | DELETED | P | I |
| T | A | F | R | I | Y | V | S | S | DELETED | DELETED | P | M |
| T | A | F | R | I | Y | V | S | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | I | Y | V | S | S | DELETED | P | DELETED | M |
| T | A | F | R | I | Y | V | S | S | DELETED | P | P | I |
| T | A | F | R | I | Y | V | S | S | DELETED | P | P | M |
| T | A | F | R | I | Y | V | S | S | N | DELETED | DELETED | I |
| T | A | F | R | I | Y | V | S | S | N | DELETED | DELETED | M |
| T | A | F | R | I | Y | V | S | S | N | DELETED | P | I |
| T | A | F | R | I | Y | V | S | S | N | DELETED | P | M |
| T | A | F | R | I | Y | V | S | S | N | P | DELETED | I |
| T | A | F | R | I | Y | V | S | S | N | P | DELETED | M |
| T | A | F | R | I | Y | V | S | S | N | P | P | I |
| T | A | F | R | I | Y | V | S | S | N | P | P | M |
| T | A | F | R | I | Y | V | S | T | DELETED | DELETED | DELETED | I |
| T | A | F | R | I | Y | V | S | T | DELETED | DELETED | DELETED | M |
| T | A | F | R | I | Y | V | S | T | DELETED | DELETED | P | I |
| T | A | F | R | I | Y | V | S | T | DELETED | DELETED | P | M |
| T | A | F | R | I | Y | V | S | T | DELETED | P | DELETED | I |
| T | A | F | R | I | Y | V | S | T | DELETED | P | DELETED | M |
| T | A | F | R | I | Y | V | S | T | DELETED | P | P | I |
| T | A | F | R | I | Y | V | S | T | DELETED | P | P | M |
| T | A | F | R | I | Y | V | S | T | N | DELETED | DELETED | I |
| T | A | F | R | I | Y | V | S | T | N | DELETED | DELETED | M |
| T | A | F | R | I | Y | V | S | T | N | DELETED | P | I |
| T | A | F | R | I | Y | V | S | T | N | DELETED | P | M |
| T | A | F | R | I | Y | V | S | T | N | P | DELETED | I |
| T | A | F | R | I | Y | V | S | T | N | P | DELETED | M |
| T | A | F | R | I | Y | V | S | T | N | P | P | I |
| T | A | F | R | I | Y | V | S | T | N | P | P | M |
| T | A | F | R | I | Y | V | G | S | DELETED | DELETED | DELETED | I |
| T | A | F | R | I | Y | V | G | S | DELETED | DELETED | DELETED | M |
| T | A | F | R | I | Y | V | G | S | DELETED | DELETED | P | I |
| T | A | F | R | I | Y | V | G | S | DELETED | DELETED | P | M |
| T | A | F | R | I | Y | V | G | S | DELETED | P | DELETED | I |
| T | A | F | R | I | Y | V | G | S | DELETED | P | DELETED | M |
| T | A | F | R | I | Y | V | G | S | DELETED | P | P | I |
| T | A | F | R | I | Y | V | G | S | DELETED | P | P | M |
| T | A | F | R | I | Y | V | G | S | N | DELETED | DELETED | I |
| T | A | F | R | I | Y | V | G | S | N | DELETED | DELETED | M |
| T | A | F | R | I | Y | V | G | S | N | DELETED | P | I |
| T | A | F | R | I | Y | V | G | S | N | DELETED | P | M |
| T | A | F | R | I | Y | V | G | S | N | P | DELETED | I |
| T | A | F | R | I | Y | V | G | S | N | P | DELETED | M |
| T | A | F | R | I | Y | V | G | S | N | P | P | I |
| T | A | F | R | I | Y | V | G | S | N | P | P | M |
| T | A | F | R | I | Y | V | G | T | DELETED | DELETED | DELETED | I |
| T | A | F | R | I | Y | V | G | T | DELETED | DELETED | DELETED | M |
| T | A | F | R | I | Y | V | G | T | DELETED | DELETED | P | I |
| T | A | F | R | I | Y | V | G | T | DELETED | DELETED | P | M |
| T | A | F | R | I | Y | V | G | T | DELETED | P | DELETED | I |
| T | A | F | R | I | Y | V | G | T | DELETED | P | DELETED | M |
| T | A | F | R | I | Y | V | G | T | DELETED | P | P | I |
| T | A | F | R | I | Y | V | G | T | DELETED | P | P | M |
| T | A | F | R | I | Y | V | G | T | N | DELETED | DELETED | I |
| T | A | F | R | I | Y | V | G | T | N | DELETED | DELETED | M |
| T | A | F | R | I | Y | V | G | T | N | DELETED | P | I |
| T | A | F | R | I | Y | V | G | T | N | DELETED | P | M |
| T | A | F | R | I | Y | V | G | T | N | P | DELETED | I |
| T | A | F | R | I | Y | V | G | T | N | P | DELETED | M |
| T | A | F | R | I | Y | V | G | T | N | P | P | I |
| T | A | F | R | I | Y | V | G | T | N | P | P | M |
| T | A | F | R | I | H | Q | S | S | DELETED | DELETED | DELETED | I |
| T | A | F | R | I | H | Q | S | S | DELETED | DELETED | DELETED | M |
| T | A | F | R | I | H | Q | S | S | DELETED | DELETED | P | I |
| T | A | F | R | I | H | Q | S | S | DELETED | DELETED | P | M |
| T | A | F | R | I | H | Q | S | S | DELETED | P | DELETED | I |
| T | A | F | R | I | H | Q | S | S | DELETED | P | DELETED | M |
| T | A | F | R | I | H | Q | S | S | DELETED | P | P | I |
| T | A | F | R | I | H | Q | S | S | DELETED | P | P | M |
| T | A | F | R | I | H | Q | S | S | N | DELETED | DELETED | I |
| T | A | F | R | I | H | Q | S | S | N | DELETED | DELETED | M |
| T | A | F | R | I | H | Q | S | S | N | DELETED | P | I |
| T | A | F | R | I | H | Q | S | S | N | DELETED | P | M |
| T | A | F | R | I | H | Q | S | S | N | P | DELETED | I |
| T | A | F | R | I | H | Q | S | S | N | P | DELETED | M |
| T | A | F | R | I | H | Q | S | S | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | I | H | Q | S | S | N | P | P | M |
| T | A | F | R | I | H | Q | S | T | DELETED | DELETED | DELETED | I |
| T | A | F | R | I | H | Q | S | T | DELETED | DELETED | DELETED | M |
| T | A | F | R | I | H | Q | S | T | DELETED | DELETED | P | I |
| T | A | F | R | I | H | Q | S | T | DELETED | DELETED | P | M |
| T | A | F | R | I | H | Q | S | T | DELETED | P | DELETED | I |
| T | A | F | R | I | H | Q | S | T | DELETED | P | DELETED | M |
| T | A | F | R | I | H | Q | S | T | DELETED | P | P | I |
| T | A | F | R | I | H | Q | S | T | DELETED | P | P | M |
| T | A | F | R | I | H | Q | S | T | N | DELETED | DELETED | I |
| T | A | F | R | I | H | Q | S | T | N | DELETED | DELETED | M |
| T | A | F | R | I | H | Q | S | T | N | DELETED | P | I |
| T | A | F | R | I | H | Q | S | T | N | DELETED | P | M |
| T | A | F | R | I | H | Q | S | T | N | P | DELETED | I |
| T | A | F | R | I | H | Q | S | T | N | P | DELETED | M |
| T | A | F | R | I | H | Q | S | T | N | P | P | I |
| T | A | F | R | I | H | Q | S | T | N | P | P | M |
| T | A | F | R | I | H | Q | G | S | DELETED | DELETED | DELETED | I |
| T | A | F | R | I | H | Q | G | S | DELETED | DELETED | DELETED | M |
| T | A | F | R | I | H | Q | G | S | DELETED | DELETED | P | I |
| T | A | F | R | I | H | Q | G | S | DELETED | DELETED | P | M |
| T | A | F | R | I | H | Q | G | S | DELETED | P | DELETED | I |
| T | A | F | R | I | H | Q | G | S | DELETED | P | DELETED | M |
| T | A | F | R | I | H | Q | G | S | DELETED | P | P | I |
| T | A | F | R | I | H | Q | G | S | DELETED | P | P | M |
| T | A | F | R | I | H | Q | G | S | N | DELETED | DELETED | I |
| T | A | F | R | I | H | Q | G | S | N | DELETED | DELETED | M |
| T | A | F | R | I | H | Q | G | S | N | DELETED | P | I |
| T | A | F | R | I | H | Q | G | S | N | DELETED | P | M |
| T | A | F | R | I | H | Q | G | S | N | P | DELETED | I |
| T | A | F | R | I | H | Q | G | S | N | P | DELETED | M |
| T | A | F | R | I | H | Q | G | S | N | P | P | I |
| T | A | F | R | I | H | Q | G | S | N | P | P | M |
| T | A | F | R | I | H | Q | G | T | DELETED | DELETED | DELETED | I |
| T | A | F | R | I | H | Q | G | T | DELETED | DELETED | DELETED | M |
| T | A | F | R | I | H | Q | G | T | DELETED | DELETED | P | I |
| T | A | F | R | I | H | Q | G | T | DELETED | DELETED | P | M |
| T | A | F | R | I | H | Q | G | T | DELETED | P | DELETED | I |
| T | A | F | R | I | H | Q | G | T | DELETED | P | DELETED | M |
| T | A | F | R | I | H | Q | G | T | DELETED | P | P | I |
| T | A | F | R | I | H | Q | G | T | DELETED | P | P | M |
| T | A | F | R | I | H | Q | G | T | N | DELETED | DELETED | I |
| T | A | F | R | I | H | Q | G | T | N | DELETED | DELETED | M |
| T | A | F | R | I | H | Q | G | T | N | DELETED | P | I |
| T | A | F | R | I | H | Q | G | T | N | DELETED | P | M |
| T | A | F | R | I | H | Q | G | T | N | P | DELETED | I |
| T | A | F | R | I | H | Q | G | T | N | P | DELETED | M |
| T | A | F | R | I | H | Q | G | T | N | P | P | I |
| T | A | F | R | I | H | Q | G | T | N | P | P | M |
| T | A | F | R | I | H | V | S | S | DELETED | DELETED | DELETED | I |
| T | A | F | R | I | H | V | S | S | DELETED | DELETED | DELETED | M |
| T | A | F | R | I | H | V | S | S | DELETED | DELETED | P | I |
| T | A | F | R | I | H | V | S | S | DELETED | DELETED | P | M |
| T | A | F | R | I | H | V | S | S | DELETED | P | DELETED | I |
| T | A | F | R | I | H | V | S | S | DELETED | P | DELETED | M |
| T | A | F | R | I | H | V | S | S | DELETED | P | P | I |
| T | A | F | R | I | H | V | S | S | DELETED | P | P | M |
| T | A | F | R | I | H | V | S | S | N | DELETED | DELETED | I |
| T | A | F | R | I | H | V | S | S | N | DELETED | DELETED | M |
| T | A | F | R | I | H | V | S | S | N | DELETED | P | I |
| T | A | F | R | I | H | V | S | S | N | DELETED | P | M |
| T | A | F | R | I | H | V | S | S | N | P | DELETED | I |
| T | A | F | R | I | H | V | S | S | N | P | DELETED | M |
| T | A | F | R | I | H | V | S | S | N | P | P | I |
| T | A | F | R | I | H | V | S | S | N | P | P | M |
| T | A | F | R | I | H | V | S | T | DELETED | DELETED | DELETED | I |
| T | A | F | R | I | H | V | S | T | DELETED | DELETED | DELETED | M |
| T | A | F | R | I | H | V | S | T | DELETED | DELETED | P | I |
| T | A | F | R | I | H | V | S | T | DELETED | DELETED | P | M |
| T | A | F | R | I | H | V | S | T | DELETED | P | DELETED | I |
| T | A | F | R | I | H | V | S | T | DELETED | P | DELETED | M |
| T | A | F | R | I | H | V | S | T | DELETED | P | P | I |
| T | A | F | R | I | H | V | S | T | DELETED | P | P | M |
| T | A | F | R | I | H | V | S | T | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | A | F | R | I | H | V | S | T | N | DELETED | DELETED | M |
| T | A | F | R | I | H | V | S | T | N | DELETED | P | I |
| T | A | F | R | I | H | V | S | T | N | DELETED | P | M |
| T | A | F | R | I | H | V | S | T | N | P | DELETED | I |
| T | A | F | R | I | H | V | S | T | N | P | DELETED | M |
| T | A | F | R | I | H | V | S | T | N | P | P | I |
| T | A | F | R | I | H | V | S | T | N | P | P | M |
| T | A | F | R | I | H | V | G | S | DELETED | DELETED | DELETED | I |
| T | A | F | R | I | H | V | G | S | DELETED | DELETED | DELETED | M |
| T | A | F | R | I | H | V | G | S | DELETED | DELETED | P | I |
| T | A | F | R | I | H | V | G | S | DELETED | DELETED | P | M |
| T | A | F | R | I | H | V | G | S | DELETED | P | DELETED | I |
| T | A | F | R | I | H | V | G | S | DELETED | P | DELETED | M |
| T | A | F | R | I | H | V | G | S | DELETED | P | P | I |
| T | A | F | R | I | H | V | G | S | DELETED | P | P | M |
| T | A | F | R | I | H | V | G | S | N | DELETED | DELETED | I |
| T | A | F | R | I | H | V | G | S | N | DELETED | DELETED | M |
| T | A | F | R | I | H | V | G | S | N | DELETED | P | I |
| T | A | F | R | I | H | V | G | S | N | DELETED | P | M |
| T | A | F | R | I | H | V | G | S | N | P | DELETED | I |
| T | A | F | R | I | H | V | G | S | N | P | DELETED | M |
| T |  | F | R | I | H | V | G | S | N | P | P | I |
| T | A | F | R | I | H | V | G | S | N | P | P | M |
| T | A | F | R | I | H | V | G | T | DELETED | DELETED | DELETED | I |
| T | A | F | R | I | H | V | G | T | DELETED | DELETED | DELETED | M |
| T | A | F | R | I | H | V | G | T | DELETED | DELETED | P | I |
| T | A | F | R | I | H | V | G | T | DELETED | DELETED | P | M |
| T | A | F | R | I | H | V | G | T | DELETED | P | DELETED | I |
| T | A | F | R | I | H | V | G | T | DELETED | P | DELETED | M |
| T | A | F | R | I | H | V | G | T | DELETED | P | P | I |
| T | A | F | R | I | H | V | G | T | DELETED | P | P | M |
| T | A | F | R | I | H | V | G | T | N | DELETED | DELETED | I |
| T | A | F | R | I | H | V | G | T | N | DELETED | DELETED | M |
| T | A | F | R | I | H | V | G | T | N | DELETED | P | I |
| T | A | F | R | I | H | V | G | T | N | DELETED | P | M |
| T | A | F | R | I | H | V | G | T | N | P | DELETED | I |
| T | A | F | R | I | H | V | G | T | N | P | DELETED | M |
| T | A | F | R | I | H | V | G | T | N | P | P | I |
| T | A | F | R | I | H | V | G | T | N | P | P | M |
| T | P | I | S | L | Y | Q | S | S | DELETED | DELETED | DELETED | I |
| T | P | I | S | L | Y | Q | S | S | DELETED | DELETED | DELETED | M |
| T | P | I | S | L | Y | Q | S | S | DELETED | DELETED | P | I |
| T | P | I | S | L | Y | Q | S | S | DELETED | DELETED | P | M |
| T | P | I | S | L | Y | Q | S | S | DELETED | P | DELETED | I |
| T | P | I | S | L | Y | Q | S | S | DELETED | P | DELETED | M |
| T | P | I | S | L | Y | Q | S | S | DELETED | P | P | I |
| T | P | I | S | L | Y | Q | S | S | DELETED | P | P | M |
| T | P | I | S | L | Y | Q | S | S | N | DELETED | DELETED | I |
| T | P | I | S | L | Y | Q | S | S | N | DELETED | DELETED | M |
| T | P | I | S | L | Y | Q | S | S | N | DELETED | P | I |
| T | P | I | S | L | Y | Q | S | S | N | DELETED | P | M |
| T | P | I | S | L | Y | Q | S | S | N | P | DELETED | I |
| T | P | I | S | L | Y | Q | S | S | N | P | DELETED | M |
| T | P | I | S | L | Y | Q | S | S | N | P | P | I |
| T | P | I | S | L | Y | Q | S | S | N | P | P | M |
| T | P | I | S | L | Y | Q | S | T | DELETED | DELETED | DELETED | I |
| T | P | I | S | L | Y | Q | S | T | DELETED | DELETED | DELETED | M |
| T | P | I | S | L | Y | Q | S | T | DELETED | DELETED | P | I |
| T | P | I | S | L | Y | Q | S | T | DELETED | DELETED | P | M |
| T | P | I | S | L | Y | Q | S | T | DELETED | P | DELETED | I |
| T | P | I | S | L | Y | Q | S | T | DELETED | P | DELETED | M |
| T | P | I | S | L | Y | Q | S | T | DELETED | P | P | I |
| T | P | I | S | L | Y | Q | S | T | DELETED | P | P | M |
| T | P | I | S | L | Y | Q | S | T | N | DELETED | DELETED | I |
| T | P | I | S | L | Y | Q | S | T | N | DELETED | DELETED | M |
| T | P | I | S | L | Y | Q | S | T | N | DELETED | P | I |
| T | P | I | S | L | Y | Q | S | T | N | DELETED | P | M |
| T | P | I | S | L | Y | Q | S | T | N | P | DELETED | I |
| T | P | I | S | L | Y | Q | S | T | N | P | DELETED | M |
| T | P | I | S | L | Y | Q | S | T | N | P | P | I |
| T | P | I | S | L | Y | Q | S | T | N | P | P | M |
| T | P | I | S | L | Y | Q | G | S | DELETED | DELETED | DELETED | I |
| T | P | I | S | L | Y | Q | G | S | DELETED | DELETED | DELETED | M |
| T | P | I | S | L | Y | Q | G | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | L | Y | Q | G | S | DELETED | DELETED | P | M |
| T | P | I | S | L | Y | Q | G | S | DELETED | P | DELETED | I |
| T | P | I | S | L | Y | Q | G | S | DELETED | P | DELETED | M |
| T | P | I | S | L | Y | Q | G | S | DELETED | P | P | I |
| T | P | I | S | L | Y | Q | G | S | DELETED | P | P | M |
| T | P | I | S | L | Y | Q | G | S | N | DELETED | DELETED | I |
| T | P | I | S | L | Y | Q | G | S | N | DELETED | DELETED | M |
| T | P | I | S | L | Y | Q | G | S | N | DELETED | P | I |
| T | P | I | S | L | Y | Q | G | S | N | DELETED | P | M |
| T | P | I | S | L | Y | Q | G | S | N | P | DELETED | I |
| T | P | I | S | L | Y | Q | G | S | N | P | DELETED | M |
| T | P | I | S | L | Y | Q | G | S | N | P | P | I |
| T | P | I | S | L | Y | Q | G | S | N | P | P | M |
| T | P | I | S | L | Y | Q | G | T | DELETED | DELETED | DELETED | I |
| T | P | I | S | L | Y | Q | G | T | DELETED | DELETED | DELETED | M |
| T | P | I | S | L | Y | Q | G | T | DELETED | DELETED | P | I |
| T | P | I | S | L | Y | Q | G | T | DELETED | DELETED | P | M |
| T | P | I | S | L | Y | Q | G | T | DELETED | P | DELETED | I |
| T | P | I | S | L | Y | Q | G | T | DELETED | P | DELETED | M |
| T | P | I | S | L | Y | Q | G | T | DELETED | P | P | I |
| T | P | I | S | L | Y | Q | G | T | DELETED | P | P | M |
| T | P | I | S | L | Y | Q | G | T | N | DELETED | DELETED | I |
| T | P | I | S | L | Y | Q | G | T | N | DELETED | DELETED | M |
| T | P | I | S | L | Y | Q | G | T | N | DELETED | P | I |
| T | P | I | S | L | Y | Q | G | T | N | DELETED | P | M |
| T | P | I | S | L | Y | Q | G | T | N | P | DELETED | I |
| T | P | I | S | L | Y | Q | G | T | N | P | DELETED | M |
| T | P | I | S | L | Y | Q | G | T | N | P | P | I |
| T | P | I | S | L | Y | Q | G | T | N | P | P | M |
| T | P | I | S | L | Y | V | S | S | DELETED | DELETED | DELETED | I |
| T | P | I | S | L | Y | V | S | S | DELETED | DELETED | DELETED | M |
| T | P | I | S | L | Y | V | S | S | DELETED | DELETED | P | I |
| T | P | I | S | L | Y | V | S | S | DELETED | DELETED | P | M |
| T | P | I | S | L | Y | V | S | S | DELETED | P | DELETED | I |
| T | P | I | S | L | Y | V | S | S | DELETED | P | DELETED | M |
| T | P | I | S | L | Y | V | S | S | DELETED | P | P | I |
| T | P | I | S | L | Y | V | S | S | DELETED | P | P | M |
| T | P | I | S | L | Y | V | S | S | N | DELETED | DELETED | I |
| T | P | I | S | L | Y | V | S | S | N | DELETED | DELETED | M |
| T | P | I | S | L | Y | V | S | S | N | DELETED | P | I |
| T | P | I | S | L | Y | V | S | S | N | DELETED | P | M |
| T | P | I | S | L | Y | V | S | S | N | P | DELETED | I |
| T | P | I | S | L | Y | V | S | S | N | P | DELETED | M |
| T | P | I | S | L | Y | V | S | S | N | P | P | I |
| T | P | I | S | L | Y | V | S | S | N | P | P | M |
| T | P | I | S | L | Y | V | S | T | DELETED | DELETED | DELETED | I |
| T | P | I | S | L | Y | V | S | T | DELETED | DELETED | DELETED | M |
| T | P | I | S | L | Y | V | S | T | DELETED | DELETED | P | I |
| T | P | I | S | L | Y | V | S | T | DELETED | DELETED | P | M |
| T | P | I | S | L | Y | V | S | T | DELETED | P | DELETED | I |
| T | P | I | S | L | Y | V | S | T | DELETED | P | DELETED | M |
| T | P | I | S | L | Y | V | S | T | DELETED | P | P | I |
| T | P | I | S | L | Y | V | S | T | DELETED | P | P | M |
| T | P | I | S | L | Y | V | S | T | N | DELETED | DELETED | I |
| T | P | I | S | L | Y | V | S | T | N | DELETED | DELETED | M |
| T | P | I | S | L | Y | V | S | T | N | DELETED | P | I |
| T | P | I | S | L | Y | V | S | T | N | DELETED | P | M |
| T | P | I | S | L | Y | V | S | T | N | P | DELETED | I |
| T | P | I | S | L | Y | V | S | T | N | P | DELETED | M |
| T | P | I | S | L | Y | V | S | T | N | P | P | I |
| T | P | I | S | L | Y | V | S | T | N | P | P | M |
| T | P | I | S | L | Y | V | G | S | DELETED | DELETED | DELETED | I |
| T | P | I | S | L | Y | V | G | S | DELETED | DELETED | DELETED | M |
| T | P | I | S | L | Y | V | G | S | DELETED | DELETED | P | I |
| T | P | I | S | L | Y | V | G | S | DELETED | DELETED | P | M |
| T | P | I | S | L | Y | V | G | S | DELETED | P | DELETED | I |
| T | P | I | S | L | Y | V | G | S | DELETED | P | DELETED | M |
| T | P | I | S | L | Y | V | G | S | DELETED | P | P | I |
| T | P | I | S | L | Y | V | G | S | DELETED | P | P | M |
| T | P | I | S | L | Y | V | G | S | N | DELETED | DELETED | I |
| T | P | I | S | L | Y | V | G | S | N | DELETED | DELETED | M |
| T | P | I | S | L | Y | V | G | S | N | DELETED | P | I |
| T | P | I | S | L | Y | V | G | S | N | DELETED | P | M |
| T | P | I | S | L | Y | V | G | S | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | L | Y | V | G | S | N | P | DELETED | M |
| T | P | I | S | L | Y | V | G | S | N | P | P | I |
| T | P | I | S | L | Y | V | G | S | N | P | P | M |
| T | P | I | S | L | Y | V | G | T | DELETED | DELETED | DELETED | I |
| T | P | I | S | L | Y | V | G | T | DELETED | DELETED | DELETED | M |
| T | P | I | S | L | Y | V | G | T | DELETED | DELETED | P | I |
| T | P | I | S | L | Y | V | G | T | DELETED | DELETED | P | M |
| T | P | I | S | L | Y | V | G | T | DELETED | P | DELETED | I |
| T | P | I | S | L | Y | V | G | T | DELETED | P | DELETED | M |
| T | P | I | S | L | Y | V | G | T | DELETED | P | P | I |
| T | P | I | S | L | Y | V | G | T | DELETED | P | P | M |
| T | P | I | S | L | Y | V | G | T | N | DELETED | DELETED | I |
| T | P | I | S | L | Y | V | G | T | N | DELETED | DELETED | M |
| T | P | I | S | L | Y | V | G | T | N | DELETED | P | I |
| T | P | I | S | L | Y | V | G | T | N | DELETED | P | M |
| T | P | I | S | L | Y | V | G | T | N | P | DELETED | I |
| T | P | I | S | L | Y | V | G | T | N | P | DELETED | M |
| T | P | I | S | L | Y | V | G | T | N | P | P | I |
| T | P | I | S | L | Y | V | G | T | N | P | P | M |
| T | P | I | S | L | H | Q | S | S | DELETED | DELETED | DELETED | I |
| T | P | I | S | L | H | Q | S | S | DELETED | DELETED | DELETED | M |
| T | P | I | S | L | H | Q | S | S | DELETED | DELETED | P | I |
| T | P | I | S | L | H | Q | S | S | DELETED | DELETED | P | M |
| T | P | I | S | L | H | Q | S | S | DELETED | P | DELETED | I |
| T | P | I | S | L | H | Q | S | S | DELETED | P | DELETED | M |
| T | P | I | S | L | H | Q | S | S | DELETED | P | P | I |
| T | P | I | S | L | H | Q | S | S | DELETED | P | P | M |
| T | P | I | S | L | H | Q | S | S | N | DELETED | DELETED | I |
| T | P | I | S | L | H | Q | S | S | N | DELETED | DELETED | M |
| T | P | I | S | L | H | Q | S | S | N | DELETED | P | I |
| T | P | I | S | L | H | Q | S | S | N | DELETED | P | M |
| T | P | I | S | L | H | Q | S | S | N | P | DELETED | I |
| T | P | I | S | L | H | Q | S | S | N | P | DELETED | M |
| T | P | I | S | L | H | Q | S | S | N | P | P | I |
| T | P | I | S | L | H | Q | S | S | N | P | P | M |
| T | P | I | S | L | H | Q | S | T | DELETED | DELETED | DELETED | I |
| T | P | I | S | L | H | Q | S | T | DELETED | DELETED | DELETED | M |
| T | P | I | S | L | H | Q | S | T | DELETED | DELETED | P | I |
| T | P | I | S | L | H | Q | S | T | DELETED | DELETED | P | M |
| T | P | I | S | L | H | Q | S | T | DELETED | P | DELETED | I |
| T | P | I | S | L | H | Q | S | T | DELETED | P | DELETED | M |
| T | P | I | S | L | H | Q | S | T | DELETED | P | P | I |
| T | P | I | S | L | H | Q | S | T | DELETED | P | P | M |
| T | P | I | S | L | H | Q | S | T | N | DELETED | DELETED | I |
| T | P | I | S | L | H | Q | S | T | N | DELETED | DELETED | M |
| T | P | I | S | L | H | Q | S | T | N | DELETED | P | I |
| T | P | I | S | L | H | Q | S | T | N | DELETED | P | M |
| T | P | I | S | L | H | Q | S | T | N | P | DELETED | I |
| T | P | I | S | L | H | Q | S | T | N | P | DELETED | M |
| T | P | I | S | L | H | Q | S | T | N | P | P | I |
| T | P | I | S | L | H | Q | S | T | N | P | P | M |
| T | P | I | S | L | H | Q | G | S | DELETED | DELETED | DELETED | I |
| T | P | I | S | L | H | Q | G | S | DELETED | DELETED | DELETED | M |
| T | P | I | S | L | H | Q | G | S | DELETED | DELETED | P | I |
| T | P | I | S | L | H | Q | G | S | DELETED | DELETED | P | M |
| T | P | I | S | L | H | Q | G | S | DELETED | P | DELETED | I |
| T | P | I | S | L | H | Q | G | S | DELETED | P | DELETED | M |
| T | P | I | S | L | H | Q | G | S | DELETED | P | P | I |
| T | P | I | S | L | H | Q | G | S | DELETED | P | P | M |
| T | P | I | S | L | H | Q | G | S | N | DELETED | DELETED | I |
| T | P | I | S | L | H | Q | G | S | N | DELETED | DELETED | M |
| T | P | I | S | L | H | Q | G | S | N | DELETED | P | I |
| T | P | I | S | L | H | Q | G | S | N | DELETED | P | M |
| T | P | I | S | L | H | Q | G | S | N | P | DELETED | I |
| T | P | I | S | L | H | Q | G | S | N | P | DELETED | M |
| T | P | I | S | L | H | Q | G | S | N | P | P | I |
| T | P | I | S | L | H | Q | G | S | N | P | P | M |
| T | P | I | S | L | H | Q | G | T | DELETED | DELETED | DELETED | I |
| T | P | I | S | L | H | Q | G | T | DELETED | DELETED | DELETED | M |
| T | P | I | S | L | H | Q | G | T | DELETED | DELETED | P | I |
| T | P | I | S | L | H | Q | G | T | DELETED | DELETED | P | M |
| T | P | I | S | L | H | Q | G | T | DELETED | P | DELETED | I |
| T | P | I | S | L | H | Q | G | T | DELETED | P | DELETED | M |
| T | P | I | S | L | H | Q | G | T | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | L | H | Q | G | T | DELETED | P | P | M |
| T | P | I | S | L | H | Q | G | T | N | DELETED | DELETED | I |
| T | P | I | S | L | H | Q | G | T | N | DELETED | DELETED | M |
| T | P | I | S | L | H | Q | G | T | N | DELETED | P | I |
| T | P | I | S | L | H | Q | G | T | N | DELETED | P | M |
| T | P | I | S | L | H | Q | G | T | N | P | DELETED | I |
| T | P | I | S | L | H | Q | G | T | N | P | DELETED | M |
| T | P | I | S | L | H | Q | G | T | N | P | P | I |
| T | P | I | S | L | H | Q | G | T | N | P | P | M |
| T | P | I | S | L | H | V | S | S | DELETED | DELETED | DELETED | I |
| T | P | I | S | L | H | V | S | S | DELETED | DELETED | DELETED | M |
| T | P | I | S | L | H | V | S | S | DELETED | DELETED | P | I |
| T | P | I | S | L | H | V | S | S | DELETED | DELETED | P | M |
| T | P | I | S | L | H | V | S | S | DELETED | P | DELETED | I |
| T | P | I | S | L | H | V | S | S | DELETED | P | DELETED | M |
| T | P | I | S | L | H | V | S | S | DELETED | P | P | I |
| T | P | I | S | L | H | V | S | S | DELETED | P | P | M |
| T | P | I | S | L | H | V | S | S | N | DELETED | DELETED | I |
| T | P | I | S | L | H | V | S | S | N | DELETED | DELETED | M |
| T | P | I | S | L | H | V | S | S | N | DELETED | P | I |
| T | P | I | S | L | H | V | S | S | N | DELETED | P | M |
| T | P | I | S | L | H | V | S | S | N | P | DELETED | I |
| T | P | I | S | L | H | V | S | S | N | P | DELETED | M |
| T | P | I | S | L | H | V | S | S | N | P | P | I |
| T | P | I | S | L | H | V | S | S | N | P | P | M |
| T | P | I | S | L | H | V | S | T | DELETED | DELETED | DELETED | I |
| T | P | I | S | L | H | V | S | T | DELETED | DELETED | DELETED | M |
| T | P | I | S | L | H | V | S | T | DELETED | DELETED | P | I |
| T | P | I | S | L | H | V | S | T | DELETED | DELETED | P | M |
| T | P | I | S | L | H | V | S | T | DELETED | P | DELETED | I |
| T | P | I | S | L | H | V | S | T | DELETED | P | DELETED | M |
| T | P | I | S | L | H | V | S | T | DELETED | P | P | I |
| T | P | I | S | L | H | V | S | T | DELETED | P | P | M |
| T | P | I | S | L | H | V | S | T | N | DELETED | DELETED | I |
| T | P | I | S | L | H | V | S | T | N | DELETED | DELETED | M |
| T | P | I | S | L | H | V | S | T | N | DELETED | P | I |
| T | P | I | S | L | H | V | S | T | N | DELETED | P | M |
| T | P | I | S | L | H | V | S | T | N | P | DELETED | I |
| T | P | I | S | L | H | V | S | T | N | P | DELETED | M |
| T | P | I | S | L | H | V | S | T | N | P | P | I |
| T | P | I | S | L | H | V | S | T | N | P | P | M |
| T | P | I | S | L | H | V | G | S | DELETED | DELETED | DELETED | I |
| T | P | I | S | L | H | V | G | S | DELETED | DELETED | DELETED | M |
| T | P | I | S | L | H | V | G | S | DELETED | DELETED | P | I |
| T | P | I | S | L | H | V | G | S | DELETED | DELETED | P | M |
| T | P | I | S | L | H | V | G | S | DELETED | P | DELETED | I |
| T | P | I | S | L | H | V | G | S | DELETED | P | DELETED | M |
| T | P | I | S | L | H | V | G | S | DELETED | P | P | I |
| T | P | I | S | L | H | V | G | S | DELETED | P | P | M |
| T | P | I | S | L | H | V | G | S | N | DELETED | DELETED | I |
| T | P | I | S | L | H | V | G | S | N | DELETED | DELETED | M |
| T | P | I | S | L | H | V | G | S | N | DELETED | P | I |
| T | P | I | S | L | H | V | G | S | N | DELETED | P | M |
| T | P | I | S | L | H | V | G | S | N | P | DELETED | I |
| T | P | I | S | L | H | V | G | S | N | P | DELETED | M |
| T | P | I | S | L | H | V | G | S | N | P | P | I |
| T | P | I | S | L | H | V | G | S | N | P | P | M |
| T | P | I | S | L | H | V | G | T | DELETED | DELETED | DELETED | I |
| T | P | I | S | L | H | V | G | T | DELETED | DELETED | DELETED | M |
| T | P | I | S | L | H | V | G | T | DELETED | DELETED | P | I |
| T | P | I | S | L | H | V | G | T | DELETED | DELETED | P | M |
| T | P | I | S | L | H | V | G | T | DELETED | P | DELETED | I |
| T | P | I | S | L | H | V | G | T | DELETED | P | DELETED | M |
| T | P | I | S | L | H | V | G | T | DELETED | P | P | I |
| T | P | I | S | L | H | V | G | T | DELETED | P | P | M |
| T | P | I | S | L | H | V | G | T | N | DELETED | DELETED | I |
| T | P | I | S | L | H | V | G | T | N | DELETED | DELETED | M |
| T | P | I | S | L | H | V | G | T | N | DELETED | P | I |
| T | P | I | S | L | H | V | G | T | N | DELETED | P | M |
| T | P | I | S | L | H | V | G | T | N | P | DELETED | I |
| T | P | I | S | L | H | V | G | T | N | P | DELETED | M |
| T | P | I | S | L | H | V | G | T | N | P | P | I |
| T | P | I | S | L | H | V | G | T | N | P | P | M |
| T | P | I | S | I | Y | Q | S | S | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | I | Y | Q | S | S | DELETED | DELETED | DELETED | M |
| T | P | I | S | I | Y | Q | S | S | DELETED | DELETED | P | I |
| T | P | I | S | I | Y | Q | S | S | DELETED | DELETED | P | M |
| T | P | I | S | I | Y | Q | S | S | DELETED | P | DELETED | I |
| T | P | I | S | I | Y | Q | S | S | DELETED | P | DELETED | M |
| T | P | I | S | I | Y | Q | S | S | DELETED | P | P | I |
| T | P | I | S | I | Y | Q | S | S | DELETED | P | P | M |
| T | P | I | S | I | Y | Q | S | S | N | DELETED | DELETED | I |
| T | P | I | S | I | Y | Q | S | S | N | DELETED | DELETED | M |
| T | P | I | S | I | Y | Q | S | S | N | DELETED | P | I |
| T | P | I | S | I | Y | Q | S | S | N | DELETED | P | M |
| T | P | I | S | I | Y | Q | S | S | N | P | DELETED | I |
| T | P | I | S | I | Y | Q | S | S | N | P | DELETED | M |
| T | P | I | S | I | Y | Q | S | S | N | P | P | I |
| T | P | I | S | I | Y | Q | S | S | N | P | P | M |
| T | P | I | S | I | Y | Q | S | T | DELETED | DELETED | DELETED | I |
| T | P | I | S | I | Y | Q | S | T | DELETED | DELETED | DELETED | M |
| T | P | I | S | I | Y | Q | S | T | DELETED | DELETED | P | I |
| T | P | I | S | I | Y | Q | S | T | DELETED | DELETED | P | M |
| T | P | I | S | I | Y | Q | S | T | DELETED | P | DELETED | I |
| T | P | I | S | I | Y | Q | S | T | DELETED | P | DELETED | M |
| T | P | I | S | I | Y | Q | S | T | DELETED | P | P | I |
| T | P | I | S | I | Y | Q | S | T | DELETED | P | P | M |
| T | P | I | S | I | Y | Q | S | T | N | DELETED | DELETED | I |
| T | P | I | S | I | Y | Q | S | T | N | DELETED | DELETED | M |
| T | P | I | S | I | Y | Q | S | T | N | DELETED | P | I |
| T | P | I | S | I | Y | Q | S | T | N | DELETED | P | M |
| T | P | I | S | I | Y | Q | S | T | N | P | DELETED | I |
| T | P | I | S | I | Y | Q | S | T | N | P | DELETED | M |
| T | P | I | S | I | Y | Q | S | T | N | P | P | I |
| T | P | I | S | I | Y | Q | S | T | N | P | P | M |
| T | P | I | S | I | Y | Q | G | S | DELETED | DELETED | DELETED | I |
| T | P | I | S | I | Y | Q | G | S | DELETED | DELETED | DELETED | M |
| T | P | I | S | I | Y | Q | G | S | DELETED | DELETED | P | I |
| T | P | I | S | I | Y | Q | G | S | DELETED | DELETED | P | M |
| T | P | I | S | I | Y | Q | G | S | DELETED | P | DELETED | I |
| T | P | I | S | I | Y | Q | G | S | DELETED | P | DELETED | M |
| T | P | I | S | I | Y | Q | G | S | DELETED | P | P | I |
| T | P | I | S | I | Y | Q | G | S | DELETED | P | P | M |
| T | P | I | S | I | Y | Q | G | S | N | DELETED | DELETED | I |
| T | P | I | S | I | Y | Q | G | S | N | DELETED | DELETED | M |
| T | P | I | S | I | Y | Q | G | S | N | DELETED | P | I |
| T | P | I | S | I | Y | Q | G | S | N | DELETED | P | M |
| T | P | I | S | I | Y | Q | G | S | N | P | DELETED | I |
| T | P | I | S | I | Y | Q | G | S | N | P | DELETED | M |
| T | P | I | S | I | Y | Q | G | S | N | P | P | I |
| T | P | I | S | I | Y | Q | G | S | N | P | P | M |
| T | P | I | S | I | Y | Q | G | T | DELETED | DELETED | DELETED | I |
| T | P | I | S | I | Y | Q | G | T | DELETED | DELETED | DELETED | M |
| T | P | I | S | I | Y | Q | G | T | DELETED | DELETED | P | I |
| T | P | I | S | I | Y | Q | G | T | DELETED | DELETED | P | M |
| T | P | I | S | I | Y | Q | G | T | DELETED | P | DELETED | I |
| T | P | I | S | I | Y | Q | G | T | DELETED | P | DELETED | M |
| T | P | I | S | I | Y | Q | G | T | DELETED | P | P | I |
| T | P | I | S | I | Y | Q | G | T | DELETED | P | P | M |
| T | P | I | S | I | Y | Q | G | T | N | DELETED | DELETED | I |
| T | P | I | S | I | Y | Q | G | T | N | DELETED | DELETED | M |
| T | P | I | S | I | Y | Q | G | T | N | DELETED | P | I |
| T | P | I | S | I | Y | Q | G | T | N | DELETED | P | M |
| T | P | I | S | I | Y | Q | G | T | N | P | DELETED | I |
| T | P | I | S | I | Y | Q | G | T | N | P | DELETED | M |
| T | P | I | S | I | Y | Q | G | T | N | P | P | I |
| T | P | I | S | I | Y | Q | G | T | N | P | P | M |
| T | P | I | S | I | Y | V | S | S | DELETED | DELETED | DELETED | I |
| T | P | I | S | I | Y | V | S | S | DELETED | DELETED | DELETED | M |
| T | P | I | S | I | Y | V | S | S | DELETED | DELETED | P | I |
| T | P | I | S | I | Y | V | S | S | DELETED | DELETED | P | M |
| T | P | I | S | I | Y | V | S | S | DELETED | P | DELETED | I |
| T | P | I | S | I | Y | V | S | S | DELETED | P | DELETED | M |
| T | P | I | S | I | Y | V | S | S | DELETED | P | P | I |
| T | P | I | S | I | Y | V | S | S | DELETED | P | P | M |
| T | P | I | S | I | Y | V | S | S | N | DELETED | DELETED | I |
| T | P | I | S | I | Y | V | S | S | N | DELETED | DELETED | M |
| T | P | I | S | I | Y | V | S | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | I | Y | V | S | S | N | DELETED | P | M |
| T | P | I | S | I | Y | V | S | S | N | P | DELETED | I |
| T | P | I | S | I | Y | V | S | S | N | P | DELETED | M |
| T | P | I | S | I | Y | V | S | S | N | P | P | I |
| T | P | I | S | I | Y | V | S | S | N | P | P | M |
| T | P | I | S | I | Y | V | S | T | DELETED | DELETED | DELETED | I |
| T | P | I | S | I | Y | V | S | T | DELETED | DELETED | DELETED | M |
| T | P | I | S | I | Y | V | S | T | DELETED | DELETED | P | I |
| T | P | I | S | I | Y | V | S | T | DELETED | DELETED | P | M |
| T | P | I | S | I | Y | V | S | T | DELETED | P | DELETED | I |
| T | P | I | S | I | Y | V | S | T | DELETED | P | DELETED | M |
| T | P | I | S | I | Y | V | S | T | DELETED | P | P | I |
| T | P | I | S | I | Y | V | S | T | DELETED | P | P | M |
| T | P | I | S | I | Y | V | S | T | N | DELETED | DELETED | I |
| T | P | I | S | I | Y | V | S | T | N | DELETED | DELETED | M |
| T | P | I | S | I | Y | V | S | T | N | DELETED | P | I |
| T | P | I | S | I | Y | V | S | T | N | DELETED | P | M |
| T | P | I | S | I | Y | V | S | T | N | P | DELETED | I |
| T | P | I | S | I | Y | V | S | T | N | P | DELETED | M |
| T | P | I | S | I | Y | V | S | T | N | P | P | I |
| T | P | I | S | I | Y | V | S | T | N | P | P | M |
| T | P | I | S | I | Y | V | G | S | DELETED | DELETED | DELETED | I |
| T | P | I | S | I | Y | V | G | S | DELETED | DELETED | DELETED | M |
| T | P | I | S | I | Y | V | G | S | DELETED | DELETED | P | I |
| T | P | I | S | I | Y | V | G | S | DELETED | DELETED | P | M |
| T | P | I | S | I | Y | V | G | S | DELETED | P | DELETED | I |
| T | P | I | S | I | Y | V | G | S | DELETED | P | DELETED | M |
| T | P | I | S | I | Y | V | G | S | DELETED | P | P | I |
| T | P | I | S | I | Y | V | G | S | DELETED | P | P | M |
| T | P | I | S | I | Y | V | G | S | N | DELETED | DELETED | I |
| T | P | I | S | I | Y | V | G | S | N | DELETED | DELETED | M |
| T | P | I | S | I | Y | V | G | S | N | DELETED | P | I |
| T | P | I | S | I | Y | V | G | S | N | DELETED | P | M |
| T | P | I | S | I | Y | V | G | S | N | P | DELETED | I |
| T | P | I | S | I | Y | V | G | S | N | P | DELETED | M |
| T | P | I | S | I | Y | V | G | S | N | P | P | I |
| T | P | I | S | I | Y | V | G | S | N | P | P | M |
| T | P | I | S | I | Y | V | G | T | DELETED | DELETED | DELETED | I |
| T | P | I | S | I | Y | V | G | T | DELETED | DELETED | DELETED | M |
| T | P | I | S | I | Y | V | G | T | DELETED | DELETED | P | I |
| T | P | I | S | I | Y | V | G | T | DELETED | DELETED | P | M |
| T | P | I | S | I | Y | V | G | T | DELETED | P | DELETED | I |
| T | P | I | S | I | Y | V | G | T | DELETED | P | DELETED | M |
| T | P | I | S | I | Y | V | G | T | DELETED | P | P | I |
| T | P | I | S | I | Y | V | G | T | DELETED | P | P | M |
| T | P | I | S | I | Y | V | G | T | N | DELETED | DELETED | I |
| T | P | I | S | I | Y | V | G | T | N | DELETED | DELETED | M |
| T | P | I | S | I | Y | V | G | T | N | DELETED | P | I |
| T | P | I | S | I | Y | V | G | T | N | DELETED | P | M |
| T | P | I | S | I | Y | V | G | T | N | P | DELETED | I |
| T | P | I | S | I | Y | V | G | T | N | P | DELETED | M |
| T | P | I | S | I | Y | V | G | T | N | P | P | I |
| T | P | I | S | I | Y | V | G | T | N | P | P | M |
| T | P | I | S | I | H | Q | S | S | DELETED | DELETED | DELETED | I |
| T | P | I | S | I | H | Q | S | S | DELETED | DELETED | DELETED | M |
| T | P | I | S | I | H | Q | S | S | DELETED | DELETED | P | I |
| T | P | I | S | I | H | Q | S | S | DELETED | DELETED | P | M |
| T | P | I | S | I | H | Q | S | S | DELETED | P | DELETED | I |
| T | P | I | S | I | H | Q | S | S | DELETED | P | DELETED | M |
| T | P | I | S | I | H | Q | S | S | DELETED | P | P | I |
| T | P | I | S | I | H | Q | S | S | DELETED | P | P | M |
| T | P | I | S | I | H | Q | S | S | N | DELETED | DELETED | I |
| T | P | I | S | I | H | Q | S | S | N | DELETED | DELETED | M |
| T | P | I | S | I | H | Q | S | S | N | DELETED | P | I |
| T | P | I | S | I | H | Q | S | S | N | DELETED | P | M |
| T | P | I | S | I | H | Q | S | S | N | P | DELETED | I |
| T | P | I | S | I | H | Q | S | S | N | P | DELETED | M |
| T | P | I | S | I | H | Q | S | S | N | P | P | I |
| T | P | I | S | I | H | Q | S | S | N | P | P | M |
| T | P | I | S | I | H | Q | S | T | DELETED | DELETED | DELETED | I |
| T | P | I | S | I | H | Q | S | T | DELETED | DELETED | DELETED | M |
| T | P | I | S | I | H | Q | S | T | DELETED | DELETED | P | I |
| T | P | I | S | I | H | Q | S | T | DELETED | DELETED | P | M |
| T | P | I | S | I | H | Q | S | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | I | H | Q | S | T | DELETED | P | DELETED | M |
| T | P | I | S | I | H | Q | S | T | DELETED | P | P | I |
| T | P | I | S | I | H | Q | S | T | DELETED | P | P | M |
| T | P | I | S | I | H | Q | S | T | N | DELETED | DELETED | I |
| T | P | I | S | I | H | Q | S | T | N | DELETED | DELETED | M |
| T | P | I | S | I | H | Q | S | T | N | DELETED | P | I |
| T | P | I | S | I | H | Q | S | T | N | DELETED | P | M |
| T | P | I | S | I | H | Q | S | T | N | P | DELETED | I |
| T | P | I | S | I | H | Q | S | T | N | P | DELETED | M |
| T | P | I | S | I | H | Q | S | T | N | P | P | I |
| T | P | I | S | I | H | Q | S | T | N | P | P | M |
| T | P | I | S | I | H | Q | G | S | DELETED | DELETED | DELETED | I |
| T | P | I | S | I | H | Q | G | S | DELETED | DELETED | DELETED | M |
| T | P | I | S | I | H | Q | G | S | DELETED | DELETED | P | I |
| T | P | I | S | I | H | Q | G | S | DELETED | DELETED | P | M |
| T | P | I | S | I | H | Q | G | S | DELETED | P | DELETED | I |
| T | P | I | S | I | H | Q | G | S | DELETED | P | DELETED | M |
| T | P | I | S | I | H | Q | G | S | DELETED | P | P | I |
| T | P | I | S | I | H | Q | G | S | DELETED | P | P | M |
| T | P | I | S | I | H | Q | G | S | N | DELETED | DELETED | I |
| T | P | I | S | I | H | Q | G | S | N | DELETED | DELETED | M |
| T | P | I | S | I | H | Q | G | S | N | DELETED | P | I |
| T | P | I | S | I | H | Q | G | S | N | DELETED | P | M |
| T | P | I | S | I | H | Q | G | S | N | P | DELETED | I |
| T | P | I | S | I | H | Q | G | S | N | P | DELETED | M |
| T | P | I | S | I | H | Q | G | S | N | P | P | I |
| T | P | I | S | I | H | Q | G | S | N | P | P | M |
| T | P | I | S | I | H | Q | G | T | DELETED | DELETED | DELETED | I |
| T | P | I | S | I | H | Q | G | T | DELETED | DELETED | DELETED | M |
| T | P | I | S | I | H | Q | G | T | DELETED | DELETED | P | I |
| T | P | I | S | I | H | Q | G | T | DELETED | DELETED | P | M |
| T | P | I | S | I | H | Q | G | T | DELETED | P | DELETED | I |
| T | P | I | S | I | H | Q | G | T | DELETED | P | DELETED | M |
| T | P | I | S | I | H | Q | G | T | DELETED | P | P | I |
| T | P | I | S | I | H | Q | G | T | DELETED | P | P | M |
| T | P | I | S | I | H | Q | G | T | N | DELETED | DELETED | I |
| T | P | I | S | I | H | Q | G | T | N | DELETED | DELETED | M |
| T | P | I | S | I | H | Q | G | T | N | DELETED | P | I |
| T | P | I | S | I | H | Q | G | T | N | DELETED | P | M |
| T | P | I | S | I | H | Q | G | T | N | P | DELETED | I |
| T | P | I | S | I | H | Q | G | T | N | P | DELETED | M |
| T | P | I | S | I | H | Q | G | T | N | P | P | I |
| T | P | I | S | I | H | Q | G | T | N | P | P | M |
| T | P | I | S | I | H | V | S | S | DELETED | DELETED | DELETED | I |
| T | P | I | S | I | H | V | S | S | DELETED | DELETED | DELETED | M |
| T | P | I | S | I | H | V | S | S | DELETED | DELETED | P | I |
| T | P | I | S | I | H | V | S | S | DELETED | DELETED | P | M |
| T | P | I | S | I | H | V | S | S | DELETED | P | DELETED | I |
| T | P | I | S | I | H | V | S | S | DELETED | P | DELETED | M |
| T | P | I | S | I | H | V | S | S | DELETED | P | P | I |
| T | P | I | S | I | H | V | S | S | DELETED | P | P | M |
| T | P | I | S | I | H | V | S | S | N | DELETED | DELETED | I |
| T | P | I | S | I | H | V | S | S | N | DELETED | DELETED | M |
| T | P | I | S | I | H | V | S | S | N | DELETED | P | I |
| T | P | I | S | I | H | V | S | S | N | DELETED | P | M |
| T | P | I | S | I | H | V | S | S | N | P | DELETED | I |
| T | P | I | S | I | H | V | S | S | N | P | DELETED | M |
| T | P | I | S | I | H | V | S | S | N | P | P | I |
| T | P | I | S | I | H | V | S | S | N | P | P | M |
| T | P | I | S | I | H | V | S | T | DELETED | DELETED | DELETED | I |
| T | P | I | S | I | H | V | S | T | DELETED | DELETED | DELETED | M |
| T | P | I | S | I | H | V | S | T | DELETED | DELETED | P | I |
| T | P | I | S | I | H | V | S | T | DELETED | DELETED | P | M |
| T | P | I | S | I | H | V | S | T | DELETED | P | DELETED | I |
| T | P | I | S | I | H | V | S | T | DELETED | P | DELETED | M |
| T | P | I | S | I | H | V | S | T | DELETED | P | P | I |
| T | P | I | S | I | H | V | S | T | DELETED | P | P | M |
| T | P | I | S | I | H | V | S | T | N | DELETED | DELETED | I |
| T | P | I | S | I | H | V | S | T | N | DELETED | DELETED | M |
| T | P | I | S | I | H | V | S | T | N | DELETED | P | I |
| T | P | I | S | I | H | V | S | T | N | DELETED | P | M |
| T | P | I | S | I | H | V | S | T | N | P | DELETED | I |
| T | P | I | S | I | H | V | S | T | N | P | DELETED | M |
| T | P | I | S | I | H | V | S | T | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | S | I | H | V | S | T | N | P | P | M |
| T | P | I | S | I | H | V | G | S | DELETED | DELETED | DELETED | I |
| T | P | I | S | I | H | V | G | S | DELETED | DELETED | DELETED | M |
| T | P | I | S | I | H | V | G | S | DELETED | DELETED | P | I |
| T | P | I | S | I | H | V | G | S | DELETED | DELETED | P | M |
| T | P | I | S | I | H | V | G | S | DELETED | P | DELETED | I |
| T | P | I | S | I | H | V | G | S | DELETED | P | DELETED | M |
| T | P | I | S | I | H | V | G | S | DELETED | P | P | I |
| T | P | I | S | I | H | V | G | S | DELETED | P | P | M |
| T | P | I | S | I | H | V | G | S | N | DELETED | DELETED | I |
| T | P | I | S | I | H | V | G | S | N | DELETED | DELETED | M |
| T | P | I | S | I | H | V | G | S | N | DELETED | P | I |
| T | P | I | S | I | H | V | G | S | N | DELETED | P | M |
| T | P | I | S | I | H | V | G | S | N | P | DELETED | I |
| T | P | I | S | I | H | V | G | S | N | P | DELETED | M |
| T | P | I | S | I | H | V | G | S | N | P | P | I |
| T | P | I | S | I | H | V | G | S | N | P | P | M |
| T | P | I | S | I | H | V | G | T | DELETED | DELETED | DELETED | I |
| T | P | I | S | I | H | V | G | T | DELETED | DELETED | DELETED | M |
| T | P | I | S | I | H | V | G | T | DELETED | DELETED | P | I |
| T | P | I | S | I | H | V | G | T | DELETED | DELETED | P | M |
| T | P | I | S | I | H | V | G | T | DELETED | P | DELETED | I |
| T | P | I | S | I | H | V | G | T | DELETED | P | DELETED | M |
| T | P | I | S | I | H | V | G | T | DELETED | P | P | I |
| T | P | I | S | I | H | V | G | T | DELETED | P | P | M |
| T | P | I | S | I | H | V | G | T | N | DELETED | DELETED | I |
| T | P | I | S | I | H | V | G | T | N | DELETED | DELETED | M |
| T | P | I | S | I | H | V | G | T | N | DELETED | P | I |
| T | P | I | S | I | H | V | G | T | N | DELETED | P | M |
| T | P | I | S | I | H | V | G | T | N | P | DELETED | I |
| T | P | I | S | I | H | V | G | T | N | P | DELETED | M |
| T | P | I | S | I | H | V | G | T | N | P | P | I |
| T | P | I | S | I | H | V | G | T | N | P | P | M |
| T | P | I | R | L | Y | Q | S | S | DELETED | DELETED | DELETED | I |
| T | P | I | R | L | Y | Q | S | S | DELETED | DELETED | DELETED | M |
| T | P | I | R | L | Y | Q | S | S | DELETED | DELETED | P | I |
| T | P | I | R | L | Y | Q | S | S | DELETED | DELETED | P | M |
| T | P | I | R | L | Y | Q | S | S | DELETED | P | DELETED | I |
| T | P | I | R | L | Y | Q | S | S | DELETED | P | DELETED | M |
| T | P | I | R | L | Y | Q | S | S | DELETED | P | P | I |
| T | P | I | R | L | Y | Q | S | S | DELETED | P | P | M |
| T | P | I | R | L | Y | Q | S | S | N | DELETED | DELETED | I |
| T | P | I | R | L | Y | Q | S | S | N | DELETED | DELETED | M |
| T | P | I | R | L | Y | Q | S | S | N | DELETED | P | I |
| T | P | I | R | L | Y | Q | S | S | N | DELETED | P | M |
| T | P | I | R | L | Y | Q | S | S | N | P | DELETED | I |
| T | P | I | R | L | Y | Q | S | S | N | P | DELETED | M |
| T | P | I | R | L | Y | Q | S | S | N | P | P | I |
| T | P | I | R | L | Y | Q | S | S | N | P | P | M |
| T | P | I | R | L | Y | Q | S | T | DELETED | DELETED | DELETED | I |
| T | P | I | R | L | Y | Q | S | T | DELETED | DELETED | DELETED | M |
| T | P | I | R | L | Y | Q | S | T | DELETED | DELETED | P | I |
| T | P | I | R | L | Y | Q | S | T | DELETED | DELETED | P | M |
| T | P | I | R | L | Y | Q | S | T | DELETED | P | DELETED | I |
| T | P | I | R | L | Y | Q | S | T | DELETED | P | DELETED | M |
| T | P | I | R | L | Y | Q | S | T | DELETED | P | P | I |
| T | P | I | R | L | Y | Q | S | T | DELETED | P | P | M |
| T | P | I | R | L | Y | Q | S | T | N | DELETED | DELETED | I |
| T | P | I | R | L | Y | Q | S | T | N | DELETED | DELETED | M |
| T | P | I | R | L | Y | Q | S | T | N | DELETED | P | I |
| T | P | I | R | L | Y | Q | S | T | N | DELETED | P | M |
| T | P | I | R | L | Y | Q | S | T | N | P | DELETED | I |
| T | P | I | R | L | Y | Q | S | T | N | P | DELETED | M |
| T | P | I | R | L | Y | Q | S | T | N | P | P | I |
| T | P | I | R | L | Y | Q | S | T | N | P | P | M |
| T | P | I | R | L | Y | Q | G | S | DELETED | DELETED | DELETED | I |
| T | P | I | R | L | Y | Q | G | S | DELETED | DELETED | DELETED | M |
| T | P | I | R | L | Y | Q | G | S | DELETED | DELETED | P | I |
| T | P | I | R | L | Y | Q | G | S | DELETED | DELETED | P | M |
| T | P | I | R | L | Y | Q | G | S | DELETED | P | DELETED | I |
| T | P | I | R | L | Y | Q | G | S | DELETED | P | DELETED | M |
| T | P | I | R | L | Y | Q | G | S | DELETED | P | P | I |
| T | P | I | R | L | Y | Q | G | S | DELETED | P | P | M |
| T | P | I | R | L | Y | Q | G | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | L | Y | Q | G | S | N | DELETED | DELETED | M |
| T | P | I | R | L | Y | Q | G | S | N | DELETED | P | I |
| T | P | I | R | L | Y | Q | G | S | N | DELETED | P | M |
| T | P | I | R | L | Y | Q | G | S | N | P | DELETED | I |
| T | P | I | R | L | Y | Q | G | S | N | P | DELETED | M |
| T | P | I | R | L | Y | Q | G | S | N | P | P | I |
| T | P | I | R | L | Y | Q | G | S | N | P | P | M |
| T | P | I | R | L | Y | Q | G | T | DELETED | DELETED | DELETED | I |
| T | P | I | R | L | Y | Q | G | T | DELETED | DELETED | DELETED | M |
| T | P | I | R | L | Y | Q | G | T | DELETED | DELETED | P | I |
| T | P | I | R | L | Y | Q | G | T | DELETED | DELETED | P | M |
| T | P | I | R | L | Y | Q | G | T | DELETED | P | DELETED | I |
| T | P | I | R | L | Y | Q | G | T | DELETED | P | DELETED | M |
| T | P | I | R | L | Y | Q | G | T | DELETED | P | P | I |
| T | P | I | R | L | Y | Q | G | T | DELETED | P | P | M |
| T | P | I | R | L | Y | Q | G | T | N | DELETED | DELETED | I |
| T | P | I | R | L | Y | Q | G | T | N | DELETED | DELETED | M |
| T | P | I | R | L | Y | Q | G | T | N | DELETED | P | I |
| T | P | I | R | L | Y | Q | G | T | N | DELETED | P | M |
| T | P | I | R | L | Y | Q | G | T | N | P | DELETED | I |
| T | P | I | R | L | Y | Q | G | T | N | P | DELETED | M |
| T | P | I | R | L | Y | Q | G | T | N | P | P | I |
| T | P | I | R | L | Y | Q | G | T | N | P | P | M |
| T | P | I | R | L | Y | V | S | S | DELETED | DELETED | DELETED | I |
| T | P | I | R | L | Y | V | S | S | DELETED | DELETED | DELETED | M |
| T | P | I | R | L | Y | V | S | S | DELETED | DELETED | P | I |
| T | P | I | R | L | Y | V | S | S | DELETED | DELETED | P | M |
| T | P | I | R | L | Y | V | S | S | DELETED | P | DELETED | I |
| T | P | I | R | L | Y | V | S | S | DELETED | P | DELETED | M |
| T | P | I | R | L | Y | V | S | S | DELETED | P | P | I |
| T | P | I | R | L | Y | V | S | S | DELETED | P | P | M |
| T | P | I | R | L | Y | V | S | S | N | DELETED | DELETED | I |
| T | P | I | R | L | Y | V | S | S | N | DELETED | DELETED | M |
| T | P | I | R | L | Y | V | S | S | N | DELETED | P | I |
| T | P | I | R | L | Y | V | S | S | N | DELETED | P | M |
| T | P | I | R | L | Y | V | S | S | N | P | DELETED | I |
| T | P | I | R | L | Y | V | S | S | N | P | DELETED | M |
| T | P | I | R | L | Y | V | S | S | N | P | P | I |
| T | P | I | R | L | Y | V | S | S | N | P | P | M |
| T | P | I | R | L | Y | V | S | T | DELETED | DELETED | DELETED | I |
| T | P | I | R | L | Y | V | S | T | DELETED | DELETED | DELETED | M |
| T | P | I | R | L | Y | V | S | T | DELETED | DELETED | P | I |
| T | P | I | R | L | Y | V | S | T | DELETED | DELETED | P | M |
| T | P | I | R | L | Y | V | S | T | DELETED | P | DELETED | I |
| T | P | I | R | L | Y | V | S | T | DELETED | P | DELETED | M |
| T | P | I | R | L | Y | V | S | T | DELETED | P | P | I |
| T | P | I | R | L | Y | V | S | T | DELETED | P | P | M |
| T | P | I | R | L | Y | V | S | T | N | DELETED | DELETED | I |
| T | P | I | R | L | Y | V | S | T | N | DELETED | DELETED | M |
| T | P | I | R | L | Y | V | S | T | N | DELETED | P | I |
| T | P | I | R | L | Y | V | S | T | N | DELETED | P | M |
| T | P | I | R | L | Y | V | S | T | N | P | DELETED | I |
| T | P | I | R | L | Y | V | S | T | N | P | DELETED | M |
| T | P | I | R | L | Y | V | S | T | N | P | P | I |
| T | P | I | R | L | Y | V | S | T | N | P | P | M |
| T | P | I | R | L | Y | V | G | S | DELETED | DELETED | DELETED | I |
| T | P | I | R | L | Y | V | G | S | DELETED | DELETED | DELETED | M |
| T | P | I | R | L | Y | V | G | S | DELETED | DELETED | P | I |
| T | P | I | R | L | Y | V | G | S | DELETED | DELETED | P | M |
| T | P | I | R | L | Y | V | G | S | DELETED | P | DELETED | I |
| T | P | I | R | L | Y | V | G | S | DELETED | P | DELETED | M |
| T | P | I | R | L | Y | V | G | S | DELETED | P | P | I |
| T | P | I | R | L | Y | V | G | S | DELETED | P | P | M |
| T | P | I | R | L | Y | V | G | S | N | DELETED | DELETED | I |
| T | P | I | R | L | Y | V | G | S | N | DELETED | DELETED | M |
| T | P | I | R | L | Y | V | G | S | N | DELETED | P | I |
| T | P | I | R | L | Y | V | G | S | N | DELETED | P | M |
| T | P | I | R | L | Y | V | G | S | N | P | DELETED | I |
| T | P | I | R | L | Y | V | G | S | N | P | DELETED | M |
| T | P | I | R | L | Y | V | G | S | N | P | P | I |
| T | P | I | R | L | Y | V | G | S | N | P | P | M |
| T | P | I | R | L | Y | V | G | T | DELETED | DELETED | DELETED | I |
| T | P | I | R | L | Y | V | G | T | DELETED | DELETED | DELETED | M |
| T | P | I | R | L | Y | V | G | T | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | L | Y | V | G | T | DELETED | DELETED | P | M |
| T | P | I | R | L | Y | V | G | T | DELETED | P | DELETED | I |
| T | P | I | R | L | Y | V | G | T | DELETED | P | DELETED | M |
| T | P | I | R | L | Y | V | G | T | DELETED | P | P | I |
| T | P | I | R | L | Y | V | G | T | DELETED | P | P | M |
| T | P | I | R | L | Y | V | G | T | N | DELETED | DELETED | I |
| T | P | I | R | L | Y | V | G | T | N | DELETED | DELETED | M |
| T | P | I | R | L | Y | V | G | T | N | DELETED | P | I |
| T | P | I | R | L | Y | V | G | T | N | DELETED | P | M |
| T | P | I | R | L | Y | V | G | T | N | P | DELETED | I |
| T | P | I | R | L | Y | V | G | T | N | P | DELETED | M |
| T | P | I | R | L | Y | V | G | T | N | P | P | I |
| T | P | I | R | L | Y | V | G | T | N | P | P | M |
| T | P | I | R | L | H | Q | S | S | DELETED | DELETED | DELETED | I |
| T | P | I | R | L | H | Q | S | S | DELETED | DELETED | DELETED | M |
| T | P | I | R | L | H | Q | S | S | DELETED | DELETED | P | I |
| T | P | I | R | L | H | Q | S | S | DELETED | DELETED | P | M |
| T | P | I | R | L | H | Q | S | S | DELETED | P | DELETED | I |
| T | P | I | R | L | H | Q | S | S | DELETED | P | DELETED | M |
| T | P | I | R | L | H | Q | S | S | DELETED | P | P | I |
| T | P | I | R | L | H | Q | S | S | DELETED | P | P | M |
| T | P | I | R | L | H | Q | S | S | N | DELETED | DELETED | I |
| T | P | I | R | L | H | Q | S | S | N | DELETED | DELETED | M |
| T | P | I | R | L | H | Q | S | S | N | DELETED | P | I |
| T | P | I | R | L | H | Q | S | S | N | DELETED | P | M |
| T | P | I | R | L | H | Q | S | S | N | P | DELETED | I |
| T | P | I | R | L | H | Q | S | S | N | P | DELETED | M |
| T | P | I | R | L | H | Q | S | S | N | P | P | I |
| T | P | I | R | L | H | Q | S | S | N | P | P | M |
| T | P | I | R | L | H | Q | S | T | DELETED | DELETED | DELETED | I |
| T | P | I | R | L | H | Q | S | T | DELETED | DELETED | DELETED | M |
| T | P | I | R | L | H | Q | S | T | DELETED | DELETED | P | I |
| T | P | I | R | L | H | Q | S | T | DELETED | DELETED | P | M |
| T | P | I | R | L | H | Q | S | T | DELETED | P | DELETED | I |
| T | P | I | R | L | H | Q | S | T | DELETED | P | DELETED | M |
| T | P | I | R | L | H | Q | S | T | DELETED | P | P | I |
| T | P | I | R | L | H | Q | S | T | DELETED | P | P | M |
| T | P | I | R | L | H | Q | S | T | N | DELETED | DELETED | I |
| T | P | I | R | L | H | Q | S | T | N | DELETED | DELETED | M |
| T | P | I | R | L | H | Q | S | T | N | DELETED | P | I |
| T | P | I | R | L | H | Q | S | T | N | DELETED | P | M |
| T | P | I | R | L | H | Q | S | T | N | P | DELETED | I |
| T | P | I | R | L | H | Q | S | T | N | P | DELETED | M |
| T | P | I | R | L | H | Q | S | T | N | P | P | I |
| T | P | I | R | L | H | Q | S | T | N | P | P | M |
| T | P | I | R | L | H | Q | G | S | DELETED | DELETED | DELETED | I |
| T | P | I | R | L | H | Q | G | S | DELETED | DELETED | DELETED | M |
| T | P | I | R | L | H | Q | G | S | DELETED | DELETED | P | I |
| T | P | I | R | L | H | Q | G | S | DELETED | DELETED | P | M |
| T | P | I | R | L | H | Q | G | S | DELETED | P | DELETED | I |
| T | P | I | R | L | H | Q | G | S | DELETED | P | DELETED | M |
| T | P | I | R | L | H | Q | G | S | DELETED | P | P | I |
| T | P | I | R | L | H | Q | G | S | DELETED | P | P | M |
| T | P | I | R | L | H | Q | G | S | N | DELETED | DELETED | I |
| T | P | I | R | L | H | Q | G | S | N | DELETED | DELETED | M |
| T | P | I | R | L | H | Q | G | S | N | DELETED | P | I |
| T | P | I | R | L | H | Q | G | S | N | DELETED | P | M |
| T | P | I | R | L | H | Q | G | S | N | P | DELETED | I |
| T | P | I | R | L | H | Q | G | S | N | P | DELETED | M |
| T | P | I | R | L | H | Q | G | S | N | P | P | I |
| T | P | I | R | L | H | Q | G | S | N | P | P | M |
| T | P | I | R | L | H | Q | G | T | DELETED | DELETED | DELETED | I |
| T | P | I | R | L | H | Q | G | T | DELETED | DELETED | DELETED | M |
| T | P | I | R | L | H | Q | G | T | DELETED | DELETED | P | I |
| T | P | I | R | L | H | Q | G | T | DELETED | DELETED | P | M |
| T | P | I | R | L | H | Q | G | T | DELETED | P | DELETED | I |
| T | P | I | R | L | H | Q | G | T | DELETED | P | DELETED | M |
| T | P | I | R | L | H | Q | G | T | DELETED | P | P | I |
| T | P | I | R | L | H | Q | G | T | DELETED | P | P | M |
| T | P | I | R | L | H | Q | G | T | N | DELETED | DELETED | I |
| T | P | I | R | L | H | Q | G | T | N | DELETED | DELETED | M |
| T | P | I | R | L | H | Q | G | T | N | DELETED | P | I |
| T | P | I | R | L | H | Q | G | T | N | DELETED | P | M |
| T | P | I | R | L | H | Q | G | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | L | H | Q | G | T | N | P | DELETED | M |
| T | P | I | R | L | H | Q | G | T | N | P | P | I |
| T | P | I | R | L | H | Q | G | T | N | P | P | M |
| T | P | I | R | L | H | V | S | S | DELETED | DELETED | DELETED | I |
| T | P | I | R | L | H | V | S | S | DELETED | DELETED | DELETED | M |
| T | P | I | R | L | H | V | S | S | DELETED | DELETED | P | I |
| T | P | I | R | L | H | V | S | S | DELETED | DELETED | P | M |
| T | P | I | R | L | H | V | S | S | DELETED | P | DELETED | I |
| T | P | I | R | L | H | V | S | S | DELETED | P | DELETED | M |
| T | P | I | R | L | H | V | S | S | DELETED | P | P | I |
| T | P | I | R | L | H | V | S | S | DELETED | P | P | M |
| T | P | I | R | L | H | V | S | S | N | DELETED | DELETED | I |
| T | P | I | R | L | H | V | S | S | N | DELETED | DELETED | M |
| T | P | I | R | L | H | V | S | S | N | DELETED | P | I |
| T | P | I | R | L | H | V | S | S | N | DELETED | P | M |
| T | P | I | R | L | H | V | S | S | N | P | DELETED | I |
| T | P | I | R | L | H | V | S | S | N | P | DELETED | M |
| T | P | I | R | L | H | V | S | S | N | P | P | I |
| T | P | I | R | L | H | V | S | S | N | P | P | M |
| T | P | I | R | L | H | V | S | T | DELETED | DELETED | DELETED | I |
| T | P | I | R | L | H | V | S | T | DELETED | DELETED | DELETED | M |
| T | P | I | R | L | H | V | S | T | DELETED | DELETED | P | I |
| T | P | I | R | L | H | V | S | T | DELETED | DELETED | P | M |
| T | P | I | R | L | H | V | S | T | DELETED | P | DELETED | I |
| T | P | I | R | L | H | V | S | T | DELETED | P | DELETED | M |
| T | P | I | R | L | H | V | S | T | DELETED | P | P | I |
| T | P | I | R | L | H | V | S | T | DELETED | P | P | M |
| T | P | I | R | L | H | V | S | T | N | DELETED | DELETED | I |
| T | P | I | R | L | H | V | S | T | N | DELETED | DELETED | M |
| T | P | I | R | L | H | V | S | T | N | DELETED | P | I |
| T | P | I | R | L | H | V | S | T | N | DELETED | P | M |
| T | P | I | R | L | H | V | S | T | N | P | DELETED | I |
| T | P | I | R | L | H | V | S | T | N | P | DELETED | M |
| T | P | I | R | L | H | V | S | T | N | P | P | I |
| T | P | I | R | L | H | V | S | T | N | P | P | M |
| T | P | I | R | L | H | V | G | S | DELETED | DELETED | DELETED | I |
| T | P | I | R | L | H | V | G | S | DELETED | DELETED | DELETED | M |
| T | P | I | R | L | H | V | G | S | DELETED | DELETED | P | I |
| T | P | I | R | L | H | V | G | S | DELETED | DELETED | P | M |
| T | P | I | R | L | H | V | G | S | DELETED | P | DELETED | I |
| T | P | I | R | L | H | V | G | S | DELETED | P | DELETED | M |
| T | P | I | R | L | H | V | G | S | DELETED | P | P | I |
| T | P | I | R | L | H | V | G | S | DELETED | P | P | M |
| T | P | I | R | L | H | V | G | S | N | DELETED | DELETED | I |
| T | P | I | R | L | H | V | G | S | N | DELETED | DELETED | M |
| T | P | I | R | L | H | V | G | S | N | DELETED | P | I |
| T | P | I | R | L | H | V | G | S | N | DELETED | P | M |
| T | P | I | R | L | H | V | G | S | N | P | DELETED | I |
| T | P | I | R | L | H | V | G | S | N | P | DELETED | M |
| T | P | I | R | L | H | V | G | S | N | P | P | I |
| T | P | I | R | L | H | V | G | S | N | P | P | M |
| T | P | I | R | L | H | V | G | T | DELETED | DELETED | DELETED | I |
| T | P | I | R | L | H | V | G | T | DELETED | DELETED | DELETED | M |
| T | P | I | R | L | H | V | G | T | DELETED | DELETED | P | I |
| T | P | I | R | L | H | V | G | T | DELETED | DELETED | P | M |
| T | P | I | R | L | H | V | G | T | DELETED | P | DELETED | I |
| T | P | I | R | L | H | V | G | T | DELETED | P | DELETED | M |
| T | P | I | R | L | H | V | G | T | DELETED | P | P | I |
| T | P | I | R | L | H | V | G | T | DELETED | P | P | M |
| T | P | I | R | L | H | V | G | T | N | DELETED | DELETED | I |
| T | P | I | R | L | H | V | G | T | N | DELETED | DELETED | M |
| T | P | I | R | L | H | V | G | T | N | DELETED | P | I |
| T | P | I | R | L | H | V | G | T | N | DELETED | P | M |
| T | P | I | R | L | H | V | G | T | N | P | DELETED | I |
| T | P | I | R | L | H | V | G | T | N | P | DELETED | M |
| T | P | I | R | L | H | V | G | T | N | P | P | I |
| T | P | I | R | L | H | V | G | T | N | P | P | M |
| T | P | I | R | I | Y | Q | S | S | DELETED | DELETED | DELETED | I |
| T | P | I | R | I | Y | Q | S | S | DELETED | DELETED | DELETED | M |
| T | P | I | R | I | Y | Q | S | S | DELETED | DELETED | P | I |
| T | P | I | R | I | Y | Q | S | S | DELETED | DELETED | P | M |
| T | P | I | R | I | Y | Q | S | S | DELETED | P | DELETED | I |
| T | P | I | R | I | Y | Q | S | S | DELETED | P | DELETED | M |
| T | P | I | R | I | Y | Q | S | S | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | I | Y | Q | S | S | DELETED | P | P | M |
| T | P | I | R | I | Y | Q | S | S | N | DELETED | DELETED | I |
| T | P | I | R | I | Y | Q | S | S | N | DELETED | DELETED | M |
| T | P | I | R | I | Y | Q | S | S | N | DELETED | P | I |
| T | P | I | R | I | Y | Q | S | S | N | DELETED | P | M |
| T | P | I | R | I | Y | Q | S | S | N | P | DELETED | I |
| T | P | I | R | I | Y | Q | S | S | N | P | DELETED | M |
| T | P | I | R | I | Y | Q | S | S | N | P | P | I |
| T | P | I | R | I | Y | Q | S | S | N | P | P | M |
| T | P | I | R | I | Y | Q | S | T | DELETED | DELETED | DELETED | I |
| T | P | I | R | I | Y | Q | S | T | DELETED | DELETED | DELETED | M |
| T | P | I | R | I | Y | Q | S | T | DELETED | DELETED | P | I |
| T | P | I | R | I | Y | Q | S | T | DELETED | DELETED | P | M |
| T | P | I | R | I | Y | Q | S | T | DELETED | P | DELETED | I |
| T | P | I | R | I | Y | Q | S | T | DELETED | P | DELETED | M |
| T | P | I | R | I | Y | Q | S | T | DELETED | P | P | I |
| T | P | I | R | I | Y | Q | S | T | DELETED | P | P | M |
| T | P | I | R | I | Y | Q | S | T | N | DELETED | DELETED | I |
| T | P | I | R | I | Y | Q | S | T | N | DELETED | DELETED | M |
| T | P | I | R | I | Y | Q | S | T | N | DELETED | P | I |
| T | P | I | R | I | Y | Q | S | T | N | DELETED | P | M |
| T | P | I | R | I | Y | Q | S | T | N | P | DELETED | I |
| T | P | I | R | I | Y | Q | S | T | N | P | DELETED | M |
| T | P | I | R | I | Y | Q | S | T | N | P | P | I |
| T | P | I | R | I | Y | Q | S | T | N | P | P | M |
| T | P | I | R | I | Y | Q | G | S | DELETED | DELETED | DELETED | I |
| T | P | I | R | I | Y | Q | G | S | DELETED | DELETED | DELETED | M |
| T | P | I | R | I | Y | Q | G | S | DELETED | DELETED | P | I |
| T | P | I | R | I | Y | Q | G | S | DELETED | DELETED | P | M |
| T | P | I | R | I | Y | Q | G | S | DELETED | P | DELETED | I |
| T | P | I | R | I | Y | Q | G | S | DELETED | P | DELETED | M |
| T | P | I | R | I | Y | Q | G | S | DELETED | P | P | I |
| T | P | I | R | I | Y | Q | G | S | DELETED | P | P | M |
| T | P | I | R | I | Y | Q | G | S | N | DELETED | DELETED | I |
| T | P | I | R | I | Y | Q | G | S | N | DELETED | DELETED | M |
| T | P | I | R | I | Y | Q | G | S | N | DELETED | P | I |
| T | P | I | R | I | Y | Q | G | S | N | DELETED | P | M |
| T | P | I | R | I | Y | Q | G | S | N | P | DELETED | I |
| T | P | I | R | I | Y | Q | G | S | N | P | DELETED | M |
| T | P | I | R | I | Y | Q | G | S | N | P | P | I |
| T | P | I | R | I | Y | Q | G | S | N | P | P | M |
| T | P | I | R | I | Y | Q | G | T | DELETED | DELETED | DELETED | I |
| T | P | I | R | I | Y | Q | G | T | DELETED | DELETED | DELETED | M |
| T | P | I | R | I | Y | Q | G | T | DELETED | DELETED | P | I |
| T | P | I | R | I | Y | Q | G | T | DELETED | DELETED | P | M |
| T | P | I | R | I | Y | Q | G | T | DELETED | P | DELETED | I |
| T | P | I | R | I | Y | Q | G | T | DELETED | P | DELETED | M |
| T | P | I | R | I | Y | Q | G | T | DELETED | P | P | I |
| T | P | I | R | I | Y | Q | G | T | DELETED | P | P | M |
| T | P | I | R | I | Y | Q | G | T | N | DELETED | DELETED | I |
| T | P | I | R | I | Y | Q | G | T | N | DELETED | DELETED | M |
| T | P | I | R | I | Y | Q | G | T | N | DELETED | P | I |
| T | P | I | R | I | Y | Q | G | T | N | DELETED | P | M |
| T | P | I | R | I | Y | Q | G | T | N | P | DELETED | I |
| T | P | I | R | I | Y | Q | G | T | N | P | DELETED | M |
| T | P | I | R | I | Y | Q | G | T | N | P | P | I |
| T | P | I | R | I | Y | Q | G | T | N | P | P | M |
| T | P | I | R | I | Y | V | S | S | DELETED | DELETED | DELETED | I |
| T | P | I | R | I | Y | V | S | S | DELETED | DELETED | DELETED | M |
| T | P | I | R | I | Y | V | S | S | DELETED | DELETED | P | I |
| T | P | I | R | I | Y | V | S | S | DELETED | DELETED | P | M |
| T | P | I | R | I | Y | V | S | S | DELETED | P | DELETED | I |
| T | P | I | R | I | Y | V | S | S | DELETED | P | DELETED | M |
| T | P | I | R | I | Y | V | S | S | DELETED | P | P | I |
| T | P | I | R | I | Y | V | S | S | DELETED | P | P | M |
| T | P | I | R | I | Y | V | S | S | N | DELETED | DELETED | I |
| T | P | I | R | I | Y | V | S | S | N | DELETED | DELETED | M |
| T | P | I | R | I | Y | V | S | S | N | DELETED | P | I |
| T | P | I | R | I | Y | V | S | S | N | DELETED | P | M |
| T | P | I | R | I | Y | V | S | S | N | P | DELETED | I |
| T | P | I | R | I | Y | V | S | S | N | P | DELETED | M |
| T | P | I | R | I | Y | V | S | S | N | P | P | I |
| T | P | I | R | I | Y | V | S | S | N | P | P | M |
| T | P | I | R | I | Y | V | S | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | I | Y | V | S | T | DELETED | DELETED | DELETED | M |
| T | P | I | R | I | Y | V | S | T | DELETED | DELETED | P | I |
| T | P | I | R | I | Y | V | S | T | DELETED | DELETED | P | M |
| T | P | I | R | I | Y | V | S | T | DELETED | P | DELETED | I |
| T | P | I | R | I | Y | V | S | T | DELETED | P | DELETED | M |
| T | P | I | R | I | Y | V | S | T | DELETED | P | P | I |
| T | P | I | R | I | Y | V | S | T | DELETED | P | P | M |
| T | P | I | R | I | Y | V | S | T | N | DELETED | DELETED | I |
| T | P | I | R | I | Y | V | S | T | N | DELETED | DELETED | M |
| T | P | I | R | I | Y | V | S | T | N | DELETED | P | I |
| T | P | I | R | I | Y | V | S | T | N | DELETED | P | M |
| T | P | I | R | I | Y | V | S | T | N | P | DELETED | I |
| T | P | I | R | I | Y | V | S | T | N | P | DELETED | M |
| T | P | I | R | I | Y | V | S | T | N | P | P | I |
| T | P | I | R | I | Y | V | S | T | N | P | P | M |
| T | P | I | R | I | Y | V | G | S | DELETED | DELETED | DELETED | I |
| T | P | I | R | I | Y | V | G | S | DELETED | DELETED | DELETED | M |
| T | P | I | R | I | Y | V | G | S | DELETED | DELETED | P | I |
| T | P | I | R | I | Y | V | G | S | DELETED | DELETED | P | M |
| T | P | I | R | I | Y | V | G | S | DELETED | P | DELETED | I |
| T | P | I | R | I | Y | V | G | S | DELETED | P | DELETED | M |
| T | P | I | R | I | Y | V | G | S | DELETED | P | P | I |
| T | P | I | R | I | Y | V | G | S | DELETED | P | P | M |
| T | P | I | R | I | Y | V | G | S | N | DELETED | DELETED | I |
| T | P | I | R | I | Y | V | G | S | N | DELETED | DELETED | M |
| T | P | I | R | I | Y | V | G | S | N | DELETED | P | I |
| T | P | I | R | I | Y | V | G | S | N | DELETED | P | M |
| T | P | I | R | I | Y | V | G | S | N | P | DELETED | I |
| T | P | I | R | I | Y | V | G | S | N | P | DELETED | M |
| T | P | I | R | I | Y | V | G | S | N | P | P | I |
| T | P | I | R | I | Y | V | G | S | N | P | P | M |
| T | P | I | R | I | Y | V | G | T | DELETED | DELETED | DELETED | I |
| T | P | I | R | I | Y | V | G | T | DELETED | DELETED | DELETED | M |
| T | P | I | R | I | Y | V | G | T | DELETED | DELETED | P | I |
| T | P | I | R | I | Y | V | G | T | DELETED | DELETED | P | M |
| T | P | I | R | I | Y | V | G | T | DELETED | P | DELETED | I |
| T | P | I | R | I | Y | V | G | T | DELETED | P | DELETED | M |
| T | P | I | R | I | Y | V | G | T | DELETED | P | P | I |
| T | P | I | R | I | Y | V | G | T | DELETED | P | P | M |
| T | P | I | R | I | Y | V | G | T | N | DELETED | DELETED | I |
| T | P | I | R | I | Y | V | G | T | N | DELETED | DELETED | M |
| T | P | I | R | I | Y | V | G | T | N | DELETED | P | I |
| T | P | I | R | I | Y | V | G | T | N | DELETED | P | M |
| T | P | I | R | I | Y | V | G | T | N | P | DELETED | I |
| T | P | I | R | I | Y | V | G | T | N | P | DELETED | M |
| T | P | I | R | I | Y | V | G | T | N | P | P | I |
| T | P | I | R | I | Y | V | G | T | N | P | P | M |
| T | P | I | R | I | H | Q | S | S | DELETED | DELETED | DELETED | I |
| T | P | I | R | I | H | Q | S | S | DELETED | DELETED | DELETED | M |
| T | P | I | R | I | H | Q | S | S | DELETED | DELETED | P | I |
| T | P | I | R | I | H | Q | S | S | DELETED | DELETED | P | M |
| T | P | I | R | I | H | Q | S | S | DELETED | P | DELETED | I |
| T | P | I | R | I | H | Q | S | S | DELETED | P | DELETED | M |
| T | P | I | R | I | H | Q | S | S | DELETED | P | P | I |
| T | P | I | R | I | H | Q | S | S | DELETED | P | P | M |
| T | P | I | R | I | H | Q | S | S | N | DELETED | DELETED | I |
| T | P | I | R | I | H | Q | S | S | N | DELETED | DELETED | M |
| T | P | I | R | I | H | Q | S | S | N | DELETED | P | I |
| T | P | I | R | I | H | Q | S | S | N | DELETED | P | M |
| T | P | I | R | I | H | Q | S | S | N | P | DELETED | I |
| T | P | I | R | I | H | Q | S | S | N | P | DELETED | M |
| T | P | I | R | I | H | Q | S | S | N | P | P | I |
| T | P | I | R | I | H | Q | S | S | N | P | P | M |
| T | P | I | R | I | H | Q | S | T | DELETED | DELETED | DELETED | I |
| T | P | I | R | I | H | Q | S | T | DELETED | DELETED | DELETED | M |
| T | P | I | R | I | H | Q | S | T | DELETED | DELETED | P | I |
| T | P | I | R | I | H | Q | S | T | DELETED | DELETED | P | M |
| T | P | I | R | I | H | Q | S | T | DELETED | P | DELETED | I |
| T | P | I | R | I | H | Q | S | T | DELETED | P | DELETED | M |
| T | P | I | R | I | H | Q | S | T | DELETED | P | P | I |
| T | P | I | R | I | H | Q | S | T | DELETED | P | P | M |
| T | P | I | R | I | H | Q | S | T | N | DELETED | DELETED | I |
| T | P | I | R | I | H | Q | S | T | N | DELETED | DELETED | M |
| T | P | I | R | I | H | Q | S | T | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | I | H | Q | S | T | N | DELETED | P | M |
| T | P | I | R | I | H | Q | S | T | N | P | DELETED | I |
| T | P | I | R | I | H | Q | S | T | N | P | DELETED | M |
| T | P | I | R | I | H | Q | S | T | N | P | P | I |
| T | P | I | R | I | H | Q | S | T | N | P | P | M |
| T | P | I | R | I | H | Q | G | S | DELETED | DELETED | DELETED | I |
| T | P | I | R | I | H | Q | G | S | DELETED | DELETED | DELETED | M |
| T | P | I | R | I | H | Q | G | S | DELETED | DELETED | P | I |
| T | P | I | R | I | H | Q | G | S | DELETED | DELETED | P | M |
| T | P | I | R | I | H | Q | G | S | DELETED | P | DELETED | I |
| T | P | I | R | I | H | Q | G | S | DELETED | P | DELETED | M |
| T | P | I | R | I | H | Q | G | S | DELETED | P | P | I |
| T | P | I | R | I | H | Q | G | S | DELETED | P | P | M |
| T | P | I | R | I | H | Q | G | S | N | DELETED | DELETED | I |
| T | P | I | R | I | H | Q | G | S | N | DELETED | DELETED | M |
| T | P | I | R | I | H | Q | G | S | N | DELETED | P | I |
| T | P | I | R | I | H | Q | G | S | N | DELETED | P | M |
| T | P | I | R | I | H | Q | G | S | N | P | DELETED | I |
| T | P | I | R | I | H | Q | G | S | N | P | DELETED | M |
| T | P | I | R | I | H | Q | G | S | N | P | P | I |
| T | P | I | R | I | H | Q | G | S | N | P | P | M |
| T | P | I | R | I | H | Q | G | T | DELETED | DELETED | DELETED | I |
| T | P | I | R | I | H | Q | G | T | DELETED | DELETED | DELETED | M |
| T | P | I | R | I | H | Q | G | T | DELETED | DELETED | P | I |
| T | P | I | R | I | H | Q | G | T | DELETED | DELETED | P | M |
| T | P | I | R | I | H | Q | G | T | DELETED | P | DELETED | I |
| T | P | I | R | I | H | Q | G | T | DELETED | P | DELETED | M |
| T | P | I | R | I | H | Q | G | T | DELETED | P | P | I |
| T | P | I | R | I | H | Q | G | T | DELETED | P | P | M |
| T | P | I | R | I | H | Q | G | T | N | DELETED | DELETED | I |
| T | P | I | R | I | H | Q | G | T | N | DELETED | DELETED | M |
| T | P | I | R | I | H | Q | G | T | N | DELETED | P | I |
| T | P | I | R | I | H | Q | G | T | N | DELETED | P | M |
| T | P | I | R | I | H | Q | G | T | N | P | DELETED | I |
| T | P | I | R | I | H | Q | G | T | N | P | DELETED | M |
| T | P | I | R | I | H | Q | G | T | N | P | P | I |
| T | P | I | R | I | H | Q | G | T | N | P | P | M |
| T | P | I | R | I | H | V | S | S | DELETED | DELETED | DELETED | I |
| T | P | I | R | I | H | V | S | S | DELETED | DELETED | DELETED | M |
| T | P | I | R | I | H | V | S | S | DELETED | DELETED | P | I |
| T | P | I | R | I | H | V | S | S | DELETED | DELETED | P | M |
| T | P | I | R | I | H | V | S | S | DELETED | P | DELETED | I |
| T | P | I | R | I | H | V | S | S | DELETED | P | DELETED | M |
| T | P | I | R | I | H | V | S | S | DELETED | P | P | I |
| T | P | I | R | I | H | V | S | S | DELETED | P | P | M |
| T | P | I | R | I | H | V | S | S | N | DELETED | DELETED | I |
| T | P | I | R | I | H | V | S | S | N | DELETED | DELETED | M |
| T | P | I | R | I | H | V | S | S | N | DELETED | P | I |
| T | P | I | R | I | H | V | S | S | N | DELETED | P | M |
| T | P | I | R | I | H | V | S | S | N | P | DELETED | I |
| T | P | I | R | I | H | V | S | S | N | P | DELETED | M |
| T | P | I | R | I | H | V | S | S | N | P | P | I |
| T | P | I | R | I | H | V | S | S | N | P | P | M |
| T | P | I | R | I | H | V | S | T | DELETED | DELETED | DELETED | I |
| T | P | I | R | I | H | V | S | T | DELETED | DELETED | DELETED | M |
| T | P | I | R | I | H | V | S | T | DELETED | DELETED | P | I |
| T | P | I | R | I | H | V | S | T | DELETED | DELETED | P | M |
| T | P | I | R | I | H | V | S | T | DELETED | P | DELETED | I |
| T | P | I | R | I | H | V | S | T | DELETED | P | DELETED | M |
| T | P | I | R | I | H | V | S | T | DELETED | P | P | I |
| T | P | I | R | I | H | V | S | T | DELETED | P | P | M |
| T | P | I | R | I | H | V | S | T | N | DELETED | DELETED | I |
| T | P | I | R | I | H | V | S | T | N | DELETED | DELETED | M |
| T | P | I | R | I | H | V | S | T | N | DELETED | P | I |
| T | P | I | R | I | H | V | S | T | N | DELETED | P | M |
| T | P | I | R | I | H | V | S | T | N | P | DELETED | I |
| T | P | I | R | I | H | V | S | T | N | P | DELETED | M |
| T | P | I | R | I | H | V | S | T | N | P | P | I |
| T | P | I | R | I | H | V | S | T | N | P | P | M |
| T | P | I | R | I | H | V | G | S | DELETED | DELETED | DELETED | I |
| T | P | I | R | I | H | V | G | S | DELETED | DELETED | DELETED | M |
| T | P | I | R | I | H | V | G | S | DELETED | DELETED | P | I |
| T | P | I | R | I | H | V | G | S | DELETED | DELETED | P | M |
| T | P | I | R | I | H | V | G | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | I | R | I | H | V | G | S | DELETED | P | DELETED | M |
| T | P | I | R | I | H | V | G | S | DELETED | P | P | I |
| T | P | I | R | I | H | V | G | S | DELETED | P | P | M |
| T | P | I | R | I | H | V | G | S | N | DELETED | DELETED | I |
| T | P | I | R | I | H | V | G | S | N | DELETED | DELETED | M |
| T | P | I | R | I | H | V | G | S | N | DELETED | P | I |
| T | P | I | R | I | H | V | G | S | N | DELETED | P | M |
| T | P | I | R | I | H | V | G | S | N | P | DELETED | I |
| T | P | I | R | I | H | V | G | S | N | P | DELETED | M |
| T | P | I | R | I | H | V | G | S | N | P | P | I |
| T | P | I | R | I | H | V | G | S | N | P | P | M |
| T | P | I | R | I | H | V | G | T | DELETED | DELETED | DELETED | I |
| T | P | I | R | I | H | V | G | T | DELETED | DELETED | DELETED | M |
| T | P | I | R | I | H | V | G | T | DELETED | DELETED | P | I |
| T | P | I | R | I | H | V | G | T | DELETED | DELETED | P | M |
| T | P | I | R | I | H | V | G | T | DELETED | P | DELETED | I |
| T | P | I | R | I | H | V | G | T | DELETED | P | DELETED | M |
| T | P | I | R | I | H | V | G | T | DELETED | P | P | I |
| T | P | I | R | I | H | V | G | T | DELETED | P | P | M |
| T | P | I | R | I | H | V | G | T | N | DELETED | DELETED | I |
| T | P | I | R | I | H | V | G | T | N | DELETED | DELETED | M |
| T | P | I | R | I | H | V | G | T | N | DELETED | P | I |
| T | P | I | R | I | H | V | G | T | N | DELETED | P | M |
| T | P | I | R | I | H | V | G | T | N | P | DELETED | I |
| T | P | I | R | I | H | V | G | T | N | P | DELETED | M |
| T | P | I | R | I | H | V | G | T | N | P | P | I |
| T | P | I | R | I | H | V | G | T | N | P | P | M |
| T | P | F | S | L | Y | Q | S | S | DELETED | DELETED | DELETED | I |
| T | P | F | S | L | Y | Q | S | S | DELETED | DELETED | DELETED | M |
| T | P | F | S | L | Y | Q | S | S | DELETED | DELETED | P | I |
| T | P | F | S | L | Y | Q | S | S | DELETED | DELETED | P | M |
| T | P | F | S | L | Y | Q | S | S | DELETED | P | DELETED | I |
| T | P | F | S | L | Y | Q | S | S | DELETED | P | DELETED | M |
| T | P | F | S | L | Y | Q | S | S | DELETED | P | P | I |
| T | P | F | S | L | Y | Q | S | S | DELETED | P | P | M |
| T | P | F | S | L | Y | Q | S | S | N | DELETED | DELETED | I |
| T | P | F | S | L | Y | Q | S | S | N | DELETED | DELETED | M |
| T | P | F | S | L | Y | Q | S | S | N | DELETED | P | I |
| T | P | F | S | L | Y | Q | S | S | N | DELETED | P | M |
| T | P | F | S | L | Y | Q | S | S | N | P | DELETED | I |
| T | P | F | S | L | Y | Q | S | S | N | P | DELETED | M |
| T | P | F | S | L | Y | Q | S | S | N | P | P | I |
| T | P | F | S | L | Y | Q | S | S | N | P | P | M |
| T | P | F | S | L | Y | Q | S | T | DELETED | DELETED | DELETED | I |
| T | P | F | S | L | Y | Q | S | T | DELETED | DELETED | DELETED | M |
| T | P | F | S | L | Y | Q | S | T | DELETED | DELETED | P | I |
| T | P | F | S | L | Y | Q | S | T | DELETED | DELETED | P | M |
| T | P | F | S | L | Y | Q | S | T | DELETED | P | DELETED | I |
| T | P | F | S | L | Y | Q | S | T | DELETED | P | DELETED | M |
| T | P | F | S | L | Y | Q | S | T | DELETED | P | P | I |
| T | P | F | S | L | Y | Q | S | T | DELETED | P | P | M |
| T | P | F | S | L | Y | Q | S | T | N | DELETED | DELETED | I |
| T | P | F | S | L | Y | Q | S | T | N | DELETED | DELETED | M |
| T | P | F | S | L | Y | Q | S | T | N | DELETED | P | I |
| T | P | F | S | L | Y | Q | S | T | N | DELETED | P | M |
| T | P | F | S | L | Y | Q | S | T | N | P | DELETED | I |
| T | P | F | S | L | Y | Q | S | T | N | P | DELETED | M |
| T | P | F | S | L | Y | Q | S | T | N | P | P | I |
| T | P | F | S | L | Y | Q | S | T | N | P | P | M |
| T | P | F | S | L | Y | Q | G | S | DELETED | DELETED | DELETED | I |
| T | P | F | S | L | Y | Q | G | S | DELETED | DELETED | DELETED | M |
| T | P | F | S | L | Y | Q | G | S | DELETED | DELETED | P | I |
| T | P | F | S | L | Y | Q | G | S | DELETED | DELETED | P | M |
| T | P | F | S | L | Y | Q | G | S | DELETED | P | DELETED | I |
| T | P | F | S | L | Y | Q | G | S | DELETED | P | DELETED | M |
| T | P | F | S | L | Y | Q | G | S | DELETED | P | P | I |
| T | P | F | S | L | Y | Q | G | S | DELETED | P | P | M |
| T | P | F | S | L | Y | Q | G | S | N | DELETED | DELETED | I |
| T | P | F | S | L | Y | Q | G | S | N | DELETED | DELETED | M |
| T | P | F | S | L | Y | Q | G | S | N | DELETED | P | I |
| T | P | F | S | L | Y | Q | G | S | N | DELETED | P | M |
| T | P | F | S | L | Y | Q | G | S | N | P | DELETED | I |
| T | P | F | S | L | Y | Q | G | S | N | P | DELETED | M |
| T | P | F | S | L | Y | Q | G | S | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | L | Y | Q | G | S | N | P | P | M |
| T | P | F | S | L | Y | Q | G | T | DELETED | DELETED | DELETED | I |
| T | P | F | S | L | Y | Q | G | T | DELETED | DELETED | DELETED | M |
| T | P | F | S | L | Y | Q | G | T | DELETED | DELETED | P | I |
| T | P | F | S | L | Y | Q | G | T | DELETED | DELETED | P | M |
| T | P | F | S | L | Y | Q | G | T | DELETED | P | DELETED | I |
| T | P | F | S | L | Y | Q | G | T | DELETED | P | DELETED | M |
| T | P | F | S | L | Y | Q | G | T | DELETED | P | P | I |
| T | P | F | S | L | Y | Q | G | T | DELETED | P | P | M |
| T | P | F | S | L | Y | Q | G | T | N | DELETED | DELETED | I |
| T | P | F | S | L | Y | Q | G | T | N | DELETED | DELETED | M |
| T | P | F | S | L | Y | Q | G | T | N | DELETED | P | I |
| T | P | F | S | L | Y | Q | G | T | N | DELETED | P | M |
| T | P | F | S | L | Y | Q | G | T | N | P | DELETED | I |
| T | P | F | S | L | Y | Q | G | T | N | P | DELETED | M |
| T | P | F | S | L | Y | Q | G | T | N | P | P | I |
| T | P | F | S | L | Y | Q | G | T | N | P | P | M |
| T | P | F | S | L | Y | V | S | S | DELETED | DELETED | DELETED | I |
| T | P | F | S | L | Y | V | S | S | DELETED | DELETED | DELETED | M |
| T | P | F | S | L | Y | V | S | S | DELETED | DELETED | P | I |
| T | P | F | S | L | Y | V | S | S | DELETED | DELETED | P | M |
| T | P | F | S | L | Y | V | S | S | DELETED | P | DELETED | I |
| T | P | F | S | L | Y | V | S | S | DELETED | P | DELETED | M |
| T | P | F | S | L | Y | V | S | S | DELETED | P | P | I |
| T | P | F | S | L | Y | V | S | S | DELETED | P | P | M |
| T | P | F | S | L | Y | V | S | S | N | DELETED | DELETED | I |
| T | P | F | S | L | Y | V | S | S | N | DELETED | DELETED | M |
| T | P | F | S | L | Y | V | S | S | N | DELETED | P | I |
| T | P | F | S | L | Y | V | S | S | N | DELETED | P | M |
| T | P | F | S | L | Y | V | S | S | N | P | DELETED | I |
| T | P | F | S | L | Y | V | S | S | N | P | DELETED | M |
| T | P | F | S | L | Y | V | S | S | N | P | P | I |
| T | P | F | S | L | Y | V | S | S | N | P | P | M |
| T | P | F | S | L | Y | V | S | T | DELETED | DELETED | DELETED | I |
| T | P | F | S | L | Y | V | S | T | DELETED | DELETED | DELETED | M |
| T | P | F | S | L | Y | V | S | T | DELETED | DELETED | P | I |
| T | P | F | S | L | Y | V | S | T | DELETED | DELETED | P | M |
| T | P | F | S | L | Y | V | S | T | DELETED | P | DELETED | I |
| T | P | F | S | L | Y | V | S | T | DELETED | P | DELETED | M |
| T | P | F | S | L | Y | V | S | T | DELETED | P | P | I |
| T | P | F | S | L | Y | V | S | T | DELETED | P | P | M |
| T | P | F | S | L | Y | V | S | T | N | DELETED | DELETED | I |
| T | P | F | S | L | Y | V | S | T | N | DELETED | DELETED | M |
| T | P | F | S | L | Y | V | S | T | N | DELETED | P | I |
| T | P | F | S | L | Y | V | S | T | N | DELETED | P | M |
| T | P | F | S | L | Y | V | S | T | N | P | DELETED | I |
| T | P | F | S | L | Y | V | S | T | N | P | DELETED | M |
| T | P | F | S | L | Y | V | S | T | N | P | P | I |
| T | P | F | S | L | Y | V | S | T | N | P | P | M |
| T | P | F | S | L | Y | V | G | S | DELETED | DELETED | DELETED | I |
| T | P | F | S | L | Y | V | G | S | DELETED | DELETED | DELETED | M |
| T | P | F | S | L | Y | V | G | S | DELETED | DELETED | P | I |
| T | P | F | S | L | Y | V | G | S | DELETED | DELETED | P | M |
| T | P | F | S | L | Y | V | G | S | DELETED | P | DELETED | I |
| T | P | F | S | L | Y | V | G | S | DELETED | P | DELETED | M |
| T | P | F | S | L | Y | V | G | S | DELETED | P | P | I |
| T | P | F | S | L | Y | V | G | S | DELETED | P | P | M |
| T | P | F | S | L | Y | V | G | S | N | DELETED | DELETED | I |
| T | P | F | S | L | Y | V | G | S | N | DELETED | DELETED | M |
| T | P | F | S | L | Y | V | G | S | N | DELETED | P | I |
| T | P | F | S | L | Y | V | G | S | N | DELETED | P | M |
| T | P | F | S | L | Y | V | G | S | N | P | DELETED | I |
| T | P | F | S | L | Y | V | G | S | N | P | DELETED | M |
| T | P | F | S | L | Y | V | G | S | N | P | P | I |
| T | P | F | S | L | Y | V | G | S | N | P | P | M |
| T | P | F | S | L | Y | V | G | T | DELETED | DELETED | DELETED | I |
| T | P | F | S | L | Y | V | G | T | DELETED | DELETED | DELETED | M |
| T | P | F | S | L | Y | V | G | T | DELETED | DELETED | P | I |
| T | P | F | S | L | Y | V | G | T | DELETED | DELETED | P | M |
| T | P | F | S | L | Y | V | G | T | DELETED | P | DELETED | I |
| T | P | F | S | L | Y | V | G | T | DELETED | P | DELETED | M |
| T | P | F | S | L | Y | V | G | T | DELETED | P | P | I |
| T | P | F | S | L | Y | V | G | T | DELETED | P | P | M |
| T | P | F | S | L | Y | V | G | T | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | L | Y | V | G | T | N | DELETED | DELETED | M |
| T | P | F | S | L | Y | V | G | T | N | DELETED | P | I |
| T | P | F | S | L | Y | V | G | T | N | DELETED | P | M |
| T | P | F | S | L | Y | V | G | T | N | P | DELETED | I |
| T | P | F | S | L | Y | V | G | T | N | P | DELETED | M |
| T | P | F | S | L | Y | V | G | T | N | P | P | I |
| T | P | F | S | L | Y | V | G | T | N | P | P | M |
| T | P | F | S | L | H | Q | S | S | DELETED | DELETED | DELETED | I |
| T | P | F | S | L | H | Q | S | S | DELETED | DELETED | DELETED | M |
| T | P | F | S | L | H | Q | S | S | DELETED | DELETED | P | I |
| T | P | F | S | L | H | Q | S | S | DELETED | DELETED | P | M |
| T | P | F | S | L | H | Q | S | S | DELETED | P | DELETED | I |
| T | P | F | S | L | H | Q | S | S | DELETED | P | DELETED | M |
| T | P | F | S | L | H | Q | S | S | DELETED | P | P | I |
| T | P | F | S | L | H | Q | S | S | DELETED | P | P | M |
| T | P | F | S | L | H | Q | S | S | N | DELETED | DELETED | I |
| T | P | F | S | L | H | Q | S | S | N | DELETED | DELETED | M |
| T | P | F | S | L | H | Q | S | S | N | DELETED | P | I |
| T | P | F | S | L | H | Q | S | S | N | DELETED | P | M |
| T | P | F | S | L | H | Q | S | S | N | P | DELETED | I |
| T | P | F | S | L | H | Q | S | S | N | P | DELETED | M |
| T | P | F | S | L | H | Q | S | S | N | P | P | I |
| T | P | F | S | L | H | Q | S | S | N | P | P | M |
| T | P | F | S | L | H | Q | S | T | DELETED | DELETED | DELETED | I |
| T | P | F | S | L | H | Q | S | T | DELETED | DELETED | DELETED | M |
| T | P | F | S | L | H | Q | S | T | DELETED | DELETED | P | I |
| T | P | F | S | L | H | Q | S | T | DELETED | DELETED | P | M |
| T | P | F | S | L | H | Q | S | T | DELETED | P | DELETED | I |
| T | P | F | S | L | H | Q | S | T | DELETED | P | DELETED | M |
| T | P | F | S | L | H | Q | S | T | DELETED | P | P | I |
| T | P | F | S | L | H | Q | S | T | DELETED | P | P | M |
| T | P | F | S | L | H | Q | S | T | N | DELETED | DELETED | I |
| T | P | F | S | L | H | Q | S | T | N | DELETED | DELETED | M |
| T | P | F | S | L | H | Q | S | T | N | DELETED | P | I |
| T | P | F | S | L | H | Q | S | T | N | DELETED | P | M |
| T | P | F | S | L | H | Q | S | T | N | P | DELETED | I |
| T | P | F | S | L | H | Q | S | T | N | P | DELETED | M |
| T | P | F | S | L | H | Q | S | T | N | P | P | I |
| T | P | F | S | L | H | Q | S | T | N | P | P | M |
| T | P | F | S | L | H | Q | G | S | DELETED | DELETED | DELETED | I |
| T | P | F | S | L | H | Q | G | S | DELETED | DELETED | DELETED | M |
| T | P | F | S | L | H | Q | G | S | DELETED | DELETED | P | I |
| T | P | F | S | L | H | Q | G | S | DELETED | DELETED | P | M |
| T | P | F | S | L | H | Q | G | S | DELETED | P | DELETED | I |
| T | P | F | S | L | H | Q | G | S | DELETED | P | DELETED | M |
| T | P | F | S | L | H | Q | G | S | DELETED | P | P | I |
| T | P | F | S | L | H | Q | G | S | DELETED | P | P | M |
| T | P | F | S | L | H | Q | G | S | N | DELETED | DELETED | I |
| T | P | F | S | L | H | Q | G | S | N | DELETED | DELETED | M |
| T | P | F | S | L | H | Q | G | S | N | DELETED | P | I |
| T | P | F | S | L | H | Q | G | S | N | DELETED | P | M |
| T | P | F | S | L | H | Q | G | S | N | P | DELETED | I |
| T | P | F | S | L | H | Q | G | S | N | P | DELETED | M |
| T | P | F | S | L | H | Q | G | S | N | P | P | I |
| T | P | F | S | L | H | Q | G | S | N | P | P | M |
| T | P | F | S | L | H | Q | G | T | DELETED | DELETED | DELETED | I |
| T | P | F | S | L | H | Q | G | T | DELETED | DELETED | DELETED | M |
| T | P | F | S | L | H | Q | G | T | DELETED | DELETED | P | I |
| T | P | F | S | L | H | Q | G | T | DELETED | DELETED | P | M |
| T | P | F | S | L | H | Q | G | T | DELETED | P | DELETED | I |
| T | P | F | S | L | H | Q | G | T | DELETED | P | DELETED | M |
| T | P | F | S | L | H | Q | G | T | DELETED | P | P | I |
| T | P | F | S | L | H | Q | G | T | DELETED | P | P | M |
| T | P | F | S | L | H | Q | G | T | N | DELETED | DELETED | I |
| T | P | F | S | L | H | Q | G | T | N | DELETED | DELETED | M |
| T | P | F | S | L | H | Q | G | T | N | DELETED | P | I |
| T | P | F | S | L | H | Q | G | T | N | DELETED | P | M |
| T | P | F | S | L | H | Q | G | T | N | P | DELETED | I |
| T | P | F | S | L | H | Q | G | T | N | P | DELETED | M |
| T | P | F | S | L | H | Q | G | T | N | P | P | I |
| T | P | F | S | L | H | Q | G | T | N | P | P | M |
| T | P | F | S | L | H | V | S | S | DELETED | DELETED | DELETED | I |
| T | P | F | S | L | H | V | S | S | DELETED | DELETED | DELETED | M |
| T | P | F | S | L | H | V | S | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | L | H | V | S | S | DELETED | DELETED | P | M |
| T | P | F | S | L | H | V | S | S | DELETED | P | DELETED | I |
| T | P | F | S | L | H | V | S | S | DELETED | P | DELETED | M |
| T | P | F | S | L | H | V | S | S | DELETED | P | P | I |
| T | P | F | S | L | H | V | S | S | DELETED | P | P | M |
| T | P | F | S | L | H | V | S | S | N | DELETED | DELETED | I |
| T | P | F | S | L | H | V | S | S | N | DELETED | DELETED | M |
| T | P | F | S | L | H | V | S | S | N | DELETED | P | I |
| T | P | F | S | L | H | V | S | S | N | DELETED | P | M |
| T | P | F | S | L | H | V | S | S | N | P | DELETED | I |
| T | P | F | S | L | H | V | S | S | N | P | DELETED | M |
| T | P | F | S | L | H | V | S | S | N | P | P | I |
| T | P | F | S | L | H | V | S | S | N | P | P | M |
| T | P | F | S | L | H | V | S | T | DELETED | DELETED | DELETED | I |
| T | P | F | S | L | H | V | S | T | DELETED | DELETED | DELETED | M |
| T | P | F | S | L | H | V | S | T | DELETED | DELETED | P | I |
| T | P | F | S | L | H | V | S | T | DELETED | DELETED | P | M |
| T | P | F | S | L | H | V | S | T | DELETED | P | DELETED | I |
| T | P | F | S | L | H | V | S | T | DELETED | P | DELETED | M |
| T | P | F | S | L | H | V | S | T | DELETED | P | P | I |
| T | P | F | S | L | H | V | S | T | DELETED | P | P | M |
| T | P | F | S | L | H | V | S | T | N | DELETED | DELETED | I |
| T | P | F | S | L | H | V | S | T | N | DELETED | DELETED | M |
| T | P | F | S | L | H | V | S | T | N | DELETED | P | I |
| T | P | F | S | L | H | V | S | T | N | DELETED | P | M |
| T | P | F | S | L | H | V | S | T | N | P | DELETED | I |
| T | P | F | S | L | H | V | S | T | N | P | DELETED | M |
| T | P | F | S | L | H | V | S | T | N | P | P | I |
| T | P | F | S | L | H | V | S | T | N | P | P | M |
| T | P | F | S | L | H | V | G | S | DELETED | DELETED | DELETED | I |
| T | P | F | S | L | H | V | G | S | DELETED | DELETED | DELETED | M |
| T | P | F | S | L | H | V | G | S | DELETED | DELETED | P | I |
| T | P | F | S | L | H | V | G | S | DELETED | DELETED | P | M |
| T | P | F | S | L | H | V | G | S | DELETED | P | DELETED | I |
| T | P | F | S | L | H | V | G | S | DELETED | P | DELETED | M |
| T | P | F | S | L | H | V | G | S | DELETED | P | P | I |
| T | P | F | S | L | H | V | G | S | DELETED | P | P | M |
| T | P | F | S | L | H | V | G | S | N | DELETED | DELETED | I |
| T | P | F | S | L | H | V | G | S | N | DELETED | DELETED | M |
| T | P | F | S | L | H | V | G | S | N | DELETED | P | I |
| T | P | F | S | L | H | V | G | S | N | DELETED | P | M |
| T | P | F | S | L | H | V | G | S | N | P | DELETED | I |
| T | P | F | S | L | H | V | G | S | N | P | DELETED | M |
| T | P | F | S | L | H | V | G | S | N | P | P | I |
| T | P | F | S | L | H | V | G | S | N | P | P | M |
| T | P | F | S | L | H | V | G | T | DELETED | DELETED | DELETED | I |
| T | P | F | S | L | H | V | G | T | DELETED | DELETED | DELETED | M |
| T | P | F | S | L | H | V | G | T | DELETED | DELETED | P | I |
| T | P | F | S | L | H | V | G | T | DELETED | DELETED | P | M |
| T | P | F | S | L | H | V | G | T | DELETED | P | DELETED | I |
| T | P | F | S | L | H | V | G | T | DELETED | P | DELETED | M |
| T | P | F | S | L | H | V | G | T | DELETED | P | P | I |
| T | P | F | S | L | H | V | G | T | DELETED | P | P | M |
| T | P | F | S | L | H | V | G | T | N | DELETED | DELETED | I |
| T | P | F | S | L | H | V | G | T | N | DELETED | DELETED | M |
| T | P | F | S | L | H | V | G | T | N | DELETED | P | I |
| T | P | F | S | L | H | V | G | T | N | DELETED | P | M |
| T | P | F | S | L | H | V | G | T | N | P | DELETED | I |
| T | P | F | S | L | H | V | G | T | N | P | DELETED | M |
| T | P | F | S | L | H | V | G | T | N | P | P | I |
| T | P | F | S | L | H | V | G | T | N | P | P | M |
| T | P | F | S | I | Y | Q | S | S | DELETED | DELETED | DELETED | I |
| T | P | F | S | I | Y | Q | S | S | DELETED | DELETED | DELETED | M |
| T | P | F | S | I | Y | Q | S | S | DELETED | DELETED | P | I |
| T | P | F | S | I | Y | Q | S | S | DELETED | DELETED | P | M |
| T | P | F | S | I | Y | Q | S | S | DELETED | P | DELETED | I |
| T | P | F | S | I | Y | Q | S | S | DELETED | P | DELETED | M |
| T | P | F | S | I | Y | Q | S | S | DELETED | P | P | I |
| T | P | F | S | I | Y | Q | S | S | DELETED | P | P | M |
| T | P | F | S | I | Y | Q | S | S | N | DELETED | DELETED | I |
| T | P | F | S | I | Y | Q | S | S | N | DELETED | DELETED | M |
| T | P | F | S | I | Y | Q | S | S | N | DELETED | P | I |
| T | P | F | S | I | Y | Q | S | S | N | DELETED | P | M |
| T | P | F | S | I | Y | Q | S | S | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | I | Y | Q | S | S | N | P | DELETED | M |
| T | P | F | S | I | Y | Q | S | S | N | P | P | I |
| T | P | F | S | I | Y | Q | S | S | N | P | P | M |
| T | P | F | S | I | Y | Q | S | T | DELETED | DELETED | DELETED | I |
| T | P | F | S | I | Y | Q | S | T | DELETED | DELETED | DELETED | M |
| T | P | F | S | I | Y | Q | S | T | DELETED | DELETED | P | I |
| T | P | F | S | I | Y | Q | S | T | DELETED | DELETED | P | M |
| T | P | F | S | I | Y | Q | S | T | DELETED | P | DELETED | I |
| T | P | F | S | I | Y | Q | S | T | DELETED | P | DELETED | M |
| T | P | F | S | I | Y | Q | S | T | DELETED | P | P | I |
| T | P | F | S | I | Y | Q | S | T | DELETED | P | P | M |
| T | P | F | S | I | Y | Q | S | T | N | DELETED | DELETED | I |
| T | P | F | S | I | Y | Q | S | T | N | DELETED | DELETED | M |
| T | P | F | S | I | Y | Q | S | T | N | DELETED | P | I |
| T | P | F | S | I | Y | Q | S | T | N | DELETED | P | M |
| T | P | F | S | I | Y | Q | S | T | N | P | DELETED | I |
| T | P | F | S | I | Y | Q | S | T | N | P | DELETED | M |
| T | P | F | S | I | Y | Q | S | T | N | P | P | I |
| T | P | F | S | I | Y | Q | S | T | N | P | P | M |
| T | P | F | S | I | Y | Q | G | S | DELETED | DELETED | DELETED | I |
| T | P | F | S | I | Y | Q | G | S | DELETED | DELETED | DELETED | M |
| T | P | F | S | I | Y | Q | G | S | DELETED | DELETED | P | I |
| T | P | F | S | I | Y | Q | G | S | DELETED | DELETED | P | M |
| T | P | F | S | I | Y | Q | G | S | DELETED | P | DELETED | I |
| T | P | F | S | I | Y | Q | G | S | DELETED | P | DELETED | M |
| T | P | F | S | I | Y | Q | G | S | DELETED | P | P | I |
| T | P | F | S | I | Y | Q | G | S | DELETED | P | P | M |
| T | P | F | S | I | Y | Q | G | S | N | DELETED | DELETED | I |
| T | P | F | S | I | Y | Q | G | S | N | DELETED | DELETED | M |
| T | P | F | S | I | Y | Q | G | S | N | DELETED | P | I |
| T | P | F | S | I | Y | Q | G | S | N | DELETED | P | M |
| T | P | F | S | I | Y | Q | G | S | N | P | DELETED | I |
| T | P | F | S | I | Y | Q | G | S | N | P | DELETED | M |
| T | P | F | S | I | Y | Q | G | S | N | P | P | I |
| T | P | F | S | I | Y | Q | G | S | N | P | P | M |
| T | P | F | S | I | Y | Q | G | T | DELETED | DELETED | DELETED | I |
| T | P | F | S | I | Y | Q | G | T | DELETED | DELETED | DELETED | M |
| T | P | F | S | I | Y | Q | G | T | DELETED | DELETED | P | I |
| T | P | F | S | I | Y | Q | G | T | DELETED | DELETED | P | M |
| T | P | F | S | I | Y | Q | G | T | DELETED | P | DELETED | I |
| T | P | F | S | I | Y | Q | G | T | DELETED | P | DELETED | M |
| T | P | F | S | I | Y | Q | G | T | DELETED | P | P | I |
| T | P | F | S | I | Y | Q | G | T | DELETED | P | P | M |
| T | P | F | S | I | Y | Q | G | T | N | DELETED | DELETED | I |
| T | P | F | S | I | Y | Q | G | T | N | DELETED | DELETED | M |
| T | P | F | S | I | Y | Q | G | T | N | DELETED | P | I |
| T | P | F | S | I | Y | Q | G | T | N | DELETED | P | M |
| T | P | F | S | I | Y | Q | G | T | N | P | DELETED | I |
| T | P | F | S | I | Y | Q | G | T | N | P | DELETED | M |
| T | P | F | S | I | Y | Q | G | T | N | P | P | I |
| T | P | F | S | I | Y | Q | G | T | N | P | P | M |
| T | P | F | S | I | Y | V | S | S | DELETED | DELETED | DELETED | I |
| T | P | F | S | I | Y | V | S | S | DELETED | DELETED | DELETED | M |
| T | P | F | S | I | Y | V | S | S | DELETED | DELETED | P | I |
| T | P | F | S | I | Y | V | S | S | DELETED | DELETED | P | M |
| T | P | F | S | I | Y | V | S | S | DELETED | P | DELETED | I |
| T | P | F | S | I | Y | V | S | S | DELETED | P | DELETED | M |
| T | P | F | S | I | Y | V | S | S | DELETED | P | P | I |
| T | P | F | S | I | Y | V | S | S | DELETED | P | P | M |
| T | P | F | S | I | Y | V | S | S | N | DELETED | DELETED | I |
| T | P | F | S | I | Y | V | S | S | N | DELETED | DELETED | M |
| T | P | F | S | I | Y | V | S | S | N | DELETED | P | I |
| T | P | F | S | I | Y | V | S | S | N | DELETED | P | M |
| T | P | F | S | I | Y | V | S | S | N | P | DELETED | I |
| T | P | F | S | I | Y | V | S | S | N | P | DELETED | M |
| T | P | F | S | I | Y | V | S | S | N | P | P | I |
| T | P | F | S | I | Y | V | S | S | N | P | P | M |
| T | P | F | S | I | Y | V | S | T | DELETED | DELETED | DELETED | I |
| T | P | F | S | I | Y | V | S | T | DELETED | DELETED | DELETED | M |
| T | P | F | S | I | Y | V | S | T | DELETED | DELETED | P | I |
| T | P | F | S | I | Y | V | S | T | DELETED | DELETED | P | M |
| T | P | F | S | I | Y | V | S | T | DELETED | P | DELETED | I |
| T | P | F | S | I | Y | V | S | T | DELETED | P | DELETED | M |
| T | P | F | S | I | Y | V | S | T | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | I | Y | V | S | T | DELETED | P | P | M |
| T | P | F | S | I | Y | V | S | T | N | DELETED | DELETED | I |
| T | P | F | S | I | Y | V | S | T | N | DELETED | DELETED | M |
| T | P | F | S | I | Y | V | S | T | N | DELETED | P | I |
| T | P | F | S | I | Y | V | S | T | N | DELETED | P | M |
| T | P | F | S | I | Y | V | S | T | N | P | DELETED | I |
| T | P | F | S | I | Y | V | S | T | N | P | DELETED | M |
| T | P | F | S | I | Y | V | S | T | N | P | P | I |
| T | P | F | S | I | Y | V | S | T | N | P | P | M |
| T | P | F | S | I | Y | V | G | S | DELETED | DELETED | DELETED | I |
| T | P | F | S | I | Y | V | G | S | DELETED | DELETED | DELETED | M |
| T | P | F | S | I | Y | V | G | S | DELETED | DELETED | P | I |
| T | P | F | S | I | Y | V | G | S | DELETED | DELETED | P | M |
| T | P | F | S | I | Y | V | G | S | DELETED | P | DELETED | I |
| T | P | F | S | I | Y | V | G | S | DELETED | P | DELETED | M |
| T | P | F | S | I | Y | V | G | S | DELETED | P | P | I |
| T | P | F | S | I | Y | V | G | S | DELETED | P | P | M |
| T | P | F | S | I | Y | V | G | S | N | DELETED | DELETED | I |
| T | P | F | S | I | Y | V | G | S | N | DELETED | DELETED | M |
| T | P | F | S | I | Y | V | G | S | N | DELETED | P | I |
| T | P | F | S | I | Y | V | G | S | N | DELETED | P | M |
| T | P | F | S | I | Y | V | G | S | N | P | DELETED | I |
| T | P | F | S | I | Y | V | G | S | N | P | DELETED | M |
| T | P | F | S | I | Y | V | G | S | N | P | P | I |
| T | P | F | S | I | Y | V | G | S | N | P | P | M |
| T | P | F | S | I | Y | V | G | T | DELETED | DELETED | DELETED | I |
| T | P | F | S | I | Y | V | G | T | DELETED | DELETED | DELETED | M |
| T | P | F | S | I | Y | V | G | T | DELETED | DELETED | P | I |
| T | P | F | S | I | Y | V | G | T | DELETED | DELETED | P | M |
| T | P | F | S | I | Y | V | G | T | DELETED | P | DELETED | I |
| T | P | F | S | I | Y | V | G | T | DELETED | P | DELETED | M |
| T | P | F | S | I | Y | V | G | T | DELETED | P | P | I |
| T | P | F | S | I | Y | V | G | T | DELETED | P | P | M |
| T | P | F | S | I | Y | V | G | T | N | DELETED | DELETED | I |
| T | P | F | S | I | Y | V | G | T | N | DELETED | DELETED | M |
| T | P | F | S | I | Y | V | G | T | N | DELETED | P | I |
| T | P | F | S | I | Y | V | G | T | N | DELETED | P | M |
| T | P | F | S | I | Y | V | G | T | N | P | DELETED | I |
| T | P | F | S | I | Y | V | G | T | N | P | DELETED | M |
| T | P | F | S | I | Y | V | G | T | N | P | P | I |
| T | P | F | S | I | Y | V | G | T | N | P | P | M |
| T | P | F | S | I | H | Q | S | S | DELETED | DELETED | DELETED | I |
| T | P | F | S | I | H | Q | S | S | DELETED | DELETED | DELETED | M |
| T | P | F | S | I | H | Q | S | S | DELETED | DELETED | P | I |
| T | P | F | S | I | H | Q | S | S | DELETED | DELETED | P | M |
| T | P | F | S | I | H | Q | S | S | DELETED | P | DELETED | I |
| T | P | F | S | I | H | Q | S | S | DELETED | P | DELETED | M |
| T | P | F | S | I | H | Q | S | S | DELETED | P | P | I |
| T | P | F | S | I | H | Q | S | S | DELETED | P | P | M |
| T | P | F | S | I | H | Q | S | S | N | DELETED | DELETED | I |
| T | P | F | S | I | H | Q | S | S | N | DELETED | DELETED | M |
| T | P | F | S | I | H | Q | S | S | N | DELETED | P | I |
| T | P | F | S | I | H | Q | S | S | N | DELETED | P | M |
| T | P | F | S | I | H | Q | S | S | N | P | DELETED | I |
| T | P | F | S | I | H | Q | S | S | N | P | DELETED | M |
| T | P | F | S | I | H | Q | S | S | N | P | P | I |
| T | P | F | S | I | H | Q | S | S | N | P | P | M |
| T | P | F | S | I | H | Q | S | T | DELETED | DELETED | DELETED | I |
| T | P | F | S | I | H | Q | S | T | DELETED | DELETED | DELETED | M |
| T | P | F | S | I | H | Q | S | T | DELETED | DELETED | P | I |
| T | P | F | S | I | H | Q | S | T | DELETED | DELETED | P | M |
| T | P | F | S | I | H | Q | S | T | DELETED | P | DELETED | I |
| T | P | F | S | I | H | Q | S | T | DELETED | P | DELETED | M |
| T | P | F | S | I | H | Q | S | T | DELETED | P | P | I |
| T | P | F | S | I | H | Q | S | T | DELETED | P | P | M |
| T | P | F | S | I | H | Q | S | T | N | DELETED | DELETED | I |
| T | P | F | S | I | H | Q | S | T | N | DELETED | DELETED | M |
| T | P | F | S | I | H | Q | S | T | N | DELETED | P | I |
| T | P | F | S | I | H | Q | S | T | N | DELETED | P | M |
| T | P | F | S | I | H | Q | S | T | N | P | DELETED | I |
| T | P | F | S | I | H | Q | S | T | N | P | DELETED | M |
| T | P | F | S | I | H | Q | S | T | N | P | P | I |
| T | P | F | S | I | H | Q | S | T | N | P | P | M |
| T | P | F | S | I | H | Q | G | S | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | I | H | Q | G | S | DELETED | DELETED | DELETED | M |
| T | P | F | S | I | H | Q | G | S | DELETED | DELETED | P | I |
| T | P | F | S | I | H | Q | G | S | DELETED | DELETED | P | M |
| T | P | F | S | I | H | Q | G | S | DELETED | P | DELETED | I |
| T | P | F | S | I | H | Q | G | S | DELETED | P | DELETED | M |
| T | P | F | S | I | H | Q | G | S | DELETED | P | P | I |
| T | P | F | S | I | H | Q | G | S | DELETED | P | P | M |
| T | P | F | S | I | H | Q | G | S | N | DELETED | DELETED | I |
| T | P | F | S | I | H | Q | G | S | N | DELETED | DELETED | M |
| T | P | F | S | I | H | Q | G | S | N | DELETED | P | I |
| T | P | F | S | I | H | Q | G | S | N | DELETED | P | M |
| T | P | F | S | I | H | Q | G | S | N | P | DELETED | I |
| T | P | F | S | I | H | Q | G | S | N | P | DELETED | M |
| T | P | F | S | I | H | Q | G | S | N | P | P | I |
| T | P | F | S | I | H | Q | G | S | N | P | P | M |
| T | P | F | S | I | H | Q | G | T | DELETED | DELETED | DELETED | I |
| T | P | F | S | I | H | Q | G | T | DELETED | DELETED | DELETED | M |
| T | P | F | S | I | H | Q | G | T | DELETED | DELETED | P | I |
| T | P | F | S | I | H | Q | G | T | DELETED | DELETED | P | M |
| T | P | F | S | I | H | Q | G | T | DELETED | P | DELETED | I |
| T | P | F | S | I | H | Q | G | T | DELETED | P | DELETED | M |
| T | P | F | S | I | H | Q | G | T | DELETED | P | P | I |
| T | P | F | S | I | H | Q | G | T | DELETED | P | P | M |
| T | P | F | S | I | H | Q | G | T | N | DELETED | DELETED | I |
| T | P | F | S | I | H | Q | G | T | N | DELETED | DELETED | M |
| T | P | F | S | I | H | Q | G | T | N | DELETED | P | I |
| T | P | F | S | I | H | Q | G | T | N | DELETED | P | M |
| T | P | F | S | I | H | Q | G | T | N | P | DELETED | I |
| T | P | F | S | I | H | Q | G | T | N | P | DELETED | M |
| T | P | F | S | I | H | Q | G | T | N | P | P | I |
| T | P | F | S | I | H | Q | G | T | N | P | P | M |
| T | P | F | S | I | H | V | S | S | DELETED | DELETED | DELETED | I |
| T | P | F | S | I | H | V | S | S | DELETED | DELETED | DELETED | M |
| T | P | F | S | I | H | V | S | S | DELETED | DELETED | P | I |
| T | P | F | S | I | H | V | S | S | DELETED | DELETED | P | M |
| T | P | F | S | I | H | V | S | S | DELETED | P | DELETED | I |
| T | P | F | S | I | H | V | S | S | DELETED | P | DELETED | M |
| T | P | F | S | I | H | V | S | S | DELETED | P | P | I |
| T | P | F | S | I | H | V | S | S | DELETED | P | P | M |
| T | P | F | S | I | H | V | S | S | N | DELETED | DELETED | I |
| T | P | F | S | I | H | V | S | S | N | DELETED | DELETED | M |
| T | P | F | S | I | H | V | S | S | N | DELETED | P | I |
| T | P | F | S | I | H | V | S | S | N | DELETED | P | M |
| T | P | F | S | I | H | V | S | S | N | P | DELETED | I |
| T | P | F | S | I | H | V | S | S | N | P | DELETED | M |
| T | P | F | S | I | H | V | S | S | N | P | P | I |
| T | P | F | S | I | H | V | S | S | N | P | P | M |
| T | P | F | S | I | H | V | S | T | DELETED | DELETED | DELETED | I |
| T | P | F | S | I | H | V | S | T | DELETED | DELETED | DELETED | M |
| T | P | F | S | I | H | V | S | T | DELETED | DELETED | P | I |
| T | P | F | S | I | H | V | S | T | DELETED | DELETED | P | M |
| T | P | F | S | I | H | V | S | T | DELETED | P | DELETED | I |
| T | P | F | S | I | H | V | S | T | DELETED | P | DELETED | M |
| T | P | F | S | I | H | V | S | T | DELETED | P | P | I |
| T | P | F | S | I | H | V | S | T | DELETED | P | P | M |
| T | P | F | S | I | H | V | S | T | N | DELETED | DELETED | I |
| T | P | F | S | I | H | V | S | T | N | DELETED | DELETED | M |
| T | P | F | S | I | H | V | S | T | N | DELETED | P | I |
| T | P | F | S | I | H | V | S | T | N | DELETED | P | M |
| T | P | F | S | I | H | V | S | T | N | P | DELETED | I |
| T | P | F | S | I | H | V | S | T | N | P | DELETED | M |
| T | P | F | S | I | H | V | S | T | N | P | P | I |
| T | P | F | S | I | H | V | S | T | N | P | P | M |
| T | P | F | S | I | H | V | G | S | DELETED | DELETED | DELETED | I |
| T | P | F | S | I | H | V | G | S | DELETED | DELETED | DELETED | M |
| T | P | F | S | I | H | V | G | S | DELETED | DELETED | P | I |
| T | P | F | S | I | H | V | G | S | DELETED | DELETED | P | M |
| T | P | F | S | I | H | V | G | S | DELETED | P | DELETED | I |
| T | P | F | S | I | H | V | G | S | DELETED | P | DELETED | M |
| T | P | F | S | I | H | V | G | S | DELETED | P | P | I |
| T | P | F | S | I | H | V | G | S | DELETED | P | P | M |
| T | P | F | S | I | H | V | G | S | N | DELETED | DELETED | I |
| T | P | F | S | I | H | V | G | S | N | DELETED | DELETED | M |
| T | P | F | S | I | H | V | G | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | S | I | H | V | G | S | N | DELETED | P | M |
| T | P | F | S | I | H | V | G | S | N | P | DELETED | I |
| T | P | F | S | I | H | V | G | S | N | P | DELETED | M |
| T | P | F | S | I | H | V | G | S | N | P | P | I |
| T | P | F | S | I | H | V | G | S | N | P | P | M |
| T | P | F | S | I | H | V | G | T | DELETED | DELETED | DELETED | I |
| T | P | F | S | I | H | V | G | T | DELETED | DELETED | DELETED | M |
| T | P | F | S | I | H | V | G | T | DELETED | DELETED | P | I |
| T | P | F | S | I | H | V | G | T | DELETED | DELETED | P | M |
| T | P | F | S | I | H | V | G | T | DELETED | P | DELETED | I |
| T | P | F | S | I | H | V | G | T | DELETED | P | DELETED | M |
| T | P | F | S | I | H | V | G | T | DELETED | P | P | I |
| T | P | F | S | I | H | V | G | T | DELETED | P | P | M |
| T | P | F | S | I | H | V | G | T | N | DELETED | DELETED | I |
| T | P | F | S | I | H | V | G | T | N | DELETED | DELETED | M |
| T | P | F | S | I | H | V | G | T | N | DELETED | P | I |
| T | P | F | S | I | H | V | G | T | N | DELETED | P | M |
| T | P | F | S | I | H | V | G | T | N | P | DELETED | I |
| T | P | F | S | I | H | V | G | T | N | P | DELETED | M |
| T | P | F | S | I | H | V | G | T | N | P | P | I |
| T | P | F | S | I | H | V | G | T | N | P | P | M |
| T | P | F | R | L | Y | Q | S | S | DELETED | DELETED | DELETED | I |
| T | P | F | R | L | Y | Q | S | S | DELETED | DELETED | DELETED | M |
| T | P | F | R | L | Y | Q | S | S | DELETED | DELETED | P | I |
| T | P | F | R | L | Y | Q | S | S | DELETED | DELETED | P | M |
| T | P | F | R | L | Y | Q | S | S | DELETED | P | DELETED | I |
| T | P | F | R | L | Y | Q | S | S | DELETED | P | DELETED | M |
| T | P | F | R | L | Y | Q | S | S | DELETED | P | P | I |
| T | P | F | R | L | Y | Q | S | S | DELETED | P | P | M |
| T | P | F | R | L | Y | Q | S | S | N | DELETED | DELETED | I |
| T | P | F | R | L | Y | Q | S | S | N | DELETED | DELETED | M |
| T | P | F | R | L | Y | Q | S | S | N | DELETED | P | I |
| T | P | F | R | L | Y | Q | S | S | N | DELETED | P | M |
| T | P | F | R | L | Y | Q | S | S | N | P | DELETED | I |
| T | P | F | R | L | Y | Q | S | S | N | P | DELETED | M |
| T | P | F | R | L | Y | Q | S | S | N | P | P | I |
| T | P | F | R | L | Y | Q | S | S | N | P | P | M |
| T | P | F | R | L | Y | Q | S | T | DELETED | DELETED | DELETED | I |
| T | P | F | R | L | Y | Q | S | T | DELETED | DELETED | DELETED | M |
| T | P | F | R | L | Y | Q | S | T | DELETED | DELETED | P | I |
| T | P | F | R | L | Y | Q | S | T | DELETED | DELETED | P | M |
| T | P | F | R | L | Y | Q | S | T | DELETED | P | DELETED | I |
| T | P | F | R | L | Y | Q | S | T | DELETED | P | DELETED | M |
| T | P | F | R | L | Y | Q | S | T | DELETED | P | P | I |
| T | P | F | R | L | Y | Q | S | T | DELETED | P | P | M |
| T | P | F | R | L | Y | Q | S | T | N | DELETED | DELETED | I |
| T | P | F | R | L | Y | Q | S | T | N | DELETED | DELETED | M |
| T | P | F | R | L | Y | Q | S | T | N | DELETED | P | I |
| T | P | F | R | L | Y | Q | S | T | N | DELETED | P | M |
| T | P | F | R | L | Y | Q | S | T | N | P | DELETED | I |
| T | P | F | R | L | Y | Q | S | T | N | P | DELETED | M |
| T | P | F | R | L | Y | Q | S | T | N | P | P | I |
| T | P | F | R | L | Y | Q | S | T | N | P | P | M |
| T | P | F | R | L | Y | Q | G | S | DELETED | DELETED | DELETED | I |
| T | P | F | R | L | Y | Q | G | S | DELETED | DELETED | DELETED | M |
| T | P | F | R | L | Y | Q | G | S | DELETED | DELETED | P | I |
| T | P | F | R | L | Y | Q | G | S | DELETED | DELETED | P | M |
| T | P | F | R | L | Y | Q | G | S | DELETED | P | DELETED | I |
| T | P | F | R | L | Y | Q | G | S | DELETED | P | DELETED | M |
| T | P | F | R | L | Y | Q | G | S | DELETED | P | P | I |
| T | P | F | R | L | Y | Q | G | S | DELETED | P | P | M |
| T | P | F | R | L | Y | Q | G | S | N | DELETED | DELETED | I |
| T | P | F | R | L | Y | Q | G | S | N | DELETED | DELETED | M |
| T | P | F | R | L | Y | Q | G | S | N | DELETED | P | I |
| T | P | F | R | L | Y | Q | G | S | N | DELETED | P | M |
| T | P | F | R | L | Y | Q | G | S | N | P | DELETED | I |
| T | P | F | R | L | Y | Q | G | S | N | P | DELETED | M |
| T | P | F | R | L | Y | Q | G | S | N | P | P | I |
| T | P | F | R | L | Y | Q | G | S | N | P | P | M |
| T | P | F | R | L | Y | Q | G | T | DELETED | DELETED | DELETED | I |
| T | P | F | R | L | Y | Q | G | T | DELETED | DELETED | DELETED | M |
| T | P | F | R | L | Y | Q | G | T | DELETED | DELETED | P | I |
| T | P | F | R | L | Y | Q | G | T | DELETED | DELETED | P | M |
| T | P | F | R | L | Y | Q | G | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | R | L | Y | Q | G | T | DELETED | P | DELETED | M |
| T | P | F | R | L | Y | Q | G | T | DELETED | P | P | I |
| T | P | F | R | L | Y | Q | G | T | DELETED | P | P | M |
| T | P | F | R | L | Y | Q | G | T | N | DELETED | DELETED | I |
| T | P | F | R | L | Y | Q | G | T | N | DELETED | DELETED | M |
| T | P | F | R | L | Y | Q | G | T | N | DELETED | P | I |
| T | P | F | R | L | Y | Q | G | T | N | DELETED | P | M |
| T | P | F | R | L | Y | Q | G | T | N | P | DELETED | I |
| T | P | F | R | L | Y | Q | G | T | N | P | DELETED | M |
| T | P | F | R | L | Y | Q | G | T | N | P | P | I |
| T | P | F | R | L | Y | Q | G | T | N | P | P | M |
| T | P | F | R | L | Y | V | S | S | DELETED | DELETED | DELETED | I |
| T | P | F | R | L | Y | V | S | S | DELETED | DELETED | DELETED | M |
| T | P | F | R | L | Y | V | S | S | DELETED | DELETED | P | I |
| T | P | F | R | L | Y | V | S | S | DELETED | DELETED | P | M |
| T | P | F | R | L | Y | V | S | S | DELETED | P | DELETED | I |
| T | P | F | R | L | Y | V | S | S | DELETED | P | DELETED | M |
| T | P | F | R | L | Y | V | S | S | DELETED | P | P | I |
| T | P | F | R | L | Y | V | S | S | DELETED | P | P | M |
| T | P | F | R | L | Y | V | S | S | N | DELETED | DELETED | I |
| T | P | F | R | L | Y | V | S | S | N | DELETED | DELETED | M |
| T | P | F | R | L | Y | V | S | S | N | DELETED | P | I |
| T | P | F | R | L | Y | V | S | S | N | DELETED | P | M |
| T | P | F | R | L | Y | V | S | S | N | P | DELETED | I |
| T | P | F | R | L | Y | V | S | S | N | P | DELETED | M |
| T | P | F | R | L | Y | V | S | S | N | P | P | I |
| T | P | F | R | L | Y | V | S | S | N | P | P | M |
| T | P | F | R | L | Y | V | S | T | DELETED | DELETED | DELETED | I |
| T | P | F | R | L | Y | V | S | T | DELETED | DELETED | DELETED | M |
| T | P | F | R | L | Y | V | S | T | DELETED | DELETED | P | I |
| T | P | F | R | L | Y | V | S | T | DELETED | DELETED | P | M |
| T | P | F | R | L | Y | V | S | T | DELETED | P | DELETED | I |
| T | P | F | R | L | Y | V | S | T | DELETED | P | DELETED | M |
| T | P | F | R | L | Y | V | S | T | DELETED | P | P | I |
| T | P | F | R | L | Y | V | S | T | DELETED | P | P | M |
| T | P | F | R | L | Y | V | S | T | N | DELETED | DELETED | I |
| T | P | F | R | L | Y | V | S | T | N | DELETED | DELETED | M |
| T | P | F | R | L | Y | V | S | T | N | DELETED | P | I |
| T | P | F | R | L | Y | V | S | T | N | DELETED | P | M |
| T | P | F | R | L | Y | V | S | T | N | P | DELETED | I |
| T | P | F | R | L | Y | V | S | T | N | P | DELETED | M |
| T | P | F | R | L | Y | V | S | T | N | P | P | I |
| T | P | F | R | L | Y | V | S | T | N | P | P | M |
| T | P | F | R | L | Y | V | G | S | DELETED | DELETED | DELETED | I |
| T | P | F | R | L | Y | V | G | S | DELETED | DELETED | DELETED | M |
| T | P | F | R | L | Y | V | G | S | DELETED | DELETED | P | I |
| T | P | F | R | L | Y | V | G | S | DELETED | DELETED | P | M |
| T | P | F | R | L | Y | V | G | S | DELETED | P | DELETED | I |
| T | P | F | R | L | Y | V | G | S | DELETED | P | DELETED | M |
| T | P | F | R | L | Y | V | G | S | DELETED | P | P | I |
| T | P | F | R | L | Y | V | G | S | DELETED | P | P | M |
| T | P | F | R | L | Y | V | G | S | N | DELETED | DELETED | I |
| T | P | F | R | L | Y | V | G | S | N | DELETED | DELETED | M |
| T | P | F | R | L | Y | V | G | S | N | DELETED | P | I |
| T | P | F | R | L | Y | V | G | S | N | DELETED | P | M |
| T | P | F | R | L | Y | V | G | S | N | P | DELETED | I |
| T | P | F | R | L | Y | V | G | S | N | P | DELETED | M |
| T | P | F | R | L | Y | V | G | S | N | P | P | I |
| T | P | F | R | L | Y | V | G | S | N | P | P | M |
| T | P | F | R | L | Y | V | G | T | DELETED | DELETED | DELETED | I |
| T | P | F | R | L | Y | V | G | T | DELETED | DELETED | DELETED | M |
| T | P | F | R | L | Y | V | G | T | DELETED | DELETED | P | I |
| T | P | F | R | L | Y | V | G | T | DELETED | DELETED | P | M |
| T | P | F | R | L | Y | V | G | T | DELETED | P | DELETED | I |
| T | P | F | R | L | Y | V | G | T | DELETED | P | DELETED | M |
| T | P | F | R | L | Y | V | G | T | DELETED | P | P | I |
| T | P | F | R | L | Y | V | G | T | DELETED | P | P | M |
| T | P | F | R | L | Y | V | G | T | N | DELETED | DELETED | I |
| T | P | F | R | L | Y | V | G | T | N | DELETED | DELETED | M |
| T | P | F | R | L | Y | V | G | T | N | DELETED | P | I |
| T | P | F | R | L | Y | V | G | T | N | DELETED | P | M |
| T | P | F | R | L | Y | V | G | T | N | P | DELETED | I |
| T | P | F | R | L | Y | V | G | T | N | P | DELETED | M |
| T | P | F | R | L | Y | V | G | T | N | P | P | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| T | P | F | R | L | Y | V | G | T | N | P | P | M |
| T | P | F | R | L | H | Q | S | S | DELETED | DELETED | DELETED | I |
| T | P | F | R | L | H | Q | S | S | DELETED | DELETED | DELETED | M |
| T | P | F | R | L | H | Q | S | S | DELETED | DELETED | P | I |
| T | P | F | R | L | H | Q | S | S | DELETED | DELETED | P | M |
| T | P | F | R | L | H | Q | S | S | DELETED | P | DELETED | I |
| T | P | F | R | L | H | Q | S | S | DELETED | P | DELETED | M |
| T | P | F | R | L | H | Q | S | S | DELETED | P | P | I |
| T | P | F | R | L | H | Q | S | S | DELETED | P | P | M |
| T | P | F | R | L | H | Q | S | S | N | DELETED | DELETED | I |
| T | P | F | R | L | H | Q | S | S | N | DELETED | DELETED | M |
| T | P | F | R | L | H | Q | S | S | N | DELETED | P | I |
| T | P | F | R | L | H | Q | S | S | N | DELETED | P | M |
| T | P | F | R | L | H | Q | S | S | N | P | DELETED | I |
| T | P | F | R | L | H | Q | S | S | N | P | DELETED | M |
| T | P | F | R | L | H | Q | S | S | N | P | P | I |
| T | P | F | R | L | H | Q | S | S | N | P | P | M |
| T | P | F | R | L | H | Q | S | T | DELETED | DELETED | DELETED | I |
| T | P | F | R | L | H | Q | S | T | DELETED | DELETED | DELETED | M |
| T | P | F | R | L | H | Q | S | T | DELETED | DELETED | P | I |
| T | P | F | R | L | H | Q | S | T | DELETED | DELETED | P | M |
| T | P | F | R | L | H | Q | S | T | DELETED | P | DELETED | I |
| T | P | F | R | L | H | Q | S | T | DELETED | P | DELETED | M |
| T | P | F | R | L | H | Q | S | T | DELETED | P | P | I |
| T | P | F | R | L | H | Q | S | T | DELETED | P | P | M |
| T | P | F | R | L | H | Q | S | T | N | DELETED | DELETED | I |
| T | P | F | R | L | H | Q | S | T | N | DELETED | DELETED | M |
| T | P | F | R | L | H | Q | S | T | N | DELETED | P | I |
| T | P | F | R | L | H | Q | S | T | N | DELETED | P | M |
| T | P | F | R | L | H | Q | S | T | N | P | DELETED | I |
| T | P | F | R | L | H | Q | S | T | N | P | DELETED | M |
| T | P | F | R | L | H | Q | S | T | N | P | P | I |
| T | P | F | R | L | H | Q | S | T | N | P | P | M |
| T | P | F | R | L | H | Q | G | S | DELETED | DELETED | DELETED | I |
| T | P | F | R | L | H | Q | G | S | DELETED | DELETED | DELETED | M |
| T | P | F | R | L | H | Q | G | S | DELETED | DELETED | P | I |
| T | P | F | R | L | H | Q | G | S | DELETED | DELETED | P | M |
| T | P | F | R | L | H | Q | G | S | DELETED | P | DELETED | I |
| T | P | F | R | L | H | Q | G | S | DELETED | P | DELETED | M |
| T | P | F | R | L | H | Q | G | S | DELETED | P | P | I |
| T | P | F | R | L | H | Q | G | S | DELETED | P | P | M |
| T | P | F | R | L | H | Q | G | S | N | DELETED | DELETED | I |
| T | P | F | R | L | H | Q | G | S | N | DELETED | DELETED | M |
| T | P | F | R | L | H | Q | G | S | N | DELETED | P | I |
| T | P | F | R | L | H | Q | G | S | N | DELETED | P | M |
| T | P | F | R | L | H | Q | G | S | N | P | DELETED | I |
| T | P | F | R | L | H | Q | G | S | N | P | DELETED | M |
| T | P | F | R | L | H | Q | G | S | N | P | P | I |
| T | P | F | R | L | H | Q | G | S | N | P | P | M |
| T | P | F | R | L | H | Q | G | T | DELETED | DELETED | DELETED | I |
| T | P | F | R | L | H | Q | G | T | DELETED | DELETED | DELETED | M |
| T | P | F | R | L | H | Q | G | T | DELETED | DELETED | P | I |
| T | P | F | R | L | H | Q | G | T | DELETED | DELETED | P | M |
| T | P | F | R | L | H | Q | G | T | DELETED | P | DELETED | I |
| T | P | F | R | L | H | Q | G | T | DELETED | P | DELETED | M |
| T | P | F | R | L | H | Q | G | T | DELETED | P | P | I |
| T | P | F | R | L | H | Q | G | T | DELETED | P | P | M |
| T | P | F | R | L | H | Q | G | T | N | DELETED | DELETED | I |
| T | P | F | R | L | H | Q | G | T | N | DELETED | DELETED | M |
| T | P | F | R | L | H | Q | G | T | N | DELETED | P | I |
| T | P | F | R | L | H | Q | G | T | N | DELETED | P | M |
| T | P | F | R | L | H | Q | G | T | N | P | DELETED | I |
| T | P | F | R | L | H | Q | G | T | N | P | DELETED | M |
| T | P | F | R | L | H | Q | G | T | N | P | P | I |
| T | P | F | R | L | H | Q | G | T | N | P | P | M |
| T | P | F | R | L | H | V | S | S | DELETED | DELETED | DELETED | I |
| T | P | F | R | L | H | V | S | S | DELETED | DELETED | DELETED | M |
| T | P | F | R | L | H | V | S | S | DELETED | DELETED | P | I |
| T | P | F | R | L | H | V | S | S | DELETED | DELETED | P | M |
| T | P | F | R | L | H | V | S | S | DELETED | P | DELETED | I |
| T | P | F | R | L | H | V | S | S | DELETED | P | DELETED | M |
| T | P | F | R | L | H | V | S | S | DELETED | P | P | I |
| T | P | F | R | L | H | V | S | S | DELETED | P | P | M |
| T | P | F | R | L | H | V | S | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | R | L | H | V | S | S | N | DELETED | DELETED | M |
| T | P | F | R | L | H | V | S | S | N | DELETED | P | I |
| T | P | F | R | L | H | V | S | S | N | DELETED | P | M |
| T | P | F | R | L | H | V | S | S | N | P | DELETED | I |
| T | P | F | R | L | H | V | S | S | N | P | DELETED | M |
| T | P | F | R | L | H | V | S | S | N | P | P | I |
| T | P | F | R | L | H | V | S | S | N | P | P | M |
| T | P | F | R | L | H | V | S | T | DELETED | DELETED | DELETED | I |
| T | P | F | R | L | H | V | S | T | DELETED | DELETED | DELETED | M |
| T | P | F | R | L | H | V | S | T | DELETED | DELETED | P | I |
| T | P | F | R | L | H | V | S | T | DELETED | DELETED | P | M |
| T | P | F | R | L | H | V | S | T | DELETED | P | DELETED | I |
| T | P | F | R | L | H | V | S | T | DELETED | P | DELETED | M |
| T | P | F | R | L | H | V | S | T | DELETED | P | P | I |
| T | P | F | R | L | H | V | S | T | DELETED | P | P | M |
| T | P | F | R | L | H | V | S | T | N | DELETED | DELETED | I |
| T | P | F | R | L | H | V | S | T | N | DELETED | DELETED | M |
| T | P | F | R | L | H | V | S | T | N | DELETED | P | I |
| T | P | F | R | L | H | V | S | T | N | DELETED | P | M |
| T | P | F | R | L | H | V | S | T | N | P | DELETED | I |
| T | P | F | R | L | H | V | S | T | N | P | DELETED | M |
| T | P | F | R | L | H | V | S | T | N | P | P | I |
| T | P | F | R | L | H | V | S | T | N | P | P | M |
| T | P | F | R | L | H | V | G | S | DELETED | DELETED | DELETED | I |
| T | P | F | R | L | H | V | G | S | DELETED | DELETED | DELETED | M |
| T | P | F | R | L | H | V | G | S | DELETED | DELETED | P | I |
| T | P | F | R | L | H | V | G | S | DELETED | DELETED | P | M |
| T | P | F | R | L | H | V | G | S | DELETED | P | DELETED | I |
| T | P | F | R | L | H | V | G | S | DELETED | P | DELETED | M |
| T | P | F | R | L | H | V | G | S | DELETED | P | P | I |
| T | P | F | R | L | H | V | G | S | DELETED | P | P | M |
| T | P | F | R | L | H | V | G | S | N | DELETED | DELETED | I |
| T | P | F | R | L | H | V | G | S | N | DELETED | DELETED | M |
| T | P | F | R | L | H | V | G | S | N | DELETED | P | I |
| T | P | F | R | L | H | V | G | S | N | DELETED | P | M |
| T | P | F | R | L | H | V | G | S | N | P | DELETED | I |
| T | P | F | R | L | H | V | G | S | N | P | DELETED | M |
| T | P | F | R | L | H | V | G | S | N | P | P | I |
| T | P | F | R | L | H | V | G | S | N | P | P | M |
| T | P | F | R | L | H | V | G | T | DELETED | DELETED | DELETED | I |
| T | P | F | R | L | H | V | G | T | DELETED | DELETED | DELETED | M |
| T | P | F | R | L | H | V | G | T | DELETED | DELETED | P | I |
| T | P | F | R | L | H | V | G | T | DELETED | DELETED | P | M |
| T | P | F | R | L | H | V | G | T | DELETED | P | DELETED | I |
| T | P | F | R | L | H | V | G | T | DELETED | P | DELETED | M |
| T | P | F | R | L | H | V | G | T | DELETED | P | P | I |
| T | P | F | R | L | H | V | G | T | DELETED | P | P | M |
| T | P | F | R | L | H | V | G | T | N | DELETED | DELETED | I |
| T | P | F | R | L | H | V | G | T | N | DELETED | DELETED | M |
| T | P | F | R | L | H | V | G | T | N | DELETED | P | I |
| T | P | F | R | L | H | V | G | T | N | DELETED | P | M |
| T | P | F | R | L | H | V | G | T | N | P | DELETED | I |
| T | P | F | R | L | H | V | G | T | N | P | DELETED | M |
| T | P | F | R | L | H | V | G | T | N | P | P | I |
| T | P | F | R | L | H | V | G | T | N | P | P | M |
| T | P | F | R | I | Y | Q | S | S | DELETED | DELETED | DELETED | I |
| T | P | F | R | I | Y | Q | S | S | DELETED | DELETED | DELETED | M |
| T | P | F | R | I | Y | Q | S | S | DELETED | DELETED | P | I |
| T | P | F | R | I | Y | Q | S | S | DELETED | DELETED | P | M |
| T | P | F | R | I | Y | Q | S | S | DELETED | P | DELETED | I |
| T | P | F | R | I | Y | Q | S | S | DELETED | P | DELETED | M |
| T | P | F | R | I | Y | Q | S | S | DELETED | P | P | I |
| T | P | F | R | I | Y | Q | S | S | DELETED | P | P | M |
| T | P | F | R | I | Y | Q | S | S | N | DELETED | DELETED | I |
| T | P | F | R | I | Y | Q | S | S | N | DELETED | DELETED | M |
| T | P | F | R | I | Y | Q | S | S | N | DELETED | P | I |
| T | P | F | R | I | Y | Q | S | S | N | DELETED | P | M |
| T | P | F | R | I | Y | Q | S | S | N | P | DELETED | I |
| T | P | F | R | I | Y | Q | S | S | N | P | DELETED | M |
| T | P | F | R | I | Y | Q | S | S | N | P | P | I |
| T | P | F | R | I | Y | Q | S | S | N | P | P | M |
| T | P | F | R | I | Y | Q | S | T | DELETED | DELETED | DELETED | I |
| T | P | F | R | I | Y | Q | S | T | DELETED | DELETED | DELETED | M |
| T | P | F | R | I | Y | Q | S | T | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | R | I | Y | Q | S | T | DELETED | DELETED | P | M |
| T | P | F | R | I | Y | Q | S | T | DELETED | P | DELETED | I |
| T | P | F | R | I | Y | Q | S | T | DELETED | P | DELETED | M |
| T | P | F | R | I | Y | Q | S | T | DELETED | P | P | I |
| T | P | F | R | I | Y | Q | S | T | DELETED | P | P | M |
| T | P | F | R | I | Y | Q | S | T | N | DELETED | DELETED | I |
| T | P | F | R | I | Y | Q | S | T | N | DELETED | DELETED | M |
| T | P | F | R | I | Y | Q | S | T | N | DELETED | P | I |
| T | P | F | R | I | Y | Q | S | T | N | DELETED | P | M |
| T | P | F | R | I | Y | Q | S | T | N | P | DELETED | I |
| T | P | F | R | I | Y | Q | S | T | N | P | DELETED | M |
| T | P | F | R | I | Y | Q | S | T | N | P | P | I |
| T | P | F | R | I | Y | Q | S | T | N | P | P | M |
| T | P | F | R | I | Y | Q | G | S | DELETED | DELETED | DELETED | I |
| T | P | F | R | I | Y | Q | G | S | DELETED | DELETED | DELETED | M |
| T | P | F | R | I | Y | Q | G | S | DELETED | DELETED | P | I |
| T | P | F | R | I | Y | Q | G | S | DELETED | DELETED | P | M |
| T | P | F | R | I | Y | Q | G | S | DELETED | P | DELETED | I |
| T | P | F | R | I | Y | Q | G | S | DELETED | P | DELETED | M |
| T | P | F | R | I | Y | Q | G | S | DELETED | P | P | I |
| T | P | F | R | I | Y | Q | G | S | DELETED | P | P | M |
| T | P | F | R | I | Y | Q | G | S | N | DELETED | DELETED | I |
| T | P | F | R | I | Y | Q | G | S | N | DELETED | DELETED | M |
| T | P | F | R | I | Y | Q | G | S | N | DELETED | P | I |
| T | P | F | R | I | Y | Q | G | S | N | DELETED | P | M |
| T | P | F | R | I | Y | Q | G | S | N | P | DELETED | I |
| T | P | F | R | I | Y | Q | G | S | N | P | DELETED | M |
| T | P | F | R | I | Y | Q | G | S | N | P | P | I |
| T | P | F | R | I | Y | Q | G | S | N | P | P | M |
| T | P | F | R | I | Y | Q | G | T | DELETED | DELETED | DELETED | I |
| T | P | F | R | I | Y | Q | G | T | DELETED | DELETED | DELETED | M |
| T | P | F | R | I | Y | Q | G | T | DELETED | DELETED | P | I |
| T | P | F | R | I | Y | Q | G | T | DELETED | DELETED | P | M |
| T | P | F | R | I | Y | Q | G | T | DELETED | P | DELETED | I |
| T | P | F | R | I | Y | Q | G | T | DELETED | P | DELETED | M |
| T | P | F | R | I | Y | Q | G | T | DELETED | P | P | I |
| T | P | F | R | I | Y | Q | G | T | DELETED | P | P | M |
| T | P | F | R | I | Y | Q | G | T | N | DELETED | DELETED | I |
| T | P | F | R | I | Y | Q | G | T | N | DELETED | DELETED | M |
| T | P | F | R | I | Y | Q | G | T | N | DELETED | P | I |
| T | P | F | R | I | Y | Q | G | T | N | DELETED | P | M |
| T | P | F | R | I | Y | Q | G | T | N | P | DELETED | I |
| T | P | F | R | I | Y | Q | G | T | N | P | DELETED | M |
| T | P | F | R | I | Y | Q | G | T | N | P | P | I |
| T | P | F | R | I | Y | Q | G | T | N | P | P | M |
| T | P | F | R | I | Y | V | S | S | DELETED | DELETED | DELETED | I |
| T | P | F | R | I | Y | V | S | S | DELETED | DELETED | DELETED | M |
| T | P | F | R | I | Y | V | S | S | DELETED | DELETED | P | I |
| T | P | F | R | I | Y | V | S | S | DELETED | DELETED | P | M |
| T | P | F | R | I | Y | V | S | S | DELETED | P | DELETED | I |
| T | P | F | R | I | Y | V | S | S | DELETED | P | DELETED | M |
| T | P | F | R | I | Y | V | S | S | DELETED | P | P | I |
| T | P | F | R | I | Y | V | S | S | DELETED | P | P | M |
| T | P | F | R | I | Y | V | S | S | N | DELETED | DELETED | I |
| T | P | F | R | I | Y | V | S | S | N | DELETED | DELETED | M |
| T | P | F | R | I | Y | V | S | S | N | DELETED | P | I |
| T | P | F | R | I | Y | V | S | S | N | DELETED | P | M |
| T | P | F | R | I | Y | V | S | S | N | P | DELETED | I |
| T | P | F | R | I | Y | V | S | S | N | P | DELETED | M |
| T | P | F | R | I | Y | V | S | S | N | P | P | I |
| T | P | F | R | I | Y | V | S | S | N | P | P | M |
| T | P | F | R | I | Y | V | S | T | DELETED | DELETED | DELETED | I |
| T | P | F | R | I | Y | V | S | T | DELETED | DELETED | DELETED | M |
| T | P | F | R | I | Y | V | S | T | DELETED | DELETED | P | I |
| T | P | F | R | I | Y | V | S | T | DELETED | DELETED | P | M |
| T | P | F | R | I | Y | V | S | T | DELETED | P | DELETED | I |
| T | P | F | R | I | Y | V | S | T | DELETED | P | DELETED | M |
| T | P | F | R | I | Y | V | S | T | DELETED | P | P | I |
| T | P | F | R | I | Y | V | S | T | DELETED | P | P | M |
| T | P | F | R | I | Y | V | S | T | N | DELETED | DELETED | I |
| T | P | F | R | I | Y | V | S | T | N | DELETED | DELETED | M |
| T | P | F | R | I | Y | V | S | T | N | DELETED | P | I |
| T | P | F | R | I | Y | V | S | T | N | DELETED | P | M |
| T | P | F | R | I | Y | V | S | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | R | I | Y | V | S | T | N | P | DELETED | M |
| T | P | F | R | I | Y | V | S | T | N | P | P | I |
| T | P | F | R | I | Y | V | S | T | N | P | P | M |
| T | P | F | R | I | Y | V | G | S | DELETED | DELETED | DELETED | I |
| T | P | F | R | I | Y | V | G | S | DELETED | DELETED | DELETED | M |
| T | P | F | R | I | Y | V | G | S | DELETED | DELETED | P | I |
| T | P | F | R | I | Y | V | Gs | S | DELETED | DELETED | P | M |
| T | P | F | R | I | Y | V | G | S | DELETED | P | DELETED | I |
| T | P | F | R | I | Y | V | G | S | DELETED | P | DELETED | M |
| T | P | F | R | I | Y | V | G | S | DELETED | P | P | I |
| T | P | F | R | I | Y | V | G | S | DELETED | P | P | M |
| T | P | F | R | I | Y | V | G | S | N | DELETED | DELETED | I |
| T | P | F | R | I | Y | V | G | S | N | DELETED | DELETED | M |
| T | P | F | R | I | Y | V | G | S | N | DELETED | P | I |
| T | P | F | R | I | Y | V | G | S | N | DELETED | P | M |
| T | P | F | R | I | Y | V | G | S | N | P | DELETED | I |
| T | P | F | R | I | Y | V | G | S | N | P | DELETED | M |
| T | P | F | R | I | Y | V | G | S | N | P | P | I |
| T | P | F | R | I | Y | V | G | S | N | P | P | M |
| T | P | F | R | I | Y | V | G | T | DELETED | DELETED | DELETED | I |
| T | P | F | R | I | Y | V | G | T | DELETED | DELETED | DELETED | M |
| T | P | F | R | I | Y | V | G | T | DELETED | DELETED | P | I |
| T | P | F | R | I | Y | V | G | T | DELETED | DELETED | P | M |
| T | P | F | R | I | Y | V | G | T | DELETED | P | DELETED | I |
| T | P | F | R | I | Y | V | G | T | DELETED | P | DELETED | M |
| T | P | F | R | I | Y | V | G | T | DELETED | P | P | I |
| T | P | F | R | I | Y | V | G | T | DELETED | P | P | M |
| T | P | F | R | I | Y | V | G | T | N | DELETED | DELETED | I |
| T | P | F | R | I | Y | V | G | T | N | DELETED | DELETED | M |
| T | P | F | R | I | Y | V | G | T | N | DELETED | P | I |
| T | P | F | R | I | Y | V | G | T | N | DELETED | P | M |
| T | P | F | R | I | Y | V | G | T | N | P | DELETED | I |
| T | P | F | R | I | Y | V | G | T | N | P | DELETED | M |
| T | P | F | R | I | Y | V | G | T | N | P | P | I |
| T | P | F | R | I | Y | V | G | T | N | P | P | M |
| T | P | F | R | I | H | Q | S | S | DELETED | DELETED | DELETED | I |
| T | P | F | R | I | H | Q | S | S | DELETED | DELETED | DELETED | M |
| T | P | F | R | I | H | Q | S | S | DELETED | DELETED | P | I |
| T | P | F | R | I | H | Q | S | S | DELETED | DELETED | P | M |
| T | P | F | R | I | H | Q | S | S | DELETED | P | DELETED | I |
| T | P | F | R | I | H | Q | S | S | DELETED | P | DELETED | M |
| T | P | F | R | I | H | Q | S | S | DELETED | P | P | I |
| T | P | F | R | I | H | Q | S | S | DELETED | P | P | M |
| T | P | F | R | I | H | Q | S | S | N | DELETED | DELETED | I |
| T | P | F | R | I | H | Q | S | S | N | DELETED | DELETED | M |
| T | P | F | R | I | H | Q | S | S | N | DELETED | P | I |
| T | P | F | R | I | H | Q | S | S | N | DELETED | P | M |
| T | P | F | R | I | H | Q | S | S | N | P | DELETED | I |
| T | P | F | R | I | H | Q | S | S | N | P | DELETED | M |
| T | P | F | R | I | H | Q | S | S | N | P | P | I |
| T | P | F | R | I | H | Q | S | S | N | P | P | M |
| T | P | F | R | I | H | Q | S | T | DELETED | DELETED | DELETED | I |
| T | P | F | R | I | H | Q | S | T | DELETED | DELETED | DELETED | M |
| T | P | F | R | I | H | Q | S | T | DELETED | DELETED | P | I |
| T | P | F | R | I | H | Q | S | T | DELETED | DELETED | P | M |
| T | P | F | R | I | H | Q | S | T | DELETED | P | DELETED | I |
| T | P | F | R | I | H | Q | S | T | DELETED | P | DELETED | M |
| T | P | F | R | I | H | Q | S | T | DELETED | P | P | I |
| T | P | F | R | I | H | Q | S | T | DELETED | P | P | M |
| T | P | F | R | I | H | Q | S | T | N | DELETED | DELETED | I |
| T | P | F | R | I | H | Q | S | T | N | DELETED | DELETED | M |
| T | P | F | R | I | H | Q | S | T | N | DELETED | P | I |
| T | P | F | R | I | H | Q | S | T | N | DELETED | P | M |
| T | P | F | R | I | H | Q | S | T | N | P | DELETED | I |
| T | P | F | R | I | H | Q | S | T | N | P | DELETED | M |
| T | P | F | R | I | H | Q | S | T | N | P | P | I |
| T | P | F | R | I | H | Q | S | T | N | P | P | M |
| T | P | F | R | I | H | Q | G | S | DELETED | DELETED | DELETED | I |
| T | P | F | R | I | H | Q | G | S | DELETED | DELETED | DELETED | M |
| T | P | F | R | I | H | Q | G | S | DELETED | DELETED | P | I |
| T | P | F | R | I | H | Q | G | S | DELETED | DELETED | P | M |
| T | P | F | R | I | H | Q | G | S | DELETED | P | DELETED | I |
| T | P | F | R | I | H | Q | G | S | DELETED | P | DELETED | M |
| T | P | F | R | I | H | Q | G | S | DELETED | P | P | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| T | P | F | R | I | H | Q | G | S | DELETED | P | P | M |
| T | P | F | R | I | H | Q | G | S | N | DELETED | DELETED | I |
| T | P | F | R | I | H | Q | G | S | N | DELETED | DELETED | M |
| T | P | F | R | I | H | Q | G | S | N | DELETED | P | I |
| T | P | F | R | I | H | Q | G | S | N | DELETED | P | M |
| T | P | F | R | I | H | Q | G | S | N | P | DELETED | I |
| T | P | F | R | I | H | Q | G | S | N | P | DELETED | M |
| T | P | F | R | I | H | Q | G | S | N | P | P | I |
| T | P | F | R | I | H | Q | G | S | N | P | P | M |
| T | P | F | R | I | H | Q | G | T | DELETED | DELETED | DELETED | I |
| T | P | F | R | I | H | Q | G | T | DELETED | DELETED | DELETED | M |
| T | P | F | R | I | H | Q | G | T | DELETED | DELETED | P | I |
| T | P | F | R | I | H | Q | G | T | DELETED | DELETED | P | M |
| T | P | F | R | I | H | Q | G | T | DELETED | P | DELETED | I |
| T | P | F | R | I | H | Q | G | T | DELETED | P | DELETED | M |
| T | P | F | R | I | H | Q | G | T | DELETED | P | P | I |
| T | P | F | R | I | H | Q | G | T | DELETED | P | P | M |
| T | P | F | R | I | H | Q | G | T | N | DELETED | DELETED | I |
| T | P | F | R | I | H | Q | G | T | N | DELETED | DELETED | M |
| T | P | F | R | I | H | Q | G | T | N | DELETED | P | I |
| T | P | F | R | I | H | Q | G | T | N | DELETED | P | M |
| T | P | F | R | I | H | Q | G | T | N | P | DELETED | I |
| T | P | F | R | I | H | Q | G | T | N | P | DELETED | M |
| T | P | F | R | I | H | Q | G | T | N | P | P | I |
| T | P | F | R | I | H | Q | G | T | N | P | P | M |
| T | P | F | R | I | H | V | S | S | DELETED | DELETED | DELETED | I |
| T | P | F | R | I | H | V | S | S | DELETED | DELETED | DELETED | M |
| T | P | F | R | I | H | V | S | S | DELETED | DELETED | P | I |
| T | P | F | R | I | H | V | S | S | DELETED | DELETED | P | M |
| T | P | F | R | I | H | V | S | S | DELETED | P | DELETED | I |
| T | P | F | R | I | H | V | S | S | DELETED | P | DELETED | M |
| T | P | F | R | I | H | V | S | S | DELETED | P | P | I |
| T | P | F | R | I | H | V | S | S | DELETED | P | P | M |
| T | P | F | R | I | H | V | S | S | N | DELETED | DELETED | I |
| T | P | F | R | I | H | V | S | S | N | DELETED | DELETED | M |
| T | P | F | R | I | H | V | S | S | N | DELETED | P | I |
| T | P | F | R | I | H | V | S | S | N | DELETED | P | M |
| T | P | F | R | I | H | V | S | S | N | P | DELETED | I |
| T | P | F | R | I | H | V | S | S | N | P | DELETED | M |
| T | P | F | R | I | H | V | S | S | N | P | P | I |
| T | P | F | R | I | H | V | S | S | N | P | P | M |
| T | P | F | R | I | H | V | S | T | DELETED | DELETED | DELETED | I |
| T | P | F | R | I | H | V | S | T | DELETED | DELETED | DELETED | M |
| T | P | F | R | I | H | V | S | T | DELETED | DELETED | P | I |
| T | P | F | R | I | H | V | S | T | DELETED | DELETED | P | M |
| T | P | F | R | I | H | V | S | T | DELETED | P | DELETED | I |
| T | P | F | R | I | H | V | S | T | DELETED | P | DELETED | M |
| T | P | F | R | I | H | V | S | T | DELETED | P | P | I |
| T | P | F | R | I | H | V | S | T | DELETED | P | P | M |
| T | P | F | R | I | H | V | S | T | N | DELETED | DELETED | I |
| T | P | F | R | I | H | V | S | T | N | DELETED | DELETED | M |
| T | P | F | R | I | H | V | S | T | N | DELETED | P | I |
| T | P | F | R | I | H | V | S | T | N | DELETED | P | M |
| T | P | F | R | I | H | V | S | T | N | P | DELETED | I |
| T | P | F | R | I | H | V | S | T | N | P | DELETED | M |
| T | P | F | R | I | H | V | S | T | N | P | P | I |
| T | P | F | R | I | H | V | S | T | N | P | P | M |
| T | P | F | R | I | H | V | G | S | DELETED | DELETED | DELETED | I |
| T | P | F | R | I | H | V | G | S | DELETED | DELETED | DELETED | M |
| T | P | F | R | I | H | V | G | S | DELETED | DELETED | P | I |
| T | P | F | R | I | H | V | G | S | DELETED | DELETED | P | M |
| T | P | F | R | I | H | V | G | S | DELETED | P | DELETED | I |
| T | P | F | R | I | H | V | G | S | DELETED | P | DELETED | M |
| T | P | F | R | I | H | V | G | S | DELETED | P | P | I |
| T | P | F | R | I | H | V | G | S | DELETED | P | P | M |
| T | P | F | R | I | H | V | G | S | N | DELETED | DELETED | I |
| T | P | F | R | I | H | V | G | S | N | DELETED | DELETED | M |
| T | P | F | R | I | H | V | G | S | N | DELETED | P | I |
| T | P | F | R | I | H | V | G | S | N | DELETED | P | M |
| T | P | F | R | I | H | V | G | S | N | P | DELETED | I |
| T | P | F | R | I | H | V | G | S | N | P | DELETED | M |
| T | P | F | R | I | H | V | G | S | N | P | P | I |
| T | P | F | R | I | H | V | G | S | N | P | P | M |
| T | P | F | R | I | H | V | G | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| T | P | F | R | I | H | V | G | T | DELETED | DELETED | DELETED | M |
| T | P | F | R | I | H | V | G | T | DELETED | DELETED | P | I |
| T | P | F | R | I | H | V | G | T | DELETED | DELETED | P | M |
| T | P | F | R | I | H | V | G | T | DELETED | P | DELETED | I |
| T | P | F | R | I | H | V | G | T | DELETED | P | DELETED | M |
| T | P | F | R | I | H | V | G | T | DELETED | P | P | I |
| T | P | F | R | I | H | V | G | T | DELETED | P | P | M |
| T | P | F | R | I | H | V | G | T | N | DELETED | DELETED | I |
| T | P | F | R | I | H | V | G | T | N | DELETED | DELETED | M |
| T | P | F | R | I | H | V | G | T | N | DELETED | P | I |
| T | P | F | R | I | H | V | G | T | N | DELETED | P | M |
| T | P | F | R | I | H | V | G | T | N | P | DELETED | I |
| T | P | F | R | I | H | V | G | T | N | P | DELETED | M |
| T | P | F | R | I | H | V | G | T | N | P | P | I |
| T | P | F | R | I | H | V | G | T | N | P | P | M |
| S | A | I | S | L | Y | Q | S | S | DELETED | DELETED | DELETED | I |
| S | A | I | S | L | Y | Q | S | S | DELETED | DELETED | DELETED | M |
| S | A | I | S | L | Y | Q | S | S | DELETED | DELETED | P | I |
| S | A | I | S | L | Y | Q | S | S | DELETED | DELETED | P | M |
| S | A | I | S | L | Y | Q | S | S | DELETED | P | DELETED | I |
| S | A | I | S | L | Y | Q | S | S | DELETED | P | DELETED | M |
| S | A | I | S | L | Y | Q | S | S | DELETED | P | P | I |
| S | A | I | S | L | Y | Q | S | S | DELETED | P | P | M |
| S | A | I | S | L | Y | Q | S | S | N | DELETED | DELETED | I |
| S | A | I | S | L | Y | Q | S | S | N | DELETED | DELETED | M |
| S | A | I | S | L | Y | Q | S | S | N | DELETED | P | I |
| S | A | I | S | L | Y | Q | S | S | N | DELETED | P | M |
| S | A | I | S | L | Y | Q | S | S | N | P | DELETED | I |
| S | A | I | S | L | Y | Q | S | S | N | P | DELETED | M |
| S | A | I | S | L | Y | Q | S | S | N | P | P | I |
| S | A | I | S | L | Y | Q | S | S | N | P | P | M |
| S | A | I | S | L | Y | Q | S | T | DELETED | DELETED | DELETED | I |
| S | A | I | S | L | Y | Q | S | T | DELETED | DELETED | DELETED | M |
| S | A | I | S | L | Y | Q | S | T | DELETED | DELETED | P | I |
| S | A | I | S | L | Y | Q | S | T | DELETED | DELETED | P | M |
| S | A | I | S | L | Y | Q | S | T | DELETED | P | DELETED | I |
| S | A | I | S | L | Y | Q | S | T | DELETED | P | DELETED | M |
| S | A | I | S | L | Y | Q | S | T | DELETED | P | P | I |
| S | A | I | S | L | Y | Q | S | T | DELETED | P | P | M |
| S | A | I | S | L | Y | Q | S | T | N | DELETED | DELETED | I |
| S | A | I | S | L | Y | Q | S | T | N | DELETED | DELETED | M |
| S | A | I | S | L | Y | Q | S | T | N | DELETED | P | I |
| S | A | I | S | L | Y | Q | S | T | N | DELETED | P | M |
| S | A | I | S | L | Y | Q | S | T | N | P | DELETED | I |
| S | A | I | S | L | Y | Q | S | T | N | P | DELETED | M |
| S | A | I | S | L | Y | Q | S | T | N | P | P | I |
| S | A | I | S | L | Y | Q | S | T | N | P | P | M |
| S | A | I | S | L | Y | Q | G | S | DELETED | DELETED | DELETED | I |
| S | A | I | S | L | Y | Q | G | S | DELETED | DELETED | DELETED | M |
| S | A | I | S | L | Y | Q | G | S | DELETED | DELETED | P | I |
| S | A | I | S | L | Y | Q | G | S | DELETED | DELETED | P | M |
| S | A | I | S | L | Y | Q | G | S | DELETED | P | DELETED | I |
| S | A | I | S | L | Y | Q | G | S | DELETED | P | DELETED | M |
| S | A | I | S | L | Y | Q | G | S | DELETED | P | P | I |
| S | A | I | S | L | Y | Q | G | S | DELETED | P | P | M |
| S | A | I | S | L | Y | Q | G | S | N | DELETED | DELETED | I |
| S | A | I | S | L | Y | Q | G | S | N | DELETED | DELETED | M |
| S | A | I | S | L | Y | Q | G | S | N | DELETED | P | I |
| S | A | I | S | L | Y | Q | G | S | N | DELETED | P | M |
| S | A | I | S | L | Y | Q | G | S | N | P | DELETED | I |
| S | A | I | S | L | Y | Q | G | S | N | P | DELETED | M |
| S | A | I | S | L | Y | Q | G | S | N | P | P | I |
| S | A | I | S | L | Y | Q | G | S | N | P | P | M |
| S | A | I | S | L | Y | Q | G | T | DELETED | DELETED | DELETED | I |
| S | A | I | S | L | Y | Q | G | T | DELETED | DELETED | DELETED | M |
| S | A | I | S | L | Y | Q | G | T | DELETED | DELETED | P | I |
| S | A | I | S | L | Y | Q | G | T | DELETED | DELETED | P | M |
| S | A | I | S | L | Y | Q | G | T | DELETED | P | DELETED | I |
| S | A | I | S | L | Y | Q | G | T | DELETED | P | DELETED | M |
| S | A | I | S | L | Y | Q | G | T | DELETED | P | P | I |
| S | A | I | S | L | Y | Q | G | T | DELETED | P | P | M |
| S | A | I | S | L | Y | Q | G | T | N | DELETED | DELETED | I |
| S | A | I | S | L | Y | Q | G | T | N | DELETED | DELETED | M |
| S | A | I | S | L | Y | Q | G | T | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | S | L | Y | Q | G | T | N | DELETED | P | M |
| S | A | I | S | L | Y | Q | G | T | N | P | DELETED | I |
| S | A | I | S | L | Y | Q | G | T | N | P | DELETED | M |
| S | A | I | S | L | Y | Q | G | T | N | P | P | I |
| S | A | I | S | L | Y | Q | G | T | N | P | P | M |
| S | A | I | S | L | Y | V | S | S | DELETED | DELETED | DELETED | I |
| S | A | I | S | L | Y | V | S | S | DELETED | DELETED | DELETED | M |
| S | A | I | S | L | Y | V | S | S | DELETED | DELETED | P | I |
| S | A | I | S | L | Y | V | S | S | DELETED | DELETED | P | M |
| S | A | I | S | L | Y | V | S | S | DELETED | P | DELETED | I |
| S | A | I | S | L | Y | V | S | S | DELETED | P | DELETED | M |
| S | A | I | S | L | Y | V | S | S | DELETED | P | P | I |
| S | A | I | S | L | Y | V | S | S | DELETED | P | P | M |
| S | A | I | S | L | Y | V | S | S | N | DELETED | DELETED | I |
| S | A | I | S | L | Y | V | S | S | N | DELETED | DELETED | M |
| S | A | I | S | L | Y | V | S | S | N | DELETED | P | I |
| S | A | I | S | L | Y | V | S | S | N | DELETED | P | M |
| S | A | I | S | L | Y | V | S | S | N | P | DELETED | I |
| S | A | I | S | L | Y | V | S | S | N | P | DELETED | M |
| S | A | I | S | L | Y | V | S | S | N | P | P | I |
| S | A | I | S | L | Y | V | S | S | N | P | P | M |
| S | A | I | S | L | Y | V | S | T | DELETED | DELETED | DELETED | I |
| S | A | I | S | L | Y | V | S | T | DELETED | DELETED | DELETED | M |
| S | A | I | S | L | Y | V | S | T | DELETED | DELETED | P | I |
| S | A | I | S | L | Y | V | S | T | DELETED | DELETED | P | M |
| S | A | I | S | L | Y | V | S | T | DELETED | P | DELETED | I |
| S | A | I | S | L | Y | V | S | T | DELETED | P | DELETED | M |
| S | A | I | S | L | Y | V | S | T | DELETED | P | P | I |
| S | A | I | S | L | Y | V | S | T | DELETED | P | P | M |
| S | A | I | S | L | Y | V | S | T | N | DELETED | DELETED | I |
| S | A | I | S | L | Y | V | S | T | N | DELETED | DELETED | M |
| S | A | I | S | L | Y | V | S | T | N | DELETED | P | I |
| S | A | I | S | L | Y | V | S | T | N | DELETED | P | M |
| S | A | I | S | L | Y | V | S | T | N | P | DELETED | I |
| S | A | I | S | L | Y | V | S | T | N | P | DELETED | M |
| S | A | I | S | L | Y | V | S | T | N | P | P | I |
| S | A | I | S | L | Y | V | S | T | N | P | P | M |
| S | A | I | S | L | Y | V | G | S | DELETED | DELETED | DELETED | I |
| S | A | I | S | L | Y | V | G | S | DELETED | DELETED | DELETED | M |
| S | A | I | S | L | Y | V | G | S | DELETED | DELETED | P | I |
| S | A | I | S | L | Y | V | G | S | DELETED | DELETED | P | M |
| S | A | I | S | L | Y | V | G | S | DELETED | P | DELETED | I |
| S | A | I | S | L | Y | V | G | S | DELETED | P | DELETED | M |
| S | A | I | S | L | Y | V | G | S | DELETED | P | P | I |
| S | A | I | S | L | Y | V | G | S | DELETED | P | P | M |
| S | A | I | S | L | Y | V | G | S | N | DELETED | DELETED | I |
| S | A | I | S | L | Y | V | G | S | N | DELETED | DELETED | M |
| S | A | I | S | L | Y | V | G | S | N | DELETED | P | I |
| S | A | I | S | L | Y | V | G | S | N | DELETED | P | M |
| S | A | I | S | L | Y | V | G | S | N | P | DELETED | I |
| S | A | I | S | L | Y | V | G | S | N | P | DELETED | M |
| S | A | I | S | L | Y | V | G | S | N | P | P | I |
| S | A | I | S | L | Y | V | G | S | N | P | P | M |
| S | A | I | S | L | Y | V | G | T | DELETED | DELETED | DELETED | I |
| S | A | I | S | L | Y | V | G | T | DELETED | DELETED | DELETED | M |
| S | A | I | S | L | Y | V | G | T | DELETED | DELETED | P | I |
| S | A | I | S | L | Y | V | G | T | DELETED | DELETED | P | M |
| S | A | I | S | L | Y | V | G | T | DELETED | P | DELETED | I |
| S | A | I | S | L | Y | V | G | T | DELETED | P | DELETED | M |
| S | A | I | S | L | Y | V | G | T | DELETED | P | P | I |
| S | A | I | S | L | Y | V | G | T | DELETED | P | P | M |
| S | A | I | S | L | Y | V | G | T | N | DELETED | DELETED | I |
| S | A | I | S | L | Y | V | G | T | N | DELETED | DELETED | M |
| S | A | I | S | L | Y | V | G | T | N | DELETED | P | I |
| S | A | I | S | L | Y | V | G | T | N | DELETED | P | M |
| S | A | I | S | L | Y | V | G | T | N | P | DELETED | I |
| S | A | I | S | L | Y | V | G | T | N | P | DELETED | M |
| S | A | I | S | L | Y | V | G | T | N | P | P | I |
| S | A | I | S | L | Y | V | G | T | N | P | P | M |
| S | A | I | S | L | H | Q | S | S | DELETED | DELETED | DELETED | I |
| S | A | I | S | L | H | Q | S | S | DELETED | DELETED | DELETED | M |
| S | A | I | S | L | H | Q | S | S | DELETED | DELETED | P | I |
| S | A | I | S | L | H | Q | S | S | DELETED | DELETED | P | M |
| S | A | I | S | L | H | Q | S | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | S | L | H | Q | S | S | DELETED | P | DELETED | M |
| S | A | I | S | L | H | Q | S | S | DELETED | P | P | I |
| S | A | I | S | L | H | Q | S | S | DELETED | P | P | M |
| S | A | I | S | L | H | Q | S | S | N | DELETED | DELETED | I |
| S | A | I | S | L | H | Q | S | S | N | DELETED | DELETED | M |
| S | A | I | S | L | H | Q | S | S | N | DELETED | P | I |
| S | A | I | S | L | H | Q | S | S | N | DELETED | P | M |
| S | A | I | S | L | H | Q | S | S | N | P | DELETED | I |
| S | A | I | S | L | H | Q | S | S | N | P | DELETED | M |
| S | A | I | S | L | H | Q | S | S | N | P | P | I |
| S | A | I | S | L | H | Q | S | S | N | P | P | M |
| S | A | I | S | L | H | Q | S | T | DELETED | DELETED | DELETED | I |
| S | A | I | S | L | H | Q | S | T | DELETED | DELETED | DELETED | M |
| S | A | I | S | L | H | Q | S | T | DELETED | DELETED | P | I |
| S | A | I | S | L | H | Q | S | T | DELETED | DELETED | P | M |
| S | A | I | S | L | H | Q | S | T | DELETED | P | DELETED | I |
| S | A | I | S | L | H | Q | S | T | DELETED | P | DELETED | M |
| S | A | I | S | L | H | Q | S | T | DELETED | P | P | I |
| S | A | I | S | L | H | Q | S | T | DELETED | P | P | M |
| S | A | I | S | L | H | Q | S | T | N | DELETED | DELETED | I |
| S | A | I | S | L | H | Q | S | T | N | DELETED | DELETED | M |
| S | A | I | S | L | H | Q | S | T | N | DELETED | P | I |
| S | A | I | S | L | H | Q | S | T | N | DELETED | P | M |
| S | A | I | S | L | H | Q | S | T | N | P | DELETED | I |
| S | A | I | S | L | H | Q | S | T | N | P | DELETED | M |
| S | A | I | S | L | H | Q | S | T | N | P | P | I |
| S | A | I | S | L | H | Q | S | T | N | P | P | M |
| S | A | I | S | L | H | Q | G | S | DELETED | DELETED | DELETED | I |
| S | A | I | S | L | H | Q | G | S | DELETED | DELETED | DELETED | M |
| S | A | I | S | L | H | Q | G | S | DELETED | DELETED | P | I |
| S | A | I | S | L | H | Q | G | S | DELETED | DELETED | P | M |
| S | A | I | S | L | H | Q | G | S | DELETED | P | DELETED | I |
| S | A | I | S | L | H | Q | G | S | DELETED | P | DELETED | M |
| S | A | I | S | L | H | Q | G | S | DELETED | P | P | I |
| S | A | I | S | L | H | Q | G | S | DELETED | P | P | M |
| S | A | I | S | L | H | Q | G | S | N | DELETED | DELETED | I |
| S | A | I | S | L | H | Q | G | S | N | DELETED | DELETED | M |
| S | A | I | S | L | H | Q | G | S | N | DELETED | P | I |
| S | A | I | S | L | H | Q | G | S | N | DELETED | P | M |
| S | A | I | S | L | H | Q | G | S | N | P | DELETED | I |
| S | A | I | S | L | H | Q | G | S | N | P | DELETED | M |
| S | A | I | S | L | H | Q | G | S | N | P | P | I |
| S | A | I | S | L | H | Q | G | S | N | P | P | M |
| S | A | I | S | L | H | Q | G | T | DELETED | DELETED | DELETED | I |
| S | A | I | S | L | H | Q | G | T | DELETED | DELETED | DELETED | M |
| S | A | I | S | L | H | Q | G | T | DELETED | DELETED | P | I |
| S | A | I | S | L | H | Q | G | T | DELETED | DELETED | P | M |
| S | A | I | S | L | H | Q | G | T | DELETED | P | DELETED | I |
| S | A | I | S | L | H | Q | G | T | DELETED | P | DELETED | M |
| S | A | I | S | L | H | Q | G | T | DELETED | P | P | I |
| S | A | I | S | L | H | Q | G | T | DELETED | P | P | M |
| S | A | I | S | L | H | Q | G | T | N | DELETED | DELETED | I |
| S | A | I | S | L | H | Q | G | T | N | DELETED | DELETED | M |
| S | A | I | S | L | H | Q | G | T | N | DELETED | P | I |
| S | A | I | S | L | H | Q | G | T | N | DELETED | P | M |
| S | A | I | S | L | H | Q | G | T | N | P | DELETED | I |
| S | A | I | S | L | H | Q | G | T | N | P | DELETED | M |
| S | A | I | S | L | H | Q | G | T | N | P | P | I |
| S | A | I | S | L | H | Q | G | T | N | P | P | M |
| S | A | I | S | L | H | V | S | S | DELETED | DELETED | DELETED | I |
| S | A | I | S | L | H | V | S | S | DELETED | DELETED | DELETED | M |
| S | A | I | S | L | H | V | S | S | DELETED | DELETED | P | I |
| S | A | I | S | L | H | V | S | S | DELETED | DELETED | P | M |
| S | A | I | S | L | H | V | S | S | DELETED | P | DELETED | I |
| S | A | I | S | L | H | V | S | S | DELETED | P | DELETED | M |
| S | A | I | S | L | H | V | S | S | DELETED | P | P | I |
| S | A | I | S | L | H | V | S | S | DELETED | P | P | M |
| S | A | I | S | L | H | V | S | S | N | DELETED | DELETED | I |
| S | A | I | S | L | H | V | S | S | N | DELETED | DELETED | M |
| S | A | I | S | L | H | V | S | S | N | DELETED | P | I |
| S | A | I | S | L | H | V | S | S | N | DELETED | P | M |
| S | A | I | S | L | H | V | S | S | N | P | DELETED | I |
| S | A | I | S | L | H | V | S | S | N | P | DELETED | M |
| S | A | I | S | L | H | V | S | S | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | S | L | H | V | S | S | N | P | P | M |
| S | A | I | S | L | H | V | S | T | DELETED | DELETED | DELETED | I |
| S | A | I | S | L | H | V | S | T | DELETED | DELETED | DELETED | M |
| S | A | I | S | L | H | V | S | T | DELETED | DELETED | P | I |
| S | A | I | S | L | H | V | S | T | DELETED | DELETED | P | M |
| S | A | I | S | L | H | V | S | T | DELETED | P | DELETED | I |
| S | A | I | S | L | H | V | S | T | DELETED | P | DELETED | M |
| S | A | I | S | L | H | V | S | T | DELETED | P | P | I |
| S | A | I | S | L | H | V | S | T | DELETED | P | P | M |
| S | A | I | S | L | H | V | S | T | N | DELETED | DELETED | I |
| S | A | I | S | L | H | V | S | T | N | DELETED | DELETED | M |
| S | A | I | S | L | H | V | S | T | N | DELETED | P | I |
| S | A | I | S | L | H | V | S | T | N | DELETED | P | M |
| S | A | I | S | L | H | V | S | T | N | P | DELETED | I |
| S | A | I | S | L | H | V | S | T | N | P | DELETED | M |
| S | A | I | S | L | H | V | S | T | N | P | P | I |
| S | A | I | S | L | H | V | S | T | N | P | P | M |
| S | A | I | S | L | H | V | G | S | DELETED | DELETED | DELETED | I |
| S | A | I | S | L | H | V | G | S | DELETED | DELETED | DELETED | M |
| S | A | I | S | L | H | V | G | S | DELETED | DELETED | P | I |
| S | A | I | S | L | H | V | G | S | DELETED | DELETED | P | M |
| S | A | I | S | L | H | V | G | S | DELETED | P | DELETED | I |
| S | A | I | S | L | H | V | G | S | DELETED | P | DELETED | M |
| S | A | I | S | L | H | V | G | S | DELETED | P | P | I |
| S | A | I | S | L | H | V | G | S | DELETED | P | P | M |
| S | A | I | S | L | H | V | G | S | N | DELETED | DELETED | I |
| S | A | I | S | L | H | V | G | S | N | DELETED | DELETED | M |
| S | A | I | S | L | H | V | G | S | N | DELETED | P | I |
| S | A | I | S | L | H | V | G | S | N | DELETED | P | M |
| S | A | I | S | L | H | V | G | S | N | P | DELETED | I |
| S | A | I | S | L | H | V | G | S | N | P | DELETED | M |
| S | A | I | S | L | H | V | G | S | N | P | P | I |
| S | A | I | S | L | H | V | G | S | N | P | P | M |
| S | A | I | S | L | H | V | G | T | DELETED | DELETED | DELETED | I |
| S | A | I | S | L | H | V | G | T | DELETED | DELETED | DELETED | M |
| S | A | I | S | L | H | V | G | T | DELETED | DELETED | P | I |
| S | A | I | S | L | H | V | G | T | DELETED | DELETED | P | M |
| S | A | I | S | L | H | V | G | T | DELETED | P | DELETED | I |
| S | A | I | S | L | H | V | G | T | DELETED | P | DELETED | M |
| S | A | I | S | L | H | V | G | T | DELETED | P | P | I |
| S | A | I | S | L | H | V | G | T | DELETED | P | P | M |
| S | A | I | S | L | H | V | G | T | N | DELETED | DELETED | I |
| S | A | I | S | L | H | V | G | T | N | DELETED | DELETED | M |
| S | A | I | S | L | H | V | G | T | N | DELETED | P | I |
| S | A | I | S | L | H | V | G | T | N | DELETED | P | M |
| S | A | I | S | L | H | V | G | T | N | P | DELETED | I |
| S | A | I | S | L | H | V | G | T | N | P | DELETED | M |
| S | A | I | S | L | H | V | G | T | N | P | P | I |
| S | A | I | S | L | H | V | G | T | N | P | P | M |
| S | A | I | S | I | Y | Q | S | S | DELETED | DELETED | DELETED | I |
| S | A | I | S | I | Y | Q | S | S | DELETED | DELETED | DELETED | M |
| S | A | I | S | I | Y | Q | S | S | DELETED | DELETED | P | I |
| S | A | I | S | I | Y | Q | S | S | DELETED | DELETED | P | M |
| S | A | I | S | I | Y | Q | S | S | DELETED | P | DELETED | I |
| S | A | I | S | I | Y | Q | S | S | DELETED | P | DELETED | M |
| S | A | I | S | I | Y | Q | S | S | DELETED | P | P | I |
| S | A | I | S | I | Y | Q | S | S | DELETED | P | P | M |
| S | A | I | S | I | Y | Q | S | S | N | DELETED | DELETED | I |
| S | A | I | S | I | Y | Q | S | S | N | DELETED | DELETED | M |
| S | A | I | S | I | Y | Q | S | S | N | DELETED | P | I |
| S | A | I | S | I | Y | Q | S | S | N | DELETED | P | M |
| S | A | I | S | I | Y | Q | S | S | N | P | DELETED | I |
| S | A | I | S | I | Y | Q | S | S | N | P | DELETED | M |
| S | A | I | S | I | Y | Q | S | S | N | P | P | I |
| S | A | I | S | I | Y | Q | S | S | N | P | P | M |
| S | A | I | S | I | Y | Q | S | T | DELETED | DELETED | DELETED | I |
| S | A | I | S | I | Y | Q | S | T | DELETED | DELETED | DELETED | M |
| S | A | I | S | I | Y | Q | S | T | DELETED | DELETED | P | I |
| S | A | I | S | I | Y | Q | S | T | DELETED | DELETED | P | M |
| S | A | I | S | I | Y | Q | S | T | DELETED | P | DELETED | I |
| S | A | I | S | I | Y | Q | S | T | DELETED | P | DELETED | M |
| S | A | I | S | I | Y | Q | S | T | DELETED | P | P | I |
| S | A | I | S | I | Y | Q | S | T | DELETED | P | P | M |
| S | A | I | S | I | Y | Q | S | T | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | S | I | Y | Q | S | T | N | DELETED | DELETED | M |
| S | A | I | S | I | Y | Q | S | T | N | DELETED | P | I |
| S | A | I | S | I | Y | Q | S | T | N | DELETED | P | M |
| S | A | I | S | I | Y | Q | S | T | N | P | DELETED | I |
| S | A | I | S | I | Y | Q | S | T | N | P | DELETED | M |
| S | A | I | S | I | Y | Q | S | T | N | P | P | I |
| S | A | I | S | I | Y | Q | S | T | N | P | P | M |
| S | A | I | S | I | Y | Q | G | S | DELETED | DELETED | DELETED | I |
| S | A | I | S | I | Y | Q | G | S | DELETED | DELETED | DELETED | M |
| S | A | I | S | I | Y | Q | G | S | DELETED | DELETED | P | I |
| S | A | I | S | I | Y | Q | G | S | DELETED | DELETED | P | M |
| S | A | I | S | I | Y | Q | G | S | DELETED | P | DELETED | I |
| S | A | I | S | I | Y | Q | G | S | DELETED | P | DELETED | M |
| S | A | I | S | I | Y | Q | G | S | DELETED | P | P | I |
| S | A | I | S | I | Y | Q | G | S | DELETED | P | P | M |
| S | A | I | S | I | Y | Q | G | S | N | DELETED | DELETED | I |
| S | A | I | S | I | Y | Q | G | S | N | DELETED | DELETED | M |
| S | A | I | S | I | Y | Q | G | S | N | DELETED | P | I |
| S | A | I | S | I | Y | Q | G | S | N | DELETED | P | M |
| S | A | I | S | I | Y | Q | G | S | N | P | DELETED | I |
| S | A | I | S | I | Y | Q | G | S | N | P | DELETED | M |
| S | A | I | S | I | Y | Q | G | S | N | P | P | I |
| S | A | I | S | I | Y | Q | G | S | N | P | P | M |
| S | A | I | S | I | Y | Q | G | T | DELETED | DELETED | DELETED | I |
| S | A | I | S | I | Y | Q | G | T | DELETED | DELETED | DELETED | M |
| S | A | I | S | I | Y | Q | G | T | DELETED | DELETED | P | I |
| S | A | I | S | I | Y | Q | G | T | DELETED | DELETED | P | M |
| S | A | I | S | I | Y | Q | G | T | DELETED | P | DELETED | I |
| S | A | I | S | I | Y | Q | G | T | DELETED | P | DELETED | M |
| S | A | I | S | I | Y | Q | G | T | DELETED | P | P | I |
| S | A | I | S | I | Y | Q | G | T | DELETED | P | P | M |
| S | A | I | S | I | Y | Q | G | T | N | DELETED | DELETED | I |
| S | A | I | S | I | Y | Q | G | T | N | DELETED | DELETED | M |
| S | A | I | S | I | Y | Q | G | T | N | DELETED | P | I |
| S | A | I | S | I | Y | Q | G | T | N | DELETED | P | M |
| S | A | I | S | I | Y | Q | G | T | N | P | DELETED | I |
| S | A | I | S | I | Y | Q | G | T | N | P | DELETED | M |
| S | A | I | S | I | Y | Q | G | T | N | P | P | I |
| S | A | I | S | I | Y | Q | G | T | N | P | P | M |
| S | A | I | S | I | Y | V | S | S | DELETED | DELETED | DELETED | I |
| S | A | I | S | I | Y | V | S | S | DELETED | DELETED | DELETED | M |
| S | A | I | S | I | Y | V | S | S | DELETED | DELETED | P | I |
| S | A | I | S | I | Y | V | S | S | DELETED | DELETED | P | M |
| S | A | I | S | I | Y | V | S | S | DELETED | P | DELETED | I |
| S | A | I | S | I | Y | V | S | S | DELETED | P | DELETED | M |
| S | A | I | S | I | Y | V | S | S | DELETED | P | P | I |
| S | A | I | S | I | Y | V | S | S | DELETED | P | P | M |
| S | A | I | S | I | Y | V | S | S | N | DELETED | DELETED | I |
| S | A | I | S | I | Y | V | S | S | N | DELETED | DELETED | M |
| S | A | I | S | I | Y | V | S | S | N | DELETED | P | I |
| S | A | I | S | I | Y | V | S | S | N | DELETED | P | M |
| S | A | I | S | I | Y | V | S | S | N | P | DELETED | I |
| S | A | I | S | I | Y | V | S | S | N | P | DELETED | M |
| S | A | I | S | I | Y | V | S | S | N | P | P | I |
| S | A | I | S | I | Y | V | S | S | N | P | P | M |
| S | A | I | S | I | Y | V | S | T | DELETED | DELETED | DELETED | I |
| S | A | I | S | I | Y | V | S | T | DELETED | DELETED | DELETED | M |
| S | A | I | S | I | Y | V | S | T | DELETED | DELETED | P | I |
| S | A | I | S | I | Y | V | S | T | DELETED | DELETED | P | M |
| S | A | I | S | I | Y | V | S | T | DELETED | P | DELETED | I |
| S | A | I | S | I | Y | V | S | T | DELETED | P | DELETED | M |
| S | A | I | S | I | Y | V | S | T | DELETED | P | P | I |
| S | A | I | S | I | Y | V | S | T | DELETED | P | P | M |
| S | A | I | S | I | Y | V | S | T | N | DELETED | DELETED | I |
| S | A | I | S | I | Y | V | S | T | N | DELETED | DELETED | M |
| S | A | I | S | I | Y | V | S | T | N | DELETED | P | I |
| S | A | I | S | I | Y | V | S | T | N | DELETED | P | M |
| S | A | I | S | I | Y | V | S | T | N | P | DELETED | I |
| S | A | I | S | I | Y | V | S | T | N | P | DELETED | M |
| S | A | I | S | I | Y | V | S | T | N | P | P | I |
| S | A | I | S | I | Y | V | S | T | N | P | P | M |
| S | A | I | S | I | Y | V | G | S | DELETED | DELETED | DELETED | I |
| S | A | I | S | I | Y | V | G | S | DELETED | DELETED | DELETED | M |
| S | A | I | S | I | Y | V | G | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | S | I | Y | V | G | S | DELETED | DELETED | P | M |
| S | A | I | S | I | Y | V | G | S | DELETED | P | DELETED | I |
| S | A | I | S | I | Y | V | G | S | DELETED | P | DELETED | M |
| S | A | I | S | I | Y | V | G | S | DELETED | P | P | I |
| S | A | I | S | I | Y | V | G | S | DELETED | P | P | M |
| S | A | I | S | I | Y | V | G | S | N | DELETED | DELETED | I |
| S | A | I | S | I | Y | V | G | S | N | DELETED | DELETED | M |
| S | A | I | S | I | Y | V | G | S | N | DELETED | P | I |
| S | A | I | S | I | Y | V | G | S | N | DELETED | P | M |
| S | A | I | S | I | Y | V | G | S | N | P | DELETED | I |
| S | A | I | S | I | Y | V | G | S | N | P | DELETED | M |
| S | A | I | S | I | Y | V | G | S | N | P | P | I |
| S | A | I | S | I | Y | V | G | S | N | P | P | M |
| S | A | I | S | I | Y | V | G | T | DELETED | DELETED | DELETED | I |
| S | A | I | S | I | Y | V | G | T | DELETED | DELETED | DELETED | M |
| S | A | I | S | I | Y | V | G | T | DELETED | DELETED | P | I |
| S | A | I | S | I | Y | V | G | T | DELETED | DELETED | P | M |
| S | A | I | S | I | Y | V | G | T | DELETED | P | DELETED | I |
| S | A | I | S | I | Y | V | G | T | DELETED | P | DELETED | M |
| S | A | I | S | I | Y | V | G | T | DELETED | P | P | I |
| S | A | I | S | I | Y | V | G | T | DELETED | P | P | M |
| S | A | I | S | I | Y | V | G | T | N | DELETED | DELETED | I |
| S | A | I | S | I | Y | V | G | T | N | DELETED | DELETED | M |
| S | A | I | S | I | Y | V | G | T | N | DELETED | P | I |
| S | A | I | S | I | Y | V | G | T | N | DELETED | P | M |
| S | A | I | S | I | Y | V | G | T | N | P | DELETED | I |
| S | A | I | S | I | Y | V | G | T | N | P | DELETED | M |
| S | A | I | S | I | Y | V | G | T | N | P | P | I |
| S | A | I | S | I | Y | V | G | T | N | P | P | M |
| S | A | I | S | I | H | Q | S | S | DELETED | DELETED | DELETED | I |
| S | A | I | S | I | H | Q | S | S | DELETED | DELETED | DELETED | M |
| S | A | I | S | I | H | Q | S | S | DELETED | DELETED | P | I |
| S | A | I | S | I | H | Q | S | S | DELETED | DELETED | P | M |
| S | A | I | S | I | H | Q | S | S | DELETED | P | DELETED | I |
| S | A | I | S | I | H | Q | S | S | DELETED | P | DELETED | M |
| S | A | I | S | I | H | Q | S | S | DELETED | P | P | I |
| S | A | I | S | I | H | Q | S | S | DELETED | P | P | M |
| S | A | I | S | I | H | Q | S | S | N | DELETED | DELETED | I |
| S | A | I | S | I | H | Q | S | S | N | DELETED | DELETED | M |
| S | A | I | S | I | H | Q | S | S | N | DELETED | P | I |
| S | A | I | S | I | H | Q | S | S | N | DELETED | P | M |
| S | A | I | S | I | H | Q | S | S | N | P | DELETED | I |
| S | A | I | S | I | H | Q | S | S | N | P | DELETED | M |
| S | A | I | S | I | H | Q | S | S | N | P | P | I |
| S | A | I | S | I | H | Q | S | S | N | P | P | M |
| S | A | I | S | I | H | Q | S | T | DELETED | DELETED | DELETED | I |
| S | A | I | S | I | H | Q | S | T | DELETED | DELETED | DELETED | M |
| S | A | I | S | I | H | Q | S | T | DELETED | DELETED | P | I |
| S | A | I | S | I | H | Q | S | T | DELETED | DELETED | P | M |
| S | A | I | S | I | H | Q | S | T | DELETED | P | DELETED | I |
| S | A | I | S | I | H | Q | S | T | DELETED | P | DELETED | M |
| S | A | I | S | I | H | Q | S | T | DELETED | P | P | I |
| S | A | I | S | I | H | Q | S | T | DELETED | P | P | M |
| S | A | I | S | I | H | Q | S | T | N | DELETED | DELETED | I |
| S | A | I | S | I | H | Q | S | T | N | DELETED | DELETED | M |
| S | A | I | S | I | H | Q | S | T | N | DELETED | P | I |
| S | A | I | S | I | H | Q | S | T | N | DELETED | P | M |
| S | A | I | S | I | H | Q | S | T | N | P | DELETED | I |
| S | A | I | S | I | H | Q | S | T | N | P | DELETED | M |
| S | A | I | S | I | H | Q | S | T | N | P | P | I |
| S | A | I | S | I | H | Q | S | T | N | P | P | M |
| S | A | I | S | I | H | Q | G | S | DELETED | DELETED | DELETED | I |
| S | A | I | S | I | H | Q | G | S | DELETED | DELETED | DELETED | M |
| S | A | I | S | I | H | Q | G | S | DELETED | DELETED | P | I |
| S | A | I | S | I | H | Q | G | S | DELETED | DELETED | P | M |
| S | A | I | S | I | H | Q | G | S | DELETED | P | DELETED | I |
| S | A | I | S | I | H | Q | G | S | DELETED | P | DELETED | M |
| S | A | I | S | I | H | Q | G | S | DELETED | P | P | I |
| S | A | I | S | I | H | Q | G | S | DELETED | P | P | M |
| S | A | I | S | I | H | Q | G | S | N | DELETED | DELETED | I |
| S | A | I | S | I | H | Q | G | S | N | DELETED | DELETED | M |
| S | A | I | S | I | H | Q | G | S | N | DELETED | P | I |
| S | A | I | S | I | H | Q | G | S | N | DELETED | P | M |
| S | A | I | S | I | H | Q | G | S | N | P | DELETED | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| S | A | I | S | I | H | Q | G | S | N | P | DELETED | M |
| S | A | I | S | I | H | Q | G | S | N | P | P | I |
| S | A | I | S | I | H | Q | G | S | N | P | P | M |
| S | A | I | S | I | H | Q | G | T | DELETED | DELETED | DELETED | I |
| S | A | I | S | I | H | Q | G | T | DELETED | DELETED | DELETED | M |
| S | A | I | S | I | H | Q | G | T | DELETED | DELETED | P | I |
| S | A | I | S | I | H | Q | G | T | DELETED | DELETED | P | M |
| S | A | I | S | I | H | Q | G | T | DELETED | P | DELETED | I |
| S | A | I | S | I | H | Q | G | T | DELETED | P | DELETED | M |
| S | A | I | S | I | H | Q | G | T | DELETED | P | P | I |
| S | A | I | S | I | H | Q | G | T | DELETED | P | P | M |
| S | A | I | S | I | H | Q | G | T | N | DELETED | DELETED | I |
| S | A | I | S | I | H | Q | G | T | N | DELETED | DELETED | M |
| S | A | I | S | I | H | Q | G | T | N | DELETED | P | I |
| S | A | I | S | I | H | Q | G | T | N | DELETED | P | M |
| S | A | I | S | I | H | Q | G | T | N | P | DELETED | I |
| S | A | I | S | I | H | Q | G | T | N | P | DELETED | M |
| S | A | I | S | I | H | Q | G | T | N | P | P | I |
| S | A | I | S | I | H | Q | G | T | N | P | P | M |
| S | A | I | S | I | H | V | S | S | DELETED | DELETED | DELETED | I |
| S | A | I | S | I | H | V | S | S | DELETED | DELETED | DELETED | M |
| S | A | I | S | I | H | V | S | S | DELETED | DELETED | P | I |
| S | A | I | S | I | H | V | S | S | DELETED | DELETED | P | M |
| S | A | I | S | I | H | V | S | S | DELETED | P | DELETED | I |
| S | A | I | S | I | H | V | S | S | DELETED | P | DELETED | M |
| S | A | I | S | I | H | V | S | S | DELETED | P | P | I |
| S | A | I | S | I | H | V | S | S | DELETED | P | P | M |
| S | A | I | S | I | H | V | S | S | N | DELETED | DELETED | I |
| S | A | I | S | I | H | V | S | S | N | DELETED | DELETED | M |
| S | A | I | S | I | H | V | S | S | N | DELETED | P | I |
| S | A | I | S | I | H | V | S | S | N | DELETED | P | M |
| S | A | I | S | I | H | V | S | S | N | P | DELETED | I |
| S | A | I | S | I | H | V | S | S | N | P | DELETED | M |
| S | A | I | S | I | H | V | S | S | N | P | P | I |
| S | A | I | S | I | H | V | S | S | N | P | P | M |
| S | A | I | S | I | H | V | S | T | DELETED | DELETED | DELETED | I |
| S | A | I | S | I | H | V | S | T | DELETED | DELETED | DELETED | M |
| S | A | I | S | I | H | V | S | T | DELETED | DELETED | P | I |
| S | A | I | S | I | H | V | S | T | DELETED | DELETED | P | M |
| S | A | I | S | I | H | V | S | T | DELETED | P | DELETED | I |
| S | A | I | S | I | H | V | S | T | DELETED | P | DELETED | M |
| S | A | I | S | I | H | V | S | T | DELETED | P | P | I |
| S | A | I | S | I | H | V | S | T | DELETED | P | P | M |
| S | A | I | S | I | H | V | S | T | N | DELETED | DELETED | I |
| S | A | I | S | I | H | V | S | T | N | DELETED | DELETED | M |
| S | A | I | S | I | H | V | S | T | N | DELETED | P | I |
| S | A | I | S | I | H | V | S | T | N | DELETED | P | M |
| S | A | I | S | I | H | V | S | T | N | P | DELETED | I |
| S | A | I | S | I | H | V | S | T | N | P | DELETED | M |
| S | A | I | S | I | H | V | S | T | N | P | P | I |
| S | A | I | S | I | H | V | S | T | N | P | P | M |
| S | A | I | S | I | H | V | G | S | DELETED | DELETED | DELETED | I |
| S | A | I | S | I | H | V | G | S | DELETED | DELETED | DELETED | M |
| S | A | I | S | I | H | V | G | S | DELETED | DELETED | P | I |
| S | A | I | S | I | H | V | G | S | DELETED | DELETED | P | M |
| S | A | I | S | I | H | V | G | S | DELETED | P | DELETED | I |
| S | A | I | S | I | H | V | G | S | DELETED | P | DELETED | M |
| S | A | I | S | I | H | V | G | S | DELETED | P | P | I |
| S | A | I | S | I | H | V | G | S | DELETED | P | P | M |
| S | A | I | S | I | H | V | G | S | N | DELETED | DELETED | I |
| S | A | I | S | I | H | V | G | S | N | DELETED | DELETED | M |
| S | A | I | S | I | H | V | G | S | N | DELETED | P | I |
| S | A | I | S | I | H | V | G | S | N | DELETED | P | M |
| S | A | I | S | I | H | V | G | S | N | P | DELETED | I |
| S | A | I | S | I | H | V | G | S | N | P | DELETED | M |
| S | A | I | S | I | H | V | G | S | N | P | P | I |
| S | A | I | S | I | H | V | G | S | N | P | P | M |
| S | A | I | S | I | H | V | G | T | DELETED | DELETED | DELETED | I |
| S | A | I | S | I | H | V | G | T | DELETED | DELETED | DELETED | M |
| S | A | I | S | I | H | V | G | T | DELETED | DELETED | P | I |
| S | A | I | S | I | H | V | G | T | DELETED | DELETED | P | M |
| S | A | I | S | I | H | V | G | T | DELETED | P | DELETED | I |
| S | A | I | S | I | H | V | G | T | DELETED | P | DELETED | M |
| S | A | I | S | I | H | V | G | T | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | S | I | H | V | G | T | DELETED | P | P | M |
| S | A | I | S | I | H | V | G | T | N | DELETED | DELETED | I |
| S | A | I | S | I | H | V | G | T | N | DELETED | DELETED | M |
| S | A | I | S | I | H | V | G | T | N | DELETED | P | I |
| S | A | I | S | I | H | V | G | T | N | DELETED | P | M |
| S | A | I | S | I | H | V | G | T | N | P | DELETED | I |
| S | A | I | S | I | H | V | G | T | N | P | DELETED | M |
| S | A | I | S | I | H | V | G | T | N | P | P | I |
| S | A | I | S | I | H | V | G | T | N | P | P | M |
| S | A | I | R | L | Y | Q | S | S | DELETED | DELETED | DELETED | I |
| S | A | I | R | L | Y | Q | S | S | DELETED | DELETED | DELETED | M |
| S | A | I | R | L | Y | Q | S | S | DELETED | DELETED | P | I |
| S | A | I | R | L | Y | Q | S | S | DELETED | DELETED | P | M |
| S | A | I | R | L | Y | Q | S | S | DELETED | P | DELETED | I |
| S | A | I | R | L | Y | Q | S | S | DELETED | P | DELETED | M |
| S | A | I | R | L | Y | Q | S | S | DELETED | P | P | I |
| S | A | I | R | L | Y | Q | S | S | DELETED | P | P | M |
| S | A | I | R | L | Y | Q | S | S | N | DELETED | DELETED | I |
| S | A | I | R | L | Y | Q | S | S | N | DELETED | DELETED | M |
| S | A | I | R | L | Y | Q | S | S | N | DELETED | P | I |
| S | A | I | R | L | Y | Q | S | S | N | DELETED | P | M |
| S | A | I | R | L | Y | Q | S | S | N | P | DELETED | I |
| S | A | I | R | L | Y | Q | S | S | N | P | DELETED | M |
| S | A | I | R | L | Y | Q | S | S | N | P | P | I |
| S | A | I | R | L | Y | Q | S | S | N | P | P | M |
| S | A | I | R | L | Y | Q | S | T | DELETED | DELETED | DELETED | I |
| S | A | I | R | L | Y | Q | S | T | DELETED | DELETED | DELETED | M |
| S | A | I | R | L | Y | Q | S | T | DELETED | DELETED | P | I |
| S | A | I | R | L | Y | Q | S | T | DELETED | DELETED | P | M |
| S | A | I | R | L | Y | Q | S | T | DELETED | P | DELETED | I |
| S | A | I | R | L | Y | Q | S | T | DELETED | P | DELETED | M |
| S | A | I | R | L | Y | Q | S | T | DELETED | P | P | I |
| S | A | I | R | L | Y | Q | S | T | DELETED | P | P | M |
| S | A | I | R | L | Y | Q | S | T | N | DELETED | DELETED | I |
| S | A | I | R | L | Y | Q | S | T | N | DELETED | DELETED | M |
| S | A | I | R | L | Y | Q | S | T | N | DELETED | P | I |
| S | A | I | R | L | Y | Q | S | T | N | DELETED | P | M |
| S | A | I | R | L | Y | Q | S | T | N | P | DELETED | I |
| S | A | I | R | L | Y | Q | S | T | N | P | DELETED | M |
| S | A | I | R | L | Y | Q | S | T | N | P | P | I |
| S | A | I | R | L | Y | Q | S | T | N | P | P | M |
| S | A | I | R | L | Y | Q | G | S | DELETED | DELETED | DELETED | I |
| S | A | I | R | L | Y | Q | G | S | DELETED | DELETED | DELETED | M |
| S | A | I | R | L | Y | Q | G | S | DELETED | DELETED | P | I |
| S | A | I | R | L | Y | Q | G | S | DELETED | DELETED | P | M |
| S | A | I | R | L | Y | Q | G | S | DELETED | P | DELETED | I |
| S | A | I | R | L | Y | Q | G | S | DELETED | P | DELETED | M |
| S | A | I | R | L | Y | Q | G | S | DELETED | P | P | I |
| S | A | I | R | L | Y | Q | G | S | DELETED | P | P | M |
| S | A | I | R | L | Y | Q | G | S | N | DELETED | DELETED | I |
| S | A | I | R | L | Y | Q | G | S | N | DELETED | DELETED | M |
| S | A | I | R | L | Y | Q | G | S | N | DELETED | P | I |
| S | A | I | R | L | Y | Q | G | S | N | DELETED | P | M |
| S | A | I | R | L | Y | Q | G | S | N | P | DELETED | I |
| S | A | I | R | L | Y | Q | G | S | N | P | DELETED | M |
| S | A | I | R | L | Y | Q | G | S | N | P | P | I |
| S | A | I | R | L | Y | Q | G | S | N | P | P | M |
| S | A | I | R | L | Y | Q | G | T | DELETED | DELETED | DELETED | I |
| S | A | I | R | L | Y | Q | G | T | DELETED | DELETED | DELETED | M |
| S | A | I | R | L | Y | Q | G | T | DELETED | DELETED | P | I |
| S | A | I | R | L | Y | Q | G | T | DELETED | DELETED | P | M |
| S | A | I | R | L | Y | Q | G | T | DELETED | P | DELETED | I |
| S | A | I | R | L | Y | Q | G | T | DELETED | P | DELETED | M |
| S | A | I | R | L | Y | Q | G | T | DELETED | P | P | I |
| S | A | I | R | L | Y | Q | G | T | DELETED | P | P | M |
| S | A | I | R | L | Y | Q | G | T | N | DELETED | DELETED | I |
| S | A | I | R | L | Y | Q | G | T | N | DELETED | DELETED | M |
| S | A | I | R | L | Y | Q | G | T | N | DELETED | P | I |
| S | A | I | R | L | Y | Q | G | T | N | DELETED | P | M |
| S | A | I | R | L | Y | Q | G | T | N | P | DELETED | I |
| S | A | I | R | L | Y | Q | G | T | N | P | DELETED | M |
| S | A | I | R | L | Y | Q | G | T | N | P | P | I |
| S | A | I | R | L | Y | Q | G | T | N | P | P | M |
| S | A | I | R | L | Y | V | S | S | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | L | Y | V | S | S | DELETED | DELETED | DELETED | M |
| S | A | I | R | L | Y | V | S | S | DELETED | DELETED | P | I |
| S | A | I | R | L | Y | V | S | S | DELETED | DELETED | P | M |
| S | A | I | R | L | Y | V | S | S | DELETED | P | DELETED | I |
| S | A | I | R | L | Y | V | S | S | DELETED | P | DELETED | M |
| S | A | I | R | L | Y | V | S | S | DELETED | P | P | I |
| S | A | I | R | L | Y | V | S | S | DELETED | P | P | M |
| S | A | I | R | L | Y | V | S | S | N | DELETED | DELETED | I |
| S | A | I | R | L | Y | V | S | S | N | DELETED | DELETED | M |
| S | A | I | R | L | Y | V | S | S | N | DELETED | P | I |
| S | A | I | R | L | Y | V | S | S | N | DELETED | P | M |
| S | A | I | R | L | Y | V | S | S | N | P | DELETED | I |
| S | A | I | R | L | Y | V | S | S | N | P | DELETED | M |
| S | A | I | R | L | Y | V | S | S | N | P | P | I |
| S | A | I | R | L | Y | V | S | S | N | P | P | M |
| S | A | I | R | L | Y | V | S | T | DELETED | DELETED | DELETED | I |
| S | A | I | R | L | Y | V | S | T | DELETED | DELETED | DELETED | M |
| S | A | I | R | L | Y | V | S | T | DELETED | DELETED | P | I |
| S | A | I | R | L | Y | V | S | T | DELETED | DELETED | P | M |
| S | A | I | R | L | Y | V | S | T | DELETED | P | DELETED | I |
| S | A | I | R | L | Y | V | S | T | DELETED | P | DELETED | M |
| S | A | I | R | L | Y | V | S | T | DELETED | P | P | I |
| S | A | I | R | L | Y | V | S | T | DELETED | P | P | M |
| S | A | I | R | L | Y | V | S | T | N | DELETED | DELETED | I |
| S | A | I | R | L | Y | V | S | T | N | DELETED | DELETED | M |
| S | A | I | R | L | Y | V | S | T | N | DELETED | P | I |
| S | A | I | R | L | Y | V | S | T | N | DELETED | P | M |
| S | A | I | R | L | Y | V | S | T | N | P | DELETED | I |
| S | A | I | R | L | Y | V | S | T | N | P | DELETED | M |
| S | A | I | R | L | Y | V | S | T | N | P | P | I |
| S | A | I | R | L | Y | V | S | T | N | P | P | M |
| S | A | I | R | L | Y | V | G | S | DELETED | DELETED | DELETED | I |
| S | A | I | R | L | Y | V | G | S | DELETED | DELETED | DELETED | M |
| S | A | I | R | L | Y | V | G | S | DELETED | DELETED | P | I |
| S | A | I | R | L | Y | V | G | S | DELETED | DELETED | P | M |
| S | A | I | R | L | Y | V | G | S | DELETED | P | DELETED | I |
| S | A | I | R | L | Y | V | G | S | DELETED | P | DELETED | M |
| S | A | I | R | L | Y | V | G | S | DELETED | P | P | I |
| S | A | I | R | L | Y | V | G | S | DELETED | P | P | M |
| S | A | I | R | L | Y | V | G | S | N | DELETED | DELETED | I |
| S | A | I | R | L | Y | V | G | S | N | DELETED | DELETED | M |
| S | A | I | R | L | Y | V | G | S | N | DELETED | P | I |
| S | A | I | R | L | Y | V | G | S | N | DELETED | P | M |
| S | A | I | R | L | Y | V | G | S | N | P | DELETED | I |
| S | A | I | R | L | Y | V | G | S | N | P | DELETED | M |
| S | A | I | R | L | Y | V | G | S | N | P | P | I |
| S | A | I | R | L | Y | V | G | S | N | P | P | M |
| S | A | I | R | L | Y | V | G | T | DELETED | DELETED | DELETED | I |
| S | A | I | R | L | Y | V | G | T | DELETED | DELETED | DELETED | M |
| S | A | I | R | L | Y | V | G | T | DELETED | DELETED | P | I |
| S | A | I | R | L | Y | V | G | T | DELETED | DELETED | P | M |
| S | A | I | R | L | Y | V | G | T | DELETED | P | DELETED | I |
| S | A | I | R | L | Y | V | G | T | DELETED | P | DELETED | M |
| S | A | I | R | L | Y | V | G | T | DELETED | P | P | I |
| S | A | I | R | L | Y | V | G | T | DELETED | P | P | M |
| S | A | I | R | L | Y | V | G | T | N | DELETED | DELETED | I |
| S | A | I | R | L | Y | V | G | T | N | DELETED | DELETED | M |
| S | A | I | R | L | Y | V | G | T | N | DELETED | P | I |
| S | A | I | R | L | Y | V | G | T | N | DELETED | P | M |
| S | A | I | R | L | Y | V | G | T | N | P | DELETED | I |
| S | A | I | R | L | Y | V | G | T | N | P | DELETED | M |
| S | A | I | R | L | Y | V | G | T | N | P | P | I |
| S | A | I | R | L | Y | V | G | T | N | P | P | M |
| S | A | I | R | L | H | Q | S | S | DELETED | DELETED | DELETED | I |
| S | A | I | R | L | H | Q | S | S | DELETED | DELETED | DELETED | M |
| S | A | I | R | L | H | Q | S | S | DELETED | DELETED | P | I |
| S | A | I | R | L | H | Q | S | S | DELETED | DELETED | P | M |
| S | A | I | R | L | H | Q | S | S | DELETED | P | DELETED | I |
| S | A | I | R | L | H | Q | S | S | DELETED | P | DELETED | M |
| S | A | I | R | L | H | Q | S | S | DELETED | P | P | I |
| S | A | I | R | L | H | Q | S | S | DELETED | P | P | M |
| S | A | I | R | L | H | Q | S | S | N | DELETED | DELETED | I |
| S | A | I | R | L | H | Q | S | S | N | DELETED | DELETED | M |
| S | A | I | R | L | H | Q | S | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | L | H | Q | S | S | N | DELETED | P | M |
| S | A | I | R | L | H | Q | S | S | N | P | DELETED | I |
| S | A | I | R | L | H | Q | S | S | N | P | DELETED | M |
| S | A | I | R | L | H | Q | S | S | N | P | P | I |
| S | A | I | R | L | H | Q | S | S | N | P | P | M |
| S | A | I | R | L | H | Q | S | T | DELETED | DELETED | DELETED | I |
| S | A | I | R | L | H | Q | S | T | DELETED | DELETED | DELETED | M |
| S | A | I | R | L | H | Q | S | T | DELETED | DELETED | P | I |
| S | A | I | R | L | H | Q | S | T | DELETED | DELETED | P | M |
| S | A | I | R | L | H | Q | S | T | DELETED | P | DELETED | I |
| S | A | I | R | L | H | Q | S | T | DELETED | P | DELETED | M |
| S | A | I | R | L | H | Q | S | T | DELETED | P | P | I |
| S | A | I | R | L | H | Q | S | T | DELETED | P | P | M |
| S | A | I | R | L | H | Q | S | T | N | DELETED | DELETED | I |
| S | A | I | R | L | H | Q | S | T | N | DELETED | DELETED | M |
| S | A | I | R | L | H | Q | S | T | N | DELETED | P | I |
| S | A | I | R | L | H | Q | S | T | N | DELETED | P | M |
| S | A | I | R | L | H | Q | S | T | N | P | DELETED | I |
| S | A | I | R | L | H | Q | S | T | N | P | DELETED | M |
| S | A | I | R | L | H | Q | S | T | N | P | P | I |
| S | A | I | R | L | H | Q | S | T | N | P | P | M |
| S | A | I | R | L | H | Q | G | S | DELETED | DELETED | DELETED | I |
| S | A | I | R | L | H | Q | G | S | DELETED | DELETED | DELETED | M |
| S | A | I | R | L | H | Q | G | S | DELETED | DELETED | P | I |
| S | A | I | R | L | H | Q | G | S | DELETED | DELETED | P | M |
| S | A | I | R | L | H | Q | G | S | DELETED | P | DELETED | I |
| S | A | I | R | L | H | Q | G | S | DELETED | P | DELETED | M |
| S | A | I | R | L | H | Q | G | S | DELETED | P | P | I |
| S | A | I | R | L | H | Q | G | S | DELETED | P | P | M |
| S | A | I | R | L | H | Q | G | S | N | DELETED | DELETED | I |
| S | A | I | R | L | H | Q | G | S | N | DELETED | DELETED | M |
| S | A | I | R | L | H | Q | G | S | N | DELETED | P | I |
| S | A | I | R | L | H | Q | G | S | N | DELETED | P | M |
| S | A | I | R | L | H | Q | G | S | N | P | DELETED | I |
| S | A | I | R | L | H | Q | G | S | N | P | DELETED | M |
| S | A | I | R | L | H | Q | G | S | N | P | P | I |
| S | A | I | R | L | H | Q | G | S | N | P | P | M |
| S | A | I | R | L | H | Q | G | T | DELETED | DELETED | DELETED | I |
| S | A | I | R | L | H | Q | G | T | DELETED | DELETED | DELETED | M |
| S | A | I | R | L | H | Q | G | T | DELETED | DELETED | P | I |
| S | A | I | R | L | H | Q | G | T | DELETED | DELETED | P | M |
| S | A | I | R | L | H | Q | G | T | DELETED | P | DELETED | I |
| S | A | I | R | L | H | Q | G | T | DELETED | P | DELETED | M |
| S | A | I | R | L | H | Q | G | T | DELETED | P | P | I |
| S | A | I | R | L | H | Q | G | T | DELETED | P | P | M |
| S | A | I | R | L | H | Q | G | T | N | DELETED | DELETED | I |
| S | A | I | R | L | H | Q | G | T | N | DELETED | DELETED | M |
| S | A | I | R | L | H | Q | G | T | N | DELETED | P | I |
| S | A | I | R | L | H | Q | G | T | N | DELETED | P | M |
| S | A | I | R | L | H | Q | G | T | N | P | DELETED | I |
| S | A | I | R | L | H | Q | G | T | N | P | DELETED | M |
| S | A | I | R | L | H | Q | G | T | N | P | P | I |
| S | A | I | R | L | H | Q | G | T | N | P | P | M |
| S | A | I | R | L | H | V | S | S | DELETED | DELETED | DELETED | I |
| S | A | I | R | L | H | V | S | S | DELETED | DELETED | DELETED | M |
| S | A | I | R | L | H | V | S | S | DELETED | DELETED | P | I |
| S | A | I | R | L | H | V | S | S | DELETED | DELETED | P | M |
| S | A | I | R | L | H | V | S | S | DELETED | P | DELETED | I |
| S | A | I | R | L | H | V | S | S | DELETED | P | DELETED | M |
| S | A | I | R | L | H | V | S | S | DELETED | P | P | I |
| S | A | I | R | L | H | V | S | S | DELETED | P | P | M |
| S | A | I | R | L | H | V | S | S | N | DELETED | DELETED | I |
| S | A | I | R | L | H | V | S | S | N | DELETED | DELETED | M |
| S | A | I | R | L | H | V | S | S | N | DELETED | P | I |
| S | A | I | R | L | H | V | S | S | N | DELETED | P | M |
| S | A | I | R | L | H | V | S | S | N | P | DELETED | I |
| S | A | I | R | L | H | V | S | S | N | P | DELETED | M |
| S | A | I | R | L | H | V | S | S | N | P | P | I |
| S | A | I | R | L | H | V | S | S | N | P | P | M |
| S | A | I | R | L | H | V | S | T | DELETED | DELETED | DELETED | I |
| S | A | I | R | L | H | V | S | T | DELETED | DELETED | DELETED | M |
| S | A | I | R | L | H | V | S | T | DELETED | DELETED | P | I |
| S | A | I | R | L | H | V | S | T | DELETED | DELETED | P | M |
| S | A | I | R | L | H | V | S | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | L | H | V | S | T | DELETED | P | DELETED | M |
| S | A | I | R | L | H | V | S | T | DELETED | P | P | I |
| S | A | I | R | L | H | V | S | T | DELETED | P | P | M |
| S | A | I | R | L | H | V | S | T | N | DELETED | DELETED | I |
| S | A | I | R | L | H | V | S | T | N | DELETED | DELETED | M |
| S | A | I | R | L | H | V | S | T | N | DELETED | P | I |
| S | A | I | R | L | H | V | S | T | N | DELETED | P | M |
| S | A | I | R | L | H | V | S | T | N | P | DELETED | I |
| S | A | I | R | L | H | V | S | T | N | P | DELETED | M |
| S | A | I | R | L | H | V | S | T | N | P | P | I |
| S | A | I | R | L | H | V | S | T | N | P | P | M |
| S | A | I | R | L | H | V | G | S | DELETED | DELETED | DELETED | I |
| S | A | I | R | L | H | V | G | S | DELETED | DELETED | DELETED | M |
| S | A | I | R | L | H | V | G | S | DELETED | DELETED | P | I |
| S | A | I | R | L | H | V | G | S | DELETED | DELETED | P | M |
| S | A | I | R | L | H | V | G | S | DELETED | P | DELETED | I |
| S | A | I | R | L | H | V | G | S | DELETED | P | DELETED | M |
| S | A | I | R | L | H | V | G | S | DELETED | P | P | I |
| S | A | I | R | L | H | V | G | S | DELETED | P | P | M |
| S | A | I | R | L | H | V | G | S | N | DELETED | DELETED | I |
| S | A | I | R | L | H | V | G | S | N | DELETED | DELETED | M |
| S | A | I | R | L | H | V | G | S | N | DELETED | P | I |
| S | A | I | R | L | H | V | G | S | N | DELETED | P | M |
| S | A | I | R | L | H | V | G | S | N | P | DELETED | I |
| S | A | I | R | L | H | V | G | S | N | P | DELETED | M |
| S | A | I | R | L | H | V | G | S | N | P | P | I |
| S | A | I | R | L | H | V | G | S | N | P | P | M |
| S | A | I | R | L | H | V | G | T | DELETED | DELETED | DELETED | I |
| S | A | I | R | L | H | V | G | T | DELETED | DELETED | DELETED | M |
| S | A | I | R | L | H | V | G | T | DELETED | DELETED | P | I |
| S | A | I | R | L | H | V | G | T | DELETED | DELETED | P | M |
| S | A | I | R | L | H | V | G | T | DELETED | P | DELETED | I |
| S | A | I | R | L | H | V | G | T | DELETED | P | DELETED | M |
| S | A | I | R | L | H | V | G | T | DELETED | P | P | I |
| S | A | I | R | L | H | V | G | T | DELETED | P | P | M |
| S | A | I | R | L | H | V | G | T | N | DELETED | DELETED | I |
| S | A | I | R | L | H | V | G | T | N | DELETED | DELETED | M |
| S | A | I | R | L | H | V | G | T | N | DELETED | P | I |
| S | A | I | R | L | H | V | G | T | N | DELETED | P | M |
| S | A | I | R | L | H | V | G | T | N | P | DELETED | I |
| S | A | I | R | L | H | V | G | T | N | P | DELETED | M |
| S | A | I | R | L | H | V | G | T | N | P | P | I |
| S | A | I | R | L | H | V | G | T | N | P | P | M |
| S | A | I | R | I | Y | Q | S | S | DELETED | DELETED | DELETED | I |
| S | A | I | R | I | Y | Q | S | S | DELETED | DELETED | DELETED | M |
| S | A | I | R | I | Y | Q | S | S | DELETED | DELETED | P | I |
| S | A | I | R | I | Y | Q | S | S | DELETED | DELETED | P | M |
| S | A | I | R | I | Y | Q | S | S | DELETED | P | DELETED | I |
| S | A | I | R | I | Y | Q | S | S | DELETED | P | DELETED | M |
| S | A | I | R | I | Y | Q | S | S | DELETED | P | P | I |
| S | A | I | R | I | Y | Q | S | S | DELETED | P | P | M |
| S | A | I | R | I | Y | Q | S | S | N | DELETED | DELETED | I |
| S | A | I | R | I | Y | Q | S | S | N | DELETED | DELETED | M |
| S | A | I | R | I | Y | Q | S | S | N | DELETED | P | I |
| S | A | I | R | I | Y | Q | S | S | N | DELETED | P | M |
| S | A | I | R | I | Y | Q | S | S | N | P | DELETED | I |
| S | A | I | R | I | Y | Q | S | S | N | P | DELETED | M |
| S | A | I | R | I | Y | Q | S | S | N | P | P | I |
| S | A | I | R | I | Y | Q | S | S | N | P | P | M |
| S | A | I | R | I | Y | Q | S | T | DELETED | DELETED | DELETED | I |
| S | A | I | R | I | Y | Q | S | T | DELETED | DELETED | DELETED | M |
| S | A | I | R | I | Y | Q | S | T | DELETED | DELETED | P | I |
| S | A | I | R | I | Y | Q | S | T | DELETED | DELETED | P | M |
| S | A | I | R | I | Y | Q | S | T | DELETED | P | DELETED | I |
| S | A | I | R | I | Y | Q | S | T | DELETED | P | DELETED | M |
| S | A | I | R | I | Y | Q | S | T | DELETED | P | P | I |
| S | A | I | R | I | Y | Q | S | T | DELETED | P | P | M |
| S | A | I | R | I | Y | Q | S | T | N | DELETED | DELETED | I |
| S | A | I | R | I | Y | Q | S | T | N | DELETED | DELETED | M |
| S | A | I | R | I | Y | Q | S | T | N | DELETED | P | I |
| S | A | I | R | I | Y | Q | S | T | N | DELETED | P | M |
| S | A | I | R | I | Y | Q | S | T | N | P | DELETED | I |
| S | A | I | R | I | Y | Q | S | T | N | P | DELETED | M |
| S | A | I | R | I | Y | Q | S | T | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | I | Y | Q | S | T | N | P | P | M |
| S | A | I | R | I | Y | Q | G | S | DELETED | DELETED | DELETED | I |
| S | A | I | R | I | Y | Q | G | S | DELETED | DELETED | DELETED | M |
| S | A | I | R | I | Y | Q | G | S | DELETED | DELETED | P | I |
| S | A | I | R | I | Y | Q | G | S | DELETED | DELETED | P | M |
| S | A | I | R | I | Y | Q | G | S | DELETED | P | DELETED | I |
| S | A | I | R | I | Y | Q | G | S | DELETED | P | DELETED | M |
| S | A | I | R | I | Y | Q | G | S | DELETED | P | P | I |
| S | A | I | R | I | Y | Q | G | S | DELETED | P | P | M |
| S | A | I | R | I | Y | Q | G | S | N | DELETED | DELETED | I |
| S | A | I | R | I | Y | Q | G | S | N | DELETED | DELETED | M |
| S | A | I | R | I | Y | Q | G | S | N | DELETED | P | I |
| S | A | I | R | I | Y | Q | G | S | N | DELETED | P | M |
| S | A | I | R | I | Y | Q | G | S | N | P | DELETED | I |
| S | A | I | R | I | Y | Q | G | S | N | P | DELETED | M |
| S | A | I | R | I | Y | Q | G | S | N | P | P | I |
| S | A | I | R | I | Y | Q | G | S | N | P | P | M |
| S | A | I | R | I | Y | Q | G | T | DELETED | DELETED | DELETED | I |
| S | A | I | R | I | Y | Q | G | T | DELETED | DELETED | DELETED | M |
| S | A | I | R | I | Y | Q | G | T | DELETED | DELETED | P | I |
| S | A | I | R | I | Y | Q | G | T | DELETED | DELETED | P | M |
| S | A | I | R | I | Y | Q | G | T | DELETED | P | DELETED | I |
| S | A | I | R | I | Y | Q | G | T | DELETED | P | DELETED | M |
| S | A | I | R | I | Y | Q | G | T | DELETED | P | P | I |
| S | A | I | R | I | Y | Q | G | T | DELETED | P | P | M |
| S | A | I | R | I | Y | Q | G | T | N | DELETED | DELETED | I |
| S | A | I | R | I | Y | Q | G | T | N | DELETED | DELETED | M |
| S | A | I | R | I | Y | Q | G | T | N | DELETED | P | I |
| S | A | I | R | I | Y | Q | G | T | N | DELETED | P | M |
| S | A | I | R | I | Y | Q | G | T | N | P | DELETED | I |
| S | A | I | R | I | Y | Q | G | T | N | P | DELETED | M |
| S | A | I | R | I | Y | Q | G | T | N | P | P | I |
| S | A | I | R | I | Y | Q | G | T | N | P | P | M |
| S | A | I | R | I | Y | V | S | S | DELETED | DELETED | DELETED | I |
| S | A | I | R | I | Y | V | S | S | DELETED | DELETED | DELETED | M |
| S | A | I | R | I | Y | V | S | S | DELETED | DELETED | P | I |
| S | A | I | R | I | Y | V | S | S | DELETED | DELETED | P | M |
| S | A | I | R | I | Y | V | S | S | DELETED | P | DELETED | I |
| S | A | I | R | I | Y | V | S | S | DELETED | P | DELETED | M |
| S | A | I | R | I | Y | V | S | S | DELETED | P | P | I |
| S | A | I | R | I | Y | V | S | S | DELETED | P | P | M |
| S | A | I | R | I | Y | V | S | S | N | DELETED | DELETED | I |
| S | A | I | R | I | Y | V | S | S | N | DELETED | DELETED | M |
| S | A | I | R | I | Y | V | S | S | N | DELETED | P | I |
| S | A | I | R | I | Y | V | S | S | N | DELETED | P | M |
| S | A | I | R | I | Y | V | S | S | N | P | DELETED | I |
| S | A | I | R | I | Y | V | S | S | N | P | DELETED | M |
| S | A | I | R | I | Y | V | S | S | N | P | P | I |
| S | A | I | R | I | Y | V | S | S | N | P | P | M |
| S | A | I | R | I | Y | V | S | T | DELETED | DELETED | DELETED | I |
| S | A | I | R | I | Y | V | S | T | DELETED | DELETED | DELETED | M |
| S | A | I | R | I | Y | V | S | T | DELETED | DELETED | P | I |
| S | A | I | R | I | Y | V | S | T | DELETED | DELETED | P | M |
| S | A | I | R | I | Y | V | S | T | DELETED | P | DELETED | I |
| S | A | I | R | I | Y | V | S | T | DELETED | P | DELETED | M |
| S | A | I | R | I | Y | V | S | T | DELETED | P | P | I |
| S | A | I | R | I | Y | V | S | T | DELETED | P | P | M |
| S | A | I | R | I | Y | V | S | T | N | DELETED | DELETED | I |
| S | A | I | R | I | Y | V | S | T | N | DELETED | DELETED | M |
| S | A | I | R | I | Y | V | S | T | N | DELETED | P | I |
| S | A | I | R | I | Y | V | S | T | N | DELETED | P | M |
| S | A | I | R | I | Y | V | S | T | N | P | DELETED | I |
| S | A | I | R | I | Y | V | S | T | N | P | DELETED | M |
| S | A | I | R | I | Y | V | S | T | N | P | P | I |
| S | A | I | R | I | Y | V | S | T | N | P | P | M |
| S | A | I | R | I | Y | V | G | S | DELETED | DELETED | DELETED | I |
| S | A | I | R | I | Y | V | G | S | DELETED | DELETED | DELETED | M |
| S | A | I | R | I | Y | V | G | S | DELETED | DELETED | P | I |
| S | A | I | R | I | Y | V | G | S | DELETED | DELETED | P | M |
| S | A | I | R | I | Y | V | G | S | DELETED | P | DELETED | I |
| S | A | I | R | I | Y | V | G | S | DELETED | P | DELETED | M |
| S | A | I | R | I | Y | V | G | S | DELETED | P | P | I |
| S | A | I | R | I | Y | V | G | S | DELETED | P | P | M |
| S | A | I | R | I | Y | V | G | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | I | Y | V | G | S | N | DELETED | DELETED | M |
| S | A | I | R | I | Y | V | G | S | N | DELETED | P | I |
| S | A | I | R | I | Y | V | G | S | N | DELETED | P | M |
| S | A | I | R | I | Y | V | G | S | N | P | DELETED | I |
| S | A | I | R | I | Y | V | G | S | N | P | DELETED | M |
| S | A | I | R | I | Y | V | G | S | N | P | P | I |
| S | A | I | R | I | Y | V | G | S | N | P | P | M |
| S | A | I | R | I | Y | V | G | T | DELETED | DELETED | DELETED | I |
| S | A | I | R | I | Y | V | G | T | DELETED | DELETED | DELETED | M |
| S | A | I | R | I | Y | V | G | T | DELETED | DELETED | P | I |
| S | A | I | R | I | Y | V | G | T | DELETED | DELETED | P | M |
| S | A | I | R | I | Y | V | G | T | DELETED | P | DELETED | I |
| S | A | I | R | I | Y | V | G | T | DELETED | P | DELETED | M |
| S | A | I | R | I | Y | V | G | T | DELETED | P | P | I |
| S | A | I | R | I | Y | V | G | T | DELETED | P | P | M |
| S | A | I | R | I | Y | V | G | T | N | DELETED | DELETED | I |
| S | A | I | R | I | Y | V | G | T | N | DELETED | DELETED | M |
| S | A | I | R | I | Y | V | G | T | N | DELETED | P | I |
| S | A | I | R | I | Y | V | G | T | N | DELETED | P | M |
| S | A | I | R | I | Y | V | G | T | N | P | DELETED | I |
| S | A | I | R | I | Y | V | G | T | N | P | DELETED | M |
| S | A | I | R | I | Y | V | G | T | N | P | P | I |
| S | A | I | R | I | Y | V | G | T | N | P | P | M |
| S | A | I | R | I | H | Q | S | S | DELETED | DELETED | DELETED | I |
| S | A | I | R | I | H | Q | S | S | DELETED | DELETED | DELETED | M |
| S | A | I | R | I | H | Q | S | S | DELETED | DELETED | P | I |
| S | A | I | R | I | H | Q | S | S | DELETED | DELETED | P | M |
| S | A | I | R | I | H | Q | S | S | DELETED | P | DELETED | I |
| S | A | I | R | I | H | Q | S | S | DELETED | P | DELETED | M |
| S | A | I | R | I | H | Q | S | S | DELETED | P | P | I |
| S | A | I | R | I | H | Q | S | S | DELETED | P | P | M |
| S | A | I | R | I | H | Q | S | S | N | DELETED | DELETED | I |
| S | A | I | R | I | H | Q | S | S | N | DELETED | DELETED | M |
| S | A | I | R | I | H | Q | S | S | N | DELETED | P | I |
| S | A | I | R | I | H | Q | S | S | N | DELETED | P | M |
| S | A | I | R | I | H | Q | S | S | N | P | DELETED | I |
| S | A | I | R | I | H | Q | S | S | N | P | DELETED | M |
| S | A | I | R | I | H | Q | S | S | N | P | P | I |
| S | A | I | R | I | H | Q | S | S | N | P | P | M |
| S | A | I | R | I | H | Q | S | T | DELETED | DELETED | DELETED | I |
| S | A | I | R | I | H | Q | S | T | DELETED | DELETED | DELETED | M |
| S | A | I | R | I | H | Q | S | T | DELETED | DELETED | P | I |
| S | A | I | R | I | H | Q | S | T | DELETED | DELETED | P | M |
| S | A | I | R | I | H | Q | S | T | DELETED | P | DELETED | I |
| S | A | I | R | I | H | Q | S | T | DELETED | P | DELETED | M |
| S | A | I | R | I | H | Q | S | T | DELETED | P | P | I |
| S | A | I | R | I | H | Q | S | T | DELETED | P | P | M |
| S | A | I | R | I | H | Q | S | T | N | DELETED | DELETED | I |
| S | A | I | R | I | H | Q | S | T | N | DELETED | DELETED | M |
| S | A | I | R | I | H | Q | S | T | N | DELETED | P | I |
| S | A | I | R | I | H | Q | S | T | N | DELETED | P | M |
| S | A | I | R | I | H | Q | S | T | N | P | DELETED | I |
| S | A | I | R | I | H | Q | S | T | N | P | DELETED | M |
| S | A | I | R | I | H | Q | S | T | N | P | P | I |
| S | A | I | R | I | H | Q | S | T | N | P | P | M |
| S | A | I | R | I | H | Q | G | S | DELETED | DELETED | DELETED | I |
| S | A | I | R | I | H | Q | G | S | DELETED | DELETED | DELETED | M |
| S | A | I | R | I | H | Q | G | S | DELETED | DELETED | P | I |
| S | A | I | R | I | H | Q | G | S | DELETED | DELETED | P | M |
| S | A | I | R | I | H | Q | G | S | DELETED | P | DELETED | I |
| S | A | I | R | I | H | Q | G | S | DELETED | P | DELETED | M |
| S | A | I | R | I | H | Q | G | S | DELETED | P | P | I |
| S | A | I | R | I | H | Q | G | S | DELETED | P | P | M |
| S | A | I | R | I | H | Q | G | S | N | DELETED | DELETED | I |
| S | A | I | R | I | H | Q | G | S | N | DELETED | DELETED | M |
| S | A | I | R | I | H | Q | G | S | N | DELETED | P | I |
| S | A | I | R | I | H | Q | G | S | N | DELETED | P | M |
| S | A | I | R | I | H | Q | G | S | N | P | DELETED | I |
| S | A | I | R | I | H | Q | G | S | N | P | DELETED | M |
| S | A | I | R | I | H | Q | G | S | N | P | P | I |
| S | A | I | R | I | H | Q | G | S | N | P | P | M |
| S | A | I | R | I | H | Q | G | T | DELETED | DELETED | DELETED | I |
| S | A | I | R | I | H | Q | G | T | DELETED | DELETED | DELETED | M |
| S | A | I | R | I | H | Q | G | T | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | I | H | Q | G | T | DELETED | DELETED | P | M |
| S | A | I | R | I | H | Q | G | T | DELETED | P | DELETED | I |
| S | A | I | R | I | H | Q | G | T | DELETED | P | DELETED | M |
| S | A | I | R | I | H | Q | G | T | DELETED | P | P | I |
| S | A | I | R | I | H | Q | G | T | DELETED | P | P | M |
| S | A | I | R | I | H | Q | G | T | N | DELETED | DELETED | I |
| S | A | I | R | I | H | Q | G | T | N | DELETED | DELETED | M |
| S | A | I | R | I | H | Q | G | T | N | DELETED | P | I |
| S | A | I | R | I | H | Q | G | T | N | DELETED | P | M |
| S | A | I | R | I | H | Q | G | T | N | P | DELETED | I |
| S | A | I | R | I | H | Q | G | T | N | P | DELETED | M |
| S | A | I | R | I | H | Q | G | T | N | P | P | I |
| S | A | I | R | I | H | Q | G | T | N | P | P | M |
| S | A | I | R | I | H | V | S | S | DELETED | DELETED | DELETED | I |
| S | A | I | R | I | H | V | S | S | DELETED | DELETED | DELETED | M |
| S | A | I | R | I | H | V | S | S | DELETED | DELETED | P | I |
| S | A | I | R | I | H | V | S | S | DELETED | DELETED | P | M |
| S | A | I | R | I | H | V | S | S | DELETED | P | DELETED | I |
| S | A | I | R | I | H | V | S | S | DELETED | P | DELETED | M |
| S | A | I | R | I | H | V | S | S | DELETED | P | P | I |
| S | A | I | R | I | H | V | S | S | DELETED | P | P | M |
| S | A | I | R | I | H | V | S | S | N | DELETED | DELETED | I |
| S | A | I | R | I | H | V | S | S | N | DELETED | DELETED | M |
| S | A | I | R | I | H | V | S | S | N | DELETED | P | I |
| S | A | I | R | I | H | V | S | S | N | DELETED | P | M |
| S | A | I | R | I | H | V | S | S | N | P | DELETED | I |
| S | A | I | R | I | H | V | S | S | N | P | DELETED | M |
| S | A | I | R | I | H | V | S | S | N | P | P | I |
| S | A | I | R | I | H | V | S | S | N | P | P | M |
| S | A | I | R | I | H | V | S | T | DELETED | DELETED | DELETED | I |
| S | A | I | R | I | H | V | S | T | DELETED | DELETED | DELETED | M |
| S | A | I | R | I | H | V | S | T | DELETED | DELETED | P | I |
| S | A | I | R | I | H | V | S | T | DELETED | DELETED | P | M |
| S | A | I | R | I | H | V | S | T | DELETED | P | DELETED | I |
| S | A | I | R | I | H | V | S | T | DELETED | P | DELETED | M |
| S | A | I | R | I | H | V | S | T | DELETED | P | P | I |
| S | A | I | R | I | H | V | S | T | DELETED | P | P | M |
| S | A | I | R | I | H | V | S | T | N | DELETED | DELETED | I |
| S | A | I | R | I | H | V | S | T | N | DELETED | DELETED | M |
| S | A | I | R | I | H | V | S | T | N | DELETED | P | I |
| S | A | I | R | I | H | V | S | T | N | DELETED | P | M |
| S | A | I | R | I | H | V | S | T | N | P | DELETED | I |
| S | A | I | R | I | H | V | S | T | N | P | DELETED | M |
| S | A | I | R | I | H | V | S | T | N | P | P | I |
| S | A | I | R | I | H | V | S | T | N | P | P | M |
| S | A | I | R | I | H | V | G | S | DELETED | DELETED | DELETED | I |
| S | A | I | R | I | H | V | G | S | DELETED | DELETED | DELETED | M |
| S | A | I | R | I | H | V | G | S | DELETED | DELETED | P | I |
| S | A | I | R | I | H | V | G | S | DELETED | DELETED | P | M |
| S | A | I | R | I | H | V | G | S | DELETED | P | DELETED | I |
| S | A | I | R | I | H | V | G | S | DELETED | P | DELETED | M |
| S | A | I | R | I | H | V | G | S | DELETED | P | P | I |
| S | A | I | R | I | H | V | G | S | DELETED | P | P | M |
| S | A | I | R | I | H | V | G | S | N | DELETED | DELETED | I |
| S | A | I | R | I | H | V | G | S | N | DELETED | DELETED | M |
| S | A | I | R | I | H | V | G | S | N | DELETED | P | I |
| S | A | I | R | I | H | V | G | S | N | DELETED | P | M |
| S | A | I | R | I | H | V | G | S | N | P | DELETED | I |
| S | A | I | R | I | H | V | G | S | N | P | DELETED | M |
| S | A | I | R | I | H | V | G | S | N | P | P | I |
| S | A | I | R | I | H | V | G | S | N | P | P | M |
| S | A | I | R | I | H | V | G | T | DELETED | DELETED | DELETED | I |
| S | A | I | R | I | H | V | G | T | DELETED | DELETED | DELETED | M |
| S | A | I | R | I | H | V | G | T | DELETED | DELETED | P | I |
| S | A | I | R | I | H | V | G | T | DELETED | DELETED | P | M |
| S | A | I | R | I | H | V | G | T | DELETED | P | DELETED | I |
| S | A | I | R | I | H | V | G | T | DELETED | P | DELETED | M |
| S | A | I | R | I | H | V | G | T | DELETED | P | P | I |
| S | A | I | R | I | H | V | G | T | DELETED | P | P | M |
| S | A | I | R | I | H | V | G | T | N | DELETED | DELETED | I |
| S | A | I | R | I | H | V | G | T | N | DELETED | DELETED | M |
| S | A | I | R | I | H | V | G | T | N | DELETED | P | I |
| S | A | I | R | I | H | V | G | T | N | DELETED | P | M |
| S | A | I | R | I | H | V | G | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | I | R | I | H | V | G | T | N | P | DELETED | M |
| S | A | I | R | I | H | V | G | T | N | P | P | I |
| S | A | I | R | I | H | V | G | T | N | P | P | M |
| S | A | F | S | L | Y | Q | S | S | DELETED | DELETED | DELETED | I |
| S | A | F | S | L | Y | Q | S | S | DELETED | DELETED | DELETED | M |
| S | A | F | S | L | Y | Q | S | S | DELETED | DELETED | P | I |
| S | A | F | S | L | Y | Q | S | S | DELETED | DELETED | P | M |
| S | A | F | S | L | Y | Q | S | S | DELETED | P | DELETED | I |
| S | A | F | S | L | Y | Q | S | S | DELETED | P | DELETED | M |
| S | A | F | S | L | Y | Q | S | S | DELETED | P | P | I |
| S | A | F | S | L | Y | Q | S | S | DELETED | P | P | M |
| S | A | F | S | L | Y | Q | S | S | N | DELETED | DELETED | I |
| S | A | F | S | L | Y | Q | S | S | N | DELETED | DELETED | M |
| S | A | F | S | L | Y | Q | S | S | N | DELETED | P | I |
| S | A | F | S | L | Y | Q | S | S | N | DELETED | P | M |
| S | A | F | S | L | Y | Q | S | S | N | P | DELETED | I |
| S | A | F | S | L | Y | Q | S | S | N | P | DELETED | M |
| S | A | F | S | L | Y | Q | S | S | N | P | P | I |
| S | A | F | S | L | Y | Q | S | S | N | P | P | M |
| S | A | F | S | L | Y | Q | S | T | DELETED | DELETED | DELETED | I |
| S | A | F | S | L | Y | Q | S | T | DELETED | DELETED | DELETED | M |
| S | A | F | S | L | Y | Q | S | T | DELETED | DELETED | P | I |
| S | A | F | S | L | Y | Q | S | T | DELETED | DELETED | P | M |
| S | A | F | S | L | Y | Q | S | T | DELETED | P | DELETED | I |
| S | A | F | S | L | Y | Q | S | T | DELETED | P | DELETED | M |
| S | A | F | S | L | Y | Q | S | T | DELETED | P | P | I |
| S | A | F | S | L | Y | Q | S | T | DELETED | P | P | M |
| S | A | F | S | L | Y | Q | S | T | N | DELETED | DELETED | I |
| S | A | F | S | L | Y | Q | S | T | N | DELETED | DELETED | M |
| S | A | F | S | L | Y | Q | S | T | N | DELETED | P | I |
| S | A | F | S | L | Y | Q | S | T | N | DELETED | P | M |
| S | A | F | S | L | Y | Q | S | T | N | P | DELETED | I |
| S | A | F | S | L | Y | Q | S | T | N | P | DELETED | M |
| S | A | F | S | L | Y | Q | S | T | N | P | P | I |
| S | A | F | S | L | Y | Q | S | T | N | P | P | M |
| S | A | F | S | L | Y | Q | G | S | DELETED | DELETED | DELETED | I |
| S | A | F | S | L | Y | Q | G | S | DELETED | DELETED | DELETED | M |
| S | A | F | S | L | Y | Q | G | S | DELETED | DELETED | P | I |
| S | A | F | S | L | Y | Q | G | S | DELETED | DELETED | P | M |
| S | A | F | S | L | Y | Q | G | S | DELETED | P | DELETED | I |
| S | A | F | S | L | Y | Q | G | S | DELETED | P | DELETED | M |
| S | A | F | S | L | Y | Q | G | S | DELETED | P | P | I |
| S | A | F | S | L | Y | Q | G | S | DELETED | P | P | M |
| S | A | F | S | L | Y | Q | G | S | N | DELETED | DELETED | I |
| S | A | F | S | L | Y | Q | G | S | N | DELETED | DELETED | M |
| S | A | F | S | L | Y | Q | G | S | N | DELETED | P | I |
| S | A | F | S | L | Y | Q | G | S | N | DELETED | P | M |
| S | A | F | S | L | Y | Q | G | S | N | P | DELETED | I |
| S | A | F | S | L | Y | Q | G | S | N | P | DELETED | M |
| S | A | F | S | L | Y | Q | G | S | N | P | P | I |
| S | A | F | S | L | Y | Q | G | S | N | P | P | M |
| S | A | F | S | L | Y | Q | G | T | DELETED | DELETED | DELETED | I |
| S | A | F | S | L | Y | Q | G | T | DELETED | DELETED | DELETED | M |
| S | A | F | S | L | Y | Q | G | T | DELETED | DELETED | P | I |
| S | A | F | S | L | Y | Q | G | T | DELETED | DELETED | P | M |
| S | A | F | S | L | Y | Q | G | T | DELETED | P | DELETED | I |
| S | A | F | S | L | Y | Q | G | T | DELETED | P | DELETED | M |
| S | A | F | S | L | Y | Q | G | T | DELETED | P | P | I |
| S | A | F | S | L | Y | Q | G | T | DELETED | P | P | M |
| S | A | F | S | L | Y | Q | G | T | N | DELETED | DELETED | I |
| S | A | F | S | L | Y | Q | G | T | N | DELETED | DELETED | M |
| S | A | F | S | L | Y | Q | G | T | N | DELETED | P | I |
| S | A | F | S | L | Y | Q | G | T | N | DELETED | P | M |
| S | A | F | S | L | Y | Q | G | T | N | P | DELETED | I |
| S | A | F | S | L | Y | Q | G | T | N | P | DELETED | M |
| S | A | F | S | L | Y | Q | G | T | N | P | P | I |
| S | A | F | S | L | Y | Q | G | T | N | P | P | M |
| S | A | F | S | L | Y | V | S | S | DELETED | DELETED | DELETED | I |
| S | A | F | S | L | Y | V | S | S | DELETED | DELETED | DELETED | M |
| S | A | F | S | L | Y | V | S | S | DELETED | DELETED | P | I |
| S | A | F | S | L | Y | V | S | S | DELETED | DELETED | P | M |
| S | A | F | S | L | Y | V | S | S | DELETED | P | DELETED | I |
| S | A | F | S | L | Y | V | S | S | DELETED | P | DELETED | M |
| S | A | F | S | L | Y | V | S | S | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | S | L | Y | V | S | S | DELETED | P | P | M |
| S | A | F | S | L | Y | V | S | S | N | DELETED | DELETED | I |
| S | A | F | S | L | Y | V | S | S | N | DELETED | DELETED | M |
| S | A | F | S | L | Y | V | S | S | N | DELETED | P | I |
| S | A | F | S | L | Y | V | S | S | N | DELETED | P | M |
| S | A | F | S | L | Y | V | S | S | N | P | DELETED | I |
| S | A | F | S | L | Y | V | S | S | N | P | DELETED | M |
| S | A | F | S | L | Y | V | S | S | N | P | P | I |
| S | A | F | S | L | Y | V | S | S | N | P | P | M |
| S | A | F | S | L | Y | V | S | T | DELETED | DELETED | DELETED | I |
| S | A | F | S | L | Y | V | S | T | DELETED | DELETED | DELETED | M |
| S | A | F | S | L | Y | V | S | T | DELETED | DELETED | P | I |
| S | A | F | S | L | Y | V | S | T | DELETED | DELETED | P | M |
| S | A | F | S | L | Y | V | S | T | DELETED | P | DELETED | I |
| S | A | F | S | L | Y | V | S | T | DELETED | P | DELETED | M |
| S | A | F | S | L | Y | V | S | T | DELETED | P | P | I |
| S | A | F | S | L | Y | V | S | T | DELETED | P | P | M |
| S | A | F | S | L | Y | V | S | T | N | DELETED | DELETED | I |
| S | A | F | S | L | Y | V | S | T | N | DELETED | DELETED | M |
| S | A | F | S | L | Y | V | S | T | N | DELETED | P | I |
| S | A | F | S | L | Y | V | S | T | N | DELETED | P | M |
| S | A | F | S | L | Y | V | S | T | N | P | DELETED | I |
| S | A | F | S | L | Y | V | S | T | N | P | DELETED | M |
| S | A | F | S | L | Y | V | S | T | N | P | P | I |
| S | A | F | S | L | Y | V | S | T | N | P | P | M |
| S | A | F | S | L | Y | V | G | S | DELETED | DELETED | DELETED | I |
| S | A | F | S | L | Y | V | G | S | DELETED | DELETED | DELETED | M |
| S | A | F | S | L | Y | V | G | S | DELETED | DELETED | P | I |
| S | A | F | S | L | Y | V | G | S | DELETED | DELETED | P | M |
| S | A | F | S | L | Y | V | G | S | DELETED | P | DELETED | I |
| S | A | F | S | L | Y | V | G | S | DELETED | P | DELETED | M |
| S | A | F | S | L | Y | V | G | S | DELETED | P | P | I |
| S | A | F | S | L | Y | V | G | S | DELETED | P | P | M |
| S | A | F | S | L | Y | V | G | S | N | DELETED | DELETED | I |
| S | A | F | S | L | Y | V | G | S | N | DELETED | DELETED | M |
| S | A | F | S | L | Y | V | G | S | N | DELETED | P | I |
| S | A | F | S | L | Y | V | G | S | N | DELETED | P | M |
| S | A | F | S | L | Y | V | G | S | N | P | DELETED | I |
| S | A | F | S | L | Y | V | G | S | N | P | DELETED | M |
| S | A | F | S | L | Y | V | G | S | N | P | P | I |
| S | A | F | S | L | Y | V | G | S | N | P | P | M |
| S | A | F | S | L | Y | V | G | T | DELETED | DELETED | DELETED | I |
| S | A | F | S | L | Y | V | G | T | DELETED | DELETED | DELETED | M |
| S | A | F | S | L | Y | V | G | T | DELETED | DELETED | P | I |
| S | A | F | S | L | Y | V | G | T | DELETED | DELETED | P | M |
| S | A | F | S | L | Y | V | G | T | DELETED | P | DELETED | I |
| S | A | F | S | L | Y | V | G | T | DELETED | P | DELETED | M |
| S | A | F | S | L | Y | V | G | T | DELETED | P | P | I |
| S | A | F | S | L | Y | V | G | T | DELETED | P | P | M |
| S | A | F | S | L | Y | V | G | T | N | DELETED | DELETED | I |
| S | A | F | S | L | Y | V | G | T | N | DELETED | DELETED | M |
| S | A | F | S | L | Y | V | G | T | N | DELETED | P | I |
| S | A | F | S | L | Y | V | G | T | N | DELETED | P | M |
| S | A | F | S | L | Y | V | G | T | N | P | DELETED | I |
| S | A | F | S | L | Y | V | G | T | N | P | DELETED | M |
| S | A | F | S | L | Y | V | G | T | N | P | P | I |
| S | A | F | S | L | Y | V | G | T | N | P | P | M |
| S | A | F | S | L | H | Q | S | S | DELETED | DELETED | DELETED | I |
| S | A | F | S | L | H | Q | S | S | DELETED | DELETED | DELETED | M |
| S | A | F | S | L | H | Q | S | S | DELETED | DELETED | P | I |
| S | A | F | S | L | H | Q | S | S | DELETED | DELETED | P | M |
| S | A | F | S | L | H | Q | S | S | DELETED | P | DELETED | I |
| S | A | F | S | L | H | Q | S | S | DELETED | P | DELETED | M |
| S | A | F | S | L | H | Q | S | S | DELETED | P | P | I |
| S | A | F | S | L | H | Q | S | S | DELETED | P | P | M |
| S | A | F | S | L | H | Q | S | S | N | DELETED | DELETED | I |
| S | A | F | S | L | H | Q | S | S | N | DELETED | DELETED | M |
| S | A | F | S | L | H | Q | S | S | N | DELETED | P | I |
| S | A | F | S | L | H | Q | S | S | N | DELETED | P | M |
| S | A | F | S | L | H | Q | S | S | N | P | DELETED | I |
| S | A | F | S | L | H | Q | S | S | N | P | DELETED | M |
| S | A | F | S | L | H | Q | S | S | N | P | P | I |
| S | A | F | S | L | H | Q | S | S | N | P | P | M |
| S | A | F | S | L | H | Q | S | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | S | L | H | Q | S | T | DELETED | DELETED | DELETED | M |
| S | A | F | S | L | H | Q | S | T | DELETED | DELETED | P | I |
| S | A | F | S | L | H | Q | S | T | DELETED | DELETED | P | M |
| S | A | F | S | L | H | Q | S | T | DELETED | P | DELETED | I |
| S | A | F | S | L | H | Q | S | T | DELETED | P | DELETED | M |
| S | A | F | S | L | H | Q | S | T | DELETED | P | P | I |
| S | A | F | S | L | H | Q | S | T | DELETED | P | P | M |
| S | A | F | S | L | H | Q | S | T | N | DELETED | DELETED | I |
| S | A | F | S | L | H | Q | S | T | N | DELETED | DELETED | M |
| S | A | F | S | L | H | Q | S | T | N | DELETED | P | I |
| S | A | F | S | L | H | Q | S | T | N | DELETED | P | M |
| S | A | F | S | L | H | Q | S | T | N | P | DELETED | I |
| S | A | F | S | L | H | Q | S | T | N | P | DELETED | M |
| S | A | F | S | L | H | Q | S | T | N | P | P | I |
| S | A | F | S | L | H | Q | S | T | N | P | P | M |
| S | A | F | S | L | H | Q | G | S | DELETED | DELETED | DELETED | I |
| S | A | F | S | L | H | Q | G | S | DELETED | DELETED | DELETED | M |
| S | A | F | S | L | H | Q | G | S | DELETED | DELETED | P | I |
| S | A | F | S | L | H | Q | G | S | DELETED | DELETED | P | M |
| S | A | F | S | L | H | Q | G | S | DELETED | P | DELETED | I |
| S | A | F | S | L | H | Q | G | S | DELETED | P | DELETED | M |
| S | A | F | S | L | H | Q | G | S | DELETED | P | P | I |
| S | A | F | S | L | H | Q | G | S | DELETED | P | P | M |
| S | A | F | S | L | H | Q | G | S | N | DELETED | DELETED | I |
| S | A | F | S | L | H | Q | G | S | N | DELETED | DELETED | M |
| S | A | F | S | L | H | Q | G | S | N | DELETED | P | I |
| S | A | F | S | L | H | Q | G | S | N | DELETED | P | M |
| S | A | F | S | L | H | Q | G | S | N | P | DELETED | I |
| S | A | F | S | L | H | Q | G | S | N | P | DELETED | M |
| S | A | F | S | L | H | Q | G | S | N | P | P | I |
| S | A | F | S | L | H | Q | G | S | N | P | P | M |
| S | A | F | S | L | H | Q | G | T | DELETED | DELETED | DELETED | I |
| S | A | F | S | L | H | Q | G | T | DELETED | DELETED | DELETED | M |
| S | A | F | S | L | H | Q | G | T | DELETED | DELETED | P | I |
| S | A | F | S | L | H | Q | G | T | DELETED | DELETED | P | M |
| S | A | F | S | L | H | Q | G | T | DELETED | P | DELETED | I |
| S | A | F | S | L | H | Q | G | T | DELETED | P | DELETED | M |
| S | A | F | S | L | H | Q | G | T | DELETED | P | P | I |
| S | A | F | S | L | H | Q | G | T | DELETED | P | P | M |
| S | A | F | S | L | H | Q | G | T | N | DELETED | DELETED | I |
| S | A | F | S | L | H | Q | G | T | N | DELETED | DELETED | M |
| S | A | F | S | L | H | Q | G | T | N | DELETED | P | I |
| S | A | F | S | L | H | Q | G | T | N | DELETED | P | M |
| S | A | F | S | L | H | Q | G | T | N | P | DELETED | I |
| S | A | F | S | L | H | Q | G | T | N | P | DELETED | M |
| S | A | F | S | L | H | Q | G | T | N | P | P | I |
| S | A | F | S | L | H | Q | G | T | N | P | P | M |
| S | A | F | S | L | H | V | S | S | DELETED | DELETED | DELETED | I |
| S | A | F | S | L | H | V | S | S | DELETED | DELETED | DELETED | M |
| S | A | F | S | L | H | V | S | S | DELETED | DELETED | P | I |
| S | A | F | S | L | H | V | S | S | DELETED | DELETED | P | M |
| S | A | F | S | L | H | V | S | S | DELETED | P | DELETED | I |
| S | A | F | S | L | H | V | S | S | DELETED | P | DELETED | M |
| S | A | F | S | L | H | V | S | S | DELETED | P | P | I |
| S | A | F | S | L | H | V | S | S | DELETED | P | P | M |
| S | A | F | S | L | H | V | S | S | N | DELETED | DELETED | I |
| S | A | F | S | L | H | V | S | S | N | DELETED | DELETED | M |
| S | A | F | S | L | H | V | S | S | N | DELETED | P | I |
| S | A | F | S | L | H | V | S | S | N | DELETED | P | M |
| S | A | F | S | L | H | V | S | S | N | P | DELETED | I |
| S | A | F | S | L | H | V | S | S | N | P | DELETED | M |
| S | A | F | S | L | H | V | S | S | N | P | P | I |
| S | A | F | S | L | H | V | S | S | N | P | P | M |
| S | A | F | S | L | H | V | S | T | DELETED | DELETED | DELETED | I |
| S | A | F | S | L | H | V | S | T | DELETED | DELETED | DELETED | M |
| S | A | F | S | L | H | V | S | T | DELETED | DELETED | P | I |
| S | A | F | S | L | H | V | S | T | DELETED | DELETED | P | M |
| S | A | F | S | L | H | V | S | T | DELETED | P | DELETED | I |
| S | A | F | S | L | H | V | S | T | DELETED | P | DELETED | M |
| S | A | F | S | L | H | V | S | T | DELETED | P | P | I |
| S | A | F | S | L | H | V | S | T | DELETED | P | P | M |
| S | A | F | S | L | H | V | S | T | N | DELETED | DELETED | I |
| S | A | F | S | L | H | V | S | T | N | DELETED | DELETED | M |
| S | A | F | S | L | H | V | S | T | N | DELETED | P | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| S | A | F | S | L | H | V | S | T | N | DELETED | P | M |
| S | A | F | S | L | H | V | S | T | N | P | DELETED | I |
| S | A | F | S | L | H | V | S | T | N | P | DELETED | M |
| S | A | F | S | L | H | V | S | T | N | P | P | I |
| S | A | F | S | L | H | V | S | T | N | P | P | M |
| S | A | F | S | L | H | V | G | S | DELETED | DELETED | DELETED | I |
| S | A | F | S | L | H | V | G | S | DELETED | DELETED | DELETED | M |
| S | A | F | S | L | H | V | G | S | DELETED | DELETED | P | I |
| S | A | F | S | L | H | V | G | S | DELETED | DELETED | P | M |
| S | A | F | S | L | H | V | G | S | DELETED | P | DELETED | I |
| S | A | F | S | L | H | V | G | S | DELETED | P | DELETED | M |
| S | A | F | S | L | H | V | G | S | DELETED | P | P | I |
| S | A | F | S | L | H | V | G | S | DELETED | P | P | M |
| S | A | F | S | L | H | V | G | S | N | DELETED | DELETED | I |
| S | A | F | S | L | H | V | G | S | N | DELETED | DELETED | M |
| S | A | F | S | L | H | V | G | S | N | DELETED | P | I |
| S | A | F | S | L | H | V | G | S | N | DELETED | P | M |
| S | A | F | S | L | H | V | G | S | N | P | DELETED | I |
| S | A | F | S | L | H | V | G | S | N | P | DELETED | M |
| S | A | F | S | L | H | V | G | S | N | P | P | I |
| S | A | F | S | L | H | V | G | S | N | P | P | M |
| S | A | F | S | L | H | V | G | T | DELETED | DELETED | DELETED | I |
| S | A | F | S | L | H | V | G | T | DELETED | DELETED | DELETED | M |
| S | A | F | S | L | H | V | G | T | DELETED | DELETED | P | I |
| S | A | F | S | L | H | V | G | T | DELETED | DELETED | P | M |
| S | A | F | S | L | H | V | G | T | DELETED | P | DELETED | I |
| S | A | F | S | L | H | V | G | T | DELETED | P | DELETED | M |
| S | A | F | S | L | H | V | G | T | DELETED | P | P | I |
| S | A | F | S | L | H | V | G | T | DELETED | P | P | M |
| S | A | F | S | L | H | V | G | T | N | DELETED | DELETED | I |
| S | A | F | S | L | H | V | G | T | N | DELETED | DELETED | M |
| S | A | F | S | L | H | V | G | T | N | DELETED | P | I |
| S | A | F | S | L | H | V | G | T | N | DELETED | P | M |
| S | A | F | S | L | H | V | G | T | N | P | DELETED | I |
| S | A | F | S | L | H | V | G | T | N | P | DELETED | M |
| S | A | F | S | L | H | V | G | T | N | P | P | I |
| S | A | F | S | L | H | V | G | T | N | P | P | M |
| S | A | F | S | I | Y | Q | S | S | DELETED | DELETED | DELETED | I |
| S | A | F | S | I | Y | Q | S | S | DELETED | DELETED | DELETED | M |
| S | A | F | S | I | Y | Q | S | S | DELETED | DELETED | P | I |
| S | A | F | S | I | Y | Q | S | S | DELETED | DELETED | P | M |
| S | A | F | S | I | Y | Q | S | S | DELETED | P | DELETED | I |
| S | A | F | S | I | Y | Q | S | S | DELETED | P | DELETED | M |
| S | A | F | S | I | Y | Q | S | S | DELETED | P | P | I |
| S | A | F | S | I | Y | Q | S | S | DELETED | P | P | M |
| S | A | F | S | I | Y | Q | S | S | N | DELETED | DELETED | I |
| S | A | F | S | I | Y | Q | S | S | N | DELETED | DELETED | M |
| S | A | F | S | I | Y | Q | S | S | N | DELETED | P | I |
| S | A | F | S | I | Y | Q | S | S | N | DELETED | P | M |
| S | A | F | S | I | Y | Q | S | S | N | P | DELETED | I |
| S | A | F | S | I | Y | Q | S | S | N | P | DELETED | M |
| S | A | F | S | I | Y | Q | S | S | N | P | P | I |
| S | A | F | S | I | Y | Q | S | S | N | P | P | M |
| S | A | F | S | I | Y | Q | S | T | DELETED | DELETED | DELETED | I |
| S | A | F | S | I | Y | Q | S | T | DELETED | DELETED | DELETED | M |
| S | A | F | S | I | Y | Q | S | T | DELETED | DELETED | P | I |
| S | A | F | S | I | Y | Q | S | T | DELETED | DELETED | P | M |
| S | A | F | S | I | Y | Q | S | T | DELETED | P | DELETED | I |
| S | A | F | S | I | Y | Q | S | T | DELETED | P | DELETED | M |
| S | A | F | S | I | Y | Q | S | T | DELETED | P | P | I |
| S | A | F | S | I | Y | Q | S | T | DELETED | P | P | M |
| S | A | F | S | I | Y | Q | S | T | N | DELETED | DELETED | I |
| S | A | F | S | I | Y | Q | S | T | N | DELETED | DELETED | M |
| S | A | F | S | I | Y | Q | S | T | N | DELETED | P | I |
| S | A | F | S | I | Y | Q | S | T | N | DELETED | P | M |
| S | A | F | S | I | Y | Q | S | T | N | P | DELETED | I |
| S | A | F | S | I | Y | Q | S | T | N | P | DELETED | M |
| S | A | F | S | I | Y | Q | S | T | N | P | P | I |
| S | A | F | S | I | Y | Q | S | T | N | P | P | M |
| S | A | F | S | I | Y | Q | G | S | DELETED | DELETED | DELETED | I |
| S | A | F | S | I | Y | Q | G | S | DELETED | DELETED | DELETED | M |
| S | A | F | S | I | Y | Q | G | S | DELETED | DELETED | P | I |
| S | A | F | S | I | Y | Q | G | S | DELETED | DELETED | P | M |
| S | A | F | S | I | Y | Q | G | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | S | I | Y | Q | G | S | DELETED | P | DELETED | M |
| S | A | F | S | I | Y | Q | G | S | DELETED | P | P | I |
| S | A | F | S | I | Y | Q | G | S | DELETED | P | P | M |
| S | A | F | S | I | Y | Q | G | S | N | DELETED | DELETED | I |
| S | A | F | S | I | Y | Q | G | S | N | DELETED | DELETED | M |
| S | A | F | S | I | Y | Q | G | S | N | DELETED | P | I |
| S | A | F | S | I | Y | Q | G | S | N | DELETED | P | M |
| S | A | F | S | I | Y | Q | G | S | N | P | DELETED | I |
| S | A | F | S | I | Y | Q | G | S | N | P | DELETED | M |
| S | A | F | S | I | Y | Q | G | S | N | P | P | I |
| S | A | F | S | I | Y | Q | G | S | N | P | P | M |
| S | A | F | S | I | Y | Q | G | T | DELETED | DELETED | DELETED | I |
| S | A | F | S | I | Y | Q | G | T | DELETED | DELETED | DELETED | M |
| S | A | F | S | I | Y | Q | G | T | DELETED | DELETED | P | I |
| S | A | F | S | I | Y | Q | G | T | DELETED | DELETED | P | M |
| S | A | F | S | I | Y | Q | G | T | DELETED | P | DELETED | I |
| S | A | F | S | I | Y | Q | G | T | DELETED | P | DELETED | M |
| S | A | F | S | I | Y | Q | G | T | DELETED | P | P | I |
| S | A | F | S | I | Y | Q | G | T | DELETED | P | P | M |
| S | A | F | S | I | Y | Q | G | T | N | DELETED | DELETED | I |
| S | A | F | S | I | Y | Q | G | T | N | DELETED | DELETED | M |
| S | A | F | S | I | Y | Q | G | T | N | DELETED | P | I |
| S | A | F | S | I | Y | Q | G | T | N | DELETED | P | M |
| S | A | F | S | I | Y | Q | G | T | N | P | DELETED | I |
| S | A | F | S | I | Y | Q | G | T | N | P | DELETED | M |
| S | A | F | S | I | Y | Q | G | T | N | P | P | I |
| S | A | F | S | I | Y | Q | G | T | N | P | P | M |
| S | A | F | S | I | Y | V | S | S | DELETED | DELETED | DELETED | I |
| S | A | F | S | I | Y | V | S | S | DELETED | DELETED | DELETED | M |
| S | A | F | S | I | Y | V | S | S | DELETED | DELETED | P | I |
| S | A | F | S | I | Y | V | S | S | DELETED | DELETED | P | M |
| S | A | F | S | I | Y | V | S | S | DELETED | P | DELETED | I |
| S | A | F | S | I | Y | V | S | S | DELETED | P | DELETED | M |
| S | A | F | S | I | Y | V | S | S | DELETED | P | P | I |
| S | A | F | S | I | Y | V | S | S | DELETED | P | P | M |
| S | A | F | S | I | Y | V | S | S | N | DELETED | DELETED | I |
| S | A | F | S | I | Y | V | S | S | N | DELETED | DELETED | M |
| S | A | F | S | I | Y | V | S | S | N | DELETED | P | I |
| S | A | F | S | I | Y | V | S | S | N | DELETED | P | M |
| S | A | F | S | I | Y | V | S | S | N | P | DELETED | I |
| S | A | F | S | I | Y | V | S | S | N | P | DELETED | M |
| S | A | F | S | I | Y | V | S | S | N | P | P | I |
| S | A | F | S | I | Y | V | S | S | N | P | P | M |
| S | A | F | S | I | Y | V | S | T | DELETED | DELETED | DELETED | I |
| S | A | F | S | I | Y | V | S | T | DELETED | DELETED | DELETED | M |
| S | A | F | S | I | Y | V | S | T | DELETED | DELETED | P | I |
| S | A | F | S | I | Y | V | S | T | DELETED | DELETED | P | M |
| S | A | F | S | I | Y | V | S | T | DELETED | P | DELETED | I |
| S | A | F | S | I | Y | V | S | T | DELETED | P | DELETED | M |
| S | A | F | S | I | Y | V | S | T | DELETED | P | P | I |
| S | A | F | S | I | Y | V | S | T | DELETED | P | P | M |
| S | A | F | S | I | Y | V | S | T | N | DELETED | DELETED | I |
| S | A | F | S | I | Y | V | S | T | N | DELETED | DELETED | M |
| S | A | F | S | I | Y | V | S | T | N | DELETED | P | I |
| S | A | F | S | I | Y | V | S | T | N | DELETED | P | M |
| S | A | F | S | I | Y | V | S | T | N | P | DELETED | I |
| S | A | F | S | I | Y | V | S | T | N | P | DELETED | M |
| S | A | F | S | I | Y | V | S | T | N | P | P | I |
| S | A | F | S | I | Y | V | S | T | N | P | P | M |
| S | A | F | S | I | Y | V | G | S | DELETED | DELETED | DELETED | I |
| S | A | F | S | I | Y | V | G | S | DELETED | DELETED | DELETED | M |
| S | A | F | S | I | Y | V | G | S | DELETED | DELETED | P | I |
| S | A | F | S | I | Y | V | G | S | DELETED | DELETED | P | M |
| S | A | F | S | I | Y | V | G | S | DELETED | P | DELETED | I |
| S | A | F | S | I | Y | V | G | S | DELETED | P | DELETED | M |
| S | A | F | S | I | Y | V | G | S | DELETED | P | P | I |
| S | A | F | S | I | Y | V | G | S | DELETED | P | P | M |
| S | A | F | S | I | Y | V | G | S | N | DELETED | DELETED | I |
| S | A | F | S | I | Y | V | G | S | N | DELETED | DELETED | M |
| S | A | F | S | I | Y | V | G | S | N | DELETED | P | I |
| S | A | F | S | I | Y | V | G | S | N | DELETED | P | M |
| S | A | F | S | I | Y | V | G | S | N | P | DELETED | I |
| S | A | F | S | I | Y | V | G | S | N | P | DELETED | M |
| S | A | F | S | I | Y | V | G | S | N | P | P | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| S | A | F | S | I | Y | V | G | S | N | P | P | M |
| S | A | F | S | I | Y | V | G | T | DELETED | DELETED | DELETED | I |
| S | A | F | S | I | Y | V | G | T | DELETED | DELETED | DELETED | M |
| S | A | F | S | I | Y | V | G | T | DELETED | DELETED | P | I |
| S | A | F | S | I | Y | V | G | T | DELETED | DELETED | P | M |
| S | A | F | S | I | Y | V | G | T | DELETED | P | DELETED | I |
| S | A | F | S | I | Y | V | G | T | DELETED | P | DELETED | M |
| S | A | F | S | I | Y | V | G | T | DELETED | P | P | I |
| S | A | F | S | I | Y | V | G | T | DELETED | P | P | M |
| S | A | F | S | I | Y | V | G | T | N | DELETED | DELETED | I |
| S | A | F | S | I | Y | V | G | T | N | DELETED | DELETED | M |
| S | A | F | S | I | Y | V | G | T | N | DELETED | P | I |
| S | A | F | S | I | Y | V | G | T | N | DELETED | P | M |
| S | A | F | S | I | Y | V | G | T | N | P | DELETED | I |
| S | A | F | S | I | Y | V | G | T | N | P | DELETED | M |
| S | A | F | S | I | Y | V | G | T | N | P | P | I |
| S | A | F | S | I | Y | V | G | T | N | P | P | M |
| S | A | F | S | I | H | Q | S | S | DELETED | DELETED | DELETED | I |
| S | A | F | S | I | H | Q | S | S | DELETED | DELETED | DELETED | M |
| S | A | F | S | I | H | Q | S | S | DELETED | DELETED | P | I |
| S | A | F | S | I | H | Q | S | S | DELETED | DELETED | P | M |
| S | A | F | S | I | H | Q | S | S | DELETED | P | DELETED | I |
| S | A | F | S | I | H | Q | S | S | DELETED | P | DELETED | M |
| S | A | F | S | I | H | Q | S | S | DELETED | P | P | I |
| S | A | F | S | I | H | Q | S | S | DELETED | P | P | M |
| S | A | F | S | I | H | Q | S | S | N | DELETED | DELETED | I |
| S | A | F | S | I | H | Q | S | S | N | DELETED | DELETED | M |
| S | A | F | S | I | H | Q | S | S | N | DELETED | P | I |
| S | A | F | S | I | H | Q | S | S | N | DELETED | P | M |
| S | A | F | S | I | H | Q | S | S | N | P | DELETED | I |
| S | A | F | S | I | H | Q | S | S | N | P | DELETED | M |
| S | A | F | S | I | H | Q | S | S | N | P | P | I |
| S | A | F | S | I | H | Q | S | S | N | P | P | M |
| S | A | F | S | I | H | Q | S | T | DELETED | DELETED | DELETED | I |
| S | A | F | S | I | H | Q | S | T | DELETED | DELETED | DELETED | M |
| S | A | F | S | I | H | Q | S | T | DELETED | DELETED | P | I |
| S | A | F | S | I | H | Q | S | T | DELETED | DELETED | P | M |
| S | A | F | S | I | H | Q | S | T | DELETED | P | DELETED | I |
| S | A | F | S | I | H | Q | S | T | DELETED | P | DELETED | M |
| S | A | F | S | I | H | Q | S | T | DELETED | P | P | I |
| S | A | F | S | I | H | Q | S | T | DELETED | P | P | M |
| S | A | F | S | I | H | Q | S | T | N | DELETED | DELETED | I |
| S | A | F | S | I | H | Q | S | T | N | DELETED | DELETED | M |
| S | A | F | S | I | H | Q | S | T | N | DELETED | P | I |
| S | A | F | S | I | H | Q | S | T | N | DELETED | P | M |
| S | A | F | S | I | H | Q | S | T | N | P | DELETED | I |
| S | A | F | S | I | H | Q | S | T | N | P | DELETED | M |
| S | A | F | S | I | H | Q | S | T | N | P | P | I |
| S | A | F | S | I | H | Q | S | T | N | P | P | M |
| S | A | F | S | I | H | Q | G | S | DELETED | DELETED | DELETED | I |
| S | A | F | S | I | H | Q | G | S | DELETED | DELETED | DELETED | M |
| S | A | F | S | I | H | Q | G | S | DELETED | DELETED | P | I |
| S | A | F | S | I | H | Q | G | S | DELETED | DELETED | P | M |
| S | A | F | S | I | H | Q | G | S | DELETED | P | DELETED | I |
| S | A | F | S | I | H | Q | G | S | DELETED | P | DELETED | M |
| S | A | F | S | I | H | Q | G | S | DELETED | P | P | I |
| S | A | F | S | I | H | Q | G | S | DELETED | P | P | M |
| S | A | F | S | I | H | Q | G | S | N | DELETED | DELETED | I |
| S | A | F | S | I | H | Q | G | S | N | DELETED | DELETED | M |
| S | A | F | S | I | H | Q | G | S | N | DELETED | P | I |
| S | A | F | S | I | H | Q | G | S | N | DELETED | P | M |
| S | A | F | S | I | H | Q | G | S | N | P | DELETED | I |
| S | A | F | S | I | H | Q | G | S | N | P | DELETED | M |
| S | A | F | S | I | H | Q | G | S | N | P | P | I |
| S | A | F | S | I | H | Q | G | S | N | P | P | M |
| S | A | F | S | I | H | Q | G | T | DELETED | DELETED | DELETED | I |
| S | A | F | S | I | H | Q | G | T | DELETED | DELETED | DELETED | M |
| S | A | F | S | I | H | Q | G | T | DELETED | DELETED | P | I |
| S | A | F | S | I | H | Q | G | T | DELETED | DELETED | P | M |
| S | A | F | S | I | H | Q | G | T | DELETED | P | DELETED | I |
| S | A | F | S | I | H | Q | G | T | DELETED | P | DELETED | M |
| S | A | F | S | I | H | Q | G | T | DELETED | P | P | I |
| S | A | F | S | I | H | Q | G | T | DELETED | P | P | M |
| S | A | F | S | I | H | Q | G | T | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | S | I | H | Q | G | T | N | DELETED | DELETED | M |
| S | A | F | S | I | H | Q | G | T | N | DELETED | P | I |
| S | A | F | S | I | H | Q | G | T | N | DELETED | P | M |
| S | A | F | S | I | H | Q | G | T | N | P | DELETED | I |
| S | A | F | S | I | H | Q | G | T | N | P | DELETED | M |
| S | A | F | S | I | H | Q | G | T | N | P | P | I |
| S | A | F | S | I | H | Q | G | T | N | P | P | M |
| S | A | F | S | I | H | V | S | S | DELETED | DELETED | DELETED | I |
| S | A | F | S | I | H | V | S | S | DELETED | DELETED | DELETED | M |
| S | A | F | S | I | H | V | S | S | DELETED | DELETED | P | I |
| S | A | F | S | I | H | V | S | S | DELETED | DELETED | P | M |
| S | A | F | S | I | H | V | S | S | DELETED | P | DELETED | I |
| S | A | F | S | I | H | V | S | S | DELETED | P | DELETED | M |
| S | A | F | S | I | H | V | S | S | DELETED | P | P | I |
| S | A | F | S | I | H | V | S | S | DELETED | P | P | M |
| S | A | F | S | I | H | V | S | S | N | DELETED | DELETED | I |
| S | A | F | S | I | H | V | S | S | N | DELETED | DELETED | M |
| S | A | F | S | I | H | V | S | S | N | DELETED | P | I |
| S | A | F | S | I | H | V | S | S | N | DELETED | P | M |
| S | A | F | S | I | H | V | S | S | N | P | DELETED | I |
| S | A | F | S | I | H | V | S | S | N | P | DELETED | M |
| S | A | F | S | I | H | V | S | S | N | P | P | I |
| S | A | F | S | I | H | V | S | S | N | P | P | M |
| S | A | F | S | I | H | V | S | T | DELETED | DELETED | DELETED | I |
| S | A | F | S | I | H | V | S | T | DELETED | DELETED | DELETED | M |
| S | A | F | S | I | H | V | S | T | DELETED | DELETED | P | I |
| S | A | F | S | I | H | V | S | T | DELETED | DELETED | P | M |
| S | A | F | S | I | H | V | S | T | DELETED | P | DELETED | I |
| S | A | F | S | I | H | V | S | T | DELETED | P | DELETED | M |
| S | A | F | S | I | H | V | S | T | DELETED | P | P | I |
| S | A | F | S | I | H | V | S | T | DELETED | P | P | M |
| S | A | F | S | I | H | V | S | T | N | DELETED | DELETED | I |
| S | A | F | S | I | H | V | S | T | N | DELETED | DELETED | M |
| S | A | F | S | I | H | V | S | T | N | DELETED | P | I |
| S | A | F | S | I | H | V | S | T | N | DELETED | P | M |
| S | A | F | S | I | H | V | S | T | N | P | DELETED | I |
| S | A | F | S | I | H | V | S | T | N | P | DELETED | M |
| S | A | F | S | I | H | V | S | T | N | P | P | I |
| S | A | F | S | I | H | V | S | T | N | P | P | M |
| S | A | F | S | I | H | V | G | S | DELETED | DELETED | DELETED | I |
| S | A | F | S | I | H | V | G | S | DELETED | DELETED | DELETED | M |
| S | A | F | S | I | H | V | G | S | DELETED | DELETED | P | I |
| S | A | F | S | I | H | V | G | S | DELETED | DELETED | P | M |
| S | A | F | S | I | H | V | G | S | DELETED | P | DELETED | I |
| S | A | F | S | I | H | V | G | S | DELETED | P | DELETED | M |
| S | A | F | S | I | H | V | G | S | DELETED | P | P | I |
| S | A | F | S | I | H | V | G | S | DELETED | P | P | M |
| S | A | F | S | I | H | V | G | S | N | DELETED | DELETED | I |
| S | A | F | S | I | H | V | G | S | N | DELETED | DELETED | M |
| S | A | F | S | I | H | V | G | S | N | DELETED | P | I |
| S | A | F | S | I | H | V | G | S | N | DELETED | P | M |
| S | A | F | S | I | H | V | G | S | N | P | DELETED | I |
| S | A | F | S | I | H | V | G | S | N | P | DELETED | M |
| S | A | F | S | I | H | V | G | S | N | P | P | I |
| S | A | F | S | I | H | V | G | S | N | P | P | M |
| S | A | F | S | I | H | V | G | T | DELETED | DELETED | DELETED | I |
| S | A | F | S | I | H | V | G | T | DELETED | DELETED | DELETED | M |
| S | A | F | S | I | H | V | G | T | DELETED | DELETED | P | I |
| S | A | F | S | I | H | V | G | T | DELETED | DELETED | P | M |
| S | A | F | S | I | H | V | G | T | DELETED | P | DELETED | I |
| S | A | F | S | I | H | V | G | T | DELETED | P | DELETED | M |
| S | A | F | S | I | H | V | G | T | DELETED | P | P | I |
| S | A | F | S | I | H | V | G | T | DELETED | P | P | M |
| S | A | F | S | I | H | V | G | T | N | DELETED | DELETED | I |
| S | A | F | S | I | H | V | G | T | N | DELETED | DELETED | M |
| S | A | F | S | I | H | V | G | T | N | DELETED | P | I |
| S | A | F | S | I | H | V | G | T | N | DELETED | P | M |
| S | A | F | S | I | H | V | G | T | N | P | DELETED | I |
| S | A | F | S | I | H | V | G | T | N | P | DELETED | M |
| S | A | F | S | I | H | V | G | T | N | P | P | I |
| S | A | F | S | I | H | V | G | T | N | P | P | M |
| S | A | F | R | L | Y | Q | S | S | DELETED | DELETED | DELETED | I |
| S | A | F | R | L | Y | Q | S | S | DELETED | DELETED | DELETED | M |
| S | A | F | R | L | Y | Q | S | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | L | Y | Q | S | S | DELETED | DELETED | P | M |
| S | A | F | R | L | Y | Q | S | S | DELETED | P | DELETED | I |
| S | A | F | R | L | Y | Q | S | S | DELETED | P | DELETED | M |
| S | A | F | R | L | Y | Q | S | S | DELETED | P | P | I |
| S | A | F | R | L | Y | Q | S | S | DELETED | P | P | M |
| S | A | F | R | L | Y | Q | S | S | N | DELETED | DELETED | I |
| S | A | F | R | L | Y | Q | S | S | N | DELETED | DELETED | M |
| S | A | F | R | L | Y | Q | S | S | N | DELETED | P | I |
| S | A | F | R | L | Y | Q | S | S | N | DELETED | P | M |
| S | A | F | R | L | Y | Q | S | S | N | P | DELETED | I |
| S | A | F | R | L | Y | Q | S | S | N | P | DELETED | M |
| S | A | F | R | L | Y | Q | S | S | N | P | P | I |
| S | A | F | R | L | Y | Q | S | S | N | P | P | M |
| S | A | F | R | L | Y | Q | S | T | DELETED | DELETED | DELETED | I |
| S | A | F | R | L | Y | Q | S | T | DELETED | DELETED | DELETED | M |
| S | A | F | R | L | Y | Q | S | T | DELETED | DELETED | P | I |
| S | A | F | R | L | Y | Q | S | T | DELETED | DELETED | P | M |
| S | A | F | R | L | Y | Q | S | T | DELETED | P | DELETED | I |
| S | A | F | R | L | Y | Q | S | T | DELETED | P | DELETED | M |
| S | A | F | R | L | Y | Q | S | T | DELETED | P | P | I |
| S | A | F | R | L | Y | Q | S | T | DELETED | P | P | M |
| S | A | F | R | L | Y | Q | S | T | N | DELETED | DELETED | I |
| S | A | F | R | L | Y | Q | S | T | N | DELETED | DELETED | M |
| S | A | F | R | L | Y | Q | S | T | N | DELETED | P | I |
| S | A | F | R | L | Y | Q | S | T | N | DELETED | P | M |
| S | A | F | R | L | Y | Q | S | T | N | P | DELETED | I |
| S | A | F | R | L | Y | Q | S | T | N | P | DELETED | M |
| S | A | F | R | L | Y | Q | S | T | N | P | P | I |
| S | A | F | R | L | Y | Q | S | T | N | P | P | M |
| S | A | F | R | L | Y | Q | G | S | DELETED | DELETED | DELETED | I |
| S | A | F | R | L | Y | Q | G | S | DELETED | DELETED | DELETED | M |
| S | A | F | R | L | Y | Q | G | S | DELETED | DELETED | P | I |
| S | A | F | R | L | Y | Q | G | S | DELETED | DELETED | P | M |
| S | A | F | R | L | Y | Q | G | S | DELETED | P | DELETED | I |
| S | A | F | R | L | Y | Q | G | S | DELETED | P | DELETED | M |
| S | A | F | R | L | Y | Q | G | S | DELETED | P | P | I |
| S | A | F | R | L | Y | Q | G | S | DELETED | P | P | M |
| S | A | F | R | L | Y | Q | G | S | N | DELETED | DELETED | I |
| S | A | F | R | L | Y | Q | G | S | N | DELETED | DELETED | M |
| S | A | F | R | L | Y | Q | G | S | N | DELETED | P | I |
| S | A | F | R | L | Y | Q | G | S | N | DELETED | P | M |
| S | A | F | R | L | Y | Q | G | S | N | P | DELETED | I |
| S | A | F | R | L | Y | Q | G | S | N | P | DELETED | M |
| S | A | F | R | L | Y | Q | G | S | N | P | P | I |
| S | A | F | R | L | Y | Q | G | S | N | P | P | M |
| S | A | F | R | L | Y | Q | G | T | DELETED | DELETED | DELETED | I |
| S | A | F | R | L | Y | Q | G | T | DELETED | DELETED | DELETED | M |
| S | A | F | R | L | Y | Q | G | T | DELETED | DELETED | P | I |
| S | A | F | R | L | Y | Q | G | T | DELETED | DELETED | P | M |
| S | A | F | R | L | Y | Q | G | T | DELETED | P | DELETED | I |
| S | A | F | R | L | Y | Q | G | T | DELETED | P | DELETED | M |
| S | A | F | R | L | Y | Q | G | T | DELETED | P | P | I |
| S | A | F | R | L | Y | Q | G | T | DELETED | P | P | M |
| S | A | F | R | L | Y | Q | G | T | N | DELETED | DELETED | I |
| S | A | F | R | L | Y | Q | G | T | N | DELETED | DELETED | M |
| S | A | F | R | L | Y | Q | G | T | N | DELETED | P | I |
| S | A | F | R | L | Y | Q | G | T | N | DELETED | P | M |
| S | A | F | R | L | Y | Q | G | T | N | P | DELETED | I |
| S | A | F | R | L | Y | Q | G | T | N | P | DELETED | M |
| S | A | F | R | L | Y | Q | G | T | N | P | P | I |
| S | A | F | R | L | Y | Q | G | T | N | P | P | M |
| S | A | F | R | L | Y | V | S | S | DELETED | DELETED | DELETED | I |
| S | A | F | R | L | Y | V | S | S | DELETED | DELETED | DELETED | M |
| S | A | F | R | L | Y | V | S | S | DELETED | DELETED | P | I |
| S | A | F | R | L | Y | V | S | S | DELETED | DELETED | P | M |
| S | A | F | R | L | Y | V | S | S | DELETED | P | DELETED | I |
| S | A | F | R | L | Y | V | S | S | DELETED | P | DELETED | M |
| S | A | F | R | L | Y | V | S | S | DELETED | P | P | I |
| S | A | F | R | L | Y | V | S | S | DELETED | P | P | M |
| S | A | F | R | L | Y | V | S | S | N | DELETED | DELETED | I |
| S | A | F | R | L | Y | V | S | S | N | DELETED | DELETED | M |
| S | A | F | R | L | Y | V | S | S | N | DELETED | P | I |
| S | A | F | R | L | Y | V | S | S | N | DELETED | P | M |
| S | A | F | R | L | Y | V | S | S | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | L | Y | V | S | S | N | P | DELETED | M |
| S | A | F | R | L | Y | V | S | S | N | P | P | I |
| S | A | F | R | L | Y | V | S | S | N | P | P | M |
| S | A | F | R | L | Y | V | S | T | DELETED | DELETED | DELETED | I |
| S | A | F | R | L | Y | V | S | T | DELETED | DELETED | DELETED | M |
| S | A | F | R | L | Y | V | S | T | DELETED | DELETED | P | I |
| S | A | F | R | L | Y | V | S | T | DELETED | DELETED | P | M |
| S | A | F | R | L | Y | V | S | T | DELETED | P | DELETED | I |
| S | A | F | R | L | Y | V | S | T | DELETED | P | DELETED | M |
| S | A | F | R | L | Y | V | S | T | DELETED | P | P | I |
| S | A | F | R | L | Y | V | S | T | DELETED | P | P | M |
| S | A | F | R | L | Y | V | S | T | N | DELETED | DELETED | I |
| S | A | F | R | L | Y | V | S | T | N | DELETED | DELETED | M |
| S | A | F | R | L | Y | V | S | T | N | DELETED | P | I |
| S | A | F | R | L | Y | V | S | T | N | DELETED | P | M |
| S | A | F | R | L | Y | V | S | T | N | P | DELETED | I |
| S | A | F | R | L | Y | V | S | T | N | P | DELETED | M |
| S | A | F | R | L | Y | V | S | T | N | P | P | I |
| S | A | F | R | L | Y | V | S | T | N | P | P | M |
| S | A | F | R | L | Y | V | G | S | DELETED | DELETED | DELETED | I |
| S | A | F | R | L | Y | V | G | S | DELETED | DELETED | DELETED | M |
| S | A | F | R | L | Y | V | G | S | DELETED | DELETED | P | I |
| S | A | F | R | L | Y | V | G | S | DELETED | DELETED | P | M |
| S | A | F | R | L | Y | V | G | S | DELETED | P | DELETED | I |
| S | A | F | R | L | Y | V | G | S | DELETED | P | DELETED | M |
| S | A | F | R | L | Y | V | G | S | DELETED | P | P | I |
| S | A | F | R | L | Y | V | G | S | DELETED | P | P | M |
| S | A | F | R | L | Y | V | G | S | N | DELETED | DELETED | I |
| S | A | F | R | L | Y | V | G | S | N | DELETED | DELETED | M |
| S | A | F | R | L | Y | V | G | S | N | DELETED | P | I |
| S | A | F | R | L | Y | V | G | S | N | DELETED | P | M |
| S | A | F | R | L | Y | V | G | S | N | P | DELETED | I |
| S | A | F | R | L | Y | V | G | S | N | P | DELETED | M |
| S | A | F | R | L | Y | V | G | S | N | P | P | I |
| S | A | F | R | L | Y | V | G | S | N | P | P | M |
| S | A | F | R | L | Y | V | G | T | DELETED | DELETED | DELETED | I |
| S | A | F | R | L | Y | V | G | T | DELETED | DELETED | DELETED | M |
| S | A | F | R | L | Y | V | G | T | DELETED | DELETED | P | I |
| S | A | F | R | L | Y | V | G | T | DELETED | DELETED | P | M |
| S | A | F | R | L | Y | V | G | T | DELETED | P | DELETED | I |
| S | A | F | R | L | Y | V | G | T | DELETED | P | DELETED | M |
| S | A | F | R | L | Y | V | G | T | DELETED | P | P | I |
| S | A | F | R | L | Y | V | G | T | DELETED | P | P | M |
| S | A | F | R | L | Y | V | G | T | N | DELETED | DELETED | I |
| S | A | F | R | L | Y | V | G | T | N | DELETED | DELETED | M |
| S | A | F | R | L | Y | V | G | T | N | DELETED | P | I |
| S | A | F | R | L | Y | V | G | T | N | DELETED | P | M |
| S | A | F | R | L | Y | V | G | T | N | P | DELETED | I |
| S | A | F | R | L | Y | V | G | T | N | P | DELETED | M |
| S | A | F | R | L | Y | V | G | T | N | P | P | I |
| S | A | F | R | L | Y | V | G | T | N | P | P | M |
| S | A | F | R | L | H | Q | S | S | DELETED | DELETED | DELETED | I |
| S | A | F | R | L | H | Q | S | S | DELETED | DELETED | DELETED | M |
| S | A | F | R | L | H | Q | S | S | DELETED | DELETED | P | I |
| S | A | F | R | L | H | Q | S | S | DELETED | DELETED | P | M |
| S | A | F | R | L | H | Q | S | S | DELETED | P | DELETED | I |
| S | A | F | R | L | H | Q | S | S | DELETED | P | DELETED | M |
| S | A | F | R | L | H | Q | S | S | DELETED | P | P | I |
| S | A | F | R | L | H | Q | S | S | DELETED | P | P | M |
| S | A | F | R | L | H | Q | S | S | N | DELETED | DELETED | I |
| S | A | F | R | L | H | Q | S | S | N | DELETED | DELETED | M |
| S | A | F | R | L | H | Q | S | S | N | DELETED | P | I |
| S | A | F | R | L | H | Q | S | S | N | DELETED | P | M |
| S | A | F | R | L | H | Q | S | S | N | P | DELETED | I |
| S | A | F | R | L | H | Q | S | S | N | P | DELETED | M |
| S | A | F | R | L | H | Q | S | S | N | P | P | I |
| S | A | F | R | L | H | Q | S | S | N | P | P | M |
| S | A | F | R | L | H | Q | S | T | DELETED | DELETED | DELETED | I |
| S | A | F | R | L | H | Q | S | T | DELETED | DELETED | DELETED | M |
| S | A | F | R | L | H | Q | S | T | DELETED | DELETED | P | I |
| S | A | F | R | L | H | Q | S | T | DELETED | DELETED | P | M |
| S | A | F | R | L | H | Q | S | T | DELETED | P | DELETED | I |
| S | A | F | R | L | H | Q | S | T | DELETED | P | DELETED | M |
| S | A | F | R | L | H | Q | S | T | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | L | H | Q | S | T | DELETED | P | P | M |
| S | A | F | R | L | H | Q | S | T | N | DELETED | DELETED | I |
| S | A | F | R | L | H | Q | S | T | N | DELETED | DELETED | M |
| S | A | F | R | L | H | Q | S | T | N | DELETED | P | I |
| S | A | F | R | L | H | Q | S | T | N | DELETED | P | M |
| S | A | F | R | L | H | Q | S | T | N | P | DELETED | I |
| S | A | F | R | L | H | Q | S | T | N | P | DELETED | M |
| S | A | F | R | L | H | Q | S | T | N | P | P | I |
| S | A | F | R | L | H | Q | S | T | N | P | P | M |
| S | A | F | R | L | H | Q | G | S | DELETED | DELETED | DELETED | I |
| S | A | F | R | L | H | Q | G | S | DELETED | DELETED | DELETED | M |
| S | A | F | R | L | H | Q | G | S | DELETED | DELETED | P | I |
| S | A | F | R | L | H | Q | G | S | DELETED | DELETED | P | M |
| S | A | F | R | L | H | Q | G | S | DELETED | P | DELETED | I |
| S | A | F | R | L | H | Q | G | S | DELETED | P | DELETED | M |
| S | A | F | R | L | H | Q | G | S | DELETED | P | P | I |
| S | A | F | R | L | H | Q | G | S | DELETED | P | P | M |
| S | A | F | R | L | H | Q | G | S | N | DELETED | DELETED | I |
| S | A | F | R | L | H | Q | G | S | N | DELETED | DELETED | M |
| S | A | F | R | L | H | Q | G | S | N | DELETED | P | I |
| S | A | F | R | L | H | Q | G | S | N | DELETED | P | M |
| S | A | F | R | L | H | Q | G | S | N | P | DELETED | I |
| S | A | F | R | L | H | Q | G | S | N | P | DELETED | M |
| S | A | F | R | L | H | Q | G | S | N | P | P | I |
| S | A | F | R | L | H | Q | G | S | N | P | P | M |
| S | A | F | R | L | H | Q | G | T | DELETED | DELETED | DELETED | I |
| S | A | F | R | L | H | Q | G | T | DELETED | DELETED | DELETED | M |
| S | A | F | R | L | H | Q | G | T | DELETED | DELETED | P | I |
| S | A | F | R | L | H | Q | G | T | DELETED | DELETED | P | M |
| S | A | F | R | L | H | Q | G | T | DELETED | P | DELETED | I |
| S | A | F | R | L | H | Q | G | T | DELETED | P | DELETED | M |
| S | A | F | R | L | H | Q | G | T | DELETED | P | P | I |
| S | A | F | R | L | H | Q | G | T | DELETED | P | P | M |
| S | A | F | R | L | H | Q | G | T | N | DELETED | DELETED | I |
| S | A | F | R | L | H | Q | G | T | N | DELETED | DELETED | M |
| S | A | F | R | L | H | Q | G | T | N | DELETED | P | I |
| S | A | F | R | L | H | Q | G | T | N | DELETED | P | M |
| S | A | F | R | L | H | Q | G | T | N | P | DELETED | I |
| S | A | F | R | L | H | Q | G | T | N | P | DELETED | M |
| S | A | F | R | L | H | Q | G | T | N | P | P | I |
| S | A | F | R | L | H | Q | G | T | N | P | P | M |
| S | A | F | R | L | H | V | S | S | DELETED | DELETED | DELETED | I |
| S | A | F | R | L | H | V | S | S | DELETED | DELETED | DELETED | M |
| S | A | F | R | L | H | V | S | S | DELETED | DELETED | P | I |
| S | A | F | R | L | H | V | S | S | DELETED | DELETED | P | M |
| S | A | F | R | L | H | V | S | S | DELETED | P | DELETED | I |
| S | A | F | R | L | H | V | S | S | DELETED | P | DELETED | M |
| S | A | F | R | L | H | V | S | S | DELETED | P | P | I |
| S | A | F | R | L | H | V | S | S | DELETED | P | P | M |
| S | A | F | R | L | H | V | S | S | N | DELETED | DELETED | I |
| S | A | F | R | L | H | V | S | S | N | DELETED | DELETED | M |
| S | A | F | R | L | H | V | S | S | N | DELETED | P | I |
| S | A | F | R | L | H | V | S | S | N | DELETED | P | M |
| S | A | F | R | L | H | V | S | S | N | P | DELETED | I |
| S | A | F | R | L | H | V | S | S | N | P | DELETED | M |
| S | A | F | R | L | H | V | S | S | N | P | P | I |
| S | A | F | R | L | H | V | S | S | N | P | P | M |
| S | A | F | R | L | H | V | S | T | DELETED | DELETED | DELETED | I |
| S | A | F | R | L | H | V | S | T | DELETED | DELETED | DELETED | M |
| S | A | F | R | L | H | V | S | T | DELETED | DELETED | P | I |
| S | A | F | R | L | H | V | S | T | DELETED | DELETED | P | M |
| S | A | F | R | L | H | V | S | T | DELETED | P | DELETED | I |
| S | A | F | R | L | H | V | S | T | DELETED | P | DELETED | M |
| S | A | F | R | L | H | V | S | T | DELETED | P | P | I |
| S | A | F | R | L | H | V | S | T | DELETED | P | P | M |
| S | A | F | R | L | H | V | S | T | N | DELETED | DELETED | I |
| S | A | F | R | L | H | V | S | T | N | DELETED | DELETED | M |
| S | A | F | R | L | H | V | S | T | N | DELETED | P | I |
| S | A | F | R | L | H | V | S | T | N | DELETED | P | M |
| S | A | F | R | L | H | V | S | T | N | P | DELETED | I |
| S | A | F | R | L | H | V | S | T | N | P | DELETED | M |
| S | A | F | R | L | H | V | S | T | N | P | P | I |
| S | A | F | R | L | H | V | S | T | N | P | P | M |
| S | A | F | R | L | H | V | G | S | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | L | H | V | G | S | DELETED | DELETED | DELETED | M |
| S | A | F | R | L | H | V | G | S | DELETED | DELETED | P | I |
| S | A | F | R | L | H | V | G | S | DELETED | DELETED | P | M |
| S | A | F | R | L | H | V | G | S | DELETED | P | DELETED | I |
| S | A | F | R | L | H | V | G | S | DELETED | P | DELETED | M |
| S | A | F | R | L | H | V | G | S | DELETED | P | P | I |
| S | A | F | R | L | H | V | G | S | DELETED | P | P | M |
| S | A | F | R | L | H | V | G | S | N | DELETED | DELETED | I |
| S | A | F | R | L | H | V | G | S | N | DELETED | DELETED | M |
| S | A | F | R | L | H | V | G | S | N | DELETED | P | I |
| S | A | F | R | L | H | V | G | S | N | DELETED | P | M |
| S | A | F | R | L | H | V | G | S | N | P | DELETED | I |
| S | A | F | R | L | H | V | G | S | N | P | DELETED | M |
| S | A | F | R | L | H | V | G | S | N | P | P | I |
| S | A | F | R | L | H | V | G | S | N | P | P | M |
| S | A | F | R | L | H | V | G | T | DELETED | DELETED | DELETED | I |
| S | A | F | R | L | H | V | G | T | DELETED | DELETED | DELETED | M |
| S | A | F | R | L | H | V | G | T | DELETED | DELETED | P | I |
| S | A | F | R | L | H | V | G | T | DELETED | DELETED | P | M |
| S | A | F | R | L | H | V | G | T | DELETED | P | DELETED | I |
| S | A | F | R | L | H | V | G | T | DELETED | P | DELETED | M |
| S | A | F | R | L | H | V | G | T | DELETED | P | P | I |
| S | A | F | R | L | H | V | G | T | DELETED | P | P | M |
| S | A | F | R | L | H | V | G | T | N | DELETED | DELETED | I |
| S | A | F | R | L | H | V | G | T | N | DELETED | DELETED | M |
| S | A | F | R | L | H | V | G | T | N | DELETED | P | I |
| S | A | F | R | L | H | V | G | T | N | DELETED | P | M |
| S | A | F | R | L | H | V | G | T | N | P | DELETED | I |
| S | A | F | R | L | H | V | G | T | N | P | DELETED | M |
| S | A | F | R | L | H | V | G | T | N | P | P | I |
| S | A | F | R | L | H | V | G | T | N | P | P | M |
| S | A | F | R | I | Y | Q | S | S | DELETED | DELETED | DELETED | I |
| S | A | F | R | I | Y | Q | S | S | DELETED | DELETED | DELETED | M |
| S | A | F | R | I | Y | Q | S | S | DELETED | DELETED | P | I |
| S | A | F | R | I | Y | Q | S | S | DELETED | DELETED | P | M |
| S | A | F | R | I | Y | Q | S | S | DELETED | P | DELETED | I |
| S | A | F | R | I | Y | Q | S | S | DELETED | P | DELETED | M |
| S | A | F | R | I | Y | Q | S | S | DELETED | P | P | I |
| S | A | F | R | I | Y | Q | S | S | DELETED | P | P | M |
| S | A | F | R | I | Y | Q | S | S | N | DELETED | DELETED | I |
| S | A | F | R | I | Y | Q | S | S | N | DELETED | DELETED | M |
| S | A | F | R | I | Y | Q | S | S | N | DELETED | P | I |
| S | A | F | R | I | Y | Q | S | S | N | DELETED | P | M |
| S | A | F | R | I | Y | Q | S | S | N | P | DELETED | I |
| S | A | F | R | I | Y | Q | S | S | N | P | DELETED | M |
| S | A | F | R | I | Y | Q | S | S | N | P | P | I |
| S | A | F | R | I | Y | Q | S | S | N | P | P | M |
| S | A | F | R | I | Y | Q | S | T | DELETED | DELETED | DELETED | I |
| S | A | F | R | I | Y | Q | S | T | DELETED | DELETED | DELETED | M |
| S | A | F | R | I | Y | Q | S | T | DELETED | DELETED | P | I |
| S | A | F | R | I | Y | Q | S | T | DELETED | DELETED | P | M |
| S | A | F | R | I | Y | Q | S | T | DELETED | P | DELETED | I |
| S | A | F | R | I | Y | Q | S | T | DELETED | P | DELETED | M |
| S | A | F | R | I | Y | Q | S | T | DELETED | P | P | I |
| S | A | F | R | I | Y | Q | S | T | DELETED | P | P | M |
| S | A | F | R | I | Y | Q | S | T | N | DELETED | DELETED | I |
| S | A | F | R | I | Y | Q | S | T | N | DELETED | DELETED | M |
| S | A | F | R | I | Y | Q | S | T | N | DELETED | P | I |
| S | A | F | R | I | Y | Q | S | T | N | DELETED | P | M |
| S | A | F | R | I | Y | Q | S | T | N | P | DELETED | I |
| S | A | F | R | I | Y | Q | S | T | N | P | DELETED | M |
| S | A | F | R | I | Y | Q | S | T | N | P | P | I |
| S | A | F | R | I | Y | Q | S | T | N | P | P | M |
| S | A | F | R | I | Y | Q | G | S | DELETED | DELETED | DELETED | I |
| S | A | F | R | I | Y | Q | G | S | DELETED | DELETED | DELETED | M |
| S | A | F | R | I | Y | Q | G | S | DELETED | DELETED | P | I |
| S | A | F | R | I | Y | Q | G | S | DELETED | DELETED | P | M |
| S | A | F | R | I | Y | Q | G | S | DELETED | P | DELETED | I |
| S | A | F | R | I | Y | Q | G | S | DELETED | P | DELETED | M |
| S | A | F | R | I | Y | Q | G | S | DELETED | P | P | I |
| S | A | F | R | I | Y | Q | G | S | DELETED | P | P | M |
| S | A | F | R | I | Y | Q | G | S | N | DELETED | DELETED | I |
| S | A | F | R | I | Y | Q | G | S | N | DELETED | DELETED | M |
| S | A | F | R | I | Y | Q | G | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | I | Y | Q | G | S | N | DELETED | P | M |
| S | A | F | R | I | Y | Q | G | S | N | P | DELETED | I |
| S | A | F | R | I | Y | Q | G | S | N | P | DELETED | M |
| S | A | F | R | I | Y | Q | G | S | N | P | P | I |
| S | A | F | R | I | Y | Q | G | S | N | P | P | M |
| S | A | F | R | I | Y | Q | G | T | DELETED | DELETED | DELETED | I |
| S | A | F | R | I | Y | Q | G | T | DELETED | DELETED | DELETED | M |
| S | A | F | R | I | Y | Q | G | T | DELETED | DELETED | P | I |
| S | A | F | R | I | Y | Q | G | T | DELETED | DELETED | P | M |
| S | A | F | R | I | Y | Q | G | T | DELETED | P | DELETED | I |
| S | A | F | R | I | Y | Q | G | T | DELETED | P | DELETED | M |
| S | A | F | R | I | Y | Q | G | T | DELETED | P | P | I |
| S | A | F | R | I | Y | Q | G | T | DELETED | P | P | M |
| S | A | F | R | I | Y | Q | G | T | N | DELETED | DELETED | I |
| S | A | F | R | I | Y | Q | G | T | N | DELETED | DELETED | M |
| S | A | F | R | I | Y | Q | G | T | N | DELETED | P | I |
| S | A | F | R | I | Y | Q | G | T | N | DELETED | P | M |
| S | A | F | R | I | Y | Q | G | T | N | P | DELETED | I |
| S | A | F | R | I | Y | Q | G | T | N | P | DELETED | M |
| S | A | F | R | I | Y | Q | G | T | N | P | P | I |
| S | A | F | R | I | Y | Q | G | T | N | P | P | M |
| S | A | F | R | I | Y | V | S | S | DELETED | DELETED | DELETED | I |
| S | A | F | R | I | Y | V | S | S | DELETED | DELETED | DELETED | M |
| S | A | F | R | I | Y | V | S | S | DELETED | DELETED | P | I |
| S | A | F | R | I | Y | V | S | S | DELETED | DELETED | P | M |
| S | A | F | R | I | Y | V | S | S | DELETED | P | DELETED | I |
| S | A | F | R | I | Y | V | S | S | DELETED | P | DELETED | M |
| S | A | F | R | I | Y | V | S | S | DELETED | P | P | I |
| S | A | F | R | I | Y | V | S | S | DELETED | P | P | M |
| S | A | F | R | I | Y | V | S | S | N | DELETED | DELETED | I |
| S | A | F | R | I | Y | V | S | S | N | DELETED | DELETED | M |
| S | A | F | R | I | Y | V | S | S | N | DELETED | P | I |
| S | A | F | R | I | Y | V | S | S | N | DELETED | P | M |
| S | A | F | R | I | Y | V | S | S | N | P | DELETED | I |
| S | A | F | R | I | Y | V | S | S | N | P | DELETED | M |
| S | A | F | R | I | Y | V | S | S | N | P | P | I |
| S | A | F | R | I | Y | V | S | S | N | P | P | M |
| S | A | F | R | I | Y | V | S | T | DELETED | DELETED | DELETED | I |
| S | A | F | R | I | Y | V | S | T | DELETED | DELETED | DELETED | M |
| S | A | F | R | I | Y | V | S | T | DELETED | DELETED | P | I |
| S | A | F | R | I | Y | V | S | T | DELETED | DELETED | P | M |
| S | A | F | R | I | Y | V | S | T | DELETED | P | DELETED | I |
| S | A | F | R | I | Y | V | S | T | DELETED | P | DELETED | M |
| S | A | F | R | I | Y | V | S | T | DELETED | P | P | I |
| S | A | F | R | I | Y | V | S | T | DELETED | P | P | M |
| S | A | F | R | I | Y | V | S | T | N | DELETED | DELETED | I |
| S | A | F | R | I | Y | V | S | T | N | DELETED | DELETED | M |
| S | A | F | R | I | Y | V | S | T | N | DELETED | P | I |
| S | A | F | R | I | Y | V | S | T | N | DELETED | P | M |
| S | A | F | R | I | Y | V | S | T | N | P | DELETED | I |
| S | A | F | R | I | Y | V | S | T | N | P | DELETED | M |
| S | A | F | R | I | Y | V | S | T | N | P | P | I |
| S | A | F | R | I | Y | V | S | T | N | P | P | M |
| S | A | F | R | I | Y | V | G | S | DELETED | DELETED | DELETED | I |
| S | A | F | R | I | Y | V | G | S | DELETED | DELETED | DELETED | M |
| S | A | F | R | I | Y | V | G | S | DELETED | DELETED | P | I |
| S | A | F | R | I | Y | V | G | S | DELETED | DELETED | P | M |
| S | A | F | R | I | Y | V | G | S | DELETED | P | DELETED | I |
| S | A | F | R | I | Y | V | G | S | DELETED | P | DELETED | M |
| S | A | F | R | I | Y | V | G | S | DELETED | P | P | I |
| S | A | F | R | I | Y | V | G | S | DELETED | P | P | M |
| S | A | F | R | I | Y | V | G | S | N | DELETED | DELETED | I |
| S | A | F | R | I | Y | V | G | S | N | DELETED | DELETED | M |
| S | A | F | R | I | Y | V | G | S | N | DELETED | P | I |
| S | A | F | R | I | Y | V | G | S | N | DELETED | P | M |
| S | A | F | R | I | Y | V | G | S | N | P | DELETED | I |
| S | A | F | R | I | Y | V | G | S | N | P | DELETED | M |
| S | A | F | R | I | Y | V | G | S | N | P | P | I |
| S | A | F | R | I | Y | V | G | S | N | P | P | M |
| S | A | F | R | I | Y | V | G | T | DELETED | DELETED | DELETED | I |
| S | A | F | R | I | Y | V | G | T | DELETED | DELETED | DELETED | M |
| S | A | F | R | I | Y | V | G | T | DELETED | DELETED | P | I |
| S | A | F | R | I | Y | V | G | T | DELETED | DELETED | P | M |
| S | A | F | R | I | Y | V | G | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | I | Y | V | G | T | DELETED | P | DELETED | M |
| S | A | F | R | I | Y | V | G | T | DELETED | P | P | I |
| S | A | F | R | I | Y | V | G | T | DELETED | P | P | M |
| S | A | F | R | I | Y | V | G | T | N | DELETED | DELETED | I |
| S | A | F | R | I | Y | V | G | T | N | DELETED | DELETED | M |
| S | A | F | R | I | Y | V | G | T | N | DELETED | P | I |
| S | A | F | R | I | Y | V | G | T | N | DELETED | P | M |
| S | A | F | R | I | Y | V | G | T | N | P | DELETED | I |
| S | A | F | R | I | Y | V | G | T | N | P | DELETED | M |
| S | A | F | R | I | Y | V | G | T | N | P | P | I |
| S | A | F | R | I | Y | V | G | T | N | P | P | M |
| S | A | F | R | I | H | Q | S | S | DELETED | DELETED | DELETED | I |
| S | A | F | R | I | H | Q | S | S | DELETED | DELETED | DELETED | M |
| S | A | F | R | I | H | Q | S | S | DELETED | DELETED | P | I |
| S | A | F | R | I | H | Q | S | S | DELETED | DELETED | P | M |
| S | A | F | R | I | H | Q | S | S | DELETED | P | DELETED | I |
| S | A | F | R | I | H | Q | S | S | DELETED | P | DELETED | M |
| S | A | F | R | I | H | Q | S | S | DELETED | P | P | I |
| S | A | F | R | I | H | Q | S | S | DELETED | P | P | M |
| S | A | F | R | I | H | Q | S | S | N | DELETED | DELETED | I |
| S | A | F | R | I | H | Q | S | S | N | DELETED | DELETED | M |
| S | A | F | R | I | H | Q | S | S | N | DELETED | P | I |
| S | A | F | R | I | H | Q | S | S | N | DELETED | P | M |
| S | A | F | R | I | H | Q | S | S | N | P | DELETED | I |
| S | A | F | R | I | H | Q | S | S | N | P | DELETED | M |
| S | A | F | R | I | H | Q | S | S | N | P | P | I |
| S | A | F | R | I | H | Q | S | S | N | P | P | M |
| S | A | F | R | I | H | Q | S | T | DELETED | DELETED | DELETED | I |
| S | A | F | R | I | H | Q | S | T | DELETED | DELETED | DELETED | M |
| S | A | F | R | I | H | Q | S | T | DELETED | DELETED | P | I |
| S | A | F | R | I | H | Q | S | T | DELETED | DELETED | P | M |
| S | A | F | R | I | H | Q | S | T | DELETED | P | DELETED | I |
| S | A | F | R | I | H | Q | S | T | DELETED | P | DELETED | M |
| S | A | F | R | I | H | Q | S | T | DELETED | P | P | I |
| S | A | F | R | I | H | Q | S | T | DELETED | P | P | M |
| S | A | F | R | I | H | Q | S | T | N | DELETED | DELETED | I |
| S | A | F | R | I | H | Q | S | T | N | DELETED | DELETED | M |
| S | A | F | R | I | H | Q | S | T | N | DELETED | P | I |
| S | A | F | R | I | H | Q | S | T | N | DELETED | P | M |
| S | A | F | R | I | H | Q | S | T | N | P | DELETED | I |
| S | A | F | R | I | H | Q | S | T | N | P | DELETED | M |
| S | A | F | R | I | H | Q | S | T | N | P | P | I |
| S | A | F | R | I | H | Q | S | T | N | P | P | M |
| S | A | F | R | I | H | Q | G | S | DELETED | DELETED | DELETED | I |
| S | A | F | R | I | H | Q | G | S | DELETED | DELETED | DELETED | M |
| S | A | F | R | I | H | Q | G | S | DELETED | DELETED | P | I |
| S | A | F | R | I | H | Q | G | S | DELETED | DELETED | P | M |
| S | A | F | R | I | H | Q | G | S | DELETED | P | DELETED | I |
| S | A | F | R | I | H | Q | G | S | DELETED | P | DELETED | M |
| S | A | F | R | I | H | Q | G | S | DELETED | P | P | I |
| S | A | F | R | I | H | Q | G | S | DELETED | P | P | M |
| S | A | F | R | I | H | Q | G | S | N | DELETED | DELETED | I |
| S | A | F | R | I | H | Q | G | S | N | DELETED | DELETED | M |
| S | A | F | R | I | H | Q | G | S | N | DELETED | P | I |
| S | A | F | R | I | H | Q | G | S | N | DELETED | P | M |
| S | A | F | R | I | H | Q | G | S | N | P | DELETED | I |
| S | A | F | R | I | H | Q | G | S | N | P | DELETED | M |
| S | A | F | R | I | H | Q | G | S | N | P | P | I |
| S | A | F | R | I | H | Q | G | S | N | P | P | M |
| S | A | F | R | I | H | Q | G | T | DELETED | DELETED | DELETED | I |
| S | A | F | R | I | H | Q | G | T | DELETED | DELETED | DELETED | M |
| S | A | F | R | I | H | Q | G | T | DELETED | DELETED | P | I |
| S | A | F | R | I | H | Q | G | T | DELETED | DELETED | P | M |
| S | A | F | R | I | H | Q | G | T | DELETED | P | DELETED | I |
| S | A | F | R | I | H | Q | G | T | DELETED | P | DELETED | M |
| S | A | F | R | I | H | Q | G | T | DELETED | P | P | I |
| S | A | F | R | I | H | Q | G | T | DELETED | P | P | M |
| S | A | F | R | I | H | Q | G | T | N | DELETED | DELETED | I |
| S | A | F | R | I | H | Q | G | T | N | DELETED | DELETED | M |
| S | A | F | R | I | H | Q | G | T | N | DELETED | P | I |
| S | A | F | R | I | H | Q | G | T | N | DELETED | P | M |
| S | A | F | R | I | H | Q | G | T | N | P | DELETED | I |
| S | A | F | R | I | H | Q | G | T | N | P | DELETED | M |
| S | A | F | R | I | H | Q | G | T | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | A | F | R | I | H | Q | G | T | N | P | P | M |
| S | A | F | R | I | H | V | S | S | DELETED | DELETED | DELETED | I |
| S | A | F | R | I | H | V | S | S | DELETED | DELETED | DELETED | M |
| S | A | F | R | I | H | V | S | S | DELETED | DELETED | P | I |
| S | A | F | R | I | H | V | S | S | DELETED | DELETED | P | M |
| S | A | F | R | I | H | V | S | S | DELETED | P | DELETED | I |
| S | A | F | R | I | H | V | S | S | DELETED | P | DELETED | M |
| S | A | F | R | I | H | V | S | S | DELETED | P | P | I |
| S | A | F | R | I | H | V | S | S | DELETED | P | P | M |
| S | A | F | R | I | H | V | S | S | N | DELETED | DELETED | I |
| S | A | F | R | I | H | V | S | S | N | DELETED | DELETED | M |
| S | A | F | R | I | H | V | S | S | N | DELETED | P | I |
| S | A | F | R | I | H | V | S | S | N | DELETED | P | M |
| S | A | F | R | I | H | V | S | S | N | P | DELETED | I |
| S | A | F | R | I | H | V | S | S | N | P | DELETED | M |
| S | A | F | R | I | H | V | S | S | N | P | P | I |
| S | A | F | R | I | H | V | S | S | N | P | P | M |
| S | A | F | R | I | H | V | S | T | DELETED | DELETED | DELETED | I |
| S | A | F | R | I | H | V | S | T | DELETED | DELETED | DELETED | M |
| S | A | F | R | I | H | V | S | T | DELETED | DELETED | P | I |
| S | A | F | R | I | H | V | S | T | DELETED | DELETED | P | M |
| S | A | F | R | I | H | V | S | T | DELETED | P | DELETED | I |
| S | A | F | R | I | H | V | S | T | DELETED | P | DELETED | M |
| S | A | F | R | I | H | V | S | T | DELETED | P | P | I |
| S | A | F | R | I | H | V | S | T | DELETED | P | P | M |
| S | A | F | R | I | H | V | S | T | N | DELETED | DELETED | I |
| S | A | F | R | I | H | V | S | T | N | DELETED | DELETED | M |
| S | A | F | R | I | H | V | S | T | N | DELETED | P | I |
| S | A | F | R | I | H | V | S | T | N | DELETED | P | M |
| S | A | F | R | I | H | V | S | T | N | P | DELETED | I |
| S | A | F | R | I | H | V | S | T | N | P | DELETED | M |
| S | A | F | R | I | H | V | S | T | N | P | P | I |
| S | A | F | R | I | H | V | S | T | N | P | P | M |
| S | A | F | R | I | H | V | G | S | DELETED | DELETED | DELETED | I |
| S | A | F | R | I | H | V | G | S | DELETED | DELETED | DELETED | M |
| S | A | F | R | I | H | V | G | S | DELETED | DELETED | P | I |
| S | A | F | R | I | H | V | G | S | DELETED | DELETED | P | M |
| S | A | F | R | I | H | V | G | S | DELETED | P | DELETED | I |
| S | A | F | R | I | H | V | G | S | DELETED | P | DELETED | M |
| S | A | F | R | I | H | V | G | S | DELETED | P | P | I |
| S | A | F | R | I | H | V | G | S | DELETED | P | P | M |
| S | A | F | R | I | H | V | G | S | N | DELETED | DELETED | I |
| S | A | F | R | I | H | V | G | S | N | DELETED | DELETED | M |
| S | A | F | R | I | H | V | G | S | N | DELETED | P | I |
| S | A | F | R | I | H | V | G | S | N | DELETED | P | M |
| S | A | F | R | I | H | V | G | S | N | P | DELETED | I |
| S | A | F | R | I | H | V | G | S | N | P | DELETED | M |
| S | A | F | R | I | H | V | G | S | N | P | P | I |
| S | A | F | R | I | H | V | G | S | N | P | P | M |
| S | A | F | R | I | H | V | G | T | DELETED | DELETED | DELETED | I |
| S | A | F | R | I | H | V | G | T | DELETED | DELETED | DELETED | M |
| S | A | F | R | I | H | V | G | T | DELETED | DELETED | P | I |
| S | A | F | R | I | H | V | G | T | DELETED | DELETED | P | M |
| S | A | F | R | I | H | V | G | T | DELETED | P | DELETED | I |
| S | A | F | R | I | H | V | G | T | DELETED | P | DELETED | M |
| S | A | F | R | I | H | V | G | T | DELETED | P | P | I |
| S | A | F | R | I | H | V | G | T | DELETED | P | P | M |
| S | A | F | R | I | H | V | G | T | N | DELETED | DELETED | I |
| S | A | F | R | I | H | V | G | T | N | DELETED | DELETED | M |
| S | A | F | R | I | H | V | G | T | N | DELETED | P | I |
| S | A | F | R | I | H | V | G | T | N | DELETED | P | M |
| S | A | F | R | I | H | V | G | T | N | P | DELETED | I |
| S | A | F | R | I | H | V | G | T | N | P | DELETED | M |
| S | A | F | R | I | H | V | G | T | N | P | P | I |
| S | A | F | R | I | H | V | G | T | N | P | P | M |
| S | P | I | S | L | Y | Q | S | S | DELETED | DELETED | DELETED | I |
| S | P | I | S | L | Y | Q | S | S | DELETED | DELETED | DELETED | M |
| S | P | I | S | L | Y | Q | S | S | DELETED | DELETED | P | I |
| S | P | I | S | L | Y | Q | S | S | DELETED | DELETED | P | M |
| S | P | I | S | L | Y | Q | S | S | DELETED | P | DELETED | I |
| S | P | I | S | L | Y | Q | S | S | DELETED | P | DELETED | M |
| S | P | I | S | L | Y | Q | S | S | DELETED | P | P | I |
| S | P | I | S | L | Y | Q | S | S | DELETED | P | P | M |
| S | P | I | S | L | Y | Q | S | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | L | Y | Q | S | S | N | DELETED | DELETED | M |
| S | P | I | S | L | Y | Q | S | S | N | DELETED | P | I |
| S | P | I | S | L | Y | Q | S | S | N | DELETED | P | M |
| S | P | I | S | L | Y | Q | S | S | N | P | DELETED | I |
| S | P | I | S | L | Y | Q | S | S | N | P | DELETED | M |
| S | P | I | S | L | Y | Q | S | S | N | P | P | I |
| S | P | I | S | L | Y | Q | S | S | N | P | P | M |
| S | P | I | S | L | Y | Q | S | T | DELETED | DELETED | DELETED | I |
| S | P | I | S | L | Y | Q | S | T | DELETED | DELETED | DELETED | M |
| S | P | I | S | L | Y | Q | S | T | DELETED | DELETED | P | I |
| S | P | I | S | L | Y | Q | S | T | DELETED | DELETED | P | M |
| S | P | I | S | L | Y | Q | S | T | DELETED | P | DELETED | I |
| S | P | I | S | L | Y | Q | S | T | DELETED | P | DELETED | M |
| S | P | I | S | L | Y | Q | S | T | DELETED | P | P | I |
| S | P | I | S | L | Y | Q | S | T | DELETED | P | P | M |
| S | P | I | S | L | Y | Q | S | T | N | DELETED | DELETED | I |
| S | P | I | S | L | Y | Q | S | T | N | DELETED | DELETED | M |
| S | P | I | S | L | Y | Q | S | T | N | DELETED | P | I |
| S | P | I | S | L | Y | Q | S | T | N | DELETED | P | M |
| S | P | I | S | L | Y | Q | S | T | N | P | DELETED | I |
| S | P | I | S | L | Y | Q | S | T | N | P | DELETED | M |
| S | P | I | S | L | Y | Q | S | T | N | P | P | I |
| S | P | I | S | L | Y | Q | S | T | N | P | P | M |
| S | P | I | S | L | Y | Q | G | S | DELETED | DELETED | DELETED | I |
| S | P | I | S | L | Y | Q | G | S | DELETED | DELETED | DELETED | M |
| S | P | I | S | L | Y | Q | G | S | DELETED | DELETED | P | I |
| S | P | I | S | L | Y | Q | G | S | DELETED | DELETED | P | M |
| S | P | I | S | L | Y | Q | G | S | DELETED | P | DELETED | I |
| S | P | I | S | L | Y | Q | G | S | DELETED | P | DELETED | M |
| S | P | I | S | L | Y | Q | G | S | DELETED | P | P | I |
| S | P | I | S | L | Y | Q | G | S | DELETED | P | P | M |
| S | P | I | S | L | Y | Q | G | S | N | DELETED | DELETED | I |
| S | P | I | S | L | Y | Q | G | S | N | DELETED | DELETED | M |
| S | P | I | S | L | Y | Q | G | S | N | DELETED | P | I |
| S | P | I | S | L | Y | Q | G | S | N | DELETED | P | M |
| S | P | I | S | L | Y | Q | G | S | N | P | DELETED | I |
| S | P | I | S | L | Y | Q | G | S | N | P | DELETED | M |
| S | P | I | S | L | Y | Q | G | S | N | P | P | I |
| S | P | I | S | L | Y | Q | G | S | N | P | P | M |
| S | P | I | S | L | Y | Q | G | T | DELETED | DELETED | DELETED | I |
| S | P | I | S | L | Y | Q | G | T | DELETED | DELETED | DELETED | M |
| S | P | I | S | L | Y | Q | G | T | DELETED | DELETED | P | I |
| S | P | I | S | L | Y | Q | G | T | DELETED | DELETED | P | M |
| S | P | I | S | L | Y | Q | G | T | DELETED | P | DELETED | I |
| S | P | I | S | L | Y | Q | G | T | DELETED | P | DELETED | M |
| S | P | I | S | L | Y | Q | G | T | DELETED | P | P | I |
| S | P | I | S | L | Y | Q | G | T | DELETED | P | P | M |
| S | P | I | S | L | Y | Q | G | T | N | DELETED | DELETED | I |
| S | P | I | S | L | Y | Q | G | T | N | DELETED | DELETED | M |
| S | P | I | S | L | Y | Q | G | T | N | DELETED | P | I |
| S | P | I | S | L | Y | Q | G | T | N | DELETED | P | M |
| S | P | I | S | L | Y | Q | G | T | N | P | DELETED | I |
| S | P | I | S | L | Y | Q | G | T | N | P | DELETED | M |
| S | P | I | S | L | Y | Q | G | T | N | P | P | I |
| S | P | I | S | L | Y | Q | G | T | N | P | P | M |
| S | P | I | S | L | Y | V | S | S | DELETED | DELETED | DELETED | I |
| S | P | I | S | L | Y | V | S | S | DELETED | DELETED | DELETED | M |
| S | P | I | S | L | Y | V | S | S | DELETED | DELETED | P | I |
| S | P | I | S | L | Y | V | S | S | DELETED | DELETED | P | M |
| S | P | I | S | L | Y | V | S | S | DELETED | P | DELETED | I |
| S | P | I | S | L | Y | V | S | S | DELETED | P | DELETED | M |
| S | P | I | S | L | Y | V | S | S | DELETED | P | P | I |
| S | P | I | S | L | Y | V | S | S | DELETED | P | P | M |
| S | P | I | S | L | Y | V | S | S | N | DELETED | DELETED | I |
| S | P | I | S | L | Y | V | S | S | N | DELETED | DELETED | M |
| S | P | I | S | L | Y | V | S | S | N | DELETED | P | I |
| S | P | I | S | L | Y | V | S | S | N | DELETED | P | M |
| S | P | I | S | L | Y | V | S | S | N | P | DELETED | I |
| S | P | I | S | L | Y | V | S | S | N | P | DELETED | M |
| S | P | I | S | L | Y | V | S | S | N | P | P | I |
| S | P | I | S | L | Y | V | S | S | N | P | P | M |
| S | P | I | S | L | Y | V | S | T | DELETED | DELETED | DELETED | I |
| S | P | I | S | L | Y | V | S | T | DELETED | DELETED | DELETED | M |
| S | P | I | S | L | Y | V | S | T | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | L | Y | V | S | T | DELETED | DELETED | P | M |
| S | P | I | S | L | Y | V | S | T | DELETED | P | DELETED | I |
| S | P | I | S | L | Y | V | S | T | DELETED | P | DELETED | M |
| S | P | I | S | L | Y | V | S | T | DELETED | P | P | I |
| S | P | I | S | L | Y | V | S | T | DELETED | P | P | M |
| S | P | I | S | L | Y | V | S | T | N | DELETED | DELETED | I |
| S | P | I | S | L | Y | V | S | T | N | DELETED | DELETED | M |
| S | P | I | S | L | Y | V | S | T | N | DELETED | P | I |
| S | P | I | S | L | Y | V | S | T | N | DELETED | P | M |
| S | P | I | S | L | Y | V | S | T | N | P | DELETED | I |
| S | P | I | S | L | Y | V | S | T | N | P | DELETED | M |
| S | P | I | S | L | Y | V | S | T | N | P | P | I |
| S | P | I | S | L | Y | V | S | T | N | P | P | M |
| S | P | I | S | L | Y | V | G | S | DELETED | DELETED | DELETED | I |
| S | P | I | S | L | Y | V | G | S | DELETED | DELETED | DELETED | M |
| S | P | I | S | L | Y | V | G | S | DELETED | DELETED | P | I |
| S | P | I | S | L | Y | V | G | S | DELETED | DELETED | P | M |
| S | P | I | S | L | Y | V | G | S | DELETED | P | DELETED | I |
| S | P | I | S | L | Y | V | G | S | DELETED | P | DELETED | M |
| S | P | I | S | L | Y | V | G | S | DELETED | P | P | I |
| S | P | I | S | L | Y | V | G | S | DELETED | P | P | M |
| S | P | I | S | L | Y | V | G | S | N | DELETED | DELETED | I |
| S | P | I | S | L | Y | V | G | S | N | DELETED | DELETED | M |
| S | P | I | S | L | Y | V | G | S | N | DELETED | P | I |
| S | P | I | S | L | Y | V | G | S | N | DELETED | P | M |
| S | P | I | S | L | Y | V | G | S | N | P | DELETED | I |
| S | P | I | S | L | Y | V | G | S | N | P | DELETED | M |
| S | P | I | S | L | Y | V | G | S | N | P | P | I |
| S | P | I | S | L | Y | V | G | S | N | P | P | M |
| S | P | I | S | L | Y | V | G | T | DELETED | DELETED | DELETED | I |
| S | P | I | S | L | Y | V | G | T | DELETED | DELETED | DELETED | M |
| S | P | I | S | L | Y | V | G | T | DELETED | DELETED | P | I |
| S | P | I | S | L | Y | V | G | T | DELETED | DELETED | P | M |
| S | P | I | S | L | Y | V | G | T | DELETED | P | DELETED | I |
| S | P | I | S | L | Y | V | G | T | DELETED | P | DELETED | M |
| S | P | I | S | L | Y | V | G | T | DELETED | P | P | I |
| S | P | I | S | L | Y | V | G | T | DELETED | P | P | M |
| S | P | I | S | L | Y | V | G | T | N | DELETED | DELETED | I |
| S | P | I | S | L | Y | V | G | T | N | DELETED | DELETED | M |
| S | P | I | S | L | Y | V | G | T | N | DELETED | P | I |
| S | P | I | S | L | Y | V | G | T | N | DELETED | P | M |
| S | P | I | S | L | Y | V | G | T | N | P | DELETED | I |
| S | P | I | S | L | Y | V | G | T | N | P | DELETED | M |
| S | P | I | S | L | Y | V | G | T | N | P | P | I |
| S | P | I | S | L | Y | V | G | T | N | P | P | M |
| S | P | I | S | L | H | Q | S | S | DELETED | DELETED | DELETED | I |
| S | P | I | S | L | H | Q | S | S | DELETED | DELETED | DELETED | M |
| S | P | I | S | L | H | Q | S | S | DELETED | DELETED | P | I |
| S | P | I | S | L | H | Q | S | S | DELETED | DELETED | P | M |
| S | P | I | S | L | H | Q | S | S | DELETED | P | DELETED | I |
| S | P | I | S | L | H | Q | S | S | DELETED | P | DELETED | M |
| S | P | I | S | L | H | Q | S | S | DELETED | P | P | I |
| S | P | I | S | L | H | Q | S | S | DELETED | P | P | M |
| S | P | I | S | L | H | Q | S | S | N | DELETED | DELETED | I |
| S | P | I | S | L | H | Q | S | S | N | DELETED | DELETED | M |
| S | P | I | S | L | H | Q | S | S | N | DELETED | P | I |
| S | P | I | S | L | H | Q | S | S | N | DELETED | P | M |
| S | P | I | S | L | H | Q | S | S | N | P | DELETED | I |
| S | P | I | S | L | H | Q | S | S | N | P | DELETED | M |
| S | P | I | S | L | H | Q | S | S | N | P | P | I |
| S | P | I | S | L | H | Q | S | S | N | P | P | M |
| S | P | I | S | L | H | Q | S | T | DELETED | DELETED | DELETED | I |
| S | P | I | S | L | H | Q | S | T | DELETED | DELETED | DELETED | M |
| S | P | I | S | L | H | Q | S | T | DELETED | DELETED | P | I |
| S | P | I | S | L | H | Q | S | T | DELETED | DELETED | P | M |
| S | P | I | S | L | H | Q | S | T | DELETED | P | DELETED | I |
| S | P | I | S | L | H | Q | S | T | DELETED | P | DELETED | M |
| S | P | I | S | L | H | Q | S | T | DELETED | P | P | I |
| S | P | I | S | L | H | Q | S | T | DELETED | P | P | M |
| S | P | I | S | L | H | Q | S | T | N | DELETED | DELETED | I |
| S | P | I | S | L | H | Q | S | T | N | DELETED | DELETED | M |
| S | P | I | S | L | H | Q | S | T | N | DELETED | P | I |
| S | P | I | S | L | H | Q | S | T | N | DELETED | P | M |
| S | P | I | S | L | H | Q | S | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | L | H | Q | S | T | N | P | DELETED | M |
| S | P | I | S | L | H | Q | S | T | N | P | P | I |
| S | P | I | S | L | H | Q | S | T | N | P | P | M |
| S | P | I | S | L | H | Q | G | S | DELETED | DELETED | DELETED | I |
| S | P | I | S | L | H | Q | G | S | DELETED | DELETED | DELETED | M |
| S | P | I | S | L | H | Q | G | S | DELETED | DELETED | P | I |
| S | P | I | S | L | H | Q | G | S | DELETED | DELETED | P | M |
| S | P | I | S | L | H | Q | G | S | DELETED | P | DELETED | I |
| S | P | I | S | L | H | Q | G | S | DELETED | P | DELETED | M |
| S | P | I | S | L | H | Q | G | S | DELETED | P | P | I |
| S | P | I | S | L | H | Q | G | S | DELETED | P | P | M |
| S | P | I | S | L | H | Q | G | S | N | DELETED | DELETED | I |
| S | P | I | S | L | H | Q | G | S | N | DELETED | DELETED | M |
| S | P | I | S | L | H | Q | G | S | N | DELETED | P | I |
| S | P | I | S | L | H | Q | G | S | N | DELETED | P | M |
| S | P | I | S | L | H | Q | G | S | N | P | DELETED | I |
| S | P | I | S | L | H | Q | G | S | N | P | DELETED | M |
| S | P | I | S | L | H | Q | G | S | N | P | P | I |
| S | P | I | S | L | H | Q | G | S | N | P | P | M |
| S | P | I | S | L | H | Q | G | T | DELETED | DELETED | DELETED | I |
| S | P | I | S | L | H | Q | G | T | DELETED | DELETED | DELETED | M |
| S | P | I | S | L | H | Q | G | T | DELETED | DELETED | P | I |
| S | P | I | S | L | H | Q | G | T | DELETED | DELETED | P | M |
| S | P | I | S | L | H | Q | G | T | DELETED | P | DELETED | I |
| S | P | I | S | L | H | Q | G | T | DELETED | P | DELETED | M |
| S | P | I | S | L | H | Q | G | T | DELETED | P | P | I |
| S | P | I | S | L | H | Q | G | T | DELETED | P | P | M |
| S | P | I | S | L | H | Q | G | T | N | DELETED | DELETED | I |
| S | P | I | S | L | H | Q | G | T | N | DELETED | DELETED | M |
| S | P | I | S | L | H | Q | G | T | N | DELETED | P | I |
| S | P | I | S | L | H | Q | G | T | N | DELETED | P | M |
| S | P | I | S | L | H | Q | G | T | N | P | DELETED | I |
| S | P | I | S | L | H | Q | G | T | N | P | DELETED | M |
| S | P | I | S | L | H | Q | G | T | N | P | P | I |
| S | P | I | S | L | H | Q | G | T | N | P | P | M |
| S | P | I | S | L | H | V | S | S | DELETED | DELETED | DELETED | I |
| S | P | I | S | L | H | V | S | S | DELETED | DELETED | DELETED | M |
| S | P | I | S | L | H | V | S | S | DELETED | DELETED | P | I |
| S | P | I | S | L | H | V | S | S | DELETED | DELETED | P | M |
| S | P | I | S | L | H | V | S | S | DELETED | P | DELETED | I |
| S | P | I | S | L | H | V | S | S | DELETED | P | DELETED | M |
| S | P | I | S | L | H | V | S | S | DELETED | P | P | I |
| S | P | I | S | L | H | V | S | S | DELETED | P | P | M |
| S | P | I | S | L | H | V | S | S | N | DELETED | DELETED | I |
| S | P | I | S | L | H | V | S | S | N | DELETED | DELETED | M |
| S | P | I | S | L | H | V | S | S | N | DELETED | P | I |
| S | P | I | S | L | H | V | S | S | N | DELETED | P | M |
| S | P | I | S | L | H | V | S | S | N | P | DELETED | I |
| S | P | I | S | L | H | V | S | S | N | P | DELETED | M |
| S | P | I | S | L | H | V | S | S | N | P | P | I |
| S | P | I | S | L | H | V | S | S | N | P | P | M |
| S | P | I | S | L | H | V | S | T | DELETED | DELETED | DELETED | I |
| S | P | I | S | L | H | V | S | T | DELETED | DELETED | DELETED | M |
| S | P | I | S | L | H | V | S | T | DELETED | DELETED | P | I |
| S | P | I | S | L | H | V | S | T | DELETED | DELETED | P | M |
| S | P | I | S | L | H | V | S | T | DELETED | P | DELETED | I |
| S | P | I | S | L | H | V | S | T | DELETED | P | DELETED | M |
| S | P | I | S | L | H | V | S | T | DELETED | P | P | I |
| S | P | I | S | L | H | V | S | T | DELETED | P | P | M |
| S | P | I | S | L | H | V | S | T | N | DELETED | DELETED | I |
| S | P | I | S | L | H | V | S | T | N | DELETED | DELETED | M |
| S | P | I | S | L | H | V | S | T | N | DELETED | P | I |
| S | P | I | S | L | H | V | S | T | N | DELETED | P | M |
| S | P | I | S | L | H | V | S | T | N | P | DELETED | I |
| S | P | I | S | L | H | V | S | T | N | P | DELETED | M |
| S | P | I | S | L | H | V | S | T | N | P | P | I |
| S | P | I | S | L | H | V | S | T | N | P | P | M |
| S | P | I | S | L | H | V | G | S | DELETED | DELETED | DELETED | I |
| S | P | I | S | L | H | V | G | S | DELETED | DELETED | DELETED | M |
| S | P | I | S | L | H | V | G | S | DELETED | DELETED | P | I |
| S | P | I | S | L | H | V | G | S | DELETED | DELETED | P | M |
| S | P | I | S | L | H | V | G | S | DELETED | P | DELETED | I |
| S | P | I | S | L | H | V | G | S | DELETED | P | DELETED | M |
| S | P | I | S | L | H | V | G | S | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | L | H | V | G | S | DELETED | P | P | M |
| S | P | I | S | L | H | V | G | S | N | DELETED | DELETED | I |
| S | P | I | S | L | H | V | G | S | N | DELETED | DELETED | M |
| S | P | I | S | L | H | V | G | S | N | DELETED | P | I |
| S | P | I | S | L | H | V | G | S | N | DELETED | P | M |
| S | P | I | S | L | H | V | G | S | N | P | DELETED | I |
| S | P | I | S | L | H | V | G | S | N | P | DELETED | M |
| S | P | I | S | L | H | V | G | S | N | P | P | I |
| S | P | I | S | L | H | V | G | S | N | P | P | M |
| S | P | I | S | L | H | V | G | T | DELETED | DELETED | DELETED | I |
| S | P | I | S | L | H | V | G | T | DELETED | DELETED | DELETED | M |
| S | P | I | S | L | H | V | G | T | DELETED | DELETED | P | I |
| S | P | I | S | L | H | V | G | T | DELETED | DELETED | P | M |
| S | P | I | S | L | H | V | G | T | DELETED | P | DELETED | I |
| S | P | I | S | L | H | V | G | T | DELETED | P | DELETED | M |
| S | P | I | S | L | H | V | G | T | DELETED | P | P | I |
| S | P | I | S | L | H | V | G | T | DELETED | P | P | M |
| S | P | I | S | L | H | V | G | T | N | DELETED | DELETED | I |
| S | P | I | S | L | H | V | G | T | N | DELETED | DELETED | M |
| S | P | I | S | L | H | V | G | T | N | DELETED | P | I |
| S | P | I | S | L | H | V | G | T | N | DELETED | P | M |
| S | P | I | S | L | H | V | G | T | N | P | DELETED | I |
| S | P | I | S | L | H | V | G | T | N | P | DELETED | M |
| S | P | I | S | L | H | V | G | T | N | P | P | I |
| S | P | I | S | L | H | V | G | T | N | P | P | M |
| S | P | I | S | I | Y | Q | S | S | DELETED | DELETED | DELETED | I |
| S | P | I | S | I | Y | Q | S | S | DELETED | DELETED | DELETED | M |
| S | P | I | S | I | Y | Q | S | S | DELETED | DELETED | P | I |
| S | P | I | S | I | Y | Q | S | S | DELETED | DELETED | P | M |
| S | P | I | S | I | Y | Q | S | S | DELETED | P | DELETED | I |
| S | P | I | S | I | Y | Q | S | S | DELETED | P | DELETED | M |
| S | P | I | S | I | Y | Q | S | S | DELETED | P | P | I |
| S | P | I | S | I | Y | Q | S | S | DELETED | P | P | M |
| S | P | I | S | I | Y | Q | S | S | N | DELETED | DELETED | I |
| S | P | I | S | I | Y | Q | S | S | N | DELETED | DELETED | M |
| S | P | I | S | I | Y | Q | S | S | N | DELETED | P | I |
| S | P | I | S | I | Y | Q | S | S | N | DELETED | P | M |
| S | P | I | S | I | Y | Q | S | S | N | P | DELETED | I |
| S | P | I | S | I | Y | Q | S | S | N | P | DELETED | M |
| S | P | I | S | I | Y | Q | S | S | N | P | P | I |
| S | P | I | S | I | Y | Q | S | S | N | P | P | M |
| S | P | I | S | I | Y | Q | S | T | DELETED | DELETED | DELETED | I |
| S | P | I | S | I | Y | Q | S | T | DELETED | DELETED | DELETED | M |
| S | P | I | S | I | Y | Q | S | T | DELETED | DELETED | P | I |
| S | P | I | S | I | Y | Q | S | T | DELETED | DELETED | P | M |
| S | P | I | S | I | Y | Q | S | T | DELETED | P | DELETED | I |
| S | P | I | S | I | Y | Q | S | T | DELETED | P | DELETED | M |
| S | P | I | S | I | Y | Q | S | T | DELETED | P | P | I |
| S | P | I | S | I | Y | Q | S | T | DELETED | P | P | M |
| S | P | I | S | I | Y | Q | S | T | N | DELETED | DELETED | I |
| S | P | I | S | I | Y | Q | S | T | N | DELETED | DELETED | M |
| S | P | I | S | I | Y | Q | S | T | N | DELETED | P | I |
| S | P | I | S | I | Y | Q | S | T | N | DELETED | P | M |
| S | P | I | S | I | Y | Q | S | T | N | P | DELETED | I |
| S | P | I | S | I | Y | Q | S | T | N | P | DELETED | M |
| S | P | I | S | I | Y | Q | S | T | N | P | P | I |
| S | P | I | S | I | Y | Q | S | T | N | P | P | M |
| S | P | I | S | I | Y | Q | G | S | DELETED | DELETED | DELETED | I |
| S | P | I | S | I | Y | Q | G | S | DELETED | DELETED | DELETED | M |
| S | P | I | S | I | Y | Q | G | S | DELETED | DELETED | P | I |
| S | P | I | S | I | Y | Q | G | S | DELETED | DELETED | P | M |
| S | P | I | S | I | Y | Q | G | S | DELETED | P | DELETED | I |
| S | P | I | S | I | Y | Q | G | S | DELETED | P | DELETED | M |
| S | P | I | S | I | Y | Q | G | S | DELETED | P | P | I |
| S | P | I | S | I | Y | Q | G | S | DELETED | P | P | M |
| S | P | I | S | I | Y | Q | G | S | N | DELETED | DELETED | I |
| S | P | I | S | I | Y | Q | G | S | N | DELETED | DELETED | M |
| S | P | I | S | I | Y | Q | G | S | N | DELETED | P | I |
| S | P | I | S | I | Y | Q | G | S | N | DELETED | P | M |
| S | P | I | S | I | Y | Q | G | S | N | P | DELETED | I |
| S | P | I | S | I | Y | Q | G | S | N | P | DELETED | M |
| S | P | I | S | I | Y | Q | G | S | N | P | P | I |
| S | P | I | S | I | Y | Q | G | S | N | P | P | M |
| S | P | I | S | I | Y | Q | G | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | I | Y | Q | G | T | DELETED | DELETED | DELETED | M |
| S | P | I | S | I | Y | Q | G | T | DELETED | DELETED | P | I |
| S | P | I | S | I | Y | Q | G | T | DELETED | DELETED | P | M |
| S | P | I | S | I | Y | Q | G | T | DELETED | P | DELETED | I |
| S | P | I | S | I | Y | Q | G | T | DELETED | P | DELETED | M |
| S | P | I | S | I | Y | Q | G | T | DELETED | P | P | I |
| S | P | I | S | I | Y | Q | G | T | DELETED | P | P | M |
| S | P | I | S | I | Y | Q | G | T | N | DELETED | DELETED | I |
| S | P | I | S | I | Y | Q | G | T | N | DELETED | DELETED | M |
| S | P | I | S | I | Y | Q | G | T | N | DELETED | P | I |
| S | P | I | S | I | Y | Q | G | T | N | DELETED | P | M |
| S | P | I | S | I | Y | Q | G | T | N | P | DELETED | I |
| S | P | I | S | I | Y | Q | G | T | N | P | DELETED | M |
| S | P | I | S | I | Y | Q | G | T | N | P | P | I |
| S | P | I | S | I | Y | Q | G | T | N | P | P | M |
| S | P | I | S | I | Y | V | S | S | DELETED | DELETED | DELETED | I |
| S | P | I | S | I | Y | V | S | S | DELETED | DELETED | DELETED | M |
| S | P | I | S | I | Y | V | S | S | DELETED | DELETED | P | I |
| S | P | I | S | I | Y | V | S | S | DELETED | DELETED | P | M |
| S | P | I | S | I | Y | V | S | S | DELETED | P | DELETED | I |
| S | P | I | S | I | Y | V | S | S | DELETED | P | DELETED | M |
| S | P | I | S | I | Y | V | S | S | DELETED | P | P | I |
| S | P | I | S | I | Y | V | S | S | DELETED | P | P | M |
| S | P | I | S | I | Y | V | S | S | N | DELETED | DELETED | I |
| S | P | I | S | I | Y | V | S | S | N | DELETED | DELETED | M |
| S | P | I | S | I | Y | V | S | S | N | DELETED | P | I |
| S | P | I | S | I | Y | V | S | S | N | DELETED | P | M |
| S | P | I | S | I | Y | V | S | S | N | P | DELETED | I |
| S | P | I | S | I | Y | V | S | S | N | P | DELETED | M |
| S | P | I | S | I | Y | V | S | S | N | P | P | I |
| S | P | I | S | I | Y | V | S | S | N | P | P | M |
| S | P | I | S | I | Y | V | S | T | DELETED | DELETED | DELETED | I |
| S | P | I | S | I | Y | V | S | T | DELETED | DELETED | DELETED | M |
| S | P | I | S | I | Y | V | S | T | DELETED | DELETED | P | I |
| S | P | I | S | I | Y | V | S | T | DELETED | DELETED | P | M |
| S | P | I | S | I | Y | V | S | T | DELETED | P | DELETED | I |
| S | P | I | S | I | Y | V | S | T | DELETED | P | DELETED | M |
| S | P | I | S | I | Y | V | S | T | DELETED | P | P | I |
| S | P | I | S | I | Y | V | S | T | DELETED | P | P | M |
| S | P | I | S | I | Y | V | S | T | N | DELETED | DELETED | I |
| S | P | I | S | I | Y | V | S | T | N | DELETED | DELETED | M |
| S | P | I | S | I | Y | V | S | T | N | DELETED | P | I |
| S | P | I | S | I | Y | V | S | T | N | DELETED | P | M |
| S | P | I | S | I | Y | V | S | T | N | P | DELETED | I |
| S | P | I | S | I | Y | V | S | T | N | P | DELETED | M |
| S | P | I | S | I | Y | V | S | T | N | P | P | I |
| S | P | I | S | I | Y | V | S | T | N | P | P | M |
| S | P | I | S | I | Y | V | G | S | DELETED | DELETED | DELETED | I |
| S | P | I | S | I | Y | V | G | S | DELETED | DELETED | DELETED | M |
| S | P | I | S | I | Y | V | G | S | DELETED | DELETED | P | I |
| S | P | I | S | I | Y | V | G | S | DELETED | DELETED | P | M |
| S | P | I | S | I | Y | V | G | S | DELETED | P | DELETED | I |
| S | P | I | S | I | Y | V | G | S | DELETED | P | DELETED | M |
| S | P | I | S | I | Y | V | G | S | DELETED | P | P | I |
| S | P | I | S | I | Y | V | G | S | DELETED | P | P | M |
| S | P | I | S | I | Y | V | G | S | N | DELETED | DELETED | I |
| S | P | I | S | I | Y | V | G | S | N | DELETED | DELETED | M |
| S | P | I | S | I | Y | V | G | S | N | DELETED | P | I |
| S | P | I | S | I | Y | V | G | S | N | DELETED | P | M |
| S | P | I | S | I | Y | V | G | S | N | P | DELETED | I |
| S | P | I | S | I | Y | V | G | S | N | P | DELETED | M |
| S | P | I | S | I | Y | V | G | S | N | P | P | I |
| S | P | I | S | I | Y | V | G | S | N | P | P | M |
| S | P | I | S | I | Y | V | G | T | DELETED | DELETED | DELETED | I |
| S | P | I | S | I | Y | V | G | T | DELETED | DELETED | DELETED | M |
| S | P | I | S | I | Y | V | G | T | DELETED | DELETED | P | I |
| S | P | I | S | I | Y | V | G | T | DELETED | DELETED | P | M |
| S | P | I | S | I | Y | V | G | T | DELETED | P | DELETED | I |
| S | P | I | S | I | Y | V | G | T | DELETED | P | DELETED | M |
| S | P | I | S | I | Y | V | G | T | DELETED | P | P | I |
| S | P | I | S | I | Y | V | G | T | DELETED | P | P | M |
| S | P | I | S | I | Y | V | G | T | N | DELETED | DELETED | I |
| S | P | I | S | I | Y | V | G | T | N | DELETED | DELETED | M |
| S | P | I | S | I | Y | V | G | T | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | I | Y | V | G | T | N | DELETED | P | M |
| S | P | I | S | I | Y | V | G | T | N | P | DELETED | I |
| S | P | I | S | I | Y | V | G | T | N | P | DELETED | M |
| S | P | I | S | I | Y | V | G | T | N | P | P | I |
| S | P | I | S | I | Y | V | G | T | N | P | P | M |
| S | P | I | S | I | H | Q | S | S | DELETED | DELETED | DELETED | I |
| S | P | I | S | I | H | Q | S | S | DELETED | DELETED | DELETED | M |
| S | P | I | S | I | H | Q | S | S | DELETED | DELETED | P | I |
| S | P | I | S | I | H | Q | S | S | DELETED | DELETED | P | M |
| S | P | I | S | I | H | Q | S | S | DELETED | P | DELETED | I |
| S | P | I | S | I | H | Q | S | S | DELETED | P | DELETED | M |
| S | P | I | S | I | H | Q | S | S | DELETED | P | P | I |
| S | P | I | S | I | H | Q | S | S | DELETED | P | P | M |
| S | P | I | S | I | H | Q | S | S | N | DELETED | DELETED | I |
| S | P | I | S | I | H | Q | S | S | N | DELETED | DELETED | M |
| S | P | I | S | I | H | Q | S | S | N | DELETED | P | I |
| S | P | I | S | I | H | Q | S | S | N | DELETED | P | M |
| S | P | I | S | I | H | Q | S | S | N | P | DELETED | I |
| S | P | I | S | I | H | Q | S | S | N | P | DELETED | M |
| S | P | I | S | I | H | Q | S | S | N | P | P | I |
| S | P | I | S | I | H | Q | S | S | N | P | P | M |
| S | P | I | S | I | H | Q | S | T | DELETED | DELETED | DELETED | I |
| S | P | I | S | I | H | Q | S | T | DELETED | DELETED | DELETED | M |
| S | P | I | S | I | H | Q | S | T | DELETED | DELETED | P | I |
| S | P | I | S | I | H | Q | S | T | DELETED | DELETED | P | M |
| S | P | I | S | I | H | Q | S | T | DELETED | P | DELETED | I |
| S | P | I | S | I | H | Q | S | T | DELETED | P | DELETED | M |
| S | P | I | S | I | H | Q | S | T | DELETED | P | P | I |
| S | P | I | S | I | H | Q | S | T | DELETED | P | P | M |
| S | P | I | S | I | H | Q | S | T | N | DELETED | DELETED | I |
| S | P | I | S | I | H | Q | S | T | N | DELETED | DELETED | M |
| S | P | I | S | I | H | Q | S | T | N | DELETED | P | I |
| S | P | I | S | I | H | Q | S | T | N | DELETED | P | M |
| S | P | I | S | I | H | Q | S | T | N | P | DELETED | I |
| S | P | I | S | I | H | Q | S | T | N | P | DELETED | M |
| S | P | I | S | I | H | Q | S | T | N | P | P | I |
| S | P | I | S | I | H | Q | S | T | N | P | P | M |
| S | P | I | S | I | H | Q | G | S | DELETED | DELETED | DELETED | I |
| S | P | I | S | I | H | Q | G | S | DELETED | DELETED | DELETED | M |
| S | P | I | S | I | H | Q | G | S | DELETED | DELETED | P | I |
| S | P | I | S | I | H | Q | G | S | DELETED | DELETED | P | M |
| S | P | I | S | I | H | Q | G | S | DELETED | P | DELETED | I |
| S | P | I | S | I | H | Q | G | S | DELETED | P | DELETED | M |
| S | P | I | S | I | H | Q | G | S | DELETED | P | P | I |
| S | P | I | S | I | H | Q | G | S | DELETED | P | P | M |
| S | P | I | S | I | H | Q | G | S | N | DELETED | DELETED | I |
| S | P | I | S | I | H | Q | G | S | N | DELETED | DELETED | M |
| S | P | I | S | I | H | Q | G | S | N | DELETED | P | I |
| S | P | I | S | I | H | Q | G | S | N | DELETED | P | M |
| S | P | I | S | I | H | Q | G | S | N | P | DELETED | I |
| S | P | I | S | I | H | Q | G | S | N | P | DELETED | M |
| S | P | I | S | I | H | Q | G | S | N | P | P | I |
| S | P | I | S | I | H | Q | G | S | N | P | P | M |
| S | P | I | S | I | H | Q | G | T | DELETED | DELETED | DELETED | I |
| S | P | I | S | I | H | Q | G | T | DELETED | DELETED | DELETED | M |
| S | P | I | S | I | H | Q | G | T | DELETED | DELETED | P | I |
| S | P | I | S | I | H | Q | G | T | DELETED | DELETED | P | M |
| S | P | I | S | I | H | Q | G | T | DELETED | P | DELETED | I |
| S | P | I | S | I | H | Q | G | T | DELETED | P | DELETED | M |
| S | P | I | S | I | H | Q | G | T | DELETED | P | P | I |
| S | P | I | S | I | H | Q | G | T | DELETED | P | P | M |
| S | P | I | S | I | H | Q | G | T | N | DELETED | DELETED | I |
| S | P | I | S | I | H | Q | G | T | N | DELETED | DELETED | M |
| S | P | I | S | I | H | Q | G | T | N | DELETED | P | I |
| S | P | I | S | I | H | Q | G | T | N | DELETED | P | M |
| S | P | I | S | I | H | Q | G | T | N | P | DELETED | I |
| S | P | I | S | I | H | Q | G | T | N | P | DELETED | M |
| S | P | I | S | I | H | Q | G | T | N | P | P | I |
| S | P | I | S | I | H | Q | G | T | N | P | P | M |
| S | P | I | S | I | H | V | S | S | DELETED | DELETED | DELETED | I |
| S | P | I | S | I | H | V | S | S | DELETED | DELETED | DELETED | M |
| S | P | I | S | I | H | V | S | S | DELETED | DELETED | P | I |
| S | P | I | S | I | H | V | S | S | DELETED | DELETED | P | M |
| S | P | I | S | I | H | V | S | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | S | I | H | V | S | S | DELETED | P | DELETED | M |
| S | P | I | S | I | H | V | S | S | DELETED | P | P | I |
| S | P | I | S | I | H | V | S | S | DELETED | P | P | M |
| S | P | I | S | I | H | V | S | S | N | DELETED | DELETED | I |
| S | P | I | S | I | H | V | S | S | N | DELETED | DELETED | M |
| S | P | I | S | I | H | V | S | S | N | DELETED | P | I |
| S | P | I | S | I | H | V | S | S | N | DELETED | P | M |
| S | P | I | S | I | H | V | S | S | N | P | DELETED | I |
| S | P | I | S | I | H | V | S | S | N | P | DELETED | M |
| S | P | I | S | I | H | V | S | S | N | P | P | I |
| S | P | I | S | I | H | V | S | S | N | P | P | M |
| S | P | I | S | I | H | V | S | T | DELETED | DELETED | DELETED | I |
| S | P | I | S | I | H | V | S | T | DELETED | DELETED | DELETED | M |
| S | P | I | S | I | H | V | S | T | DELETED | DELETED | P | I |
| S | P | I | S | I | H | V | S | T | DELETED | DELETED | P | M |
| S | P | I | S | I | H | V | S | T | DELETED | P | DELETED | I |
| S | P | I | S | I | H | V | S | T | DELETED | P | DELETED | M |
| S | P | I | S | I | H | V | S | T | DELETED | P | P | I |
| S | P | I | S | I | H | V | S | T | DELETED | P | P | M |
| S | P | I | S | I | H | V | S | T | N | DELETED | DELETED | I |
| S | P | I | S | I | H | V | S | T | N | DELETED | DELETED | M |
| S | P | I | S | I | H | V | S | T | N | DELETED | P | I |
| S | P | I | S | I | H | V | S | T | N | DELETED | P | M |
| S | P | I | S | I | H | V | S | T | N | P | DELETED | I |
| S | P | I | S | I | H | V | S | T | N | P | DELETED | M |
| S | P | I | S | I | H | V | S | T | N | P | P | I |
| S | P | I | S | I | H | V | S | T | N | P | P | M |
| S | P | I | S | I | H | V | G | S | DELETED | DELETED | DELETED | I |
| S | P | I | S | I | H | V | G | S | DELETED | DELETED | DELETED | M |
| S | P | I | S | I | H | V | G | S | DELETED | DELETED | P | I |
| S | P | I | S | I | H | V | G | S | DELETED | DELETED | P | M |
| S | P | I | S | I | H | V | G | S | DELETED | P | DELETED | I |
| S | P | I | S | I | H | V | G | S | DELETED | P | DELETED | M |
| S | P | I | S | I | H | V | G | S | DELETED | P | P | I |
| S | P | I | S | I | H | V | G | S | DELETED | P | P | M |
| S | P | I | S | I | H | V | G | S | N | DELETED | DELETED | I |
| S | P | I | S | I | H | V | G | S | N | DELETED | DELETED | M |
| S | P | I | S | I | H | V | G | S | N | DELETED | P | I |
| S | P | I | S | I | H | V | G | S | N | DELETED | P | M |
| S | P | I | S | I | H | V | G | S | N | P | DELETED | I |
| S | P | I | S | I | H | V | G | S | N | P | DELETED | M |
| S | P | I | S | I | H | V | G | S | N | P | P | I |
| S | P | I | S | I | H | V | G | S | N | P | P | M |
| S | P | I | S | I | H | V | G | T | DELETED | DELETED | DELETED | I |
| S | P | I | S | I | H | V | G | T | DELETED | DELETED | DELETED | M |
| S | P | I | S | I | H | V | G | T | DELETED | DELETED | P | I |
| S | P | I | S | I | H | V | G | T | DELETED | DELETED | P | M |
| S | P | I | S | I | H | V | G | T | DELETED | P | DELETED | I |
| S | P | I | S | I | H | V | G | T | DELETED | P | DELETED | M |
| S | P | I | S | I | H | V | G | T | DELETED | P | P | I |
| S | P | I | S | I | H | V | G | T | DELETED | P | P | M |
| S | P | I | S | I | H | V | G | T | N | DELETED | DELETED | I |
| S | P | I | S | I | H | V | G | T | N | DELETED | DELETED | M |
| S | P | I | S | I | H | V | G | T | N | DELETED | P | I |
| S | P | I | S | I | H | V | G | T | N | DELETED | P | M |
| S | P | I | S | I | H | V | G | T | N | P | DELETED | I |
| S | P | I | S | I | H | V | G | T | N | P | DELETED | M |
| S | P | I | S | I | H | V | G | T | N | P | P | I |
| S | P | I | S | I | H | V | G | T | N | P | P | M |
| S | P | I | R | L | Y | Q | S | S | DELETED | DELETED | DELETED | I |
| S | P | I | R | L | Y | Q | S | S | DELETED | DELETED | DELETED | M |
| S | P | I | R | L | Y | Q | S | S | DELETED | DELETED | P | I |
| S | P | I | R | L | Y | Q | S | S | DELETED | DELETED | P | M |
| S | P | I | R | L | Y | Q | S | S | DELETED | P | DELETED | I |
| S | P | I | R | L | Y | Q | S | S | DELETED | P | DELETED | M |
| S | P | I | R | L | Y | Q | S | S | DELETED | P | P | I |
| S | P | I | R | L | Y | Q | S | S | DELETED | P | P | M |
| S | P | I | R | L | Y | Q | S | S | N | DELETED | DELETED | I |
| S | P | I | R | L | Y | Q | S | S | N | DELETED | DELETED | M |
| S | P | I | R | L | Y | Q | S | S | N | DELETED | P | I |
| S | P | I | R | L | Y | Q | S | S | N | DELETED | P | M |
| S | P | I | R | L | Y | Q | S | S | N | P | DELETED | I |
| S | P | I | R | L | Y | Q | S | S | N | P | DELETED | M |
| S | P | I | R | L | Y | Q | S | S | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | R | L | Y | Q | S | S | N | P | P | M |
| S | P | I | R | L | Y | Q | S | T | DELETED | DELETED | DELETED | I |
| S | P | I | R | L | Y | Q | S | T | DELETED | DELETED | DELETED | M |
| S | P | I | R | L | Y | Q | S | T | DELETED | DELETED | P | I |
| S | P | I | R | L | Y | Q | S | T | DELETED | DELETED | P | M |
| S | P | I | R | L | Y | Q | S | T | DELETED | P | DELETED | I |
| S | P | I | R | L | Y | Q | S | T | DELETED | P | DELETED | M |
| S | P | I | R | L | Y | Q | S | T | DELETED | P | P | I |
| S | P | I | R | L | Y | Q | S | T | DELETED | P | P | M |
| S | P | I | R | L | Y | Q | S | T | N | DELETED | DELETED | I |
| S | P | I | R | L | Y | Q | S | T | N | DELETED | DELETED | M |
| S | P | I | R | L | Y | Q | S | T | N | DELETED | P | I |
| S | P | I | R | L | Y | Q | S | T | N | DELETED | P | M |
| S | P | I | R | L | Y | Q | S | T | N | P | DELETED | I |
| S | P | I | R | L | Y | Q | S | T | N | P | DELETED | M |
| S | P | I | R | L | Y | Q | S | T | N | P | P | I |
| S | P | I | R | L | Y | Q | S | T | N | P | P | M |
| S | P | I | R | L | Y | Q | G | S | DELETED | DELETED | DELETED | I |
| S | P | I | R | L | Y | Q | G | S | DELETED | DELETED | DELETED | M |
| S | P | I | R | L | Y | Q | G | S | DELETED | DELETED | P | I |
| S | P | I | R | L | Y | Q | G | S | DELETED | DELETED | P | M |
| S | P | I | R | L | Y | Q | G | S | DELETED | P | DELETED | I |
| S | P | I | R | L | Y | Q | G | S | DELETED | P | DELETED | M |
| S | P | I | R | L | Y | Q | G | S | DELETED | P | P | I |
| S | P | I | R | L | Y | Q | G | S | DELETED | P | P | M |
| S | P | I | R | L | Y | Q | G | S | N | DELETED | DELETED | I |
| S | P | I | R | L | Y | Q | G | S | N | DELETED | DELETED | M |
| S | P | I | R | L | Y | Q | G | S | N | DELETED | P | I |
| S | P | I | R | L | Y | Q | G | S | N | DELETED | P | M |
| S | P | I | R | L | Y | Q | G | S | N | P | DELETED | I |
| S | P | I | R | L | Y | Q | G | S | N | P | DELETED | M |
| S | P | I | R | L | Y | Q | G | S | N | P | P | I |
| S | P | I | R | L | Y | Q | G | S | N | P | P | M |
| S | P | I | R | L | Y | Q | G | T | DELETED | DELETED | DELETED | I |
| S | P | I | R | L | Y | Q | G | T | DELETED | DELETED | DELETED | M |
| S | P | I | R | L | Y | Q | G | T | DELETED | DELETED | P | I |
| S | P | I | R | L | Y | Q | G | T | DELETED | DELETED | P | M |
| S | P | I | R | L | Y | Q | G | T | DELETED | P | DELETED | I |
| S | P | I | R | L | Y | Q | G | T | DELETED | P | DELETED | M |
| S | P | I | R | L | Y | Q | G | T | DELETED | P | P | I |
| S | P | I | R | L | Y | Q | G | T | DELETED | P | P | M |
| S | P | I | R | L | Y | Q | G | T | N | DELETED | DELETED | I |
| S | P | I | R | L | Y | Q | G | T | N | DELETED | DELETED | M |
| S | P | I | R | L | Y | Q | G | T | N | DELETED | P | I |
| S | P | I | R | L | Y | Q | G | T | N | DELETED | P | M |
| S | P | I | R | L | Y | Q | G | T | N | P | DELETED | I |
| S | P | I | R | L | Y | Q | G | T | N | P | DELETED | M |
| S | P | I | R | L | Y | Q | G | T | N | P | P | I |
| S | P | I | R | L | Y | Q | G | T | N | P | P | M |
| S | P | I | R | L | Y | V | S | S | DELETED | DELETED | DELETED | I |
| S | P | I | R | L | Y | V | S | S | DELETED | DELETED | DELETED | M |
| S | P | I | R | L | Y | V | S | S | DELETED | DELETED | P | I |
| S | P | I | R | L | Y | V | S | S | DELETED | DELETED | P | M |
| S | P | I | R | L | Y | V | S | S | DELETED | P | DELETED | I |
| S | P | I | R | L | Y | V | S | S | DELETED | P | DELETED | M |
| S | P | I | R | L | Y | V | S | S | DELETED | P | P | I |
| S | P | I | R | L | Y | V | S | S | DELETED | P | P | M |
| S | P | I | R | L | Y | V | S | S | N | DELETED | DELETED | I |
| S | P | I | R | L | Y | V | S | S | N | DELETED | DELETED | M |
| S | P | I | R | L | Y | V | S | S | N | DELETED | P | I |
| S | P | I | R | L | Y | V | S | S | N | DELETED | P | M |
| S | P | I | R | L | Y | V | S | S | N | P | DELETED | I |
| S | P | I | R | L | Y | V | S | S | N | P | DELETED | M |
| S | P | I | R | L | Y | V | S | S | N | P | P | I |
| S | P | I | R | L | Y | V | S | S | N | P | P | M |
| S | P | I | R | L | Y | V | S | T | DELETED | DELETED | DELETED | I |
| S | P | I | R | L | Y | V | S | T | DELETED | DELETED | DELETED | M |
| S | P | I | R | L | Y | V | S | T | DELETED | DELETED | P | I |
| S | P | I | R | L | Y | V | S | T | DELETED | DELETED | P | M |
| S | P | I | R | L | Y | V | S | T | DELETED | P | DELETED | I |
| S | P | I | R | L | Y | V | S | T | DELETED | P | DELETED | M |
| S | P | I | R | L | Y | V | S | T | DELETED | P | P | I |
| S | P | I | R | L | Y | V | S | T | DELETED | P | P | M |
| S | P | I | R | L | Y | V | S | T | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | R | L | Y | V | S | T | N | DELETED | DELETED | M |
| S | P | I | R | L | Y | V | S | T | N | DELETED | P | I |
| S | P | I | R | L | Y | V | S | T | N | DELETED | P | M |
| S | P | I | R | L | Y | V | S | T | N | P | DELETED | I |
| S | P | I | R | L | Y | V | S | T | N | P | DELETED | M |
| S | P | I | R | L | Y | V | S | T | N | P | P | I |
| S | P | I | R | L | Y | V | S | T | N | P | P | M |
| S | P | I | R | L | Y | V | G | S | DELETED | DELETED | DELETED | I |
| S | P | I | R | L | Y | V | G | S | DELETED | DELETED | DELETED | M |
| S | P | I | R | L | Y | V | G | S | DELETED | DELETED | P | I |
| S | P | I | R | L | Y | V | G | S | DELETED | DELETED | P | M |
| S | P | I | R | L | Y | V | G | S | DELETED | P | DELETED | I |
| S | P | I | R | L | Y | V | G | S | DELETED | P | DELETED | M |
| S | P | I | R | L | Y | V | G | S | DELETED | P | P | I |
| S | P | I | R | L | Y | V | G | S | DELETED | P | P | M |
| S | P | I | R | L | Y | V | G | S | N | DELETED | DELETED | I |
| S | P | I | R | L | Y | V | G | S | N | DELETED | DELETED | M |
| S | P | I | R | L | Y | V | G | S | N | DELETED | P | I |
| S | P | I | R | L | Y | V | G | S | N | DELETED | P | M |
| S | P | I | R | L | Y | V | G | S | N | P | DELETED | I |
| S | P | I | R | L | Y | V | G | S | N | P | DELETED | M |
| S | P | I | R | L | Y | V | G | S | N | P | P | I |
| S | P | I | R | L | Y | V | G | S | N | P | P | M |
| S | P | I | R | L | Y | V | G | T | DELETED | DELETED | DELETED | I |
| S | P | I | R | L | Y | V | G | T | DELETED | DELETED | DELETED | M |
| S | P | I | R | L | Y | V | G | T | DELETED | DELETED | P | I |
| S | P | I | R | L | Y | V | G | T | DELETED | DELETED | P | M |
| S | P | I | R | L | Y | V | G | T | DELETED | P | DELETED | I |
| S | P | I | R | L | Y | V | G | T | DELETED | P | DELETED | M |
| S | P | I | R | L | Y | V | G | T | DELETED | P | P | I |
| S | P | I | R | L | Y | V | G | T | DELETED | P | P | M |
| S | P | I | R | L | Y | V | G | T | N | DELETED | DELETED | I |
| S | P | I | R | L | Y | V | G | T | N | DELETED | DELETED | M |
| S | P | I | R | L | Y | V | G | T | N | DELETED | P | I |
| S | P | I | R | L | Y | V | G | T | N | DELETED | P | M |
| S | P | I | R | L | Y | V | G | T | N | P | DELETED | I |
| S | P | I | R | L | Y | V | G | T | N | P | DELETED | M |
| S | P | I | R | L | Y | V | G | T | N | P | P | I |
| S | P | I | R | L | Y | V | G | T | N | P | P | M |
| S | P | I | R | L | H | Q | S | S | DELETED | DELETED | DELETED | I |
| S | P | I | R | L | H | Q | S | S | DELETED | DELETED | DELETED | M |
| S | P | I | R | L | H | Q | S | S | DELETED | DELETED | P | I |
| S | P | I | R | L | H | Q | S | S | DELETED | DELETED | P | M |
| S | P | I | R | L | H | Q | S | S | DELETED | P | DELETED | I |
| S | P | I | R | L | H | Q | S | S | DELETED | P | DELETED | M |
| S | P | I | R | L | H | Q | S | S | DELETED | P | P | I |
| S | P | I | R | L | H | Q | S | S | DELETED | P | P | M |
| S | P | I | R | L | H | Q | S | S | N | DELETED | DELETED | I |
| S | P | I | R | L | H | Q | S | S | N | DELETED | DELETED | M |
| S | P | I | R | L | H | Q | S | S | N | DELETED | P | I |
| S | P | I | R | L | H | Q | S | S | N | DELETED | P | M |
| S | P | I | R | L | H | Q | S | S | N | P | DELETED | I |
| S | P | I | R | L | H | Q | S | S | N | P | DELETED | M |
| S | P | I | R | L | H | Q | S | S | N | P | P | I |
| S | P | I | R | L | H | Q | S | S | N | P | P | M |
| S | P | I | R | L | H | Q | S | T | DELETED | DELETED | DELETED | I |
| S | P | I | R | L | H | Q | S | T | DELETED | DELETED | DELETED | M |
| S | P | I | R | L | H | Q | S | T | DELETED | DELETED | P | I |
| S | P | I | R | L | H | Q | S | T | DELETED | DELETED | P | M |
| S | P | I | R | L | H | Q | S | T | DELETED | P | DELETED | I |
| S | P | I | R | L | H | Q | S | T | DELETED | P | DELETED | M |
| S | P | I | R | L | H | Q | S | T | DELETED | P | P | I |
| S | P | I | R | L | H | Q | S | T | DELETED | P | P | M |
| S | P | I | R | L | H | Q | S | T | N | DELETED | DELETED | I |
| S | P | I | R | L | H | Q | S | T | N | DELETED | DELETED | M |
| S | P | I | R | L | H | Q | S | T | N | DELETED | P | I |
| S | P | I | R | L | H | Q | S | T | N | DELETED | P | M |
| S | P | I | R | L | H | Q | S | T | N | P | DELETED | I |
| S | P | I | R | L | H | Q | S | T | N | P | DELETED | M |
| S | P | I | R | L | H | Q | S | T | N | P | P | I |
| S | P | I | R | L | H | Q | S | T | N | P | P | M |
| S | P | I | R | L | H | Q | G | S | DELETED | DELETED | DELETED | I |
| S | P | I | R | L | H | Q | G | S | DELETED | DELETED | DELETED | M |
| S | P | I | R | L | H | Q | G | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | R | L | H | Q | G | S | DELETED | DELETED | P | M |
| S | P | I | R | L | H | Q | G | S | DELETED | P | DELETED | I |
| S | P | I | R | L | H | Q | G | S | DELETED | P | DELETED | M |
| S | P | I | R | L | H | Q | G | S | DELETED | P | P | I |
| S | P | I | R | L | H | Q | G | S | DELETED | P | P | M |
| S | P | I | R | L | H | Q | G | S | N | DELETED | DELETED | I |
| S | P | I | R | L | H | Q | G | S | N | DELETED | DELETED | M |
| S | P | I | R | L | H | Q | G | S | N | DELETED | P | I |
| S | P | I | R | L | H | Q | G | S | N | DELETED | P | M |
| S | P | I | R | L | H | Q | G | S | N | P | DELETED | I |
| S | P | I | R | L | H | Q | G | S | N | P | DELETED | M |
| S | P | I | R | L | H | Q | G | S | N | P | P | I |
| S | P | I | R | L | H | Q | G | S | N | P | P | M |
| S | P | I | R | L | H | Q | G | T | DELETED | DELETED | DELETED | I |
| S | P | I | R | L | H | Q | G | T | DELETED | DELETED | DELETED | M |
| S | P | I | R | L | H | Q | G | T | DELETED | DELETED | P | I |
| S | P | I | R | L | H | Q | G | T | DELETED | DELETED | P | M |
| S | P | I | R | L | H | Q | G | T | DELETED | P | DELETED | I |
| S | P | I | R | L | H | Q | G | T | DELETED | P | DELETED | M |
| S | P | I | R | L | H | Q | G | T | DELETED | P | P | I |
| S | P | I | R | L | H | Q | G | T | DELETED | P | P | M |
| S | P | I | R | L | H | Q | G | T | N | DELETED | DELETED | I |
| S | P | I | R | L | H | Q | G | T | N | DELETED | DELETED | M |
| S | P | I | R | L | H | Q | G | T | N | DELETED | P | I |
| S | P | I | R | L | H | Q | G | T | N | DELETED | P | M |
| S | P | I | R | L | H | Q | G | T | N | P | DELETED | I |
| S | P | I | R | L | H | Q | G | T | N | P | DELETED | M |
| S | P | I | R | L | H | Q | G | T | N | P | P | I |
| S | P | I | R | L | H | Q | G | T | N | P | P | M |
| S | P | I | R | L | H | V | S | S | DELETED | DELETED | DELETED | I |
| S | P | I | R | L | H | V | S | S | DELETED | DELETED | DELETED | M |
| S | P | I | R | L | H | V | S | S | DELETED | DELETED | P | I |
| S | P | I | R | L | H | V | S | S | DELETED | DELETED | P | M |
| S | P | I | R | L | H | V | S | S | DELETED | P | DELETED | I |
| S | P | I | R | L | H | V | S | S | DELETED | P | DELETED | M |
| S | P | I | R | L | H | V | S | S | DELETED | P | P | I |
| S | P | I | R | L | H | V | S | S | DELETED | P | P | M |
| S | P | I | R | L | H | V | S | S | N | DELETED | DELETED | I |
| S | P | I | R | L | H | V | S | S | N | DELETED | DELETED | M |
| S | P | I | R | L | H | V | S | S | N | DELETED | P | I |
| S | P | I | R | L | H | V | S | S | N | DELETED | P | M |
| S | P | I | R | L | H | V | S | S | N | P | DELETED | I |
| S | P | I | R | L | H | V | S | S | N | P | DELETED | M |
| S | P | I | R | L | H | V | S | S | N | P | P | I |
| S | P | I | R | L | H | V | S | S | N | P | P | M |
| S | P | I | R | L | H | V | S | T | DELETED | DELETED | DELETED | I |
| S | P | I | R | L | H | V | S | T | DELETED | DELETED | DELETED | M |
| S | P | I | R | L | H | V | S | T | DELETED | DELETED | P | I |
| S | P | I | R | L | H | V | S | T | DELETED | DELETED | P | M |
| S | P | I | R | L | H | V | S | T | DELETED | P | DELETED | I |
| S | P | I | R | L | H | V | S | T | DELETED | P | DELETED | M |
| S | P | I | R | L | H | V | S | T | DELETED | P | P | I |
| S | P | I | R | L | H | V | S | T | DELETED | P | P | M |
| S | P | I | R | L | H | V | S | T | N | DELETED | DELETED | I |
| S | P | I | R | L | H | V | S | T | N | DELETED | DELETED | M |
| S | P | I | R | L | H | V | S | T | N | DELETED | P | I |
| S | P | I | R | L | H | V | S | T | N | DELETED | P | M |
| S | P | I | R | L | H | V | S | T | N | P | DELETED | I |
| S | P | I | R | L | H | V | S | T | N | P | DELETED | M |
| S | P | I | R | L | H | V | S | T | N | P | P | I |
| S | P | I | R | L | H | V | S | T | N | P | P | M |
| S | P | I | R | L | H | V | G | S | DELETED | DELETED | DELETED | I |
| S | P | I | R | L | H | V | G | S | DELETED | DELETED | DELETED | M |
| S | P | I | R | L | H | V | G | S | DELETED | DELETED | P | I |
| S | P | I | R | L | H | V | G | S | DELETED | DELETED | P | M |
| S | P | I | R | L | H | V | G | S | DELETED | P | DELETED | I |
| S | P | I | R | L | H | V | G | S | DELETED | P | DELETED | M |
| S | P | I | R | L | H | V | G | S | DELETED | P | P | I |
| S | P | I | R | L | H | V | G | S | DELETED | P | P | M |
| S | P | I | R | L | H | V | G | S | N | DELETED | DELETED | I |
| S | P | I | R | L | H | V | G | S | N | DELETED | DELETED | M |
| S | P | I | R | L | H | V | G | S | N | DELETED | P | I |
| S | P | I | R | L | H | V | G | S | N | DELETED | P | M |
| S | P | I | R | L | H | V | G | S | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | R | L | H | V | G | S | N | P | DELETED | M |
| S | P | I | R | L | H | V | G | S | N | P | P | I |
| S | P | I | R | L | H | V | G | S | N | P | P | M |
| S | P | I | R | L | H | V | G | T | DELETED | DELETED | DELETED | I |
| S | P | I | R | L | H | V | G | T | DELETED | DELETED | DELETED | M |
| S | P | I | R | L | H | V | G | T | DELETED | DELETED | P | I |
| S | P | I | R | L | H | V | G | T | DELETED | DELETED | P | M |
| S | P | I | R | L | H | V | G | T | DELETED | P | DELETED | I |
| S | P | I | R | L | H | V | G | T | DELETED | P | DELETED | M |
| S | P | I | R | L | H | V | G | T | DELETED | P | P | I |
| S | P | I | R | L | H | V | G | T | DELETED | P | P | M |
| S | P | I | R | L | H | V | G | T | N | DELETED | DELETED | I |
| S | P | I | R | L | H | V | G | T | N | DELETED | DELETED | M |
| S | P | I | R | L | H | V | G | T | N | DELETED | P | I |
| S | P | I | R | L | H | V | G | T | N | DELETED | P | M |
| S | P | I | R | L | H | V | G | T | N | P | DELETED | I |
| S | P | I | R | L | H | V | G | T | N | P | DELETED | M |
| S | P | I | R | L | H | V | G | T | N | P | P | I |
| S | P | I | R | L | H | V | G | T | N | P | P | M |
| S | P | I | R | I | Y | Q | S | S | DELETED | DELETED | DELETED | I |
| S | P | I | R | I | Y | Q | S | S | DELETED | DELETED | DELETED | M |
| S | P | I | R | I | Y | Q | S | S | DELETED | DELETED | P | I |
| S | P | I | R | I | Y | Q | S | S | DELETED | DELETED | P | M |
| S | P | I | R | I | Y | Q | S | S | DELETED | P | DELETED | I |
| S | P | I | R | I | Y | Q | S | S | DELETED | P | DELETED | M |
| S | P | I | R | I | Y | Q | S | S | DELETED | P | P | I |
| S | P | I | R | I | Y | Q | S | S | DELETED | P | P | M |
| S | P | I | R | I | Y | Q | S | S | N | DELETED | DELETED | I |
| S | P | I | R | I | Y | Q | S | S | N | DELETED | DELETED | M |
| S | P | I | R | I | Y | Q | S | S | N | DELETED | P | I |
| S | P | I | R | I | Y | Q | S | S | N | DELETED | P | M |
| S | P | I | R | I | Y | Q | S | S | N | P | DELETED | I |
| S | P | I | R | I | Y | Q | S | S | N | P | DELETED | M |
| S | P | I | R | I | Y | Q | S | S | N | P | P | I |
| S | P | I | R | I | Y | Q | S | S | N | P | P | M |
| S | P | I | R | I | Y | Q | S | T | DELETED | DELETED | DELETED | I |
| S | P | I | R | I | Y | Q | S | T | DELETED | DELETED | DELETED | M |
| S | P | I | R | I | Y | Q | S | T | DELETED | DELETED | P | I |
| S | P | I | R | I | Y | Q | S | T | DELETED | DELETED | P | M |
| S | P | I | R | I | Y | Q | S | T | DELETED | P | DELETED | I |
| S | P | I | R | I | Y | Q | S | T | DELETED | P | DELETED | M |
| S | P | I | R | I | Y | Q | S | T | DELETED | P | P | I |
| S | P | I | R | I | Y | Q | S | T | DELETED | P | P | M |
| S | P | I | R | I | Y | Q | S | T | N | DELETED | DELETED | I |
| S | P | I | R | I | Y | Q | S | T | N | DELETED | DELETED | M |
| S | P | I | R | I | Y | Q | S | T | N | DELETED | P | I |
| S | P | I | R | I | Y | Q | S | T | N | DELETED | P | M |
| S | P | I | R | I | Y | Q | S | T | N | P | DELETED | I |
| S | P | I | R | I | Y | Q | S | T | N | P | DELETED | M |
| S | P | I | R | I | Y | Q | S | T | N | P | P | I |
| S | P | I | R | I | Y | Q | S | T | N | P | P | M |
| S | P | I | R | I | Y | Q | G | S | DELETED | DELETED | DELETED | I |
| S | P | I | R | I | Y | Q | G | S | DELETED | DELETED | DELETED | M |
| S | P | I | R | I | Y | Q | G | S | DELETED | DELETED | P | I |
| S | P | I | R | I | Y | Q | G | S | DELETED | DELETED | P | M |
| S | P | I | R | I | Y | Q | G | S | DELETED | P | DELETED | I |
| S | P | I | R | I | Y | Q | G | S | DELETED | P | DELETED | M |
| S | P | I | R | I | Y | Q | G | S | DELETED | P | P | I |
| S | P | I | R | I | Y | Q | G | S | DELETED | P | P | M |
| S | P | I | R | I | Y | Q | G | S | N | DELETED | DELETED | I |
| S | P | I | R | I | Y | Q | G | S | N | DELETED | DELETED | M |
| S | P | I | R | I | Y | Q | G | S | N | DELETED | P | I |
| S | P | I | R | I | Y | Q | G | S | N | DELETED | P | M |
| S | P | I | R | I | Y | Q | G | S | N | P | DELETED | I |
| S | P | I | R | I | Y | Q | G | S | N | P | DELETED | M |
| S | P | I | R | I | Y | Q | G | S | N | P | P | I |
| S | P | I | R | I | Y | Q | G | S | N | P | P | M |
| S | P | I | R | I | Y | Q | G | T | DELETED | DELETED | DELETED | I |
| S | P | I | R | I | Y | Q | G | T | DELETED | DELETED | DELETED | M |
| S | P | I | R | I | Y | Q | G | T | DELETED | DELETED | P | I |
| S | P | I | R | I | Y | Q | G | T | DELETED | DELETED | P | M |
| S | P | I | R | I | Y | Q | G | T | DELETED | P | DELETED | I |
| S | P | I | R | I | Y | Q | G | T | DELETED | P | DELETED | M |
| S | P | I | R | I | Y | Q | G | T | DELETED | P | P | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| S | P | I | R | I | Y | Q | G | T | DELETED | P | P | M |
| S | P | I | R | I | Y | Q | G | T | N | DELETED | DELETED | I |
| S | P | I | R | I | Y | Q | G | T | N | DELETED | DELETED | M |
| S | P | I | R | I | Y | Q | G | T | N | DELETED | P | I |
| S | P | I | R | I | Y | Q | G | T | N | DELETED | P | M |
| S | P | I | R | I | Y | Q | G | T | N | P | DELETED | I |
| S | P | I | R | I | Y | Q | G | T | N | P | DELETED | M |
| S | P | I | R | I | Y | Q | G | T | N | P | P | I |
| S | P | I | R | I | Y | Q | G | T | N | P | P | M |
| S | P | I | R | I | Y | V | S | S | DELETED | DELETED | DELETED | I |
| S | P | I | R | I | Y | V | S | S | DELETED | DELETED | DELETED | M |
| S | P | I | R | I | Y | V | S | S | DELETED | DELETED | P | I |
| S | P | I | R | I | Y | V | S | S | DELETED | DELETED | P | M |
| S | P | I | R | I | Y | V | S | S | DELETED | P | DELETED | I |
| S | P | I | R | I | Y | V | S | S | DELETED | P | DELETED | M |
| S | P | I | R | I | Y | V | S | S | DELETED | P | P | I |
| S | P | I | R | I | Y | V | S | S | DELETED | P | P | M |
| S | P | I | R | I | Y | V | S | S | N | DELETED | DELETED | I |
| S | P | I | R | I | Y | V | S | S | N | DELETED | DELETED | M |
| S | P | I | R | I | Y | V | S | S | N | DELETED | P | I |
| S | P | I | R | I | Y | V | S | S | N | DELETED | P | M |
| S | P | I | R | I | Y | V | S | S | N | P | DELETED | I |
| S | P | I | R | I | Y | V | S | S | N | P | DELETED | M |
| S | P | I | R | I | Y | V | S | S | N | P | P | I |
| S | P | I | R | I | Y | V | S | S | N | P | P | M |
| S | P | I | R | I | Y | V | S | T | DELETED | DELETED | DELETED | I |
| S | P | I | R | I | Y | V | S | T | DELETED | DELETED | DELETED | M |
| S | P | I | R | I | Y | V | S | T | DELETED | DELETED | P | I |
| S | P | I | R | I | Y | V | S | T | DELETED | DELETED | P | M |
| S | P | I | R | I | Y | V | S | T | DELETED | P | DELETED | I |
| S | P | I | R | I | Y | V | S | T | DELETED | P | DELETED | M |
| S | P | I | R | I | Y | V | S | T | DELETED | P | P | I |
| S | P | I | R | I | Y | V | S | T | DELETED | P | P | M |
| S | P | I | R | I | Y | V | S | T | N | DELETED | DELETED | I |
| S | P | I | R | I | Y | V | S | T | N | DELETED | DELETED | M |
| S | P | I | R | I | Y | V | S | T | N | DELETED | P | I |
| S | P | I | R | I | Y | V | S | T | N | DELETED | P | M |
| S | P | I | R | I | Y | V | S | T | N | P | DELETED | I |
| S | P | I | R | I | Y | V | S | T | N | P | DELETED | M |
| S | P | I | R | I | Y | V | S | T | N | P | P | I |
| S | P | I | R | I | Y | V | S | T | N | P | P | M |
| S | P | I | R | I | Y | V | G | S | DELETED | DELETED | DELETED | I |
| S | P | I | R | I | Y | V | G | S | DELETED | DELETED | DELETED | M |
| S | P | I | R | I | Y | V | G | S | DELETED | DELETED | P | I |
| S | P | I | R | I | Y | V | G | S | DELETED | DELETED | P | M |
| S | P | I | R | I | Y | V | G | S | DELETED | P | DELETED | I |
| S | P | I | R | I | Y | V | G | S | DELETED | P | DELETED | M |
| S | P | I | R | I | Y | V | G | S | DELETED | P | P | I |
| S | P | I | R | I | Y | V | G | S | DELETED | P | P | M |
| S | P | I | R | I | Y | V | G | S | N | DELETED | DELETED | I |
| S | P | I | R | I | Y | V | G | S | N | DELETED | DELETED | M |
| S | P | I | R | I | Y | V | G | S | N | DELETED | P | I |
| S | P | I | R | I | Y | V | G | S | N | DELETED | P | M |
| S | P | I | R | I | Y | V | G | S | N | P | DELETED | I |
| S | P | I | R | I | Y | V | G | S | N | P | DELETED | M |
| S | P | I | R | I | Y | V | G | S | N | P | P | I |
| S | P | I | R | I | Y | V | G | S | N | P | P | M |
| S | P | I | R | I | Y | V | G | T | DELETED | DELETED | DELETED | I |
| S | P | I | R | I | Y | V | G | T | DELETED | DELETED | DELETED | M |
| S | P | I | R | I | Y | V | G | T | DELETED | DELETED | P | I |
| S | P | I | R | I | Y | V | G | T | DELETED | DELETED | P | M |
| S | P | I | R | I | Y | V | G | T | DELETED | P | DELETED | I |
| S | P | I | R | I | Y | V | G | T | DELETED | P | DELETED | M |
| S | P | I | R | I | Y | V | G | T | DELETED | P | P | I |
| S | P | I | R | I | Y | V | G | T | DELETED | P | P | M |
| S | P | I | R | I | Y | V | G | T | N | DELETED | DELETED | I |
| S | P | I | R | I | Y | V | G | T | N | DELETED | DELETED | M |
| S | P | I | R | I | Y | V | G | T | N | DELETED | P | I |
| S | P | I | R | I | Y | V | G | T | N | DELETED | P | M |
| S | P | I | R | I | Y | V | G | T | N | P | DELETED | I |
| S | P | I | R | I | Y | V | G | T | N | P | DELETED | M |
| S | P | I | R | I | Y | V | G | T | N | P | P | I |
| S | P | I | R | I | Y | V | G | T | N | P | P | M |
| S | P | I | R | I | H | Q | S | S | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | R | I | H | Q | S | S | DELETED | DELETED | DELETED | M |
| S | P | I | R | I | H | Q | S | S | DELETED | DELETED | P | I |
| S | P | I | R | I | H | Q | S | S | DELETED | DELETED | P | M |
| S | P | I | R | I | H | Q | S | S | DELETED | P | DELETED | I |
| S | P | I | R | I | H | Q | S | S | DELETED | P | DELETED | M |
| S | P | I | R | I | H | Q | S | S | DELETED | P | P | I |
| S | P | I | R | I | H | Q | S | S | DELETED | P | P | M |
| S | P | I | R | I | H | Q | S | S | N | DELETED | DELETED | I |
| S | P | I | R | I | H | Q | S | S | N | DELETED | DELETED | M |
| S | P | I | R | I | H | Q | S | S | N | DELETED | P | I |
| S | P | I | R | I | H | Q | S | S | N | DELETED | P | M |
| S | P | I | R | I | H | Q | S | S | N | P | DELETED | I |
| S | P | I | R | I | H | Q | S | S | N | P | DELETED | M |
| S | P | I | R | I | H | Q | S | S | N | P | P | I |
| S | P | I | R | I | H | Q | S | S | N | P | P | M |
| S | P | I | R | I | H | Q | S | T | DELETED | DELETED | DELETED | I |
| S | P | I | R | I | H | Q | S | T | DELETED | DELETED | DELETED | M |
| S | P | I | R | I | H | Q | S | T | DELETED | DELETED | P | I |
| S | P | I | R | I | H | Q | S | T | DELETED | DELETED | P | M |
| S | P | I | R | I | H | Q | S | T | DELETED | P | DELETED | I |
| S | P | I | R | I | H | Q | S | T | DELETED | P | DELETED | M |
| S | P | I | R | I | H | Q | S | T | DELETED | P | P | I |
| S | P | I | R | I | H | Q | S | T | DELETED | P | P | M |
| S | P | I | R | I | H | Q | S | T | N | DELETED | DELETED | I |
| S | P | I | R | I | H | Q | S | T | N | DELETED | DELETED | M |
| S | P | I | R | I | H | Q | S | T | N | DELETED | P | I |
| S | P | I | R | I | H | Q | S | T | N | DELETED | P | M |
| S | P | I | R | I | H | Q | S | T | N | P | DELETED | I |
| S | P | I | R | I | H | Q | S | T | N | P | DELETED | M |
| S | P | I | R | I | H | Q | S | T | N | P | P | I |
| S | P | I | R | I | H | Q | S | T | N | P | P | M |
| S | P | I | R | I | H | Q | G | S | DELETED | DELETED | DELETED | I |
| S | P | I | R | I | H | Q | G | S | DELETED | DELETED | DELETED | M |
| S | P | I | R | I | H | Q | G | S | DELETED | DELETED | P | I |
| S | P | I | R | I | H | Q | G | S | DELETED | DELETED | P | M |
| S | P | I | R | I | H | Q | G | S | DELETED | P | DELETED | I |
| S | P | I | R | I | H | Q | G | S | DELETED | P | DELETED | M |
| S | P | I | R | I | H | Q | G | S | DELETED | P | P | I |
| S | P | I | R | I | H | Q | G | S | DELETED | P | P | M |
| S | P | I | R | I | H | Q | G | S | N | DELETED | DELETED | I |
| S | P | I | R | I | H | Q | G | S | N | DELETED | DELETED | M |
| S | P | I | R | I | H | Q | G | S | N | DELETED | P | I |
| S | P | I | R | I | H | Q | G | S | N | DELETED | P | M |
| S | P | I | R | I | H | Q | G | S | N | P | DELETED | I |
| S | P | I | R | I | H | Q | G | S | N | P | DELETED | M |
| S | P | I | R | I | H | Q | G | S | N | P | P | I |
| S | P | I | R | I | H | Q | G | S | N | P | P | M |
| S | P | I | R | I | H | Q | G | T | DELETED | DELETED | DELETED | I |
| S | P | I | R | I | H | Q | G | T | DELETED | DELETED | DELETED | M |
| S | P | I | R | I | H | Q | G | T | DELETED | DELETED | P | I |
| S | P | I | R | I | H | Q | G | T | DELETED | DELETED | P | M |
| S | P | I | R | I | H | Q | G | T | DELETED | P | DELETED | I |
| S | P | I | R | I | H | Q | G | T | DELETED | P | DELETED | M |
| S | P | I | R | I | H | Q | G | T | DELETED | P | P | I |
| S | P | I | R | I | H | Q | G | T | DELETED | P | P | M |
| S | P | I | R | I | H | Q | G | T | N | DELETED | DELETED | I |
| S | P | I | R | I | H | Q | G | T | N | DELETED | DELETED | M |
| S | P | I | R | I | H | Q | G | T | N | DELETED | P | I |
| S | P | I | R | I | H | Q | G | T | N | DELETED | P | M |
| S | P | I | R | I | H | Q | G | T | N | P | DELETED | I |
| S | P | I | R | I | H | Q | G | T | N | P | DELETED | M |
| S | P | I | R | I | H | Q | G | T | N | P | P | I |
| S | P | I | R | I | H | Q | G | T | N | P | P | M |
| S | P | I | R | I | H | V | S | S | DELETED | DELETED | DELETED | I |
| S | P | I | R | I | H | V | S | S | DELETED | DELETED | DELETED | M |
| S | P | I | R | I | H | V | S | S | DELETED | DELETED | P | I |
| S | P | I | R | I | H | V | S | S | DELETED | DELETED | P | M |
| S | P | I | R | I | H | V | S | S | DELETED | P | DELETED | I |
| S | P | I | R | I | H | V | S | S | DELETED | P | DELETED | M |
| S | P | I | R | I | H | V | S | S | DELETED | P | P | I |
| S | P | I | R | I | H | V | S | S | DELETED | P | P | M |
| S | P | I | R | I | H | V | S | S | N | DELETED | DELETED | I |
| S | P | I | R | I | H | V | S | S | N | DELETED | DELETED | M |
| S | P | I | R | I | H | V | S | S | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | I | R | I | H | V | S | S | N | DELETED | P | M |
| S | P | I | R | I | H | V | S | S | N | P | DELETED | I |
| S | P | I | R | I | H | V | S | S | N | P | DELETED | M |
| S | P | I | R | I | H | V | S | S | N | P | P | I |
| S | P | I | R | I | H | V | S | S | N | P | P | M |
| S | P | I | R | I | H | V | S | T | DELETED | DELETED | DELETED | I |
| S | P | I | R | I | H | V | S | T | DELETED | DELETED | DELETED | M |
| S | P | I | R | I | H | V | S | T | DELETED | DELETED | P | I |
| S | P | I | R | I | H | V | S | T | DELETED | DELETED | P | M |
| S | P | I | R | I | H | V | S | T | DELETED | P | DELETED | I |
| S | P | I | R | I | H | V | S | T | DELETED | P | DELETED | M |
| S | P | I | R | I | H | V | S | T | DELETED | P | P | I |
| S | P | I | R | I | H | V | S | T | DELETED | P | P | M |
| S | P | I | R | I | H | V | S | T | N | DELETED | DELETED | I |
| S | P | I | R | I | H | V | S | T | N | DELETED | DELETED | M |
| S | P | I | R | I | H | V | S | T | N | DELETED | P | I |
| S | P | I | R | I | H | V | S | T | N | DELETED | P | M |
| S | P | I | R | I | H | V | S | T | N | P | DELETED | I |
| S | P | I | R | I | H | V | S | T | N | P | DELETED | M |
| S | P | I | R | I | H | V | S | T | N | P | P | I |
| S | P | I | R | I | H | V | S | T | N | P | P | M |
| S | P | I | R | I | H | V | G | S | DELETED | DELETED | DELETED | I |
| S | P | I | R | I | H | V | G | S | DELETED | DELETED | DELETED | M |
| S | P | I | R | I | H | V | G | S | DELETED | DELETED | P | I |
| S | P | I | R | I | H | V | G | S | DELETED | DELETED | P | M |
| S | P | I | R | I | H | V | G | S | DELETED | P | DELETED | I |
| S | P | I | R | I | H | V | G | S | DELETED | P | DELETED | M |
| S | P | I | R | I | H | V | G | S | DELETED | P | P | I |
| S | P | I | R | I | H | V | G | S | DELETED | P | P | M |
| S | P | I | R | I | H | V | G | S | N | DELETED | DELETED | I |
| S | P | I | R | I | H | V | G | S | N | DELETED | DELETED | M |
| S | P | I | R | I | H | V | G | S | N | DELETED | P | I |
| S | P | I | R | I | H | V | G | S | N | DELETED | P | M |
| S | P | I | R | I | H | V | G | S | N | P | DELETED | I |
| S | P | I | R | I | H | V | G | S | N | P | DELETED | M |
| S | P | I | R | I | H | V | G | S | N | P | P | I |
| S | P | I | R | I | H | V | G | S | N | P | P | M |
| S | P | I | R | I | H | V | G | T | DELETED | DELETED | DELETED | I |
| S | P | I | R | I | H | V | G | T | DELETED | DELETED | DELETED | M |
| S | P | I | R | I | H | V | G | T | DELETED | DELETED | P | I |
| S | P | I | R | I | H | V | G | T | DELETED | DELETED | P | M |
| S | P | I | R | I | H | V | G | T | DELETED | P | DELETED | I |
| S | P | I | R | I | H | V | G | T | DELETED | P | DELETED | M |
| S | P | I | R | I | H | V | G | T | DELETED | P | P | I |
| S | P | I | R | I | H | V | G | T | DELETED | P | P | M |
| S | P | I | R | I | H | V | G | T | N | DELETED | DELETED | I |
| S | P | I | R | I | H | V | G | T | N | DELETED | DELETED | M |
| S | P | I | R | I | H | V | G | T | N | DELETED | P | I |
| S | P | I | R | I | H | V | G | T | N | DELETED | P | M |
| S | P | I | R | I | H | V | G | T | N | P | DELETED | I |
| S | P | I | R | I | H | V | G | T | N | P | DELETED | M |
| S | P | I | R | I | H | V | G | T | N | P | P | I |
| S | P | I | R | I | H | V | G | T | N | P | P | M |
| S | P | F | S | L | Y | Q | S | S | DELETED | DELETED | DELETED | I |
| S | P | F | S | L | Y | Q | S | S | DELETED | DELETED | DELETED | M |
| S | P | F | S | L | Y | Q | S | S | DELETED | DELETED | P | I |
| S | P | F | S | L | Y | Q | S | S | DELETED | DELETED | P | M |
| S | P | F | S | L | Y | Q | S | S | DELETED | P | DELETED | I |
| S | P | F | S | L | Y | Q | S | S | DELETED | P | DELETED | M |
| S | P | F | S | L | Y | Q | S | S | DELETED | P | P | I |
| S | P | F | S | L | Y | Q | S | S | DELETED | P | P | M |
| S | P | F | S | L | Y | Q | S | S | N | DELETED | DELETED | I |
| S | P | F | S | L | Y | Q | S | S | N | DELETED | DELETED | M |
| S | P | F | S | L | Y | Q | S | S | N | DELETED | P | I |
| S | P | F | S | L | Y | Q | S | S | N | DELETED | P | M |
| S | P | F | S | L | Y | Q | S | S | N | P | DELETED | I |
| S | P | F | S | L | Y | Q | S | S | N | P | DELETED | M |
| S | P | F | S | L | Y | Q | S | S | N | P | P | I |
| S | P | F | S | L | Y | Q | S | S | N | P | P | M |
| S | P | F | S | L | Y | Q | S | T | DELETED | DELETED | DELETED | I |
| S | P | F | S | L | Y | Q | S | T | DELETED | DELETED | DELETED | M |
| S | P | F | S | L | Y | Q | S | T | DELETED | DELETED | P | I |
| S | P | F | S | L | Y | Q | S | T | DELETED | DELETED | P | M |
| S | P | F | S | L | Y | Q | S | T | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | S | L | Y | Q | S | T | DELETED | P | DELETED | M |
| S | P | F | S | L | Y | Q | S | T | DELETED | P | P | I |
| S | P | F | S | L | Y | Q | S | T | DELETED | P | P | M |
| S | P | F | S | L | Y | Q | S | T | N | DELETED | DELETED | I |
| S | P | F | S | L | Y | Q | S | T | N | DELETED | DELETED | M |
| S | P | F | S | L | Y | Q | S | T | N | DELETED | P | I |
| S | P | F | S | L | Y | Q | S | T | N | DELETED | P | M |
| S | P | F | S | L | Y | Q | S | T | N | P | DELETED | I |
| S | P | F | S | L | Y | Q | S | T | N | P | DELETED | M |
| S | P | F | S | L | Y | Q | S | T | N | P | P | I |
| S | P | F | S | L | Y | Q | S | T | N | P | P | M |
| S | P | F | S | L | Y | Q | G | S | DELETED | DELETED | DELETED | I |
| S | P | F | S | L | Y | Q | G | S | DELETED | DELETED | DELETED | M |
| S | P | F | S | L | Y | Q | G | S | DELETED | DELETED | P | I |
| S | P | F | S | L | Y | Q | G | S | DELETED | DELETED | P | M |
| S | P | F | S | L | Y | Q | G | S | DELETED | P | DELETED | I |
| S | P | F | S | L | Y | Q | G | S | DELETED | P | DELETED | M |
| S | P | F | S | L | Y | Q | G | S | DELETED | P | P | I |
| S | P | F | S | L | Y | Q | G | S | DELETED | P | P | M |
| S | P | F | S | L | Y | Q | G | S | N | DELETED | DELETED | I |
| S | P | F | S | L | Y | Q | G | S | N | DELETED | DELETED | M |
| S | P | F | S | L | Y | Q | G | S | N | DELETED | P | I |
| S | P | F | S | L | Y | Q | G | S | N | DELETED | P | M |
| S | P | F | S | L | Y | Q | G | S | N | P | DELETED | I |
| S | P | F | S | L | Y | Q | G | S | N | P | DELETED | M |
| S | P | F | S | L | Y | Q | G | S | N | P | P | I |
| S | P | F | S | L | Y | Q | G | S | N | P | P | M |
| S | P | F | S | L | Y | Q | G | T | DELETED | DELETED | DELETED | I |
| S | P | F | S | L | Y | Q | G | T | DELETED | DELETED | DELETED | M |
| S | P | F | S | L | Y | Q | G | T | DELETED | DELETED | P | I |
| S | P | F | S | L | Y | Q | G | T | DELETED | DELETED | P | M |
| S | P | F | S | L | Y | Q | G | T | DELETED | P | DELETED | I |
| S | P | F | S | L | Y | Q | G | T | DELETED | P | DELETED | M |
| S | P | F | S | L | Y | Q | G | T | DELETED | P | P | I |
| S | P | F | S | L | Y | Q | G | T | DELETED | P | P | M |
| S | P | F | S | L | Y | Q | G | T | N | DELETED | DELETED | I |
| S | P | F | S | L | Y | Q | G | T | N | DELETED | DELETED | M |
| S | P | F | S | L | Y | Q | G | T | N | DELETED | P | I |
| S | P | F | S | L | Y | Q | G | T | N | DELETED | P | M |
| S | P | F | S | L | Y | Q | G | T | N | P | DELETED | I |
| S | P | F | S | L | Y | Q | G | T | N | P | DELETED | M |
| S | P | F | S | L | Y | Q | G | T | N | P | P | I |
| S | P | F | S | L | Y | Q | G | T | N | P | P | M |
| S | P | F | S | L | Y | V | S | S | DELETED | DELETED | DELETED | I |
| S | P | F | S | L | Y | V | S | S | DELETED | DELETED | DELETED | M |
| S | P | F | S | L | Y | V | S | S | DELETED | DELETED | P | I |
| S | P | F | S | L | Y | V | S | S | DELETED | DELETED | P | M |
| S | P | F | S | L | Y | V | S | S | DELETED | P | DELETED | I |
| S | P | F | S | L | Y | V | S | S | DELETED | P | DELETED | M |
| S | P | F | S | L | Y | V | S | S | DELETED | P | P | I |
| S | P | F | S | L | Y | V | S | S | DELETED | P | P | M |
| S | P | F | S | L | Y | V | S | S | N | DELETED | DELETED | I |
| S | P | F | S | L | Y | V | S | S | N | DELETED | DELETED | M |
| S | P | F | S | L | Y | V | S | S | N | DELETED | P | I |
| S | P | F | S | L | Y | V | S | S | N | DELETED | P | M |
| S | P | F | S | L | Y | V | S | S | N | P | DELETED | I |
| S | P | F | S | L | Y | V | S | S | N | P | DELETED | M |
| S | P | F | S | L | Y | V | S | S | N | P | P | I |
| S | P | F | S | L | Y | V | S | S | N | P | P | M |
| S | P | F | S | L | Y | V | S | T | DELETED | DELETED | DELETED | I |
| S | P | F | S | L | Y | V | S | T | DELETED | DELETED | DELETED | M |
| S | P | F | S | L | Y | V | S | T | DELETED | DELETED | P | I |
| S | P | F | S | L | Y | V | S | T | DELETED | DELETED | P | M |
| S | P | F | S | L | Y | V | S | T | DELETED | P | DELETED | I |
| S | P | F | S | L | Y | V | S | T | DELETED | P | DELETED | M |
| S | P | F | S | L | Y | V | S | T | DELETED | P | P | I |
| S | P | F | S | L | Y | V | S | T | DELETED | P | P | M |
| S | P | F | S | L | Y | V | S | T | N | DELETED | DELETED | I |
| S | P | F | S | L | Y | V | S | T | N | DELETED | DELETED | M |
| S | P | F | S | L | Y | V | S | T | N | DELETED | P | I |
| S | P | F | S | L | Y | V | S | T | N | DELETED | P | M |
| S | P | F | S | L | Y | V | S | T | N | P | DELETED | I |
| S | P | F | S | L | Y | V | S | T | N | P | DELETED | M |
| S | P | F | S | L | Y | V | S | T | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | S | L | Y | V | S | T | N | P | P | M |
| S | P | F | S | L | Y | V | G | S | DELETED | DELETED | DELETED | I |
| S | P | F | S | L | Y | V | G | S | DELETED | DELETED | DELETED | M |
| S | P | F | S | L | Y | V | G | S | DELETED | DELETED | P | I |
| S | P | F | S | L | Y | V | G | S | DELETED | DELETED | P | M |
| S | P | F | S | L | Y | V | G | S | DELETED | P | DELETED | I |
| S | P | F | S | L | Y | V | G | S | DELETED | P | DELETED | M |
| S | P | F | S | L | Y | V | G | S | DELETED | P | P | I |
| S | P | F | S | L | Y | V | G | S | DELETED | P | P | M |
| S | P | F | S | L | Y | V | G | S | N | DELETED | DELETED | I |
| S | P | F | S | L | Y | V | G | S | N | DELETED | DELETED | M |
| S | P | F | S | L | Y | V | G | S | N | DELETED | P | I |
| S | P | F | S | L | Y | V | G | S | N | DELETED | P | M |
| S | P | F | S | L | Y | V | G | S | N | P | DELETED | I |
| S | P | F | S | L | Y | V | G | S | N | P | DELETED | M |
| S | P | F | S | L | Y | V | G | S | N | P | P | I |
| S | P | F | S | L | Y | V | G | S | N | P | P | M |
| S | P | F | S | L | Y | V | G | T | DELETED | DELETED | DELETED | I |
| S | P | F | S | L | Y | V | G | T | DELETED | DELETED | DELETED | M |
| S | P | F | S | L | Y | V | G | T | DELETED | DELETED | P | I |
| S | P | F | S | L | Y | V | G | T | DELETED | DELETED | P | M |
| S | P | F | S | L | Y | V | G | T | DELETED | P | DELETED | I |
| S | P | F | S | L | Y | V | G | T | DELETED | P | DELETED | M |
| S | P | F | S | L | Y | V | G | T | DELETED | P | P | I |
| S | P | F | S | L | Y | V | G | T | DELETED | P | P | M |
| S | P | F | S | L | Y | V | G | T | N | DELETED | DELETED | I |
| S | P | F | S | L | Y | V | G | T | N | DELETED | DELETED | M |
| S | P | F | S | L | Y | V | G | T | N | DELETED | P | I |
| S | P | F | S | L | Y | V | G | T | N | DELETED | P | M |
| S | P | F | S | L | Y | V | G | T | N | P | DELETED | I |
| S | P | F | S | L | Y | V | G | T | N | P | DELETED | M |
| S | P | F | S | L | Y | V | G | T | N | P | P | I |
| S | P | F | S | L | Y | V | G | T | N | P | P | M |
| S | P | F | S | L | H | Q | S | S | DELETED | DELETED | DELETED | I |
| S | P | F | S | L | H | Q | S | S | DELETED | DELETED | DELETED | M |
| S | P | F | S | L | H | Q | S | S | DELETED | DELETED | P | I |
| S | P | F | S | L | H | Q | S | S | DELETED | DELETED | P | M |
| S | P | F | S | L | H | Q | S | S | DELETED | P | DELETED | I |
| S | P | F | S | L | H | Q | S | S | DELETED | P | DELETED | M |
| S | P | F | S | L | H | Q | S | S | DELETED | P | P | I |
| S | P | F | S | L | H | Q | S | S | DELETED | P | P | M |
| S | P | F | S | L | H | Q | S | S | N | DELETED | DELETED | I |
| S | P | F | S | L | H | Q | S | S | N | DELETED | DELETED | M |
| S | P | F | S | L | H | Q | S | S | N | DELETED | P | I |
| S | P | F | S | L | H | Q | S | S | N | DELETED | P | M |
| S | P | F | S | L | H | Q | S | S | N | P | DELETED | I |
| S | P | F | S | L | H | Q | S | S | N | P | DELETED | M |
| S | P | F | S | L | H | Q | S | S | N | P | P | I |
| S | P | F | S | L | H | Q | S | S | N | P | P | M |
| S | P | F | S | L | H | Q | S | T | DELETED | DELETED | DELETED | I |
| S | P | F | S | L | H | Q | S | T | DELETED | DELETED | DELETED | M |
| S | P | F | S | L | H | Q | S | T | DELETED | DELETED | P | I |
| S | P | F | S | L | H | Q | S | T | DELETED | DELETED | P | M |
| S | P | F | S | L | H | Q | S | T | DELETED | P | DELETED | I |
| S | P | F | S | L | H | Q | S | T | DELETED | P | DELETED | M |
| S | P | F | S | L | H | Q | S | T | DELETED | P | P | I |
| S | P | F | S | L | H | Q | S | T | DELETED | P | P | M |
| S | P | F | S | L | H | Q | S | T | N | DELETED | DELETED | I |
| S | P | F | S | L | H | Q | S | T | N | DELETED | DELETED | M |
| S | P | F | S | L | H | Q | S | T | N | DELETED | P | I |
| S | P | F | S | L | H | Q | S | T | N | DELETED | P | M |
| S | P | F | S | L | H | Q | S | T | N | P | DELETED | I |
| S | P | F | S | L | H | Q | S | T | N | P | DELETED | M |
| S | P | F | S | L | H | Q | S | T | N | P | P | I |
| S | P | F | S | L | H | Q | S | T | N | P | P | M |
| S | P | F | S | L | H | Q | G | S | DELETED | DELETED | DELETED | I |
| S | P | F | S | L | H | Q | G | S | DELETED | DELETED | DELETED | M |
| S | P | F | S | L | H | Q | G | S | DELETED | DELETED | P | I |
| S | P | F | S | L | H | Q | G | S | DELETED | DELETED | P | M |
| S | P | F | S | L | H | Q | G | S | DELETED | P | DELETED | I |
| S | P | F | S | L | H | Q | G | S | DELETED | P | DELETED | M |
| S | P | F | S | L | H | Q | G | S | DELETED | P | P | I |
| S | P | F | S | L | H | Q | G | S | DELETED | P | P | M |
| S | P | F | S | L | H | Q | G | S | N | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | S | L | H | Q | G | S | N | DELETED | DELETED | M |
| S | P | F | S | L | H | Q | G | S | N | DELETED | P | I |
| S | P | F | S | L | H | Q | G | S | N | DELETED | P | M |
| S | P | F | S | L | H | Q | G | S | N | P | DELETED | I |
| S | P | F | S | L | H | Q | G | S | N | P | DELETED | M |
| S | P | F | S | L | H | Q | G | S | N | P | P | I |
| S | P | F | S | L | H | Q | G | S | N | P | P | M |
| S | P | F | S | L | H | Q | G | T | DELETED | DELETED | DELETED | I |
| S | P | F | S | L | H | Q | G | T | DELETED | DELETED | DELETED | M |
| S | P | F | S | L | H | Q | G | T | DELETED | DELETED | P | I |
| S | P | F | S | L | H | Q | G | T | DELETED | DELETED | P | M |
| S | P | F | S | L | H | Q | G | T | DELETED | P | DELETED | I |
| S | P | F | S | L | H | Q | G | T | DELETED | P | DELETED | M |
| S | P | F | S | L | H | Q | G | T | DELETED | P | P | I |
| S | P | F | S | L | H | Q | G | T | DELETED | P | P | M |
| S | P | F | S | L | H | Q | G | T | N | DELETED | DELETED | I |
| S | P | F | S | L | H | Q | G | T | N | DELETED | DELETED | M |
| S | P | F | S | L | H | Q | G | T | N | DELETED | P | I |
| S | P | F | S | L | H | Q | G | T | N | DELETED | P | M |
| S | P | F | S | L | H | Q | G | T | N | P | DELETED | I |
| S | P | F | S | L | H | Q | G | T | N | P | DELETED | M |
| S | P | F | S | L | H | Q | G | T | N | P | P | I |
| S | P | F | S | L | H | Q | G | T | N | P | P | M |
| S | P | F | S | L | H | V | S | S | DELETED | DELETED | DELETED | I |
| S | P | F | S | L | H | V | S | S | DELETED | DELETED | DELETED | M |
| S | P | F | S | L | H | V | S | S | DELETED | DELETED | P | I |
| S | P | F | S | L | H | V | S | S | DELETED | DELETED | P | M |
| S | P | F | S | L | H | V | S | S | DELETED | P | DELETED | I |
| S | P | F | S | L | H | V | S | S | DELETED | P | DELETED | M |
| S | P | F | S | L | H | V | S | S | DELETED | P | P | I |
| S | P | F | S | L | H | V | S | S | DELETED | P | P | M |
| S | P | F | S | L | H | V | S | S | N | DELETED | DELETED | I |
| S | P | F | S | L | H | V | S | S | N | DELETED | DELETED | M |
| S | P | F | S | L | H | V | S | S | N | DELETED | P | I |
| S | P | F | S | L | H | V | S | S | N | DELETED | P | M |
| S | P | F | S | L | H | V | S | S | N | P | DELETED | I |
| S | P | F | S | L | H | V | S | S | N | P | DELETED | M |
| S | P | F | S | L | H | V | S | S | N | P | P | I |
| S | P | F | S | L | H | V | S | S | N | P | P | M |
| S | P | F | S | L | H | V | S | T | DELETED | DELETED | DELETED | I |
| S | P | F | S | L | H | V | S | T | DELETED | DELETED | DELETED | M |
| S | P | F | S | L | H | V | S | T | DELETED | DELETED | P | I |
| S | P | F | S | L | H | V | S | T | DELETED | DELETED | P | M |
| S | P | F | S | L | H | V | S | T | DELETED | P | DELETED | I |
| S | P | F | S | L | H | V | S | T | DELETED | P | DELETED | M |
| S | P | F | S | L | H | V | S | T | DELETED | P | P | I |
| S | P | F | S | L | H | V | S | T | DELETED | P | P | M |
| S | P | F | S | L | H | V | S | T | N | DELETED | DELETED | I |
| S | P | F | S | L | H | V | S | T | N | DELETED | DELETED | M |
| S | P | F | S | L | H | V | S | T | N | DELETED | P | I |
| S | P | F | S | L | H | V | S | T | N | DELETED | P | M |
| S | P | F | S | L | H | V | S | T | N | P | DELETED | I |
| S | P | F | S | L | H | V | S | T | N | P | DELETED | M |
| S | P | F | S | L | H | V | S | T | N | P | P | I |
| S | P | F | S | L | H | V | S | T | N | P | P | M |
| S | P | F | S | L | H | V | G | S | DELETED | DELETED | DELETED | I |
| S | P | F | S | L | H | V | G | S | DELETED | DELETED | DELETED | M |
| S | P | F | S | L | H | V | G | S | DELETED | DELETED | P | I |
| S | P | F | S | L | H | V | G | S | DELETED | DELETED | P | M |
| S | P | F | S | L | H | V | G | S | DELETED | P | DELETED | I |
| S | P | F | S | L | H | V | G | S | DELETED | P | DELETED | M |
| S | P | F | S | L | H | V | G | S | DELETED | P | P | I |
| S | P | F | S | L | H | V | G | S | DELETED | P | P | M |
| S | P | F | S | L | H | V | G | S | N | DELETED | DELETED | I |
| S | P | F | S | L | H | V | G | S | N | DELETED | DELETED | M |
| S | P | F | S | L | H | V | G | S | N | DELETED | P | I |
| S | P | F | S | L | H | V | G | S | N | DELETED | P | M |
| S | P | F | S | L | H | V | G | S | N | P | DELETED | I |
| S | P | F | S | L | H | V | G | S | N | P | DELETED | M |
| S | P | F | S | L | H | V | G | S | N | P | P | I |
| S | P | F | S | L | H | V | G | S | N | P | P | M |
| S | P | F | S | L | H | V | G | T | DELETED | DELETED | DELETED | I |
| S | P | F | S | L | H | V | G | T | DELETED | DELETED | DELETED | M |
| S | P | F | S | L | H | V | G | T | DELETED | DELETED | P | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| S | P | F | S | L | H | V | G | T | DELETED | DELETED | P | M |
| S | P | F | S | L | H | V | G | T | DELETED | P | DELETED | I |
| S | P | F | S | L | H | V | G | T | DELETED | P | DELETED | M |
| S | P | F | S | L | H | V | G | T | DELETED | P | P | I |
| S | P | F | S | L | H | V | G | T | DELETED | P | P | M |
| S | P | F | S | L | H | V | G | T | N | DELETED | DELETED | I |
| S | P | F | S | L | H | V | G | T | N | DELETED | DELETED | M |
| S | P | F | S | L | H | V | G | T | N | DELETED | P | I |
| S | P | F | S | L | H | V | G | T | N | DELETED | P | M |
| S | P | F | S | L | H | V | G | T | N | P | DELETED | I |
| S | P | F | S | L | H | V | G | T | N | P | DELETED | M |
| S | P | F | S | L | H | V | G | T | N | P | P | I |
| S | P | F | S | L | H | V | G | T | N | P | P | M |
| S | P | F | S | I | Y | Q | S | S | DELETED | DELETED | DELETED | I |
| S | P | F | S | I | Y | Q | S | S | DELETED | DELETED | DELETED | M |
| S | P | F | S | I | Y | Q | S | S | DELETED | DELETED | P | I |
| S | P | F | S | I | Y | Q | S | S | DELETED | DELETED | P | M |
| S | P | F | S | I | Y | Q | S | S | DELETED | P | DELETED | I |
| S | P | F | S | I | Y | Q | S | S | DELETED | P | DELETED | M |
| S | P | F | S | I | Y | Q | S | S | DELETED | P | P | I |
| S | P | F | S | I | Y | Q | S | S | DELETED | P | P | M |
| S | P | F | S | I | Y | Q | S | S | N | DELETED | DELETED | I |
| S | P | F | S | I | Y | Q | S | S | N | DELETED | DELETED | M |
| S | P | F | S | I | Y | Q | S | S | N | DELETED | P | I |
| S | P | F | S | I | Y | Q | S | S | N | DELETED | P | M |
| S | P | F | S | I | Y | Q | S | S | N | P | DELETED | I |
| S | P | F | S | I | Y | Q | S | S | N | P | DELETED | M |
| S | P | F | S | I | Y | Q | S | S | N | P | P | I |
| S | P | F | S | I | Y | Q | S | S | N | P | P | M |
| S | P | F | S | I | Y | Q | S | T | DELETED | DELETED | DELETED | I |
| S | P | F | S | I | Y | Q | S | T | DELETED | DELETED | DELETED | M |
| S | P | F | S | I | Y | Q | S | T | DELETED | DELETED | P | I |
| S | P | F | S | I | Y | Q | S | T | DELETED | DELETED | P | M |
| S | P | F | S | I | Y | Q | S | T | DELETED | P | DELETED | I |
| S | P | F | S | I | Y | Q | S | T | DELETED | P | DELETED | M |
| S | P | F | S | I | Y | Q | S | T | DELETED | P | P | I |
| S | P | F | S | I | Y | Q | S | T | DELETED | P | P | M |
| S | P | F | S | I | Y | Q | S | T | N | DELETED | DELETED | I |
| S | P | F | S | I | Y | Q | S | T | N | DELETED | DELETED | M |
| S | P | F | S | I | Y | Q | S | T | N | DELETED | P | I |
| S | P | F | S | I | Y | Q | S | T | N | DELETED | P | M |
| S | P | F | S | I | Y | Q | S | T | N | P | DELETED | I |
| S | P | F | S | I | Y | Q | S | T | N | P | DELETED | M |
| S | P | F | S | I | Y | Q | S | T | N | P | P | I |
| S | P | F | S | I | Y | Q | S | T | N | P | P | M |
| S | P | F | S | I | Y | Q | G | S | DELETED | DELETED | DELETED | I |
| S | P | F | S | I | Y | Q | G | S | DELETED | DELETED | DELETED | M |
| S | P | F | S | I | Y | Q | G | S | DELETED | DELETED | P | I |
| S | P | F | S | I | Y | Q | G | S | DELETED | DELETED | P | M |
| S | P | F | S | I | Y | Q | G | S | DELETED | P | DELETED | I |
| S | P | F | S | I | Y | Q | G | S | DELETED | P | DELETED | M |
| S | P | F | S | I | Y | Q | G | S | DELETED | P | P | I |
| S | P | F | S | I | Y | Q | G | S | DELETED | P | P | M |
| S | P | F | S | I | Y | Q | G | S | N | DELETED | DELETED | I |
| S | P | F | S | I | Y | Q | G | S | N | DELETED | DELETED | M |
| S | P | F | S | I | Y | Q | G | S | N | DELETED | P | I |
| S | P | F | S | I | Y | Q | G | S | N | DELETED | P | M |
| S | P | F | S | I | Y | Q | G | S | N | P | DELETED | I |
| S | P | F | S | I | Y | Q | G | S | N | P | DELETED | M |
| S | P | F | S | I | Y | Q | G | S | N | P | P | I |
| S | P | F | S | I | Y | Q | G | S | N | P | P | M |
| S | P | F | S | I | Y | Q | G | T | DELETED | DELETED | DELETED | I |
| S | P | F | S | I | Y | Q | G | T | DELETED | DELETED | DELETED | M |
| S | P | F | S | I | Y | Q | G | T | DELETED | DELETED | P | I |
| S | P | F | S | I | Y | Q | G | T | DELETED | DELETED | P | M |
| S | P | F | S | I | Y | Q | G | T | DELETED | P | DELETED | I |
| S | P | F | S | I | Y | Q | G | T | DELETED | P | DELETED | M |
| S | P | F | S | I | Y | Q | G | T | DELETED | P | P | I |
| S | P | F | S | I | Y | Q | G | T | DELETED | P | P | M |
| S | P | F | S | I | Y | Q | G | T | N | DELETED | DELETED | I |
| S | P | F | S | I | Y | Q | G | T | N | DELETED | DELETED | M |
| S | P | F | S | I | Y | Q | G | T | N | DELETED | P | I |
| S | P | F | S | I | Y | Q | G | T | N | DELETED | P | M |
| S | P | F | S | I | Y | Q | G | T | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | S | I | Y | Q | G | T | N | P | DELETED | M |
| S | P | F | S | I | Y | Q | G | T | N | P | P | I |
| S | P | F | S | I | Y | Q | G | T | N | P | P | M |
| S | P | F | S | I | Y | V | S | S | DELETED | DELETED | DELETED | I |
| S | P | F | S | I | Y | V | S | S | DELETED | DELETED | DELETED | M |
| S | P | F | S | I | Y | V | S | S | DELETED | DELETED | P | I |
| S | P | F | S | I | Y | V | S | S | DELETED | DELETED | P | M |
| S | P | F | S | I | Y | V | S | S | DELETED | P | DELETED | I |
| S | P | F | S | I | Y | V | S | S | DELETED | P | DELETED | M |
| S | P | F | S | I | Y | V | S | S | DELETED | P | P | I |
| S | P | F | S | I | Y | V | S | S | DELETED | P | P | M |
| S | P | F | S | I | Y | V | S | S | N | DELETED | DELETED | I |
| S | P | F | S | I | Y | V | S | S | N | DELETED | DELETED | M |
| S | P | F | S | I | Y | V | S | S | N | DELETED | P | I |
| S | P | F | S | I | Y | V | S | S | N | DELETED | P | M |
| S | P | F | S | I | Y | V | S | S | N | P | DELETED | I |
| S | P | F | S | I | Y | V | S | S | N | P | DELETED | M |
| S | P | F | S | I | Y | V | S | S | N | P | P | I |
| S | P | F | S | I | Y | V | S | S | N | P | P | M |
| S | P | F | S | I | Y | V | S | T | DELETED | DELETED | DELETED | I |
| S | P | F | S | I | Y | V | S | T | DELETED | DELETED | DELETED | M |
| S | P | F | S | I | Y | V | S | T | DELETED | DELETED | P | I |
| S | P | F | S | I | Y | V | S | T | DELETED | DELETED | P | M |
| S | P | F | S | I | Y | V | S | T | DELETED | P | DELETED | I |
| S | P | F | S | I | Y | V | S | T | DELETED | P | DELETED | M |
| S | P | F | S | I | Y | V | S | T | DELETED | P | P | I |
| S | P | F | S | I | Y | V | S | T | DELETED | P | P | M |
| S | P | F | S | I | Y | V | S | T | N | DELETED | DELETED | I |
| S | P | F | S | I | Y | V | S | T | N | DELETED | DELETED | M |
| S | P | F | S | I | Y | V | S | T | N | DELETED | P | I |
| S | P | F | S | I | Y | V | S | T | N | DELETED | P | M |
| S | P | F | S | I | Y | V | S | T | N | P | DELETED | I |
| S | P | F | S | I | Y | V | S | T | N | P | DELETED | M |
| S | P | F | S | I | Y | V | S | T | N | P | P | I |
| S | P | F | S | I | Y | V | S | T | N | P | P | M |
| S | P | F | S | I | Y | V | G | S | DELETED | DELETED | DELETED | I |
| S | P | F | S | I | Y | V | G | S | DELETED | DELETED | DELETED | M |
| S | P | F | S | I | Y | V | G | S | DELETED | DELETED | P | I |
| S | P | F | S | I | Y | V | G | S | DELETED | DELETED | P | M |
| S | P | F | S | I | Y | V | G | S | DELETED | P | DELETED | I |
| S | P | F | S | I | Y | V | G | S | DELETED | P | DELETED | M |
| S | P | F | S | I | Y | V | G | S | DELETED | P | P | I |
| S | P | F | S | I | Y | V | G | S | DELETED | P | P | M |
| S | P | F | S | I | Y | V | G | S | N | DELETED | DELETED | I |
| S | P | F | S | I | Y | V | G | S | N | DELETED | DELETED | M |
| S | P | F | S | I | Y | V | G | S | N | DELETED | P | I |
| S | P | F | S | I | Y | V | G | S | N | DELETED | P | M |
| S | P | F | S | I | Y | V | G | S | N | P | DELETED | I |
| S | P | F | S | I | Y | V | G | S | N | P | DELETED | M |
| S | P | F | S | I | Y | V | G | S | N | P | P | I |
| S | P | F | S | I | Y | V | G | S | N | P | P | M |
| S | P | F | S | I | Y | V | G | T | DELETED | DELETED | DELETED | I |
| S | P | F | S | I | Y | V | G | T | DELETED | DELETED | DELETED | M |
| S | P | F | S | I | Y | V | G | T | DELETED | DELETED | P | I |
| S | P | F | S | I | Y | V | G | T | DELETED | DELETED | P | M |
| S | P | F | S | I | Y | V | G | T | DELETED | P | DELETED | I |
| S | P | F | S | I | Y | V | G | T | DELETED | P | DELETED | M |
| S | P | F | S | I | Y | V | G | T | DELETED | P | P | I |
| S | P | F | S | I | Y | V | G | T | DELETED | P | P | M |
| S | P | F | S | I | Y | V | G | T | N | DELETED | DELETED | I |
| S | P | F | S | I | Y | V | G | T | N | DELETED | DELETED | M |
| S | P | F | S | I | Y | V | G | T | N | DELETED | P | I |
| S | P | F | S | I | Y | V | G | T | N | DELETED | P | M |
| S | P | F | S | I | Y | V | G | T | N | P | DELETED | I |
| S | P | F | S | I | Y | V | G | T | N | P | DELETED | M |
| S | P | F | S | I | Y | V | G | T | N | P | P | I |
| S | P | F | S | I | Y | V | G | T | N | P | P | M |
| S | P | F | S | I | H | Q | S | S | DELETED | DELETED | DELETED | I |
| S | P | F | S | I | H | Q | S | S | DELETED | DELETED | DELETED | M |
| S | P | F | S | I | H | Q | S | S | DELETED | DELETED | P | I |
| S | P | F | S | I | H | Q | S | S | DELETED | DELETED | P | M |
| S | P | F | S | I | H | Q | S | S | DELETED | P | DELETED | I |
| S | P | F | S | I | H | Q | S | S | DELETED | P | DELETED | M |
| S | P | F | S | I | H | Q | S | S | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | S | I | H | Q | S | S | DELETED | P | P | M |
| S | P | F | S | I | H | Q | S | S | N | DELETED | DELETED | I |
| S | P | F | S | I | H | Q | S | S | N | DELETED | DELETED | M |
| S | P | F | S | I | H | Q | S | S | N | DELETED | P | I |
| S | P | F | S | I | H | Q | S | S | N | DELETED | P | M |
| S | P | F | S | I | H | Q | S | S | N | P | DELETED | I |
| S | P | F | S | I | H | Q | S | S | N | P | DELETED | M |
| S | P | F | S | I | H | Q | S | S | N | P | P | I |
| S | P | F | S | I | H | Q | S | S | N | P | P | M |
| S | P | F | S | I | H | Q | S | T | DELETED | DELETED | DELETED | I |
| S | P | F | S | I | H | Q | S | T | DELETED | DELETED | DELETED | M |
| S | P | F | S | I | H | Q | S | T | DELETED | DELETED | P | I |
| S | P | F | S | I | H | Q | S | T | DELETED | DELETED | P | M |
| S | P | F | S | I | H | Q | S | T | DELETED | P | DELETED | I |
| S | P | F | S | I | H | Q | S | T | DELETED | P | DELETED | M |
| S | P | F | S | I | H | Q | S | T | DELETED | P | P | I |
| S | P | F | S | I | H | Q | S | T | DELETED | P | P | M |
| S | P | F | S | I | H | Q | S | T | N | DELETED | DELETED | I |
| S | P | F | S | I | H | Q | S | T | N | DELETED | DELETED | M |
| S | P | F | S | I | H | Q | S | T | N | DELETED | P | I |
| S | P | F | S | I | H | Q | S | T | N | DELETED | P | M |
| S | P | F | S | I | H | Q | S | T | N | P | DELETED | I |
| S | P | F | S | I | H | Q | S | T | N | P | DELETED | M |
| S | P | F | S | I | H | Q | S | T | N | P | P | I |
| S | P | F | S | I | H | Q | S | T | N | P | P | M |
| S | P | F | S | I | H | Q | G | S | DELETED | DELETED | DELETED | I |
| S | P | F | S | I | H | Q | G | S | DELETED | DELETED | DELETED | M |
| S | P | F | S | I | H | Q | G | S | DELETED | DELETED | P | I |
| S | P | F | S | I | H | Q | G | S | DELETED | DELETED | P | M |
| S | P | F | S | I | H | Q | G | S | DELETED | P | DELETED | I |
| S | P | F | S | I | H | Q | G | S | DELETED | P | DELETED | M |
| S | P | F | S | I | H | Q | G | S | DELETED | P | P | I |
| S | P | F | S | I | H | Q | G | S | DELETED | P | P | M |
| S | P | F | S | I | H | Q | G | S | N | DELETED | DELETED | I |
| S | P | F | S | I | H | Q | G | S | N | DELETED | DELETED | M |
| S | P | F | S | I | H | Q | G | S | N | DELETED | P | I |
| S | P | F | S | I | H | Q | G | S | N | DELETED | P | M |
| S | P | F | S | I | H | Q | G | S | N | P | DELETED | I |
| S | P | F | S | I | H | Q | G | S | N | P | DELETED | M |
| S | P | F | S | I | H | Q | G | S | N | P | P | I |
| S | P | F | S | I | H | Q | G | S | N | P | P | M |
| S | P | F | S | I | H | Q | G | T | DELETED | DELETED | DELETED | I |
| S | P | F | S | I | H | Q | G | T | DELETED | DELETED | DELETED | M |
| S | P | F | S | I | H | Q | G | T | DELETED | DELETED | P | I |
| S | P | F | S | I | H | Q | G | T | DELETED | DELETED | P | M |
| S | P | F | S | I | H | Q | G | T | DELETED | P | DELETED | I |
| S | P | F | S | I | H | Q | G | T | DELETED | P | DELETED | M |
| S | P | F | S | I | H | Q | G | T | DELETED | P | P | I |
| S | P | F | S | I | H | Q | G | T | DELETED | P | P | M |
| S | P | F | S | I | H | Q | G | T | N | DELETED | DELETED | I |
| S | P | F | S | I | H | Q | G | T | N | DELETED | DELETED | M |
| S | P | F | S | I | H | Q | G | T | N | DELETED | P | I |
| S | P | F | S | I | H | Q | G | T | N | DELETED | P | M |
| S | P | F | S | I | H | Q | G | T | N | P | DELETED | I |
| S | P | F | S | I | H | Q | G | T | N | P | DELETED | M |
| S | P | F | S | I | H | Q | G | T | N | P | P | I |
| S | P | F | S | I | H | Q | G | T | N | P | P | M |
| S | P | F | S | I | H | V | S | S | DELETED | DELETED | DELETED | I |
| S | P | F | S | I | H | V | S | S | DELETED | DELETED | DELETED | M |
| S | P | F | S | I | H | V | S | S | DELETED | DELETED | P | I |
| S | P | F | S | I | H | V | S | S | DELETED | DELETED | P | M |
| S | P | F | S | I | H | V | S | S | DELETED | P | DELETED | I |
| S | P | F | S | I | H | V | S | S | DELETED | P | DELETED | M |
| S | P | F | S | I | H | V | S | S | DELETED | P | P | I |
| S | P | F | S | I | H | V | S | S | DELETED | P | P | M |
| S | P | F | S | I | H | V | S | S | N | DELETED | DELETED | I |
| S | P | F | S | I | H | V | S | S | N | DELETED | DELETED | M |
| S | P | F | S | I | H | V | S | S | N | DELETED | P | I |
| S | P | F | S | I | H | V | S | S | N | DELETED | P | M |
| S | P | F | S | I | H | V | S | S | N | P | DELETED | I |
| S | P | F | S | I | H | V | S | S | N | P | DELETED | M |
| S | P | F | S | I | H | V | S | S | N | P | P | I |
| S | P | F | S | I | H | V | S | S | N | P | P | M |
| S | P | F | S | I | H | V | S | T | DELETED | DELETED | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | S | I | H | V | S | T | DELETED | DELETED | DELETED | M |
| S | P | F | S | I | H | V | S | T | DELETED | DELETED | P | I |
| S | P | F | S | I | H | V | S | T | DELETED | DELETED | P | M |
| S | P | F | S | I | H | V | S | T | DELETED | P | DELETED | I |
| S | P | F | S | I | H | V | S | T | DELETED | P | DELETED | M |
| S | P | F | S | I | H | V | S | T | DELETED | P | P | I |
| S | P | F | S | I | H | V | S | T | DELETED | P | P | M |
| S | P | F | S | I | H | V | S | T | N | DELETED | DELETED | I |
| S | P | F | S | I | H | V | S | T | N | DELETED | DELETED | M |
| S | P | F | S | I | H | V | S | T | N | DELETED | P | I |
| S | P | F | S | I | H | V | S | T | N | DELETED | P | M |
| S | P | F | S | I | H | V | S | T | N | P | DELETED | I |
| S | P | F | S | I | H | V | S | T | N | P | DELETED | M |
| S | P | F | S | I | H | V | S | T | N | P | P | I |
| S | P | F | S | I | H | V | S | T | N | P | P | M |
| S | P | F | S | I | H | V | G | S | DELETED | DELETED | DELETED | I |
| S | P | F | S | I | H | V | G | S | DELETED | DELETED | DELETED | M |
| S | P | F | S | I | H | V | G | S | DELETED | DELETED | P | I |
| S | P | F | S | I | H | V | G | S | DELETED | DELETED | P | M |
| S | P | F | S | I | H | V | G | S | DELETED | P | DELETED | I |
| S | P | F | S | I | H | V | G | S | DELETED | P | DELETED | M |
| S | P | F | S | I | H | V | G | S | DELETED | P | P | I |
| S | P | F | S | I | H | V | G | S | DELETED | P | P | M |
| S | P | F | S | I | H | V | G | S | N | DELETED | DELETED | I |
| S | P | F | S | I | H | V | G | S | N | DELETED | DELETED | M |
| S | P | F | S | I | H | V | G | S | N | DELETED | P | I |
| S | P | F | S | I | H | V | G | S | N | DELETED | P | M |
| S | P | F | S | I | H | V | G | S | N | P | DELETED | I |
| S | P | F | S | I | H | V | G | S | N | P | DELETED | M |
| S | P | F | S | I | H | V | G | S | N | P | P | I |
| S | P | F | S | I | H | V | G | S | N | P | P | M |
| S | P | F | S | I | H | V | G | T | DELETED | DELETED | DELETED | I |
| S | P | F | S | I | H | V | G | T | DELETED | DELETED | DELETED | M |
| S | P | F | S | I | H | V | G | T | DELETED | DELETED | P | I |
| S | P | F | S | I | H | V | G | T | DELETED | DELETED | P | M |
| S | P | F | S | I | H | V | G | T | DELETED | P | DELETED | I |
| S | P | F | S | I | H | V | G | T | DELETED | P | DELETED | M |
| S | P | F | S | I | H | V | G | T | DELETED | P | P | I |
| S | P | F | S | I | H | V | G | T | DELETED | P | P | M |
| S | P | F | S | I | H | V | G | T | N | DELETED | DELETED | I |
| S | P | F | S | I | H | V | G | T | N | DELETED | DELETED | M |
| S | P | F | S | I | H | V | G | T | N | DELETED | P | I |
| S | P | F | S | I | H | V | G | T | N | DELETED | P | M |
| S | P | F | S | I | H | V | G | T | N | P | DELETED | I |
| S | P | F | S | I | H | V | G | T | N | P | DELETED | M |
| S | P | F | S | I | H | V | G | T | N | P | P | I |
| S | P | F | S | I | H | V | G | T | N | P | P | M |
| S | P | F | R | L | Y | Q | S | S | DELETED | DELETED | DELETED | I |
| S | P | F | R | L | Y | Q | S | S | DELETED | DELETED | DELETED | M |
| S | P | F | R | L | Y | Q | S | S | DELETED | DELETED | P | I |
| S | P | F | R | L | Y | Q | S | S | DELETED | DELETED | P | M |
| S | P | F | R | L | Y | Q | S | S | DELETED | P | DELETED | I |
| S | P | F | R | L | Y | Q | S | S | DELETED | P | DELETED | M |
| S | P | F | R | L | Y | Q | S | S | DELETED | P | P | I |
| S | P | F | R | L | Y | Q | S | S | DELETED | P | P | M |
| S | P | F | R | L | Y | Q | S | S | N | DELETED | DELETED | I |
| S | P | F | R | L | Y | Q | S | S | N | DELETED | DELETED | M |
| S | P | F | R | L | Y | Q | S | S | N | DELETED | P | I |
| S | P | F | R | L | Y | Q | S | S | N | DELETED | P | M |
| S | P | F | R | L | Y | Q | S | S | N | P | DELETED | I |
| S | P | F | R | L | Y | Q | S | S | N | P | DELETED | M |
| S | P | F | R | L | Y | Q | S | S | N | P | P | I |
| S | P | F | R | L | Y | Q | S | S | N | P | P | M |
| S | P | F | R | L | Y | Q | S | T | DELETED | DELETED | DELETED | I |
| S | P | F | R | L | Y | Q | S | T | DELETED | DELETED | DELETED | M |
| S | P | F | R | L | Y | Q | S | T | DELETED | DELETED | P | I |
| S | P | F | R | L | Y | Q | S | T | DELETED | DELETED | P | M |
| S | P | F | R | L | Y | Q | S | T | DELETED | P | DELETED | I |
| S | P | F | R | L | Y | Q | S | T | DELETED | P | DELETED | M |
| S | P | F | R | L | Y | Q | S | T | DELETED | P | P | I |
| S | P | F | R | L | Y | Q | S | T | DELETED | P | P | M |
| S | P | F | R | L | Y | Q | S | T | N | DELETED | DELETED | I |
| S | P | F | R | L | Y | Q | S | T | N | DELETED | DELETED | M |
| S | P | F | R | L | Y | Q | S | T | N | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | R | L | Y | Q | S | T | N | DELETED | P | M |
| S | P | F | R | L | Y | Q | S | T | N | P | DELETED | I |
| S | P | F | R | L | Y | Q | S | T | N | P | DELETED | M |
| S | P | F | R | L | Y | Q | S | T | N | P | P | I |
| S | P | F | R | L | Y | Q | S | T | N | P | P | M |
| S | P | F | R | L | Y | Q | G | S | DELETED | DELETED | DELETED | I |
| S | P | F | R | L | Y | Q | G | S | DELETED | DELETED | DELETED | M |
| S | P | F | R | L | Y | Q | G | S | DELETED | DELETED | P | I |
| S | P | F | R | L | Y | Q | G | S | DELETED | DELETED | P | M |
| S | P | F | R | L | Y | Q | G | S | DELETED | P | DELETED | I |
| S | P | F | R | L | Y | Q | G | S | DELETED | P | DELETED | M |
| S | P | F | R | L | Y | Q | G | S | DELETED | P | P | I |
| S | P | F | R | L | Y | Q | G | S | DELETED | P | P | M |
| S | P | F | R | L | Y | Q | G | S | N | DELETED | DELETED | I |
| S | P | F | R | L | Y | Q | G | S | N | DELETED | DELETED | M |
| S | P | F | R | L | Y | Q | G | S | N | DELETED | P | I |
| S | P | F | R | L | Y | Q | G | S | N | DELETED | P | M |
| S | P | F | R | L | Y | Q | G | S | N | P | DELETED | I |
| S | P | F | R | L | Y | Q | G | S | N | P | DELETED | M |
| S | P | F | R | L | Y | Q | G | S | N | P | P | I |
| S | P | F | R | L | Y | Q | G | S | N | P | P | M |
| S | P | F | R | L | Y | Q | G | T | DELETED | DELETED | DELETED | I |
| S | P | F | R | L | Y | Q | G | T | DELETED | DELETED | DELETED | M |
| S | P | F | R | L | Y | Q | G | T | DELETED | DELETED | P | I |
| S | P | F | R | L | Y | Q | G | T | DELETED | DELETED | P | M |
| S | P | F | R | L | Y | Q | G | T | DELETED | P | DELETED | I |
| S | P | F | R | L | Y | Q | G | T | DELETED | P | DELETED | M |
| S | P | F | R | L | Y | Q | G | T | DELETED | P | P | I |
| S | P | F | R | L | Y | Q | G | T | DELETED | P | P | M |
| S | P | F | R | L | Y | Q | G | T | N | DELETED | DELETED | I |
| S | P | F | R | L | Y | Q | G | T | N | DELETED | DELETED | M |
| S | P | F | R | L | Y | Q | G | T | N | DELETED | P | I |
| S | P | F | R | L | Y | Q | G | T | N | DELETED | P | M |
| S | P | F | R | L | Y | Q | G | T | N | P | DELETED | I |
| S | P | F | R | L | Y | Q | G | T | N | P | DELETED | M |
| S | P | F | R | L | Y | Q | G | T | N | P | P | I |
| S | P | F | R | L | Y | Q | G | T | N | P | P | M |
| S | P | F | R | L | Y | V | S | S | DELETED | DELETED | DELETED | I |
| S | P | F | R | L | Y | V | S | S | DELETED | DELETED | DELETED | M |
| S | P | F | R | L | Y | V | S | S | DELETED | DELETED | P | I |
| S | P | F | R | L | Y | V | S | S | DELETED | DELETED | P | M |
| S | P | F | R | L | Y | V | S | S | DELETED | P | DELETED | I |
| S | P | F | R | L | Y | V | S | S | DELETED | P | DELETED | M |
| S | P | F | R | L | Y | V | S | S | DELETED | P | P | I |
| S | P | F | R | L | Y | V | S | S | DELETED | P | P | M |
| S | P | F | R | L | Y | V | S | S | N | DELETED | DELETED | I |
| S | P | F | R | L | Y | V | S | S | N | DELETED | DELETED | M |
| S | P | F | R | L | Y | V | S | S | N | DELETED | P | I |
| S | P | F | R | L | Y | V | S | S | N | DELETED | P | M |
| S | P | F | R | L | Y | V | S | S | N | P | DELETED | I |
| S | P | F | R | L | Y | V | S | S | N | P | DELETED | M |
| S | P | F | R | L | Y | V | S | S | N | P | P | I |
| S | P | F | R | L | Y | V | S | S | N | P | P | M |
| S | P | F | R | L | Y | V | S | T | DELETED | DELETED | DELETED | I |
| S | P | F | R | L | Y | V | S | T | DELETED | DELETED | DELETED | M |
| S | P | F | R | L | Y | V | S | T | DELETED | DELETED | P | I |
| S | P | F | R | L | Y | V | S | T | DELETED | DELETED | P | M |
| S | P | F | R | L | Y | V | S | T | DELETED | P | DELETED | I |
| S | P | F | R | L | Y | V | S | T | DELETED | P | DELETED | M |
| S | P | F | R | L | Y | V | S | T | DELETED | P | P | I |
| S | P | F | R | L | Y | V | S | T | DELETED | P | P | M |
| S | P | F | R | L | Y | V | S | T | N | DELETED | DELETED | I |
| S | P | F | R | L | Y | V | S | T | N | DELETED | DELETED | M |
| S | P | F | R | L | Y | V | S | T | N | DELETED | P | I |
| S | P | F | R | L | Y | V | S | T | N | DELETED | P | M |
| S | P | F | R | L | Y | V | S | T | N | P | DELETED | I |
| S | P | F | R | L | Y | V | S | T | N | P | DELETED | M |
| S | P | F | R | L | Y | V | S | T | N | P | P | I |
| S | P | F | R | L | Y | V | S | T | N | P | P | M |
| S | P | F | R | L | Y | V | G | S | DELETED | DELETED | DELETED | I |
| S | P | F | R | L | Y | V | G | S | DELETED | DELETED | DELETED | M |
| S | P | F | R | L | Y | V | G | S | DELETED | DELETED | P | I |
| S | P | F | R | L | Y | V | G | S | DELETED | DELETED | P | M |
| S | P | F | R | L | Y | V | G | S | DELETED | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | R | L | Y | V | G | S | DELETED | P | DELETED | M |
| S | P | F | R | L | Y | V | G | S | DELETED | P | P | I |
| S | P | F | R | L | Y | V | G | S | DELETED | P | P | M |
| S | P | F | R | L | Y | V | G | S | N | DELETED | DELETED | I |
| S | P | F | R | L | Y | V | G | S | N | DELETED | DELETED | M |
| S | P | F | R | L | Y | V | G | S | N | DELETED | P | I |
| S | P | F | R | L | Y | V | G | S | N | DELETED | P | M |
| S | P | F | R | L | Y | V | G | S | N | P | DELETED | I |
| S | P | F | R | L | Y | V | G | S | N | P | DELETED | M |
| S | P | F | R | L | Y | V | G | S | N | P | P | I |
| S | P | F | R | L | Y | V | G | S | N | P | P | M |
| S | P | F | R | L | Y | V | G | T | DELETED | DELETED | DELETED | I |
| S | P | F | R | L | Y | V | G | T | DELETED | DELETED | DELETED | M |
| S | P | F | R | L | Y | V | G | T | DELETED | DELETED | P | I |
| S | P | F | R | L | Y | V | G | T | DELETED | DELETED | P | M |
| S | P | F | R | L | Y | V | G | T | DELETED | P | DELETED | I |
| S | P | F | R | L | Y | V | G | T | DELETED | P | DELETED | M |
| S | P | F | R | L | Y | V | G | T | DELETED | P | P | I |
| S | P | F | R | L | Y | V | G | T | DELETED | P | P | M |
| S | P | F | R | L | Y | V | G | T | N | DELETED | DELETED | I |
| S | P | F | R | L | Y | V | G | T | N | DELETED | DELETED | M |
| S | P | F | R | L | Y | V | G | T | N | DELETED | P | I |
| S | P | F | R | L | Y | V | G | T | N | DELETED | P | M |
| S | P | F | R | L | Y | V | G | T | N | P | DELETED | I |
| S | P | F | R | L | Y | V | G | T | N | P | DELETED | M |
| S | P | F | R | L | Y | V | G | T | N | P | P | I |
| S | P | F | R | L | Y | V | G | T | N | P | P | M |
| S | P | F | R | L | H | Q | S | S | DELETED | DELETED | DELETED | I |
| S | P | F | R | L | H | Q | S | S | DELETED | DELETED | DELETED | M |
| S | P | F | R | L | H | Q | S | S | DELETED | DELETED | P | I |
| S | P | F | R | L | H | Q | S | S | DELETED | DELETED | P | M |
| S | P | F | R | L | H | Q | S | S | DELETED | P | DELETED | I |
| S | P | F | R | L | H | Q | S | S | DELETED | P | DELETED | M |
| S | P | F | R | L | H | Q | S | S | DELETED | P | P | I |
| S | P | F | R | L | H | Q | S | S | DELETED | P | P | M |
| S | P | F | R | L | H | Q | S | S | N | DELETED | DELETED | I |
| S | P | F | R | L | H | Q | S | S | N | DELETED | DELETED | M |
| S | P | F | R | L | H | Q | S | S | N | DELETED | P | I |
| S | P | F | R | L | H | Q | S | S | N | DELETED | P | M |
| S | P | F | R | L | H | Q | S | S | N | P | DELETED | I |
| S | P | F | R | L | H | Q | S | S | N | P | DELETED | M |
| S | P | F | R | L | H | Q | S | S | N | P | P | I |
| S | P | F | R | L | H | Q | S | S | N | P | P | M |
| S | P | F | R | L | H | Q | S | T | DELETED | DELETED | DELETED | I |
| S | P | F | R | L | H | Q | S | T | DELETED | DELETED | DELETED | M |
| S | P | F | R | L | H | Q | S | T | DELETED | DELETED | P | I |
| S | P | F | R | L | H | Q | S | T | DELETED | DELETED | P | M |
| S | P | F | R | L | H | Q | S | T | DELETED | P | DELETED | I |
| S | P | F | R | L | H | Q | S | T | DELETED | P | DELETED | M |
| S | P | F | R | L | H | Q | S | T | DELETED | P | P | I |
| S | P | F | R | L | H | Q | S | T | DELETED | P | P | M |
| S | P | F | R | L | H | Q | S | T | N | DELETED | DELETED | I |
| S | P | F | R | L | H | Q | S | T | N | DELETED | DELETED | M |
| S | P | F | R | L | H | Q | S | T | N | DELETED | P | I |
| S | P | F | R | L | H | Q | S | T | N | DELETED | P | M |
| S | P | F | R | L | H | Q | S | T | N | P | DELETED | I |
| S | P | F | R | L | H | Q | S | T | N | P | DELETED | M |
| S | P | F | R | L | H | Q | S | T | N | P | P | I |
| S | P | F | R | L | H | Q | S | T | N | P | P | M |
| S | P | F | R | L | H | Q | G | S | DELETED | DELETED | DELETED | I |
| S | P | F | R | L | H | Q | G | S | DELETED | DELETED | DELETED | M |
| S | P | F | R | L | H | Q | G | S | DELETED | DELETED | P | I |
| S | P | F | R | L | H | Q | G | S | DELETED | DELETED | P | M |
| S | P | F | R | L | H | Q | G | S | DELETED | P | DELETED | I |
| S | P | F | R | L | H | Q | G | S | DELETED | P | DELETED | M |
| S | P | F | R | L | H | Q | G | S | DELETED | P | P | I |
| S | P | F | R | L | H | Q | G | S | DELETED | P | P | M |
| S | P | F | R | L | H | Q | G | S | N | DELETED | DELETED | I |
| S | P | F | R | L | H | Q | G | S | N | DELETED | DELETED | M |
| S | P | F | R | L | H | Q | G | S | N | DELETED | P | I |
| S | P | F | R | L | H | Q | G | S | N | DELETED | P | M |
| S | P | F | R | L | H | Q | G | S | N | P | DELETED | I |
| S | P | F | R | L | H | Q | G | S | N | P | DELETED | M |
| S | P | F | R | L | H | Q | G | S | N | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | R | L | H | Q | G | S | N | P | P | M |
| S | P | F | R | L | H | Q | G | T | DELETED | DELETED | DELETED | I |
| S | P | F | R | L | H | Q | G | T | DELETED | DELETED | DELETED | M |
| S | P | F | R | L | H | Q | G | T | DELETED | DELETED | P | I |
| S | P | F | R | L | H | Q | G | T | DELETED | DELETED | P | M |
| S | P | F | R | L | H | Q | G | T | DELETED | P | DELETED | I |
| S | P | F | R | L | H | Q | G | T | DELETED | P | DELETED | M |
| S | P | F | R | L | H | Q | G | T | DELETED | P | P | I |
| S | P | F | R | L | H | Q | G | T | DELETED | P | P | M |
| S | P | F | R | L | H | Q | G | T | N | DELETED | DELETED | I |
| S | P | F | R | L | H | Q | G | T | N | DELETED | DELETED | M |
| S | P | F | R | L | H | Q | G | T | N | DELETED | P | I |
| S | P | F | R | L | H | Q | G | T | N | DELETED | P | M |
| S | P | F | R | L | H | Q | G | T | N | P | DELETED | I |
| S | P | F | R | L | H | Q | G | T | N | P | DELETED | M |
| S | P | F | R | L | H | Q | G | T | N | P | P | I |
| S | P | F | R | L | H | Q | G | T | N | P | P | M |
| S | P | F | R | L | H | V | S | S | DELETED | DELETED | DELETED | I |
| S | P | F | R | L | H | V | S | S | DELETED | DELETED | DELETED | M |
| S | P | F | R | L | H | V | S | S | DELETED | DELETED | P | I |
| S | P | F | R | L | H | V | S | S | DELETED | DELETED | P | M |
| S | P | F | R | L | H | V | S | S | DELETED | P | DELETED | I |
| S | P | F | R | L | H | V | S | S | DELETED | P | DELETED | M |
| S | P | F | R | L | H | V | S | S | DELETED | P | P | I |
| S | P | F | R | L | H | V | S | S | DELETED | P | P | M |
| S | P | F | R | L | H | V | S | S | N | DELETED | DELETED | I |
| S | P | F | R | L | H | V | S | S | N | DELETED | DELETED | M |
| S | P | F | R | L | H | V | S | S | N | DELETED | P | I |
| S | P | F | R | L | H | V | S | S | N | DELETED | P | M |
| S | P | F | R | L | H | V | S | S | N | P | DELETED | I |
| S | P | F | R | L | H | V | S | S | N | P | DELETED | M |
| S | P | F | R | L | H | V | S | S | N | P | P | I |
| S | P | F | R | L | H | V | S | S | N | P | P | M |
| S | P | F | R | L | H | V | S | T | DELETED | DELETED | DELETED | I |
| S | P | F | R | L | H | V | S | T | DELETED | DELETED | DELETED | M |
| S | P | F | R | L | H | V | S | T | DELETED | DELETED | P | I |
| S | P | F | R | L | H | V | S | T | DELETED | DELETED | P | M |
| S | P | F | R | L | H | V | S | T | DELETED | P | DELETED | I |
| S | P | F | R | L | H | V | S | T | DELETED | P | DELETED | M |
| S | P | F | R | L | H | V | S | T | DELETED | P | P | I |
| S | P | F | R | L | H | V | S | T | DELETED | P | P | M |
| S | P | F | R | L | H | V | S | T | N | DELETED | DELETED | I |
| S | P | F | R | L | H | V | S | T | N | DELETED | DELETED | M |
| S | P | F | R | L | H | V | S | T | N | DELETED | P | I |
| S | P | F | R | L | H | V | S | T | N | DELETED | P | M |
| S | P | F | R | L | H | V | S | T | N | P | DELETED | I |
| S | P | F | R | L | H | V | S | T | N | P | DELETED | M |
| S | P | F | R | L | H | V | S | T | N | P | P | I |
| S | P | F | R | L | H | V | S | T | N | P | P | M |
| S | P | F | R | L | H | V | G | S | DELETED | DELETED | DELETED | I |
| S | P | F | R | L | H | V | G | S | DELETED | DELETED | DELETED | M |
| S | P | F | R | L | H | V | G | S | DELETED | DELETED | P | I |
| S | P | F | R | L | H | V | G | S | DELETED | DELETED | P | M |
| S | P | F | R | L | H | V | G | S | DELETED | P | DELETED | I |
| S | P | F | R | L | H | V | G | S | DELETED | P | DELETED | M |
| S | P | F | R | L | H | V | G | S | DELETED | P | P | I |
| S | P | F | R | L | H | V | G | S | DELETED | P | P | M |
| S | P | F | R | L | H | V | G | S | N | DELETED | DELETED | I |
| S | P | F | R | L | H | V | G | S | N | DELETED | DELETED | M |
| S | P | F | R | L | H | V | G | S | N | DELETED | P | I |
| S | P | F | R | L | H | V | G | S | N | DELETED | P | M |
| S | P | F | R | L | H | V | G | S | N | P | DELETED | I |
| S | P | F | R | L | H | V | G | S | N | P | DELETED | M |
| S | P | F | R | L | H | V | G | S | N | P | P | I |
| S | P | F | R | L | H | V | G | S | N | P | P | M |
| S | P | F | R | L | H | V | G | T | DELETED | DELETED | DELETED | I |
| S | P | F | R | L | H | V | G | T | DELETED | DELETED | DELETED | M |
| S | P | F | R | L | H | V | G | T | DELETED | DELETED | P | I |
| S | P | F | R | L | H | V | G | T | DELETED | DELETED | P | M |
| S | P | F | R | L | H | V | G | T | DELETED | P | DELETED | I |
| S | P | F | R | L | H | V | G | T | DELETED | P | DELETED | M |
| S | P | F | R | L | H | V | G | T | DELETED | P | P | I |
| S | P | F | R | L | H | V | G | T | DELETED | P | P | M |
| S | P | F | R | L | H | V | G | T | N | DELETED | DELETED | I |

TABLE 9-continued

| Exemplary Mutations of mAb 2.449.1.3 Light Chain (SEQ ID NO: 12) to Germline at the Indicated Residue Number. | | | | | | | | | | | | |
|---|---|---|---|---|---|---|---|---|---|---|---|---|
| 20 | 25 | 29 | 31 | 33 | 49 | 55 | 56 | 91 | 94 | 95 | 96 | 107 |
| S | P | F | R | L | H | V | G | T | N | DELETED | DELETED | M |
| S | P | F | R | L | H | V | G | T | N | DELETED | P | I |
| S | P | F | R | L | H | V | G | T | N | DELETED | P | M |
| S | P | F | R | L | H | V | G | T | N | P | DELETED | I |
| S | P | F | R | L | H | V | G | T | N | P | DELETED | M |
| S | P | F | R | L | H | V | G | T | N | P | P | I |
| S | P | F | R | L | H | V | G | T | N | P | P | M |
| S | P | F | R | I | Y | Q | S | S | DELETED | DELETED | DELETED | I |
| S | P | F | R | I | Y | Q | S | S | DELETED | DELETED | DELETED | M |
| S | P | F | R | I | Y | Q | S | S | DELETED | DELETED | P | I |
| S | P | F | R | I | Y | Q | S | S | DELETED | DELETED | P | M |
| S | P | F | R | I | Y | Q | S | S | DELETED | P | DELETED | I |
| S | P | F | R | I | Y | Q | S | S | DELETED | P | DELETED | M |
| S | P | F | R | I | Y | Q | S | S | DELETED | P | P | I |
| S | P | F | R | I | Y | Q | S | S | DELETED | P | P | M |
| S | P | F | R | I | Y | Q | S | S | N | DELETED | DELETED | I |
| S | P | F | R | I | Y | Q | S | S | N | DELETED | DELETED | M |
| S | P | F | R | I | Y | Q | S | S | N | DELETED | P | I |
| S | P | F | R | I | Y | Q | S | S | N | DELETED | P | M |
| S | P | F | R | I | Y | Q | S | S | N | P | DELETED | I |
| S | P | F | R | I | Y | Q | S | S | N | P | DELETED | M |
| S | P | F | R | I | Y | Q | S | S | N | P | P | I |
| S | P | F | R | I | Y | Q | S | S | N | P | P | M |
| S | P | F | R | I | Y | Q | S | T | DELETED | DELETED | DELETED | I |
| S | P | F | R | I | Y | Q | S | T | DELETED | DELETED | DELETED | M |
| S | P | F | R | I | Y | Q | S | T | DELETED | DELETED | P | I |
| S | P | F | R | I | Y | Q | S | T | DELETED | DELETED | P | M |
| S | P | F | R | I | Y | Q | S | T | DELETED | P | DELETED | I |
| S | P | F | R | I | Y | Q | S | T | DELETED | P | DELETED | M |
| S | P | F | R | I | Y | Q | S | T | DELETED | P | P | I |
| S | P | F | R | I | Y | Q | S | T | DELETED | P | P | M |
| S | P | F | R | I | Y | Q | S | T | N | DELETED | DELETED | I |
| S | P | F | R | I | Y | Q | S | T | N | DELETED | DELETED | M |
| S | P | F | R | I | Y | Q | S | T | N | DELETED | P | I |
| S | P | F | R | I | Y | Q | S | T | N | DELETED | P | M |
| S | P | F | R | I | Y | Q | S | T | N | P | DELETED | I |
| S | P | F | R | I | Y | Q | S | T | N | P | DELETED | M |
| S | P | F | R | I | Y | Q | S | T | N | P | P | I |
| S | P | F | R | I | Y | Q | S | T | N | P | P | M |
| S | P | F | R | I | Y | Q | G | S | DELETED | DELETED | DELETED | I |
| S | P | F | R | I | Y | Q | G | S | DELETED | DELETED | DELETED | M |
| S | P | F | R | I | Y | Q | G | S | DELETED | DELETED | P | I |
| S | P | F | R | I | Y | Q | G | S | DELETED | DELETED | P | M |
| S | P | F | R | I | Y | Q | G | S | DELETED | P | DELETED | I |
| S | P | F | R | I | Y | Q | G | S | DELETED | P | DELETED | M |
| S | P | F | R | I | Y | Q | G | S | DELETED | P | P | I |
| S | P | F | R | I | Y | Q | G | S | DELETED | P | P | M |
| S | P | F | R | I | Y | Q | G | S | N | DELETED | DELETED | I |
| S | P | F | R | I | Y | Q | G | S | N | DELETED | DELETED | M |
| S | P | F | R | I | Y | Q | G | S | N | DELETED | P | I |
| S | P | F | R | I | Y | Q | G | S | N | DELETED | P | M |
| S | P | F | R | I | Y | Q | G | S | N | P | DELETED | I |
| S | P | F | R | I | Y | Q | G | S | N | P | DELETED | M |
| S | P | F | R | I | Y | Q | G | S | N | P | P | I |
| S | P | F | R | I | Y | Q | G | S | N | P | P | M |
| S | P | F | R | I | Y | Q | G | T | DELETED | DELETED | DELETED | I |
| S | P | F | R | I | Y | Q | G | T | DELETED | DELETED | DELETED | M |
| S | P | F | R | I | Y | Q | G | T | DELETED | DELETED | P | I |
| S | P | F | R | I | Y | Q | G | T | DELETED | DELETED | P | M |
| S | P | F | R | I | Y | Q | G | T | DELETED | P | DELETED | I |
| S | P | F | R | I | Y | Q | G | T | DELETED | P | DELETED | M |
| S | P | F | R | I | Y | Q | G | T | DELETED | P | P | I |
| S | P | F | R | I | Y | Q | G | T | DELETED | P | P | M |
| S | P | F | R | I | Y | Q | G | T | N | DELETED | DELETED | I |
| S | P | F | R | I | Y | Q | G | T | N | DELETED | DELETED | M |
| S | P | F | R | I | Y | Q | G | T | N | DELETED | P | I |
| S | P | F | R | I | Y | Q | G | T | N | DELETED | P | M |
| S | P | F | R | I | Y | Q | G | T | N | P | DELETED | I |
| S | P | F | R | I | Y | Q | G | T | N | P | DELETED | M |
| S | P | F | R | I | Y | Q | G | T | N | P | P | I |
| S | P | F | R | I | Y | Q | G | T | N | P | P | M |
| S | P | F | R | I | Y | V | S | S | DELETED | DELETED | DELETED | I |
| S | P | F | R | I | Y | V | S | S | DELETED | DELETED | DELETED | M |
| S | P | F | R | I | Y | V | S | S | DELETED | DELETED | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | R | I | Y | V | S | S | DELETED | DELETED | P | M |
| S | P | F | R | I | Y | V | S | S | DELETED | P | DELETED | I |
| S | P | F | R | I | Y | V | S | S | DELETED | P | DELETED | M |
| S | P | F | R | I | Y | V | S | S | DELETED | P | P | I |
| S | P | F | R | I | Y | V | S | S | DELETED | P | P | M |
| S | P | F | R | I | Y | V | S | S | N | DELETED | DELETED | I |
| S | P | F | R | I | Y | V | S | S | N | DELETED | DELETED | M |
| S | P | F | R | I | Y | V | S | S | N | DELETED | P | I |
| S | P | F | R | I | Y | V | S | S | N | DELETED | P | M |
| S | P | F | R | I | Y | V | S | S | N | P | DELETED | I |
| S | P | F | R | I | Y | V | S | S | N | P | DELETED | M |
| S | P | F | R | I | Y | V | S | S | N | P | P | I |
| S | P | F | R | I | Y | V | S | S | N | P | P | M |
| S | P | F | R | I | Y | V | S | T | DELETED | DELETED | DELETED | I |
| S | P | F | R | I | Y | V | S | T | DELETED | DELETED | DELETED | M |
| S | P | F | R | I | Y | V | S | T | DELETED | DELETED | P | I |
| S | P | F | R | I | Y | V | S | T | DELETED | DELETED | P | M |
| S | P | F | R | I | Y | V | S | T | DELETED | P | DELETED | I |
| S | P | F | R | I | Y | V | S | T | DELETED | P | DELETED | M |
| S | P | F | R | I | Y | V | S | T | DELETED | P | P | I |
| S | P | F | R | I | Y | V | S | T | DELETED | P | P | M |
| S | P | F | R | I | Y | V | S | T | N | DELETED | DELETED | I |
| S | P | F | R | I | Y | V | S | T | N | DELETED | DELETED | M |
| S | P | F | R | I | Y | V | S | T | N | DELETED | P | I |
| S | P | F | R | I | Y | V | S | T | N | DELETED | P | M |
| S | P | F | R | I | Y | V | S | T | N | P | DELETED | I |
| S | P | F | R | I | Y | V | S | T | N | P | DELETED | M |
| S | P | F | R | I | Y | V | S | T | N | P | P | I |
| S | P | F | R | I | Y | V | S | T | N | P | P | M |
| S | P | F | R | I | Y | V | G | S | DELETED | DELETED | DELETED | I |
| S | P | F | R | I | Y | V | G | S | DELETED | DELETED | DELETED | M |
| S | P | F | R | I | Y | V | G | S | DELETED | DELETED | P | I |
| S | P | F | R | I | Y | V | G | S | DELETED | DELETED | P | M |
| S | P | F | R | I | Y | V | G | S | DELETED | P | DELETED | I |
| S | P | F | R | I | Y | V | G | S | DELETED | P | DELETED | M |
| S | P | F | R | I | Y | V | G | S | DELETED | P | P | I |
| S | P | F | R | I | Y | V | G | S | DELETED | P | P | M |
| S | P | F | R | I | Y | V | G | S | N | DELETED | DELETED | I |
| S | P | F | R | I | Y | V | G | S | N | DELETED | DELETED | M |
| S | P | F | R | I | Y | V | G | S | N | DELETED | P | I |
| S | P | F | R | I | Y | V | G | S | N | DELETED | P | M |
| S | P | F | R | I | Y | V | G | S | N | P | DELETED | I |
| S | P | F | R | I | Y | V | G | S | N | P | DELETED | M |
| S | P | F | R | I | Y | V | G | S | N | P | P | I |
| S | P | F | R | I | Y | V | G | S | N | P | P | M |
| S | P | F | R | I | Y | V | G | T | DELETED | DELETED | DELETED | I |
| S | P | F | R | I | Y | V | G | T | DELETED | DELETED | DELETED | M |
| S | P | F | R | I | Y | V | G | T | DELETED | DELETED | P | I |
| S | P | F | R | I | Y | V | G | T | DELETED | DELETED | P | M |
| S | P | F | R | I | Y | V | G | T | DELETED | P | DELETED | I |
| S | P | F | R | I | Y | V | G | T | DELETED | P | DELETED | M |
| S | P | F | R | I | Y | V | G | T | DELETED | P | P | I |
| S | P | F | R | I | Y | V | G | T | DELETED | P | P | M |
| S | P | F | R | I | Y | V | G | T | N | DELETED | DELETED | I |
| S | P | F | R | I | Y | V | G | T | N | DELETED | DELETED | M |
| S | P | F | R | I | Y | V | G | T | N | DELETED | P | I |
| S | P | F | R | I | Y | V | G | T | N | DELETED | P | M |
| S | P | F | R | I | Y | V | G | T | N | P | DELETED | I |
| S | P | F | R | I | Y | V | G | T | N | P | DELETED | M |
| S | P | F | R | I | Y | V | G | T | N | P | P | I |
| S | P | F | R | I | Y | V | G | T | N | P | P | M |
| S | P | F | R | I | H | Q | S | S | DELETED | DELETED | DELETED | I |
| S | P | F | R | I | H | Q | S | S | DELETED | DELETED | DELETED | M |
| S | P | F | R | I | H | Q | S | S | DELETED | DELETED | P | I |
| S | P | F | R | I | H | Q | S | S | DELETED | DELETED | P | M |
| S | P | F | R | I | H | Q | S | S | DELETED | P | DELETED | I |
| S | P | F | R | I | H | Q | S | S | DELETED | P | DELETED | M |
| S | P | F | R | I | H | Q | S | S | DELETED | P | P | I |
| S | P | F | R | I | H | Q | S | S | DELETED | P | P | M |
| S | P | F | R | I | H | Q | S | S | N | DELETED | DELETED | I |
| S | P | F | R | I | H | Q | S | S | N | DELETED | DELETED | M |
| S | P | F | R | I | H | Q | S | S | N | DELETED | P | I |
| S | P | F | R | I | H | Q | S | S | N | DELETED | P | M |
| S | P | F | R | I | H | Q | S | S | N | P | DELETED | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | R | I | H | Q | S | S | N | P | DELETED | M |
| S | P | F | R | I | H | Q | S | S | N | P | P | I |
| S | P | F | R | I | H | Q | S | S | N | P | P | M |
| S | P | F | R | I | H | Q | S | T | DELETED | DELETED | DELETED | I |
| S | P | F | R | I | H | Q | S | T | DELETED | DELETED | DELETED | M |
| S | P | F | R | I | H | Q | S | T | DELETED | DELETED | P | I |
| S | P | F | R | I | H | Q | S | T | DELETED | DELETED | P | M |
| S | P | F | R | I | H | Q | S | T | DELETED | P | DELETED | I |
| S | P | F | R | I | H | Q | S | T | DELETED | P | DELETED | M |
| S | P | F | R | I | H | Q | S | T | DELETED | P | P | I |
| S | P | F | R | I | H | Q | S | T | DELETED | P | P | M |
| S | P | F | R | I | H | Q | S | T | N | DELETED | DELETED | I |
| S | P | F | R | I | H | Q | S | T | N | DELETED | DELETED | M |
| S | P | F | R | I | H | Q | S | T | N | DELETED | P | I |
| S | P | F | R | I | H | Q | S | T | N | DELETED | P | M |
| S | P | F | R | I | H | Q | S | T | N | P | DELETED | I |
| S | P | F | R | I | H | Q | S | T | N | P | DELETED | M |
| S | P | F | R | I | H | Q | S | T | N | P | P | I |
| S | P | F | R | I | H | Q | S | T | N | P | P | M |
| S | P | F | R | I | H | Q | G | S | DELETED | DELETED | DELETED | I |
| S | P | F | R | I | H | Q | G | S | DELETED | DELETED | DELETED | M |
| S | P | F | R | I | H | Q | G | S | DELETED | DELETED | P | I |
| S | P | F | R | I | H | Q | G | S | DELETED | DELETED | P | M |
| S | P | F | R | I | H | Q | G | S | DELETED | P | DELETED | I |
| S | P | F | R | I | H | Q | G | S | DELETED | P | DELETED | M |
| S | P | F | R | I | H | Q | G | S | DELETED | P | P | I |
| S | P | F | R | I | H | Q | G | S | DELETED | P | P | M |
| S | P | F | R | I | H | Q | G | S | N | DELETED | DELETED | I |
| S | P | F | R | I | H | Q | G | S | N | DELETED | DELETED | M |
| S | P | F | R | I | H | Q | G | S | N | DELETED | P | I |
| S | P | F | R | I | H | Q | G | S | N | DELETED | P | M |
| S | P | F | R | I | H | Q | G | S | N | P | DELETED | I |
| S | P | F | R | I | H | Q | G | S | N | P | DELETED | M |
| S | P | F | R | I | H | Q | G | S | N | P | P | I |
| S | P | F | R | I | H | Q | G | S | N | P | P | M |
| S | P | F | R | I | H | Q | G | T | DELETED | DELETED | DELETED | I |
| S | P | F | R | I | H | Q | G | T | DELETED | DELETED | DELETED | M |
| S | P | F | R | I | H | Q | G | T | DELETED | DELETED | P | I |
| S | P | F | R | I | H | Q | G | T | DELETED | DELETED | P | M |
| S | P | F | R | I | H | Q | G | T | DELETED | P | DELETED | I |
| S | P | F | R | I | H | Q | G | T | DELETED | P | DELETED | M |
| S | P | F | R | I | H | Q | G | T | DELETED | P | P | I |
| S | P | F | R | I | H | Q | G | T | DELETED | P | P | M |
| S | P | F | R | I | H | Q | G | T | N | DELETED | DELETED | I |
| S | P | F | R | I | H | Q | G | T | N | DELETED | DELETED | M |
| S | P | F | R | I | H | Q | G | T | N | DELETED | P | I |
| S | P | F | R | I | H | Q | G | T | N | DELETED | P | M |
| S | P | F | R | I | H | Q | G | T | N | P | DELETED | I |
| S | P | F | R | I | H | Q | G | T | N | P | DELETED | M |
| S | P | F | R | I | H | Q | G | T | N | P | P | I |
| S | P | F | R | I | H | Q | G | T | N | P | P | M |
| S | P | F | R | I | H | V | S | S | DELETED | DELETED | DELETED | I |
| S | P | F | R | I | H | V | S | S | DELETED | DELETED | DELETED | M |
| S | P | F | R | I | H | V | S | S | DELETED | DELETED | P | I |
| S | P | F | R | I | H | V | S | S | DELETED | DELETED | P | M |
| S | P | F | R | I | H | V | S | S | DELETED | P | DELETED | I |
| S | P | F | R | I | H | V | S | S | DELETED | P | DELETED | M |
| S | P | F | R | I | H | V | S | S | DELETED | P | P | I |
| S | P | F | R | I | H | V | S | S | DELETED | P | P | M |
| S | P | F | R | I | H | V | S | S | N | DELETED | DELETED | I |
| S | P | F | R | I | H | V | S | S | N | DELETED | DELETED | M |
| S | P | F | R | I | H | V | S | S | N | DELETED | P | I |
| S | P | F | R | I | H | V | S | S | N | DELETED | P | M |
| S | P | F | R | I | H | V | S | S | N | P | DELETED | I |
| S | P | F | R | I | H | V | S | S | N | P | DELETED | M |
| S | P | F | R | I | H | V | S | S | N | P | P | I |
| S | P | F | R | I | H | V | S | S | N | P | P | M |
| S | P | F | R | I | H | V | S | T | DELETED | DELETED | DELETED | I |
| S | P | F | R | I | H | V | S | T | DELETED | DELETED | DELETED | M |
| S | P | F | R | I | H | V | S | T | DELETED | DELETED | P | I |
| S | P | F | R | I | H | V | S | T | DELETED | DELETED | P | M |
| S | P | F | R | I | H | V | S | T | DELETED | P | DELETED | I |
| S | P | F | R | I | H | V | S | T | DELETED | P | DELETED | M |
| S | P | F | R | I | H | V | S | T | DELETED | P | P | I |

TABLE 9-continued

Exemplary Mutations of mAb 2.449.1.3 Light Chain (SEQ ID NO: 12) to Germline at the Indicated Residue Number.

| 20 | 25 | 29 | 31 | 33 | 49 | 55 | 56 | 91 | 94 | 95 | 96 | 107 |
|---|---|---|---|---|---|---|---|---|---|---|---|---|
| S | P | F | R | I | H | V | S | T | DELETED | P | P | M |
| S | P | F | R | I | H | V | S | T | N | DELETED | DELETED | I |
| S | P | F | R | I | H | V | S | T | N | DELETED | DELETED | M |
| S | P | F | R | I | H | V | S | T | N | DELETED | P | I |
| S | P | F | R | I | H | V | S | T | N | DELETED | P | M |
| S | P | F | R | I | H | V | S | T | N | P | DELETED | I |
| S | P | F | R | I | H | V | S | T | N | P | DELETED | M |
| S | P | F | R | I | H | V | S | T | N | P | P | I |
| S | P | F | R | I | H | V | S | T | N | P | P | M |
| S | P | F | R | I | H | V | G | S | DELETED | DELETED | DELETED | I |
| S | P | F | R | I | H | V | G | S | DELETED | DELETED | DELETED | M |
| S | P | F | R | I | H | V | G | S | DELETED | DELETED | P | I |
| S | P | F | R | I | H | V | G | S | DELETED | DELETED | P | M |
| S | P | F | R | I | H | V | G | S | DELETED | P | DELETED | I |
| S | P | F | R | I | H | V | G | S | DELETED | P | DELETED | M |
| S | P | F | R | I | H | V | G | S | DELETED | P | P | I |
| S | P | F | R | I | H | V | G | S | DELETED | P | P | M |
| S | P | F | R | I | H | V | G | S | N | DELETED | DELETED | I |
| S | P | F | R | I | H | V | G | S | N | DELETED | DELETED | M |
| S | P | F | R | I | H | V | G | S | N | DELETED | P | I |
| S | P | F | R | I | H | V | G | S | N | DELETED | P | M |
| S | P | F | R | I | H | V | G | S | N | P | DELETED | I |
| S | P | F | R | I | H | V | G | S | N | P | DELETED | M |
| S | P | F | R | I | H | V | G | S | N | P | P | I |
| S | P | F | R | I | H | V | G | S | N | P | P | M |
| S | P | F | R | I | H | V | G | T | DELETED | DELETED | DELETED | I |
| S | P | F | R | I | H | V | G | T | DELETED | DELETED | DELETED | M |
| S | P | F | R | I | H | V | G | T | DELETED | DELETED | P | I |
| S | P | F | R | I | H | V | G | T | DELETED | DELETED | P | M |
| S | P | F | R | I | H | V | G | T | DELETED | P | DELETED | I |
| S | P | F | R | I | H | V | G | T | DELETED | P | DELETED | M |
| S | P | F | R | I | H | V | G | T | DELETED | P | P | I |
| S | P | F | R | I | H | V | G | T | DELETED | P | P | M |
| S | P | F | R | I | H | V | G | T | N | DELETED | DELETED | I |
| S | P | F | R | I | H | V | G | T | N | DELETED | DELETED | M |
| S | P | F | R | I | H | V | G | T | N | DELETED | P | I |
| S | P | F | R | I | H | V | G | T | N | DELETED | P | M |
| S | P | F | R | I | H | V | G | T | N | P | DELETED | I |
| S | P | F | R | I | H | V | G | T | N | P | DELETED | M |
| S | P | F | R | I | H | V | G | T | N | P | P | I |
| S | P | F | R | I | H | V | G | T | N | P | P | M |

TABLE 10

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| G | S | S | S | S | DELETED | DELETED | DELETED | L |
| G | S | S | S | S | DELETED | DELETED | DELETED | Q |
| G | S | S | S | S | DELETED | DELETED | V | L |
| G | S | S | S | S | DELETED | DELETED | V | Q |
| G | S | S | S | S | DELETED | H | DELETED | L |
| G | S | S | S | S | DELETED | H | DELETED | Q |
| G | S | S | S | S | DELETED | H | V | L |
| G | S | S | S | S | DELETED | H | V | Q |
| G | S | S | S | S | H | DELETED | DELETED | L |
| G | S | S | S | S | H | DELETED | DELETED | Q |
| G | S | S | S | S | H | DELETED | V | L |
| G | S | S | S | S | H | DELETED | V | Q |
| G | S | S | S | S | H | H | DELETED | L |
| G | S | S | S | S | H | H | DELETED | Q |
| G | S | S | S | S | H | H | V | L |
| G | S | S | S | S | H | H | V | Q |
| G | S | S | S | R | DELETED | DELETED | DELETED | L |
| G | S | S | S | R | DELETED | DELETED | DELETED | Q |
| G | S | S | S | R | DELETED | DELETED | V | L |
| G | S | S | S | R | DELETED | DELETED | V | Q |
| G | S | S | S | R | DELETED | H | DELETED | L |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| G | S | S | S | R | DELETED | H | DELETED | Q |
| G | S | S | S | R | DELETED | H | V | L |
| G | S | S | S | R | DELETED | H | V | Q |
| G | S | S | S | R | H | DELETED | DELETED | L |
| G | S | S | S | R | H | DELETED | DELETED | Q |
| G | S | S | S | R | H | DELETED | V | L |
| G | S | S | S | R | H | DELETED | V | Q |
| G | S | S | S | R | H | H | DELETED | L |
| G | S | S | S | R | H | H | DELETED | Q |
| G | S | S | S | R | H | H | V | L |
| G | S | S | S | R | H | H | V | Q |
| G | S | S | T | S | DELETED | DELETED | DELETED | L |
| G | S | S | T | S | DELETED | DELETED | DELETED | Q |
| G | S | S | T | S | DELETED | DELETED | V | L |
| G | S | S | T | S | DELETED | DELETED | V | Q |
| G | S | S | T | S | DELETED | H | DELETED | L |
| G | S | S | T | S | DELETED | H | DELETED | Q |
| G | S | S | T | S | DELETED | H | V | L |
| G | S | S | T | S | DELETED | H | V | Q |
| G | S | S | T | S | H | DELETED | DELETED | L |
| G | S | S | T | S | H | DELETED | DELETED | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| G | S | S | T | S | H | DELETED | V | L |
| G | S | S | T | S | H | DELETED | V | Q |
| G | S | S | T | S | H | H | DELETED | L |
| G | S | S | T | S | H | H | DELETED | Q |
| G | S | S | T | S | H | H | V | L |
| G | S | S | T | S | H | H | V | Q |
| G | S | S | T | R | DELETED | DELETED | DELETED | L |
| G | S | S | T | R | DELETED | DELETED | DELETED | Q |
| G | S | S | T | R | DELETED | DELETED | V | L |
| G | S | S | T | R | DELETED | DELETED | V | Q |
| G | S | S | T | R | DELETED | H | DELETED | L |
| G | S | S | T | R | DELETED | H | DELETED | Q |
| G | S | S | T | R | DELETED | H | V | L |
| G | S | S | T | R | DELETED | H | V | Q |
| G | S | S | T | R | H | DELETED | DELETED | L |
| G | S | S | T | R | H | DELETED | DELETED | Q |
| G | S | S | T | R | H | DELETED | V | L |
| G | S | S | T | R | H | DELETED | V | Q |
| G | S | S | T | R | H | H | DELETED | L |
| G | S | S | T | R | H | H | DELETED | Q |
| G | S | S | T | R | H | H | V | L |
| G | S | S | T | R | H | H | V | Q |
| G | S | I | S | S | DELETED | DELETED | DELETED | L |
| G | S | I | S | S | DELETED | DELETED | DELETED | Q |
| G | S | I | S | S | DELETED | DELETED | V | L |
| G | S | I | S | S | DELETED | DELETED | V | Q |
| G | S | I | S | S | DELETED | H | DELETED | L |
| G | S | I | S | S | DELETED | H | DELETED | Q |
| G | S | I | S | S | DELETED | H | V | L |
| G | S | I | S | S | DELETED | H | V | Q |
| G | S | I | S | S | H | DELETED | DELETED | L |
| G | S | I | S | S | H | DELETED | DELETED | Q |
| G | S | I | S | S | H | DELETED | V | L |
| G | S | I | S | S | H | DELETED | V | Q |
| G | S | I | S | S | H | H | DELETED | L |
| G | S | I | S | S | H | H | DELETED | Q |
| G | S | I | S | S | H | H | V | L |
| G | S | I | S | S | H | H | V | Q |
| G | S | I | S | R | DELETED | DELETED | DELETED | L |
| G | S | I | S | R | DELETED | DELETED | DELETED | Q |
| G | S | I | S | R | DELETED | DELETED | V | L |
| G | S | I | S | R | DELETED | DELETED | V | Q |
| G | S | I | S | R | DELETED | H | DELETED | L |
| G | S | I | S | R | DELETED | H | DELETED | Q |
| G | S | I | S | R | DELETED | H | V | L |
| G | S | I | S | R | DELETED | H | V | Q |
| G | S | I | S | R | H | DELETED | DELETED | L |
| G | S | I | S | R | H | DELETED | DELETED | Q |
| G | S | I | S | R | H | DELETED | V | L |
| G | S | I | S | R | H | DELETED | V | Q |
| G | S | I | S | R | H | H | DELETED | L |
| G | S | I | S | R | H | H | DELETED | Q |
| G | S | I | S | R | H | H | V | L |
| G | S | I | S | R | H | H | V | Q |
| G | S | I | T | S | DELETED | DELETED | DELETED | L |
| G | S | I | T | S | DELETED | DELETED | DELETED | Q |
| G | S | I | T | S | DELETED | DELETED | V | L |
| G | S | I | T | S | DELETED | DELETED | V | Q |
| G | S | I | T | S | DELETED | H | DELETED | L |
| G | S | I | T | S | DELETED | H | DELETED | Q |
| G | S | I | T | S | DELETED | H | V | L |
| G | S | I | T | S | DELETED | H | V | Q |
| G | S | I | T | S | H | DELETED | DELETED | L |
| G | S | I | T | S | H | DELETED | DELETED | Q |
| G | S | I | T | S | H | DELETED | V | L |
| G | S | I | T | S | H | DELETED | V | Q |
| G | S | I | T | S | H | H | DELETED | L |
| G | S | I | T | S | H | H | DELETED | Q |
| G | S | I | T | S | H | H | V | L |
| G | S | I | T | S | H | H | V | Q |
| G | S | I | T | R | DELETED | DELETED | DELETED | L |
| G | S | I | T | R | DELETED | DELETED | DELETED | Q |
| G | S | I | T | R | DELETED | DELETED | V | L |
| G | S | I | T | R | DELETED | DELETED | V | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| G | S | I | T | R | DELETED | H | DELETED | L |
| G | S | I | T | R | DELETED | H | DELETED | Q |
| G | S | I | T | R | DELETED | H | V | L |
| G | S | I | T | R | DELETED | H | V | Q |
| G | S | I | T | R | H | DELETED | DELETED | L |
| G | S | I | T | R | H | DELETED | DELETED | Q |
| G | S | I | T | R | H | DELETED | V | L |
| G | S | I | T | R | H | DELETED | V | Q |
| G | S | I | T | R | H | H | DELETED | L |
| G | S | I | T | R | H | H | DELETED | Q |
| G | S | I | T | R | H | H | V | L |
| G | S | I | T | R | H | H | V | Q |
| G | F | S | S | S | DELETED | DELETED | DELETED | L |
| G | F | S | S | S | DELETED | DELETED | DELETED | Q |
| G | F | S | S | S | DELETED | DELETED | V | L |
| G | F | S | S | S | DELETED | DELETED | V | Q |
| G | F | S | S | S | DELETED | H | DELETED | L |
| G | F | S | S | S | DELETED | H | DELETED | Q |
| G | F | S | S | S | DELETED | H | V | L |
| G | F | S | S | S | DELETED | H | V | Q |
| G | F | S | S | S | H | DELETED | DELETED | L |
| G | F | S | S | S | H | DELETED | DELETED | Q |
| G | F | S | S | S | H | DELETED | V | L |
| G | F | S | S | S | H | DELETED | V | Q |
| G | F | S | S | S | H | H | DELETED | L |
| G | F | S | S | S | H | H | DELETED | Q |
| G | F | S | S | S | H | H | V | L |
| G | F | S | S | S | H | H | V | Q |
| G | F | S | S | R | DELETED | DELETED | DELETED | L |
| G | F | S | S | R | DELETED | DELETED | DELETED | Q |
| G | F | S | S | R | DELETED | DELETED | V | L |
| G | F | S | S | R | DELETED | DELETED | V | Q |
| G | F | S | S | R | DELETED | H | DELETED | L |
| G | F | S | S | R | DELETED | H | DELETED | Q |
| G | F | S | S | R | DELETED | H | V | L |
| G | F | S | S | R | DELETED | H | V | Q |
| G | F | S | S | R | H | DELETED | DELETED | L |
| G | F | S | S | R | H | DELETED | DELETED | Q |
| G | F | S | S | R | H | DELETED | V | L |
| G | F | S | S | R | H | DELETED | V | Q |
| G | F | S | S | R | H | H | DELETED | L |
| G | F | S | S | R | H | H | DELETED | Q |
| G | F | S | S | R | H | H | V | L |
| G | F | S | S | R | H | H | V | Q |
| G | F | S | T | S | DELETED | DELETED | DELETED | L |
| G | F | S | T | S | DELETED | DELETED | DELETED | Q |
| G | F | S | T | S | DELETED | DELETED | V | L |
| G | F | S | T | S | DELETED | DELETED | V | Q |
| G | F | S | T | S | DELETED | H | DELETED | L |
| G | F | S | T | S | DELETED | H | DELETED | Q |
| G | F | S | T | S | DELETED | H | V | L |
| G | F | S | T | S | DELETED | H | V | Q |
| G | F | S | T | S | H | DELETED | DELETED | L |
| G | F | S | T | S | H | DELETED | DELETED | Q |
| G | F | S | T | S | H | DELETED | V | L |
| G | F | S | T | S | H | DELETED | V | Q |
| G | F | S | T | S | H | H | DELETED | L |
| G | F | S | T | S | H | H | DELETED | Q |
| G | F | S | T | S | H | H | V | L |
| G | F | S | T | S | H | H | V | Q |
| G | F | S | T | R | DELETED | DELETED | DELETED | L |
| G | F | S | T | R | DELETED | DELETED | DELETED | Q |
| G | F | S | T | R | DELETED | DELETED | V | L |
| G | F | S | T | R | DELETED | DELETED | V | Q |
| G | F | S | T | R | DELETED | H | DELETED | L |
| G | F | S | T | R | DELETED | H | DELETED | Q |
| G | F | S | T | R | DELETED | H | V | L |
| G | F | S | T | R | DELETED | H | V | Q |
| G | F | S | T | R | H | DELETED | DELETED | L |
| G | F | S | T | R | H | DELETED | DELETED | Q |
| G | F | S | T | R | H | DELETED | V | L |
| G | F | S | T | R | H | DELETED | V | Q |
| G | F | S | T | R | H | H | DELETED | L |
| G | F | S | T | R | H | H | DELETED | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| G | F | S | T | R | H | H | V | L |
| G | F | S | T | R | H | H | V | Q |
| G | F | I | S | S | DELETED | DELETED | DELETED | L |
| G | F | I | S | S | DELETED | DELETED | DELETED | Q |
| G | F | I | S | S | DELETED | DELETED | V | L |
| G | F | I | S | S | DELETED | DELETED | V | Q |
| G | F | I | S | S | DELETED | H | DELETED | L |
| G | F | I | S | S | DELETED | H | DELETED | Q |
| G | F | I | S | S | DELETED | H | V | L |
| G | F | I | S | S | DELETED | H | V | Q |
| G | F | I | S | S | H | DELETED | DELETED | L |
| G | F | I | S | S | H | DELETED | DELETED | Q |
| G | F | I | S | S | H | DELETED | V | L |
| G | F | I | S | S | H | DELETED | V | Q |
| G | F | I | S | S | H | H | DELETED | L |
| G | F | I | S | S | H | H | DELETED | Q |
| G | F | I | S | S | H | H | V | L |
| G | F | I | S | S | H | H | V | Q |
| G | F | I | S | R | DELETED | DELETED | DELETED | L |
| G | F | I | S | R | DELETED | DELETED | DELETED | Q |
| G | F | I | S | R | DELETED | DELETED | V | L |
| G | F | I | S | R | DELETED | DELETED | V | Q |
| G | F | I | S | R | DELETED | H | DELETED | L |
| G | F | I | S | R | DELETED | H | DELETED | Q |
| G | F | I | S | R | DELETED | H | V | L |
| G | F | I | S | R | DELETED | H | V | Q |
| G | F | I | S | R | H | DELETED | DELETED | L |
| G | F | I | S | R | H | DELETED | DELETED | Q |
| G | F | I | S | R | H | DELETED | V | L |
| G | F | I | S | R | H | DELETED | V | Q |
| G | F | I | S | R | H | H | DELETED | L |
| G | F | I | S | R | H | H | DELETED | Q |
| G | F | I | S | R | H | H | V | L |
| G | F | I | S | R | H | H | V | Q |
| G | F | I | T | S | DELETED | DELETED | DELETED | L |
| G | F | I | T | S | DELETED | DELETED | DELETED | Q |
| G | F | I | T | S | DELETED | DELETED | V | L |
| G | F | I | T | S | DELETED | DELETED | V | Q |
| G | F | I | T | S | DELETED | H | DELETED | L |
| G | F | I | T | S | DELETED | H | DELETED | Q |
| G | F | I | T | S | DELETED | H | V | L |
| G | F | I | T | S | DELETED | H | V | Q |
| G | F | I | T | S | H | DELETED | DELETED | L |
| G | F | I | T | S | H | DELETED | DELETED | Q |
| G | F | I | T | S | H | DELETED | V | L |
| G | F | I | T | S | H | DELETED | V | Q |
| G | F | I | T | S | H | H | DELETED | L |
| G | F | I | T | S | H | H | DELETED | Q |
| G | F | I | T | S | H | H | V | L |
| G | F | I | T | S | H | H | V | Q |
| G | F | I | T | R | DELETED | DELETED | DELETED | L |
| G | F | I | T | R | DELETED | DELETED | DELETED | Q |
| G | F | I | T | R | DELETED | DELETED | V | L |
| G | F | I | T | R | DELETED | DELETED | V | Q |
| G | F | I | T | R | DELETED | H | DELETED | L |
| G | F | I | T | R | DELETED | H | DELETED | Q |
| G | F | I | T | R | DELETED | H | V | L |
| G | F | I | T | R | DELETED | H | V | Q |
| G | F | I | T | R | H | DELETED | DELETED | L |
| G | F | I | T | R | H | DELETED | DELETED | Q |
| G | F | I | T | R | H | DELETED | V | L |
| G | F | I | T | R | H | DELETED | V | Q |
| G | F | I | T | R | H | H | DELETED | L |
| G | F | I | T | R | H | H | DELETED | Q |
| G | F | I | T | R | H | H | V | L |
| G | F | I | T | R | H | H | V | Q |
| D | S | S | S | S | DELETED | DELETED | DELETED | L |
| D | S | S | S | S | DELETED | DELETED | DELETED | Q |
| D | S | S | S | S | DELETED | DELETED | V | L |
| D | S | S | S | S | DELETED | DELETED | V | Q |
| D | S | S | S | S | DELETED | H | DELETED | L |
| D | S | S | S | S | DELETED | H | DELETED | Q |
| D | S | S | S | S | DELETED | H | V | L |
| D | S | S | S | S | DELETED | H | V | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| D | S | S | S | S | H | DELETED | DELETED | L |
| D | S | S | S | S | H | DELETED | DELETED | Q |
| D | S | S | S | S | H | DELETED | V | L |
| D | S | S | S | S | H | DELETED | V | Q |
| D | S | S | S | S | H | H | DELETED | L |
| D | S | S | S | S | H | H | DELETED | Q |
| D | S | S | S | S | H | H | V | L |
| D | S | S | S | S | H | H | V | Q |
| D | S | S | S | R | DELETED | DELETED | DELETED | L |
| D | S | S | S | R | DELETED | DELETED | DELETED | Q |
| D | S | S | S | R | DELETED | DELETED | V | L |
| D | S | S | S | R | DELETED | DELETED | V | Q |
| D | S | S | S | R | DELETED | H | DELETED | L |
| D | S | S | S | R | DELETED | H | DELETED | Q |
| D | S | S | S | R | DELETED | H | V | L |
| D | S | S | S | R | DELETED | H | V | Q |
| D | S | S | S | R | H | DELETED | DELETED | L |
| D | S | S | S | R | H | DELETED | DELETED | Q |
| D | S | S | S | R | H | DELETED | V | L |
| D | S | S | S | R | H | DELETED | V | Q |
| D | S | S | S | R | H | H | DELETED | L |
| D | S | S | S | R | H | H | DELETED | Q |
| D | S | S | S | R | H | H | V | L |
| D | S | S | S | R | H | H | V | Q |
| D | S | S | T | S | DELETED | DELETED | DELETED | L |
| D | S | S | T | S | DELETED | DELETED | DELETED | Q |
| D | S | S | T | S | DELETED | DELETED | V | L |
| D | S | S | T | S | DELETED | DELETED | V | Q |
| D | S | S | T | S | DELETED | H | DELETED | L |
| D | S | S | T | S | DELETED | H | DELETED | Q |
| D | S | S | T | S | DELETED | H | V | L |
| D | S | S | T | S | DELETED | H | V | Q |
| D | S | S | T | S | H | DELETED | DELETED | L |
| D | S | S | T | S | H | DELETED | DELETED | Q |
| D | S | S | T | S | H | DELETED | V | L |
| D | S | S | T | S | H | DELETED | V | Q |
| D | S | S | T | S | H | H | DELETED | L |
| D | S | S | T | S | H | H | DELETED | Q |
| D | S | S | T | S | H | H | V | L |
| D | S | S | T | S | H | H | V | Q |
| D | S | S | T | R | DELETED | DELETED | DELETED | L |
| D | S | S | T | R | DELETED | DELETED | DELETED | Q |
| D | S | S | T | R | DELETED | DELETED | V | L |
| D | S | S | T | R | DELETED | DELETED | V | Q |
| D | S | S | T | R | DELETED | H | DELETED | L |
| D | S | S | T | R | DELETED | H | DELETED | Q |
| D | S | S | T | R | DELETED | H | V | L |
| D | S | S | T | R | DELETED | H | V | Q |
| D | S | S | T | R | H | DELETED | DELETED | L |
| D | S | S | T | R | H | DELETED | DELETED | Q |
| D | S | S | T | R | H | DELETED | V | L |
| D | S | S | T | R | H | DELETED | V | Q |
| D | S | S | T | R | H | H | DELETED | L |
| D | S | S | T | R | H | H | DELETED | Q |
| D | S | S | T | R | H | H | V | L |
| D | S | S | T | R | H | H | V | Q |
| D | S | I | S | S | DELETED | DELETED | DELETED | L |
| D | S | I | S | S | DELETED | DELETED | DELETED | Q |
| D | S | I | S | S | DELETED | DELETED | V | L |
| D | S | I | S | S | DELETED | DELETED | V | Q |
| D | S | I | S | S | DELETED | H | DELETED | L |
| D | S | I | S | S | DELETED | H | DELETED | Q |
| D | S | I | S | S | DELETED | H | V | L |
| D | S | I | S | S | DELETED | H | V | Q |
| D | S | I | S | S | H | DELETED | DELETED | L |
| D | S | I | S | S | H | DELETED | DELETED | Q |
| D | S | I | S | S | H | DELETED | V | L |
| D | S | I | S | S | H | DELETED | V | Q |
| D | S | I | S | S | H | H | DELETED | L |
| D | S | I | S | S | H | H | DELETED | Q |
| D | S | I | S | S | H | H | V | L |
| D | S | I | S | S | H | H | V | Q |
| D | S | I | S | R | DELETED | DELETED | DELETED | L |
| D | S | I | S | R | DELETED | DELETED | DELETED | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| D | S | I | S | R | DELETED | DELETED | V | L |
| D | S | I | S | R | DELETED | DELETED | V | Q |
| D | S | I | S | R | DELETED | H | DELETED | L |
| D | S | I | S | R | DELETED | H | DELETED | Q |
| D | S | I | S | R | DELETED | H | V | L |
| D | S | I | S | R | DELETED | H | V | Q |
| D | S | I | S | R | H | DELETED | DELETED | L |
| D | S | I | S | R | H | DELETED | DELETED | Q |
| D | S | I | S | R | H | DELETED | V | L |
| D | S | I | S | R | H | DELETED | V | Q |
| D | S | I | S | R | H | H | DELETED | L |
| D | S | I | S | R | H | H | DELETED | Q |
| D | S | I | S | R | H | H | V | L |
| D | S | I | S | R | H | H | V | Q |
| D | S | I | T | S | DELETED | DELETED | DELETED | L |
| D | S | I | T | S | DELETED | DELETED | DELETED | Q |
| D | S | I | T | S | DELETED | DELETED | V | L |
| D | S | I | T | S | DELETED | DELETED | V | Q |
| D | S | I | T | S | DELETED | H | DELETED | L |
| D | S | I | T | S | DELETED | H | DELETED | Q |
| D | S | I | T | S | DELETED | H | V | L |
| D | S | I | T | S | DELETED | H | V | Q |
| D | S | I | T | S | H | DELETED | DELETED | L |
| D | S | I | T | S | H | DELETED | DELETED | Q |
| D | S | I | T | S | H | DELETED | V | L |
| D | S | I | T | S | H | DELETED | V | Q |
| D | S | I | T | S | H | H | DELETED | L |
| D | S | I | T | S | H | H | DELETED | Q |
| D | S | I | T | S | H | H | V | L |
| D | S | I | T | S | H | H | V | Q |
| D | S | I | T | R | DELETED | DELETED | DELETED | L |
| D | S | I | T | R | DELETED | DELETED | DELETED | Q |
| D | S | I | T | R | DELETED | DELETED | V | L |
| D | S | I | T | R | DELETED | DELETED | V | Q |
| D | S | I | T | R | DELETED | H | DELETED | L |
| D | S | I | T | R | DELETED | H | DELETED | Q |
| D | S | I | T | R | DELETED | H | V | L |
| D | S | I | T | R | DELETED | H | V | Q |
| D | S | I | T | R | H | DELETED | DELETED | L |
| D | S | I | T | R | H | DELETED | DELETED | Q |
| D | S | I | T | R | H | DELETED | V | L |
| D | S | I | T | R | H | DELETED | V | Q |
| D | S | I | T | R | H | H | DELETED | L |
| D | S | I | T | R | H | H | DELETED | Q |
| D | S | I | T | R | H | H | V | L |
| D | S | I | T | R | H | H | V | Q |
| D | F | S | S | S | DELETED | DELETED | DELETED | L |
| D | F | S | S | S | DELETED | DELETED | DELETED | Q |
| D | F | S | S | S | DELETED | DELETED | V | L |
| D | F | S | S | S | DELETED | DELETED | V | Q |
| D | F | S | S | S | DELETED | H | DELETED | L |
| D | F | S | S | S | DELETED | H | DELETED | Q |
| D | F | S | S | S | DELETED | H | V | L |
| D | F | S | S | S | DELETED | H | V | Q |
| D | F | S | S | S | H | DELETED | DELETED | L |
| D | F | S | S | S | H | DELETED | DELETED | Q |
| D | F | S | S | S | H | DELETED | V | L |
| D | F | S | S | S | H | DELETED | V | Q |
| D | F | S | S | S | H | H | DELETED | L |
| D | F | S | S | S | H | H | DELETED | Q |
| D | F | S | S | S | H | H | V | L |
| D | F | S | S | S | H | H | V | Q |
| D | F | S | S | R | DELETED | DELETED | DELETED | L |
| D | F | S | S | R | DELETED | DELETED | DELETED | Q |
| D | F | S | S | R | DELETED | DELETED | V | L |
| D | F | S | S | R | DELETED | DELETED | V | Q |
| D | F | S | S | R | DELETED | H | DELETED | L |
| D | F | S | S | R | DELETED | H | DELETED | Q |
| D | F | S | S | R | DELETED | H | V | L |
| D | F | S | S | R | DELETED | H | V | Q |
| D | F | S | S | R | H | DELETED | DELETED | L |
| D | F | S | S | R | H | DELETED | DELETED | Q |
| D | F | S | S | R | H | DELETED | V | L |
| D | F | S | S | R | H | DELETED | V | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| D | F | S | S | R | H | H | DELETED | L |
| D | F | S | S | R | H | H | DELETED | Q |
| D | F | S | S | R | H | H | V | L |
| D | F | S | S | R | H | H | V | Q |
| D | F | S | T | S | DELETED | DELETED | DELETED | L |
| D | F | S | T | S | DELETED | DELETED | DELETED | Q |
| D | F | S | T | S | DELETED | DELETED | V | L |
| D | F | S | T | S | DELETED | DELETED | V | Q |
| D | F | S | T | S | DELETED | H | DELETED | L |
| D | F | S | T | S | DELETED | H | DELETED | Q |
| D | F | S | T | S | DELETED | H | V | L |
| D | F | S | T | S | DELETED | H | V | Q |
| D | F | S | T | S | H | DELETED | DELETED | L |
| D | F | S | T | S | H | DELETED | DELETED | Q |
| D | F | S | T | S | H | DELETED | V | L |
| D | F | S | T | S | H | DELETED | V | Q |
| D | F | S | T | S | H | H | DELETED | L |
| D | F | S | T | S | H | H | DELETED | Q |
| D | F | S | T | S | H | H | V | L |
| D | F | S | T | S | H | H | V | Q |
| D | F | S | T | R | DELETED | DELETED | DELETED | L |
| D | F | S | T | R | DELETED | DELETED | DELETED | Q |
| D | F | S | T | R | DELETED | DELETED | V | L |
| D | F | S | T | R | DELETED | DELETED | V | Q |
| D | F | S | T | R | DELETED | H | DELETED | L |
| D | F | S | T | R | DELETED | H | DELETED | Q |
| D | F | S | T | R | DELETED | H | V | L |
| D | F | S | T | R | DELETED | H | V | Q |
| D | F | S | T | R | H | DELETED | DELETED | L |
| D | F | S | T | R | H | DELETED | DELETED | Q |
| D | F | S | T | R | H | DELETED | V | L |
| D | F | S | T | R | H | DELETED | V | Q |
| D | F | S | T | R | H | H | DELETED | L |
| D | F | S | T | R | H | H | DELETED | Q |
| D | F | S | T | R | H | H | V | L |
| D | F | S | T | R | H | H | V | Q |
| D | F | I | S | S | DELETED | DELETED | DELETED | L |
| D | F | I | S | S | DELETED | DELETED | DELETED | Q |
| D | F | I | S | S | DELETED | DELETED | V | L |
| D | F | I | S | S | DELETED | DELETED | V | Q |
| D | F | I | S | S | DELETED | H | DELETED | L |
| D | F | I | S | S | DELETED | H | DELETED | Q |
| D | F | I | S | S | DELETED | H | V | L |
| D | F | I | S | S | DELETED | H | V | Q |
| D | F | I | S | S | H | DELETED | DELETED | L |
| D | F | I | S | S | H | DELETED | DELETED | Q |
| D | F | I | S | S | H | DELETED | V | L |
| D | F | I | S | S | H | DELETED | V | Q |
| D | F | I | S | S | H | H | DELETED | L |
| D | F | I | S | S | H | H | DELETED | Q |
| D | F | I | S | S | H | H | V | L |
| D | F | I | S | S | H | H | V | Q |
| D | F | I | S | R | DELETED | DELETED | DELETED | L |
| D | F | I | S | R | DELETED | DELETED | DELETED | Q |
| D | F | I | S | R | DELETED | DELETED | V | L |
| D | F | I | S | R | DELETED | DELETED | V | Q |
| D | F | I | S | R | DELETED | H | DELETED | L |
| D | F | I | S | R | DELETED | H | DELETED | Q |
| D | F | I | S | R | DELETED | H | V | L |
| D | F | I | S | R | DELETED | H | V | Q |
| D | F | I | S | R | H | DELETED | DELETED | L |
| D | F | I | S | R | H | DELETED | DELETED | Q |
| D | F | I | S | R | H | DELETED | V | L |
| D | F | I | S | R | H | DELETED | V | Q |
| D | F | I | S | R | H | H | DELETED | L |
| D | F | I | S | R | H | H | DELETED | Q |
| D | F | I | S | R | H | H | V | L |
| D | F | I | S | R | H | H | V | Q |
| D | F | I | T | S | DELETED | DELETED | DELETED | L |
| D | F | I | T | S | DELETED | DELETED | DELETED | Q |
| D | F | I | T | S | DELETED | DELETED | V | L |
| D | F | I | T | S | DELETED | DELETED | V | Q |
| D | F | I | T | S | DELETED | H | DELETED | L |
| D | F | I | T | S | DELETED | H | DELETED | Q |

TABLE 10-continued

Exemplary Mutations of mAb 2.998.2 Heavy Chain (SEQ ID NO: 14) to Germline at the Indicated Residue Number.

| 27 | 32 | 33 | 52 | 85 | 100 | 101 | 103 | 112 |
|---|---|---|---|---|---|---|---|---|
| D | F | I | T | S | DELETED | H | V | L |
| D | F | I | T | S | DELETED | H | V | Q |
| D | F | I | T | S | H | DELETED | DELETED | L |
| D | F | I | T | S | H | DELETED | DELETED | Q |
| D | F | I | T | S | H | DELETED | V | L |
| D | F | I | T | S | H | DELETED | V | Q |
| D | F | I | T | S | H | H | DELETED | L |
| D | F | I | T | S | H | H | DELETED | Q |
| D | F | I | T | S | H | H | V | L |
| D | F | I | T | S | H | H | V | Q |
| D | F | I | T | R | DELETED | DELETED | DELETED | L |
| D | F | I | T | R | DELETED | DELETED | DELETED | Q |
| D | F | I | T | R | DELETED | DELETED | V | L |
| D | F | I | T | R | DELETED | DELETED | V | Q |
| D | F | I | T | R | DELETED | H | DELETED | L |
| D | F | I | T | R | DELETED | H | DELETED | Q |
| D | F | I | T | R | DELETED | H | V | L |
| D | F | I | T | R | DELETED | H | V | Q |
| D | F | I | T | R | H | DELETED | DELETED | L |
| D | F | I | T | R | H | DELETED | DELETED | Q |
| D | F | I | T | R | H | DELETED | V | L |
| D | F | I | T | R | H | DELETED | V | Q |
| D | F | I | T | R | H | H | DELETED | L |
| D | F | I | T | R | H | H | DELETED | Q |
| D | F | I | T | R | H | H | V | L |
| D | F | I | T | R | H | H | V | Q |

TABLE 11

Exemplary Mutations of mAb 2.998.2 Light Chain (SEQ ID NO: 16) to Germline at the Indicated Residue Number.

| 1 | 7 | 28 | 80 | 92 | 93 | 106 |
|---|---|---|---|---|---|---|
| E | S | S | A | S | S | I |
| E | S | S | A | S | S | V |
| E | S | S | A | S | I | I |
| E | S | S | A | S | I | V |
| E | S | S | A | T | S | I |
| E | S | S | A | T | S | V |
| E | S | S | A | T | I | I |
| E | S | S | A | T | I | V |
| E | S | S | V | S | S | I |
| E | S | S | V | S | S | V |
| E | S | S | V | S | I | I |
| E | S | S | V | S | I | V |
| E | S | S | V | T | S | I |
| E | S | S | V | T | S | V |
| E | S | S | V | T | I | I |
| E | S | S | V | T | I | V |
| E | S | V | A | S | S | I |
| E | S | V | A | S | S | V |
| E | S | V | A | S | I | I |
| E | S | V | A | S | I | V |
| E | S | V | A | T | S | I |
| E | S | V | A | T | S | V |
| E | S | V | A | T | I | I |
| E | S | V | A | T | I | V |
| E | S | V | V | S | S | I |
| E | S | V | V | S | S | V |
| E | S | V | V | S | I | I |
| E | S | V | V | S | I | V |
| E | S | V | V | T | S | I |
| E | S | V | V | T | S | V |
| E | S | V | V | T | I | I |
| E | S | V | V | T | I | V |
| E | F | S | A | S | S | I |
| E | F | S | A | S | S | V |
| E | F | S | A | S | I | I |
| E | F | S | A | S | I | V |
| E | F | S | A | T | S | I |

TABLE 11-continued

Exemplary Mutations of mAb 2.998.2 Light Chain (SEQ ID NO: 16) to Germline at the Indicated Residue Number.

| 1 | 7 | 28 | 80 | 92 | 93 | 106 |
|---|---|---|---|---|---|---|
| E | F | S | A | T | S | V |
| E | F | S | A | T | I | I |
| E | F | S | A | T | I | V |
| E | F | S | V | S | S | I |
| E | F | S | V | S | S | V |
| E | F | S | V | S | I | I |
| E | F | S | V | S | I | V |
| E | F | S | V | T | S | I |
| E | F | S | V | T | S | V |
| E | F | S | V | T | I | I |
| E | F | S | V | T | I | V |
| E | F | V | A | S | S | I |
| E | F | V | A | S | S | V |
| E | F | V | A | S | I | I |
| E | F | V | A | S | I | V |
| E | F | V | A | T | S | I |
| E | F | V | A | T | S | V |
| E | F | V | A | T | I | I |
| E | F | V | A | T | I | V |
| E | F | V | V | S | S | I |
| E | F | V | V | S | S | V |
| E | F | V | V | S | I | I |
| E | F | V | V | S | I | V |
| E | F | V | V | T | S | I |
| E | F | V | V | T | S | V |
| E | F | V | V | T | I | I |
| E | F | V | V | T | I | V |
| D | S | S | A | S | S | I |
| D | S | S | A | S | S | V |
| D | S | S | A | S | I | I |
| D | S | S | A | S | I | V |
| D | S | S | A | T | S | I |
| D | S | S | A | T | S | V |
| D | S | S | A | T | I | I |
| D | S | S | A | T | I | V |
| D | S | S | V | S | S | I |
| D | S | S | V | S | S | V |
| D | S | S | V | S | I | I |
| D | S | S | V | S | I | V |
| D | S | S | V | T | S | I |
| D | S | S | V | T | S | V |
| D | S | S | V | T | I | I |
| D | S | S | V | T | I | V |
| D | S | V | A | S | S | I |
| D | S | V | A | S | S | V |
| D | S | V | A | S | I | I |
| D | S | V | A | S | I | V |
| D | S | V | A | T | S | I |
| D | S | V | A | T | S | V |
| D | S | V | A | T | I | I |
| D | S | V | A | T | I | V |
| D | S | V | V | S | S | I |
| D | S | V | V | S | S | V |
| D | S | V | V | S | I | I |
| D | S | V | V | S | I | V |
| D | S | V | V | T | S | I |
| D | S | V | V | T | S | V |
| D | S | V | V | T | I | I |
| D | S | V | V | T | I | V |
| D | F | S | A | S | S | I |
| D | F | S | A | S | S | V |
| D | F | S | A | S | I | I |
| D | F | S | A | S | I | V |
| D | F | S | A | T | S | I |
| D | F | S | A | T | S | V |
| D | F | S | A | T | I | I |
| D | F | S | A | T | I | V |
| D | F | S | V | S | S | I |
| D | F | S | V | S | S | V |
| D | F | S | V | S | I | I |
| D | F | S | V | S | I | V |
| D | F | S | V | T | S | I |
| D | F | S | V | T | S | V |
| D | F | S | V | T | I | I |

TABLE 11-continued

| Exemplary Mutations of mAb 2.998.2 Light Chain (SEQ ID NO: 16) to Germline at the Indicated Residue Number. | | | | | | |
|---|---|---|---|---|---|---|
| 1 | 7 | 28 | 80 | 92 | 93 | 106 |
| D | F | S | V | T | I | V |
| D | F | V | A | S | S | I |
| D | F | V | A | S | S | V |
| D | F | V | A | S | I | I |
| D | F | V | A | S | I | V |
| D | F | V | A | T | S | I |
| D | F | V | A | T | S | V |
| D | F | V | A | T | I | I |
| D | F | V | A | T | I | V |
| D | F | V | V | S | S | I |
| D | F | V | V | S | S | V |
| D | F | V | V | S | I | I |
| D | F | V | V | S | I | V |
| D | F | V | V | T | S | I |
| D | F | V | V | T | S | V |
| D | F | V | V | T | I | I |
| D | F | V | V | T | I | V |

TABLE 12

| ANTI-PDGFR-ALPHA ANTIBODY HEAVY CHAIN SEQUENCES | | | | | | |
|---|---|---|---|---|---|---|
| Chain Name | V | D | J | FR1 | CDR1 | FR2 |
| | | Germline | | QVQLVESGGGLVKPGGSLRLSCAAS | GFTFSDYYMS | WIRQAPGKGLEWVS |
| 2.175.3 | VH3-11 | D1-26 | JH4B | --H---------------------- | ---------H | -------------- |
| | | Germline | | QVQLVESGGGLVKPGGSLRLSCAAS | GFTFSDYYMS | WIRQAPGKGLEWVS |
| 2.451.1.1 | V3-11 | D6-6 | JH6B | ------------------------- | ---------N | -------------- |
| 2.449.1.3 | V3-11 | D6-6 | JH6B | ------------------------- | ---------N | -------------- |
| | | Germline | | QLQLQESGPGLVKPSETLSLTCTVS | GGSISSSSYYWG | WIRQPPGKGLEWIG |
| 2.84.1 | V4-39 | D7-27 | JH4B | ------------------------- | --F--------- | -------------- |
| 2.998.2 | V4-39 | D7-27 | JH4B | ------------------------- | -D----FI---- | -------------- |

| CDR2 | FR3 | CDR3 | FR4 | SEQ ID NO. |
|---|---|---|---|---|
| YISSSGSTIYYADSVKG | RFTISRDNAKNSLYLQMNSLRAEDTAVYYCAR | ###YSGS#FDY | WGQGTLVTVSS | 127 |
| ---R---L---V----- | -------------N------------------ | GGP----P--- | ----------- | 2 |
| YISSSGSTIYYADSVKG | RFTISRDNAKNSLYLQMNSLRAEDTAVYYCAR | ##SIAARGMDV | WGQGTTVTVSS | 128 |
| F---------------- | -------------------------------- | DGH-------- | ----------- | 6 |
| -------I--------- | -------------------------------- | EGR-------- | ----------- | 10 |
| SIYYSGSTYYNPSLKS | RVTISVDTSKNQFSLKLSSVTAADTAVYYCAR | ##W#FDY | WGQGTLVTVSS | 129 |
| T-----T----S---- | ---------Q---------------------- | HH-VFDY | ----------- | 18 |
| T--------------- | -----------------R-------------- | HH-VFDY | -----Q----- | 14 |

TABLE 13

| ANTI-PDGFR-ALPHA ANTIBODY LIGHT CHAIN SEQUENCES | | | | | |
|---|---|---|---|---|---|
| Chain Name | V | J | FR1 | CDR1 | FR2 |
| | Germline | | DIQMTQSPSSLSASVGDRVTITC | RASQSISSYLN | WYQQKPGKAPKLLIY |
| 2.175.3 | O12 | JK1 | ----------------------- | -P--R--R--- | -----------F--- |
| | Germline | | DIQMTQSPSSLSASVGDRVTITC | RASQGISNYLA | WYQQKPGKVPKLLIY |
| 2.451.1.1 | A20 | JK5 | V---------------------- | ----V-T---- | --------------F |
| | Germline | | EIVLTQSPDFQSVTPKEKVTITC | RASQSIGSSLH | WYQQKPDQSPKLLIK |
| 2.84.1 | A26 | JK1 | -V----------------I---- | ----I--T--- | ---K----------- |
| 2.998.2 | A26 | JK1 | D-----F---------------- | ----V------ | --------------- |

TABLE 13-continued

| ANTI-PDGFR-ALPHA ANTIBODY LIGHT CHAIN SEQUENCES | | | | | |
|---|---|---|---|---|---|
| | Germline | | DIQMTQSPSSLSASVGDRVTITC | RASQSISSYLN | WYQQKPGKAPKLLIY |
| 2.449.1.3 | O12 | JK5 | -------------------S--- | -P---F-R-I- | --------------H |
| 2.451.1.1 | O12 | JK5 | ----------------------- | ---H--TR-I- | ----------N---- |

| CDR2 | FR3 | CDR3 | FR4 | SEQ ID NO. |
|---|---|---|---|---|
| AASSLQS | GVPSRFSGSGSGTDFTLTISSLQPEDFATYYC | QQSYSTPPWT | FGQGTKVEIK | 130 |
| -----P- | --------------------T----------- | ---------- | ---------- | 4 |
| AASTLQS | GVPSRFSGSGSGTDFTLTISSLQPEDVATYYC | QKYNSAP#####IT | FGQGTRLEIK | 131 |
| -S----- | -------------------------------- | -------PRTRS-- | ---------- | 22 |
| YASQSFS | GVPSRFSGSGSGTDFTLTINSLEAEDAATYYC | HQSSSLPWT | FGQGTKVEIK | 132 |
| ------- | -------------E------------T----- | ---TN---- | ---------- | 20 |
| ------- | ----------------------V--------- | ---TI---- | --------V- | 16 |
| AASSLQS | GVPSRFSGSGSGTDFTLTISSLQPEDFATYYC | QQSYS###IT | FGQGTRLEIK | 133 |
| -----VG | -------------------------------- | --T--NPP-- | --------M- | 12 |
| ------- | -------------------------------- | --T--NPP-- | ---------- | 8 |

Example 8

Affinity Determination by Biacore Analysis

Biacore experiments were performed using a Biacore T100 instrument at 22° C. Standard aldehyde coupling of the biosensor surface with the antibody was utilized. Specifically, 50 μg of each mAb was reacted with ~1 mM NaIO4 for 25 min. on ice in 0.1 M NaOAc, pH 5.5, and then the oxidation reaction was stopped by desalting the sample on a Sephadex G-25 Nucleic Acid Purification-5 column (NAP-5, GE biosciences) with 10 mM NaOAC, pH 4.0. The mAbs were then flowed over a CM5 biosensor surface that had been reacted with EDC/NHS, carbohydrazide, and ethanolamine. After the desired surface capacity had been reached, the hydrazone bonds between the mAb and the surface were reduced by flowing 0.1 M NaBH3CN in 0.1 M NaOAc, pH 4.0 across the immobilized mAbs for 20 mins.

Mabs 2.998.2 (SEQ ID Nos:14 and 16), 2.175.3 (SEQ ID Nos: 2 and 4), 2.175.3 variant A (SEQ ID NO: 2 with 3Q, 80Y (SEQ ID NO:134); SEQ ID NO: 4 with 46L, 77S (SEQ ID NO:135)), 2.449.1 (SEQ ID NO: 10 and 12), and 2.449.1 variant A (SEQ ID NO: 10; SEQ ID NO: 12 with 49Y, 1071 (SEQ ID NO:136)) were immobilized on a CM5 biosensor chip. Recombinant human sPDGFR-alpha (R&D catalog# 322-PR/CF; lot#QY056081) was injected for 90 seconds at a concentration range of 51.6-0.806 nM (2× serial dilution) followed by a 3 minute dissociation. Since the dissociation phase was obviously extremely slow for all the interactions studied, an additional six injections, three at 25.8 nM and three blank buffer injections, were performed with a 90 second injection with a dissociation phase of 14,400 seconds (4 hrs.) after the initial 30 injections had been completed. The samples were prepared in Hepes-buffered saline, 0.005% polysorbate 20, pH 7.4 (HBS-P) with 100 μg/ml of BSA added. All samples were randomly injected in triplicate with over ten buffer injections interspersed for double referencing. All sensorgram data were processed with Scrubber 2.0 and globally fit to a 1:1 interaction model including a term for mass transport using CLAMP. The resulting binding constants are listed in the table below. MAbs are listed in order from highest to lowest affinity.

TABLE 14

| AFFINITY OF SELECTED ANTIBODIES | | | |
|---|---|---|---|
| Sample | $k_a$ ($M^{-1}s^{-1}$) | $k_d$ ($s^{-1}$) | $K_D$ (pM) |
| 2.175.3 variant A | $3.55 \times 10^5$ | $2.53 \times 10^{-6}$ | 7.1 |
| 2.449.1 variant A | $4.40 \times 10^5$ | $3.80 \times 10^{-6}$ | 8.6 |
| 2.175.3 | $5.16 \times 10^5$ | $2.59 \times 10^{-5}$ | 50 |
| 2.449.1 | $4.40 \times 10^5$ | $6.16 \times 10^{-5}$ | 140 |
| 2.998.2 | $2.98 \times 10^5$ | $4.89 \times 10^{-5}$ | 164 |

The results in Table 14 show that the germlined variants of 2.175.3 and 2.449.1 showed increased affinity for soluble PDGFRa as determined by Biacore analysis compared to the respective non-germlined antibodies. Both germlined antibodies show reduced dissociation constants compared to their normal counterparts which contributes to the observed increase in affinity. Four of the antibodies with the highest affinity in Table 14 were tested in a soluble PDGFRa binding ELISA as described in Example 2 and an MG-63 phosphorylation assay as described in Example 4. The resulting IC50 values are listed in Table 15.

TABLE 15

| ACTIVITY OF SELECTED ANTIBODIES IN THE sPDGFRa BINDING ELISA AND RECEPTOR PHOSPHORYLATION ASSAY | | |
|---|---|---|
| Antibody | sPDGFRa Elisa IC50 (ng/ml) | PTYR Assay IC50 (ng/ml) |
| 2.175.3 | 38 | 28 |
| 2.175.3 Variant A | 46 | 29 |
| 2.449.1.3 | 44 | 21 |
| 2.449.1.3 Variant A | 45 | 31 |

Example 9

Evaluation of Antitumor Efficacy in Human Tumor Xenograft Models

Figure 2A:
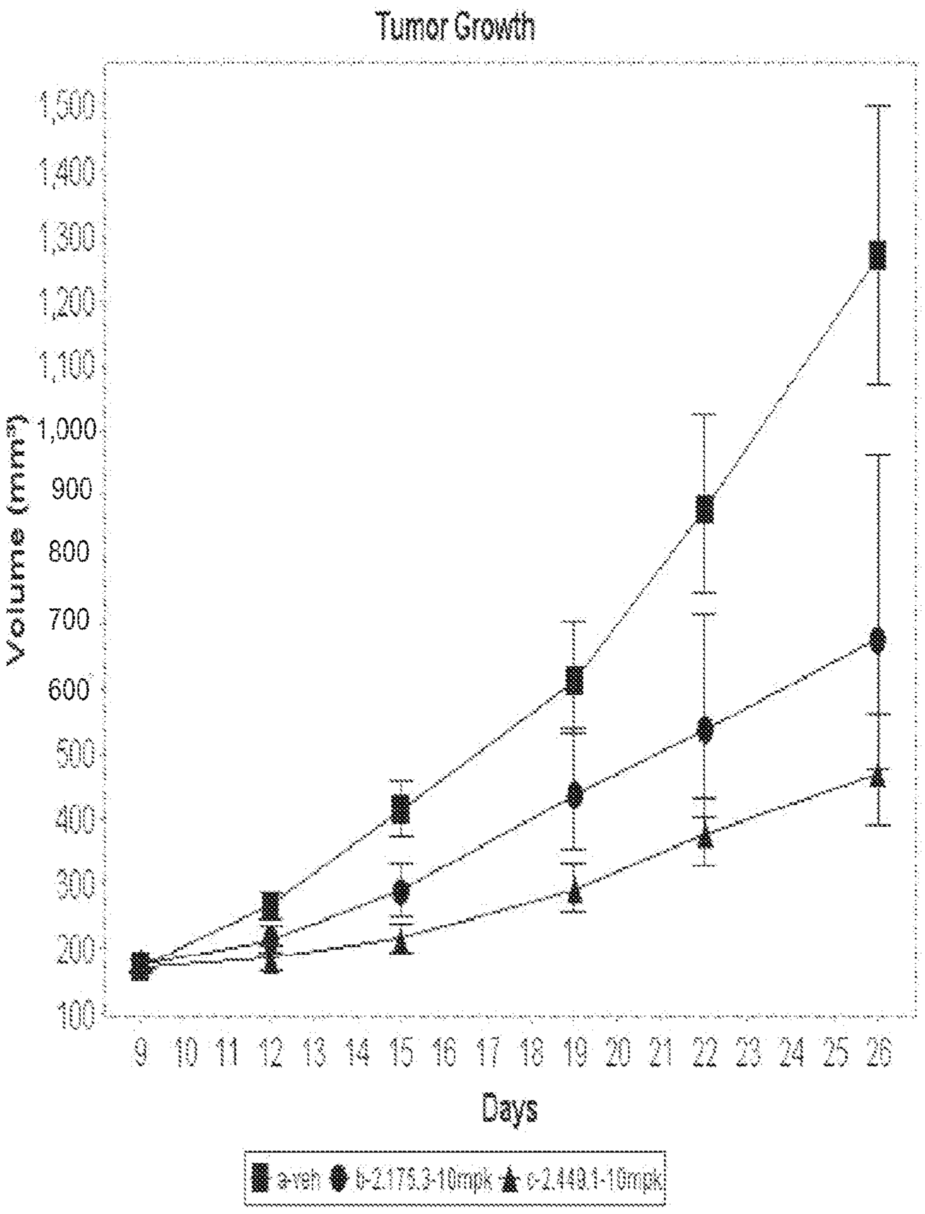
FIGS. 2*a*-2*b* show the results of in vivo antitumor evaluation of 2.175.3 and 2.449.1.3 in the Calu-6 non-small cell lung carcinoma xenograft model.
Figure 2B:
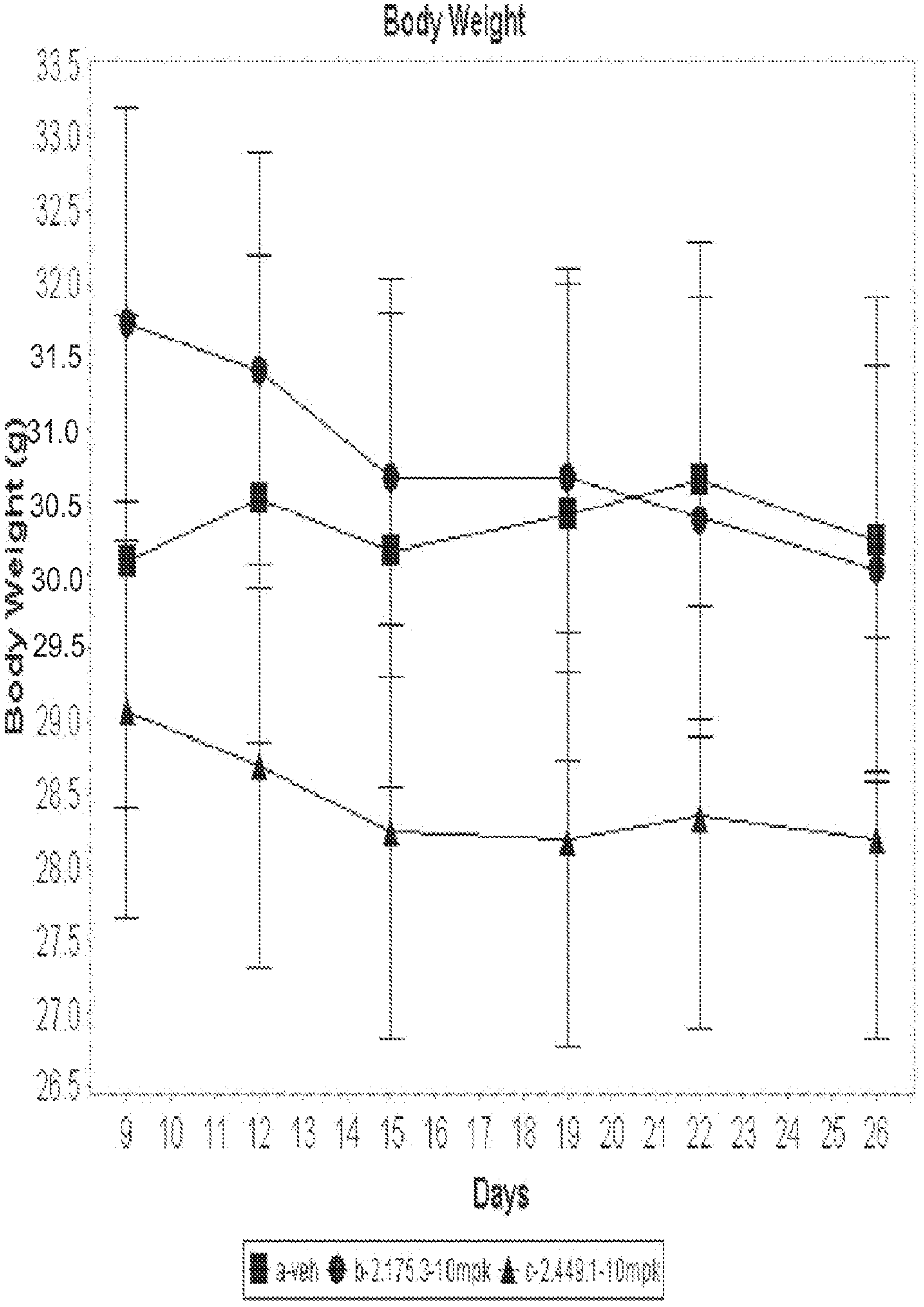

The antitumor efficacy of two of the above antibodies were evaluated in a xenograft model of non small cell lung carcinoma, Calu-6. The host mice were derived from a cross between Black6/129 mice that had the murine PDGFRa gene replaced with the human PDGFRa by homologous recombination and SCID mice. The resulting mice expressed the human PDGFRa receptor and not the murine receptor. These knockin/knockout mice 19 weeks of age (10/group) were injected with 2×106 Calu-6 cells in 0.1 ml of matrigel into the right flank. When the tumors reached the average of 170 mm3 in size, the antibodies in a phosphate buffered saline vehicle or empty saline vehicle were administered intraperitoneally at 10 mg of antibody per kilogram two times per week for the duration of the study. FIG. 2*a* shows the average tumor size per treatment group over time, while FIG. 2*b* shows the average body weight over time. Treatment with both antibodies reduced the tumor growth rate significantly; treatment with 2.175.3 produced a 55% reduced growth (p=0.06) while treatment with 2.449.1.3 producing a 73% reduced growth rate ($p<0.001$). There was no significant difference between groups with respect to body weight change during the study (FIG. 2*b*).

Figure 3:
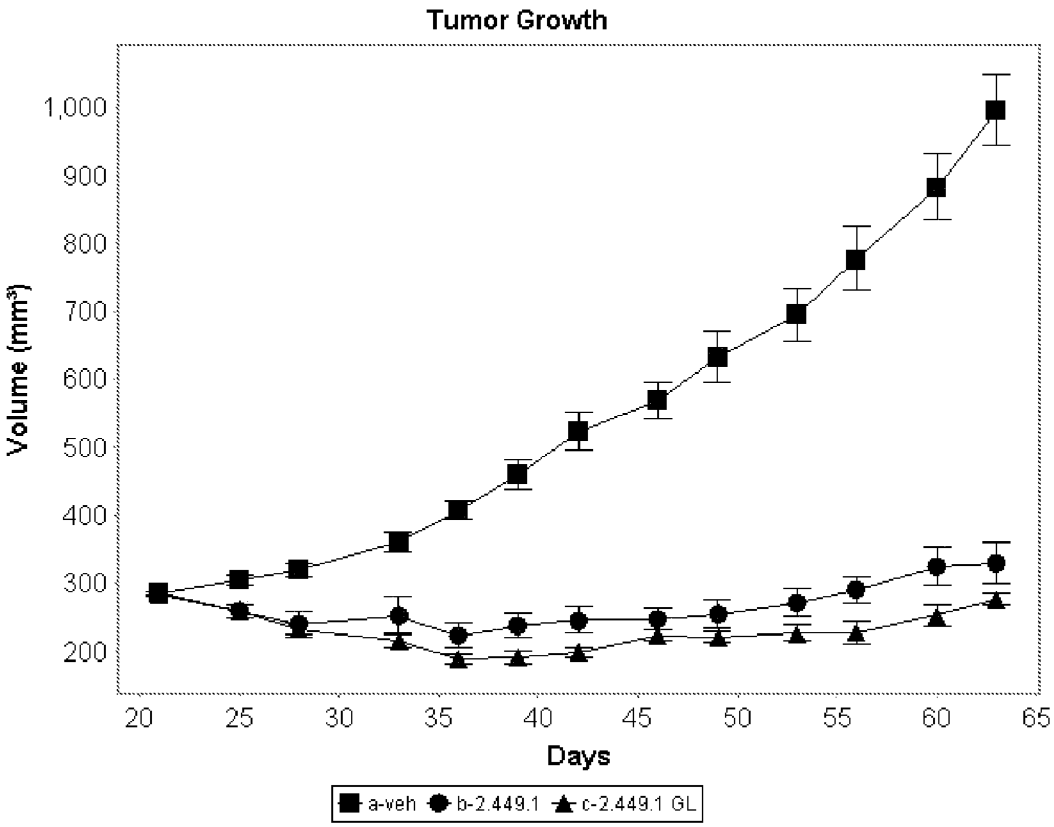
FIG. 3 shows the results of in vivo evaluation of the antibodies in the U118 glioma xenograft model in SCID mice. Tumor size (mm3) versus time (days) of treatment with antibodies is graphed. The square points show the vehicle treatment group; the circular points show the 2.175.3 10 mg/kg treatment group; the triangular points show the 2.449.1.3 10 mg/kg treatment group.

The antitumor efficacy of 2.449.1.3 and 2.449.1.3 variant A was further evaluated in the U118 glioma xenograft model. SCID mice 19 weeks of age (10/group) were injected with 2×106 cells in 0.1 ml of matrigel into the right flank of the animals. When the tumors reached an average of 280 mm3 in size, the antibodies were administered as described above for the Calu-6 model. The results are shown in FIG. 3. The antibody 2.449.1.3 reduced growth of the U118 tumors by 94% ($p<0.000001$). Variant A of 2.449.1.3 reduced growth by 101%. Therefore both 2.449.1.3 and 2.449.1.3 Variant A are highly active in reducing growth of this glioma xenograft, and the mutations of Variant A do not reduce in vivo activity in this model.

INCORPORATION BY REFERENCE

All references cited herein, including patents, patent applications, papers, text books, and the like, and the references cited therein, to the extent that they are not already, are hereby incorporated herein by reference in their entirety.

EQUIVALENTS

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention can be practiced in many ways and the invention should be construed in accordance with the appended claims and any equivalents thereof.

What is claimed is:

1. An isolated antibody, or binding fragment thereof, that specifically binds to PDGFR-alpha and inhibits the growth of cells that express PDGFR-alpha, wherein said antibody comprises a heavy chain polypeptide comprising the sequence of SEQ ID NO.: 10, or SEQ ID NO.:10 comprising any one of the combinations of residues indicated by each row of table 8.

2. The antibody of claim 1, wherein said antibody comprises a heavy chain polypeptide comprising the sequence of SEQ ID NO.: 10.

3. The antibody of claim 1, wherein said antibody further comprises a light chain polypeptide comprising the sequence of SEQ ID NO.: 12, or SEQ ID NO.:12 comprising any one of the combinations of residues indicated by each row of table 9.

4. The antibody of claim 3, wherein said antibody comprises a light chain polypeptide comprising the sequence of SEQ ID NO.: 12.

5. An isolated antibody, or binding fragment thereof, which competes for binding to PDGFR-alpha with the antibody of claims 1, 2, or 3-4.

6. An isolated antibody, or binding fragment thereof, that binds to the same epitope on PDGFR-alpha as the antibody of claim 1, 2, or 3-4.

7. An isolated antibody, or binding fragment thereof, that specifically binds to PDGFR-alpha and inhibits the growth of cells that express PDGFR-alpha, wherein the antibody comprises;

a heavy chain complementarity determining region 1 (CDR1) having the amino acid sequence of SEQ ID NO: 143;

a heavy chain complementarity determining region 2 (CDR2) having the amino acid sequence of SEQ ID NO: 144;

a heavy chain complementarity determining region 3 (CDR3) having the amino acid sequence of SEQ ID NO: 145;

a light chain complementarity determining region 1 (CDR1) having the amino acid sequence of SEQ ID NO: 146;

a light chain complementarity determining region 2 (CDR2) having the amino acid sequence of SEQ ID NO: 147; and a light chain complementarity determining region 3 (CDR3) having the amino acid sequence of SEQ ID NO: 148.

8. An antibody according to claim 7, wherein said antibody is a fully human monoclonal antibody.

9. A conjugate comprising an antibody of claims 1, 2, 3, 4, 7 or 8 or a binding fragment thereof.

10. The conjugate of claim 9, comprising a therapeutic agent.

11. The conjugate of claim 10, wherein the therapeutic agent is a toxin or radioisotope.

12. The conjugate of claim 10, wherein the therapeutic agent is a pharmaceutical agent.

13. The antibody of claim 3, wherein said antibody comprises a light chain polypeptide comprising the following residues:

residue 20 is T;

residue 49 is Y; and residue 107 is I.

14. The antibody of claim 13, wherein the light chain polypeptide further comprises the following residues:

residue 25 is P;

residue 29 is F;

residue 31 is R;

residue 33 is I;

residue 55 is V;

residue 56 is G;

residue 91 is T;

residue 94 is N;

residue 95 is P; and residue 96 is P.

15. The antibody of any of claims 1, 2, 3, 4, 7, or 8, wherein said antibody binding fragment is selected from the group consisting of Fab, Fab', $F(ab')_2$ and Fv.

16. A composition comprising the antibody of claim 1 and a pharmaceutically acceptable carrier.

17. A composition comprising the antibody of claim 7 and a pharmaceutically acceptable carrier.

18. A composition comprising the antibody of any of claims 3, 8, 13, or 14 and a pharmaceutically acceptable carrier.

* * * * *